US012527779B2

(12) United States Patent
Blayo et al.

(10) Patent No.: US 12,527,779 B2
(45) Date of Patent: Jan. 20, 2026

(54) PROSTAGLANDIN $E_2$ ($PGE_2$) $EP_4$ RECEPTOR ANTAGONISTS

(71) Applicant: Domain Therapeutics, Illkirch-Graffenstaden (FR)

(72) Inventors: Anne-Laure Blayo, Illkirch-Graffenstaden (FR); Ismet Dorange, Illkirch-Graffenstaden (FR); Gaël Hommet, Illkirch-Graffenstaden (FR); Baptiste Manteau, Illkirch-Graffenstaden (FR); Stanislas Mayer, Illkirch-Graffenstaden (FR); Stephan Schann, Illkirch-Graffenstaden (FR)

(73) Assignee: Domain Therapeutics, Illkirch-Graffenstaden (FR)

( * ) Notice: Subject to any disclaimer, the term of this patent is extended or adjusted under 35 U.S.C. 154(b) by 628 days.

(21) Appl. No.: 17/766,161

(22) PCT Filed: Oct. 2, 2020

(86) PCT No.: PCT/EP2020/077690
§ 371 (c)(1),
(2) Date: Apr. 1, 2022

(87) PCT Pub. No.: WO2021/064189
PCT Pub. Date: Apr. 8, 2021

(65) Prior Publication Data

US 2022/0378772 A1 Dec. 1, 2022

(30) Foreign Application Priority Data

Oct. 2, 2019 (EP) .................................... 19306267

(51) Int. Cl.
*A61K 31/453* (2006.01)
*A61K 31/196* (2006.01)
(Continued)

(52) U.S. Cl.
CPC .......... *A61K 31/453* (2013.01); *A61K 31/196* (2013.01); *A61K 31/341* (2013.01); *A61K 31/351* (2013.01); *A61K 31/382* (2013.01); *A61K 31/40* (2013.01); *A61K 31/4025* (2013.01); *A61K 31/4155* (2013.01); *A61K 31/4245* (2013.01); *A61K 31/4418* (2013.01); *A61K 31/4433* (2013.01); *A61K 31/4439* (2013.01); *A61K 31/4468* (2013.01);
(Continued)

(58) Field of Classification Search
CPC ................ A61K 31/453; A61K 31/341; A61K 31/352; A61K 31/40; A61K 31/4025; A61K 31/4155; A61K 31/4245; A61K 31/4418; A61K 31/4439; A61K 31/4468; A61K 39/3955; C07C 233/63; C07C 237/24; C07C 2601/04; C07C 2601/08; C07C 2601/14; C07C 2602/38; C07C 2602/50; C07D 207/09; C07D 211/66; C07D 213/65; C07D 309/08; C07D 309/10; C07D 405/14; C07D 413/12; C07D 211/58; C07D 307/22; C07D 335/18; C07D 407/04; C07D 311/02; A61P 15/00; A61P 19/02; A61P 27/02; A61P 29/00; A61P 35/00; A61P 35/02
See application file for complete search history.

(56) References Cited

U.S. PATENT DOCUMENTS

2005/0107364 A1 5/2005 Hutchinson et al.

FOREIGN PATENT DOCUMENTS

CN 103249727 8/2013
EP 0134337 A1 3/1985
(Continued)

OTHER PUBLICATIONS

CAS Registry No. 2172145-99-0 (Entered STN date: Jan. 31, 2018). (Year: 2018).*
Experimental and Predicted Properties of CAS Registry No. 2172145-99-0 (Entered STN date: Jan. 31, 2018). (Year: 2025).*
Albu D. et al., "EP4 Antagonism by E7046 diminishes Myeloid immunosuppression and synergizes with Treg-reducing IL-2-Diphtheria toxin fusion protein in restoring anti-tumor immunity", *Oncoimmunology*, 2017, e1338239.
Bao X. et al., "Combination of EP4 antagonist and checkpoint inhibitors promotes anti- tumor effector T cells in preclinical tumor models", *Journal for ImmunoTherapy of Cancer*, 2015, 350.
(Continued)

*Primary Examiner* — Kamal A Saeed
*Assistant Examiner* — Sagar Patel
(74) *Attorney, Agent, or Firm* — pH IP Law

(57) ABSTRACT

The present invention relates to novel compounds of formula (I) and pharmaceutical compositions containing these compounds. The compounds provided herein can act as prostaglandin E2 (PGE2) EP4 receptor antagonists, which renders them highly advantageous for use in therapy, particularly in the treatment or prevention of cancer, a neovascular eye disease, inflammatory pain, or an inflammatory disease, such as, e.g., multiple sclerosis, rheumatoid arthritis or endometriosis.

(I)

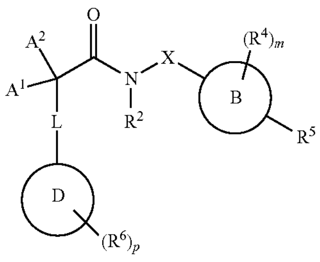

26 Claims, 2 Drawing Sheets

Figure 1:
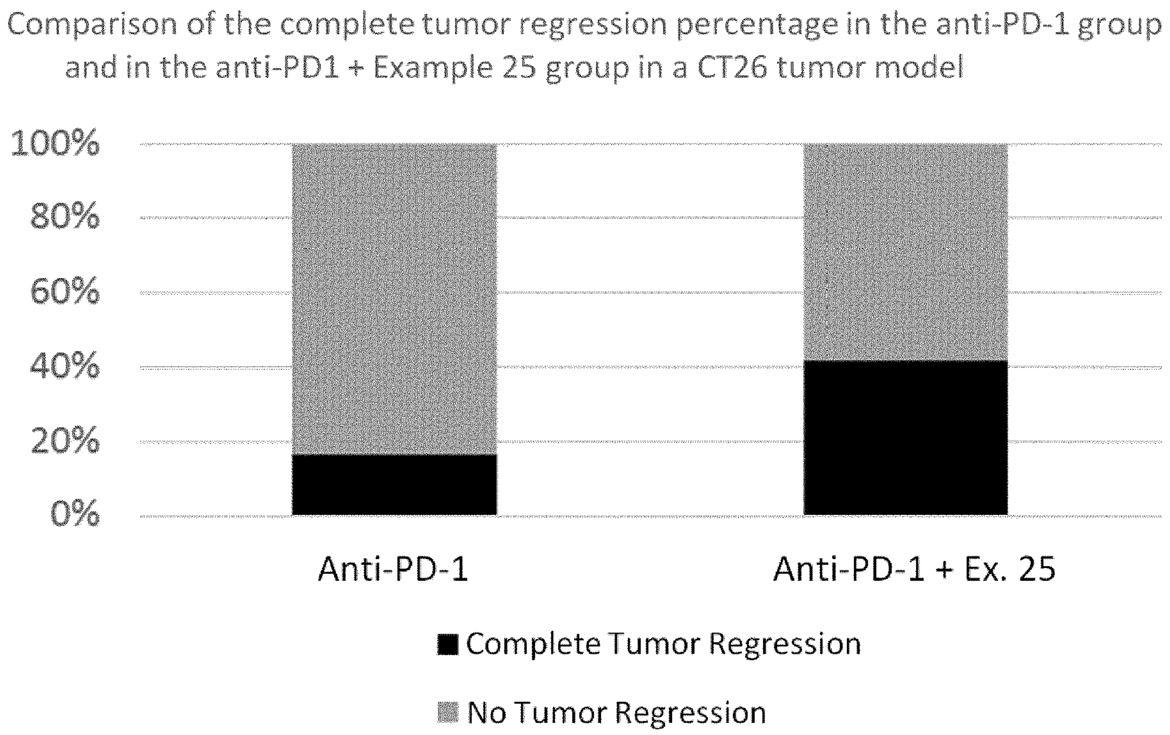

(51) Int. Cl.

| | |
|---|---|
| ***A61K 31/341*** | (2006.01) |
| ***A61K 31/351*** | (2006.01) |
| ***A61K 31/382*** | (2006.01) |
| ***A61K 31/40*** | (2006.01) |
| ***A61K 31/4025*** | (2006.01) |
| ***A61K 31/4155*** | (2006.01) |
| ***A61K 31/4245*** | (2006.01) |
| ***A61K 31/4418*** | (2006.01) |
| ***A61K 31/4433*** | (2006.01) |
| ***A61K 31/4439*** | (2006.01) |
| ***A61K 31/4468*** | (2006.01) |
| ***A61K 39/395*** | (2006.01) |
| ***A61P 35/00*** | (2006.01) |
| ***C07C 233/63*** | (2006.01) |
| ***C07D 207/09*** | (2006.01) |
| ***C07D 207/12*** | (2006.01) |
| ***C07D 211/66*** | (2006.01) |
| ***C07D 213/64*** | (2006.01) |
| ***C07D 213/65*** | (2006.01) |
| ***C07D 213/68*** | (2006.01) |
| ***C07D 307/24*** | (2006.01) |
| ***C07D 309/08*** | (2006.01) |
| ***C07D 309/10*** | (2006.01) |
| ***C07D 309/14*** | (2006.01) |
| ***C07D 311/94*** | (2006.01) |
| ***C07D 335/02*** | (2006.01) |
| ***C07D 405/04*** | (2006.01) |
| ***C07D 405/12*** | (2006.01) |
| ***C07D 405/14*** | (2006.01) |
| ***C07D 407/12*** | (2006.01) |
| ***C07D 413/12*** | (2006.01) |

(52) U.S. Cl.

CPC .......... *A61K 39/3955* (2013.01); *A61P 35/00* (2018.01); *C07C 233/63* (2013.01); *C07D 207/09* (2013.01); *C07D 207/12* (2013.01); *C07D 211/66* (2013.01); *C07D 213/64* (2013.01); *C07D 213/65* (2013.01); *C07D 213/68* (2013.01); *C07D 307/24* (2013.01); *C07D 309/08* (2013.01); *C07D 309/10* (2013.01); *C07D 309/14* (2013.01); *C07D 311/94* (2013.01); *C07D 335/02* (2013.01); *C07D 405/04* (2013.01); *C07D 405/12* (2013.01); *C07D 405/14* (2013.01); *C07D 407/12* (2013.01); *C07D 413/12* (2013.01)

(56) References Cited

FOREIGN PATENT DOCUMENTS

| | | | |
|---|---|---|---|
| EP | 0252524 | A2 | 1/1988 |
| EP | 2351744 | A1 | 8/2011 |
| JP | 2005-314407 | A | 11/2005 |
| JP | 2010-516810 | | 5/2010 |
| JP | 2014-501266 | | 1/2014 |
| JP | 2014-511359 | | 5/2014 |
| WO | WO 94/04494 | A1 | 3/1994 |
| WO | WO 2003/065789 | A2 | 8/2003 |
| WO | WO 2005/003084 | A1 | 1/2005 |
| WO | WO 2008/016676 | A2 | 2/2008 |
| WO | WO 2008/094476 | | 8/2008 |
| WO | WO 2012/076063 | | 6/2012 |
| WO | WO 2012/089601 | | 7/2012 |
| WO | WO 2012/101011 | | 8/2012 |
| WO | WO 2012/116151 | A2 | 8/2012 |
| WO | WO 2013/171316 | A1 | 11/2013 |
| WO | WO 2013/171317 | A1 | 11/2013 |
| WO | WO 2016/148145 | | 9/2016 |
| WO | WO 2017/068412 | A1 | 4/2017 |

OTHER PUBLICATIONS

Huang H. et al., "Inhibition of PGE2/EP4 receptor signaling enhances oxaliplatin efficacy in resistant colon cancer cells through modulation of oxidative stress", *Scientific Reports*, 2019, 4954.

Inada M. et al., "Direct Melanoma Cell Contact Induces Stromal Cell Autocrine. Prostaglandin E2-EP4 Receptor Signaling That Drives Tumor Growth, Angiogenesis, and Metastasis", *The Journal of Biological Chemistry*, 2015, 29781.

Kalinski P., "Regulation of Immune Responses by Prostaglandin $E_2$", *The Journal of Immunology*, 2012, 21.

Konya V. et al., "E-type prostanoid receptor 4 (EP4) in disease and therapy", *Pharmacology & Therapeutics*, 2013, 485.

Ma X. et al., "Prostaglandin E Receptor EP4 Antagonism Inhibits Breast Cancer Metastasis", *Cancer Research*, 2006, 2923.

Ma X. et al., "A prostaglandin E (PGE) receptor EP4 antagonist protects natural killer cells from $PGE_2$-mediated immunosuppression and inhibits breast cancer metastasis", *Oncoimmunology*, 2013, e22647.

Majumder M. et al., "Prostaglandin E2 receptor EP4 as the common target on cancer cells and macrophages to abolish angiogenesis, lymphangiogenesis, metastasis, and stem-like cell functions", *Cancer science*, 2014, 1142.

O'Callaghan G. et al., "Prostaglandin E2 and the EP receptors in malignancy: possible therapeutic targets?", *British Journal of Pharmacology*, 2015, 5239.

Prima et al., "COX2/mPGES1/PGE2 pathway regulates PD-L1 expression in tumor-associated macrophages and myeloid-derived suppressor cells", *Proceedings of the National Academy of Science*, 2017, 1117.

Yang L., "Host and Direct Antitumor Effects and Profound Reduction in Tumor Metastasis with Selective EP4 Receptor Antagonism", *Cancer research*, 2006, 9665.

Yokoyama U. et al., "The Prostanoid EP4 Receptor and Its Signaling Pathway", *Pharmacological reviews*, 2013, 65(3)1010-1052.

Bellucci, M. C. et al., "Design, synthesis, and conformational analysis of 3-cyclo-butylcarbamoyl hydantoins as novel hydrogen bond driven universal peptidomimetics," *Org. Biomol. Chem.*, 16 (2018): 521-525.

Khoury, K. et al., "Efficient Assembly of Iminodicarboxamides by a "Truly" Four-Component Reaction," *Angew. Chem.*, 124 (2012): 10426-10429.

Kozian, D. H. et al., "Modulation of Hexadecyl-LPA-Mediated Activation of Mast Cells and Microglia by a Chemical Probe for LPA5," *ChemBioChem*, 17 (2016): 861-865.

Extended European Search Report issued in European Patent Application 19306267.6, dated Jul. 9, 2020.

PCT International Search Report and Written Opinion issued in International Patent Application No. PCT/EP2020/077690, mailed Apr. 20, 2021.

Pct International Preliminary report on Patentability issued in International Patent Application No. PCT/EP2020/077690, mailed Feb. 1, 2022.

Xu, F. et al., "Synthesis of 4H-1,3-benzoxazines via Metal- and Oxidizing Reagent-Free Aromatic C—H Oxygenation," *Organic Letters*, 19.23 (2017): 1-115.

CAS Registry No. 1070455-71-8; Entered STN Nov. 8, 2008.

CAS Registry No. 1134776-81-0; Entered STN Apr. 15, 2009.

CAS Registry No. 1147329-21-2; Entered STN May 19, 2009.

CAS Registry No. 1147497-09-3; Entered STN May 19, 2009.

CAS Registry No. 1241133-20-9; Entered STN Sep. 15, 2010.

CAS Registry No. 1252497-45-2; Entered STN Nov. 10, 2010.

CAS Registry No. 1277480-02-0; Entered STN Apr. 10, 2011.

CAS Registry No. 1278131-37-5; Entered STN Apr. 10, 2011.

CAS Registry No. 1278751-62-4; Entered STN Apr. 12, 2011.

CAS Registry No. 1278754-76-9; Entered STN Apr. 12, 2011.

CAS Registry No. 1278836-61-5; Entered STN Apr. 12, 2011.

CAS Registry No. 1294117-63-7; Entered STN May 13, 2011.

CAS Registry No. 1298710-55-0; Entered STN May 22, 2011.

CAS Registry No. 1300449-99-3; Entered STN May 25, 2011.

CAS Registry No. 1301385-86-3; Entered STN May 27, 2011.

CAS Registry No. 1301548-38-8; Entered STN May 27, 2011.

(56) References Cited

OTHER PUBLICATIONS

CAS Registry No. 1302585-58-5; Entered STN May 30, 2011.
CAS Registry No. 1370839-62-5; Entered STN Apr. 29, 2012.
CAS Registry No. 1390225-25-8; Entered STN Aug. 12, 2012.
CAS Registry No. 1573883-64-3; Entered STN Mar. 26, 2014.
CAS Registry No. 1625929-33-0; Entered STN Sep. 25, 2014.
CAS Registry No. 1794057-76-3; Entered STN Jul. 5, 2015.
CAS Registry No. 1825599-06-1; Entered STN Dec. 9, 2015.
CAS Registry No. 2037269-54-6; Entered STN Nov. 25, 2016.
CAS Registry No. 2171884-57-2; Entered STN Jan. 31, 2018.
CAS Registry No. 2172145-91-2; Entered STN Jan. 31, 2018.
CAS Registry No. 2172145-99-0; Entered STN Jan. 31, 2018.
CAS Registry No. 2172202-80-9; Entered STN Jan. 31, 2018.
CAS Registry No. 2172273-86-6; Entered STN Jan. 31, 2018.
CAS Registry No. 2323193-57-1; Entered STN Jun. 3, 2019.
CAS Registry No. 2172463-30-6; Entered STN Feb. 1, 2018.
CAS Registry No. 1797110-63-4; Entered STN Jul. 8, 2015.
CAS Registry No. 1626016-75-8; Entered STN Sep. 25, 2014.
CAS Registry No. 1624788-47-1; Entered STN Sep. 23, 2014.
CAS Registry No. 1318941-96-6; Entered STN Aug. 17, 2011.
CAS Registry No. 1070455-71-8; Entered STN Nov. 4, 2008.

* cited by examiner

PROSTAGLANDIN $E_2$ ($PGE_2$) $EP_4$ RECEPTOR ANTAGONISTS

This application is a § 371 national phase of International Application No. PCT/EP2023/064898 filed Jun. 2, 2023, which claims priority to European Application No. 22305814.0 filed Jun. 3, 2022.

The present invention relates to novel compounds of formula (I) and pharmaceutical compositions containing these compounds. The compounds provided herein can act as prostaglandin $E_2$ ($PGE_2$) $EP_4$ receptor antagonists, which renders them highly advantageous for use in therapy, particularly in the treatment or prevention of cancer, a neovascular eye disease, inflammatory pain, or an inflammatory disease, such as, e.g., multiple sclerosis, rheumatoid arthritis or endometriosis.

Prostaglandin $E_2$ ($PGE_2$) is an eicosanoid described as a major mediator of inflammation, displaying pro- and anti-inflammatory effects depending on the context. This bioactive lipid, the most widely produced prostanoid in animal species and in humans, is synthesized from arachidonic acid by cyclooxygenases, COX-1 or COX-2, and specific prostanoid synthases, cPGES-1, m-PGES-1 and m-PGES-2. $PGE_2$ is involved in a wide variety of physiological effects including pain, fever, inflammation, regulation of vascular tone, mucosal integrity, bone healing, renal function, angiogenesis and tumor growth. Signaling of $PGE_2$ is mediated by four G-protein-coupled receptors (GPCRs): $EP_1$, $EP_2$, $EP_3$ and $EP_4$. The $EP_4$ receptor is primary coupled to the Gas protein, leading to elevated intracellular cyclic adenosine monophosphate (cAMP) levels upon $PGE_2$ activation (Konya V. et al. Pharmacology & Therapeutics, 2013, 485; Yokoyama U. et al., Pharmacological reviews, 2013, 1010). Additionally, the $EP_4$ receptor can signal through other pathways involving a $G_{\alpha i}$ protein or β-Arrestin.

Interfering with the $PGE_2$ signaling provides tools to modulate the pattern of immunity in a wide range of diseases from autoimmunity to cancer (Kalinski P., *The Journal of Immunology,* 2012, 21). Indeed, sustained levels of $PGE_2$ in the tumor microenvironment promote immune suppression across a diverse range of immune cells leading to subsequent cancer immune evasion. Notably, this immunosuppression operates through a shift from Th1 to Th2 immune responses, the alteration of antigen-presenting cell infiltration and function, impaired cytotoxic activity of $CD8^+$ T cells and natural killer cells, and enhancement of immunosuppressive cells, including myeloid-derived suppressor cells (MDSCs) and regulatory T cells (Tregs). Elevated COX-2 expression and resulting increased levels of $PGE_2$ are found in numerous cancers and associated with tumor development and progression (O'Callaghan G. et al., *British Journal of Pharmacology,* 2015, 5239). Especially, COX-2 overexpression was reported to promote breast cancer progression and metastasis (Majumder M. et al., *Cancer science,* 2014, 1142). The $PGE_2$ produced by host tissues was also shown to be critical for 816 melanoma growth, angiogenesis and metastasis to bone and soft tissues (Inada M. et al., *The Journal of Biological Chemistry,* 2015, 29781). Alternatively, a critical role of $PGE_2$/$EP_4$ signaling pathway was highlighted in the promotion of the oxaliplatin resistance in human colorectal cancer cells (Huang H. et al., *Scientific Reports,* 2019, 4954). $PGE_2$ was also shown to be involved in the regulation of PD-L1 expression in tumor infiltrating myeloid cells, therefore mediating tumor evasion from the immune system (Prima et al., *Proceedings of the National Academy of Science,* 2017, 1117).

Previous studies support a key role of the $EP_4$ receptor in mediating the immunosuppressive effects of $PGE_2$. Selective $EP_4$ antagonism was previously shown to prevent lung and breast cancer metastasis (Yang L., *Cancer research,* 2006, 9665; Ma X. et al., *Cancer Research,* 2006, 2923). Metastatic tumor growth and vascularization in soft tissues were abrogated by an $EP_4$ receptor antagonist in a B16 melanoma model (Inada M. et al., *The Journal of Biological Chemistry,* 2015, 29781). An $EP_4$ receptor antagonist was also shown to abolish tumor growth, lymphangiogenesis and metastasis to lymph nodes and lungs in a breast cancer model (Majumder M. et al., *Cancer science,* 2014, 1142). $EP_4$ blockade was shown to prevent tumor-mediated NK cell immunosuppression as well as to reduce the immune tolerance generated by myeloid-derived suppressor cells and tumor associated macrophages (Ma X. et al., *Oncoimmunology,* 2013, e22647; Albu D. et al., *Oncoimmunology,* 2017, e1338239). Successful combination therapies of $EP_4$ antagonists with immune checkpoint inhibitors were reported (Bao X. et al., *Journal for ImmunoTherapy of Cancer,* 2015, 350). Notably, concomitant blockade of the $EP_4$ receptor and use of an anti-PD-1 antibody provides an effective anti-tumor response.

While various antagonists of the $EP_4$ receptor have already been reported in the literature (as mentioned above), there is still an ongoing need for novel and/or improved $EP_4$ receptor antagonists, particularly for the therapy of cancer and other $EP_4$-related pathologies.

The present invention addresses this need and solves the problem of providing novel and highly potent $EP_4$ receptor antagonists. In particular, it has surprisingly been found that the compounds provided herein have a strong $EP_4$ antagonistic activity and, furthermore, exhibit an outstanding therapeutic efficacy against cancer, as reflected by a considerable tumor growth inhibition and even a complete tumor regression achieved in a high percentage of cases in a xenograft mouse model (as further described in the examples section).

The present invention thus provides a compound of the following formula (I)

(I)

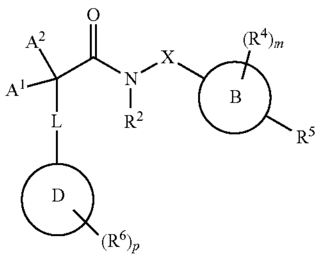

or a pharmaceutically acceptable salt thereof.

In formula (I), the groups $A^1$ and $A^2$ are each independently $C_{1-5}$ alkyl; or the groups $A^1$ and $A^2$ are mutually joined to form, together with the carbon atom that they are attached to, a carbocyclic group or a heterocyclic group, wherein said carbocyclic group or said heterocyclic group is optionally substituted with one or more groups $R^1$. The aforementioned carbocyclic or heterocyclic group (which is formed from $A^1$, $A^2$ and the carbon atom carrying $A^1$ and $A^2$) is also referred to herein as "ring A".

In the context of the present invention, it has surprisingly been found that the presence of two alkyl groups (particularly two methyl groups) as $A^1$ and $A^2$, or the presence of a carbocyclic or heterocyclic group formed from $A^1$ and $A^2$ (ring A), is highly advantageous with respect to the antagonistic activity of the compounds of formula (I) on the prostaglandin $E_2$ ($PGE_2$) $EP_4$ receptor.

Ring B is a carbocyclic group or a heterocyclic group.

Ring D is carbocyclyl or heterocyclyl.

L is $C_{1-6}$ alkylene or a covalent bond, wherein one or more —$CH_2$— units comprised in said $C_{1-6}$ alkylene are each optionally replaced by a group independently selected from —O—, —CO—, —NH—, —N($C_{1-5}$ alkyl)-, —N[—CO—($C_{1-5}$ alkyl)]-, —N[—($C_{0-4}$ alkylene)-cycloalkyl]-, —N[—($C_{0-4}$ alkylene)-heterocycloalkyl]-, —S—, —SO—, —$SO_2$—, —CH($C_{1-5}$ alkyl)-, —C($C_{1-5}$ alkyl)($C_{1-5}$ alkyl)-, carbocyclylene, and heterocyclylene, wherein said carbocyclylene and said heterocyclylene are each optionally substituted with one or more groups -$L^A$-$R^A$.

m is an integer of 0 to 4.

p is an integer of 0 to 4.

Each $R^1$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{0-3}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^A$-$R^A$.

$R^2$ is selected from hydrogen, $C_{1-5}$ alkyl, and —CO($C_{1-5}$ alkyl).

X is C($R^{3a}$)($R^{3b}$) or N($R^{3c}$). Accordingly, X is a carbon atom carrying the substituents $R^{3a}$ and $R^{3b}$, or X is a nitrogen atom carrying the substituent $R^{3c}$.

$R^{3a}$ and $R^{3b}$ are each independently selected from hydrogen, $C_{1-5}$ alkyl, and $C_{2-5}$ alkenyl; or $R^{3a}$ and $R^{3b}$ are mutually linked to form, together with the carbon atom that they are attached to, a cycloalkyl or a heterocycloalkyl, wherein said cycloalkyl or said heterocycloalkyl is optionally substituted with one or more groups $R^{31}$; or $R^{3a}$ is a divalent group selected from linear $C_{2-4}$ alkylene and linear $C_{2-4}$ alkenylene, wherein said divalent group is attached via one end to the carbon atom carrying $R^{3b}$ and is attached via the other end to a ring atom of ring B which is adjacent to the ring atom carrying the group X, wherein said alkylene or said alkenylene is optionally substituted with one or more groups $R^{31}$, wherein one —$CH_2$— unit in said alkylene or said alkenylene is optionally replaced by —O—, —S—, —NH— or —N($C_{1-5}$ alkyl)-, and $R^{3b}$ is selected from hydrogen, $C_{1-6}$ alkyl, and $C_{2-5}$ alkenyl.

$R^{3c}$ is selected from hydrogen, $C_{1-5}$ alkyl, and $C_{2-5}$ alkenyl.

Each $R^{31}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl) ($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{0-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), and —$SO_2$—($C_{1-5}$ alkyl).

Each $R^4$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{0-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-6}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{0-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^A$-$R^A$.

$R^5$ is selected from —COOH, —CO—$NH_2$, —CO—NH($C_{1-5}$ alkyl), —CO—N($C_{1-5}$ alkyl)($C_{1-5}$ alkyl), —$SO_2$—OH, —$SO_2$—O—($C_{1-5}$alkyl), —$SO_2$—$NH_2$, —$SO_2$—NH($C_{1-5}$ alkyl), —$SO_2$—N($C_{1-5}$ alkyl)($C_{1-5}$ alkyl), —$SO_2$—($C_{1-5}$ alkyl), —S(═O)(═NH)—($C_{1-5}$ alkyl), halogen, $C_{1-5}$ haloalkyl, —CN, hydrogen, $C_{1-4}$ alkyl, —OH, —O($C_{1-4}$ alkyl), carbocyclyl, and heterocyclyl, wherein said carbocyclyl or said heterocyclyl is optionally substituted with one or more groups -$L^A$-$R^A$.

Each $R^6$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-6}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-

COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^1$-$R^{61}$.

$L^1$ is $C_6$ alkylene or a covalent bond, wherein one or more —$CH_2$— units comprised in said $C_{1-6}$ alkylene are each optionally replaced by a group independently selected from —O—, —CO—, —NH—, —N($C_{1-5}$ alkyl)-, —N[—CO—($C_{0-3}$ alkyl)]-, —S—, —SO—, —$SO_2$—, —CH($C_{1-5}$ alkyl)- and —C($C_{1-5}$ alkyl)($C_{1-5}$ alkyl)-.

$R^{61}$ is carbocyclyl or heterocyclyl, wherein said carbocyclyl or said heterocyclyl is optionally substituted with one or more groups $R^{62}$.

Each $R^{62}$ is independently selected from $C_{1-6}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{0-3}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{0-3}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{0-3}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, and —($C_{0-3}$ alkylene)-heterocycloalkyl.

Each $L^A$ is independently selected from a covalent bond, $C_{1-5}$ alkylene, $C_{2-5}$ alkenylene, and $C_{2-5}$ alkynylene, wherein said alkylene, said alkenylene and said alkynylene are each optionally substituted with one or more groups independently selected from halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl), and further wherein one or more —$CH_2$— units comprised in said alkylene, said alkenylene or said alkynylene are each optionally replaced by a group independently selected from —O—, —NH—, —N($C_{1-5}$ alkyl)-, —CO—, —S—, —SO—, and —$SO_2$—.

Each $R^A$ is independently selected from —OH, —O($C_{1-5}$ alkyl), —O($C_{1-5}$ alkylene)-OH, —O($C_{1-5}$ alkylene)-O($C_{1-5}$ alkyl), —SH, —S($C_{0-3}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O($C_{1-5}$ haloalkyl), —CN, —CHO, —CO($C_{1-5}$ alkyl), —COOH, —COO($C_{1-5}$ alkyl), —O—CO($C_{1-5}$ alkyl), —CO—$NH_2$, —CO—NH($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-6}$ alkyl), —NH—$SO_2$—($C_{1-5}$ alkyl), —N($C_{1-5}$ alkyl)-$SO_2$—($C_{1-5}$ alkyl), —$SO_2$—($C_{1-5}$ alkyl), —SO—($C_{1-5}$ alkyl), hydrogen, aryl, heteroaryl, cycloalkyl, and heterocycloalkyl, wherein said aryl, said heteroaryl, said cycloalkyl, and said heterocycloalkyl are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl).

The present invention also relates to a pharmaceutical composition comprising a compound of formula (I), or a pharmaceutically acceptable salt thereof, in combination with a pharmaceutically acceptable excipient. Accordingly, the invention relates to a compound of formula (I) or a pharmaceutically acceptable salt thereof, or a pharmaceutical composition comprising any of the aforementioned entities and a pharmaceutically acceptable excipient, for use as a medicament.

The invention further relates to a compound of formula (I) or a pharmaceutically acceptable salt thereof, or a pharmaceutical composition comprising any of the aforementioned entities and a pharmaceutically acceptable excipient, for use in the treatment or prevention of cancer, inflammatory pain, an inflammatory disease, or a neovascular eye disease. Thus, the invention in particular provides a pharmaceutical composition comprising, as an active ingredient, a compound of formula (I) or a pharmaceutically acceptable salt thereof, together with a pharmaceutically acceptable excipient, for use in the treatment or prevention of cancer, inflammatory pain, an inflammatory disease, or a neovascular eye disease.

Moreover, the present invention relates to the use of a compound of formula (I) or a pharmaceutically acceptable salt thereof in the preparation of a medicament for the treatment or prevention of cancer, inflammatory pain, an inflammatory disease, or a neovascular eye disease.

The invention likewise relates to a method of treating or preventing cancer, inflammatory pain, an inflammatory disease, or a neovascular eye disease, the method comprising administering a compound of formula (I) or a pharmaceutically acceptable salt thereof, or a pharmaceutical composition comprising any of the aforementioned entities in combination with a pharmaceutically acceptable excipient, to a subject (preferably a human) in need thereof. It will be understood that a therapeutically effective amount of the compound of formula (I) or the pharmaceutically acceptable salt thereof (or of the pharmaceutical composition) is to be administered in accordance with this method.

As explained above, the diseases/disorders to be treated or prevented with a compound of formula (I) or a pharmaceutically acceptable salt thereof (or a corresponding pharmaceutical composition) in accordance with the present invention include, in particular, cancer, inflammatory pain, an inflammatory disease, or a neovascular eye disease. It is particularly preferred that the disease/disorder to be treated or prevented in accordance with the invention is cancer.

The cancer to be treated or prevented in accordance with the present invention may be a solid cancer or a hematological cancer, and is preferably selected from lung cancer (e.g., small cell lung cancer or non-small cell lung cancer; particularly non-small cell lung cancer), renal carcinoma, gastro-intestinal cancer, stomach cancer, colorectal cancer, colon cancer, anal cancer, genitourinary cancer, bladder cancer, liver cancer (e.g., hepatocellular carcinoma), pancreatic cancer (e.g., pancreatic adenocarcinoma or pancreatic ductal adenocarcinoma), ovarian cancer, cervical cancer, endometrial cancer, vaginal cancer, vulvar cancer, prostate cancer (e.g., hormone-refractory prostate cancer), testicular cancer, biliary tract cancer, hepatobiliary cancer, neuroblastoma, brain cancer (e.g., glioblastoma), breast cancer (e.g., triple-negative breast cancer, including in particular COX-2 expressing triple-negative breast cancer), head and/or neck cancer (e.g., head and neck squamous cell carcinoma), skin cancer, melanoma, Merkel-cell carcinoma, epidermoid cancer, squamous cell carcinoma (e.g., oral squamous cell carcinoma), bone cancer (or osteosarcoma), fibrosarcoma, Ewing's sarcoma, malignant mesothelioma, esophageal cancer, laryngeal cancer, mouth cancer, thymoma, neuroendocrine cancer, hematological cancer, leukemia (e.g., acute lymphoblastic leukemia, acute myeloid leukemia, chronic lymphocytic leukemia, or chronic myeloid leukemia; particularly acute myeloid leukemia), lymphoma (e.g., Hodgkin lymphoma or non-Hodgkin lymphoma), and multiple myeloma. Moreover, the cancer to be treated or prevented (including any one of the aforementioned specific types of cancer) may also be a metastatic cancer.

As explained above, the cancer to be treated or prevented in accordance with the present invention may be a hematological cancer. In that case, the hematological cancer is preferably selected from: Hodgkin's lymphoma, including, e.g., nodular sclerosing subtype of Hodgkin's lymphoma, mixed-cellularity subtype of Hodgkin's lymphoma, lymphocyte-rich subtype of Hodgkin's lymphoma, or lymphocyte-depleted subtype of Hodgkin's lymphoma; non-Hodgkin's lymphoma, including, e.g., follicular non-Hodgkin's lymphoma, mantle cell lymphoma, or diffuse non-Hodgkin's lymphoma (e.g., diffuse large B-cell lymphoma or Burkitt's lymphoma); nodular lymphocyte predominant Hodgkin's lymphoma; peripheral/cutaneous T-cell lymphoma, including, e.g., mycosis fungoides, Sézary's disease, T-zone lymphoma, lymphoepithelioid lymphoma (e.g., Lennert's lymphoma), or peripheral T-cell lymphoma; lymphosarcoma; a malignant immunoproliferative disorder, including, e.g., Waldenström's macroglobulinaemia, alpha heavy chain disease, gamma heavy chain disease (e.g., Franklin's disease), or an immunoproliferative small intestinal disease (e.g., Mediterranean disease); multiple myeloma, including, e.g., Kahler's disease, or myelomatosis; plasma cell leukemia; lymphoid leukemia, including, e.g., acute lymphoblastic leukemia, chronic lymphocytic leukemia, subacute lymphocytic leukemia, prolymphocytic leukemia, hairy-cell leukemia (e.g., leukemic reticuloendotheliosis), or adult T-cell leukemia; myeloid leukemia, including, e.g., acute myeloid leukemia, chronic myeloid leukemia, subacute myeloid leukemia, myeloid sarcoma (e.g., chloroma, or granulocytic sarcoma), acute promyelocytic leukemia, or acute myelomonocytic leukemia; a myeloproliferative neoplastic disorder, including, e.g., polycythaemia vera, essential thrombocythemia, or idiopathic myelofibrosis; monocytic leukemia; acute erythraemia or erythroleukemia, including, e.g., acute erythraemic myelosis, or Di Guglielmo's disease; chronic erythraemia, including, e.g., Heilmeyer-Schöner disease; acute megakaryoblastic leukemia; mast cell leukemia; acute panmyelosis; acute myelofibrosis; and Letterer-Siwe disease.

The inflammatory pain to be treated or prevented in accordance with the present invention may be acute inflammatory pain or chronic inflammatory pain, and may be, in particular, osteoarthritic pain, inflammatory pain associated with rheumatoid arthritis, or inflammatory post-operative pain.

The inflammatory disease to be treated or prevented in accordance with the present invention may be an acute inflammatory disease or a chronic inflammatory disease, and it is preferably selected from multiple sclerosis, rheumatoid arthritis, endometriosis, and osteoarthritis.

The neovascular eye disease to be treated or prevented in accordance with the present invention is preferably selected from neovascular degenerative maculopathy (or "wet" macular degeneration), proliferative diabetic retinopathy, neovascular glaucoma, and retinopathy of prematurity.

The present invention furthermore relates to the use of a compound of formula (I) or a pharmaceutically acceptable salt thereof as an antagonist of the prostaglandin $E_2$ receptor subtype 4 ($EP_4$) in research, particularly as a research tool compound for antagonizing the $EP_4$ receptor. Accordingly, the invention refers to the in vitro use of a compound of formula (I) or a pharmaceutically acceptable salt thereof as an $EP_4$ receptor antagonist and, in particular, to the in vitro use of a compound of formula (I) or a pharmaceutically acceptable salt thereof as a research tool compound acting as an $EP_4$ receptor antagonist. The invention likewise relates to a method, particularly an in vitro method, of antagonizing the $EP_4$ receptor, the method comprising the application of a compound of formula (I) or a pharmaceutically acceptable salt thereof. The invention further relates to a method of antagonizing the $EP_4$ receptor, the method comprising applying a compound of formula (I) or a pharmaceutically acceptable salt thereof to a test sample (e.g., a biological sample) or a test animal (i.e., a non-human test animal). The invention also refers to a method, particularly an in vitro method, of antagonizing the $EP_4$ receptor in a sample (e.g., a biological sample), the method comprising applying a compound of formula (I) or a pharmaceutically acceptable salt thereof to said sample. The present invention further provides a method of antagonizing the $EP_4$ receptor, the method comprising contacting a test sample (e.g., a biological sample) or a test animal (i.e., a non-human test animal) with a compound of formula (I) or a pharmaceutically acceptable salt thereof. The terms "sample", "test sample" and "biological sample" include, without being limited thereto: a cell, a cell culture or a cellular or subcellular extract; biopsied material obtained from an animal (e.g., a human), or an extract thereof; or blood, serum, plasma, saliva, urine, feces, or any other body fluid, or an extract thereof. It is to be understood that the term "in vitro" is used in this specific context in the sense of "outside a living human or animal body", which includes, in particular, experiments performed with cells, cellular or subcellular extracts, and/or biological molecules in an artificial environment such as an aqueous solution or a culture medium which may be provided, e.g., in a flask, a test tube, a Petri dish, a microtiter plate, etc.

The compounds of formula (I) as well as the pharmaceutically acceptable salts thereof will be described in more detail in the following:

(I)

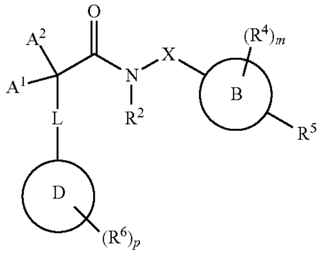

In formula (I), the groups $A^1$ and $A^2$ are each independently $C_{1-5}$ alkyl (e.g., methyl or ethyl); or the groups $A^1$ and $A^2$ are mutually joined to form, together with the carbon atom that they are attached to, a carbocyclic group or a heterocyclic group, wherein said carbocyclic group or said heterocyclic group is optionally substituted with one or more (e.g., one, two, three, or four) groups $R^1$. The aforementioned carbocyclic or heterocyclic group (which is formed from $A^1$, $A^2$ and the carbon atom carrying $A^1$ and $A^2$) is also referred to herein as "ring A". It is preferred that $A^1$ and $A^2$ are each independently $C_{1-6}$ alkyl (e.g., methyl).

In the context of the present invention, it has surprisingly been found that the presence of two alkyl groups (particularly two methyl groups) as $A^1$ and $A^2$, or the presence of a carbocyclic or heterocyclic group formed from $A^1$ and $A^2$ (ring A), is highly advantageous with respect to the antagonistic activity of the compounds of formula (I) on the prostaglandin $E_2$ ($PGE_2$) $EP_4$ receptor.

Preferably, $A^1$ and $A^2$ are each independently $C_{1-5}$ alkyl. More preferably, $A^1$ and $A^2$ are each independently methyl or ethyl. Even more preferably, $A^1$ and $A^2$ are each methyl.

As described above, the groups $A^1$ and $A^2$ may also be mutually joined to form, together with the carbon atom that they are attached to, a carbocyclic group or a heterocyclic group, wherein said carbocyclic group or said heterocyclic group is optionally substituted with one or more (e.g., one, two, three, or four) groups $R^1$. In this case, the compound of formula (I) may be a compound having the following formula (Ia) or a pharmaceutically acceptable salt thereof:

(Ia)

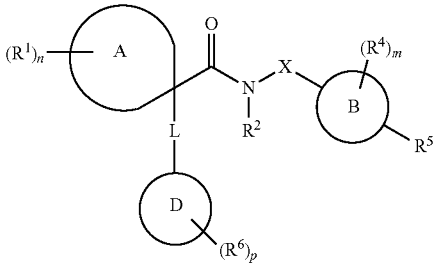

wherein ring A in formula (Ia) is a carbocyclic group or a heterocyclic group, wherein n is an integer of 0 to 4, and wherein the further groups/variables in formula (Ia) (including, in particular, ring B, ring D, $R^1$, $R^2$, $R^4$, $R^5$, $R^6$, X, L, m and p) have the same meanings, including the same preferred meanings, as described and defined in connection with formula (I).

As also depicted in formula (Ia), both the moiety —CO—N($R^2$)—X—B[(—$R^4$)$_m$]—$R^5$ and the moiety -L-D[(—$R^6$)$_p$] are attached to the same ring carbon atom of ring A which is thus a divalent carbocyclic or heterocyclic group. It will be understood that the following description of ring A, as depicted in formula (Ia), likewise applies to the carbocyclic or heterocyclic group which is formed from $A^1$ and $A^2$ (and the carbon atom that they are attached to) in formula (I), wherein said carbocyclic or heterocyclic group is optionally substituted with one or more groups $R^1$.

Ring A is preferably saturated. Accordingly, it is preferred that ring A is cycloalkylene or heterocycloalkylene. Said cycloalkylene or said heterocycloalkylene is preferably monocyclic or bicyclic. More preferably, A is monocyclic cycloalkylene or monocyclic heterocycloalkylene. Even more preferably, A is a monocyclic $C_{3-9}$ cycloalkylene or a monocyclic 4 to 9-membered heterocycloalkylene.

Preferred examples of ring A include, in particular, cyclopropylene, cyclobutylene, cyclopentylene, cyclohexylene, tetrahydrofuranylene (e.g., tetrahydrofuran-2,2-diyl or tetrahydrofuran-3,3-diyl), tetrahydrothiophenylene (e.g., tetrahydrothiophen-2,2-diyl or tetrahydrothiophen-3,3-diyl), tetrahydropyranylene (e.g. tetrahydropyran-2,2-diyl, tetrahydropyran-3,3-diyl, or tetrahydropyran-4,4-diyl), or thianylene (e.g., thian-2,2-diyl, thian-3,3-diyl, or thian-4,4-diyl). It is particularly preferred that ring A is tetrahydrofuranylene (preferably tetrahydrofuran-3,3-diyl), tetrahydropyranylene (preferably tetrahydropyran-4,4-diyl), cyclopropylene (i.e., cyclopropan-1,1-diyl), cyclobutylene (i.e., cyclobutan-1,1-diyl), cyclopentylene (i.e., cyclopentan-1,1-diyl), or cyclohexylene (i.e., cyclohexan-1,1-diyl), and it is even more preferred that ring A is cyclopropylene (i.e., cyclopropan-1,1-diyl).

Ring B is a carbocyclic group or a heterocyclic group.

As also depicted in formula (I), ring B is a divalent group which is attached to X and is furthermore attached to the group $R^5$.

Preferably, ring B is selected from arylene, heteroarylene (e.g., pyridinylene; including, in particular, pyridin-2,5-diyl or pyridin-3,6-diyl), cycloalkylene and heterocycloalkylene. More preferably, ring B is arylene or cycloalkylene. Even more preferably, ring B is phenylene or $C_{3-6}$ cycloalkylene (such as, e.g., cyclopentylene, cyclohexylene, cycloheptylene, spiro[3.3]heptylene (e.g., spiro[3.3]hept-2,6-diyl), or bicyclo[1.1.1]pentylene). Even more preferably, ring B is phenylene (particularly phen-1,4-diyl) or cyclohexylene (particularly cyclohexan-1,4-diyl). Yet even more preferably, ring B is phenylene (e.g., phen-1,4-diyl, pheny-1,3-diyl, or phen-1,2-diyl). Still more preferably, ring B is phen-1,4-diyl.

Ring D is carbocyclyl or heterocyclyl. Preferably, ring D is selected from aryl, heteroaryl, cycloalkyl, and heterocycloalkyl. More preferably, ring D is selected from phenyl, monocyclic heteroaryl, monocyclic cycloalkyl, and monocyclic heterocycloalkyl. Even more preferably, ring D is selected from phenyl, pyridinyl (e.g., pyridin-2-yl, pyridin-3-yl, or pyridin-4-yl), azetidinyl (e.g., azetidin-1-yl or azetidin-2-yl), pyrrolidinyl (e.g., pyrrolidin-1-yl, pyrrolidin-2-yl, or pyrrolidin-3-yl), piperidinyl (e.g., piperidin-1-yl, piperidin-2-yl, piperidin-3-yl, or piperidin-4-yl), and cyclohexyl. Yet even more preferably, ring D is phenyl or pyridinyl. Still more preferably, ring D is phenyl.

L is $C_{1-6}$ alkylene or a covalent bond, wherein one or more (e.g., one, two or three) —$CH_2$— units comprised in said $C_{1-6}$ alkylene are each optionally replaced by a group independently selected from —O—, —CO—, —NH—, —N($C_{1-5}$ alkyl)-, —N[—CO—($C_{1-5}$ alkyl)]-, —N[—($C_{0-4}$ alkylene)-cycloalkyl]-, —N[—($C_{0-4}$ alkylene)-heterocycloalkyl]-, —S—, —SO—, —$SO_2$—, —CH($C_{1-5}$ alkyl)-, —C($C_{1-5}$ alkyl)($C_{1-5}$ alkyl)-, carbocyclylene, and heterocyclylene, wherein said carbocyclylene and said heterocyclylene are each optionally substituted with one or more (e.g., one, two, or three) groups $-L^A-R^A$.

It is preferred that at most one —$CH_2$— unit comprised in said $C_{1-6}$ alkylene is optionally replaced by carbocyclylene (e.g., cycloalkylene or arylene) or heterocyclylene (e.g., heterocycloalkylene or heteroarylene), preferably by heterocyclylene, more preferably by heterocycloalkylene, wherein said carbocyclylene or said heterocyclylene (or said heterocycloalkylene) is optionally substituted with one or more groups $-L^A-R^A$. Said carbocyclylene or heterocyclylene (or said heterocycloalkylene) is preferably attached in a 1,3-orientation (e.g., as in the compound of Example 134 or Example 138). Corresponding preferred examples include, in particular, pyrrolidin-1,3-diyl or piperidin-1,3-diyl.

Preferably, L is $C_{3-6}$ alkylene (e.g., propylene, butylene or pentylene), wherein one or more (e.g., one, two or three) —$CH_2$— units comprised in said $C_{3-6}$ alkylene are each optionally replaced by a group independently selected from —O—, —CO—, —NH—, —N($C_{1-5}$ alkyl)-, —N[—CO—($C_{1-5}$ alkyl)]-, —N[—($C_{0-4}$ alkylene)-cycloalkyl]-, —N[—($C_{0-4}$ alkylene)-heterocycloalkyl]-, —S—, —SO—, —$SO_2$—, —CH($C_{1-5}$ alkyl)- and —C($C_{1-5}$ alkyl)($C_{1-5}$ alkyl)-, particularly by a group independently selected from —O—, —CO—, —NH—, —N($C_{1-5}$ alkyl)-, —N[—CO—($C_{1-5}$ alkyl)]-, —N[—($C_{0-4}$ alkylene)-($C_{3-7}$ cycloalkyl)]- (e.g., —N[—($C_{0-4}$ alkylene)-cyclopropyl]-), —CH($C_{1-5}$ alkyl)- and —C($C_{1-5}$ alkyl)($C_{1-5}$ alkyl)-, more preferably by a group independently selected from —O—, —NH—, and —N($C_{1-5}$ alkyl)- (e.g., —N(—$CH_3$)— or —N(—$CH_2CH_3$)—); or, alternatively, L is $C_{2-4}$ alkylene (e.g., ethylene, n-propylene or n-butylene), wherein one —$CH_2$— unit comprised in said $C_{2-4}$ alkylene (preferably the —$CH_2$— unit which is attached to ring A or to the carbon atom carrying $A^1$ and $A^2$) is replaced by carbocyclylene or heterocyclylene (preferably by heterocyclylene), wherein one further —$CH_2$— unit comprised in said $C_{2-4}$ alkylene (preferably the —$CH_2$— unit which is attached to ring D) is optionally replaced by a group selected from —O—, —CO—, —NH—, —N($C_{1-6}$ alkyl)-, —N[—CO—($C_{1-5}$ alkyl)]-, —N[—($C_{0-4}$ alkylene)-cycloalkyl]-, —N[—($C_{0-4}$ alkylene)-heterocycloalkyl]-, —S—, —SO—, and —$SO_2$— (preferably by a group selected from —O—, —NH—, and —N($C_{1-5}$ alkyl)-, more preferably by a group —O—), wherein said carbocyclylene or said heterocyclylene is preferably attached in a 1,3-orientation, and further wherein said carbocyclylene or said heterocyclylene is optionally substituted with one or more groups $-L^A-R^A$.

More preferably, L is —$(CH_2)_{3-5}$—, wherein one or more (e.g., one, two or three) —$CH_2$— units comprised in said —$(CH_2)_{3-5}$— are each optionally replaced by a group independently selected from —O—, —CO—, —NH—, —N($C_{1-5}$ alkyl)-, —N[—CO—($C_{1-5}$ alkyl)]-, —N[—($C_{0-4}$ alkylene)-($C_{3-7}$ cycloalkyl)]- (e.g., —N(—$CH_2$-cyclopropyl)-), —CH($C_{1-5}$ alkyl)- and —C($C_{1-5}$ alkyl)($C_{1-5}$ alkyl)-, particularly from —O—, —NH—, and —N($C_{1-5}$ alkyl)-; or L is -heterocyclylene-$(CH_2)_{1-2}$—, wherein one —$CH_2$— unit comprised in said -heterocyclylene-$(CH_2)_{1-2}$— is optionally replaced by a group selected from —O—, —CO—, —NH—, —N($C_{1-5}$ alkyl)- and —N[—CO—($C_{1-5}$ alkyl)]- (particularly from —O—, —NH—, and —N($C_{1-5}$ alkyl)-), wherein the heterocyclylene in said -heterocyclylene-$(CH_2)_{1-2}$— is optionally substituted with one or more groups $-L^A-R^A$, and further wherein the heterocyclylene in said -heterocyclylene-$(CH_2)_{1-2}$— is preferably attached in a 1,3-orientation.

Even more preferably, L is —$CH_2$—$CH_2$—$CH_2$—$CH_2$—, wherein one or more (e.g., one, two or three) —$CH_2$— units comprised in said —$CH_2$—$CH_2$—$CH_2$—$CH_2$— are each optionally replaced by a group independently selected from —O—, —CO—, —NH—, —N($C_{1-6}$ alkyl)-, —N[—CO—($C_{1-5}$ alkyl)]-, —N[—($C_{0-4}$ alkylene)-($C_{3-7}$ cycloalkyl)]- (e.g., —N(—$CH_2$-cyclopropyl)-), —CH($C_{1-5}$ alkyl)- and —C($C_{1-5}$ alkyl)($C_{1-5}$ alkyl)-, particularly from —O—, —NH—, and —N($C_{1-5}$ alkyl)-; or L is -heterocycloalkylene-$CH_2$—, wherein the —$CH_2$— unit in said -heterocycloalkylene-$CH_2$— is optionally replaced by a group selected from —O—, —CO—, —NH—, —N($C_{1-5}$ alkyl)- and —N[—CO—($C_{1-5}$ alkyl)]- (particularly a group selected from —O—, —NH—, and —N($C_{1-5}$ alkyl)-, more preferably a group —O—), and wherein the heterocycloalkylene in said -heterocycloalkylene-$CH_2$— is preferably attached in a 1,3-orientation. It is furthermore preferred that said -heterocycloalkylene-$CH_2$— is attached to ring D via the —$CH_2$— unit (which may be optionally replaced, as described above) in said -heterocycloalkylene-$CH_2$—.

In accordance with the above-described general and preferred definitions of L, it is particularly preferred that, in any one of these definitions of L, the respective group L is attached to ring D via —$CH_2$— or via —O—, even more preferably via —O— (i.e., that the respective group L contains a —$CH_2$— unit which is replaced by —O—, and that the group L is connected to ring D via said —O—).

Yet even more preferably, L is —$CH_2$—$CH_2$—$CH_2$—O— which is attached to ring D via the oxygen atom (—O—) in said group —$CH_2$—$CH_2$—$CH_2$—O—, and wherein one or more (e.g., one or two) —$CH_2$— units comprised in said —$CH_2$—$CH_2$—$CH_2$—O— are each optionally replaced by a group independently selected from —O—, —CO—, —NH—, —N($C_{1-4}$ alkyl)-, —N[—CO—($C_{1-4}$ alkyl)]-, —N[—($C_{1-3}$ alkylene)-cyclopropyl]-, —CH($C_{1-4}$ alkyl)- and —C($C_{1-4}$ alkyl)($C_{1-4}$alkyl)-, particularly from —O—, —NH—, and —N($C_{1-4}$ alkyl)-, wherein it is furthermore preferred that the terminal —$CH_2$— unit (which is most distant to the oxygen atom in —$CH_2$—$CH_2$—$CH_2$—O—) is replaced by a group as defined above (e.g., by —N($C_{1-4}$ alkyl)-, particularly by —N($CH_3$)—); or L is -heterocycloalkylene-O— which is attached to ring D via the oxygen atom in said group -heterocycloalkylene-O—, and wherein the heterocycloalkylene in said -heterocycloalkylene-O— is attached in a 1,3-orientation. The heterocycloalkylene in said -heterocycloalkylene-O— is preferably a monocyclic 4- to 9-membered (more preferably a monocyclic 5-, 6- or 7-membered) heterocycloalkylene which is attached via a nitrogen ring atom to ring A (or to the carbon atom carrying $A^1$ and $A^2$) and is attached via a carbon ring atom to the oxygen (—O—) in said -heterocycloalkylene-O—, wherein said nitrogen ring atom and said carbon ring atom are separated by one carbon ring atom. Thus, L may be, for example, a group

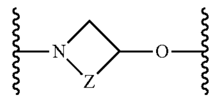

which is attached via the oxygen atom (—O—) to ring D, wherein Z refers to 1, 2, 3, 4 or 5 ring atoms connected via single bonds, wherein 1 or 2 of said ring atoms (Z) are each independently selected from nitrogen, oxygen, sulfur and carbon, and the remaining ring atoms (Z), if any, are all carbon atoms. In particular, L may be a group

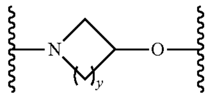

which is attached via the oxygen atom (—O—) to ring D, wherein y is 1, 2, 3, 4 or 5, and wherein y is preferably 2, 3 or 4 (so that the heterocycloalkylene ring preferably has a total of 5, 6 or 7 ring members).

Corresponding preferred examples of L include, in particular, $—CH_2—CH_2—CH_2—O—$, $—NH—CH_2—CH_2—O—$, $—N(—CH_3)—CH_2—CH_2—O—$, $—N(—CH_2CH_3)—CH_2—CH_2—O—$, $—N(—CH_2CH_2CH_3)—CH_2—CH_2—O—$, $—N(isopropyl)\text{-}CH_2—CH_2—O—$, $—N(—CH_2\text{-}cyclopropyl)\text{-}CH_2—CH_2—O—$, $—N(—CO—CH_3)—CH_2—CH_2—O—$, $—NH—CO—CH_2—O—$, $—O—CH_2—CH_2—O—$,

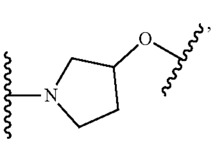

or

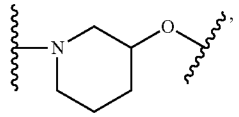

wherein each of these groups is attached to ring D via the terminal oxygen atom (—O—) contained therein.

Further examples of L include any one of the groups listed in the preceding paragraph, wherein the terminal oxygen atom (through which these groups are attached to ring D) is replaced by methylene ($—CH_2$)—.

Particularly preferred examples of L include $—N(—CH_3)—CH_2—CH_2—O—$, $—N(—CH_2CH_3)—CH_2—CH_2—O—$, $—N(—CH_2\text{-}cyclopropyl)\text{-}CH_2—CH_2—O—$, $—O—CH_2—CH_2—O—$,

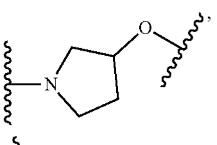

or

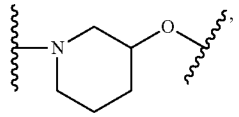

wherein each of these groups is attached to ring D via the terminal oxygen atom contained therein. Even more preferred examples of L include $—N(—CH_3)—CH_2—CH_2—O—$,

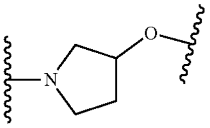

, or

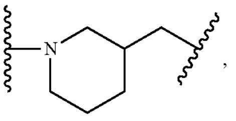

wherein each of these groups is attached to ring D via the terminal oxygen atom contained therein.

If L is a group

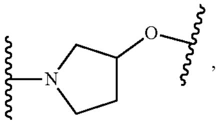 [SMILES: *OC1CCN(*)C1]

then it is furthermore preferred that this group is present in the compound of formula (I) in the following stereochemical configuration:

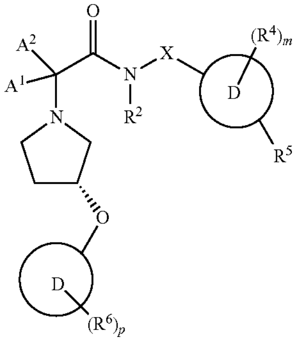

If L is a group

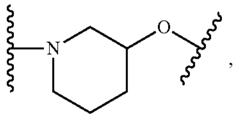 [SMILES: *OC1CCCN(*)C1]

then it is further preferred that this group is present in the compound of formula (I) in the following stereochemical configuration:

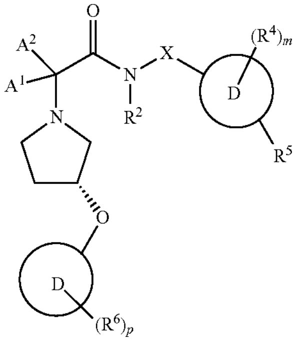

If the groups $A^1$ and $A^2$ in formula (I) are each $C_{1-5}$ alkyl (e.g., methyl), then it is particularly preferred that L is

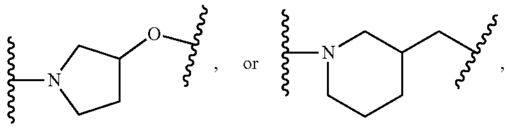 [SMILES: *OC1CCN(*)C1 ; *CC1CCCN(*)C1]

wherein each of these groups is attached to ring D via the terminal oxygen atom contained therein.

n is an integer of 0 to 4 (i.e., 0, 1, 2, 3 or 4). Preferably, n is 0, 1 or 2. More preferably, n is 0 or 1. Even more preferably, n is 0.

m is an integer of 0 to 4 (i.e., 0, 1, 2, 3 or 4). Preferably, m is 0, 1 or 2. More preferably, m is 0 or 1. Even more preferably, m is 0.

p is an integer of 0 to 4 (i.e., 0, 1, 2, 3 or 4). Preferably, p is 0, 1 or 2. More preferably, p is 1.

It is to be understood that m indicates the number of substituents $R^4$ that are attached to ring B in the compound of formula (I) or (Ia). If m is 0, then ring B is not substituted with any group $R^4$, i.e. is substituted with hydrogen instead of $R^4$. Moreover, p indicates the number of substituents $R^6$ that are bound to ring D in the compound of formula (I) or (Ia). If p is 0, then ring D is not substituted with any group $R^5$, i.e. is substituted with hydrogen instead of $R^5$. Likewise, n indicates the number of substituents $R^1$ that are bound to ring A in the compound of formula (Ia); if n is 0, then ring A is not substituted with any group $R^1$, i.e. is substituted with hydrogen instead of $R^1$. It will further be understood that the maximum number of substituents $R^1$, $R^4$ and $R^5$ is limited by the number of attachment sites available on the respective ring group, i.e. on ring A, ring B and ring D, respectively.

Each $R^1$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-6}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{0-3}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-6}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^A$-$R^A$.

Preferably, each $R^1$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-6}$ alkyl), —SH, —S($C_{1-5}$ alkyl), —S($C_{1-5}$ alkylene)-SH, —S($C_{1-5}$ alkylene)-S($CO_1$-alkyl), —$NH_2$, —NH($C_{1-6}$ alkyl), —N($C_{1-5}$ alkyl)($C_{1-5}$ alkyl), halogen, $C_{2-5}$ haloalkyl, —O—($C_{1-5}$ haloalkyl), —CN, —CHO, —CO—($C_{1-5}$ alkyl), —COOH, —CO—O—($C_{1-6}$ alkyl), —O—CO—($C_{1-5}$ alkyl), —CO—$NH_2$, —CO—NH($C_{1-6}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{0-3}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl (e.g., —$CH_2$-cyclopropyl), —($C_{0-3}$ alkylene)-heterocycloalkyl, and -$L^A$-$R^A$. More preferably, each $R^1$ is independently selected from $C_{1-6}$ alkyl, —OH, —O($C_{1-5}$ alkyl), —O($C_{1-6}$ alkylene)-OH, —O($C_{0-3}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN. Even more preferably, each $R^1$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-4}$ alkyl) (e.g., —N$(CH_3)_2$), halogen (e.g., —F, —Cl, —Br, or —I), —$CF_3$, and —CN.

A preferred example of ring A substituted with two groups $R^1$ is 4,4-difluoro-cyclohexan-1,1-diyl, i.e. a cyclohexylene (as ring A) which is substituted in para-position with two fluoro atoms (as $R^1$).

$R^2$ is selected from hydrogen, $C_{1-6}$ alkyl, and —CO($C_{1-5}$ alkyl). Preferably, $R^2$ is hydrogen or $C_{1-6}$ alkyl. More preferably, $R^2$ is hydrogen, methyl or ethyl. Even more preferably, $R^2$ is hydrogen.

X is C($R^{3a}$)($R^{3b}$) or N($R^3$). Accordingly, X is a carbon atom carrying the substituents $R^{3a}$ and $R^{3b}$, or X is a nitrogen atom carrying the substituent $R^{3c}$. Preferably, X is C($R^{3a}$)($R^{3b}$).

$R^{3a}$ and $R^{3b}$ are each independently selected from hydrogen, $C_{1-5}$ alkyl, and $C_{2-5}$ alkenyl; or $R^{3a}$ and $R^{3b}$ are mutually linked to form, together with the carbon atom that they are attached to, a cycloalkyl or a heterocycloalkyl, wherein said cycloalkyl or said heterocycloalkyl is optionally substituted with one or more (e.g., one, two or three) groups $R^{31}$; or $R^{3a}$ is a divalent group selected from linear $C_{2-4}$ alkylene and linear $C_{2-4}$ alkenylene, wherein said divalent group is attached via one end to the carbon atom carrying $R^{3b}$ and is attached via the other end to a ring atom of ring B which is adjacent to the ring atom (of ring B) carrying the group X, wherein said alkylene or said alkenylene is optionally substituted with one or more (e.g., one, two or three) groups $R^{31}$, wherein one —$CH_2$— unit in said alkylene or said alkenylene is optionally replaced by —O—, —S—, —NH— or —N($C_{1-5}$ alkyl)-, and $R^{3b}$ is selected from hydrogen, $C_{1-6}$ alkyl, and $C_{2-5}$ alkenyl.

As indicated above, $R^{3a}$ may be a divalent group selected from linear $C_{2-4}$ alkylene (e.g., —$CH_2CH_2$— or —$CH_2CH_2CH_2$—) and linear $C_{2-4}$ alkenylene (e.g., —CH═CH—, —CH═CH—$CH_2$—, or —$CH_2$—CH═CH—), wherein said divalent group is attached via one end to the carbon atom carrying $R^{3b}$ and is attached via the other end to a ring atom of ring B which is adjacent to the ring atom (of ring B) carrying the group X, wherein said alkylene or said alkenylene is optionally substituted with one or more groups $R^{31}$, wherein one —$CH_2$— unit in said alkylene or said alkenylene is optionally replaced by —O—, —S—, —NH— or —N($C_{1-5}$ alkyl)-, and $R^{3b}$ is selected from hydrogen, $C_{1-5}$ alkyl, and $C_{2-5}$ alkenyl. In particular, $R^{3a}$ may be a divalent group selected from —$CH_2CH_2$— and —$CH_2CH_2CH_2$—, wherein said divalent group is attached via one end to the carbon atom carrying $R^{3b}$ and is attached via the other end to a ring atom of ring B which is adjacent to the ring atom (of ring B) carrying the group X, wherein said divalent group is optionally substituted with one or more groups $R^{31}$, and $R^{3b}$ may be hydrogen, $C_{1-6}$ alkyl or $C_{2-5}$ alkenyl, particularly hydrogen. Thus,

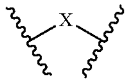

may be a group

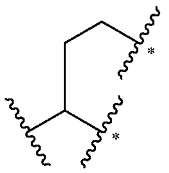

or

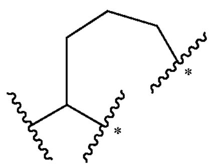

(particularly

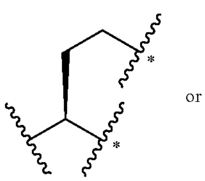

or

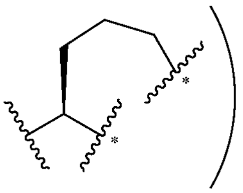

, wherein said group is attached via the two bonds marked with an asterisk (*) to two adjacent ring atoms of ring B, and wherein said group is optionally substituted with one or more (e.g., one, two or three) $R^{31}$.

Moreover, as indicated above, $R^{3a}$ and $R^{3b}$ may be mutually linked to form, together with the carbon atom that they are attached to, a cycloalkyl or a heterocycloalkyl, wherein said cycloalkyl or said heterocycloalkyl is optionally substituted with one or more groups $R^{31}$. It will be understood that the cycloalkyl or heterocycloalkyl which is formed from $R^{3a}$ and $R^{3b}$ is attached to the remainder of the compound of formula (I) through the carbon atom which carries $R^{3a}$ and $R^{3b}$. The said cycloalkyl or heterocycloalkyl is thus a divalent group which is attached via the same ring carbon atom to ring B and to the nitrogen atom carrying $R^2$, respectively. For example, if $R^{3a}$ and $R^{3b}$ are mutually linked to form, together with the carbon atom that they are attached to, a cyclopropyl, then said cyclopropyl is a cycloprop-1,1-diyl group, i.e. a group.

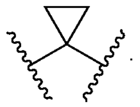 [SMILES: *C1(*)CC1]

Furthermore, as indicated above, $R^{3a}$ and $R^{3b}$ may each be independently selected from hydrogen, $C_{1-5}$ alkyl, and $C_{2-5}$ alkenyl. For example, $R^{3a}$ may be $C_{1-5}$ alkyl or $C_{2-5}$ alkenyl, and $R^{3b}$ may be hydrogen, $C_{1-5}$ alkyl, or $C_{2-5}$ alkenyl. In particular, $R^{3a}$ may be $C_{1-5}$ alkyl, and $R^{3b}$ may be hydrogen or $C_{1-6}$ alkyl.

Preferably, $R^{3a}$ and $R^{3b}$ are each independently selected from hydrogen and $C_{1-5}$ alkyl, or $R^{3a}$ and $R^{3b}$ are mutually linked to form, together with the carbon atom that they are attached to, a $C_{3-5}$ cycloalkyl or a 3- to 5-membered heterocycloalkyl, wherein said cycloalkyl or said heterocycloalkyl is optionally substituted with one or more (e.g., one or two) groups $R^{31}$. More preferably, $R^{3a}$ and $R^{3b}$ are each independently selected from hydrogen and $C_{1-6}$ alkyl (e.g., methyl or ethyl), or $R^{3a}$ and $R^{3b}$ are mutually linked to form, together with the carbon atom that they are attached to, a cyclopropyl. Even more preferably, $R^{3a}$ is $C_{1-5}$ alkyl (e.g., methyl or ethyl) and $R^{3b}$ is hydrogen or $C_{1-6}$ alkyl (e.g., methyl or ethyl), or $R^{3a}$ and $R^{3b}$ are mutually linked to form, together with the carbon atom that they are attached to, a cyclopropyl. Yet even more preferably, $R^{3a}$ is methyl and $R^{3b}$ is hydrogen, or $R^{3a}$ and $R^{3b}$ are mutually linked to form, together with the carbon atom that they are attached to, a cyclopropyl.

$R^{3c}$ is selected from hydrogen, $C_{1-5}$ alkyl, and $C_{2-5}$ alkenyl.

Preferably, $R^{3c}$ is hydrogen or $C_{1-5}$ alkyl (e.g., methyl or ethyl). More preferably, $R^{3c}$ is hydrogen or methyl. Even more preferably, $R^{3c}$ is methyl.

In accordance with the above definitions of X, $R^{3a}$ and $R^{3b}$, it is particularly preferred that the moiety

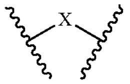

in formula (I) or (Ia) is

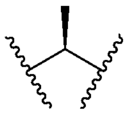

(e.g., as in the compound of Example 1) or

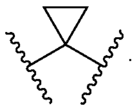 [SMILES: *C1(*)CC1]

Each $R^{31}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-6}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{0-3}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-6}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—

($C_{1-5}$ alkyl), and —$SO_2$—($C_{1-5}$ alkyl). Preferably, each $R^{31}$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN.

Each $R^4$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-6}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-6}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-6}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-6}$ alkyl)($C_{1-6}$ alkyl), —($C_{0-3}$ alkylene)-NH—$SO_2$—($C_{1-6}$ alkyl), —($C_{0-3}$ alkylene)-N($C_{1-6}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^A$-$R^A$.

Preferably, each $R^4$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-6}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl, —($C_{0-3}$ alkylene)-heterocycloalkyl, and -$L^A$-$R^A$. More preferably, each $R^4$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN. Even more preferably, each $R^4$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$alkyl)($C_{1-4}$ alkyl) (e.g., —$N(CH_3)_2$), halogen (e.g., —F, —Cl, —Br, or —I), —$CF_3$, and —CN.

$R^5$ is selected from —COOH, —CO—$NH_2$, —CO—NH($C_{1-5}$ alkyl), —CO—N($C_{1-5}$ alkyl)($C_{1-5}$ alkyl), —$SO_2$—OH, —$SO_2$—O—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —$SO_2$—($C_{1-5}$ alkyl), —S(=O)(=NH)—($C_{1-5}$ alkyl), halogen (e.g., —F or —Cl), $C_{1-5}$ haloalkyl (e.g., —$CF_3$), —CN, hydrogen, $C_{1-4}$ alkyl, —OH, —O($C_{1-4}$ alkyl), carbocyclyl (e.g., aryl or cycloalkyl), and heterocyclyl (e.g., heteroaryl or heterocycloalkyl), wherein said carbocyclyl or said heterocyclyl is optionally substituted with one or more (e.g., one, two or three) groups -$L^A$-$R^A$.

Preferably, $R^5$ is selected from —COOH, —CO—$NH_2$, —CO—NH($C_{1-6}$ alkyl), —CO—N($C_{1-5}$ alkyl)($C_{1-5}$ alkyl), —$SO_2$—OH, —$SO_2$—O—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —$SO_2$—($C_{1-6}$ alkyl), —S(=O)(=NH)—($C_{1-5}$ alkyl), halogen, $C_{1-5}$ haloalkyl, —CN, $C_{1-4}$ alkyl, —OH, —O($C_{1-4}$ alkyl), carbocyclyl, and heterocyclyl, wherein said carbocyclyl or said heterocyclyl is optionally substituted with one or more groups -$L^A$-$R^A$. More preferably, $R^5$ is selected from —COOH, —CO—$NH_2$, —CO—NH($C_{1-6}$ alkyl), —CO—N($C_{1-5}$ alkyl)($C_{1-6}$ alkyl), —$SO_2$—OH, —$SO_2$—O—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —$SO_2$—($C_{1-5}$ alkyl), —S(=O)(=NH)—($C_{1-5}$ alkyl), —CN, —O($C_{1-4}$ alkyl) (e.g., —$OCH_3$), and heteroaryl (e.g., tetrazolyl). More preferably, $R^5$ is selected from —COOH, —CO—$NH_2$, —CO—NH($C_{1-5}$ alkyl), —CO—N($C_{1-5}$ alkyl)($C_{1-5}$ alkyl), —$SO_2$—OH, —$SO_2$—O—($C_{1-5}$ alkyl), —$SO_2$—$NH_2$, —$SO_2$—NH($C_{1-6}$ alkyl), —$SO_2$—N($C_{1-6}$ alkyl)($C_{1-5}$ alkyl), —$SO_2$—($C_{1-5}$ alkyl), —S(=O)(=NH)—($C_{1-5}$ alkyl), —CN, and heteroaryl (e.g., tetrazolyl). More preferably, $R^5$ is selected from —COOH, —CO—$NH_2$, —CO—NH($C_{1-5}$ alkyl) (e.g., —CO—NH—$CH_3$), —CO—N($C_{1-5}$ alkyl)($C_{1-5}$ alkyl) (e.g., —CO—N($CH_3$)—$CH_3$), —$SO_2$—($C_{1-5}$ alkyl) (e.g., —$SO_2$—$CH_3$), —S(=O)(=NH)—($C_{1-6}$ alkyl) (e.g., —S(=O)(=NH)—$CH_3$), and tetrazolyl (e.g., 1H-tetrazol-5-yl or 2H-tetrazol-5-yl). More preferably, $R^5$ is —COOH, —CO—$NH_2$, or tetrazolyl (particularly 1H-tetrazol-5-yl or 2H-tetrazol-5-yl). Even more preferably, $R^5$ is —COOH or tetrazolyl (particularly 1H-tetrazol-5-yl or 2H-tetrazol-5-yl). Yet even more preferably, $R^5$ is —COOH.

In accordance with the above definitions of ring B, X, $R^2$, $R^{3a}$, $R^{3b}$, $R^4$, $R^5$ and m, it is particularly preferred that the moiety

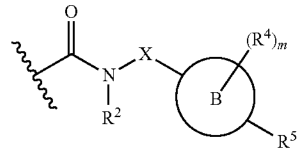

has the following structure:

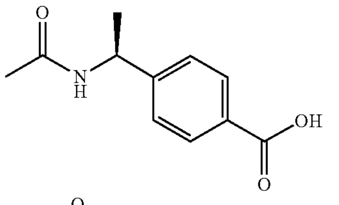

or

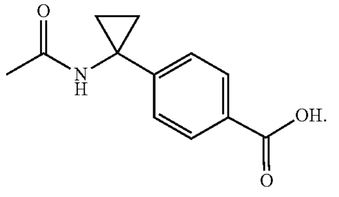

Moreover, if ring B is cyclohexylene, then the moiety

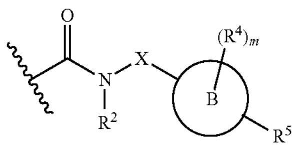

may, for example, have the following structure:

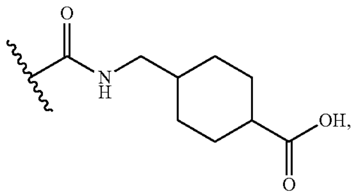 [SMILES: *C(=O)NCC1CCC(C(=O)O)CC1]

particularly

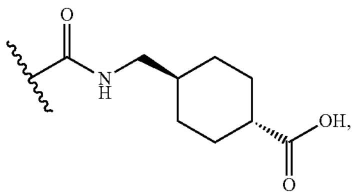 [SMILES: *C(=O)NC[C@H]1CC[C@H](C(=O)O)CC1]

Each $R^6$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-6}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^1$-$R^{61}$.

Preferably, each $R^6$ is independently selected from $C_{1-5}$ alkyl, $C_{2-5}$ alkenyl, $C_{2-5}$ alkynyl, —OH, —O($C_{1-6}$ alkyl), —O($C_{1-5}$ alkylene)-OH, —O($C_{1-6}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl, —($C_{0-3}$ alkylene)-heterocycloalkyl, and -$L^1$-$R^{61}$. More preferably, each $R^6$ is independently selected from $C_{1-6}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), —O—($C_{1-5}$ haloalkyl) (e.g., —$OCF_3$), —CN, and -$L^1$-$R^{61}$. Even more preferably, each $R^6$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-5}$ alkyl) (e.g., —$NHCH_3$), —N($C_{1-5}$ alkyl)($C_{1-4}$ alkyl) (e.g., —$N(CH_3)_2$), halogen (e.g., —F, —Cl, —Br, or —I), —$CF_3$, —$OCF_3$, —CN, and -$L^1$-$R^{61}$. Yet even more preferably, each $R^6$ is independently selected from —$CH_3$, —OH, —$OCH_3$, halogen (e.g., —F, —Cl, —Br, or —I), —$CF_3$, —$OCF_3$, —CN, and -$L^1$-$R^{61}$. Yet even more preferably, each $R^6$ is independently selected from —$CH_3$, —$OCH_3$, —F, —Cl, —$CF_3$, and —$OCF_3$. Still more preferably, each $R^6$ is independently selected from —$CH_3$, —$OCH_3$, —F, —Cl, and —$CF_3$. It is particularly preferred that each $R^6$ is independently —Cl or —$CF_3$.

If p is 1, then it is preferred that $R^6$ is attached to ring D in a 1,2-orientation, a 1,3-orientation or a 1,4-orientation with respect to the attachment point of group L to ring D, more preferably $R^6$ is attached to ring D in a 1,3-orientation with respect to the attachment point of group L to ring D. It will be understood in this regard that the attachment point of group L on ring D (i.e., the ring atom of ring D which is bound to L), is numbered as position 1, and either one of the two directly adjacent ring atoms is numbered as position 2, etc. Accordingly, if p is 1 and ring D is phenyl, then it is preferred that $R^6$ is attached to ring D in meta-position (corresponding to the 1,3-orientation) with respect to the attachment point of group L to ring D. Likewise, if p is greater than 1 (e.g., 2, 3 or 4), then it is preferred that at least one of the groups $R^6$ is attached to ring D in a 1,3-orientation with respect to the attachment point of group L to ring D; for example, if p is 2 and ring D is phenyl, the two groups $R^6$ may each be attached to said phenyl in meta-position (i.e., one group $R^6$ in position 3 and the other group $R^6$ in position 5) with respect to the attachment point of group L to said phenyl.

In accordance with the above definitions of p and $R^6$, it is particularly preferred that p is 1, the group $R^6$ is attached to ring D (which may be, e.g., phenyl) in a 1,3-orientation with respect to the attachment point of group L to ring D, and said group $R^6$ is selected from —$CH_3$, —OH, —$OCH_3$, halogen (e.g., —F, —Cl, —Br, or —I), —$CF_3$, —$OCF_3$, —CN, and -$L^1$-$R^{61}$, more preferably said group $R^6$ is selected from —$CH_3$, —$OCH_3$, —F, —Cl, —$CF_3$, and —$OCF_3$, even more preferably said group $R^6$ is selected from —$CH_3$, —$OCH_3$, —F, —Cl, and —$CF_3$, and still more preferably said group $R^6$ is selected from —Cl and —$CF_3$.

$L^1$ is $C_{1-6}$ alkylene or a covalent bond, wherein one or more (e.g., one, two or three) —$CH_2$— units comprised in said $C_{1-6}$ alkylene are each optionally replaced by a group independently selected from —O—, —CO—, —NH—, —N($C_{1-5}$ alkyl)-, —N[—CO—($C_{1-5}$ alkyl)]-, —S—, —SO—, —$SO_2$—, —CH($C_{1-5}$ alkyl)- and —C($C_{1-5}$ alkyl)($C_{1-5}$ alkyl)-.

Preferably, $L^1$ is $C_{1-4}$ alkylene, wherein one or more (e.g., one or two) —$CH_2$— units comprised in said $C_{1-4}$ alkylene are each optionally replaced by a group independently selected from —O—, —CO—, —NH—, —N($C_{1-5}$ alkyl)-, —N[—CO—($C_{1-5}$ alkyl)]-, —S—, —SO—, —$SO_2$—, —CH($C_{1-5}$ alkyl)- and —C($C_{1-5}$ alkyl)($C_{1-5}$ alkyl)-. Said alkylene is preferably $C_{2-4}$ alkylene (e.g., ethylene, propylene or butylene), more preferably —$(CH_2)_2$—, —$(CH_2)_3$— or —$(CH_2)_4$—, and is even more preferably —$(CH_2)_2$—. Moreover, it is preferred that said one or more —$CH_2$— units are each optionally replaced by a group independently selected from —O—, —S—, —NH—, and —N($C_{1-5}$ alkyl)-, particularly by —O—. It is furthermore preferred that $L^1$ is attached to ring D via —O— (i.e., that $L^1$ contains a terminal —$CH_2$— unit which is replaced by —O—, and that $L^1$ is connected to ring D via said —O—).

More preferably, $L^1$ is —$(CH_2)_{2-4}$—, wherein one —$CH_2$— unit comprised in said —$(CH_2)_{2-4}$— is optionally replaced by a group selected from —O—, —S—, —NH—, and —N($C_{1-5}$ alkyl)-, particularly by a group —O—. Even more preferably, $L^1$ is —O—$(CH_2)_{1-3}$—, wherein $L^1$ is attached to ring D via the oxygen atom (—O—) comprised in said —O—$(CH_2)_{1-3}$—. Yet even more preferably, $L^1$ is —O—$CH_2$— or —O—$CH_2$—$CH_2$—, wherein $L^1$ is attached to ring D via the oxygen atom in said —O—$CH_2$— or said —O—$CH_2$—$CH_2$—. Still more preferably, $L^1$ is —O—$CH_2$— which is attached to ring D via the oxygen atom (—O—) comprised in said —O—$CH_2$—.

$R^{61}$ is carbocyclyl or heterocyclyl, wherein said carbocyclyl or said heterocyclyl is optionally substituted with one or more (e.g., one, two or three) groups $R^{62}$.

Preferably, $R^{61}$ is selected from cycloalkyl, aryl, heterocycloalkyl (e.g., tetrahydrofuranyl or tetrahydropyranyl) and heteroaryl (e.g., pyridinyl), wherein said cycloalkyl, said aryl, said heterocycloalkyl and said heteroaryl are each optionally substituted with one or more (e.g., one, two or three) groups $R^{62}$. More preferably, $R^{61}$ is cycloalkyl or aryl, wherein said cycloalkyl or said aryl is optionally substituted with one or more $R^{62}$. Even more preferably, $R^{61}$ is selected from $C_{3-9}$ cycloalkyl (e.g., cyclopropyl, cyclobutyl, cyclopentyl, cyclohexyl, cycloheptyl, cyclooctyl, or cyclononyl) or phenyl, wherein said $C_{3-9}$ cycloalkyl or said phenyl is optionally substituted with one or more $R^{52}$. Yet even more preferably, $R^{61}$ is $C_{5-9}$ cycloalkyl (e.g., cyclopentyl, cyclohexyl, cycloheptyl, cyclooctyl, or cyclononyl) which is optionally substituted with one or more $R^{62}$. Yet even more preferably, $R^{61}$ is cyclohexyl or cycloheptyl, wherein said cyclohexyl or said cycloheptyl is optionally substituted with one or more $R^{62}$. Still more preferably, $R^{61}$ is cyclohexyl which is optionally substituted with one or more $R^{62}$. It is furthermore preferred that the aforementioned cyclic groups ($R^{61}$) are not substituted with any groups $R^{62}$.

Each $R^{62}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{0-3}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, and —($C_{0-3}$ alkylene)-heterocycloalkyl.

Preferably, each $R^{62}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{0-3}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl, and —($C_{0-3}$ alkylene)-heterocycloalkyl. More preferably, each $R^{62}$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN. Even more preferably, each $R^{62}$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-4}$ alkyl) (e.g., —$N(CH_3)_2$), halogen (e.g., —F, —Cl, —Br, or —I), —$CF_3$, and —CN.

Each $L^A$ is independently selected from a covalent bond, $C_{1-5}$ alkylene, $C_{2-5}$ alkenylene, and $C_{2-5}$ alkynylene, wherein said alkylene, said alkenylene and said alkynylene are each optionally substituted with one or more (e.g., one, two, or three) groups independently selected from halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl), and further wherein one or more (e.g., one, two, or three) —$CH_2$— units comprised in said alkylene, said alkenylene or said alkynylene are each optionally replaced by a group independently selected from —O—, —NH—, —N($C_{1-5}$ alkyl)-, —CO—, —S—, —SO—, and —$SO_2$—.

Each $R^A$ is independently selected from —OH, —O($C_{1-5}$ alkyl), —O($C_{1-5}$ alkylene)-OH, —O($C_{1-5}$ alkylene)-O($C_{1-5}$ alkyl), —SH, —S($C_{1-6}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O($C_{1-5}$ haloalkyl), —CN, —CHO, —CO($C_{1-5}$ alkyl), —COOH, —COO($C_{1-5}$ alkyl), —O—CO($C_{1-5}$ alkyl), —CO—$NH_2$, —CO—NH($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—

N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —$SO_2$—($C_{1-6}$ alkyl), —SO—($C_{1-5}$ alkyl), hydrogen, aryl, heteroaryl, cycloalkyl, and heterocycloalkyl, wherein said aryl, said heteroaryl, said cycloalkyl, and said heterocycloalkyl are each optionally substituted with one or more (e.g., one, two or three) groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl).

It is particularly preferred that the compound of formula (I) is any one of the specific compounds of formula (I) described in the examples section of this specification, including any one of Examples 1 to 210 described further below, either in non-salt form or as a pharmaceutically acceptable salt of the respective compound.

Accordingly, it is particularly preferred that the compound of formula (I) is selected from:

4-[(1S)-1-[[4-(2-Phenoxyethylamino)tetrahydropyran-4-carbonyl]amino]ethyl]benzoic acid;
4-[(1S)-1-[[4-[Methyl(2-phenoxyethyl)amino]tetrahydropyran-4-carbonyl]amino]ethyl]benzoic acid;
N-[(1S)-1-(4-Carbamoylphenyl)ethyl]-4-[methyl(2-phenoxyethyl)amino]tetrahydropyran-4-carboxamide;
N-[(1S)-1-[4-(Methylcarbamoyl)phenyl]ethyl]-4-[methyl(2-phenoxyethyl)amino]tetrahydropyran-4-carboxamide;
N-[(1S)-1-[4-(Dimethylcarbamoyl)phenyl]ethyl]-4-[methyl(2-phenoxyethyl)amino]tetrahydropyran-4-carboxamide;
4-[(1S)-1-[[4-[Acetyl(2-phenoxyethyl)amino]tetrahydropyran-4-carbonyl]amino]ethyl]benzoic acid;
4-[(1S)-1-[[4-[(2-Phenoxyacetyl)amino]tetrahydropyran-4-carbonyl]amino]ethyl]benzoic acid;
4-[(1S)-1-[[4-[2-(3-Chlorophenoxy)ethylamino]tetrahydropyran-4-carbonyl]amino]ethyl]benzoic acid;
4-[(1S)-1-[[4-[2-(3-Chlorophenoxy)ethyl-methyl-amino]tetrahydropyran-4-carbonyl]amino]ethyl]benzoic acid;
4-[(1S)-1-[[4-[2-(3-Chlorophenoxy)ethyl-ethyl-amino]tetrahydropyran-4-carbonyl]amino]ethyl]benzoic acid;
4-[(1S)-1-[[4-[2-(4-Chlorophenoxy)ethylamino]tetrahydropyran-4-carbonyl]amino]ethyl]benzoic acid;
4-[(1S)-1-[[4-[2-[3-(Trifluoromethyl)phenoxy]ethylamino]tetrahydropyran-4-carbonyl]amino]ethyl]benzoic acid;
4-[(1S)-1-[[4-[2-[3-Methoxyphenoxy]ethylamino]tetrahydropyran-4-carbonyl]amino]ethyl]benzoic acid;
4-[(1S)-1-[[4-[2-(3-Methylphenoxy)ethylamino]tetrahydropyran-4-carbonyl]amino]ethyl]benzoic acid;
4-[(1S)-1-[[4-[2-(4-Cyanophenoxy)ethylamino]tetrahydropyran-4-carbonyl]amino]ethyl]benzoic acid;
4-[(1S)-1-[[4-[2-(3,5-Difluorophenoxy)ethylamino]tetrahydropyran-4-carbonyl]amino]ethyl]benzoic acid;
4-[(1S)-1-[[4-[2-(3,4-Dichlorophenoxy)ethylamino]tetrahydropyran-4-carbonyl]amino]ethyl]benzoic acid;
4-[(1S)-1-[[4-(3-Phenylpropylamino)tetrahydropyran-4-carbonyl]amino]ethyl]benzoic acid;
4-[(1S)-1-[[4-(2-Phenylethylamino)tetrahydropyran-4-carbonyl]amino]ethyl]benzoic acid;
4-[(1S)-1-[[4-[(3-Fluorophenyl)methylamino]tetrahydropyran-4-carbonyl]amino]ethyl]benzoic acid;
4-[(1S)-1-[[4-(Cyclohexylmethylamino)tetrahydropyran-4-carbonyl]amino]ethyl]benzoic acid;
4-[(1S)-1-[[4-(3-Pyridylmethylamino)tetrahydropyran-4-carbonyl]amino]ethyl]benzoic acid;
4-[(1S)-1-[[4-(2-Pyridylmethylamino)tetrahydropyran-4-carbonyl]amino]ethyl]benzoic acid;
4-[1-[[4-(2-Phenoxyethylamino)tetrahydropyran-4-carbonyl]amino]cyclopropyl]benzoic acid;
4-[1-[[4-[Methyl(2-phenoxyethyl)amino]tetrahydropyran-4-carbonyl]amino]cyclopropyl]benzoic acid;
4-[1-[[4-[Propyl(2-phenoxyethyl)amino]tetrahydropyran-4-carbonyl]amino]cyclopropyl]benzoic acid;
4-[1-[[4-[Cyclopropylmethyl(2-phenoxyethyl)amino]tetrahydropyran-4-carbonyl]amino]cyclopropyl]benzoic acid;
4-[1-[[4-[2-(3-Chlorophenoxy)ethylamino]tetrahydropyran-4-carbonyl]amino]cyclopropyl]benzoic acid;
4-[1-[[4-[2-(3-Chlorophenoxy)ethyl-methyl-amino]tetrahydropyran-4-carbonyl]amino]cyclopropyl]benzoic acid;
4-[1-[[4-[2-(2-Chlorophenoxy)ethyl-methyl-amino]tetrahydropyran-4-carbonyl]amino]cyclopropyl]benzoic acid;
4-[1-[[4-[2-(4-Chlorophenoxy)ethyl-methyl-amino]tetrahydropyran-4-carbonyl]amino]cyclopropyl]benzoic acid;
4-[1-[[4-[2-(3-Fluorophenoxy)ethyl-methyl-amino]tetrahydropyran-4-carbonyl]amino]cyclopropyl]benzoic acid;
4-[1-[[4-[2-(2-Fluorophenoxy)ethyl-methyl-amino]tetrahydropyran-4-carbonyl]amino]cyclopropyl]benzoic acid;
4-[1-[[4-[2-(4-Fluorophenoxy)ethyl-methyl-amino]tetrahydropyran-4-carbonyl]amino]cyclopropyl]benzoic acid;
4-[1-[[4-[2-(3-Methylphenoxy)ethyl-methyl-amino]tetrahydropyran-4-carbonyl]amino]cyclopropyl]benzoic acid;
4-[1-[[4-[2-(2-Methylphenoxy)ethyl-methyl-amino]tetrahydropyran-4-carbonyl]amino]cyclopropyl]benzoic acid;
4-[1-[[4-[2-(4-Methylphenoxy)ethyl-methyl-amino]tetrahydropyran-4-carbonyl]amino]cyclopropyl]benzoic acid;
4-[1-[[4-[2-(3-Methoxyphenoxy)ethyl-methyl-amino]tetrahydropyran-4-carbonyl]amino]cyclopropyl]benzoic acid;
4-[1-[[4-[2-(2-Methoxyphenoxy)ethyl-methyl-amino]tetrahydropyran-4-carbonyl]amino]cyclopropyl]benzoic acid;
4-[1-[[4-[2-(4-Methoxyphenoxy)ethyl-methyl-amino]tetrahydropyran-4-carbonyl]amino]cyclopropyl]benzoic acid;
4-[1-[[4-[2-(3-Trifluoromethylphenoxy)ethyl-methyl-amino]tetrahydropyran-4-carbonyl]amino]cyclopropyl]benzoic acid;
4-[1-[[4-[2-(2-Trifluoromethylphenoxy)ethyl-methyl-amino]tetrahydropyran-4-carbonyl]amino]cyclopropyl]benzoic acid;
4-[1-[[4-[2-(3-Trifluoromethoxyphenoxy)ethyl-methyl-amino]tetrahydropyran-4-carbonyl]amino]cyclopropyl]benzoic acid;
4-[1-[[4-[2-(2-Trifluoromethoxyphenoxy)ethyl-methyl-amino]tetrahydropyran-4-carbonyl]amino]cyclopropyl]benzoic acid;
4-[1-[[4-[2-(4-Trifluoromethoxyphenoxy)ethyl-methyl-amino]tetrahydropyran-4-carbonyl]amino]cyclopropyl]benzoic acid;
4-[1-[[4-[2-(3-Cyanophenoxy)ethyl-methyl-amino]tetrahydropyran-4-carbonyl]amino]cyclopropyl]benzoic acid;
4-[1-[[4-[2-(2-Cyanophenoxy)ethyl-methyl-amino]tetrahydropyran-4-carbonyl]amino]cyclopropyl]benzoic acid;
4-[1-[[4-[2-(4-Cyanophenoxy)ethyl-methyl-amino]tetrahydropyran-4-carbonyl]amino]cyclopropyl]benzoic acid;
2-Fluoro-4-[1-[[4-[methyl(2-phenoxyethyl)amino]tetrahydropyran-4-carbonyl]amino]cyclopropyl]benzoic acid;
3-Fluoro-4-[1-[[4-[methyl(2-phenoxyethyl)amino]tetrahydropyran-4-carbonyl]amino]cyclopropyl]benzoic acid;
2-Chloro-4-[1-[[4-[methyl(2-phenoxyethyl)amino]tetrahydropyran-4-carbonyl]amino]cyclopropyl]benzoic acid;
3-Chloro-4-[1-[[4-[methyl(2-phenoxyethyl)amino]tetrahydropyran-4-carbonyl]amino]cyclopropyl]benzoic acid;
5-[1-[[4-[Methyl(2-phenoxyethyl)amino]tetrahydropyran-4-carbonyl]amino]cyclopropyl]pyridine-2-carboxylic acid;
6-[1-[[4-[Methyl(2-phenoxyethyl)amino]tetrahydropyran-4-carbonyl]amino]cyclopropyl]pyridine-3-carboxylic acid;

4-[(1S)-1-[[1-(2-Phenoxyethylamino)cyclohexanecarbonyl]amino]ethyl]benzoic acid;
4-[(1S)-1-[[1-[2-(3-Chlorophenoxy)ethylamino]cyclohexanecarbonyl]amino]ethyl]benzoic acid;
4-[(1S)-1-[[1-[2-(3-Chlorophenoxy)ethyl-methyl-amino]cyclohexanecarbonyl]amino]ethyl]benzoic acid;
4-[(1S)-1-[[1-[2-(3-Methylphenoxy)ethylamino]cyclohexanecarbonyl]amino]ethyl]benzoic acid;
4-[(1S)-1-[[1-[Methyl-[2-(3-methylphenoxy)ethyl]amino]cyclohexanecarbonyl]amino]ethyl]benzoic acid;
4-[(1S)-1-[[1-[2-(3-Methoxyphenoxy)ethyl-methyl-amino]cyclohexanecarbonyl]amino]ethyl]benzoic acid;
4-[(1S)-1-[[1-(2-Phenoxyethylamino)cyclopentanecarbonyl]amino]ethyl]benzoic acid;
4-[(1S)-1-[[1-[Methyl(2-phenoxyethyl)amino]cyclopentanecarbonyl]amino]ethyl]benzoic acid;
4-[(1S)-1-[[1-[2-(3-Chlorophenoxy)ethylamino]cyclopentanecarbonyl]amino]ethyl]benzoic acid;
3-[(1S)-1-[[1-[2-(3-Chlorophenoxy)ethylamino]cyclopentanecarbonyl]amino]ethyl]bicyclo[1.1.1]pentane-1-carboxylic acid;
4-[(1S)-1-[[4,4-Difluoro-1-(2-phenoxyethylamino)cyclohexanecarbonyl]amino]ethyl]benzoic acid;
4-[(1S)-1-[[4-(2-Phenoxyethylamino)tetrahydrothiopyran-4-carbonyl]amino]ethyl]benzoic acid;
4-[(1S)-1-[[1,1-Dioxo-4-(2-phenoxyethylamino)thiane-4-carbonyl]amino]ethyl]benzoic acid;
4-[(1S)-1-[[2-(2-Phenoxyethylamino)spiro[3.3]heptane-2-carbonyl]amino]ethyl]benzoic acid;
4-[(1S)-1-[[1-(2-Phenoxyethylamino)cyclobutanecarbonyl]amino]ethyl]benzoic acid;
4-[(1S)-1-[[8,8-Dimethyl-7-(2-phenoxyethylamino)-2-oxabicyclo[4.2.0]octane-7-carbonyl]amino]ethyl]benzoic acid;
4-[(1S)-1-[[2,2-Dimethyl-4-(2-phenoxyethylamino)tetrahydropyran-4-carbonyl]amino]ethyl]benzoic acid;
4-[(1S)-1-[[2,2-Dimethyl-4-(2-phenoxyethylamino)tetrahydropyran-4-carbonyl]amino]ethyl]benzoic acid;
4-[(1S)-1-[[3-[Methyl(2-phenoxyethyl)amino]tetrahydropyran-3-carbonyl]amino]ethyl]benzoic acid;
4-[(1S)-1-[[3-[Methyl(2-phenoxyethyl)amino]tetrahydrofuran-3-carbonyl]amino]ethyl]benzoic acid;
4-[(1S)-1-[[3-[2-(3-Chlorophenoxy)ethyl-methyl-amino]tetrahydrofuran-3-carbonyl]amino]ethyl]benzoic acid;
4-[i-[[3-[Methyl(2-phenoxyethyl)amino]tetrahydrofuran-3-carbonyl]amino]cyclopropyl]benzoic acid;
4-[i-[[3-[2-(3-Chlorophenoxy)ethyl-methyl-amino]tetrahydrofuran-3-carbonyl]amino]cyclopropyl]benzoic acid;
4-[(1S)-1-[[1-Methyl-4-(2-phenoxyethylamino)piperidine-4-carbonyl]amino]ethyl]benzoic acid;
4-[(1S)-1-[[1-(2-Methoxyethyl)-4-(2-phenoxyethylamino)piperidine-4-carbonyl]amino]ethyl]benzoic acid;
4-[(1S)-1-[[1-(Cyclopropylmethyl)-4-(2-phenoxyethylamino)piperidine-4-carbonyl]amino]ethyl]benzoic acid;
4-[(1S)-1-[[4-(3-Phenoxypropyl)tetrahydropyran-4-carbonyl]amino]ethyl]benzoic acid;
4-[1-[[4-[2-(3-Chlorophenoxy)ethoxy]tetrahydropyran-4-carbonyl]amino]cyclopropyl]benzoic acid;
4-[(1S)-1-[[4-(3-Fluorophenyl)tetrahydropyran-4-carbonyl]amino]ethyl]benzoic acid;
4-[(1S)-1-[[4-[4-(2-Methylpentoxy)phenyl]tetrahydropyran-4-carbonyl]amino]ethyl]benzoic acid;
4-[(1S)-1-[[4-(4-Methoxyphenyl)tetrahydropyran-4-carbonyl]amino]ethyl]benzoic acid;
4-[(1S)-1-[[4-(3-Isopropoxyphenyl)tetrahydropyran-4-carbonyl]amino]ethyl]benzoic acid;
4-[(1S)-1-[[4-[3-(2,2,2-Trifluoroethoxy)phenyl]tetrahydropyran-4-carbonyl]amino]ethyl]benzoic acid;
4-[(1S)-1-[[4-(4-Benzyloxyphenyl)tetrahydropyran-4-carbonyl]amino]ethyl]benzoic acid;
4-[(1S)-1-[[4-[4-(Cyclohexylmethoxy)phenyl]tetrahydropyran-4-carbonyl]amino]ethyl]benzoic acid;
4-[(1S)-1-[[4-[4-(Tetrahydropyran-4-ylmethoxy)phenyl]tetrahydropyran-4-carbonyl]amino]ethyl]benzoic acid;
4-[(1S)-1-[[4-[4-(2,2,2-Trifluoroethoxy)phenyl]tetrahydropyran-4-carbonyl]amino]ethyl]benzoic acid;
4-[(1S)-1-[[4-[4-(3-Phenylpropoxy)phenyl]tetrahydropyran-4-carbonyl]amino]ethyl]benzoic acid;
4-[(1S)-1-[[4-[4-(2-Tetrahydropyran-4-ylethoxy)phenyl]tetrahydropyran-4-carbonyl]amino]ethyl]benzoic acid;
4-[(1S)-1-[[4-[4-(3-Phenylethoxy)phenyl]tetrahydropyran-4-carbonyl]amino]ethyl]benzoic acid;
4-[(1S)-1-[[4-[4-(2-Cyclohexylethoxy)phenyl]tetrahydropyran-4-carbonyl]amino]ethyl]benzoic acid;
4-[(1S)-1-[[4-[4-(3-Pyridylmethoxy)phenyl]tetrahydropyran-4-carbonyl]amino]ethyl]benzoic acid;
4-[(1S)-1-[[4-[3-(Cyclohexylmethoxy)phenyl]tetrahydropyran-4-carbonyl]amino]ethyl]benzoic acid;
4-[(1S)-1-[[4-[3-(Tetrahydropyran-4-ylmethoxy)phenyl]tetrahydropyran-4-carbonyl]amino]ethyl]benzoic acid;
4-[(1S)-1-[[4-(3-Benzyloxyphenyl)tetrahydropyran-4-carbonyl]amino]ethyl]benzoic acid;
4-[(1S)-1-[[4-[3-(Cyclohexoxy)phenyl]tetrahydropyran-4-carbonyl]amino]ethyl]benzoic acid;
4-[(1S)-1-[[4-[3-(Cyclopropylmethoxy)phenyl]tetrahydropyran-4-carbonyl]amino]ethyl]benzoic acid;
4-[(1S)-1-[[4-[3-(Cyclopentylmethoxy)phenyl]tetrahydropyran-4-carbonyl]amino]ethyl]benzoic acid;
4-[(1S)-1-[[4-[3-(Cycloheptylmethoxy)phenyl]tetrahydropyran-4-carbonyl]amino]ethyl]benzoic acid;
4-[(1S)-1-[[4-(3-Isopentyloxyphenyl)tetrahydropyran-4-carbonyl]amino]ethyl]benzoic acid;
4-[(1S)-1-[[4-[3-(2-Cyclohexylethoxy)phenyl]tetrahydropyran-4-carbonyl]amino]ethyl]benzoic acid;
4-[(1S)-1-[[4-[3-[[(3S)-Tetrahydrofuran-3-yl]methoxy]phenyl]tetrahydropyran-4-carbonyl]amino]ethyl]benzoic acid;
4-[(1S)-1-[[4-[3-[[(3R)-Tetrahydrofuran-3-yl]methoxy]phenyl]tetrahydropyran-4-carbonyl]amino]ethyl]benzoic acid;
4-[(1S)-1-[[1-[4-(Cyclohexylmethoxy)phenyl]cyclopentanecarbonyl]amino]ethyl]benzoic acid;
4-[(1S)-1-[[1-(4-Benzyloxyphenyl)cyclopentanecarbonyl]amino]ethyl]benzoic acid;
4-[(1S)-1-[[1-[4-(2-Cyclohexylethoxy)phenyl]cyclopentanecarbonyl]amino]ethyl]benzoic acid;
4-[(1S)-1-[[1-[4-(2-Cyclohexylethoxy)phenyl]cyclopentanecarbonyl]-methyl-amino]ethyl]benzoic acid;
4-[(1S)-1-[[1-[3-(Cyclohexylmethoxy)phenyl]cyclopentanecarbonyl]amino]ethyl]benzoic acid;
4-[(1S)-1-[[1-(3-Benzyloxyphenyl)cyclopentanecarbonyl]amino]ethyl]benzoic acid;
4-[(1S)-1-[[1-[2-(Cyclohexylmethoxy)phenyl]cyclopentanecarbonyl]amino]ethyl]benzoic acid;
4-[(1S)-1-[[4-[6-(Cyclohexylmethoxy)-2-pyridyl]tetrahydropyran-4-carbonyl]amino]ethyl]benzoic acid;
4-[(1S)-1-[[4-[2-(Cyclohexylmethoxy)-4-pyridyl]tetrahydropyran-4-carbonyl]amino]ethyl]benzoic acid;
4-[(1S)-1-[[4-[4-(Cyclohexylmethoxy)-2-pyridyl]tetrahydropyran-4-carbonyl]amino]ethyl]benzoic acid;
4-[(1S)-1-[[4-[5-(Cyclohexylmethoxy)-3-pyridyl]tetrahydropyran-4-carbonyl]amino]ethyl]benzoic acid;

4-[(1S)-1-[[4-[5-(Cyclohexylmethoxy)-2-pyridyl]tetrahydropyran-4-carbonyl]amino]ethyl]benzoic acid;
4-[(1S)-1-[[4-[5-(2-Cyclohexylethoxy)-2-pyridyl]tetrahydropyran-4-carbonyl]amino]ethyl]benzoic acid;
4-[(1S)-1-[[4-[6-(Cyclohexylmethoxy)-3-pyridyl]tetrahydropyran-4-carbonyl]amino]ethyl]benzoic acid;
4-[(1S)-1-[[4-[6-(2-Cyclohexylethoxy)-3-pyridyl]tetrahydropyran-4-carbonyl]amino]ethyl]benzoic acid;
4-[(1S)-1-[[1-[6-(Cyclohexylmethoxy)-2-pyridyl]cyclopentanecarbonyl]amino]ethyl]benzoic acid;
4-[(1S)-1-[[1-[2-(Cyclohexylmethoxy)-4-pyridyl]cyclopentanecarbonyl]amino]ethyl]benzoic acid;
4-[(1S)-1-[[1-[4-(Cyclohexylmethoxy)-2-pyridyl]cyclopentanecarbonyl]amino]ethyl]benzoic acid;
4-[(1S)-1-[[1-[5-(Cyclohexylmethoxy)-3-pyridyl]cyclopentanecarbonyl]amino]ethyl]benzoic acid;
4-[(1S)-1-[[1-[5-(Cyclohexylmethoxy)-2-pyridyl]cyclopentanecarbonyl]amino]ethyl]benzoic acid;
4-[(1S)-1-[[1-[5-(2-Cyclohexylethoxy)-2-pyridyl]cyclopentanecarbonyl]amino]ethyl]benzoic acid;
4-[(1S)-1-[[1-[6-(Cyclohexylmethoxy)-3-pyridyl]cyclopentanecarbonyl]amino]ethyl]benzoic acid;
4-[(1S)-1-[[1-[6-(2-Cyclohexylethoxy)-3-pyridyl]cyclopentanecarbonyl]amino]ethyl]benzoic acid;
4-[(1S)-1-[[4-[4-(3-Chlorophenoxy)-1-piperidyl]tetrahydropyran-4-carbonyl]amino]ethyl]benzoic acid;
4-[(1S)-1-[[4-[4-[(3-chlorophenyl)methoxy]-1-piperidyl]tetrahydropyran-4-carbonyl]amino]ethyl]benzoic acid;
4-[1-[[4-[4-[(3-Chlorophenyl)methoxy]-1-piperidyl]tetrahydropyran-4-carbonyl]amino]cyclopropyl]benzoic acid;
4-[(1S)-1-[[4-[(3S)-3-(3-Chlorophenoxy)-1-piperidyl]tetrahydropyran-4-carbonyl]amino]ethyl]benzoic acid;
4-[1-[[4-[(3S)-3-(3-Chlorophenoxy)-1-piperidyl]tetrahydropyran-4-carbonyl]amino]cyclopropyl]benzoic acid;
4-[(1S)-1-[[4-[(3R)-3-(3-Chlorophenoxy)-1-piperidyl]tetrahydropyran-4-carbonyl]amino]ethyl]benzoic acid;
4-[1-[[4-[(3R)-3-(3-Chlorophenoxy)-1-piperidyl]tetrahydropyran-4-carbonyl]amino]cyclopropyl]benzoic acid;
4-[(1S)-1-[[4-[(3S)-3-(3-Chlorophenoxy)pyrrolidin-1-yl]tetrahydropyran-4-carbonyl]amino]ethyl]benzoic acid;
4-[1-[[4-[(3S)-3-(3-Chlorophenoxy)pyrrolidin-1-yl]tetrahydropyran-4-carbonyl]amino]cyclopropyl]benzoic acid;
4-[(1S)-1-[[4-[(3R)-3-(3-Chlorophenoxy)pyrrolidin-1-yl]tetrahydropyran-4-carbonyl]amino]ethyl]benzoic acid;
4-[1-[[4-[(3R)-3-(3-Chlorophenoxy)pyrrolidin-1-yl]tetrahydropyran-4-carbonyl]amino]cyclopropyl]benzoic acid;
4-[(1S)-1-[[4-[(3R)-3-(3-Fluorophenoxy)pyrrolidin-1-yl]tetrahydropyran-4-carbonyl]amino]ethyl]benzoic acid;
4-[1-[[4-[(3R)-3-(3-Fluorophenoxy)pyrrolidin-1-yl]tetrahydropyran-4-carbonyl]amino]cyclopropyl]benzoic acid;
4-[(1S)-1-[[4-[(3R)-3-[3-(Trifluoromethyl)phenoxy]pyrrolidin-1-yl]tetrahydropyran-4-carbonyl]amino]ethyl]benzoic acid;
4-[1-[[4-[(3R)-3-[3-(Trifluoromethyl)phenoxy]pyrrolidin-1-yl]tetrahydropyran-4-carbonyl]amino]cyclopropyl]benzoic acid;
4-[(1S)-1-[[4-[(3R)-3-[3-(Trifluoromethoxy)phenoxy]pyrrolidin-1-yl]tetrahydropyran-4-carbonyl]amino]ethyl]benzoic acid;
4-[1-[[4-[(3R)-3-[3-(Trifluoromethoxy)phenoxy]pyrrolidin-1-yl]tetrahydropyran-4-carbonyl]amino]cyclopropyl]benzoic acid;
4-[(1S)-1-[[4-[(3R)-3-(3-Methoxyphenoxy)pyrrolidin-1-yl]tetrahydropyran-4-carbonyl]amino]ethyl]benzoic acid;
4-[1-[[4-[(3R)-3-(3-Methoxyphenoxy)pyrrolidin-1-yl]tetrahydropyran-4-carbonyl]amino]cyclopropyl]benzoic acid;
4-[(1S)-1-[[4-[(3R)-3-(3-Methylphenoxy)pyrrolidin-1-yl]tetrahydropyran-4-carbonyl]amino]ethyl]benzoic acid;
4-[1-[[4-[(3R)-3-(3-Methylphenoxy)pyrrolidin-1-yl]tetrahydropyran-4-carbonyl]amino]cyclopropyl]benzoic acid;
4-[(1S)-1-[[4-((3R)-3-Phenoxypyrrolidin-1-yl)tetrahydropyran-4-carbonyl]amino]ethyl]benzoic acid;
4-[1-[[4-((3R)-3-Phenoxypyrrolidin-1-yl)tetrahydropyran-4-carbonyl]amino]cyclopropyl]benzoic acid;
4-[(1S)-1-[[4-[(3R)-3-(Cyclohexyloxy]pyrrolidin-1-yl]tetrahydropyran-4-carbonyl]amino]ethyl]benzoic acid;
4-[(1S)-1-[[1-[(3R)-3-(3-Chlorophenoxy)pyrrolidin-1-yl]cyclohexane-1-carbonyl]amino]ethyl]benzoic acid;
4-[(1S)-1-[[1-[(3R)-3-(3-Chlorophenoxy)pyrrolidin-1-yl]-4,4-difluorocyclohexane-1-carbonyl]amino]ethyl]benzoic acid;
4-[(1S)-1-[[1-[(3R)-3-(3-Chlorophenoxy)pyrrolidin-1-yl]cyclopentane-1-carbonyl]amino]ethyl]benzoic acid;
4-[1-[[4-[(3R)-3-(3-Chlorophenoxy)pyrrolidin-1-ylcyclopentane-1-carbonyl]amino]cyclopropyl]benzoic acid;
4-[(1S)-1-[[1-[(3R)-3-(3-Chlorophenoxy)pyrrolidin-1-yl]cyclobutane-1-carbonyl]amino]ethyl]benzoic acid;
4-[(1S)-1-[[1-[(3R)-3-(3-Chlorophenoxy)pyrrolidin-1-yl]cyclopropane-1-carbonyl]amino]ethyl]benzoic acid;
4-[(1S)-1-[[2-[(3R)-3-(3-Chlorophenoxy)pyrrolidin-1-yl]-2-methylpropane-carbonyl]amino]ethyl]benzoic acid;
4-[(1S)-1-[[1-[(3R)-3-[3-(Trifluoromethyl)phenoxy]pyrrolidin-1-yl]cyclohexane-1-carbonyl]amino]ethyl]benzoic acid;
4-[(1S)-1-[[1-[(3R)-3-[3-(Trifluoromethyl)phenoxy]pyrrolidin-1-yl]-4,4-difluorocyclohexane-1-carbonyl]amino]ethyl]benzoic acid;
4-[(1S)-1-[[1-[(3R)-3-[3-Trifluoromethyl)phenoxy]pyrrolidin-1-yl]cyclopentane-1-carbonyl]amino]ethyl]benzoic acid;
4-[(1S)-1-[[1-[(3R)-3-[3-(Trifluoromethyl)phenoxy]pyrrolidin-1-yl]cyclobutane-1-carbonyl]amino]ethyl]benzoic acid;
4-[(1S)-1-[[1-[(3R)-3-[3-(Trifluoromethyl)phenoxy]pyrrolidin-1-yl]cyclopropane-1-carbonyl]amino]ethyl]benzoic acid;
4-[(1S)-1-[[2-[(3R)-3-[3-(Trifluoromethyl)phenoxy]pyrrolidin-1-yl]-2-methylpropane-carbonyl]amino]ethyl]benzoic acid;
4-[(1S)-1-[[4-[(3R)-3-[3-(Trifluoromethyl)phenoxy]pyrrolidin-1-yl]tetrahydropyran-4-carbonyl]amino]ethyl]benzamide;
4-[(1S)-1-[[4-[(3R)-3-[3-(Trifluoromethyl)phenoxy]pyrrolidin-1-yl]tetrahydropyran-4-carbonyl]methylamino]ethyl]benzamide;
4-[(1S)-1-[[4-[(3R)-3-[3-(Trifluoromethyl)phenoxy]pyrrolidin-1-yl]tetrahydropyran-4-carbonyl]dimethylamino]ethyl]benzamide;
4-[(1S)-1-[[1-[(3R)-3-[3-(Trifluoromethyl)phenoxy]pyrrolidin-1-yl]cyclobutane-1-carbonyl]amino]ethyl]benzamide;
4-[(1S)-1-[[1-[(3R)-3-(3-Chlorophenoxy)pyrrolidin-1-yl]cyclobutane-1-carbonyl]amino]ethyl]benzamide;
4-[(1S)-1-[[2-[(3R)-3-[3-(Trifluoromethyl)phenoxy]pyrrolidin-1-yl]-2-methylpropane-carbonyl]amino]ethyl]benzamide;
4-[(1S)-1-[[2-[(3R)-3-(3-Chlorophenoxy)pyrrolidin-1-yl]-2-methylpropane-carbonyl]amino]ethyl]benzamide;
N—((S)-1-(4-(2H-Tetrazol-5-yl)phenyl)ethyl)-4-((R)-3-(3-(trifluoromethyl)phenoxy)pyrrolidin-1-yl)tetrahydro-2H-pyran-4-carboxamide;

N—((S)-1-(4-(1H-Pyrazol-4-yl)phenyl)ethyl)-4-((R)-3-(3-(trifluoromethyl)phenoxy)pyrrolidin-1-yl)tetrahydro-2H-pyran-4-carboxamide;

N—((S)-1-(4-(1H-Pyrazol-5-yl)phenyl)ethyl)-4-((R)-3-(3-(trifluoromethyl)phenoxy)pyrrolidin-1-yl)tetrahydro-2H-pyran-4-carboxamide;

N—((S)-1-(4-Sulfamoylphenyl)ethyl)-4-((R)-3-(3-(trifluoromethyl)phenoxy)pyrrolidin-1-yl)tetrahydro-2H-pyran-4-carboxamide;

N—((S)-1-(4-(Methylsulfonyl)phenyl)ethyl)-4-((R)-3-(3-(trifluoromethyl)phenoxy)pyrrolidin-1-yl)tetrahydro-2H-pyran-4-carboxamide;

N-((1S)-1-(4-(S-Methylsulfonimidoyl)phenyl)ethyl)-4-((R)-3-(3-(trifluoromethyl)phenoxy)pyrrolidin-1-yl)tetrahydro-2H-pyran-4-carboxamide;

N—((S)-1-(4-Hydroxyphenyl)ethyl)-4-((R)-3-(3-(trifluoromethyl)phenoxy)pyrrolidin-1-yl)tetrahydro-2H-pyran-4-carboxamide;

N—((S)-1-(4-Cyanophenyl)ethyl)-4-((R)-3-(3-(trifluoromethyl)phenoxy)pyrrolidin-1-yl)tetrahydro-2H-pyran-4-carboxamide;

N—((S)-1-Phenylethyl)-4-((R)-3-(3-(trifluoromethyl)phenoxy)pyrrolidin-1-yl)tetrahydro-2H-pyran-4-carboxamide;

N—((S)-1-(Pyridin-4-yl)ethyl)-4-((R)-3-(3-(trifluoromethyl)phenoxy)pyrrolidin-1-yl)tetrahydro-2H-pyran-4-carboxamide;

N—((S)-1-(Pyridin-3-yl)ethyl)-4-((R)-3-(3-(trifluoromethyl)phenoxy)pyrrolidin-1-yl)tetrahydro-2H-pyran-4-carboxamide;

N—((S)-1-(Pyridin-2-yl)ethyl)-4-((R)-3-(3-(trifluoromethyl)phenoxy)pyrrolidin-1-yl)tetrahydro-2H-pyran-4-carboxamide;

N—((S)-1-(4-Fluorophenyl)ethyl)-4-((R)-3-(3-(trifluoromethyl)phenoxy)pyrrolidin-1-yl)tetrahydro-2H-pyran-4-carboxamide;

N—((S)-1-(3-Fluorophenyl)ethyl)-4-((R)-3-(3-(trifluoromethyl)phenoxy)pyrrolidin-1-yl)tetrahydro-2H-pyran-4-carboxamide;

N—((S)-1-(2-Fluorophenyl)ethyl)-4-((R)-3-(3-(trifluoromethyl)phenoxy)pyrrolidin-1-yl)tetrahydro-2H-pyran-4-carboxamide;

N—((S)-1-(4-Bromophenyl)ethyl)-4-((R)-3-(3-(trifluoromethyl)phenoxy)pyrrolidin-1-yl)tetrahydro-2H-pyran-4-carboxamide;

N—((S)-1-(3-Chlorophenyl)ethyl)-4-((R)-3-(3-(trifluoromethyl)phenoxy)pyrrolidin-1-yl)tetrahydro-2H-pyran-4-carboxamide;

N—((S)-1-(2-Chlorophenyl)ethyl)-4-((R)-3-(3-(trifluoromethyl)phenoxy)pyrrolidin-1-yl)tetrahydro-2H-pyran-4-carboxamide;

N—((S)-1-(4-Methylphenyl)ethyl)-4-((R)-3-(3-(trifluoromethyl)phenoxy)pyrrolidin-1-yl)tetrahydro-2H-pyran-4-carboxamide;

N—((S)-1-(3-Methylphenyl)ethyl)-4-((R)-3-(3-(trifluoromethyl)phenoxy)pyrrolidin-1-yl)tetrahydro-2H-pyran-4-carboxamide;

N—((S)-1-(4-Methoxyphenyl)ethyl)-4-((R)-3-(3-(trifluoromethyl)phenoxy)pyrrolidin-1-yl)tetrahydro-2H-pyran-4-carboxamide;

N—((S)-1-(3-Methoxyphenyl)ethyl)-4-((R)-3-(3-(trifluoromethyl)phenoxy)pyrrolidin-1-yl)tetrahydro-2H-pyran-4-carboxamide;

N—((S)-1-(2-Methoxyphenyl)ethyl)-4-((R)-3-(3-(trifluoromethyl)phenoxy)pyrrolidin-1-yl)tetrahydro-2H-pyran-4-carboxamide;

(R)-2-Methyl-4-(1-(4-(3-(3-(trifluoromethyl)phenoxy)pyrrolidin-1-yl)tetrahydro-2H-pyran-4-carboxamido)cyclopropyl)benzoic acid;

(R)-6-(4-(3-(3-(Trifluoromethyl)phenoxy)pyrrolidin-1-yl)tetrahydro-2H-pyran-4-carboxamido)spiro[3.3]heptane-2-carboxylic acid;

(1R,4R)-4-((4-((R)-3-(3-(Trifluoromethyl)phenoxy)pyrrolidin-1-yl)tetrahydro-2H-pyran-4-carboxamido)methyl)cyclohexane-1-carboxylic acid;

(1R,4R)-4-((2-Methyl-2-((R)-3-(3-(trifluoromethyl)phenoxy)pyrrolidin-1-yl)propanamido)methyl)cyclohexane-1-carboxylic acid;

(1R,4R)-4-((2-Methyl-2-((R)-3-(3-(trifluoromethyl)phenoxy)pyrrolidin-1-yl)propanamido)methyl)cyclohexane-1-carboxamide;

2-Methyl-N—((S)-1-(4-sulfamoylphenyl)ethyl)-2-((R)-3-(3-(trifluoromethyl)phenoxy)pyrrolidin-1-yl)propanamide;

2-Methyl-N—((S)-1-(4-(methylsulfonyl)phenyl)ethyl)-2-((R)-3-(3-(trifluoromethyl)phenoxy)pyrrolidin-1-yl)propanamide;

2-Methyl-N-((1S)-1-(4-(S-methylsulfonimidoyl)phenyl)ethyl)-2-((R)-3-(3-(trifluoromethyl)phenoxy)pyrrolidin-1-yl)propanamide;

N—((S)-1-(4-(1,2,4-Oxadiazol-3-yl)phenyl)ethyl)-2-methyl-2-((R)-3-(3-(trifluoromethyl)phenoxy)pyrrolidin-1-yl)propanamide;

N—((S)-1-(4-(1,2,4-Oxadiazol-5-yl)phenyl)ethyl)-2-methyl-2-((R)-3-(3-(trifluoromethyl)phenoxy)pyrrolidin-1-yl)propanamide;

4-((1S)-1-(2-(3-Benzylpyrrolidin-1-yl)-2-methylpropanamido)ethyl)benzoic acid;

4-((S)-1-(2-((R)-3-((3-Chlorophenoxy)methyl)pyrrolidin-1-yl)-2-methylpropanamido)ethyl)benzoic acid;

4-[(1S)-1-[[2-[(3R)-3-(3-Chlorophenoxy)pyrrolidin-1-yl]-2-ethylbutane-carbonyl]amino]ethyl]benzoic acid;

and a pharmaceutically acceptable salt of any one of the above-mentioned compounds.

The present invention also relates to each of the intermediates described further below in the examples section of this specification, including any one of these intermediates in non-salt form or in the form of a salt (e.g., a pharmaceutically acceptable salt) of the respective compound. Such intermediates can be used, in particular, in the synthesis of the compounds of formula (I).

In a $1^{st}$ specific embodiment, the compound of formula (I) is a compound of the following formula

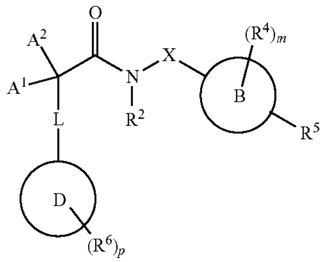

or a pharmaceutically acceptable salt thereof.

In this $1^{st}$ specific embodiment, $A^1$ and $A^2$ are each independently $C_{1-5}$ alkyl. More preferably, $A^1$ and $A^2$ are each independently methyl or ethyl. Even more preferably, $A^1$ and $A^2$ are each methyl.

In this 1st specific embodiment, ring B is a carbocyclic group or a heterocyclic group. Preferably, ring B is selected from arylene, heteroarylene (e.g., pyridinylene; including, in particular, pyridin-2,5-diyl or pyridin-3,6-diyl), cycloalkylene and heterocycloalkylene. It is furthermore preferred that ring B is monocyclic. More preferably, ring B is arylene or cycloalkylene. Even more preferably, ring B is phenylene or $C_{3-9}$ cycloalkylene. Even more preferably, ring B is phenylene (particularly phen-1,4-diyl) or cyclohexylene (particularly cyclohexan-1,4-diyl). Yet even more preferably, ring B is phenylene (e.g., phen-1,4-diyl, pheny-1,3-diyl, or phen-1,2-diyl). Still more preferably, ring B is phen-1,4-diyl.

In this 1st specific embodiment, ring D is phenyl.

In this 1st specific embodiment, L is $C_{2-4}$ alkylene (e.g., ethylene, n-propylene or n-butylene), wherein one —$CH_2$— unit comprised in said $C_{2-4}$ alkylene (preferably the —$CH_2$— unit which is attached to the carbon atom carrying $A^1$ and $A^2$) is replaced by carbocyclylene or heterocyclylene (preferably by heterocyclylene), wherein one further —$CH_2$— unit comprised in said $C_{2-4}$ alkylene (preferably the —$CH_2$— unit which is attached to ring D) is optionally replaced by a group selected from —O—, —CO—, —NH—, —N($C_{1-5}$ alkyl)-, —N[—CO—($C_{1-5}$ alkyl)]-, —N[—($C_{0-4}$ alkylene)-cycloalkyl]-, —N[—($C_{0-4}$ alkylene)-heterocycloalkyl]-, —S—, —SO—, and —$SO_2$— (preferably by a group selected from —O—, —NH—, and —N($C_{1-5}$ alkyl)-, more preferably by a group —O—), wherein said carbocyclylene or said heterocyclylene is preferably attached in a 1,3-orientation, and further wherein said carbocyclylene or said heterocyclylene is optionally substituted with one or more groups -$L^A$-$R^A$. Preferably, L is -heterocyclylene-$(CH_2)_{1-2}$—, wherein one —$CH_2$— unit comprised in said -heterocyclylene-$(CH_2)_{1-2}$— is optionally replaced by a group selected from —O—, —CO—, —NH—, —N($C_{1-5}$ alkyl)- and —N[—CO—($C_{1-5}$ alkyl)]- (particularly from —O—, —NH—, and —N($C_{1-5}$ alkyl)-), wherein the heterocyclylene in said -heterocyclylene-$(CH_2)_{1-2}$— is optionally substituted with one or more groups -$L^A$-$R^A$, and further wherein the heterocyclylene in said -heterocyclylene-$(CH_2)_{1-2}$— is preferably attached in a 1,3-orientation. More preferably, L is -heterocycloalkylene-$CH_2$—, wherein the —$CH_2$— unit in said -heterocycloalkylene-$CH_2$— is optionally replaced by a group selected from —O—, —CO—, —NH—, —N($C_{1-5}$ alkyl)- and —N[—CO—($C_{1-5}$ alkyl)]- (particularly a group selected from —O—, —NH—, and —N($C_{1-5}$ alkyl)-, more preferably a group —O—), and wherein the heterocycloalkylene in said -heterocycloalkylene-$CH_2$— is preferably attached in a 1,3-orientation; it is furthermore preferred that said -heterocycloalkylene-$CH_2$— is attached to ring D via the —$CH_2$— unit (which may be optionally replaced, as described above) in said -heterocycloalkylene-$CH_2$—. Even more preferably, L is -heterocycloalkylene-O— which is attached to ring D via the oxygen atom in said group -heterocycloalkylene-O—, and wherein the heterocycloalkylene in said -heterocycloalkylene-O— is attached in a 1,3-orientation; the heterocycloalkylene in said -heterocycloalkylene-O— is preferably a monocyclic 4- to 9-membered (more preferably a monocyclic 5-, 6- or 7-membered) heterocycloalkylene which is attached via a nitrogen ring atom to the carbon atom carrying $A^1$ and $A^2$ and is attached via a carbon ring atom to the oxygen (—O—) in said -heterocycloalkylene-O—, wherein said nitrogen ring atom and said carbon ring atom are separated by one carbon ring atom. Thus, L may be, for example, a group

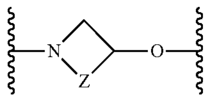

which is attached via the oxygen atom (—O—) to ring D, wherein Z refers to 1, 2, 3, 4 or 5 ring atoms connected via single bonds, wherein 1 or 2 of said ring atoms (Z) are each independently selected from nitrogen, oxygen, sulfur and carbon, and the remaining ring atoms (Z), if any, are all carbon atoms. In particular, L may be a group

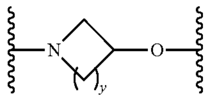

which is attached via the oxygen atom (—O— to ring D, wherein y is 1, 2, 3, 4 or 5, and wherein y is preferably 2, 3 or 4 (so that the heterocycloalkylene ring preferably has a total of 5, 6 or 7 ring members). Particularly preferred examples of L include

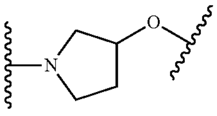

or

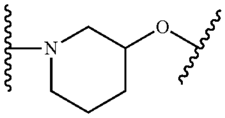

, wherein each of these groups is attached to ring D via the terminal oxygen atom contained therein. If L is a group

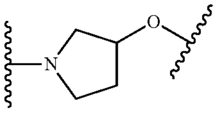

or

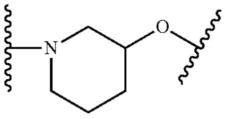

, then it is furthermore preferred that the corresponding group L is present in the following stereochemical configuration:

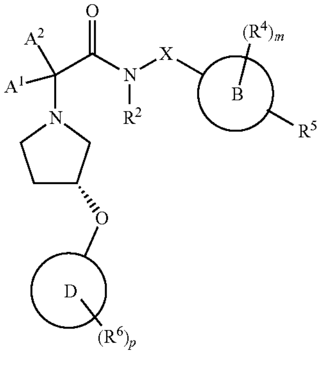

or

-continued

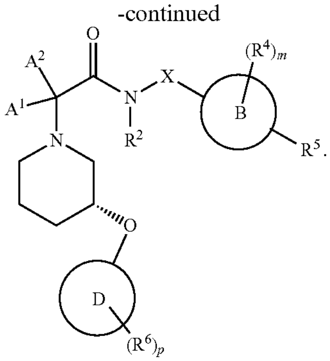

In this $1^{st}$ specific embodiment, m is 0, 1, 2, 3 or 4. Preferably, m is 0, 1 or 2. More preferably, m is 0 or 1. Even more preferably, m is 0.

In this $1^{st}$ specific embodiment, p is 0, 1, 2, 3 or 4. Preferably, p is 0, 1 or 2. More preferably, p is 1.

In this $1^{51}$ specific embodiment, $R^2$ is selected from hydrogen, $C_{1-5}$ alkyl, and —CO($C_{1-5}$ alkyl). Preferably, $R^2$ is hydrogen or $C_{1-5}$ alkyl. More preferably, $R^2$ is hydrogen, methyl or ethyl. Even more preferably, $R^2$ is hydrogen.

In this $1^{st}$ specific embodiment, X is C($R^{3a}$)($R^{3b}$). Accordingly, X is a carbon atom carrying the substituents $R^{3b}$ and $R^{3b}$.

In this $1^{st}$ specific embodiment, $R^{3a}$ and $R^{3b}$ are each independently selected from hydrogen, $C_{1-6}$ alkyl, and $C_{2-5}$ alkenyl. Preferably, $R^{3a}$ and $R^{3b}$ are each independently selected from hydrogen and $C_{1-6}$ alkyl (e.g., methyl or ethyl). More preferably, $R^{3a}$ is $C_{1-5}$ alkyl (e.g., methyl or ethyl), and $R^{3b}$ is hydrogen or $C_{1-5}$ alkyl (e.g., methyl or ethyl). Even more preferably, $R^{3a}$ is methyl and $R^{3b}$ is hydrogen.

In accordance with the above definitions of X, $R^{33}$ and $R^{3b}$, it is particularly preferred that the moiety

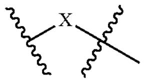

is

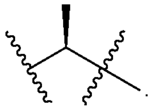

In this $1^{st}$ specific embodiment, each $R^4$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{0-3}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-6}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^A$-$R^A$. Preferably, each $R^4$ is independently selected from $C_{1-6}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-6}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-6}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-6}$ alkyl), —($C_{0-3}$ alkylene)-cycloalkyl, —($C_{0-3}$ alkylene)-heterocycloalkyl, and -$L^A$-$R^A$. More preferably, each $R^4$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN. Even more preferably, each $R^4$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-4}$ alkyl) (e.g., —N$(CH_3)_2$), halogen (e.g., —F, —Cl, —Br, or —I), —$CF_3$, and —CN.

In this $1^{st}$ specific embodiment, $R^5$ is selected from —COOH, —CO—$NH_2$, —CO—NH($C_{1-5}$ alkyl), —CO—N($C_{1-5}$ alkyl)($C_{1-5}$ alkyl), —$SO_2$—OH, —$SO_2$—O—($C_{1-5}$ alkyl), —$SO_2$—$NH_2$, —SO—NH($C_{1-5}$ alkyl), —$SO_2$—N($C_{1-5}$ alkyl)($C_{1-5}$ alkyl), —$SO_2$—($C_{1-5}$ alkyl), —S(═O)(═NH)—($C_{1-5}$ alkyl), halogen (e.g., —F or —Cl), $C_{1-5}$ haloalkyl (e.g., —$CF_3$), —CN, hydrogen, $C_{1-4}$ alkyl, —OH, —O($C_{1-4}$ alkyl), carbocyclyl (e.g., aryl or cycloalkyl), and heterocyclyl (e.g., heteroaryl or heterocycloalkyl), wherein said carbocyclyl or said heterocyclyl is optionally substituted with one or more (e.g., one, two or three) groups -$L^A$-$R^A$.

Preferably, $R^5$ is selected from —COOH, —CO—$NH_2$, —CO—NH($C_{1-5}$ alkyl), —CO—N($C_{1-5}$ alkyl)($C_{1-5}$ alkyl), —$SO_2$—OH, —$SO_2$—O—($C_{1-3}$ alkyl), —$SO_2$—$NH_2$, —$SO_2$—NH($C_{1-5}$ alkyl), —$SO_2$—N($C_{1-5}$ alkyl)($C_{1-5}$ alkyl), —$SO_2$—($C_{1-5}$ alkyl), —S(═O)(═NH)—($C_{1-5}$ alkyl), —CN, —O($C_{1-4}$ alkyl) (e.g., —$OCH_3$), and heteroaryl (e.g., tetrazolyl). More preferably, $R^5$ is selected from —COOH, —CO—$NH_2$, —CO—NH($C_{1-5}$ alkyl) (e.g., —CO—NH—$CH_3$), —CO—N($C_{1-5}$ alkyl)($C_{1-5}$ alkyl) (e.g., —CO—N($CH_3$)—$CH_3$), —$SO_2$—($C_{1-5}$ alkyl) (e.g., —$SO_2$—$CH_3$), —S(═O)(═NH)—($C_{1-5}$ alkyl) (e.g., —S(═O)(═NH)—$CH_3$), and tetrazolyl (e.g., 1H-tetrazol-5-yl or 2H-tetrazol-5-yl). More preferably, $R^5$ is —COOH, —CO—$NH_2$, or tetrazolyl (particularly 1H-tetrazol-5-yl or 2H-tetrazol-5-yl).

Even more preferably, $R^5$ is —COOH or tetrazolyl (particularly 1H-tetrazol-5-yl or 2H-tetrazol-5-yl). Yet even more preferably, $R^5$ is —COOH.

In this $1^{st}$ specific embodiment, each $R^6$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-6}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-6}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-6}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^1$-$R^{61}$. Preferably, each $R^6$ is independently selected from $C_{1-5}$ alkyl, $C_{2-5}$ alkenyl, $C_{2-5}$ alkynyl, —OH, —O($C_{1-6}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl, —($C_{0-3}$ alkylene)-heterocycloalkyl, and -$L^1$-$R^{61}$. More preferably, each $R^6$ is independently selected from $C_{1-5}$ alkyl, —OH, —O($C_{1-6}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), —O—($C_{1-5}$ haloalkyl) (e.g., —$OCF_3$), —CN, and -$L^1$-$R^{61}$. Even more preferably, each $R^6$ is independently selected from $C_{1-4}$ alkyl (e.g., methyl or ethyl), —OH, —O($C_{1-5}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-5}$ alkyl) (e.g., —N($CH_3$)$_2$), halogen (e.g., —F, —Cl, —Br, or —I), —$CF_3$, —$OCF_3$, —CN, and -$L^1$-$R^{61}$. Yet even more preferably, each $R^6$ is independently selected from —$CH_3$, —OH, —$OCH_3$, halogen (e.g., —F, —Cl, —Br, or —I), —$CF_3$, —$OCF_3$, —CN, and -$L^1$-$R^{61}$. Yet even more preferably, each $R^6$ is independently selected from —$CH_3$, —$OCH_3$, —F, —Cl, —$CF_3$, and —$OCF_3$. Still more preferably, each $R^6$ is independently selected from —$CH_3$, —$OCH_3$, —F, —Cl, and —$CF_3$. It is particularly preferred that each $R^6$ is independently —Cl or —$CF_3$.

In this $1^{st}$ specific embodiment, if p is 1, then it is preferred that $R^6$ is attached to ring D in a 1,2-orientation, a 1,3-orientation or a 1,4-orientation with respect to the attachment point of group L to ring D, more preferably $R^6$ is attached to ring D in a 1,3-orientation with respect to the attachment point of group L to ring D. Moreover, if p is greater than 1 (e.g., 2, 3 or 4), then it is preferred that at least one of the groups $R^6$ is attached to ring D in a 1,3-orientation with respect to the attachment point of group L to ring D.

In this $1^{st}$ specific embodiment, in accordance with the above definitions of p and $R^6$, it is particularly preferred that p is 1, the group $R^6$ is attached to ring D in a 1,3-orientation with respect to the attachment point of group L to ring D, and said group $R^6$ is selected from —$CH_3$, —OH, —$OCH_3$, halogen (e.g., —F, —Cl, —Br, or —I), —$CF_3$, —$OCF_3$, —CN, and -$L^1$-$R^{61}$, more preferably said group $R^6$ is selected from —$CH_3$, —$OCH_3$, —F, —C, —$CF_3$, and —$OCF_3$, even more preferably said group $R^6$ is selected from —$CH_3$, —$OCH_3$, —F, —C, and —$CF_3$, and still more preferably said group $R^6$ is selected from —C and —$CF_3$.

In this $1^{st}$ specific embodiment, $L^1$ is $C_{1-6}$ alkylene or a covalent bond, wherein one or more (e.g., one, two or three) —$CH_2$— units comprised in said $C_{1-6}$ alkylene are each optionally replaced by a group independently selected from —O—, —CO—, —NH—, —N($C_{1-5}$ alkyl)-, —N[—CO—($C_{1-5}$ alkyl)]-, —S—, —SO—, —$SO_2$—, —CH($C_{1-5}$ alkyl)- and —C($C_{1-5}$ alkyl)($C_{1-5}$ alkyl)-. Preferably, $L^1$ is $C_{1-4}$ alkylene, wherein one or more (e.g., one or two) —$CH_2$— units comprised in said $C_{1-4}$ alkylene are each optionally replaced by a group independently selected from —O—, —CO—, —NH—, —N($C_{1-5}$ alkyl)-, —N[—CO—($C_{1-5}$ alkyl)]-, —S—, —SO—, —$SO_2$—, —CH($C_{1-5}$ alkyl)- and —C($C_{1-5}$ alkyl)($C_{1-5}$ alkyl)-. Said alkylene is preferably $C_{2-4}$ alkylene (e.g., ethylene, propylene or butylene), more preferably —($CH_2$)$_2$—, —($CH_2$)$_3$— or —($CH_2$)$_4$—, and is even more preferably —($CH_2$)$_2$—. Moreover, it is preferred that said one or more —$CH_2$— units are each optionally replaced by a group independently selected from —O—, —S—, —NH—, and —N($C_{1-5}$ alkyl)-, particularly by —O—. It is furthermore preferred that $L^1$ is attached to ring D via —O— (i.e., that $L^1$ contains a terminal —$CH_2$— unit which is replaced by —O—, and that $L^1$ is connected to ring D via said —O—). More preferably, $L^1$ is —($CH_2$)$_{2-4}$—, wherein one —$CH_2$— unit comprised in said —($CH_2$)$_{2-4}$— is optionally replaced by a group selected from —O—, —S—, —NH—, and —N($C_{1-5}$ alkyl)-, particularly by a group —O—. Even more preferably, $L^1$ is —O—($CH_2$)$_{1-3}$—, wherein $L^1$ is attached to ring D via the oxygen atom (—O—) comprised in said —O—($CH_2$)$_{1-3}$—, Yet even more preferably, $L^1$ is —O—$CH_2$— or —O—$CH_2$—$CH_2$—, wherein $L^1$ is attached to ring D via the oxygen atom in said —O—$CH_2$— or said —O—$CH_2$—$CH_2$—. Still more preferably, $L^1$ is —O—$CH_2$— which is attached to ring D via the oxygen atom (—O—) comprised in said —O—$CH_2$—.

In this $1^{st}$ specific embodiment, $R^{61}$ is carbocyclyl or heterocyclyl, wherein said carbocyclyl or said heterocyclyl is optionally substituted with one or more (e.g., one, two or three) groups $R^{62}$. Preferably, $R^{61}$ is selected from cycloalkyl, aryl, heterocycloalkyl (e.g., tetrahydrofuranyl or tetrahydropyranyl) and heteroaryl (e.g., pyridinyl), wherein said cycloalkyl, said aryl, said heterocycloalkyl and said heteroaryl are each optionally substituted with one or more (e.g., one, two or three) groups $R^{62}$. More preferably, $R^{61}$ is cycloalkyl or aryl, wherein said cycloalkyl or said aryl is optionally substituted with one or more $R^{62}$. Even more preferably, $R^{61}$ is selected from $C_{3-9}$ cycloalkyl (e.g., cyclopropyl, cyclobutyl, cyclopentyl, cyclohexyl, cycloheptyl, cyclooctyl, or cyclononyl) or phenyl, wherein said $C_{3-9}$ cycloalkyl or said phenyl is optionally substituted with one or more $R^{62}$. Yet even more preferably, $R^{61}$ is $C_{5-9}$ cycloalkyl (e.g., cyclopentyl, cyclohexyl, cycloheptyl, cyclooctyl, or cyclononyl) which is optionally substituted with one or more $R^{62}$.

Yet even more preferably, $R^{61}$ is cyclohexyl or cycloheptyl, wherein said cyclohexyl or said cycloheptyl is optionally substituted with one or more $R^{62}$. Still more preferably, $R^{61}$ is cyclohexyl which is optionally substituted with one or more $R^{62}$. It is furthermore preferred that the aforementioned cyclic groups ($R^{61}$) are not substituted with any groups $R^{62}$.

In this $1^{st}$ specific embodiment, each $R^{62}$ is independently selected from $C_{1-6}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{3-7}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{1-5}$ alkylene)-N($C_{1-5}$ alkyl)-COO($C_{1-5}$ alkyl), —($C_{0-3}$ alkylene)-O—CO—NH($C_{1-5}$ alkyl), —($C_{1-5}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, and —($C_{0-3}$ alkylene)-heterocycloalkyl. Preferably, each $R^{62}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, COs haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{0-3}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl, and —($C_{0-3}$ alkylene)-heterocycloalkyl. More preferably, each $R^{62}$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-6}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN. Even more preferably, each $R^{62}$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-4}$ alkyl) (e.g., —$N(CH_3)_2$), halogen (e.g., —F, —Cl, —Br, or —I), —$CF_3$, and —CN.

In this $1^{st}$ specific embodiment, each $L^A$ is independently selected from a covalent bond, $C_{1-5}$ alkylene, $C_{2-5}$ alkenylene, and $C_{2-5}$ alkynylene, wherein said alkylene, said alkenylene and said alkynylene are each optionally substituted with one or more (e.g., one, two, or three) groups independently selected from halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl), and further wherein one or more (e.g., one, two, or three) —$CH_2$— units comprised in said alkylene, said alkenylene or said alkynylene are each optionally replaced by a group independently selected from —O—, —NH—, —N($C_{1-5}$ alkyl)-, —CO—, —S—, —SO—, and —$SO_2$—.

In this $1^{st}$ specific embodiment, each $R^A$ is independently selected from —OH, —O($C_{1-5}$ alkyl), —O($C_{0-3}$ alkylene)-OH, —O($C_{0-3}$ alkylene)-O($C_{1-5}$ alkyl), —SH, —S($C_{1-6}$ alkyl), —S($C_{0-3}$ alkylene)-SH, —S($C_{1-5}$ alkylene)-S($C_{1-5}$alkyl), —$NH_2$, —NH($C_{1-5}$ alkyl), —N($C_{1-5}$ alkyl)($C_{1-5}$ alkyl), halogen, $C_{1-5}$ haloalkyl, —O($C_{1-5}$ haloalkyl), —CN, —CHO, —CO($C_{1-5}$ alkyl), —COOH, —COO($C_{1-5}$ alkyl), —O—CO($C_{0-3}$ alkyl), —CO—$NH_2$, —CO—NH($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —$SO_2$—($C_{1-5}$ alkyl), —SO—($C_{1-5}$ alkyl), hydrogen, aryl, heteroaryl, cycloalkyl, and heterocycloalkyl, wherein said aryl, said heteroaryl, said cycloalkyl, and said heterocycloalkyl are each optionally substituted with one or more (e.g., one, two or three) groups independently selected from $C_{1-6}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl).

In a $2^{nd}$ specific embodiment, the compound of formula (I) or the pharmaceutically acceptable salt thereof is as defined in the $1^{st}$ specific embodiment, except that $R^{3a}$ and $R^{3b}$ are mutually linked to form, together with the carbon atom that they are attached to, a cycloalkyl or a heterocycloalkyl, wherein said cycloalkyl or said heterocycloalkyl is optionally substituted with one or more (e.g., one, two or three) groups $R^{31}$.

In this $2^{nd}$ specific embodiment, it is preferred that $R^{3a}$ and $R^{3b}$ are mutually linked to form, together with the carbon atom that they are attached to, a $C_{3-5}$ cycloalkyl or a 3- to 5-membered heterocycloalkyl, wherein said cycloalkyl or said heterocycloalkyl is optionally substituted with one or more (e.g., one or two) groups $R^{31}$. More preferably, $R^{3a}$ and $R^{3b}$ are mutually linked to form, together with the carbon atom that they are attached to, a cyclopropyl.

In this $2^{nd}$ specific embodiment, it is thus particularly preferred that the moiety

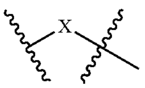

is.

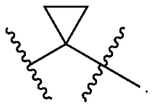 [SMILES: *C1(*)CC1]

In this $2^{nd}$ specific embodiment, each $R^{31}$ is independently selected from $C_{1-5}$ alkyl, $C_{2-5}$ alkenyl, $C_{2-5}$ alkynyl, —OH, —O($C_{1-6}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{0-3}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), and —$SO_2$—($C_{1-5}$ alkyl). Preferably, each $R^{31}$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN.

In a $3^{rd}$ specific embodiment, the compound of formula (I) or the pharmaceutically acceptable salt thereof is as defined in the $1^{st}$ specific embodiment, except that ring D is monocyclic heteroaryl or monocyclic heterocycloalkyl.

In this $3^{rd}$ specific embodiment, it is preferred that ring D is selected from pyridinyl (e.g., pyridin-2-yl, pyridin-3-yl, or pyridin-4-yl), azetidinyl (e.g., azetidin-1-yl or azetidin-2-yl), pyrrolidinyl (e.g., pyrrolidin-1-yl, pyrrolidin-2-yl, or pyrrolidin-3-yl), and piperidinyl (e.g., piperidin-1-yl, piperidin-2-yl, piperidin-3-yl, or piperidin-4-yl). More preferably, ring D is pyridinyl.

In a $4^{th}$ specific embodiment, the compound of formula (I) or the pharmaceutically acceptable salt thereof is as defined in the $2^{nd}$ specific embodiment, except that ring D is monocyclic heteroaryl or monocyclic heterocycloalkyl.

In this $4^{th}$ specific embodiment, it is preferred that ring D is selected from pyridinyl (e.g., pyridin-2-yl, pyridin-3-yl, or pyridin-4-yl), azetidinyl (e.g., azetidin-1-yl or azetidin-2-yl), pyrrolidinyl (e.g., pyrrolidin-1-yl, pyrrolidin-2-yl, or pyrrolidin-3-yl), and piperidinyl (e.g., piperidin-1-yl, piperidin-2-yl, piperidin-3-yl, or piperidin-4-yl). More preferably, ring D is pyridinyl.

In a $5^{th}$ specific embodiment, the compound of formula (I) is a compound of the following formula

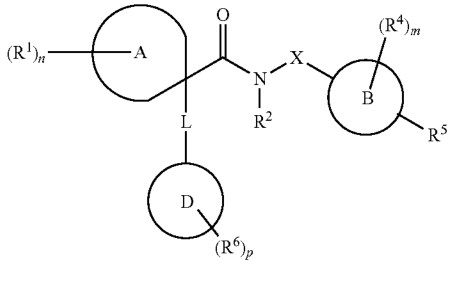

or a pharmaceutically acceptable salt thereof.

In this $5^{th}$ specific embodiment, ring A is a carbocyclic group or a heterocyclic group. As also depicted in formula above, both the moiety —CO—N($R^2$)—X—B[(—$R^4$)$_m$]—$R^5$ and the moiety -L-D[(—$R^6$)$_p$] are attached to the same ring carbon atom of ring A which is thus a divalent carbocyclic or heterocyclic group. Ring A is preferably saturated. Accordingly, it is preferred that ring A is cycloalkylene or heterocycloalkylene; said cycloalkylene or said heterocycloalkylene is preferably monocyclic or bicyclic. More preferably, A is monocyclic cycloalkylene or monocyclic heterocycloalkylene. Even more preferably, A is a monocyclic $C_{3-9}$ cycloalkylene or a monocyclic 4 to 9-membered heterocycloalkylene. Preferred examples of ring A include, in particular, cyclopropylene, cyclobutylene, cyclopentylene, cyclohexylene, tetrahydrofuranylene (e.g., tetrahydrofuran-2,2-diyl or tetrahydrofuran-3,3-diyl), tetrahydrothiophenylene (e.g., tetrahydrothiophen-2,2-diyl or tetrahydrothiophen-3,3-diyl), tetrahydropyranylene (e.g., tetrahydropyran-2,2-diyl, tetrahydropyran-3,3-diyl, or tetrahydropyran-4,4-diyl), or thianylene (e.g., thian-2,2-diyl, thian-3,3-diyl, or thian-4,4-diyl). It is particularly preferred that ring A is tetrahydrofuranylene (preferably tetrahydrofuran-3,3-diyl), tetrahydropyranylene (preferably tetrahydropyran-4,4-diyl), cyclopropylene (i.e., cyclopropan-1,1-diyl), cyclobutylene (i.e., cyclobutan-1,1-diyl), cyclopentylene (i.e., cyclopentan-1,1-diyl), or cyclohexylene (i.e., cyclohexan-1,1-diyl).

In this $5^{th}$ specific embodiment, ring B is a carbocyclic group or a heterocyclic group. Preferably, ring B is selected from arylene, heteroarylene (e.g., pyridinylene; including, in particular, pyridin-2,5-diyl or pyridin-3,6-diyl), cycloalkylene and heterocycloalkylene. It is furthermore preferred that ring B is monocyclic. More preferably, ring B is arylene or cycloalkylene. Even more preferably, ring B is phenylene or $C_{3-9}$ cycloalkylene. Even more preferably, ring B is phenylene (particularly phen-1,4-diyl) or cyclohexylene (particularly cyclohexan-1,4-diyl). Yet even more preferably, ring B is phenylene (e.g., phen-1,4-diyl, pheny-1,3-diyl, or phen-1,2-diyl). Still more preferably, ring B is phen-1,4-diyl.

In this $5^{th}$ specific embodiment, ring D is phenyl.

In this $5^{th}$ specific embodiment, L is $C_{2-4}$ alkylene (e.g., ethylene, n-propylene or n-butylene), wherein one —$CH_2$— unit comprised in said $C_{2-4}$ alkylene (preferably the —$CH_2$— unit which is attached to ring A) is replaced by carbocyclylene or heterocyclylene (preferably by heterocyclylene), wherein one further —$CH_2$— unit comprised in said $C_{2-4}$ alkylene (preferably the —$CH_2$— unit which is attached to ring D) is optionally replaced by a group selected from —O—, —CO—, —NH—, —N($C_{1-5}$ alkyl)-, —N[—CO—($C_{1-5}$ alkyl)]-, —N[—($C_{0-4}$ alkylene)-cycloalkyl]-, —N[—($C_{0-4}$ alkylene)-heterocycloalkyl]-, —S—, —SO—, and —$SO_2$— (preferably by a group selected from —O—, —NH—, and —N($C_{1-5}$ alkyl)-, more preferably by a group —O—), wherein said carbocyclylene or said heterocyclylene is preferably attached in a 1,3-orientation, and further wherein said carbocyclylene or said heterocyclylene is optionally substituted with one or more groups -$L^A$-$R^A$. Preferably, L is -heterocyclylene-($CH_2$)$_{1-2}$—, wherein one —$CH_2$— unit comprised in said -heterocyclylene-($CH_2$)$_{1-2}$— is optionally replaced by a group selected from —O—, —CO—, —NH—, —N($C_{1-5}$ alkyl)- and —N[—CO—($C_{1-5}$ alkyl)]- (particularly from —O—, —NH—, and —N($C_{1-5}$ alkyl)-), wherein the heterocyclylene in said -heterocyclylene-($CH_2$)$_{1-2}$— is optionally substituted with one or more groups -$L^A$-$R^A$, and further wherein the heterocyclylene in said -heterocyclylene-($CH_2$)$_{1-2}$— is preferably attached in a 1,3-orientation. More preferably, L is -heterocycloalkylene-$CH_2$—, wherein the —$CH_2$— unit in said -heterocycloalkylene-$CH_2$— is optionally replaced by a group selected from —O—, —CO—, —NH—, —N($C_{1-5}$ alkyl)- and —N[—CO—($C_{1-5}$ alkyl)]- (particularly a group selected from —O—, —NH—, and —N($C_{1-5}$ alkyl)-, more preferably a group —O—), and wherein the heterocycloalkylene in said -heterocycloalkylene-$CH_2$— is preferably attached in a 1,3-orientation; it is furthermore preferred that said -heterocycloalkylene-$CH_2$— is attached to ring D via the —$CH_2$— unit (which may be optionally replaced, as described above) in said -heterocycloalkylene-$CH_2$—.

Even more preferably, L is -heterocycloalkylene-O— which is attached to ring D via the oxygen atom in said group -heterocycloalkylene-O—, and wherein the heterocycloalkylene in said -heterocycloalkylene-O— is attached in a 1,3-orientation; the heterocycloalkylene in said -heterocycloalkylene-O— is preferably a monocyclic 4- to 9-membered (more preferably a monocyclic 5-, 6- or 7-membered) heterocycloalkylene which is attached via a nitrogen ring atom to ring A and is attached via a carbon ring atom to the oxygen (—O—) in said -heterocycloalkylene-O—, wherein said nitrogen ring atom and said carbon ring atom are separated by one carbon ring atom. Thus, L may be, for example, a group

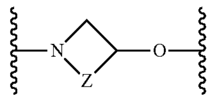

which is attached via the oxygen atom (—O—) to ring D, wherein Z refers to 1, 2, 3, 4 or 5 ring atoms connected via single bonds, wherein 1 or 2 of said ring atoms (Z) are each independently selected from nitrogen, oxygen, sulfur and carbon, and the remaining ring atoms (Z), if any, are all carbon atoms. In particular, L may be a group

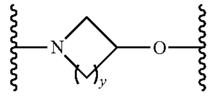

which is attached via the oxygen atom (—O—) to ring D, wherein y is 1, 2, 3, 4 or 5, and wherein y is preferably 2, 3 or 4 (so that the heterocycloalkylene ring preferably has a total of 5, 6 or 7 ring members). Particularly preferred examples of L include

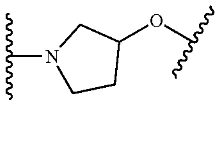

or

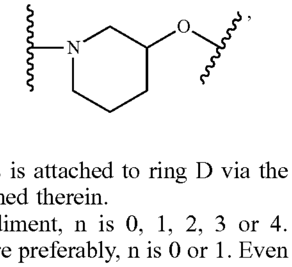

, wherein each of these groups is attached to ring D via the terminal oxygen atom contained therein.

In this $5^{th}$ specific embodiment, n is 0, 1, 2, 3 or 4. Preferably, n is 0, 1 or 2. More preferably, n is 0 or 1. Even more preferably, n is 0.

In this $5^{th}$ specific embodiment, m is 0, 1, 2, 3 or 4. Preferably, m is 0, 1 or 2. More preferably, m is 0 or 1. Even more preferably, m is 0.

In this $5^{th}$ specific embodiment, p is 0, 1, 2, 3 or 4. Preferably, p is 0, 1 or 2. More preferably, p is 1.

In this $5^{th}$ specific embodiment, each $R^1$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{1-5}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{0-3}$ alkyl)($C_{1-5}$ alkyl), —($C_{0-3}$ alkylene)-NH—CO—($C_{1-5}$ alkyl), —($C_{0-3}$ alkylene)-N($C_{1-5}$alkyl)-CO—($C_{0-3}$ alkyl), —($C_{0-3}$ alkylene)-NH—COO($C_{1-5}$ alkyl), —($C_{0-3}$ alkylene)-N($C_{1-5}$ alkyl)-COO($C_{0-3}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^A$-$R^A$. Preferably, each $R^1$ is independently selected from $C_{1-6}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-6}$ alkyl), —COOH, —CO—O—($C_{1-5}$ alkyl), —O—CO—($C_{1-5}$ alkyl), —CO—$NH_2$—COCO—NH($C_{1-5}$ alkyl)C—CO—($C_{1-5}$ alkyl)C, —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-6}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl (e.g., —$CH_2$-cyclopropyl), —($C_{0-3}$ alkylene)-heterocycloalkyl, and -$L^A$-$R^A$. More preferably, each $R^1$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN. Even more preferably, each $R^1$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-4}$ alkyl) (e.g., —N$(CH_3)_2$), halogen (e.g., —F, —Cl, —Br, or —I), —$CF_3$, and —CN. A preferred example of ring A substituted with two groups $R^1$ is 4,4-difluoro-cyclohexan-1,1-diyl, i.e. a cyclohexylene (as ring A) which is substituted in para-position with two fluoro atoms (as $R^1$).

In this $5^{th}$ specific embodiment, $R^2$ is selected from hydrogen, $C_{1-5}$ alkyl, and —CO($C_{1-5}$ alkyl). Preferably, $R^2$ is hydrogen or $C_{1-5}$ alkyl. More preferably, $R^2$ is hydrogen, methyl or ethyl. Even more preferably, $R^2$ is hydrogen.

In this $5^{th}$ specific embodiment, X is $C(R^{3a})(R^{3b})$. Accordingly, X is a carbon atom carrying the substituents $R^{3a}$ and $R^{3b}$.

In this $5^{th}$ specific embodiment, $R^{3a}$ and $R^{3b}$ are each independently selected from hydrogen, $C_{1-6}$ alkyl, and $C_{2-5}$ alkenyl. Preferably, $R^{3a}$ and $R^{3b}$ are each independently selected from hydrogen and $C_{1-5}$ alkyl (e.g., methyl or ethyl).

More preferably, $R^{3a}$ is $C_{1-5}$ alkyl (e.g., methyl or ethyl), and $R^{3b}$ is hydrogen or $C_{1-5}$ alkyl (e.g., methyl or ethyl). Even more preferably, $R^{3a}$ is methyl and $R^{3b}$ is hydrogen.

In accordance with the above definitions of X, $R^{3a}$ and $R^{3b}$, it is particularly preferred that the moiety

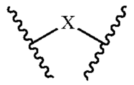

is

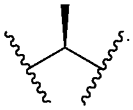.

In this $5^{th}$ specific embodiment, each $R^4$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{0-3}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-6}$ alkyl)-COO($C_{1-5}$ alkyl), —($C_{0-3}$ alkylene)-O—CO—NH($C_{1-6}$ alkyl), —($C_{0-3}$ alkylene)-O—CO—N($C_{1-6}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^A$-$R^A$. Preferably, each $R^4$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl, —($C_{0-3}$ alkylene)-heterocycloalkyl, and -$L^A$-$R^A$. More preferably, each $R^4$ is independently selected from $C_{1-5}$ alkyl, —OH, —O($C_{1-6}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN. Even more preferably, each $R^4$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-4}$ alkyl) (e.g., —N$(CH_3)_2$), halogen (e.g., —F, —Cl, —Br, or —I), —$CF_3$, and —CN.

In this $5^{th}$ specific embodiment, $R^5$ is selected from —COOH, —CO—$NH_2$, —CO—NH($C_{1-5}$ alkyl), —CO—N($C_{1-6}$ alkyl)($C_{1-5}$ alkyl), —$SO_2$—OH, —$SO_2$—O—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —$SO_2$—($C_{1-5}$ alkyl), —S(═O)(═NH)—($C_{1-5}$ alkyl), halogen (e.g., —F or —Cl), $C_{1-5}$ haloalkyl (e.g., —$CF_3$), —CN, hydrogen, $C_{1-4}$ alkyl, —OH, —O($C_{1-4}$ alkyl), carbocyclyl (e.g., aryl or cycloalkyl), and heterocyclyl (e.g., heteroaryl or heterocycloalkyl), wherein said carbocyclyl or said heterocyclyl is optionally substituted with one or more (e.g., one, two or three) groups -$L^A$-$R^A$.

Preferably, $R^5$ is selected from —COOH, —CO—$NH_2$, —CO—NH($C_{1-5}$ alkyl), —CO—N($C_{1-5}$ alkyl)($C_{1-5}$ alkyl), —$SO_2$—OH, —$SO_2$—O—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —$SO_2$—($C_{1-5}$ alkyl), —S(═O)(═NH)—($C_{1-5}$ alkyl), —CN, —O($C_{1-4}$ alkyl) (e.g., —$OCH_3$), and heteroaryl (e.g., tetrazolyl). More preferably, $R^5$ is selected from —COOH, —CO—$NH_2$, —CO—NH($C_{1-5}$ alkyl) (e.g., —CO—NH—$CH_3$), —CO—N($C_{1-5}$ alkyl)($C_{1-5}$ alkyl) (e.g., —CO—N($CH_3$)—$CH_3$), —$SO_2$—($C_{1-5}$ alkyl) (e.g., —$SO_2$—$CH_3$), —S(═O)(═NH)—($C_{1-5}$ alkyl) (e.g., —S(═O)(═NH)—$CH_3$), and tetrazolyl (e.g., 1H-tetrazol-5-yl or 2H-tetrazol-5-yl). More preferably, $R^5$ is —COOH, —CO—$NH_2$, or tetrazolyl (particularly 1H-tetrazol-5-yl or 2H-tetrazol-5-yl). Even more preferably, $R^5$ is —COOH or tetrazolyl (particularly 1H-tetrazol-5-yl or 2H-tetrazol-5-yl).

Yet even more preferably, $R^5$ is —COOH.

In this $5^{th}$ specific embodiment, each $R^6$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O(Cos alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^1$-$R^{61}$. Preferably, each $R^6$ is independently selected from $C_{1-6}$ alkyl, $C_{2-5}$ alkenyl, $C_{2-5}$ alkynyl, —OH, —O($C_{1-6}$ alkyl), —O($C_{1-5}$ alkylene)-OH, —O($C_{1-6}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO ($C_{1-5}$ alkyl), —O—CO—NH($C_{1-5}$ alkyl), —O—CO—N ($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl, —($C_{0-3}$ alkylene)-heterocycloalkyl, and -$L^1$-$R^{61}$. More preferably, each $R^6$ is independently selected from $C_{1-5}$ alkyl, —OH, —O($C_{1-6}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), —O—($C_{1-5}$ haloalkyl) (e.g., —$OCF_3$), —CN, and -$L^1$-$R^{61}$. Even more preferably, each $R^6$ is independently selected from $C_{1-4}$ alkyl (e.g., methyl or ethyl), —OH, —O($C_{1-5}$ alkyl) (e.g., —$OCH_3$ or —$OCH_2CH_3$), —$NH_2$, —NH($C_{1-5}$ alkyl) (e.g., —$NHCH_3$), —N($C_{1-5}$ alkyl)($C_{1-5}$ alkyl) (e.g., —N($CH_3$)$_2$), halogen (e.g., —F, —Cl, —Br, or —I), —$CF_3$, —$OCF_3$, —CN, and -$L^1$-$R^{61}$. Yet even more preferably, each $R^6$ is independently selected from —$CH_3$, —OH, —$OCH_3$, halogen (e.g., —F, —Cl, —Br, or —I), —$CF_3$, —$OCF_3$, —CN, and -$L^1$-$R^{61}$. Yet even more preferably, each $R^6$ is independently selected from —$CH_3$, —$OCH_3$, —F, —Cl, —$CF_3$, and —$OCF_3$. Still more preferably, each $R^6$ is independently selected from —$CH_3$, —$OCH_3$, —F, —Cl, and —$CF_3$. It is particularly preferred that each $R^6$ is independently —Cl or —$CF_3$.

In this $5^{th}$ specific embodiment, if p is 1, then it is preferred that $R^6$ is attached to ring D in a 1,2-orientation, a 1,3-orientation or a 1,4-orientation with respect to the attachment point of group L to ring D, more preferably $R^6$ is attached to ring D in a 1,3-orientation with respect to the attachment point of group L to ring D. Moreover, if p is greater than 1 (e.g., 2, 3 or 4), then it is preferred that at least one of the groups $R^6$ is attached to ring D in a 1,3-orientation with respect to the attachment point of group L to ring D.

In this $5^{th}$ specific embodiment, in accordance with the above definitions of p and $R^6$, it is particularly preferred that p is 1, the group $R^6$ is attached to ring D in a 1,3-orientation with respect to the attachment point of group L to ring D, and said group $R^6$ is selected from —$CH_3$, —OH, —$OCH_3$, halogen (e.g., —F, —Cl, —Br, or —I), —$CF_3$, —$OCF_3$, —CN, and -$L^1$-$R^{61}$, more preferably said group $R^6$ is selected from —$CH_3$, —$OCH_3$, —F, —Cl, —$CF_3$, and —$OCF_3$, even more preferably said group $R^6$ is selected from —$CH_3$, —$OCH_3$, —F, —Cl, and —$CF_3$, and still more preferably said group $R^6$ is selected from —Cl and —$CF_3$.

In this $5^{th}$ specific embodiment, $L^1$ is $C_{1-6}$ alkylene or a covalent bond, wherein one or more (e.g., one, two or three) —$CH_2$— units comprised in said $C_{1-6}$ alkylene are each optionally replaced by a group independently selected from —O—, —CO—, —NH—, —N($C_{1-5}$ alkyl)-, —N[—CO—($C_{0-3}$ alkyl)]-, —S—, —SO—, —$SO_2$—, —CH($C_{1-5}$ alkyl)- and —C($C_{0-3}$ alkyl)($C_{1-5}$ alkyl)-. Preferably, $L^1$ is $C_{1-4}$ alkylene, wherein one or more (e.g., one or two) —$CH_2$— units comprised in said $C_{1-4}$ alkylene are each optionally replaced by a group independently selected from —O—, —CO—, —NH—, —N($C_{1-5}$ alkyl)-, —N[—CO—($C_{1-5}$ alkyl)]-, —S—, —SO—, —$SO_2$—, —CH($C_{1-5}$ alkyl)- and —C($C_{1-5}$ alkyl)($C_{1-5}$ alkyl)-. Said alkylene is preferably $C_{2-4}$ alkylene (e.g., ethylene, propylene or butylene), more preferably —$(CH_2)_2$—, —$(CH_2)_3$— or —$(CH_2)_4$—, and is even more preferably —$(CH_2)_2$—. Moreover, it is preferred that said one or more —$CH_2$— units are each optionally replaced by a group independently selected from —O—, —S—, —NH—, and —N($C_{1-5}$ alkyl)-, particularly by —O—. It is furthermore preferred that $L^1$ is attached to ring D via —O— (i.e., that $L^1$ contains a terminal —$CH_2$— unit which is replaced by —O—, and that $L^1$ is connected to ring D via said —O—). More preferably, $L^1$ is —$(CH_2)_{2-4}$—, wherein one —$CH_2$— unit comprised in said —$(CH_2)_{2-4}$— is optionally replaced by a group selected from —O—, —S—, —NH—, and —N($C_{1-5}$ alkyl)-, particularly by a group —O—. Even more preferably, $L^1$ is —O—$(CH_2)_{1-3}$—, wherein $L^1$ is attached to ring D via the oxygen atom (—O—) comprised in said —O—$(CH_2)_{13}$—. Yet even more preferably, $L^1$ is —O—$CH_2$— or —O—$CH_2$—$CH_2$—, wherein $L^1$ is attached to ring D via the oxygen atom in said —O—$CH_2$— or said —O—$CH_2$—$CH_2$—. Still more preferably, $L^1$ is —O—$CH_2$— which is attached to ring D via the oxygen atom (—O—) comprised in said —O—$CH_2$—.

In this $5^{th}$ specific embodiment, $R^{61}$ is carbocyclyl or heterocyclyl, wherein said carbocyclyl or said heterocyclyl is optionally substituted with one or more (e.g., one, two or three) groups $R^{62}$. Preferably, $R^{61}$ is selected from cycloalkyl, aryl, heterocycloalkyl (e.g., tetrahydrofuranyl or tetrahydropyranyl) and heteroaryl (e.g., pyridinyl), wherein said cycloalkyl, said aryl, said heterocycloalkyl and said heteroaryl are each optionally substituted with one or more (e.g., one, two or three) groups $R^{62}$. More preferably, $R^{61}$ is cycloalkyl or aryl, wherein said cycloalkyl or said aryl is optionally substituted with one or more $R^{62}$. Even more preferably, $R^{61}$ is selected from $C_{3-9}$ cycloalkyl (e.g., cyclopropyl, cyclobutyl, cyclopentyl, cyclohexyl, cycloheptyl, cyclooctyl, or cyclononyl) or phenyl, wherein said $C_{3-9}$ cycloalkyl or said phenyl is optionally substituted with one or more $R^{62}$. Yet even more preferably, $R^{61}$ is $C_{5-9}$ cycloalkyl (e.g., cyclopentyl, cyclohexyl, cycloheptyl, cyclooctyl, or cyclononyl) which is optionally substituted with one or more $R^{62}$.

Yet even more preferably, $R^{61}$ is cyclohexyl or cycloheptyl, wherein said cyclohexyl or said cycloheptyl is optionally substituted with one or more $R^{62}$. Still more preferably, $R^{61}$ is cyclohexyl which is optionally substituted with one or more $R^{62}$. It is furthermore preferred that the aforementioned cyclic groups ($R^{61}$) are not substituted with any groups $R^{62}$.

In this $5^{th}$ specific embodiment, each $R^{62}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-

CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, and —($C_{0-3}$ alkylene)-heterocycloalkyl. Preferably, each $R^{62}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl, and —($C_{0-3}$ alkylene)-heterocycloalkyl. More preferably, each $R^{62}$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN. Even more preferably, each $R^{62}$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-4}$ alkyl) (e.g., —$N(CH_3)_2$), halogen (e.g., —F, —Cl, —Br, or —I), —$CF_3$, and —CN.

In this $5^{th}$ specific embodiment, each $L^A$ is independently selected from a covalent bond, $C_{1-5}$ alkylene, $C_{2-5}$ alkenylene, and $C_{2-5}$ alkynylene, wherein said alkylene, said alkenylene and said alkynylene are each optionally substituted with one or more (e.g., one, two, or three) groups independently selected from halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl), and further wherein one or more (e.g., one, two, or three) —$CH_2$— units comprised in said alkylene, said alkenylene or said alkynylene are each optionally replaced by a group independently selected from —O—, —NH—, —N($C_{1-5}$ alkyl)-, —CO—, —S—, —SO—, and —$SO_2$—.

In this $5^{th}$ specific embodiment, each $R^A$ is independently selected from —OH, —O($C_{1-5}$ alkyl), —O($C_{1-5}$ alkylene)-OH, —O($C_{0-3}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O($C_{1-5}$ haloalkyl), —CN, —CHO, —CO($C_{1-5}$ alkyl), —COOH, —COO($C_{0-3}$ alkyl), —O—CO($C_{1-5}$ alkyl), —CO—$NH_2$, —CO—NH($C_{1-6}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-6}$ alkyl)-COO($C_{1-5}$ alkyl), —O—CO—NH($C_{1-5}$ alkyl), —O—CO—N($C_{1-6}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-6}$ alkyl), —N($C_{1-5}$ alkyl)-$SO_2$—($C_{1-6}$ alkyl), —$SO_2$—($C_{1-6}$ alkyl), —SO—($C_{1-5}$ alkyl), hydrogen, aryl, heteroaryl, cycloalkyl, and heterocycloalkyl, wherein said aryl, said heteroaryl, said cycloalkyl, and said heterocycloalkyl are each optionally substituted with one or more (e.g., one, two or three) groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl).

In a $6^{th}$ specific embodiment, the compound of formula (I) or the pharmaceutically acceptable salt thereof is as defined in the $5^{th}$ specific embodiment, except that $R^{3a}$ and $R^{3b}$ are mutually linked to form, together with the carbon atom that they are attached to, a cycloalkyl or a heterocycloalkyl, wherein said cycloalkyl or said heterocycloalkyl is optionally substituted with one or more (e.g., one, two or three) groups $R^{31}$.

In this $6^{th}$ specific embodiment, it is preferred that $R^{3a}$ and $R^{3b}$ are mutually linked to form, together with the carbon atom that they are attached to, a $C_{3-5}$ cycloalkyl or a 3- to 5-membered heterocycloalkyl, wherein said cycloalkyl or said heterocycloalkyl is optionally substituted with one or more (e.g., one or two) groups $R^{31}$. More preferably, $R^{3a}$ and $R^{3b}$ are mutually linked to form, together with the carbon atom that they are attached to, a cyclopropyl.

In this $6^{th}$ specific embodiment, it is thus particularly preferred that the moiety

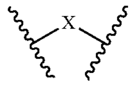

is

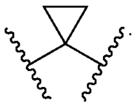 [SMILES: *C1(*)CC1].

In this $6^{th}$ specific embodiment, each $R^{31}$ is independently selected from $C_{1-6}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{0-3}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-6}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—SO—($C_{1-5}$ alkyl), —N($C_{1-5}$ alkyl)-$SO_2$—($C_{1-5}$alkyl), —SO—($C_{1-5}$ alkyl), and —$SO_2$—($C_{1-5}$ alkyl). Preferably, each $R^{31}$ is independently selected from $C_{1-5}$ alkyl, —OH, —O($C_{1-5}$ alkyl), —O($C_{1-5}$ alkylene)-OH, —O($C_{7-5}$ alkylene)-O($C_{1-5}$ alkyl), —SH, —$S(C_{1-5}$ alkyl), —$NH_2$, —$NH(C_{1-5}$ alkyl), —$N(C_{1-6}$ alkyl)($C_{1-5}$ alkyl), halogen, $C_{1-5}$ haloalkyl (e.g., —$CF_3$), and —CN.

In a 7$^{th}$ specific embodiment, the compound of formula (I) or the pharmaceutically acceptable salt thereof is as defined in the 5$^{th}$ specific embodiment, except that L is $C_{3-6}$ alkylene (e.g., propylene, butylene or pentylene), wherein one or more (e.g., one, two or three) —$CH_2$— units comprised in said $C_{3-6}$ alkylene are each optionally replaced by a group independently selected from —O—, —CO—, —NH—, —$N(C_{1-5}$ alkyl)-, —N[—CO—($C_{1-5}$ alkyl)]-, —N[—($C_{0-4}$ alkylene)-cycloalkyl]-, —N[—($C_{0-4}$ alkylene)-heterocycloalkyl]-, —S—, —SO—, —$SO_2$—, —$CH(C_{1-5}$ alkyl)- and —$C(C_{0-3}$ alkyl)($C_{1-5}$ alkyl)-, particularly by a group independently selected from —O—, —CO—, —NH—, —$N(C_{1-5}$ alkyl)-, —N[—CO—($C_{1-5}$ alkyl)]-, —N[—($C_{0-4}$ alkylene)-cycloalkyl]-, —N[—($C_{0-4}$ alkylene)-heterocycloalkyl]-, —$CH(C_{1-5}$ alkyl)- and —$C(C_{1-5}$ alkyl)($C_{1-5}$ alkyl)-, more preferably by a group independently selected from —O—, —NH—, and —$N(C_{1-5}$ alkyl)- (e.g., —N(—$CH_3$)— or —N(—$CH_2CH_3$)—). Preferably, L is —$(CH_2)_{3-5}$—, wherein one or more (e.g., one, two or three) —$CH_2$— units comprised in said —$(CH_2)_{3-5}$— are each optionally replaced by a group independently selected from —O—, —CO—, —NH—, —$N(C_{1-5}$ alkyl)-, —N[—CO—($C_{1-5}$ alkyl)]-, —N[—($C_{0-4}$ alkylene)-($C_{3-5}$ cycloalkyl)]-, —$CH(C_{1-5}$ alkyl)- and —$C(C_{1-5}$ alkyl)($C_{1-5}$ alkyl)-, particularly from —O—, —NH—, and —$N(C_{1-5}$ alkyl)-. More preferably, L is —$CH_2$—$CH_2$—CH—$CH_2$—, wherein one or more (e.g., one, two or three) —$CH_2$— units comprised in said —$CH_2$—$CH_2$—$CH_2$—$CH_2$— are each optionally replaced by a group independently selected from —O—, —CO—, —NH—, —$N(C_{1-5}$ alkyl)-, —N[—CO—($C_{1-5}$ alkyl)]-, —N[—($C_{1-4}$ alkylene)-($C_{3-7}$ cycloalkyl)]- (e.g., —N(—$CH_2$-cyclopropyl)-), —$CH(C_{1-5}$ alkyl)- and —$C(C_{0-3}$ alkyl)($C_{1-6}$ alkyl)-, particularly from —O—, —NH—, and —$N(C_{1-5}$ alkyl)-. Even more preferably, L is —$CH_2$—$CH_2$—$CH_2$—O— which is attached to ring D via the oxygen atom (—O—) in said group —$CH_2$—$CH_2$—$CH_2$—O—, and wherein one or more (e.g., one or two) —$CH_2$— units comprised in said —$CH_2$—$CH_2$—$CH_2$—O— are each optionally replaced by a group independently selected from —O—, —CO—, —NH—, —$N(C_{1-4}$ alkyl)-, —N[—CO—($C_{1-4}$ alkyl)]-, —N[—($C_{1-3}$ alkylene)-cyclopropyl]-, —$CH(C_{1-4}$ alkyl)- and —$C(C_{1-4}$ alkyl)($C_{1-4}$ alkyl)-, particularly from —O—, —NH—, and —$N(C_{1-4}$ alkyl)-, wherein it is furthermore preferred that the terminal —$CH_2$— unit (which is most distant to the oxygen atom in —$CH_2$—$CH_2$—$CH_2$—O—) is replaced by a group as defined above (e.g., by —$N(C_{1-4}$ alkyl)-, particularly by —$N(CH_3)$—). Corresponding preferred examples of L include, in particular, —$CH_2$—$CH_2$—$CH_2$—O—, —NH—$CH_2$—$CH_2$—O—, —N(—$CH_3$)—$CH_2$—$CH_2$—O—, —N(—$CH_2CH_3$)—$CH_2$—$CH_2$—O—, —N(—$CH_2CH_2CH_3$)—$CH_2$—$CH_2$—O—, —N(isopropyl)-$CH_2$—$CH_2$—O—, —N(—$CH_2$-cyclopropyl)-$CH_2$—$CH_2$—O—, —N(—CO—$CH_3$)—$CH_2$—$CH_2$—O—, —NH—CO—$CH_2$—O—, or —O—$CH_2$—$CH_2$—O—, wherein each of these groups is attached to ring D via the terminal oxygen atom (—O—) contained therein. Particularly preferred examples of L include —N(—$CH_3$)—$CH_2$—$CH_2$-0-, —N(—$CH_2CH_3$)—$CH_2$—$CH_2$—O—, —N(—$CH_2$-cyclopropyl)-$CH_2$—$CH_2$—O—, or —O—$CH_2$—$CH_2$—O—, wherein each of these groups is attached to ring D via the terminal oxygen atom contained therein. An even more preferred example of L is —N(—$CH_3$)—$CH_2$—$CH_2$—O— which is attached to ring D via the terminal oxygen atom contained therein.

In an 8$^{th}$ specific embodiment, the compound of formula (I) or the pharmaceutically acceptable salt thereof is as defined in the 6$^{th}$ specific embodiment, except that L is $C_{3-6}$ alkylene (e.g., propylene, butylene or pentylene), wherein one or more (e.g., one, two or three) —$CH_2$— units comprised in said $C_{3-5}$ alkylene are each optionally replaced by a group independently selected from —O—, —CO—, —NH—, —$N(C_{1-6}$ alkyl)-, —N[—CO—($C_{1-5}$ alkyl)]-, —N[—($C_{0-4}$ alkylene)-cycloalkyl]-, —N[—($C_{0-4}$ alkylene)-heterocycloalkyl]-, —S—, —SO—, —$SO_2$—, —$CH(C_{1-5}$ alkyl)- and —$C(C_{1-6}$ alkyl)($C_{1-5}$ alkyl)-, particularly by a group independently selected from —O—, —CO—, —NH—, —$N(C_{1-5}$ alkyl)-, —N[—CO—($C_{1-5}$ alkyl)]-, —N[—($C_{0-4}$ alkylene)-cycloalkyl]-, —N[—($C_{0-4}$ alkylene)-heterocycloalkyl]-, —$CH(C_{1-5}$ alkyl)- and —$C(C_{1-5}$ alkyl)($C_{1-5}$ alkyl)-, more preferably by a group independently selected from —O—, —NH—, and —$N(C_{1-5}$ alkyl)- (e.g., —N(—$CH_3$)— or —N(—$CH_2CH_3$)—). Preferably, L is —$(CH_2)_{3-5}$—, wherein one or more (e.g., one, two or three) —$CH_2$— units comprised in said —$(CH_2)_{3-5}$— are each optionally replaced by a group independently selected from —O—, —CO—, —NH—, —$N(C_{1-5}$ alkyl)-, —N[—CO—($C_{1-5}$alkyl)]-, —N[—($C_{0-4}$ alkylene)-($C_{3-7}$ cycloalkyl)]- (e.g., —N(—$CH_2$-cyclopropyl)-), —$CH(C_{1-4}$ alkyl)- and —$C(C_{1-5}$ alkyl)($C_{1-5}$ alkyl)-, particularly from —O—, —NH—, and —$N(C_{1-5}$ alkyl)-. More preferably, L is —$CH_2$—$CH_2$—$CH_2$—$CH_2$—, wherein one or more (e.g., one, two or three) —$CH_2$— units comprised in said —$CH_2$—$CH_2$—$CH_2$—$CH_2$— are each optionally replaced by a group independently selected from —O—, —CO—, —NH—, —$N(C_{1-5}$ alkyl)-, —N[—CO—($C_{1-5}$ alkyl)]-, —N[—($C_{0-4}$ alkylene)-($C_{3-7}$ cycloalkyl)]- (e.g., —N(—$CH_2$-cyclopropyl)-), —$CH(C_{1-5}$ alkyl)- and —$C(C_{1-5}$ alkyl)($C_{1-5}$ alkyl)-, particularly from —O—, —NH—, and —$N(C_{1-5}$ alkyl)-. Even more preferably, L is —$CH_2$—$CH_2$—$CH_2$—O— which is attached to ring D via the oxygen atom (—O—) in said group —$CH_2$—$CH_2$—$CH_2$—O—, and wherein one or more (e.g., one or two) —$CH_2$— units comprised in said —$CH_2$—$CH_2$—$CH_2$—O— are each optionally replaced by a group independently selected from —O—, —CO—, —NH—, —$N(C_{1-4}$ alkyl)-, —N[—CO—($C_{1-4}$ alkyl)]-, —N[—($C_{1-3}$ alkylene)-cyclopropyl]-, —$CH(C_{1-4}$ alkyl)- and —$C(C_{1-4}$ alkyl)($C_{1-4}$ alkyl)-, particularly from —O—, —NH—, and —$N(C_{1-4}$ alkyl)-, wherein it is furthermore preferred that the terminal —$CH_2$— unit (which is most distant to the oxygen atom in —$CH_2$—$CH_2$—$CH_2$—O—) is replaced by a group as defined above (e.g., by —$N(C_{1-4}$ alkyl)-, particularly by —$N(CH_3)$—). Corresponding preferred examples of L include, in particular, —$CH_2$—$CH_2$—$CH_2$—O—, —NH—$CH_2$—$CH_2$—O—, —N(—$CH_3$)—$CH_2$—$CH_2$—O—, —N(—$CH_2CH_3$)—$CH_2$—$CH_2$—O—, —N(—$CH_2CH_2CH_3$)—$CH_2$—$CH_2$—O—, —N(isopropyl)-$CH_2$—$CH_2$—O—, —N(—$CH_2$-cyclopropyl)-$CH_2$—$CH_2$—O—, —N(—CO—$CH_3$)—$CH_2$—$CH_2$—O—, —NH—CO—$CH_2$—O—, or —O—$CH_2$—$CH_2$—O—, wherein each of these groups is attached to ring D via the terminal oxygen atom (—O—) contained therein. Particularly preferred examples of L include —N(—$CH_3$)—$CH_2$—$CH_2$—O—, —N(—$CH_2CH_3$)—$CH_2$—$CH_2$—O—, —N(—$CH_2$-cyclopropyl)-$CH_2$—$CH_2$—O—, or —O—$CH_2$—$CH_2$—O—, wherein each of these groups is attached to ring D via the terminal oxygen atom contained therein. An even more preferred example of L is —N(—

$CH_3$)—$CH_2$—$CH_2$—O— which is attached to ring D via the terminal oxygen atom contained therein.

In a 9$^{th}$ specific embodiment, the compound of formula (I) or the pharmaceutically acceptable salt thereof is as defined in the 5$^{th}$ specific embodiment, except that ring D is monocyclic heteroaryl or monocyclic heterocycloalkyl. It is preferred that ring D is selected from pyridinyl (e.g., pyridin-2-yl, pyridin-3-yl, or pyridin-4-yl), azetidinyl (e.g., azetidin-1-yl or azetidin-2-yl), pyrrolidinyl (e.g., pyrrolidin-1-yl, pyrrolidin-2-yl, or pyrrolidin-3-yl), and piperidinyl (e.g., piperidin-1-yl, piperidin-2-yl, piperidin-3-yl, or piperidin-4-yl). More preferably, ring D is pyridinyl.

In a 10$^{th}$ specific embodiment, the compound of formula (I) or the pharmaceutically acceptable salt thereof is as defined in the 6$^{th}$ specific embodiment, except that ring D is monocyclic heteroaryl or monocyclic heterocycloalkyl. It is preferred that ring D is selected from pyridinyl (e.g., pyridin-2-yl, pyridin-3-yl, or pyridin-4-yl), azetidinyl (e.g., azetidin-1-yl or azetidin-2-yl), pyrrolidinyl (e.g., pyrrolidin-1-yl, pyrrolidin-2-yl, or pyrrolidin-3-yl), and piperidinyl (e.g., piperidin-1-yl, piperidin-2-yl, piperidin-3-yl, or piperidin-4-yl). More preferably, ring D is pyridinyl.

In an 11$^{th}$ specific embodiment, the compound of formula (I) or the pharmaceutically acceptable salt thereof is as defined in the 7$^{th}$ specific embodiment, except that ring D is monocyclic heteroaryl or monocyclic heterocycloalkyl. It is preferred that ring D is selected from pyridinyl (e.g., pyridin-2-yl, pyridin-3-yl, or pyridin-4-yl), azetidinyl (e.g., azetidin-1-yl or azetidin-2-yl), pyrrolidinyl (e.g., pyrrolidin-1-yl, pyrrolidin-2-yl, or pyrrolidin-3-yl), and piperidinyl (e.g., piperidin-1-yl, piperidin-2-yl, piperidin-3-yl, or piperidin-4-yl). More preferably, ring D is pyridinyl.

In a 12$^{th}$ specific embodiment, the compound of formula (I) or the pharmaceutically acceptable salt thereof is as defined in the 8$^{th}$ specific embodiment, except that ring D is monocyclic heteroaryl or monocyclic heterocycloalkyl. It is preferred that ring D is selected from pyridinyl (e.g., pyridin-2-yl, pyridin-3-yl, or pyridin-4-yl), azetidinyl (e.g., azetidin-1-yl or azetidin-2-yl), pyrrolidinyl (e.g., pyrrolidin-1-yl, pyrrolidin-2-yl, or pyrrolidin-3-yl), and piperidinyl (e.g., piperidin-1-yl, piperidin-2-yl, piperidin-3-yl, or piperidin-4-yl). More preferably, ring D is pyridinyl.

In a 13$^{th}$ specific embodiment, the compound of formula (I) or the pharmaceutically acceptable salt thereof is as defined in the 1$^{st}$ specific embodiment, except that X is $C(R^{3a})(R^{3b})$, wherein $R^{3a}$ and $R^{3b}$ are each hydrogen (i.e., X is —$CH_2$—), and except that ring B is cyclohexylene (preferably, ring B is cyclohexan-1,4-diyl).

In a 14$^{th}$ specific embodiment, the compound of formula (I) or the pharmaceutically acceptable salt thereof is as defined in the 3$^{rd}$ specific embodiment, except that X is $C(R^{3a})(R^{3b})$, wherein $R^{3b}$ and $R^{3b}$ are each hydrogen (i.e., X is —$CH_2$—), and except that ring B is cyclohexylene (preferably, ring B is cyclohexan-1,4-diyl).

In a 15$^{th}$ specific embodiment, the compound of formula (I) or the pharmaceutically acceptable salt thereof is as defined in the 5$^{th}$ specific embodiment, except that X is $C(R^{3a})(R^{3b})$, wherein $R^{3a}$ and $R^{3b}$ are each hydrogen (i.e., X is —$CH_2$—), and except that ring B is cyclohexylene (preferably, ring B is cyclohexan-1,4-diyl).

In a 16$^{th}$ specific embodiment, the compound of formula (I) or the pharmaceutically acceptable salt thereof is as defined in the 7$^{th}$ specific embodiment, except that X is $C(R^{3a})(R^{31})$, wherein $R^{3a}$ and $R^{3b}$ are each hydrogen (i.e., X is —$CH_2$—), and except that ring B is cyclohexylene (preferably, ring B is cyclohexan-1,4-diyl).

In a 17$^{th}$ specific embodiment, the compound of formula (I) or the pharmaceutically acceptable salt thereof is as defined in the 9$^{th}$ specific embodiment, except that X is $C(R^{3a})(R^{3b})$, wherein $R^{3a}$ and $R^{3b}$ are each hydrogen (i.e., X is —$CH_2$—), and except that ring B is cyclohexylene (preferably, ring B is cyclohexan-1,4-diyl).

In a 18$^{th}$ specific embodiment, the compound of formula (I) or the pharmaceutically acceptable salt thereof is as defined in the 11$^{th}$ specific embodiment, except that X is $C(R^{3a})(R^{3b})$, wherein $R^{3a}$ and $R^{3b}$ are each hydrogen (i.e., X is —$CH_2$—), and except that ring B is cyclohexylene (preferably, ring B is cyclohexan-1,4-diyl).

In a 19$^{th}$ specific embodiment, the compound of formula (I) is a compound of the following formula

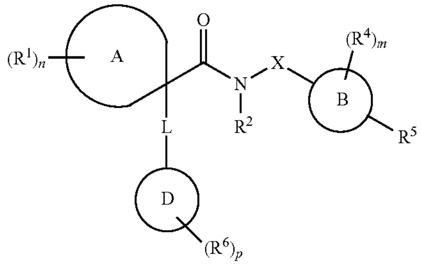

or a pharmaceutically acceptable salt thereof.

In this 19$^{th}$ specific embodiment, L is a covalent bond.

In this 19$^{th}$ specific embodiment, ring D is phenyl or pyridinyl (e.g., pyridin-2-yl, pyridin-3-yl, or pyridin-4-yl). Preferably, ring D is phenyl.

In this 19$^{th}$ specific embodiment, p is 0, 1 or 2. More preferably, p is 1. If p is 1, then it is preferred that $R^6$ is attached to ring D in a 1,3-orientation or a 1,4-orientation with respect to the attachment point of ring A (via group L which is a covalent bond) to ring D, more preferably $R^6$ is attached to ring D in a 1,3-orientation with respect to the attachment point of ring A to ring D. Thus, if p is 1 and ring D is phenyl, then it is preferred that $R^6$ is attached to said phenyl (as ring D) in meta-position or para-position, more preferably in meta-position (corresponding to the 1,3-orientation), with respect to the attachment point of ring A to said phenyl (as ring D). Moreover, if p is 1 and ring D is pyridinyl, then it is preferred that $R^6$ is attached to said pyridinyl (as ring D) in a 1,3-orientation or a 1,4-orientation with respect to the attachment point of ring A to ring D. In particular, if p is 1 and ring D is pyridin-2-yl or pyridin-3-yl, then $R^6$ may be attached to said pyridin-2-yl or said pyridin-3-yl, e.g., in a 1,4-orientation with respect to the attachment point of ring A to ring D. If p is 1 and ring D is pyridin-4-yl, then $R^b$ may be attached to said pyridin-4-yl, e.g., in a 1,3-orientation with respect to the attachment point of ring A to ring D.

In this 19$^{th}$ specific embodiment, each $R^6$ is independently a group $-L^1-R^{61}$.

In this 19$^{th}$ specific embodiment, Lt is $C_{1-6}$ alkylene or a covalent bond, wherein one or more (e.g., one, two or three) —$CH_2$— units comprised in said $C_{1-6}$ alkylene are each optionally replaced by a group independently selected from —O—, —CO—, —NH—, —N($C_{1-5}$ alkyl)-, —N[—CO—($C_{1-5}$ alkyl)]-, —S—, —SO—, —$SO_2$—, —CH($C_{1-5}$ alkyl)- and —C($C_{1-5}$ alkyl)($C_{1-5}$ alkyl)-.

Preferably, $L^1$ is $C_{1-4}$ alkylene, wherein one or more (e.g., one or two) —$CH_2$— units comprised in said $C_{1-4}$ alkylene are each optionally replaced by a group independently selected from —O—, —CO—, —NH—, —N($C_{1-5}$ alkyl)-, —N[—CO—($C_{1-5}$ alkyl)]-, —S—, —SO—, —$SO_2$—, —CH($C_{1-5}$ alkyl)- and —C($C_{1-5}$ alkyl)($C_{1-5}$ alkyl)-. Said alkylene is preferably $C_{2-4}$ alkylene (e.g., ethylene, propylene or butylene), more preferably —$(CH_2)_2$—, —$(CH_2)_3$— or —$(CH_2)_4$—, and is even more preferably —$(CH_2)_2$—. Moreover, it is preferred that said one or more —$CH_2$— units are each optionally replaced by a group independently selected from —O—, —S—, —NH—, and —N($C_{1-5}$ alkyl)-, particularly by —O—. It is furthermore preferred that $L^1$ is attached to ring D via —O— (i.e., that $L^1$ contains a terminal —$CH_2$— unit which is replaced by —O—, and that $L^1$ is connected to ring D via said —O—).

More preferably, $L^1$ is —$(CH_2)_{2-4}$—, wherein one —$CH_2$— unit comprised in said —$(CH_2)_{2-4}$— is optionally replaced by a group selected from —O—, —S—, —NH—, and —N($C_{1-5}$ alkyl)-, particularly by a group —O—. Even more preferably, $L^1$ is —O—$(CH_2)_{1-3}$—, wherein $L^1$ is attached to ring D via the oxygen atom (—O—) comprised in said —O—$(CH_2)_{1-3}$—. Yet even more preferably, $L^1$ is —O—$CH_2$— or —O—$CH_2$—$CH_2$—, wherein $L^1$ is attached to ring D via the oxygen atom in said —O—$CH_2$— or said —O—$CH_2$—$CH_2$—. Still more preferably, $L^1$ is —O—$CH_2$— which is attached to ring D via the oxygen atom (—O—) comprised in said —O—$CH_2$—.

In this $19^{th}$ specific embodiment, $R^{61}$ is carbocyclyl or heterocyclyl, wherein said carbocyclyl or said heterocyclyl is optionally substituted with one or more (e.g., one, two or three) groups $R^{62}$. Preferably, $R^{61}$ is selected from cycloalkyl, aryl, heterocycloalkyl (e.g., tetrahydrofuranyl or tetrahydropyranyl) and heteroaryl (e.g., pyridinyl), wherein said cycloalkyl, said aryl, said heterocycloalkyl and said heteroaryl are each optionally substituted with one or more (e.g., one, two or three) groups $R^{62}$. More preferably, $R^{61}$ is cycloalkyl or aryl, wherein said cycloalkyl or said aryl is optionally substituted with one or more $R^{62}$. Even more preferably, $R^{61}$ is selected from $C_{3-9}$ cycloalkyl (e.g., cyclopropyl, cyclobutyl, cyclopentyl, cyclohexyl, cycloheptyl, cyclooctyl, or cyclononyl) or phenyl, wherein said $C_{3-9}$ cycloalkyl or said phenyl is optionally substituted with one or more $R^{62}$. Yet even more preferably, $R^{61}$ is $C_{1-5}$ cycloalkyl (e.g., cyclopentyl, cyclohexyl, cycloheptyl, cyclooctyl, or cyclononyl) which is optionally substituted with one or more $R^{62}$. Yet even more preferably, $R^{61}$ is cyclohexyl or cycloheptyl, wherein said cyclohexyl or said cycloheptyl is optionally substituted with one or more $R^{62}$. Still more preferably, $R^{61}$ is cyclohexyl which is optionally substituted with one or more $R^{62}$. It is furthermore preferred that the aforementioned cyclic groups ($R^{61}$) are not substituted with any groups $R^{62}$.

In this $19^{th}$ specific embodiment, each $R^{62}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-6}$ alkylene)-OH, —($C_{0-3}$ alkylene)-O($C_{1-5}$ alkylene)-O($C_{0-3}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{0-3}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, and —($C_{0-3}$ alkylene)-heterocycloalkyl. Preferably, each $R^{62}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{0-3}$ alkyl), —O—CO—($C_{1-5}$ alkyl), —CO—$NH_2$, —CO—NH($C_{1-6}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-6}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl, and —($C_{0-3}$ alkylene)-heterocycloalkyl. More preferably, each $R^{62}$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN. Even more preferably, each $R^{62}$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-4}$ alkyl) (e.g., —$N(CH_3)_2$), halogen (e.g., —F, —Cl, —Br, or —I), —$CF_3$, and —CN.

In this $19^{th}$ specific embodiment, ring A is cycloalkylene or heterocycloalkylene. Preferably, ring A is monocyclic cycloalkylene or monocyclic heterocycloalkylene. Even more preferably, ring A is a monocyclic $C_{4-9}$ cycloalkylene or a monocyclic 4 to 9-membered heterocycloalkylene.

Preferred examples of ring A include, in particular, cyclobutylene, cyclopentylene, cyclohexylene, tetrahydrofuranylene (e.g., tetrahydrofuran-2,2-diyl or tetrahydrofuran-3,3-diyl), tetrahydrothiophenylene (e.g., tetrahydrothiophen-2,2-diyl or tetrahydrothiophen-3,3-diyl), tetrahydropyranylene (e.g., tetrahydropyran-2,2-diyl, tetrahydropyran-3,3-diyl, or tetrahydropyran-4,4-diyl), or thianylene (e.g., thian-2,2-diyl, thian-3,3-diyl, or thian-4,4-diyl). It is particularly preferred that ring A is tetrahydropyranylene (preferably tetrahydropyran-4,4-diyl) or cyclopentylene (i.e., cyclopentan-1,1-diyl).

In this $19^{th}$ specific embodiment, ring B is a carbocyclic group or a heterocyclic group. Preferably, ring B is selected from arylene, heteroarylene (e.g., pyridinylene; including, in particular, pyridin-2,5-diyl or pyridin-3,6-diyl), cycloalkylene and heterocycloalkylene. It is furthermore preferred that ring B is monocyclic. More preferably, ring B is arylene or cycloalkylene. Even more preferably, ring B is phenylene or $C_{3-9}$ cycloalkylene. Even more preferably, ring B is phenylene (particularly phen-1,4-diyl) or cyclohexylene (particularly cyclohexan-1,4-diyl). Yet even more preferably, ring B is phenylene (e.g., phen-1,4-diyl, pheny-1,3-diyl, or phen-1,2-diyl). Still more preferably, ring B is phen-1,4-diyl.

In this $19^{th}$ specific embodiment, n is 0, 1, 2, 3 or 4. Preferably, n is 0, 1 or 2. More preferably, n is 0 or 1. Even more preferably, n is 0.

In this $19^{th}$ specific embodiment, m is 0, 1, 2, 3 or 4. Preferably, m is 0, 1 or 2. More preferably, m is 0 or 1. Even more preferably, m is 0.

In this $19^{th}$ specific embodiment, each $R^1$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-6}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{0-3}$ alkyl)($C_{1-6}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^A$-$R^A$. Preferably, each $R^1$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl (e.g., —$CH_2$-cyclopropyl), —($C_{0-3}$ alkylene)-heterocycloalkyl, and -$L^A$-$R^A$. More preferably, each $R^1$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN. Even more preferably, each $R^1$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-4}$ alkyl) (e.g., —$N(CH_3)_2$), halogen (e.g., —F, —Cl, —Br, or —I), —$CF_3$, and —CN.

In this $19^{th}$ specific embodiment, $R^2$ is selected from hydrogen, $C_{1-5}$ alkyl, and —CO($C_{1-5}$ alkyl). Preferably, $R^2$ is hydrogen or $C_{1-5}$ alkyl. More preferably, $R^2$ is hydrogen, methyl or ethyl. Even more preferably, $R^2$ is hydrogen.

In this 19*h specific embodiment, X is $C(R^{3a})(R^{3b})$ or $N(R^{3c})$. Accordingly, X is a carbon atom carrying the substituents $R^{3a}$ and $R^{31}$, or X is a nitrogen atom carrying the substituent $R^{3c}$. Preferably, X is $C(R^{3a})(R^{3b})$.

In this $19^{th}$ specific embodiment, $R^{3a}$ and $R^{3b}$ are each independently selected from hydrogen, $C_{1-5}$ alkyl, and $C_{2-5}$ alkenyl; or $R^{3a}$ and $R^{3b}$ are mutually linked to form, together with the carbon atom that they are attached to, a cycloalkyl or a heterocycloalkyl, wherein said cycloalkyl or said heterocycloalkyl is optionally substituted with one or more (e.g., one, two or three) groups $R^{31}$; or $R^{3a}$ is a divalent group selected from linear $C_{2-4}$ alkylene and linear $C_{2-4}$ alkenylene, wherein said divalent group is attached via one end to the carbon atom carrying $R^{3b}$ and is attached via the other end to a ring atom of ring B which is adjacent to the ring atom (of ring B) carrying the group X, wherein said alkylene or said alkenylene is optionally substituted with one or more (e.g., one, two or three) groups $R^{31}$, wherein one —$CH_2$— unit in said alkylene or said alkenylene is optionally replaced by —O—, —S—, —NH— or —N($C_{1-5}$ alkyl)-, and $R^{3b}$ is selected from hydrogen, $C_{1-5}$ alkyl, and $C_{2-5}$ alkenyl. Preferably, $R^{3a}$ and $R^{3b}$ are each independently selected from hydrogen and $C_{1-5}$ alkyl, or $R^{3a}$ and $R^{3b}$ are mutually linked to form, together with the carbon atom that they are attached to, a $C_{3-5}$ cycloalkyl or a 3- to 5-membered heterocycloalkyl, wherein said cycloalkyl or said heterocycloalkyl is optionally substituted with one or more (e.g., one or two) groups $R^{31}$. More preferably, $R^{3a}$ and $R^{3b}$ are each independently selected from hydrogen and $C_{1-5}$ alkyl (e.g., methyl or ethyl), or $R^{3a}$ and $R^{3b}$ are mutually linked to form, together with the carbon atom that they are attached to, a cyclopropyl. Even more preferably, $R^{3a}$ is $C_{1-5}$ alkyl (e.g., methyl or ethyl) and $R^{3b}$ is hydrogen or $C_{1-5}$ alkyl (e.g., methyl or ethyl), or $R^{3a}$ and $R^{3b}$ are mutually linked to form, together with the carbon atom that they are attached to, a cyclopropyl. Yet even more preferably, $R^{3a}$ is methyl and $R^{3b}$ is hydrogen, or $R^{3a}$ and $R^{3b}$ are mutually linked to form, together with the carbon atom that they are attached to, a cyclopropyl.

In this $19^{th}$ specific embodiment, $R^{3c}$ is selected from hydrogen, $C_{1-6}$ alkyl, and $C_{2-5}$ alkenyl. Preferably, $R^{3c}$ is hydrogen or $C_{1-5}$ alkyl (e.g., methyl or ethyl). More preferably, $R^{3c}$ is hydrogen or methyl. Even more preferably, $R^{3c}$ is methyl.

In this $19^{th}$ specific embodiment in accordance with the above definitions of X, $R^{3a}$ and $R^{3b}$, it is particularly preferred that the moiety

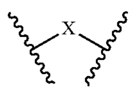

is

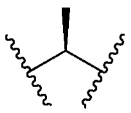

or

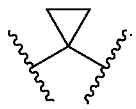

.

In this $19^{th}$ specific embodiment, each $R^{31}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-6}$ alkyl), —SH, —S($C_{1-5}$ alkyl), —S($C_{1-5}$ alkylene)-SH, —S($C_{1-5}$ alkylene)-S($C_{1-6}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), and —$SO_2$—($C_{1-5}$ alkyl). Preferably, each $R^{31}$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN.

In this 19$^{th}$ specific embodiment, each $R^4$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{0-3}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-6}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl)($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^A$-$R^A$. Preferably, each $R^4$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), —($C_{0-3}$ alkylene)-cycloalkyl, —($C_{0-3}$ alkylene)-heterocycloalkyl, and -$L^A$-$R^A$. More preferably, each $R^4$ is independently selected from $C_{1-5}$ alkyl, —OH, —O($C_{1-5}$ alkyl), —O($C_{1-5}$alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl (e.g., —$CF_3$), and —CN. Even more preferably, each $R^4$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-4}$ alkyl) (e.g., —$N(CH_3)_2$), halogen (e.g., —F, —Cl, —Br, or —I), —$CF_3$, and —CN.

In this 19$^{th}$ specific embodiment, $R^5$ is selected from —COOH, —CO—$NH_2$, —CO—NH($C_{1-5}$ alkyl), —CO—N($C_{1-5}$ alkyl)($C_{1-5}$ alkyl), —$SO_2$—OH, —$SO_2$—O—($C_{1-5}$ alkyl), —SO—$NH_2$, —$SO_2$—NH($C_{1-5}$ alkyl), —$SO_2$—N($C_{1-5}$ alkyl)($C_{1-5}$ alkyl), —$SO_2$—($C_{1-5}$ alkyl), —S(═O)(═NH)—($C_{1-5}$ alkyl), halogen (e.g., —F or —Cl), $C_{1-5}$ haloalkyl (e.g., —$CF_3$), —CN, hydrogen, $C_{1-4}$ alkyl, —OH, —O($C_{1-4}$ alkyl), carbocyclyl (e.g., aryl or cycloalkyl), and heterocyclyl (e.g., heteroaryl or heterocycloalkyl), wherein said carbocyclyl or said heterocyclyl is optionally substituted with one or more (e.g., one, two or three) groups -$L^A$-$R^A$. Preferably, $R^5$ is selected from —COOH, —CO—$NH_2$, —CO—NH($C_{1-5}$ alkyl), —CO—N($C_{1-5}$ alkyl)($C_{1-5}$ alkyl), —$SO_2$—OH, —$SO_2$—O—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —$SO_2$—($C_{1-5}$ alkyl), —S(═O)(═NH)—($C_{1-5}$ alkyl), —CN, —O($C_{1-4}$ alkyl) (e.g., —$OCH_3$), and heteroaryl (e.g., tetrazolyl). More preferably, $R^5$ is selected from —COOH, —CO—$NH_2$, —CO—NH($C_{1-5}$ alkyl) (e.g., —CO—NH—$CH_3$), —CO—N($C_{1-5}$ alkyl)($C_{1-5}$ alkyl) (e.g., —CO—N($CH_3$)—$CH_3$), —$SO_2$—($C_{1-5}$ alkyl) (e.g., —$SO_2$—$CH_3$), —S(═O)(═NH)—($C_{1-5}$ alkyl) (e.g., —S(═O)(═NH)—$CH_3$), and tetrazolyl (e.g., 1H-tetrazol-5-yl or 2H-tetrazol-5-yl). More preferably, $R^5$ is —COOH, —CO—$NH_2$, or tetrazolyl (particularly 1H-tetrazol-5-yl or 2H-tetrazol-5-yl). Even more preferably, $R^5$ is —COOH or tetrazolyl (particularly 1H-tetrazol-5-yl or 2H-tetrazol-5-yl). Yet even more preferably. $R^5$ is —COOH.

In this 19$^{th}$ specific embodiment, in accordance with the above definitions of ring B, X, $R^2$, $R^{3a}$, $R^{3b}$, $R^4$, $R^5$ and m, it is particularly preferred that the moiety

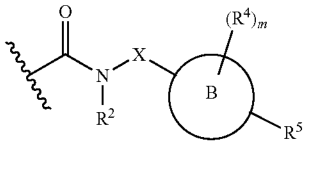

has the following structure:

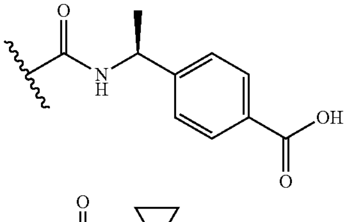

or

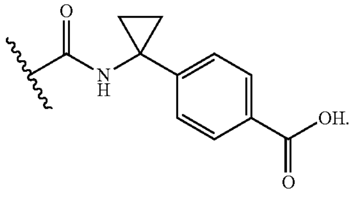

In this 19$^{th}$ specific embodiment, each $L^A$ is independently selected from a covalent bond, $C_5$ alkylene, $C_{2-5}$ alkenylene, and $C_{2-5}$ alkynylene, wherein said alkylene, said alkenylene and said alkynylene are each optionally substituted with one or more (e.g., one, two, or three) groups independently selected from halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl), and further wherein one or more (e.g., one, two, or three) —$CH_2$— units comprised in said alkylene, said alkenylene or said alkynylene are each optionally replaced by a group independently selected from —O—, —NH—, —N($C_{1-5}$ alkyl)-, —CO—, —S—, —SO—, and —$SO_2$—.

In this $19^{th}$ specific embodiment, each $R^A$ is independently selected from —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{0-3}$ alkylene)-S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O($C_{1-5}$ haloalkyl), —CN, —CHO, —CO($C_{1-5}$ alkyl), —COOH, —COO($C_{1-5}$ alkyl), —O—CO($C_{1-5}$ alkyl), —CO—$NH_2$, —CO—NH($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-6}$ alkyl)-$SO_2$—($C_{1-5}$ alkyl), —$SO_2$—($C_{1-5}$ alkyl), —SO—($C_{1-5}$ alkyl), hydrogen, aryl, heteroaryl, cycloalkyl, and heterocycloalkyl, wherein said aryl, said heteroaryl, said cycloalkyl, and said heterocycloalkyl are each optionally substituted with one or more (e.g., one, two or three) groups independently selected from $C_{1-5}$ alkyl, $C_{2-5}$ alkenyl, $C_{2-5}$ alkynyl, halogen, $C_{1-5}$ haloalkyl, —CN, —OH, —O($C_{1-5}$ alkyl), —SH, —S($C_{1-5}$ alkyl), —$NH_2$, —NH($C_{1-5}$ alkyl), and —N($C_{1-5}$ alkyl)($C_{1-5}$ alkyl).

In a $20^{th}$ specific embodiment, the compound of formula (I) or the pharmaceutically acceptable salt thereof is as defined in the $19^{th}$ specific embodiment, except that ring A is tetrahydropyranylene (preferably tetrahydropyran-4,4-diyl) and ring D is phenyl.

In a $21^{st}$ specific embodiment, the compound of formula (I) or the pharmaceutically acceptable salt thereof is as defined in the $19^{th}$ specific embodiment, except that ring A is cyclopentylene (i.e., cyclopentan-1,1-diyl) and ring D is pyridinyl (e.g., pyridin-2-yl, pyridin-3-yl, or pyridin-4-yl; preferably pyridin-4-yl).

For a person skilled in the field of synthetic chemistry, various ways for the preparation of the compounds of general formula (I) and their pharmaceutically acceptable salts will be readily apparent. For example, the compounds of the invention can be prepared in accordance with, or in analogy to, the synthetic routes described in detail in the examples section. In particular, the compounds of formula (I) can be generally synthesized in accordance with the methods described in the following schemes.

Examples F, O, X and AI can be obtained by saponification or acid hydrolysis of esters E, N, W and AH respectively (scheme 1, 2, 3, 4). Saponification can generally be performed in basic aqueous conditions, using typically an aqueous sodium hydroxide or an aqueous lithium hydroxide solution. If necessary, a mixture with an organic solvent like THF or dioxane can be used. Acid hydrolysis can be generally performed in an acidic aqueous solution, using typically aqueous HCl. If necessary, a mixture with an organic solvent like dioxane can be used. Examples G and AJ can be obtained by amide coupling starting from Examples F and AI respectively with the appropriate amine, via an activated acid intermediate (scheme 1 and 4). Typically, this activated acid intermediate can be the corresponding acyl chloride or can be obtained by using a coupling agent such as BOP or HATU.

Intermediate E can be obtained from Intermediate D (scheme 1). The $Y_3$ moiety can be introduced by using the appropriate electrophile. For instance, it can be introduced by reductive amination in presence of the appropriate aldehyde or ketone and a reductant, such as sodium triacetoxyborohydride. It can also be introduced by amide coupling by reaction with an activated acid intermediate, like an acyl chloride or a carboxylic acid in presence of a coupling agent such as BOP or HATU. In a similar manner, Intermediate D can be obtained from Intermediate C. The $Y_2$ moiety can be introduced by using the appropriate electrophile, typically the appropriate aldehyde or ketone or by reaction with an activated acid intermediate, like previously described. Intermediate C can be obtained in 2 steps from protected amino-acid A and amine B. The first step can consist in an amide coupling via an activated acid intermediate, using typically an acyl chloride or a coupling agent such as BOP or HATU, followed by a deprotection step. This later one is adapted to the protectiong group used for Intermediate A: typically, in case of a Boc-protected amino acid A, the Boc group can be removed in acidic conditions such as a TFA/organic solvent mixture.

Scheme 1: General preparation of Examples F and G

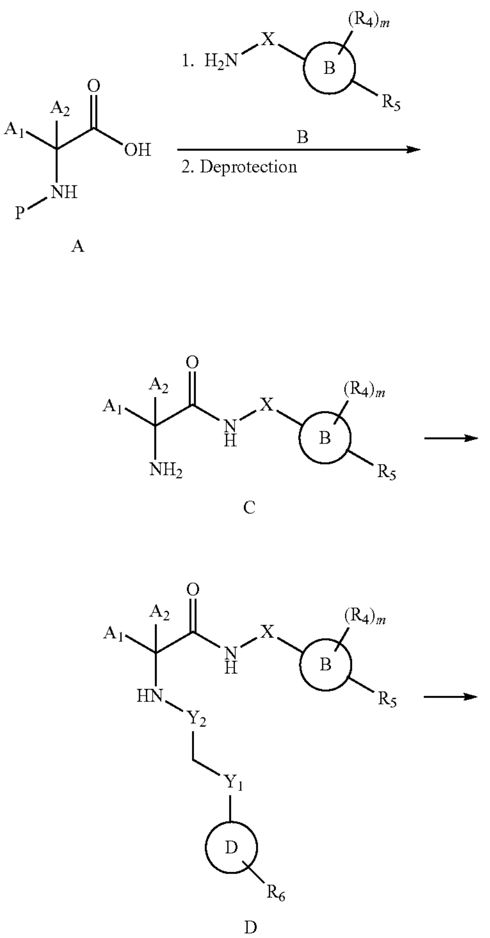

A

C

D

-continued

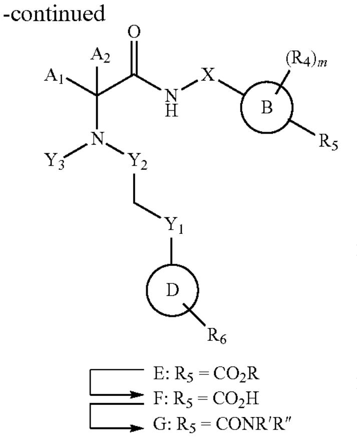

Intermediates N and W can be obtained in 2 steps from amine B and Intermediates J and V respectively (scheme 2 and 3). First, a saponification of esters J or V in basic aqueous conditions, using typically an aqueous sodium hydroxide or an aqueous lithium hydroxide solution. If necessary, a mixture with an organic solvent like THF or dioxane can be used. Then, the obtained carboxylic acid can undergo an amide coupling with the appropriate amine B via the preparation of an activated acid intermediate, like previously described.

Intermediates J and L can be obtained from Intermediates H and K respectively via α-arylation of an ester I, catalyzed with a transition metal such as palladium (scheme 2). Intermediate J can be alternatively obtained by functionalization of phenol M, typically via a Mitsunobu reaction with an aliphatic alcohol, in presence of a dialkyl azodicarboxylate, like DIAD, and triphenylphosphine, either in solution or polymer bound. Intermediate J can also be obtained from phenol M via a nucleophilic substitution, using the appropriate electrophile and a base such as potassium carbonate.

Intermediate M can be obtained by deprotection of the protected phenol L. In the case of a trimethylsilyl protected phenol L, a simple acidic work up can generate phenol M. Likewise, a silyl protected phenol L can be cleaved in acid conditions, typically a HCl solution in an organic solvent, or in presence of fluoride anion, like TBAF for example.

Scheme 2: General preparation of Examples O

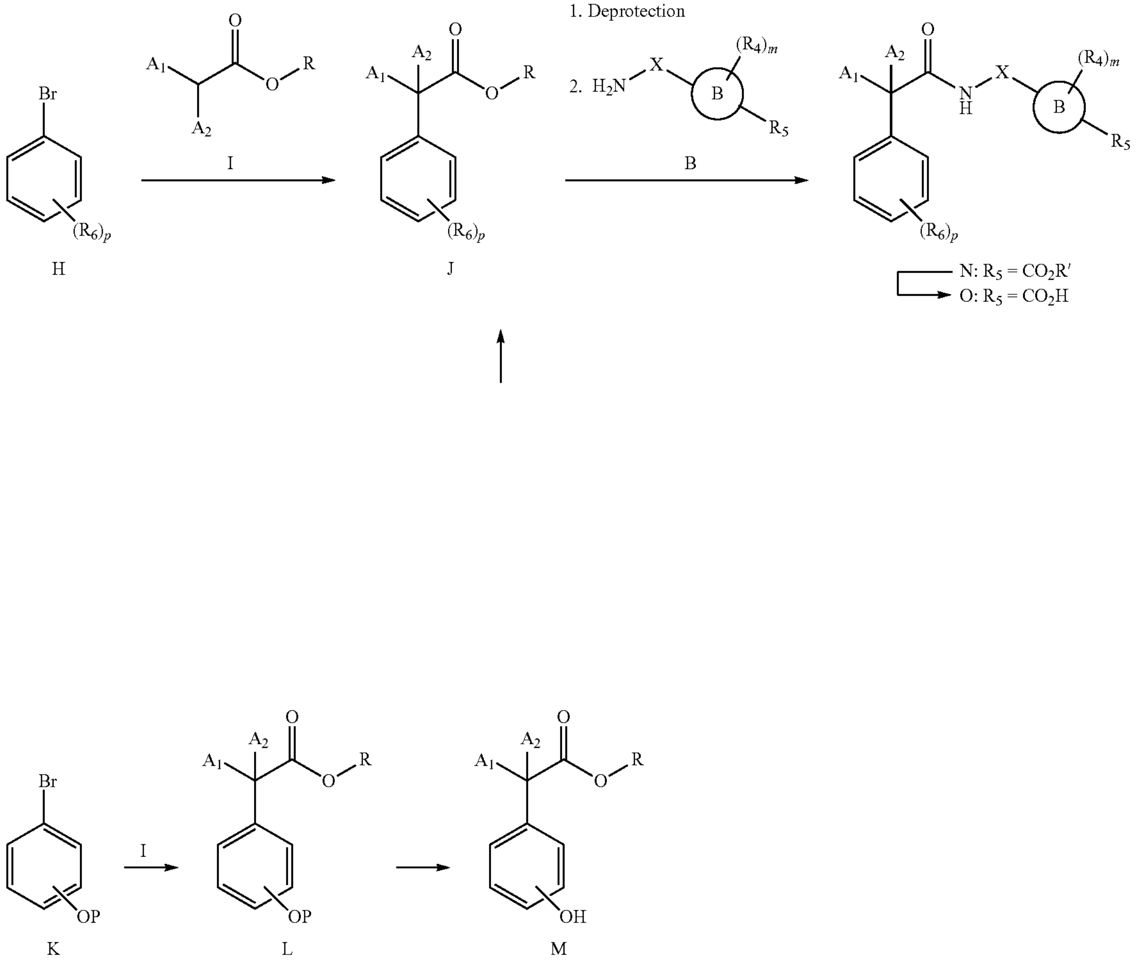

Intermediate V can be obtained from Intermediate T in a 2-step sequence (scheme 3). First, hydration of the cyanide T can generate the corresponding primary amide, typically in presence of $H_2O_2$ in basic aqueous conditions, which can ultimately yield the ester V by treatment with DMF-DMA in methanol or in a mixture of methanol and another organic solvent. If appropriate, Intermediate T can be obtained from a halogeno-heteroaryl R by aromatic nucleophilic substitution in presence of a nucleophile, such as an alcoholate generated in situ from an aliphatic alcohol and a strong base like sodium hydride. Otherwise, Intermediate T can be obtained by coupling between the halogeno-heteroaryl R and an appropriate aliphatic alcohol catalyzed with a transition metal such as palladium. This 2-step sequence can also be reversed to generate intermediate V via intermediate U. Intermediate R can be directly obtained from a di-halogeno-heteroaryl P by aromatic nucleophilic substitution with the appropriate nucleophile, such as a carbanion generated in the α-position of a cyanide with a strong base like n-BuLi or KHMDS. Otherwise, it can be generated in a 2 step-sequence from a di-halogeno-heteroaryl P. First, an aromatic nucleophilic substitution with the carbanion of acetonitrile, generated by treatment of acetonitrile with a strong base like n-Buli or KHMDS, can yield the intermediate Q. Then, intermediate R can be obtained by nucleophilic substitution with the appropriate electrophile, in presence of a strong base, such as sodium hydride.

Intermediate AH can be obtained by amide coupling between Intermediate AG and amine B, via preparation of the activated acid intermediate, like previously described (scheme 4). Intermediate AG can be obtained in 2 different ways from Intermediate AD. A di-nucleophilic substitution of amino-ester AE on Intermediate AD in basic conditions, typically by using potassium carbonate as a base in an organic solvent, followed by the saponification of the ester in basic aqueous conditions can generate Intermediate AG. Otherwise, a di-nucleophilic substitution of amino-alcohol AF on Intermediate AD in basic conditions, typically by using potassium carbonate as a base in an organic solvent, followed by oxidation of the primary alcohol can also generate Intermediate AG. In some cases, addition of sodium iodide can facilitate these di-nucleophilic substitutions. The dibrominated Intermediate AD can be obtained form the corresponding di-alcohol Intermediate AC, using a brominating agent such as N-bromosuccinimide in presence of triphenylphosphine. Intermediate AC can be obtained by deprotection of the primary alcohol of Intermediate AB. This deprotection is adapted to the used protecting group. For instance, in case of ester groups, a reduction step, using a reductant such as lithium aluminium hydride, can be performed to generate Intermediate AC. In case of silyl protecting groups, the di-alcohol Intermediate AC can be obtained in presence of of fluoride anion, like TBAF for example. Intermediate AB can be obtained from the sec Scheme 3: General preparation of Examples X

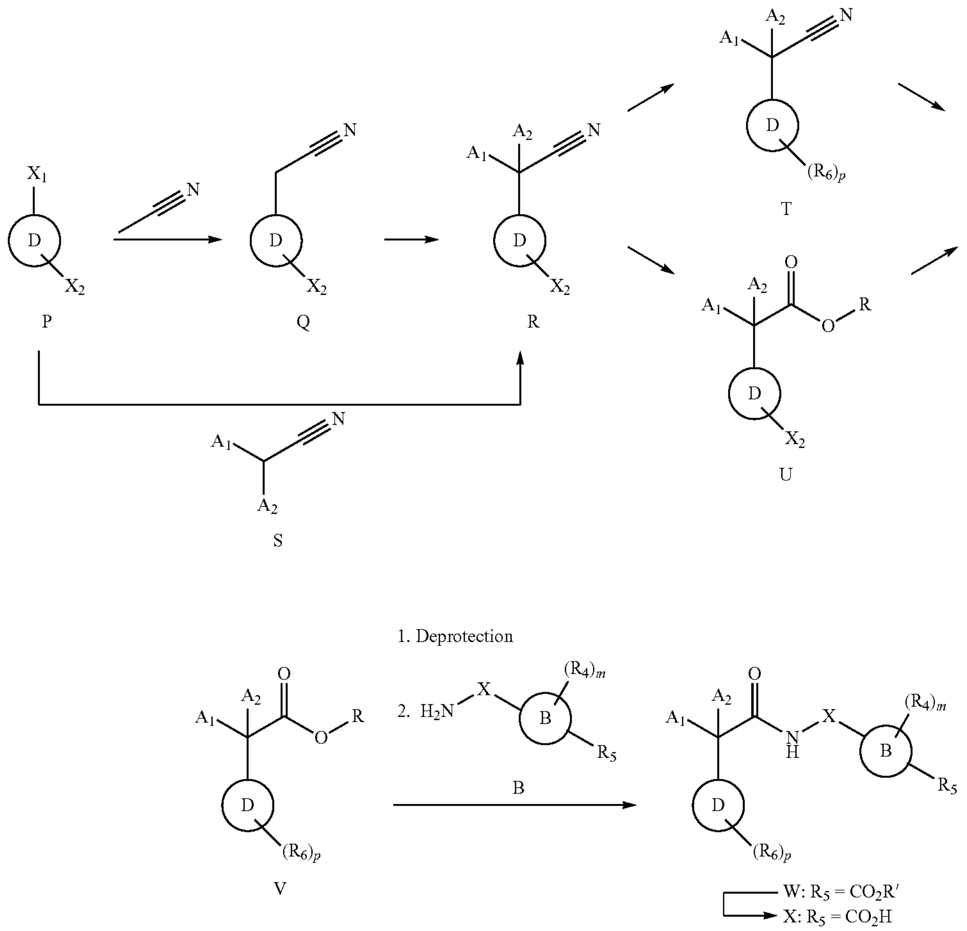

ondary alcohol AA, either via a Mitsunobu reaction when appropriate, otherwise via nucleophilic substitution on the appropriate electrophile in basic conditions.

Scheme 4: General preparation of Examples AH, AI and AJ

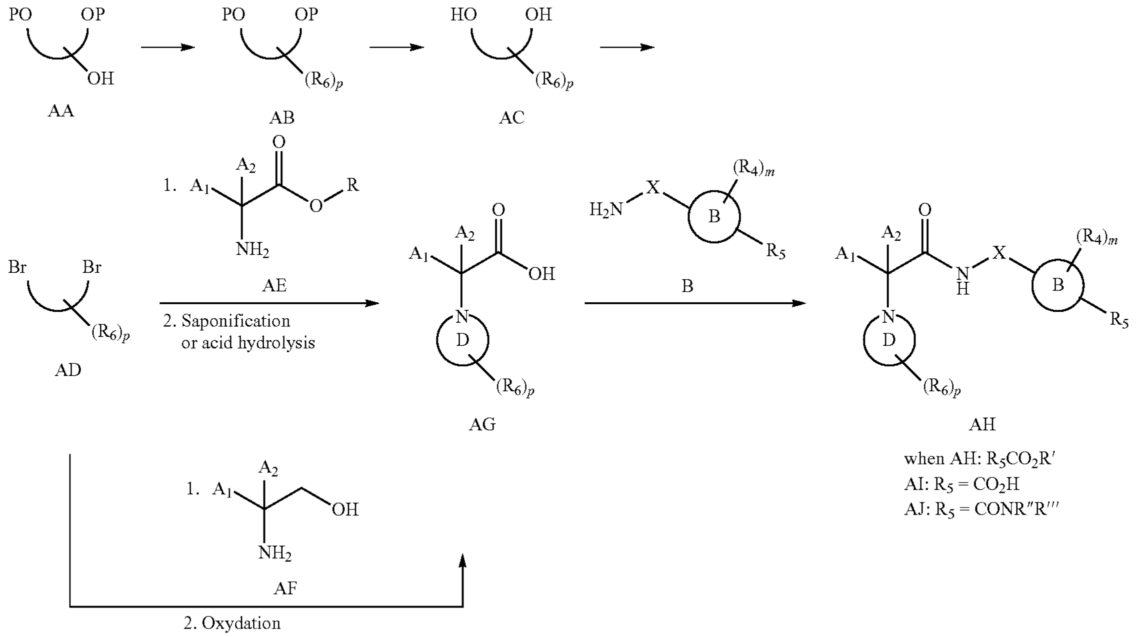

The following definitions apply throughout the present specification and the claims, unless specifically indicated otherwise.

The term "hydrocarbon group" refers to a group consisting of carbon atoms and hydrogen atoms.

The term "alicyclic" is used in connection with cyclic groups and denotes that the corresponding cyclic group is non-aromatic.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_{1-5}$ alkyl" denotes an alkyl group having 1 to 5 carbon atoms. Preferred exemplary alkyl groups are methyl, ethyl, propyl (e.g., n-propyl or isopropyl), or butyl (e.g., n-butyl, isobutyl, sec-butyl, or tert-butyl). Unless defined otherwise, the term "alkyl" preferably refers to $C_{1-4}$ alkyl, more preferably to methyl or ethyl, and even more preferably to methyl.

As used herein, the term "alkenyl" refers to a monovalent unsaturated acyclic hydrocarbon group which may be linear or branched and comprises one or more (e.g., one or two) carbon-to-carbon double bonds while it does not comprise any carbon-to-carbon triple bond. The term "$C_{2-5}$ alkenyl" denotes an alkenyl group having 2 to 5 carbon atoms. Preferred exemplary alkenyl groups are ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl). Unless defined otherwise, the term "alkenyl" preferably refers to $C_{2-4}$ alkenyl.

As used herein, the term "alkynyl" refers to a monovalent unsaturated acyclic hydrocarbon group which may be linear or branched and comprises one or more (e.g., one or two) carbon-to-carbon triple bonds and optionally one or more (e.g., one or two) carbon-to-carbon double bonds. The term "$C_{2-5}$ alkynyl" denotes an alkynyl group having 2 to 5 carbon atoms. Preferred exemplary alkynyl groups are ethynyl, propynyl (e.g., propargyl), or butynyl. Unless defined otherwise, the term "alkynyl" preferably refers to $C_{2-4}$ alkynyl.

As used herein, the term "alkylene" refers to an alkanediyl group, i.e. a divalent saturated acyclic hydrocarbon group which may be linear or branched. A "$C_{1-5}$ alkylene" denotes an alkylene group having 1 to 5 carbon atoms, and the term "$C_{0-3}$ alkylene" indicates that a covalent bond (corresponding to the option "$C_0$ alkylene") or a $C_{1-3}$ alkylene is present. Preferred exemplary alkylene groups are methylene ($-CH_2-$), ethylene (e.g., $-CH_2-CH_2-$ or $-CH(-CH_3)-$), propylene (e.g., $-CH_2-CH_2-CH_2-$, $-CH(-CH_2-CH_3)-$, $-CH_2-CH(-CH_3)-$, or $-CH(-CH_3)-CH_2-$), or butylene (e.g., $-CH_2-CH_2-CH_2-CH_2-$). Unless defined otherwise, the term "alkylene" preferably refers to $C_{1-4}$ alkylene (including, in particular, linear $C_{1-4}$ alkylene), more preferably to methylene or ethylene, and even more preferably to methylene.

As used herein, the term "alkenylene" refers to an alkenediyl group, i.e. a divalent unsaturated acyclic hydrocarbon group which may be linear or branched and comprises one or more (e.g., one or two) carbon-to-carbon double bonds while it does not comprise any carbon-to-carbon triple bond. A "$C_{2-5}$ alkenylene" denotes an alkenylene group having 2 to 5 carbon atoms. Unless defined otherwise, the term "alkenylene" preferably refers to $C_{2-4}$ alkenylene (including, in particular, linear $C_{2-4}$ alkenylene).

As used herein, the term "alkynylene" refers to an alkynediyl group, i.e. a divalent unsaturated acyclic hydrocarbon group which may be linear or branched and comprises one or more (e.g., one or two) carbon-to-carbon triple bonds and optionally one or more (e.g., one or two) carbon-to-carbon double bonds. A "$C_{2-5}$ alkynylene" denotes an alkynylene group having 2 to 5 carbon atoms. Unless defined otherwise, the term “alkynylene” preferably refers to $C_{2-4}$ alkynylene (including, in particular, linear $C_{2-4}$ alkynylene).

As used herein, the term “carbocyclyl” refers to a hydrocarbon ring group, including monocyclic rings as well as bridged ring, spiro ring and/or fused ring systems (which may be composed, e.g., of two or three rings), wherein said ring group may be saturated, partially unsaturated (i.e., unsaturated but not aromatic) or aromatic. Unless defined otherwise, “carbocycyl” preferably refers to aryl, cycloalkyl or cycloalkenyl.

As used herein, the term “heterocyclyl” refers to a ring group, including monocyclic rings as well as bridged ring, spiro ring and/or fused ring systems (which may be composed, e.g., of two or three rings), wherein said ring group comprises one or more (such as, e.g., one, two, three, or four) ring heteroatoms independently selected from 0, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group may be saturated, partially unsaturated (i.e., unsaturated but not aromatic) or aromatic. For example, each heteroatom-containing ring comprised in said ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. Unless defined otherwise, “heterocyclyl” preferably refers to heteroaryl, heterocycloalkyl or heterocycloalkenyl.

As used herein, the term “carbocyclic group” has the same meaning as “carbocyclyl”, and the term “heterocyclic group” has the same meaning as “heterocyclyl”. It will be understood that the rings A and B, which may each be a carbocyclic group or a heterocyclic group, are divalent ring groups (i.e., ring A is attached to —CO—N($R^2$)—X—B[(—$R^4$),]—$R^5$ and to -L-D[(—$R^5$)$_p$]; ring B is attached to the atom X and to the group $R^5$), and furthermore that ring A is attached via the same ring carbon atom (of ring A) to both the moiety —CO—N($R^2$)—X—B[(—$R^4$)$_m$]—$R^5$ and the moiety -L-D[(—$R^6$)$_p$], as also depicted in formula (Ia); these features of the rings A and B also apply to the definitions of the respective ring groups provided herein, including the exemplary ring groups indicated in each definition (insofar as ring A or B is concerned), For example, if ring A is arylene, it will be understood that phenylene (as ring A), which is disclosed herein as an exemplary arylene group, must be present as phen-1,1-diyl.

As used herein, the term “carbocyclylene” refers to a carbocyclyl group, as defined herein above, but having two points of attachment (i.e., a divalent carbocyclyl group). Unless defined otherwise, “carbocyclylene” preferably refers to cycloalkylene or arylene.

As used herein, the term “heterocyclylene” refers to a heterocyclyl group, as defined herein above, but having two points of attachment (i.e., a divalent heterocyclyl group). Unless defined otherwise, “heterocyclylene” preferably refers to heterocycloalkylene or heteroarylene.

As used herein, the term “aryl” refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). “Aryl” may, e.g., refer to phenyl, naphthyl, dialinyl (i.e., 1,2-dihydronaphthyl), tetralinyl (i.e., 1,2,3,4-tetrahydronaphthyl), indanyl, indenyl (e.g., 1H-indenyl), anthracenyl, phenanthrenyl, 9H-fluorenyl, or azulenyl. Unless defined otherwise, an “aryl” preferably has 6 to 14 ring atoms, more preferably 6 to 10 ring atoms, even more preferably refers to phenyl or naphthyl, and most preferably refers to phenyl.

As used herein, the term “arylene” refers to an aryl group, as defined herein above, but having two points of attachment, i.e. a divalent aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). “Arylene” may, e.g., refer to phenylene (e.g., phen-1,2-diyl, phen-1,3-diyl, or phen-1,4-diyl), naphthylene (e.g., naphthalen-1,2-diyl, naphthalen-1,3-diyl, naphthalen-1,4-diyl, naphthalen-1,5-diyl, naphthalen-1,6-diyl, naphthalen-1,7-diyl, naphthalen-2,3-diyl, naphthalen-2,5-diyl, naphthalen-2,6-diyl, naphthalen-2,7-diyl, or naphthalen-2,8-diyl), 1,2-dihydronaphthylene, 1,2,3,4-tetrahydronaphthylene, indanylene, indenylene, anthracenylene, phenanthrenylene, 9H-fluorenylene, or azulenylene.

Unless defined otherwise, an “arylene” preferably has 6 to 14 ring atoms, more preferably 6 to 10 ring atoms, even more preferably refers to phenylene or naphthylene, and most preferably refers to phenylene (particularly phen-1,4-diyl).

As used herein, the term “heteroaryl” refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. “Heteroaryl” may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromanyl, chromenyl (e.g., 2H-1-benzopyranyl or 4H-1-benzopyranyl), isochromenyl (e.g., 1H-2-benzopyranyl), chromonyl, xanthenyl, phenoxathiinyl, pyrrolyl (e.g., 1H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolyl (e.g., 3H-indolyl), isoindolyl, indazolyl, indolizinyl, purinyl, quinolyl, isoquinolyl, phthalazinyl, naphthyridinyl, quinoxalinyl, cinnolinyl, pteridinyl, carbazolyl, β-carbolinyl, phenanthridinyl, acridinyl, perimidinyl, phenanthrolinyl (e.g., [1,10]phenanthrolinyl, [1,7]phenanthrolinyl, or [4,7] phenanthrolinyl), phenazinyl, thiazolyl, isothiazolyl, phenothiazinyl, oxazolyl, isoxazolyl, oxadiazolyl (e.g., 1,2,4-oxadiazolyl, 1,2,5-oxadiazolyl (i.e., furazanyl), or 1,3,4-oxadiazolyl), thiadiazolyl (e.g., 1,2,4-thiadiazolyl, 1,2,5-thiadiazolyl, or 1,3,4-thiadiazolyl), phenoxazinyl, pyrazolo [1,5-a]pyrimidinyl (e.g., pyrazolo[1,5-a]pyrimidin-3-yl), 1,2-benzoisoxazol-3-yl, benzothiazolyl, benzothiadiazolyl, benzoxazolyl, benzisoxazolyl, benzimidazolyl, benzo[b] thiophenyl (i.e., benzothienyl), triazolyl (e.g., 1H-1,2,3-triazolyl, 2H-1,2,3-triazolyl, 1H-1,2,4-triazolyl, or 4H-1,2,4-triazolyl), benzotriazolyl, 1H-tetrazolyl, 2H-tetrazolyl, triazinyl (e.g., 1,2,3-triazinyl, 1,2,4-triazinyl, or 1,3,5-triazinyl), furo[2,3-c]pyrdinyl, dihydrofuropyridinyl (e.g., 2,3-dihydrofuro[2,3-c]pyridinyl or 1,3-dihydrofuro[3,4-c] pyridinyl), imidazopyridinyl (e.g., imidazo[1,2-a]pyridinyl or imidazo[3,2-a]pyridinyl), quinazolinyl, thienopyridinyl, tetrahydrothienopyridinyl (e.g., 4,5,6,7-tetrahydrothieno[3,2-c]pyridinyl), dibenzofuranyl, 1,3-benzodioxolyl, benzodioxanyl (e.g., 1,3-benzodioxanyl or 1,4-benzodioxanyl), or coumarinyl. Unless defined otherwise, the term "heteroaryl" preferably refers to a 5 to 14 membered (more preferably 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroaryl" refers to a 5 or 6 membered monocyclic ring comprising one or more (e.g., one, two or three) ring heteroatoms independently selected from O, S and N, wherein one or more S ring atoms (if present) and/or one or more N ring atoms (if present) are optionally oxidized, and wherein one or more carbon ring atoms are optionally oxidized.

As used herein, the term "heteroarylene" refers to a heteroaryl group, as defined herein above, but having two points of attachment, i.e. a divalent aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three, or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroarylene" may, e.g., refer to thienylene (i.e., thiophenylene; e.g., thien-2,3-diyl, thien-2,4-diyl, or thien-2,5-diyl), benzo[b]thienylene, naphtho[2,3-b]thienylene, thianthrenylene, furylene (i.e., furanylene; e.g., furan-2,3-diyl, furan-2,4-diyl, or furan-2,5-diyl), benzofuranylene, isobenzofuranylene, chromanylene, chromenylene, isochromenylene, chromonylene, xanthenylene, phenoxathiinylene, pyrrolylene, imidazolylene, pyrazolylene, pyridylene (i.e., pyridinylene), pyrazinylene, pyrimidinylene, pyridazinylene, indolylene, isoindolylene, indazolylene, indolizinylene, purinylene, quinolylene, isoquinolylene, phthalazinylene, naphthyridinylene, quinoxalinylene, cinnolinylene, pteridinylene, carbazolylene, s-carbolinylene, phenanthridinylene, acridinylene, perimidinylene, phenanthrolinylene, phenazinylene, thiazolylene (e.g., thiazol-2,4-diyl, thiazol-2,5-diyl, or thiazol-4,5-diyl), isothiazolylene (e.g., isothiazol-3,4-diyl, isothiazol-3,5-diyl, or isothiazol-4,5-diyl), phenothiazinylene, oxazolylene (e.g., oxazol-2,4-diyl, oxazol-2,5-diyl, or oxazol-4,5-diyl), isoxazolylene (e.g., isoxazol-3,4-diyl, isoxazol-3,5-diyl, or isoxazol-4,5-diyl), oxadiazolylene (e.g., 1,2,4-oxadiazol-3,5-diyl, 1,2,5-oxadiazol-3,4-diyl, or 1,3,4-oxadiazol-2,5-diyl), thiadiazolylene (e.g., 1,2,4-thiadiazol-3,5-diyl, 1,2,5-thiadiazol-3,4-diyl, or 1,3,4-thiadiazol-2,5-diyl), phenoxazinylene, pyrazolo[1,5-a]pyrimidinylene, 1,2-benzoisoxazolylene, benzothiazolylene, benzothiadiazolylene, benzoxazolylene, benzisoxazolylene, benzimidazolylene, benzo[b]thiophenylene (i.e., benzothienylene), triazolylene (e.g., 1H-1,2,3-triazolylene, 2H-1,2,3-triazolylene, 1H-1,2,4-triazolylene, or 4H-1,2,4-triazolylene), benzotriazolylene, 1H-tetrazolylene, 2H-tetrazolylene, triazinylene (e.g., 1,2,3-triazinylene, 1,2,4-triazinylene, or 1,3,5-triazinylene), furo[2,3-c]pyridinylene, dihydrofuropyridinylene (e.g., 2,3-dihydrofuro[2,3-c]pyridinylene or 1,3-dihydrofuro[3,4-c]pyridinylene), imidazopyridinylene (e.g., imidazo[1,2-a]pyridinylene or imidazo[3,2-a]pyridinylene), quinazolinylene, thienopyridinylene, tetrahydrothienopyridinylene (e.g., 4,5,6,7-tetrahydrothieno[3,2-c]pyridinylene), dibenzofuranylene, 1,3-benzodioxolylene, benzodioxanylene (e.g., 1,3-benzodioxanylene or 1,4-benzodioxanylene), or coumarinylene. Unless defined otherwise, the term "heteroarylene" preferably refers to a divalent 5 to 14 membered (more preferably 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroarylene" refers to a divalent 5 or 6 membered monocyclic ring comprising one or more (e.g., one, two or three) ring heteroatoms independently selected from O, S, and N, wherein one or more S ring atoms (if present) and/or one or more N ring atoms (if present) are optionally oxidized, and wherein one or more carbon ring atoms are optionally oxidized. A "heteroarylene", including any of the specific heteroarylene groups described herein, may be attached through two carbon ring atoms, particularly through those two carbon ring atoms that have the greatest distance from one another (in terms of the number of ring atoms separating them by the shortest possible connection) within one single ring or within the entire ring system of the corresponding heteroarylene.

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, decalinyl (i.e., decahydronaphthyl), or adamantyl. Unless defined otherwise, "cycloalkyl" preferably refers to a $C_{3-11}$ cycloalkyl, and more preferably refers to a $C_{3-7}$ cycloalkyl. A particularly preferred "cycloalkyl" is a monocyclic saturated hydrocarbon ring having 3 to 7 ring members (e.g., cyclopropyl or cyclohexyl).

As used herein, the term "cycloalkylene" refers to a cycloalkyl group, as defined herein above, but having two points of attachment, i.e. a divalent saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkylene" may, e.g., refer to cyclopropylene (e.g., cyclopropan-1,1-diyl or cyclopropan-1,2-diyl), cyclobutylene (e.g., cyclobutan-1,1-diyl, cyclobutan-1,2-diyl, or cyclobutan-1,3-diyl), cyclopentylene (e.g., cyclopentan-1,1-diyl, cyclopentan-1,2-diyl, or cyclopentan-1,3-diyl), cyclohexylene (e.g., cyclohexan-1,1-diyl, cyclohexan-1,2-diyl, cyclohexan-1,3-diyl, or cyclohexan-1,4-diyl), cycloheptylene, decalinylene (i.e., decahydronaphthylene), or adamantylene. Unless defined otherwise, "cycloalkylene" preferably refers to a $C_{3-11}$ cycloalkylene, and more preferably refers to a $C_{3-7}$ cycloalkylene. A particularly preferred "cycloalkylene" is a divalent monocyclic saturated hydrocarbon ring having 3 to 7 ring members (e.g., cyclopropylene or cyclohexylene).

As used herein, the term "heterocycloalkyl" refers to a saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkyl" may, e.g., refer to aziridinyl, azetidinyl, pyrrolidinyl, imidazolidinyl, pyrazolidinyl, piperidinyl, piperazinyl, azepanyl, diazepanyl (e.g., 1,4-diazepanyl), oxazolidinyl, isoxazolidinyl, thiazolidinyl, isothiazolidinyl, morpholinyl (e.g., morpholin-4-yl), thiomorpholinyl (e.g., thiomorpholin-4-yl), oxazepanyl, oxiranyl, oxetanyl, tetrahydrofuranyl, 1,3-dioxolanyl, tetrahydropyranyl, 1,4-dioxanyl, oxepanyl, thiiranyl, thietanyl, tetrahydrothiophenyl (i.e., thiolanyl), 1,3-dithiolanyl, thianyl, 1,1-dioxothianyl, thiepanyl, decahydroquinolinyl, decahydroisoquinolinyl, or 2-oxa-5-aza-bicyclo[2.2.1]hept-5-yl. Unless defined otherwise, "heterocycloalkyl" preferably refers to a 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized; more preferably, "heterocycloalkyl" refers to a 5 to 7 membered saturated monocyclic ring group containing one or more (e.g., one, two, or three) ring heteroatoms independently selected from O, S and N, wherein one or more S ring atoms (if present) and/or one or more N ring atoms (if present) are optionally oxidized, and wherein one or more carbon ring atoms are optionally oxidized.

As used herein, the term "heterocycloalkylene" refers to a heterocycloalkyl group, as defined herein above, but having two points of attachment, i.e. a divalent saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkylene" may, e.g., refer to aziridinylene, azetidinylene, pyrrolidinylene, imidazolidinylene, pyrazolidinylene, piperidinylene, piperazinylene, azepanylene, diazepanylene (e.g., 1,4-diazepanylene), oxazolidinylene, isoxazolidinylene, thiazolidinylene, isothiazolidinylene, morpholinylene, thiomorpholinylene, oxazepanylene, oxiranylene, oxetanylene, tetrahydrofuranylene, 1,3-dioxolanylene, tetrahydropyranylene, 1,4-dioxanylene, oxepanylene, thiiranylene, thietanylene, tetrahydrothiophenylene (i.e., thiolanylene), 1,3-dithiolanylene, thianylene, 1,1-dioxothianylene, thiepanylene, decahydroquinolinylene, decahydroisoquinolinylene, or 2-oxa-5-aza-bicyclo[2.2.1]hept-5-ylene. Unless defined otherwise, "heterocycloalkylene" preferably refers to a divalent 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized; more preferably, "heterocycloalkylene" refers to a divalent 5 to 7 membered saturated monocyclic ring group containing one or more (e.g., one, two, or three) ring heteroatoms independently selected from O, S and N, wherein one or more S ring atoms (if present) and/or one or more N ring atoms (if present) are optionally oxidized, and wherein one or more carbon ring atoms are optionally oxidized.

As used herein, the term "cycloalkenyl" refers to an unsaturated alicyclic (non-aromatic) hydrocarbon ring group, including monocyclic rings as well as bridged ring, spiro ring and/or fused ring systems (which may be composed, e.g., of two or three rings; such as, e.g., a fused ring system composed of two or three fused rings), wherein said hydrocarbon ring group comprises one or more (e.g., one or two) carbon-to-carbon double bonds and does not comprise any carbon-to-carbon triple bond. "Cycloalkenyl" may, e.g., refer to cyclopropenyl, cyclobutenyl, cyclopentenyl, cyclohexenyl, cyclohexadienyl, cycloheptenyl, or cycloheptadienyl. Unless defined otherwise, "cycloalkenyl" preferably refers to a $C_{31}$ cycloalkenyl, and more preferably refers to a $C_{3-7}$ cycloalkenyl. A particularly preferred "cycloalkenyl" is a monocyclic unsaturated alicyclic hydrocarbon ring having 3 to 7 ring members and containing one or more (e.g., one or two; preferably one) carbon-to-carbon double bonds.

As used herein, the term "heterocycloalkenyl" refers to an unsaturated alicyclic (non-aromatic) ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from 0, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group comprises at least one double bond between adjacent ring atoms and does not comprise any triple bond between adjacent ring atoms. For example, each heteroatom-containing ring comprised in said unsaturated alicyclic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkenyl" may, e.g., refer to imidazolinyl (e.g., 2-imidazolinyl (i.e., 4,5-dihydro-1H-imidazolyl), 3-imidazolinyl, or 4-imidazolinyl), tetrahydropyridinyl (e.g., 1,2,3,6-tetrahydropyridinyl), dihydropyridinyl (e.g., 1,2-dihydropyridinyl or 2,3-dihydropyridinyl), pyranyl (e.g., 2H-pyranyl or 4H-pyranyl), thiopyranyl (e.g., 2H-thiopyranyl or 4H-thiopyranyl), dihydropyranyl, dihydrofuranyl, dihydropyrazolyl, dihydropyrazinyl, dihydroisoindolyl, octahydroquinolinyl (e.g., 1,2,3,4,4a,5,6,7-octahydroquinolinyl), or octahydroisoquinolinyl (e.g., 1,2,3,4,5,6,7,8-octahydroisoquinolinyl). Unless defined otherwise, "heterocycloalkenyl" preferably refers to a 3 to 11 membered unsaturated alicyclic ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms; more preferably, "heterocycloalkenyl" refers to a 5 to 7 membered monocyclic unsaturated non-aromatic ring group containing one or more (e.g., one, two, or three) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms.

As used herein, the term "halogen" refers to fluoro (—F), chloro (—Cl), bromo (—Br), or iodo (—I).

As used herein, the term "haloalkyl" refers to an alkyl group substituted with one or more (preferably 1 to 6, more preferably 1 to 3) halogen atoms which are selected independently from fluoro, chloro, bromo and iodo, and are preferably all fluoro atoms. It will be understood that the maximum number of halogen atoms is limited by the number of available attachment sites and, thus, depends on the number of carbon atoms comprised in the alkyl moiety of the haloalkyl group. "Haloalkyl" may, e.g., refer to $—CF_3$, $—CHF_2$, $—CH_2F$, $—CF_2—CH_3$, $—CH_2—CF_3$, $—CH_2—CHF_2$, $—CH_2—CF_2—CH_3$, $—CH_2—CF_2—CF_3$, or $—CH(CF_3)_2$. A particularly preferred "haloalkyl" group is $—CF_3$.

The terms "bond" and "covalent bond" are used herein synonymously, unless explicitly indicated otherwise or contradicted by context.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

Various groups are referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

A skilled person will appreciate that the substituent groups comprised in the compounds of the present invention may be attached to the remainder of the respective compound via a number of different positions of the corresponding specific substituent group. Unless defined otherwise, the preferred attachment positions for the various specific substituent groups are as illustrated in the examples.

As used herein, unless explicitly indicated otherwise or contradicted by context, the terms "a", "an" and "the" are used interchangeably with "one or more" and "at least one". Thus, for example, a composition comprising "a" compound of formula (I) can be interpreted as referring to a composition comprising "one or more" compounds of formula (I).

It is to be understood that wherever numerical ranges are provided/disclosed herein, all values and subranges encompassed by the respective numerical range are meant to be encompassed within the scope of the invention. Accordingly, the present invention specifically and individually relates to each value that falls within a numerical range disclosed herein, as well as each subrange encompassed by a numerical range disclosed herein.

As used herein, the term "about" preferably refers to ±10% of the indicated numerical value, more preferably to ±5% of the indicated numerical value, and in particular to the exact numerical value indicated. If the term "about" is used in connection with the endpoints of a range, it preferably refers to the range from the lower endpoint −10% of its indicated numerical value to the upper endpoint ±10% of its indicated numerical value, more preferably to the range from of the lower endpoint −5% to the upper endpoint ±5%, and even more preferably to the range defined by the exact numerical values of the lower endpoint and the upper endpoint.

As used herein, the term "comprising" (or "comprise", "comprises", "contain", "contains", or "containing"), unless explicitly indicated otherwise or contradicted by context, has the meaning of "containing, inter alia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

The scope of the invention embraces all pharmaceutically acceptable salt forms of the compounds of formula (I) which may be formed, e.g., by protonation of an atom carrying an electron lone pair which is susceptible to protonation, such as an amino group, with an inorganic or organic acid, or as a salt of an acid group (such as a carboxylic acid group) with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts (such as, e.g., sulfate or hydrogensulfate salts), nitrate salts, phosphate salts (such as, e.g., phosphate, hydrogenphosphate, or dihydrogenphosphate salts), carbonate salts, hydrogencarbonate salts, perchlorate salts, borate salts, or thiocyanate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, adipate, gluconate, glycolate, nicotinate, benzoate, salicylate, ascorbate, pamoate (embonate), camphorate, glucoheptanoate, or pivalate salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; glycerophosphate salts; and acidic amino acid salts such as aspartate or glutamate salts. Preferred pharmaceutically acceptable salts of the compounds of formula (I) include a hydrochloride salt, a hydrobromide salt, a mesylate salt, a sulfate salt, a tartrate salt, a fumarate salt, an acetate salt, a citrate salt, and a phosphate salt. A particularly preferred pharmaceutically acceptable salt of the compound of formula (I) is a hydrochloride salt. Accordingly, it is preferred that the compound of formula (I), including any one of the specific compounds of formula (I) described herein, is in the form of a hydrochloride salt, a hydrobromide salt, a mesylate salt, a sulfate salt, a tartrate salt, a fumarate salt, an acetate salt, a citrate salt, or a phosphate salt, and it is particularly preferred that the compound of formula (I) is in the form of a hydrochloride salt.

The present invention also specifically relates to the compound of formula (I), including any one of the specific compounds of formula (I) described herein, in non-salt form.

Moreover, the scope of the invention embraces the compounds of formula (I) in any solvated form, including, e.g., solvates with water (i.e., as a hydrate) or solvates with organic solvents such as, e.g., methanol, ethanol, isopropanol, acetic acid, ethyl acetate, ethanolamine, DMSO, or acetonitrile. All physical forms, including any amorphous or crystalline forms (i.e., polymorphs), of the compounds of formula (I) are also encompassed within the scope of the invention. It is to be understood that such solvates and physical forms of pharmaceutically acceptable salts of the compounds of the formula (I) are likewise embraced by the invention.

Furthermore, the compounds of formula (I) may exist in the form of different isomers, in particular stereoisomers (including, e.g., geometric isomers (or cis/trans isomers), enantiomers and diastereomers) or tautomers (including, in particular, prototropic tautomers, such as keto/enol tautomers or thione/thiol tautomers). All such isomers of the compounds of formula (I) are contemplated as being part of the present invention, either in admixture or in pure or substantially pure form. As for stereoisomers, the invention embraces the isolated optical isomers of the compounds according to the invention as well as any mixtures thereof (including, in particular, racemic mixtures/racemates). The racemates can be resolved by physical methods, such as, e.g., fractional crystallization, separation or crystallization of diastereomeric derivatives, or separation by chiral column chromatography. The individual optical isomers can also be obtained from the racemates via salt formation with an optically active acid followed by crystallization. The present invention further encompasses any tautomers of the compounds of formula (I). It will be understood that some compounds may exhibit tautomerism. In such cases, the formulae provided herein expressly depict only one of the possible tautomeric forms. The formulae and chemical names as provided herein are intended to encompass any tautomeric form of the corresponding compound and not to be limited merely to the specific tautomeric form depicted by the drawing or identified by the name of the compound.

The scope of the invention also embraces compounds of formula (I), in which one or more atoms are replaced by a specific isotope of the corresponding atom. For example, the invention encompasses compounds of formula (I), in which one or more hydrogen atoms (or, e.g., all hydrogen atoms) are replaced by deuterium atoms (i.e., $^2H$; also referred to as "D"). Accordingly, the invention also embraces compounds of formula (I) which are enriched in deuterium. Naturally occurring hydrogen is an isotopic mixture comprising about 99.98 mol-% hydrogen-1 ($^1H$) and about 0.0156 mol-% deuterium ($^2H$ or D). The content of deuterium in one or more hydrogen positions in the compounds of formula (I) can be increased using deuteration techniques known in the art. For example, a compound of formula (I) or a reactant or precursor to be used in the synthesis of the compound of formula (I) can be subjected to an H/D exchange reaction using, e.g., heavy water ($D_2O$). Further suitable deuteration techniques are described in: Atzrodt J et al., *Bioorg Med*

*Chem*, 20(18), 5658-5667, 2012; William J S et al., *Journal of Labelled Compounds and Radiopharmaceuticals*, 53(11-12), 635-644, 2010; Modvig A et al., *J Org Chem*, 79, 5861-5868, 2014. The content of deuterium can be determined, e.g., using mass spectrometry or NMR spectroscopy. Unless specifically indicated otherwise, it is preferred that the compound of formula (I) is not enriched in deuterium. Accordingly, the presence of naturally occurring hydrogen atoms or $^{1}H$ hydrogen atoms in the compounds of formula (I) is preferred.

The present invention also embraces compounds of formula (I), in which one or more atoms are replaced by a positron-emitting isotope of the corresponding atom, such as, e.g., $^{18}F$, $^{11}C$, $^{13}N$, $^{15}O$, $^{76}Br$, $^{77}Br$, $^{120}I$ and/or $^{124}I$. Such compounds can be used as tracers, trackers or imaging probes in positron emission tomography (PET). The invention thus includes (i) compounds of formula (I), in which one or more fluorine atoms (or, e.g., all fluorine atoms) are replaced by $^{18}F$ atoms, (ii) compounds of formula (I), in which one or more carbon atoms (or, e.g., all carbon atoms) are replaced by $^{11}C$ atoms, (iii) compounds of formula (I), in which one or more nitrogen atoms (or, e.g., all nitrogen atoms) are replaced by $^{13}N$ atoms, (iv) compounds of formula (I), in which one or more oxygen atoms (or, e.g., all oxygen atoms) are replaced by $^{15}O$ atoms, (v) compounds of formula (I), in which one or more bromine atoms (or, e.g., all bromine atoms) are replaced by $^{76}Br$ atoms, (vi) compounds of formula (I), in which one or more bromine atoms (or, e.g., all bromine atoms) are replaced by $^{77}Br$ atoms, (vii) compounds of formula (I), in which one or more iodine atoms (or, e.g., all iodine atoms) are replaced by $^{120}I$ atoms, and (viii) compounds of formula (I), in which one or more iodine atoms (or, e.g., all iodine atoms) are replaced by $^{124}I$ atoms. In general, it is preferred that none of the atoms in the compounds of formula (I) are replaced by specific isotopes.

The compounds provided herein may be administered as compounds per se or may be formulated as medicaments. The medicaments/pharmaceutical compositions may optionally comprise one or more pharmaceutically acceptable excipients, such as carriers, diluents, fillers, disintegrants, lubricating agents, binders, colorants, pigments, stabilizers, preservatives, antioxidants, and/or solubility enhancers.

The pharmaceutical compositions may comprise one or more solubility enhancers, such as, e.g., poly(ethylene glycol), including poly(ethylene glycol) having a molecular weight in the range of about 200 to about 5,000 Da (e.g., PEG 200, PEG 300, PEG 400, or PEG 600), ethylene glycol, propylene glycol, glycerol, a non-ionic surfactant, tyloxapol, polysorbate 80, macrogol-15-hydroxystearate (e.g., Kolliphor® HS 15, CAS 70142-34-6), a phospholipid, lecithin, dimyristoyl phosphatidylcholine, dipalmitoyl phosphatidylcholine, distearoyl phosphatidylcholine, a cyclodextrin, α-cyclodextrin, β-cyclodextrin, γ-cyclodextrin, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, sulfobutylether-β-cyclodextrin, sulfobutylether-γ-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, a carboxyalkyl thioether, hydroxypropyl methylcellulose, hydroxypropylcellulose, polyvinylpyrrolidone, a vinyl acetate copolymer, vinyl pyrrolidone, sodium lauryl sulfate, dioctyl sodium sulfosuccinate, or any combination thereof.

The pharmaceutical compositions may also comprise one or more preservatives, particularly one or more antimicrobial preservatives, such as, e.g., benzyl alcohol, chlorobutanol, 2-ethoxyethanol, m-cresol, chlorocresol (e.g., 2-chloro-3-methyl-phenol or 4-chloro-3-methyl-phenol), benzalkonium chloride, benzethonium chloride, benzoic acid (or a pharmaceutically acceptable salt thereof), sorbic acid (or a pharmaceutically acceptable salt thereof), chlorhexidine, thimerosal, or any combination thereof.

The pharmaceutical compositions can be formulated by techniques known to the person skilled in the art, such as the techniques published in "Remington: The Science and Practice of Pharmacy", Pharmaceutical Press, 22$^{nd}$ edition. The pharmaceutical compositions can be formulated as dosage forms for oral, parenteral, such as intramuscular, intravenous, subcutaneous, intradermal, intraarterial, intracardial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds of formula (I) or the above described pharmaceutical compositions comprising a compound of formula (I) may be administered to a subject by any convenient route of administration, whether systemically/peripherally or at the site of desired action, including but not limited to one or more of: oral (e.g., as a tablet, capsule, or as an ingestible solution), topical (e.g., transdermal, intranasal, ocular, buccal, and sublingual), parenteral (e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, intraocular, subcutaneous, ophthalmic (including intravitreal or intracameral), rectal, or vaginal administration.

If said compounds or pharmaceutical compositions are administered parenterally, then examples of such administration include one or more of: intravenously, intraarterially, intraperitoneally, intrathecally, intraventricularly, intraurethrally, intrasternally, intracardially, intracranially, intramuscularly or subcutaneously administering the compounds or pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

For oral administration, the compounds or pharmaceutical compositions are preferably administered by oral ingestion, particularly by swallowing. The compounds or pharmaceutical compositions can thus be administered to pass through the mouth into the gastrointestinal tract, which can also be referred to as "oral-gastrointestinal" administration.

Alternatively, said compounds or pharmaceutical compositions can be administered in the form of a suppository or pessary, or may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by sustained release systems. Suitable examples of sustained-release compositions include semi-permeable polymer matrices in the form of shaped articles, e.g., films, or microcapsules. Sustained-release matrices include, e.g., polylactides, copolymers of L-glutamic acid and gamma-ethyl-L-glutamate, poly(2-hydroxyethyl methacrylate), ethylene vinyl acetate, or poly-D-(−)-3-hydroxybutyric acid. Sustained-release pharmaceutical compositions also include liposomally entrapped compounds. The present invention thus also relates to liposomes containing a compound of the invention.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

It is also envisaged to prepare dry powder formulations of the compounds of formula (I) for pulmonary administration, particularly inhalation. Such dry powders may be prepared by spray drying under conditions which result in a substantially amorphous glassy or a substantially crystalline bioactive powder. Accordingly, dry powders of the compounds of the present invention can be made according to an emulsification/spray drying process.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

The present invention thus relates to the compounds or the pharmaceutical compositions provided herein, wherein the corresponding compound or pharmaceutical composition is to be administered by any one of: an oral route; topical route, including by transdermal, intranasal, ocular, buccal, or sublingual route; parenteral route using injection techniques or infusion techniques, including by subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intrasternal, intraventricular, intraurethral, or intracranial route; pulmonary route, including by inhalation or insufflation therapy; gastrointestinal route; intrauterine route; intraocular route; subcutaneous route; ophthalmic route, including by intravitreal, or intracameral route; rectal route; or vaginal route. Preferred routes of administration are oral administration or parenteral administration. For each of the compounds or pharmaceutical compositions provided herein, it is particularly preferred that the respective compound or pharmaceutical composition is to be administered orally (particularly by oral ingestion).

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds according to the invention for oral administration to a human (of approximately 70 kg body weight) may be 0.05 to 2000 mg, preferably 0.1 mg to 1000 mg, of the active ingredient per unit dose. The unit dose may be administered, e.g. 1 to 3 times per day. The unit dose may also be administered 1 to 7 times per week, e.g., with not more than one administration per day. It will be appreciated that it may be necessary to make routine variations to the dosage depending on the age and weight of the patient/subject as well as the severity of the condition to be treated. The precise dose and also the route of administration will ultimately be at the discretion of the attendant physician or veterinarian.

The compound of formula (I) or a pharmaceutical composition comprising the compound of formula (I) can be administered in monotherapy (e.g., without concomitantly administering any further therapeutic agents, or without concomitantly administering any further therapeutic agents against the same disease that is to be treated or prevented with the compound of formula (I)). Thus, the present invention relates to the compound of formula (I) or a corresponding pharmaceutical composition for use in the monotherapeutic treatment of cancer, a neovascular eye disease, inflammatory pain, or an inflammatory disease. In particular, the invention relates to the monotherapeutic administration of the compound of formula (I), or a corresponding pharmaceutical composition, without concomitantly administering any further anticancer agents and/or without concomitantly administering any further active agents against neovascular eye disease and/or without concomitantly administering any further analgesics and/or without concomitantly administering any further anti-inflammatory agents.

However, the compound of formula (I) or a pharmaceutical composition comprising the compound of formula (I) can also be administered in combination with one or more further therapeutic agents. If the compound of formula (I) is used in combination with a second therapeutic agent active against the same disease or condition, the dose of each compound may differ from that when the corresponding compound is used alone, in particular, a lower dose of each compound may be used. The combination of the compound of formula (I) with one or more further therapeutic agents may comprise the simultaneous/concomitant administration of the compound of formula (I) and the further therapeutic agent(s) (either in a single pharmaceutical formulation or in separate pharmaceutical formulations), or the sequential/separate administration of the compound of formula (I) and the further therapeutic agent(s). If administration is sequential, either the compound of formula (I) according to the invention or the one or more further therapeutic agents may be administered first. If administration is simultaneous, the one or more further therapeutic agents may be included in the same pharmaceutical formulation as the compound of formula (I), or they may be administered in two or more different (separate) pharmaceutical formulations.

Preferably, in the context of the treatment or prevention of cancer, the one or more further therapeutic agents to be administered in combination with a compound of the present invention are anticancer drugs. The anticancer drug(s) to be administered in combination with a compound of formula (I) according to the invention may, e.g., be selected from: a tumor angiogenesis inhibitor (e.g., a protease inhibitor, an epidermal growth factor receptor kinase inhibitor, or a vascular endothelial growth factor receptor kinase inhibitor); a cytotoxic drug (e.g., an antimetabolite, such as purine and pyrimidine analog antimetabolites); an antimitotic agent (e.g., a microtubule stabilizing drug or an antimitotic alkaloid); a platinum coordination complex; an anti-tumor antibiotic; an alkylating agent (e.g., a nitrogen mustard or a nitrosourea); an endocrine agent (e.g., an adrenocorticosteroid, an androgen, an anti-androgen, an estrogen, an anti-estrogen, an aromatase inhibitor, a gonadotropin-releasing hormone agonist, or a somatostatin analog); or a compound that targets an enzyme or receptor that is overexpressed and/or otherwise involved in a specific metabolic pathway that is deregulated (or misregulated) in the tumor cell (e.g., ATP and GTP phosphodiesterase inhibitors, histone deacetylase inhibitors, protein kinase inhibitors (such as serine, threonine and tyrosine kinase inhibitors, e.g., Abelson protein tyrosine kinase inhibitors) and the various growth factors, their receptors and corresponding kinase inhibitors (such as epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors)); methionine, aminopeptidase inhibitors, proteasome inhibitors, cyclooxygenase inhibitors (e.g., cyclooxygenase-1 or cyclooxygenase-2 inhibitors), topoisomerase inhibitors (e.g., topoisomerase I inhibitors or topoisomerase II inhibitors), poly ADP ribose polymerase inhibitors (PARP inhibitors), and epidermal growth factor receptor (EGFR) inhibitors/antagonists.

An alkylating agent which can be used as an anticancer drug in combination with a compound of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazine (such as temozolomide).

A platinum coordination complex which can be used as an anticancer drug in combination with a compound of the present invention may be, for example, cisplatin, carboplatin, nedaplatin, oxaliplatin, satraplatin, or triplatin tetranitrate.

A cytotoxic drug which can be used as an anticancer drug in combination with a compound of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent which can be used as an anticancer drug in combination with a compound of the present invention may be, for example, a taxane (such as docetaxel, larotaxel, ortataxel, paclitaxel/taxol, tesetaxel, or nab-paclitaxel (e.g., Abraxane®)), a Vinca alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/azaepothilone B).

An anti-tumor antibiotic which can be used as an anticancer drug in combination with a compound of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from *Streptomyces* (such as actinomycin (including actinomycin D), bleomycin, mitomycin (including mitomycin C), or plicamycin).

A tyrosine kinase inhibitor which can be used as an anticancer drug in combination with a compound of the present invention may be, for example, axitinib, bosutinib, cediranib, dasatinib, erlotinib, gefitinib, imatinib, lapatinib, lestaurtinib, nilotinib, semaxanib, sorafenib, sunitinib, axitinib, nintedanib, ponatinib, vandetanib, or vemurafenib.

A topoisomerase inhibitor which can be used as an anticancer drug in combination with a compound of the present invention may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

A PARP inhibitor which can be used as an anticancer drug in combination with a compound of the present invention may be, for example, niraparib, olaparib, rucaparib, talazoparib, veliparib, pamiparib (BGB-290), BMN-673, CEP 9722, MK 4827, E7016, or 3-aminobenzamide, An EGFR inhibitor/antagonist which can be used as an anticancer drug in combination with a compound of the present invention may be, for example, gefitinib, erlotinib, lapatinib, afatinib, neratinib, osimertinib, brigatinib, dacomitinib, vandetanib, pelitinib, canertinib, icotinib, poziotinib, ABT-414, AV-412, PD 153035, PKI-166, BMS-690514, CUDC-101, AP26113, XL647, cetuximab, panitumumab, zalutumumab, nimotuzumab, or matuzumab.

Further anticancer drugs may also be used in combination with a compound of the present invention. The anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, vorinostat, iniparib, or copanlisib.

Also biological drugs, like antibodies, antibody fragments, antibody constructs (for example, single-chain constructs), and/or modified antibodies (like CDR-grafted antibodies, humanized antibodies, "fully human" antibodies, etc.) directed against cancer or tumor markers/factors/cytokines involved in proliferative diseases can be employed in cotherapy approaches with the compounds of the invention. Examples of such biological molecules are anti-HER2 antibodies (e.g. trastuzumab, Herceptin®), anti-CD20 antibodies (e.g. Rituximab, Rituxan®, MabThera®, Reditux®), anti-CD19/CD3 constructs (see, e.g., EP1071752) and anti-TNF antibodies (see, e.g., Taylor P C, *Curr Opin Pharmacol,* 2003, 3(3):323-328). Further antibodies, antibody fragments, antibody constructs and/or modified antibodies to be used in cotherapy approaches with the compounds of the invention can be found, e.g., in: Taylor PC, *Curr Opin Pharmacol,* 2003, 3(3):323-328; or Roxana A, *Maedica,* 2006, 1(1):63-65.

An anticancer drug which can be used in combination with a compound of the present invention may, in particular, be an immunooncology therapeutic (such as an antibody (e.g., a monoclonal antibody or a polyclonal antibody), an antibody fragment, an antibody construct (e.g., a single-chain construct), or a modified antibody (e.g., a CDR-grafted antibody, a humanized antibody, or a "fully human" antibody) targeting any one of CTLA-4, PD-1, PD-L1, TIM3, LAG3, OX40, CSF1R, IDO, or CD40. Such immunooncology therapeutics include, e.g., an anti-CTLA-4 antibody (particularly an antagonistic or pathway-blocking anti-CTLA-4 antibody; e.g., ipilimumab or tremelimumab), an anti-PD-1 antibody (particularly an antagonistic or pathway-blocking anti-PD-1 antibody; e.g., nivolumab (BMS-936558), pembrolizumab (MK-3475), pidilizumab (CT-011), AMP-224, or APE02058), an anti-PD-L1 antibody (particularly a pathway-blocking anti-PD-L1 antibody; e.g., BMS-936559, MEDI4736, MPDL3280A (RG7446), MDX-1105, or MED16469), an anti-TIM3 antibody (particularly a pathway-blocking anti-TIM3 antibody), an anti-LAG3 antibody (particularly an antagonistic or pathway-blocking anti-LAG3 antibody; e.g., BMS-986016, IMP701, or IMP731), an anti-OX40 antibody (particularly an agonistic anti-OX40 antibody; e.g., MED10562), an anti-CSF1R antibody (particularly a pathway-blocking anti-CSF1R antibody; e.g., IMC-CS4 or RG7155), an anti-IDO antibody (particularly a pathway-blocking anti-IDO antibody), or an anti-CD40 antibody (particularly an agonistic anti-CD40 antibody; e.g., CP-870,893 or Chi Lob 7/4). Further immunooncology therapeutics are known in the art and are described, e.g., in: Kyi C et al., *FEBS Lett,* 2014, 588(2):368-76; Intlekofer A M et al., *J Leukoc Biol,* 2013, 94(1):25-39; Callahan M K et al., *J Leukoc Biol,* 2013, 94(1):41-53; Ngiow S F et al., *Cancer Res,* 2011, 71(21):6567-71; and Blattman J N et al., *Science,* 2004, 305(5681):200-5.

It is particularly advantageous to administer a compound of formula (I), or a pharmaceutical composition comprising a compound of formula (I), in combination with an immune checkpoint inhibitor, preferably an antibody (or an antigen-binding fragment thereof, or an antibody construct) directed against CTLA-4, PD-1 or PD-L1. Corresponding examples include, in particular, any one of the anti-CTLA-4 antibodies ipilimumab or tremelimumab, any one of the anti-PD-1 antibodies nivolumab, pembrolizumab, cemiplimab, spartalizumab, camrelizumab, sintilimab, tislelizumab, AMP-224 or AMP-514, and/or any one of the anti-PD-L1 antibodies atezolizumab, avelumab, durvalumab, KN035 or CK-301. The present invention thus relates to a compound of formula (I) or a pharmaceutically acceptable salt thereof, or a pharmaceutical composition comprising any of the aforementioned entities in combination with a pharmaceutically acceptable excipient, for use in the treatment or prevention of cancer, wherein the compound or the pharmaceutical composition is to be administered in combination with one or more immune checkpoint inhibitors, wherein said one or more immune checkpoint inhibitors are preferably selected from anti-CTLA-4 antibodies, anti-PD-1 antibodies and/or anti-PD-L1 antibodies; more preferably, said one or more immune checkpoint inhibitors are selected from ipilimumab, tremelimumab, nivolumab, pembrolizumab, cemiplimab, spartalizumab, camrelizumab, sintilimab, tislelizumab, AMP-224, AMP-514, atezolizumab, avelumab, durvalumab, KN035, and CK-301.

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the compound of the present invention (i.e., the compound of formula (I) or a pharmaceutically acceptable salt thereof) or the further therapeutic agent(s) may be administered first. When administration is simultaneous, the combination may be administered either in the same pharmaceutical composition or in different pharmaceutical compositions. When combined in the same formulation, it will be appreciated that the two or more compounds must be stable and compatible with each other and the other components of the formulation. When formulated separately, they may be provided in any convenient formulation.

The compounds of formula (I) can also be administered in combination with physical therapy, such as radiotherapy. Radiotherapy may commence before, after, or simultaneously with administration of the compounds of the invention. For example, radiotherapy may commence about 1 to 10 minutes, about 1 to 10 hours, or about 24 to 72 hours after administration of the compound of formula (I). The subject/ patient is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens.

The present invention thus relates to a compound of formula (I) or a pharmaceutically acceptable salt thereof, or a pharmaceutical composition comprising any of the aforementioned entities in combination with a pharmaceutically acceptable excipient, for use in the treatment or prevention of cancer, wherein the compound or the pharmaceutical composition is to be administered in combination with one or more anticancer drugs (including any one or more of the specific anticancer drugs described herein above) and/or in combination with radiotherapy.

Yet, the compounds of formula (I) can also be used in monotherapy, particularly in the monotherapeutic treatment or prevention of cancer (i.e., without administering any other anticancer agents until the treatment with the compound(s) of formula (I) is terminated). Accordingly, the invention also relates to a compound of formula (I) or a pharmaceutically acceptable salt thereof, or a pharmaceutical composition comprising any of the aforementioned entities in combination with a pharmaceutically acceptable excipient, for use in the monotherapeutic treatment or prevention of cancer.

Moreover, the compounds of formula (I)—either in combination with one or more further anticancer agents (including any of the exemplary anticancer agents described above) or without any further anticancer agents—can also be administered in combination with an antiemetic agent. The antiemetic agent may, for example, be selected from alosetron, azasetron, bemesetron, cilansetron, clozapine, dazopride, dolasetron, granisetron, lerisetron, metoclopramide, mianserin, mirtazapine, olanzapine, ondansetron, palonosetron (e.g., palonosetron alone, or palonosetron in combination with netupitant), quetiapine, ramosetron, ricasetron, tropisetron, zatosetron, clozapine, cyproheptadine, hydroxyzine, olanzapine, risperidone, ziprasidone, dronabinol, nabilone, tetrahydrocannabinol, alizapride, bromopride, chlorpromazine, clebopride, domperidone, haloperidol, hydroxyzine, itopride, metoclopramide, metopimazine, prochlorperazine, thiethylperazine, trimethobenzamide, cyclizine, dimenhydrinate, diphenhydramine, hydroxyzine, meclizine, promethazine, atropine, diphenhydramine, hyoscyamine, scopolamine, aprepitant, casopitant, ezlopitant, fosaprepitant, maropitant, netupitant, rolapitant, vestipitant, cerium oxalate, dexamethasone, lorazepam, midazolam, propofol, or a combination thereof. Preferably, the antiemetic agent is a 5-$HT_3$ antagonist (or a "setron"), such as, e.g., alosetron, azasetron, bemesetron, cilansetron, clozapine, dazopride, dolasetron, granisetron, lerisetron, metoclopramide, mianserin, mirtazapine, olanzapine, ondansetron, palonosetron (optionally in combination with netupitant), quetiapine, ramosetron, ricasetron, tropisetron, or zatosetron. A particularly preferred antiemetic agent is palonosetron.

The subject or patient to be treated in accordance with the present invention may be an animal (e.g., a non-human animal). Preferably, the subject/patient is a mammal. More preferably, the subject/patient is a human (e.g., a male human or a female human) or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, cattle, or a pig). Most preferably, the subject/patient to be treated in accordance with the invention is a human.

The term "treatment" of a disorder or disease, as used herein, is well known in the art. "Treatment" of a disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (such as the exemplary responses as described herein above). The treatment of a disorder or disease may, inter alia, comprise curative treatment (preferably leading to a complete response and eventually to healing of the disorder or disease) and palliative treatment (including symptomatic relief).

The term "prevention" of a disorder or disease, as used herein, is also well known in the art. For example, a patient/subject suspected of being prone to suffer from a disorder or disease may particularly benefit from a prevention of the disorder or disease. The subject/patient may have a susceptibility or predisposition for a disorder or disease, including but not limited to hereditary predisposition. Such a predisposition can be determined by standard methods or assays, using, e.g., genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of a compound of the present invention before any clinical and/or pathological symptoms are diagnosed or determined or can be diagnosed or determined by the attending physician.

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in formula (I) or (Ia).

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The reference in this specification to any prior publication (or information derived therefrom) is not and should not be taken as an acknowledgment or admission or any form of suggestion that the corresponding prior publication (or the information derived therefrom) forms part of the common general knowledge in the technical field to which the present specification relates.

The present invention is also described by the appended illustrative figures:

FIG. 1: Comparison of the complete tumor regression percentage in the anti-PD-1 group and in the anti-PD1+ Example 25 group in a CT26 tumor model (see Example 212).

Figure 2:
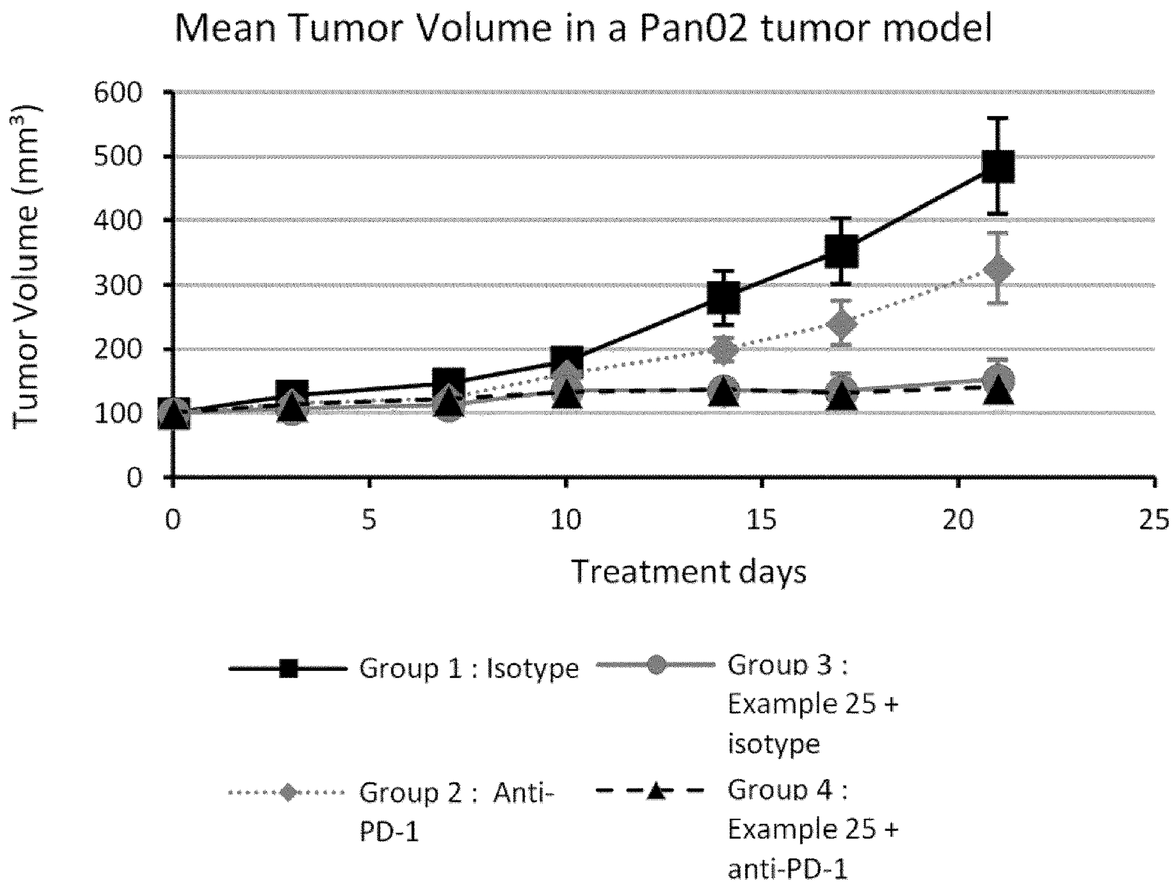

FIG. 2: Mean tumor volume in a Pan02 tumor model (see Example 213).

Figure 3:
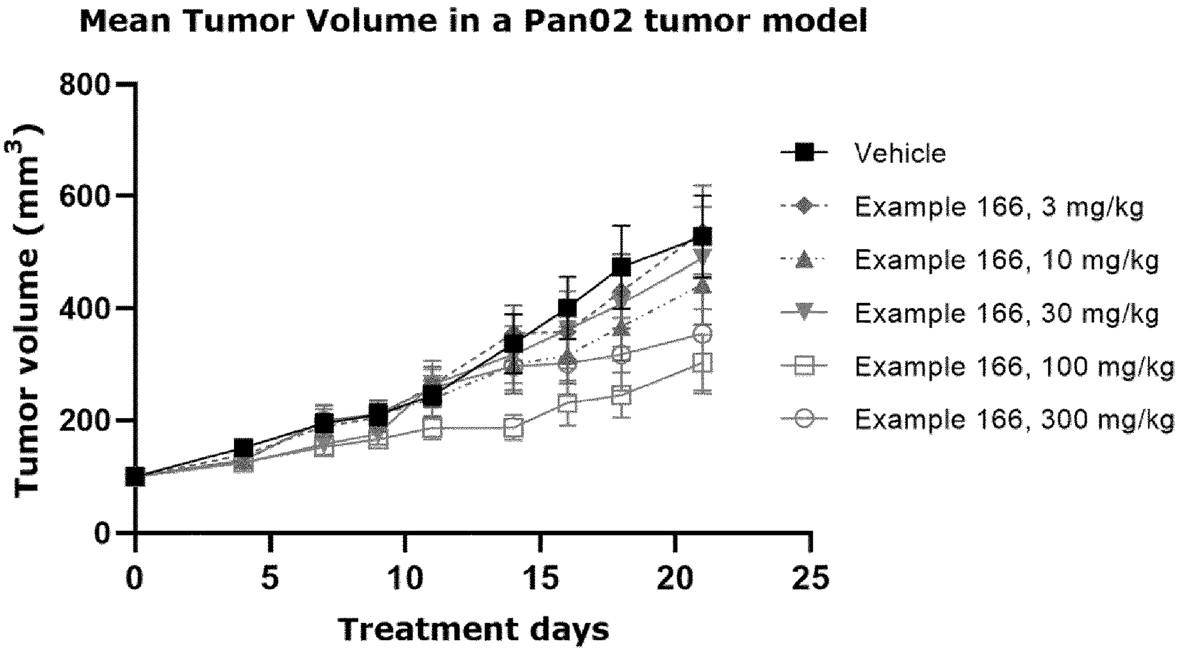

FIG. 3: Mean tumor volume in a Pan02 tumor model (see Example 214).

Figure 4:
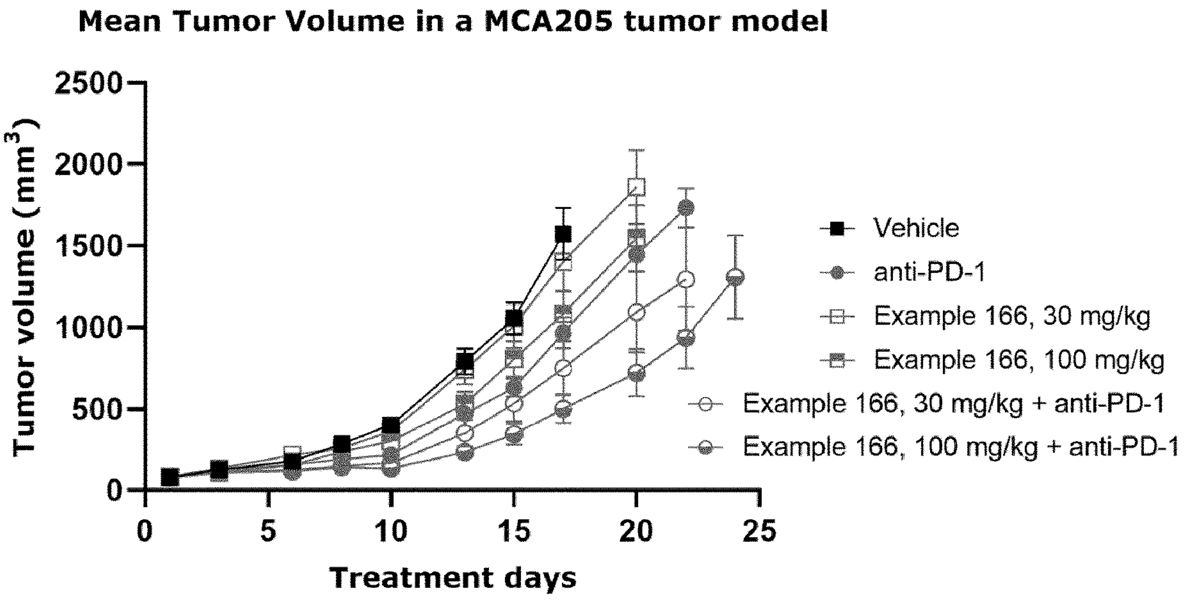

FIG. 4: Mean tumor volume in an MCA205 tumor model (see Example 215).

The invention will now be described by reference to the following examples which are merely illustrative and are not to be construed as a limitation of the scope of the present invention.

EXAMPLES

The compounds of formula (I) described in this section, including in particular Examples 1 to 210, are defined by their chemical formulae and their corresponding chemical names. In case of conflict between any chemical formula and the corresponding chemical name indicated herein, the present invention relates to both the compound defined by the chemical formula and the compound defined by the chemical name, and particularly relates to the compound defined by the chemical formula.

Abbreviations

The following abbreviations are used in the experimental procedures.

Ac Acetyl
Boc Tert-Butoxycarbonyle
BOP (Benzotriazol-1-yloxy)tris(dimethylamino)phosphonium hexafluorophosphate
BRET Bioluminescence Resonance Energy Transfer
cAMP Cyclic Adenosine Monophosphate
DCM Dichloromethane
DIAD Diisopropyl Azodicarboxylate
DIPEA N,N-Diisopropylethylamine
DMA N,N-Dimethylacetamide
DMAP 4-Dimethylaminopyridine
DMF N,N-Dimethylformamide
DMF-DMA N,N-Dimethylformamide dimethyl acetal
DMSO Dimethylsulfoxide
DNA Deoxyribonucleic acid
EPAC Exchange protein activated by cAMP
EtOAc Ethyl Acetate
GFP Green Fluorescent Protein
HATU 1-[Bis(dimethylamino)methylene]-1H-1,2,3-triazolo [4,5-b]pyridinium 3-oxid hexafluorophosphate
HEK Human Embryonic Kidney
HPLC High Performance Liquid Chromatography
KHMDS Potassium bis(trimethylsilyl)amide
LC-MS Liquid Chromatography-Mass spectrometry
LDA Lithium Diisopropylamide
MeOH Methanol
n-BuLi n-Butyllithium
NMR Nuclear Magnetic Resonance
ppm Parts per million
PS Polystyrene
rt Room temperature
TBAF Tetrabutylammonium fluoride
THF Tetrahydrofuran
TFA Trifluoroacetic Acid
TLC Thin Layer Chromatography
UPLC Ultra Performance Liquid Chromatography General Conditions:

All reagents were commercial grade and used without further purification. Reactions were typically run using anhydrous solvents under argon atmosphere. The indicated reaction temperature is the setpoint temperature. Reactions under microwave irradiation were performed under automatically regulated power; the indicated reaction time corresponds to the time at the setpoint temperature before cooling down of the reaction mixture. Organic layers were usually dried over sodium or magnesium sulphate or filtered through an Isolute® SPE Single Fritted column. Thin layer chromatography were carried out using pre-coated silica gel F-254 plate. Flash column chromatography were performed using a Biotage® isolera 4 system, with the Biotage® SNAP cartridge KP-Sil if not specified. In specific cases, a Biotage® SNAP KP-NH or Interchim PF-15SIHP-F0025 (15 µm) cartridge could be used. After purification by flash chromatography, examples were usually triturated in diethyl ether or diisopropyl ether or pentane then dried overnight under vacuum at 70° C. Examples were usually synthesized in 10 to 100 mg scale.

Reactions were monitored and compounds were characterized using a Waters Acquity UPLC H-class system with a photodiode array detector (190-400 nm). An Acquity CSH C18 1.7 µM 2.1×30 mm column was used. The mobile phase consisted in a gradient of A and B: A was water with 0.025% of trifluoroacetic acid and B was acetonitrile with 0.025% of trifluoroacetic acid. Flow rate was 0.8 ml per min. All analysis were performed at 55° C. The UPLC system was coupled to a Waters SQD2 platform. All mass spectra were full-scan experiments (mass range 100-800 amu). Mass spectra were obtained using positive electrospray ionization.

Preparative LC-MS were performed using a Waters HPLC system with a 2767 sample manager, a 2525 pump, a photodiode array detector (190-400 nm) enabling analytical and preparative modes. An Xselect CSH C18 3.5 µM 4.6×50 mm column was used in analytical mode and a Xselect CSH C18 5 µM 19×100 mm column in preparative mode. The mobile phase consisted in both cases in a gradient of A and B: A was water with 0.1% of formic acid and B was acetonitrile with 0.1% of formic acid. Flow rate was 1 ml per min in analytical mode and 25 ml per min in preparative mode. All LC-MS analysis/purification were performed at room temperature. The HPLC system was coupled with a Waters Acquity QDa detector. All mass spectra were full-scan experiments (mass range 100-800 amu). Mass spectra were obtained using positive electrospray ionization.

All NMR experiments were recorded on a Brucker AMX-400 spectrometer. Proton chemical shift are listed relative to residual DMSO (2.50 ppm). Splitting patterns are designated as s (singlet); d (doublet); dd (doublet of doublet); t (triplet); dt (doublet of triplet); td (triplet of doublet); tt (triplet of triplet); q (quartet); quint (quintuplet); m (multiplet); bs (broad singlet); bd (broad doublet).

General Procedures and Methods:

General Procedure I-a: Amide Coupling Using BOP

To a solution of a carboxylic acid (1 equiv.) in DMF (0.1 M) were added an amine (1.2 equiv.), diisopropylethylamine (2 equiv.) and BOP (1.2 equiv). The reaction mixture was stirred at rt for 1 h. The reaction mixture was diluted with EtOAc, washed with brine, dried, then concentrated. When specified, the resulting crude mixture was purified by flash chromatography to afford the desired compound.

General Procedure I-b: Amide Coupling Using HATU

To a solution of a carboxylic acid (1 equiv.) in DMF (0.1 M) were added an amine (1.2 equiv.), diisopropylethylamine (2 equiv.) and HATU (1.2 equiv). The reaction mixture was stirred at rt for 1 h. The reaction mixture was diluted with EtOAc, washed with brine, dried, then concentrated. When specified, the resulting crude mixture was purified by flash chromatography to afford the desired compound.

General Procedure II-a: Boc Cleavage

A solution of a Boc-protected amine (1 equiv.) in a DCM/TFA mixture (1/1, 0.1 M) was stirred at rt for 1 h. The reaction mixture was concentrated to dryness. The resulting residue was dissolved in DCM, washed with a saturated solution of potassium carbonate and brine, dried, then concentrated. When specified, the resulting crude was purified by flash chromatography to afford the desired compound.

General Procedure II-b: Boc Cleavage

A solution of a Boc-protected amine (1 equiv.) in a DCM/TFA mixture (1/1, 0.1 M) was stirred at rt for 1 h. The reaction mixture was concentrated to dryness. The resulting residue was dissolved in DCM, HCl 2 M in diethyl ether was added. The resulting precipitate was filtered, then dried under vacuum to afford the desired compound under its hydrochloride salt form.

General Procedure I-c: Boc Cleavage

A solution of a Boc-protected amine (1 equiv.) in a DCM/TFA mixture (1/1, 0.1 M) was stirred at rt for 1 h. The reaction mixture was concentrated to dryness. The resulting residue was dissolved in methanol, then filtered through a SCX resin to recover the free base. After concentration of the solution, the residue was dissolved in methanol, HCl 1.25 M in methanol was added. The solution was concentrated to afford the desired compound under its hydrochloride salt form.

General Procedure III-a: Reductive Amination

To a solution of an amine (1 equiv.) in THF (0.1 M) were added an aldehyde (1.2 equiv.), $NaBH(OAc)_3$ (2 equiv.) and acetic acid (1 equiv.). The reaction mixture was stirred overnight at rt. The reaction mixture was diluted with EtOAc, washed with a saturated solution of sodium bicarbonate and brine, dried, then concentrated. When specified, the resulting crude mixture was purified by flash chromatography to afford the desired compound.

General Procedure III-b: Reductive Amination

To a solution of an amine (1 equiv.) in THF (0.1 M) were added an aldehyde (1.2 equiv.), $NaBH(OAc)_3$ (2 equiv.). The reaction mixture was stirred overnight at rt. The reaction mixture was diluted with EtOAc, washed with a saturated solution of sodium bicarbonate and brine, dried, then concentrated. When specified, the resulting crude mixture was purified by flash chromatography to afford the desired compound.

General Procedure IV-a: Ester Hydrolysis

A suspension of an ester (1 equiv.) in aqueous HCl 1 N (0.1 M) was stirred at 150° C. for 5 min under microwave irradiation. The resulting solution was concentrated to dryness. If needed, the residue was purified by preparative LC-MS, otherwise it was simply triturated in diethyl ether or in pentane to afford the desired compound.

General Procedure IV-b: Ester Hydrolysis

A solution of a methyl ester (1 equiv.) in an aqueous HCl 1 N/dioxane mixture (7/3, 0.1 M) was stirred at 150° C. for 5 min under microwave irradiation. The resulting solution was concentrated to dryness. If needed, the residue was purified by preparative LC-MS, otherwise it was simply triturated in diethyl ether or in pentane to afford the desired compound.

General Procedure V-a: Saponification

To a solution of an ester (1 equiv.) in THF (0.2 M) was added an aqueous LiOH 1 M solution (2 equiv.). The reaction mixture was stirred overnight at 70° C. The reaction mixture was concentrated to dryness to afford the desired compound.

General Procedure V-b: Saponification

To a solution of an ester (1 equiv.) in THF (0.2 M) was added an aqueous LiOH 1 M solution (2 equiv.). The reaction mixture was stirred overnight at 70° C. The reaction mixture was cooled down to rt, acidified with aqueous HCl 1 N, extracted with DCM. The organic layer was washed with brine, dried, then concentrated. If needed, the residue was purified by preparative LC-MS, otherwise it was simply triturated in diethyl ether or in pentane to afford the desired compound.

General Procedure V-c: Saponification

To a solution of an ester (1 equiv.) in THF (0.2 M) was added an aqueous LiOH 1 M solution (2 equiv.). The reaction mixture was stirred overnight at rt. The reaction mixture was concentrated to remove THF, diluted with water, extracted with ethyl ether. The aqueous layer was acidified with aqueous HCl 1 N. The resulting precipitate was filtered. If needed, the residue was purified by preparative LC-MS, otherwise it was simply triturated in diethyl ether or in pentane to afford the desired compound.

General Procedure V-d: Saponification

To a solution of an ester (1 equiv.) in dioxane (0.2 M) was added an aqueous LiOH 1 M solution (4 equiv.). The reaction mixture was stirred overnight at 100° C. The reaction mixture was cooled down to rt, acidified with aqueous HCl 1 N, extracted with DCM. The organic layer was washed with brine, dried, then concentrated. If needed, the residue was purified by preparative LC-MS, otherwise it was simply triturated in diethyl ether or in pentane to afford the desired compound.

General Procedure V-e: Saponification

To a solution of an ester (1 equiv.) in THF (0.2 M) was added an aqueous LiOH 1 M solution (2 equiv.). The reaction mixture was stirred overnight at 70° C. The reaction mixture was directly purified by preparative LC-MS to afford the desired compound.

General Procedure V-f: Saponification

To a solution of an ester (1 equiv.) in Dioxane (0.2 M) was added an aqueous LiOH 1 M solution (2 equiv.). The reaction mixture was stirred overnight at 100° C. The reaction mixture was concentrated to dryness to afford the desired compound.

General Procedure VI-a: α-arylation of ester

To a solution of an ester (1.7 equiv.) in toluene (0.2 M) under argon atmosphere at −15° C. was added dropwise LDA 1 M in THF (1.6 equiv.). The reaction mixture was stirred at −15° C. for 15 min, then was allowed to warm up to rt. A bromoarene (1 equiv.) and $\{(Pt\text{-}Bus)Pdl\}_2$ (5 mol %) were added. The reaction mixture was stirred overnight at rt. The reaction mixture was hydrolyzed with aqueous HCl 1 N, extracted with EtOAc. The organic layer was washed with brine, dried, then concentrated. When specified, the resulting crude mixture was purified by flash chromatography to afford the desired compound.

General Procedure VI-b: α-Arylation of Ester

To a solution of an ester (1.7 equiv.) in toluene (0.2 M) under argon atmosphere at −15° C. was added dropwise LDA 1 M in THF (1.6 equiv.). The reaction mixture was stirred at −15° C. for 15 min, then was allowed to warm up to rt. A halogeno-(hetero)arene (1 equiv.) and $Pd(Pt\text{-}Bu_3)_2$ were added. The reaction mixture was stirred overnight at rt. The reaction mixture was hydrolyzed with aqueous HCl 1 N, extracted with EtOAc. The organic layer was washed with brine, dried, then concentrated. When specified, the resulting crude mixture was purified by flash chromatography to afford the desired compound.

General Procedure VII-a: Nucleophilic Aromatic Substitution with Carbanion

To a solution of a carbonitrile (1 equiv.) in toluene (0.2 M) under argon atmosphere at 0° C. was added dropwise KHMDS 1 M in THF (1.05 equiv.). The reaction mixture was stirred at 0° C. for 15 min, then was allowed to warm up to rt. A halogeno-heteroarene (2.5 equiv.) was added. The reaction mixture was stirred at rt for 40 min. The reaction mixture was hydrolyzed with a saturated solution of ammonium chloride, extracted with DCM. The organic layer was washed with a saturated solution of sodium bicarbonate and brine, dried, then concentrated. When specified, the resulting crude mixture was purified by flash chromatography to afford the desired compound.

General Procedure VII-b: Nucleophilic Aromatic Substitution with Acetonitrile

To a solution of acetonitrile (3.4 equiv.) in THF (0.2 M) at −78° C. was added n-BuLi 1.6 M in THF (3.3 equiv.). The reaction mixture was stirred at −78° C. for 45 min. A solution of a halogeno-heteroarene (1 equiv.) in THF (0.4 M) was added dropwise. The reaction mixture was allowed to warm up to rt, and was stirred at rt for 2 h. The reaction mixture was hydrolyzed with water, then extracted with EtOAc. The organic layer was washed with brine, dried, then concentrated. When specified, the resulting crude mixture was purified by flash chromatography to afford the desired compound.

General Procedure VII-c: Nucleophilic Aromatic Substitution with an Aliphatic Alcohol To a solution of an aliphatic alcohol (1.3 equiv.) in DMA (0.12 M) at 0° C. was added sodium hydride (1.4 equiv.). The reaction mixture was stirred at 0° C. for 10 min. A solution of a halogeno-heteroarene (1 equiv.) in DMA (0.4 M) was added. The reaction mixture was stirred at 150° C. for 10 min under microwave irradiation. The reaction mixture was hydrolyzed with a saturated solution of ammonium chloride, then extracted with EtOAc. The organic layer was washed with brine, dried, then concentrated. When specified, the resulting crude mixture was purified by flash chromatography to afford the desired compound.

General Procedure VIII-a: Saturated Carbo/Heterocyle Synthesis

To a solution of an ester or a cyanide (1 equiv.) in DMA (0.1 M) was added sodium hydride (2 equiv.). The reaction mixture was stirred at 0° C. for 10 min. A di-halogenoalkane (1 equiv.) was added. The reaction mixture was stirred at rt for 5 h. The reaction mixture was hydrolyzed with a saturated solution of ammonium chloride, then extracted with EtOAc. The organic layer was washed with brine, dried, then concentrated. When specified, the resulting crude mixture was purified by flash chromatography to afford the desired compound.

General Procedure VIII-b: Saturated Nitrogen-Containing Heterocyle Synthesis

To a solution of a primary amine (1.3 equiv.) in acetonitrile (0.1 M) were added potassium carbonate (2 equiv.) and a di-halogenoalkane compound (1 equiv.). The reaction mixture was stirred at 85° C. for 6 days. The reaction mixture was cooled down to 0° C., hydrolyzed with water, extracted with DCM. The organic layer was dried, then concentrated. When specified, the resulting crude mixture was purified by flash chromatography to afford the desired compound.

General Procedure IX-a: Mitsunobu with Polymer-Bound Triphenylphospine

To a solution of a phenol (1 equiv.) in THF (0.1 M) were added DIAD (1.6 equiv.), PS-triphenylphosphine (2.2 equiv.) and an aliphatic alcohol (1.5 equiv.). The reaction mixture was stirred overnight at rt with an orbital shaker. The reaction mixture was filtered, diluted with EtOAc, washed with brine, dried, then concentrated. When specified, the resulting crude mixture was purified by flash chromatography to afford the desired compound.

General Procedure IX-b: Mitsunobu

To a solution of a phenol (1 equiv.) in THF (0.1 M) were added DIAD (1.5 equiv.), triphenylphosphine (1.5 equiv.) and an aliphatic alcohol (1.5 equiv.). The reaction mixture was stirred at rt for 3 h. The reaction mixture was diluted with DCM, washed with brine, dried, then concentrated. When specified, the resulting crude mixture was purified by flash chromatography to afford the desired compound.

General Procedure X: Nucleophilic Substitution with Phenols

To a solution of a phenol (1 equiv.) in DMF (0.1 M) were added potassium carbonate (2 equiv.) and an electrophile (1.5 equiv.). The reaction mixture was stirred overnight at rt. The reaction mixture was cooled down to 0° C., hydrolyzed with water. The resulting precipitate was filtered. When specified, the resulting crude mixture was purified by flash chromatography to afford the desired compound.

General Procedure XI-a: Carbonitrile Hydratation

To a solution of a carbonitrile (1 equiv.) in DMSO (0.2 M) were added potassium carbonate (1 equiv.) and $H_2O_2$ 30% in water (2 equiv.). The reaction mixture was stirred overnight at rt. Water was added to the reaction mixture. The resulting precipitate was filtered, washed with water, then dried under vacuum at 70° C. with $P_2O_5$. When specified, the resulting crude mixture was purified by flash chromatography to afford the desired compound.

General Procedure XI-b: Carbonitrile Hydratation

A solution of a carbonitrile (1 equiv.) in conc. $H_2SO_4$ (0.2 M) was stirred overnight at rt. The reaction mixture was poured into crushed ice, then potassium carbonate was added until reaching pH 8. The resulting precipitate was filtered, washed with water, then dried under vacuum at 70° C. with $P_2O_5$. The obtained solid was suspended in DCM, filtered. The resulting filtrate was concentrated to afford the desired compound.

General Procedure XI-c: Carbonitrile Hydratation/Hydrolysis

A solution of a carbonitrile (1 equiv.) in an aqueous HCl 12 N solution (0.1 M) was stirred at 100° C. for 2 h. The reaction mixture was concentrated to dryness, co-evaporated with toluene, then dried under vacuum at 70° C. to afford the desired compound.

General Procedure XII: Methyl Ester Synthesis from Primary Amide

To a primary amide (1 equiv.) in methanol (0.1 M) was added DMF-DMA (6 equiv.). The reaction mixture was stirred overnight at rt. Sodium methoxide (5 equiv.) was added. The reaction mixture was stirred at rt for 5 h. The reaction mixture was hydrolyzed with water, then extracted with EtOAc. The organic layer was washed with brine, dried, then concentrated. When specified, the resulting crude mixture was purified by flash chromatography to afford the desired compound.

General Procedure XIII: Pd-Catalysed Arylation of an Aliphatic Alcohol

To a solution of a bromo-arene (1 equiv.) in dioxane (0.1 M) were added cesium carbonate (2 equiv.) and an aliphatic alcohol (6 equiv.). The reaction mixture was degassed for 10 min with argon, then RockPhosPd G3 (5 mol %) was added. The reaction mixture was heated overnight at 90° C. The reaction mixture was diluted with a saturated solution of ammonium chloride, then extracted with EtOAc. The organic layer was washed with brine, dried, then concentrated. When specified, the resulting crude mixture was purified by flash chromatography to afford the desired compound.

General Procedure XIV: Silyl Protection of Primary Alcohols

To a solution of a primary alcohol (1 equiv.) in DCM (0.3 M) were added t-butyl-chloro-dimethyl-silane (1.8 equiv.), triethylamine (2.2 equiv.) and DMAP (0.1 equiv.). The reaction mixture was stirred overnight at rt. The reaction mixture was hydrolyzed with water, then extracted with DCM. The organic layer was washed with brine, dried, then concentrated. When specified, the resulting crude mixture was purified by flash chromatography to afford the desired compound.

General Procedure XV-a: Silyl Deprotection

To a solution of a silyl-protected phenol (1 equiv.) in THF (0.1 M) was added TBAF 1 M in THF (2 equiv.). The reaction mixture was stirred at rt for 1 h, then cooled down to 0° C., hydrolyzed with water and extracted with EtOAc. The organic layer was washed with brine, dried, then concentrated. When specified, the resulting crude mixture was purified by flash chromatography to afford the desired compound.

General Procedure XV-b: Silyl Deprotection

To a solution of a silyl-protected phenol (1 equiv.) in methanol (0.2 M) was added HCl 4 N in dioxane (5 equiv.). The reaction mixture was stirred at rt for 72 h, then concentrated. When specified, the resulting crude mixture was purified by flash chromatography to afford the desired compound.

General Procedure XVI: Di-Bromination of an Diol

To a solution of N-bromosuccinimide (3 equiv.) in DCM (0.4 M) at −78° C. was added triphenylphosphine (3 equiv.). The reaction mixture was stirred at −78° C. for 5 min, then an diol (1 equiv.) in DCM (0.4M) was added. The reaction mixture was stirred at rt for 3 h, then concentrated to dryness. When specified, the resulting crude mixture was purified by flash chromatography to afford the desired compound.

General Procedure XVII: Oxydation of a Primary Alcohol

To a solution of a primary alcohol (1 equiv.) in acetone (0.2 M) was added the Jones' reagent (5 equiv.). The reaction mixture was stirred at rt for 2.5 h. The reaction mixture was hydrolyzed with an aqueous NaOH 6 N solution until reaching pH 12, then washed with ethyl ether. The aqueous layer was acidified back to pH 4 with aqueous HCl 1 N. The resulting precipitate was filtered off. The aqueous layer was extracted with EtOAc. The organic layer was dried, then concentrated to afford the carboxylic acid which was used as such in the next step.

HCl Salt Preparation:

Method 1: After purification by preparative LC-MS, aqueous HCl 1 N was added to the combined fractions. The resulting solution was lyophilized. The obtained solid was dried under vacuum at 70° C.

Method 2: After purification by preparative LC-MS, the combined fractions were concentrated. The resulting residue was dissolved in DCM. HCl 2 M in diethyl ether was added. The resulting solution was concentrated and the obtained solid was triturated in diethyl ether then dried under vacuum at 70° C.

Method 3: After purification by preparative LC-MS, HCl 4 M in dioxane, was added to the combined fractions. The resulting solution was concentrated. The obtained solid was dried under vacuum at 70° C.

Compounds and Examples Synthesis

This section describes the preparation of compounds of formula (I), which are referred to as "Examples", and the preparation of synthesis intermediates, which are referred to as "Compounds".

Compound 1: Methyl 4-[(1S)-1-[[4-(tert-butoxycarbonylamino)tetrahydropyran-4-carbonyl]amino]ethyl]benzoate Compound 1 was obtained according to General Procedure I-a, starting from 4-(tert-butoxycarbonylamino)tetrahydropyran-4-carboxylic acid and methyl 4-[(1S)-1-aminoethyl]benzoate. Purification by flash chromatography (Cyclohexane/EtOAc: 100/0 to 20/80) afforded Compound 1 as a white powder in 98% yield. M/Z $(M+Na)^+$: 429

Compound 2: Methyl 4-[(1S)-1-[(4-aminotetrahydropyran-4-carbonyl)amino]ethyl]benzoate Compound 2 was obtained according to General Procedure II-a, starting from Compound 1, as a beige powder in 99% yield. M/Z $(M+H)^+$: 307

Compound 3: Methyl 4-[(1S)-1-[[4-(2-phenoxyethylamino)tetrahydropyran-4-carbonyl]amino]ethyl]benzoate Compound 3 was obtained according to General Procedure III-a, starting from Compound 2 and 2-phenoxyacetaldehyde. Purification by flash chromatography (DCM/MeOH: 100/0 to 94/6; then, on a 15 μm cartridge, DCM/MeOH: 100/0 to 97.5/2.5) afforded Compound 3 as a white powder in 37% yield. M/Z $(M+H)^+$: 427

Example 1: 4-[(1S)-1-[[4-(2-Phenoxyethylamino)tetrahydropyran-4-carbonyl]amino]ethyl]benzoic acid, hydrochloride

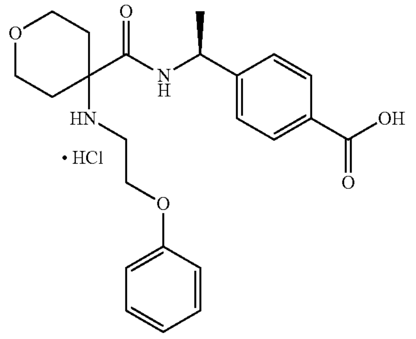 [SMILES: C[C@H](NC(=O)C1(NCCOc2ccccc2)CCOCC1)c1ccc(C(=O)O)cc1 ; "· HCl"]

Example 1 was obtained according to General Procedure IV-a, starting from Compound 3, as a white powder in 75% yield. $^1$H-NMR (DMSO-$d_6$ 400 MHz) δ (ppm): 1.46 (d, J 7.1 Hz, 3H, CH—$CH_3$); 1.90-2.02 (m, 2H, $CH_2$); 2.37-2.47 (m, 2H, $CH_2$); 2.98-3.20 (m, 2H, NH—$CH_2$); 3.27-3.34 (m, 2H, O—$CH_2$); 3.85-3.94 (m, 2H, O—$CH_2$); 4.19-4.27 (m, 2H, Ph-O—$CH_2$); 4.99 (quint, J 7.1 Hz, 1H, CONH—CH—$CH_3$); 6.96-7.01 (m, 3H, Ar); 7.32 (dd, J 8.7, 7.3 Hz, 2H, Ar); 7.52 (d, J 8.3 Hz, 2H, Ar); 7.89 (d, J 8.3 Hz, 2H, Ar); 9.13-9.24 (m, 1H, CONH—CH); 9.76-9.93 (d, J 7.1 Hz, 2H, NH+HCl salt); 12.85 (bs, 1H, $CO_2H$). M/Z $(M+H)^+$: 413

Compound 4: Methyl 4-[(1S)-1-[[4-[methyl(2-phenoxyethyl)amino))]tetrahydropyran-4-carbonyl]amino]ethyl]benzoate Compound 4 was obtained according to General Procedure III-a, starting from Compound 3 and formaldehyde. Purification by flash chromatography (15 μm cartridge, DCM/MeOH: 100/0 to 95/5) afforded Compound 4 as a white powder in 37% yield. M/Z $(M+H)^+$: 441

Example 2: 4-[(1S)-1-[[4-[Methyl(2-phenoxyethyl)amino]tetrahydropyran-4-carbonyl]amino]ethyl]benzoic acid, hydrochloride

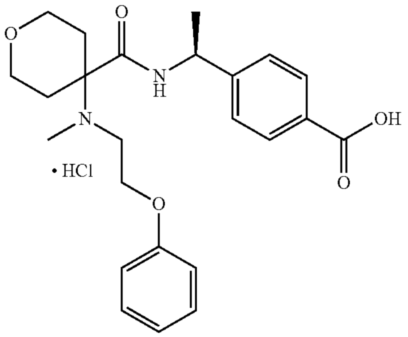 [SMILES: C[C@H](NC(=O)C1(N(C)CCOc2ccccc2)CCOCC1)c1ccc(C(=O)O)cc1 ; "· HCl"]

Example 2 was obtained according to General Procedure IV-a, starting from Compound 4. Purification by preparative LC-MS and HCl salt preparation (method 3) afforded Example 2 as a beige powder in 29% yield. $^1$H-NMR (DMSO-$d_6$ 400 MHz) δ (ppm): 1.49 (d, J 6.8 Hz, 3H, CH—$CH_3$); 1.95-2.10 (m, 2H, $CH_2$); 2.43-2.46 (m, 2H, $CH_2$); 2.74-2.90 (m, 3H, N—$CH_3$); 3.09-3.29 (m, 2H, O—$CH_2$); 3.33-3.53 (m, 1H, N—$CH_aH_b$); 3.58-3.72 (m, 1H, N—$CH_aH_b$); 3.87-4.03 (m, 2H, O—$OH_2$); 4.25-4.39 (m, 2H, PhO—$CH_2$); 5.13 (quint, J 6.8 Hz, 1H, CONH—CH—$CH_3$); 6.88-7.02 (m, 3H, Ar); 7.32 (t, J 7.6 Hz, 2H, Ar); 7.50 (d, J 7.8 Hz, 2H, Ar); 7.91 (d, J 7.8 Hz, 2H, Ar); 9.03 (bs, 1H, CONH—CH); 10.52 (bs, 1H, HCl salt); 12.86 (bs, 1H, $CO_2H$). M/Z $(M+H)^+$: 427

Example 3: N-[(1S)-1-(4-Carbamoylphenyl)ethyl]-4-[methyl(2-phenoxyethyl)amino]tetrahydropyran-4-carboxamide

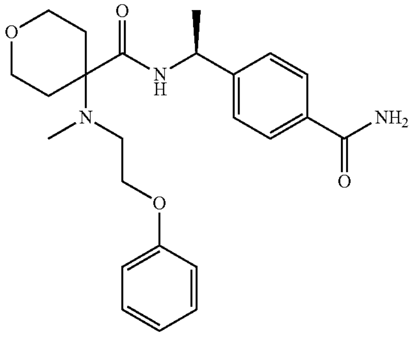 [SMILES: C[C@H](NC(=O)C1(N(C)CCOc2ccccc2)CCOCC1)c1ccc(C(N)=O)cc1]

Example 3 was obtained according to General Procedure I-a, starting from Example 2 and $NH_3$ 0.5 M in dioxane. Purification by preparative LC-MS afforded Example 3 as a white powder in 58% yield. $^1$H-NMR (DMSO-$d_6$, 400 MHz) δ (ppm): 1.41 (d, J 7.1 Hz, 3H, CH—$CH_3$); 1.60-1.73 (m, 2H, $CH_2$); 1.95-2.05 (m, 2H, $CH_2$); 2.28 (s, 3H, N—$CH_3$); 2.67-2.74 (m, 2H, N—$CH_2$); 3.26-3.39 (m, 2H, O—$CH_2$); 3.71-3.78 (m, 2H, O—$CH_2$); 3.95 (t, J 5.9 Hz, 2H, PhO—$CH_2$); 5.08 (quint, J 7.1 Hz, 1H, CONH—CH—$CH_3$); 6.85-6.94 (m, 3H, Ar); 7.22-7.32 (m, 3H, Ar+$CONH_a$—$H_b$); 7.40 (d, J 8.2 Hz, 2H, Ar); 7.80 (d, J 8.2 Hz, 2H, Ar); 7.88 (bs, 1H, $CONH_a$—$H_b$); 7.93 (d, J 7.1 Hz, 1H, CONH—CH). M/Z $(M+H)^+$: 426

Example 4: N-[(1S)-1-[4-(Methylcarbamoyl)phenyl]ethyl]-4-[methyl(2-phenoxyethyl)amino]tetrahydropyran-4-carboxamide

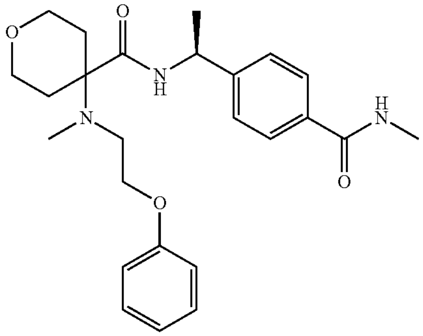 [SMILES: CNC(=O)c1ccc([C@H](C)NC(=O)C2(N(C)CCOc3ccccc3)CCOCC2)cc1]

Example 4 was obtained according to General Procedure I-a, starting from Example 2 and methylamine 2 M in THF. Purification by flash chromatography (DCM/MeOH: 100/0 to 94/6) afforded Example 4 as a white powder in 64% yield. $^1$H-NMR (DMSO-$d_6$, 400 MHz) δ (ppm): 1.41 (d, J 7.1 Hz, 3H, CH—$CH_3$); 1.61-1.73 (m, 2H, $CH_2$); 1.95-2.04 (m, 2H, $CH_2$); 2.28 (s, 3H, N—$CH_3$); 2.66-2.72 (m, 2H, N—$CH_2$); 2.77 (d, J 4.5 Hz, 3H, NH—$CH_3$); 3.26-3.39 (m, 2H, O—$CH_2$); 3.71-3.78 (m, 2H, O—$CH_2$); 3.94 (t, J 6.1 Hz, 2H, PhO—$CH_2$); 5.04-5.12 (m, 1H, CONH—CH—$CH_3$); 6.84-6.93 (m, 3H, Ar); 7.27 (dd, J 8.6, 7.3 Hz, 2H, Ar); 7.40 (d, J 8.3 Hz, 2H, Ar); 7.76 (d, J 8.3 Hz, 2H, Ar); 7.92 (d, J 8.1 Hz, 1H, CONH—CH—$CH_3$); 8.33 (q, J 4.5 Hz, 1H, CONH—$CH_3$). M/Z $(M+H)^+$: 440

Example 5: N-[(1S)-1-[4-(Dimethylcarbamoyl)phenyl]ethyl]-4-[methyl(2-phenoxyethyl)amino]tetrahydropyran-4-carboxamide

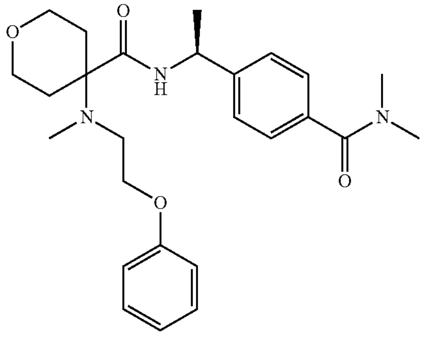 [SMILES: C[C@H](NC(=O)C1(N(C)CCOc2ccccc2)CCOCC1)c1ccc(C(=O)N(C)C)cc1]

Example 5 was obtained according to General Procedure I-a, starting from Example 2 and dimethylamine 2 M in THF. Purification by flash chromatography (DCM/MeOH: 100/0 to 95/5) afforded Example 5 as a beige powder in 56% yield. $^1$H-NMR (DMSO-de 400 MHz) δ (ppm): 1.42 (d, J 7.1 Hz, 3H, CH—$CH_3$); 1.62-1.74 (m, 2H, $CH_2$); 1.94-2.03 (m, 2H, $CH_2$); 2.28 (s, 3H, N—$CH_3$); 2.66-2.72 (m, 2H, N—$CH_2$); 2.84-2.99 (m, 6H, $N(CH_3)_2$); 3.27-3.39 (m, 2H, O—$CH_2$); 3.71-3.78 (m, 2H, O—$CH_2$); 3.96 (t, J 6.2 Hz, 2H, PhO—$CH_2$); 5.03-5.12 (m, 1H, CONH—CH—$CH_3$); 6.85-6.94 (m, 3H, Ar); 7.27 (dd, J 8.6, 7.3 Hz, 2H, Ar); 7.32 (d, J 8.2 Hz, 2H, Ar); 7.39 (d, J 8.2 Hz, 2H, Ar); 7.93 (d, J 8.1 Hz, 1H, CONH—CH). M/Z $(M+H)^+$: 454

Compound 5: Methyl 4-[(1S)-1-[[4-[acetyl(2-phenoxyethyl)amino]tetrahydropyran-4-carbonyl]amino]ethyl]benzoate To a solution of Compound 3 (1 equiv.) in DCE (0.1 M) were added acetyl chloride (3 equiv.) and triethylamine (2 equiv.). The reaction mixture was stirred at rt for 1 h. The reaction mixture was diluted with EtOAc, washed with a saturated solution of sodium bicarbonate and brine, dried, then concentrated. Purification by flash chromatography (DCM/MeOH: 100/0 to 96.5/3.5; then 15 μm cartridge, DCM/MeOH: 100/0 to 97/3) afforded Compound 5 as a white powder in 24% yield. M/Z $(M+H)^+$: 469

Example 6: 4-[(1S)-1-[[4-[Acetyl(2-phenoxyethyl)amino]tetrahydropyran-4-carbonyl]amino]ethyl]benzoic acid

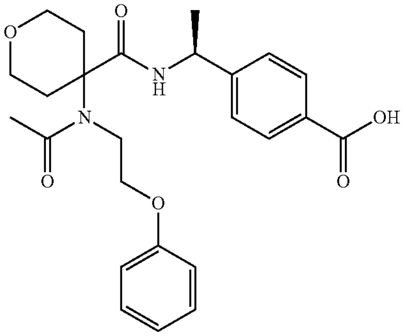 [SMILES: CC(=O)N(CCOc1ccccc1)C1(C(=O)N[C@@H](C)c2ccc(C(=O)O)cc2)CCOCC1]

Example 6 was obtained according to General Procedure V-b, starting from Compound 5, as a white solid in 86% yield. $^1$H-NMR (DMSO-de, 400 MHz) δ (ppm): 1.28 (d, J 7.1 Hz, 3H, CH—$CH_3$); 1.80-2.00 (m, 2H, $CH_2$); 2.14 (s, 3H, CO—$CH_3$); 2.17-2.27 (m, 2H, $CH_2$); 3.54-3.77 (m, 4H, CO—N—$CH_2$+O—$CH_2$); 3.87 (t, J 5.6 Hz, 2H, O—$CH_2$); 4.13 (t, J 5.6 Hz, 2H, PhO—$CH_2$); 4.93 (quint, J 7.1 Hz, 1H, CONH—CH—$CH_3$); 6.92-6.98 (m, 3H, Ar); 7.30 (dd, J 8.8, 8.0 Hz, 2H, Ar); 7.36 (d, J 8.2 Hz, 2H, Ar); 7.69 (d, J 7.1 Hz, 1H, CONH—CH); 7.84 (d, J 8.2 Hz, 2H, Ar); 12.79 (bs, 1H, $CO_2H$). M/Z $(M+H)^+$: 455

Compound 6: Methyl 4-[(1S)-1-[[4-[(2-phenoxyacetyl)amino]tetrahydropyran-4-carbonyl]amino]ethyl]benzoate Compound 6 was obtained according to General Procedure I-a, starting from Compound 2 and lithium phenoxyacetate. Purification by flash chromatography (DCM/MeOH: 100/0 to 95/5) afforded Compound 6 as a white powder in 75% yield. M/Z $(M+H)^+$: 441

Example 7: 4-[(1S)-1-[[4-[(2-Phenoxyacetyl)amino]tetrahydropyran-4-carbonyl]amino]ethyl]benzoic acid

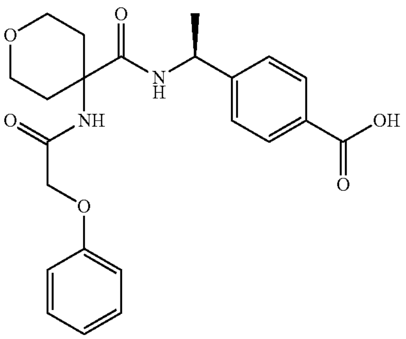 [SMILES: C[C@H](NC(=O)C1(NC(=O)COc2ccccc2)CCOCC1)c1ccc(C(=O)O)cc1]

A suspension of Compound 6 (1 equiv.) in HCl 1 N (0.1 M) was stirred at 150° C. for 5 min under microwave irradiation. As the conversion was half complete, the reaction mixture was diluted with water, extracted with EtOAc, washed with brine and dried. The resulting residue was dissolved in THF (0.2 M). LiOH in water (4 equiv.) was added. The reaction mixture was stirred at rt for 1.5 h, then acidified to pH 1 with aqueous HCl 1 N. The reaction mixture was extracted with DCM, washed with brine and dried. Purification by flash chromatography (DCM/MeOH: 100/0 to 90/10), then by preparative LC-MS afforded Example 7 as a white solid in 15% yield. $^1$H-NMR (DMSO-$d_6$, 400 MHz) δ (ppm): 1.34 (d, J 7.0 Hz, 3H, CH—$CH_3$); 1.86-2.01 (m, 4H, $CH_2$); 3.38-3.46 (m, 2H, O—$CH_2$); 3.59-3.67 (m, 2H, O—$CH_2$); 4.62 (s, 2H, Ph-O—$CH_2$); 4.94 (quint, J 7.0 Hz, 1H, CONH—CH—$CH_3$); 6.93-7.01 (m, 3H, Ar); 7.29 (dd, J 8.2, 7.7 Hz, 2H, Ar); 7.38 (d, J 8.0 Hz, 2H, Ar); 7.81-7.86 (m, 3H, Ar+O-$CH_2$—CONH); 8.02 (d, J 7.0 Hz, 1H, CONH—CH—$CH_3$); 12.80 (bs, 1H, $CO_2H$). M/Z $(M+H)^+$: 427

Compound 7: Methyl 4-[(1S)-1-[[4-[2-(3-chlorophenoxy)ethylamino]tetrahydropyran-4-carbonyl]amino]ethyl]benzoate Compound 7 was obtained according to General Procedure III-a, starting from Compound 2 and 2-(3-chlorophenoxy)acetaldehyde. Purification by flash chromatography (Cyclohexane/EtOAc: 100/0 to 0/100) afforded Compound 7 as a white powder in 49% yield. M/Z $(M[^{35}Cl]+H)^+$: 461

Example 8: 4-[(1S)-1-[[4-[2-(3-Chlorophenoxy)ethylamino]tetrahydropyran-4-carbonyl]amino]ethyl]benzoic acid, hydrochloride

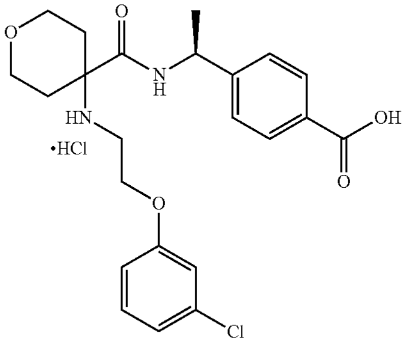 [SMILES: C[C@H](NC(=O)C1(NCCOc2cccc(Cl)c2)CCOCC1)c1ccc(C(=O)O)cc1 ; Cl]

Example 8 was obtained according to General Procedure IV-a, starting from Compound 7, as a white solid in 43% yield. $^1$H-NMR (DMSO-$d_6$, 400 MHz) (ppm): 1.46 (d, J 7.1 Hz, 3H, CH—$CH_3$); 1.90-2.02 (m, 2H, $CH_2$); 2.36-2.47 (m, 2H, $CH_2$); 2.97-3.20 (m, 2H, NH—$CH_2$); 3.30-3.46 (m, 2H, O—$CH_2$); 3.85-3.94 (m, 2H, O—$CH_2$); 4.22-4.31 (m, 2H, PhO—$CH_2$); 5.05 (quint, J 7.1 Hz, 1H, CONH—CH—$CH_3$); 6.97 (dd, J 8.1, 1.3 Hz, 1H, Ar); 7.03-7.09 (m, 2H, Ar); 7.35 (t, J 8.1 Hz, 1H, Ar); 7.52 (d, J 8.3 Hz, 2H, Ar); 7.89 (d, J 8.3 Hz, 2H, Ar); 9.24 (d, J 7.1 Hz, 1H, CONH—CH); 9.87 (bs, 2H, NH+HCl salt); 12.84 (bs, 1H, $CO_2H$). M/Z $(M[^{35}Cl]+H)^+$: 447

Compound 8: Methyl 4-[(1S)-1-[[4-[2-(3-chlorophenoxy)ethyl-methyl-amino]tetrahydropyran-4-carbonyl]amino]ethyl]benzoate Compound 8 was obtained according to General Procedure III-a, starting from Compound 7 and formaldehyde, as a colorless oil in 85% yield. M/Z $(M[^{35}Cl]+H)^+$: 475

Example 9: 4-[(1S)-1-[[4-[2-(3-Chlorophenoxy)ethyl-methyl-amino]tetrahydropyran-4-carbonyl]amino]ethyl]benzoic acid, hydrochloride

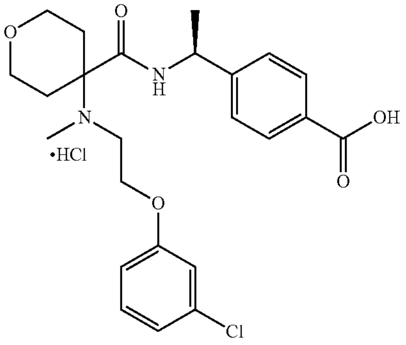 [SMILES: C[C@H](NC(=O)C1(N(C)CCOc2cccc(Cl)c2)CCOCC1)c1ccc(C(=O)O)cc1 ; Cl]

Example 9 was obtained according to General Procedure IV-b, starting from Compound 8. Purification by preparative LC-MS, then HCl salt preparation (method 2) afforded Example 9 as a beige powder in 33% yield. $^1$H-NMR (DMSO-$d_6$, 400 MHz, 80° C.): 1.49 (d, J 7.1 Hz, 3H, CH—$CH_3$); 1.83-1.96 (m, 2H, $CH_2$); 2.15-2.26 (m, 2H, $CH_2$); 3.02-3.60 (m, 7H, N—$CH_3$+N-$CH_2$+O—$CH_2$); 3.79-3.88 (m, 2H, O—$CH_2$); 4.17-4.24 (m, 2H, PhO—$CH_2$); 5.12 (quint, J 7.1 Hz, 1H, CONH—CH—$CH_3$); 6.87-6.92 (m, 1H, Ar); 6.97-7.03 (m, 2H, Ar); 7.30 (t, J 8.5 Hz, 1H, Ar); 7.48 (d, J 8.2 Hz, 2H, Ar); 7.89 (d, J 8.2 Hz, 2H, Ar); CONH signal not observed; $CO_2H$ signal not observed; HCl salt signal not observed. M/Z $(M[^{35}Cl]+H)^+$: 461

Compound 9: Ethyl 4-[(1S)-1-[[4-[2-(3-chlorophenoxy)ethyl-ethyl-amino]tetrahydropyran-4-carbonyl]amino]ethyl]benzoate Compound 9 was obtained according to General Procedure III-a, starting from Compound 7 and acetaldehyde, as a colorless oil in 73% yield. M/Z $(M[^{35}Cl]+H)^+$: 489

Example 10: 4-[(1S)-1-[[4-[2-(3-Chlorophenoxy)ethyl-ethyl-amino]tetrahydropyran-4-carbonyl]amino]ethyl]benzoic acid, hydrochloride

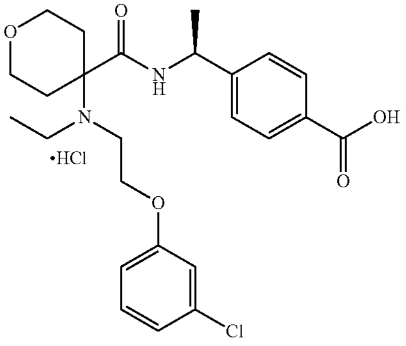 [SMILES: CCN(CCOc1cccc(Cl)c1)C1(C(=O)N[C@@H](C)c2ccc(C(=O)O)cc2)CCOCC1 ; Cl]

Example 10 was obtained according to General Procedure IV-b, starting from Compound 9. Purification by preparative LC-MS, then HCl salt preparation (method 2) afforded Example 10 as a white powder in 35% yield. $^1$H-NMR (DMSO-$d_6$ 400 MHz, 80° C.): 1.10 (d, J 6.7 Hz, 3H, $CH_2$—$CH_3$); 1.47 (d, J 7.1 Hz, 3H, CH—$CH_3$); 1.77-1.90 (m, 2H, $CH_2$); 2.09-2.18 (m, 2H, $CH_2$); 2.75-2.85 (m, 2H, N—$CH_2$); 3.05-3.45 (m, 4H, N—$CH_2$+O—$CH_2$); 3.76-3.85 (m, 2H, O—$CH_2$); 4.07-4.15 (m, 2H, PhO—$CH_2$); 5.10 (quint, J 7.1 Hz, 1H, CONH—CH—$CH_3$); 6.86-6.91 (m, 1H, Ar); 6.95-7.00 (m, 2H, Ar); 7.30 (t, J 8.5 Hz, 1H, Ar); 7.46 (d, J 8.2 Hz, 2H, Ar); 7.88 (d, J 8.2 Hz, 2H, Ar); CONH signal not observed; $CO_2H$ signal not observed; HCl salt signal not observed. M/Z $(M[^{35}Cl]+H)^+$: 475

Compound 10: Methyl 4-[(1S)-1-[[4-[2-(4-chlorophenoxy)ethylamino]tetrahydropyran-4-carbonyl]amino]ethyl]benzoate Compound 10 was obtained according to General Procedure III-a, starting from Compound 2 and 2-(4-chlorophenoxy)acetaldehyde. Purification by flash chromatography (Cyclohexane/EtOAc: 100/0 to 0/100) afforded Compound 10 as a colorless oil in 39% yield. M/Z $(M[^{35}Cl]+H)^+$: 461

Example 11: 4-[(1S)-1-[[4-[2-(4-Chlorophenoxy)ethylamino]tetrahydropyran-4-carbonyl]amino]ethyl]benzoic acid, hydrochloride

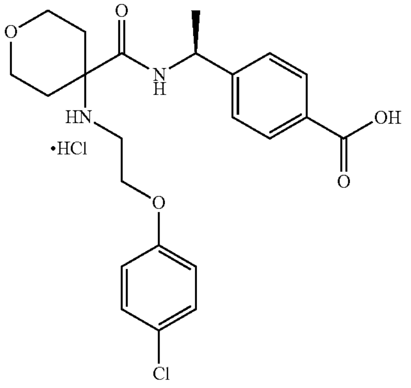 [SMILES: C[C@H](NC(=O)C1(NCCOc2ccc(Cl)cc2)CCOCC1)c1ccc(C(=O)O)cc1 ; Cl]

Example 11 was obtained according to General Procedure IV-a, starting from Compound 10, as a white solid in 34% yield. $^1$H-NMR (DMSO-$d_6$, 400 MHz) δ (ppm): 1.46 (d, J 6.9 Hz, 3H, CH—$CH_3$); 1.90-2.01 (m, 2H, $CH_2$); 2.36-2.47 (m, 2H, $CH_2$); 2.98-3.19 (m, 2H, NH—$CH_2$); 3.27-3.36 (m, 2H, O—$CH_2$); 3.82-3.94 (m, 2H, O—$CH_2$); 4.19-4.28 (m, 2H, PhO—$CH_2$); 5.05 (quint, J 6.9 Hz, 1H, CONH—CH—$CH_3$); 7.01 (d, J 8.7 Hz, 2H, Ar); 7.36 (d, J 8.7 Hz, 2H, Ar); 7.52 (d, J 8.2 Hz, 2H, Ar); 7.89 (d, J 8.2 Hz, 2H, Ar); 9.22 (d, J 6.9 Hz, 1H, CONH—CH); 9.86 (bs, 2H, NH+HCl salt); 12.84 (bs, 1H, $CO_2H$). M/Z $M[^{35}Cl]+H)^+$: 447

Compound 11: Methyl 4-[(1S)-1-[[4-[2-[3-(trifluoromethyl)phenoxy]ethylamino]tetrahydropyran-4-carbonyl]amino]ethyl]benzoate Compound 11 was obtained according to General Procedure III-a, starting from Compound 2 and 2-[3-(trifluoromethyl)phenoxy]acetaldehyde, as a yellow oil in 58% yield. M/Z $(M+H)^+$: 495

Example 12: 4-[(1S)-1-[[4-[2-[3-(Trifluoromethyl)phenoxy]ethylamino]tetrahydropyran-4-carbonyl]amino]ethyl]benzoic acid

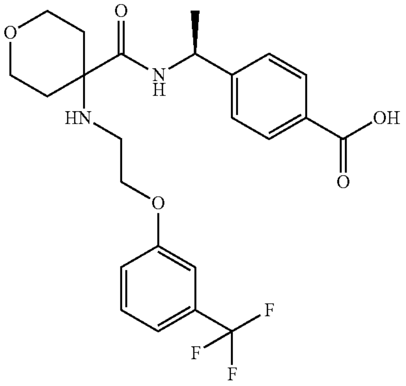 [SMILES: C[C@H](NC(=O)C1(NCCOc2cccc(C(F)(F)F)c2)CCOCC1)c1ccc(C(=O)O)cc1]

Example 12 was obtained according to General Procedure IV-a, starting from Compound 11. Purification by preparative LC-MS afforded Example 12 as a white powder in 22% yield. $^1$H-NMR (DMSO-$d_6$, 400 MHz) δ (ppm): 1.37 (d, J 6.9 Hz, 3H, CH—$CH_3$); 1.48-1.57 (m, 2H, $CH_2$); 1.83-1.97 (m, 2H, $CH_2$); 2.63-2.73 (m, 2H, NH—$CH_2$); 3.49-3.59 (m, 2H, O—$CH_2$); 3.63-3.70 (m, 2H, O—$CH_2$); 4.10 (t, J 5.4 Hz, 2H, PhO—$CH_2$); 4.94-5.02 (m, 1H, CONH—CH—$CH_3$); 7.18-7.23 (m, 2H, Ar); 7.28 (d, J 7.8 Hz, 1H, Ar); 7.41 (d, J 8.0 Hz, 2H, Ar); 7.52 (t, J 7.8 Hz, 1H, Ar); 7.84 (d, J 8.0 Hz, 2H, Ar); 8.21 (d, J 8.1 Hz, 1H, CONH—CH); signal not observed; $CO_2H$ signal not observed. M/Z $(M+H)^+$: 481

Compound 12: Methyl 4-[(1S)-1-[[4-[2-(3-methoxyphenoxy)ethylamino]tetrahydropyran-4-carbonyl]amino]ethyl]benzoate Compound 12 was obtained according to General Procedure III-a, starting from Compound 2 and 2-(3-methoxyphenoxy)acetaldehyde. Purification by flash chromatography (Cyclohexane/EtOAc: 40/60 to 20/80) afforded Compound 12 as a colorless oil in 74% yield. M/Z $(M+H)^+$: 457

Example 13: 4-[(1S)-1-[[4-[2-[3-Methoxyphenoxy]ethylamino]tetrahydropyran-4-carbonyl]amino]ethyl]benzoic acid, hydrochloride

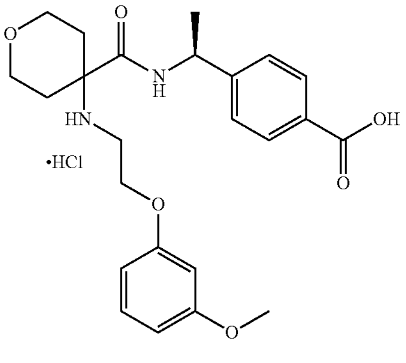 [SMILES: COc1cccc(OCCNC2(C(=O)N[C@@H](C)c3ccc(C(=O)O)cc3)CCOCC2)c1 ; Cl]

Example 13 was obtained according to General Procedure IV-a, starting from Compound 12. Purification by preparative LC-MS, then HCl salt preparation (method 2) afforded Example 13 as a beige powder in 58% yield. $^1$H-NMR (DMSO-$d_6$, 400 MHz) δ (ppm): 1.46 (d, J 6.9 Hz, 3H, CH—$CH_3$); 1.84-2.00 (m, 2H, $CH_2$); 2.36-2.47 (m, 2H, $CH_2$); 3.00-3.19 (m, 2H, NH—$CH_2$); 3.73 (s, 3H, $CH_3$); 3.27-3.42 (m, 2H, O—$CH_2$); 3.82-3.95 (m, 2H, O—$CH_2$); 4.15-4.25 (m, 2H, PhO—$CH_2$); 5.06 (quint, J 6.9 Hz, 1H, CONH—CH—$CH_3$); 6.50-6.60 (m, 3H, Ar); 7.21 (t, J 8.1 Hz, 1H, Ar); 7.50 (d, J 8.2 Hz, 2H, Ar); 7.90 (d, J 8.2 Hz, 2H, Ar); 9.02 (bs, 1H, CONH—CH); 9.63 (bs, 2H, NH+HCl salt); 12.67-12.98 (m, 1H, $CO_2H$). M/Z $(M+H)^+$: 443

Compound 13: Methyl 4-[(1S)-1-[[4-[2-(3-methylphenoxy)ethylamino]tetrahydropyran-4-carbonyl]amino]ethyl]benzoate Compound 13 was obtained according to General Procedure III-a, starting from Compound 2 and 2-(3-methylphenoxy)acetaldehyde. Purification by flash chromatography (Cyclohexane/EtOAc: 100/0 to 0/100) afforded Compound 13 as a colorless oil in 53% yield. M/Z $(M+H)^+$: 441

Example 14: 4-[(1S)-1-[[4-[2-(3-Methylphenoxy)ethylamino]tetrahydropyran-4-carbonyl]amino]ethyl]benzoic acid, hydrochloride

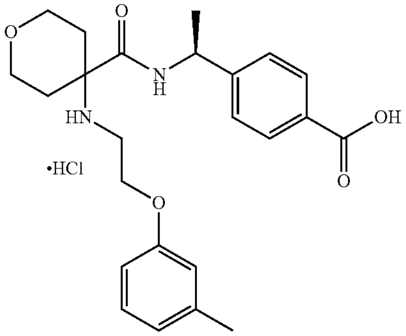 [SMILES: Cc1cccc(OCCNC2(C(=O)N[C@@H](C)c3ccc(C(=O)O)cc3)CCOCC2)c1 ; Cl]

Example 14 was obtained according to General Procedure IV-a, starting from Compound 13, as a white solid in 33% yield. $^1$H-NMR (DMSO-$d_6$, 400 MHz) δ (ppm): 1.46 (d, J 7.1 Hz, 3H, CH—$CH_3$); 1.90-2.03 (m, 2H, $CH_2$); 2.29 (s, 3H, Ph-$CH_3$); 2.35-2.47 (m, 2H, $CH_2$); 2.95-3.19 (m, 2H, NH—$CH_2$); 3.30-3.42 (m, 2H, O—$CH_2$); 3.84-3.94 (m, 2H, O—$CH_2$); 4.17-4.25 (m, 2H, PhO—$CH_2$); 5.05 (quint, J 7.1 Hz, 1H, CONH—CH—$CH_3$); 6.75-6.83 (m, 3H, Ar); 7.19 (t, J 8.1 Hz, 1H, Ar); 7.52 (d, J 8.3 Hz, 2H, Ar); 7.89 (d, J 8.3 Hz, 2H, Ar); 9.22 (d, J 7.1 Hz, 1H, CONH—CH); 9.81-9.95 (m, 2H, NH+HCl salt); 12.85 (bs, 1H, $CO_2H$). M/Z $(M+H)^+$: 427

Compound 14: Methyl 4-[(1S)-1-[[4-[2-(4-cyanophenoxy)ethylamino]tetrahydropyran-4-carbonyl]amino]ethyl]benzoate Compound 14 was obtained according to General Procedure III-a, starting from Compound 2 and 2-(4-cyanophenoxy)acetaldehyde. Purification by flash chromatography (Cyclohexane/EtOAc: 100/0 to 0/100) afforded Compound 14 as a colorless oil in 58% yield. M/Z $(M+H)^+$: 452

Example 15: 4-[(1S)-1-[[4-[2-(4-Cyanophenoxy)ethylamino]tetrahydropyran-4-carbonyl]amino]ethyl]benzoic acid, hydrochloride

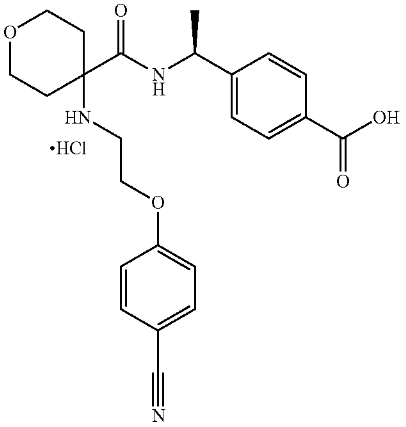 [SMILES: C[C@H](NC(=O)C1(NCCOc2ccc(C#N)cc2)CCOCC1)c1ccc(C(=O)O)cc1 ; Cl]

Example 15 was obtained according to General Procedure IV-a, starting from Compound 14. Purification by preparative LC-MS afforded Example 15 as a white solid in 13% yield. $^1$H-NMR (DMSO-$d_6$, 400 MHz) δ (ppm): 1.45 (d, J 7.0 Hz, 3H, CH—$CH_3$); 1.82-1.93 (m, 2H, $CH_2$); 2.31-2.46 (m, 2H, $CH_2$); 3.03-3.19 (m, 2H, NH—$CH_2$); 3.35-3.43 (m, 2H, O—$CH_2$); 3.81-3.90 (m, 2H, O—$CH_2$); 4.24-4.32 (m, 2H, PhO—$CH_2$); 5.06 (quint, J 7.0 Hz, 1H, CONH—CH—$CH_3$); 7.12 (d, J 8.8 Hz, 2H, Ar); 7.49 (d, J 8.3 Hz, 2H, Ar); 7.80 (d, J 8.8 Hz, 2H, Ar); 7.90 (d, J 8.3 Hz, 2H, Ar); 8.77-8.97 (m, 1H, CONH—CH); 9.34-9.72 (m, 2H, NH+HCl salt); 12.81 (bs, 1H, $CO_2H$). M/Z $(M+H)^+$: 438

Compound 15: Methyl 4-[(1S)-1-[[4-[2-(3,5-difluorophenoxy)ethylamino]tetrahydropyran-4-carbonyl]amino]ethyl]benzoate Compound 15 was obtained according to General Procedure III-a, starting from Compound 2 and 2-(3,5-difluorophenoxy)acetaldehyde. Purification by flash chromatography (DCM/MeOH: 100/0 to 97.5/2.5) afforded Compound 15 as a yellow oil in 42% yield. M/Z $(M+H)^+$: 463

Example 16: 4-[(1S)-1-[[4-[2-(3,5-Difluorophenoxy)ethylamino]tetrahydropyran-4-carbonyl]amino]ethyl]benzoic acid, hydrochloride

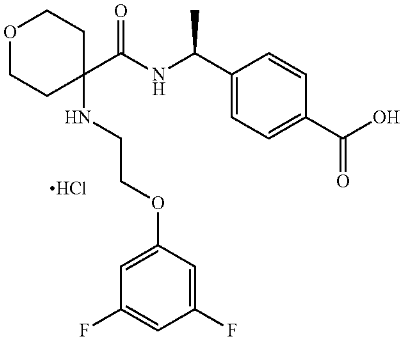 [SMILES: C[C@H](NC(=O)C1(NCCOc2cc(F)cc(F)c2)CCOCC1)c1ccc(C(=O)O)cc1 ; Cl]

Example 16 was obtained according to General Procedure IV-a, starting from Compound 15, as a white solid in 53% yield. $^1$H-NMR (DMSO-d$_6$, 400 MHz) δ (ppm): 1.47 (d, J 6.9 Hz, 3H, CH—CH$_3$); 1.89-2.00 (m, 2H, CH$_2$); 2.35-2.49 (m, 2H, CH$_2$); 3.00-3.19 (m, 2H, NH—CH$_2$); 3.31-3.40 (m, 2H, O—CH$_2$); 3.84-3.93 (m, 2H, O—CH$_2$); 4.24-4.32 (m, 2H, PhO—CH$_2$); 5.05 (quint, J 6.9 Hz, 1H, CONH—CH—CH$_3$); 6.72-6.81 (m, 2H, Ar); 6.82-6.88 (m, 1H, Ar); 7.51 (d, J 8.2 Hz, 2H, Ar); 7.89 (d, J 8.2 Hz, 2H, Ar); 9.14-9.25 (m, 1H, CONH—CH); 9.76-9.89 (m, 2H, NH+HCl salt); 12.80 (bs, 1H, CO$_2$H). M/Z (M+H)$^+$: 449

Compound 16: Methyl 4-[(1S)-1-[[4-[2-(3,4-dichlorophenoxy)ethylamino]tetrahydropyran-4-carbonyl]amino]ethyl]benzoate Compound 16 was obtained according to General Procedure III-a, starting from Compound 2 and 2-(3,4-dichlorophenoxy)acetaldehyde. Purification by flash chromatography (15 μm cartridge, DCM/MeOH: 100/0 to 94/6) afforded Compound 16 as a colorless oil in 30% yield. M/Z (M[$^{35}$Cl]+H)$^+$: 495

Example 17: 4-[(1S)-1-[[4-[2-(3,4-Dichlorophenoxy)ethylamino]tetrahydropyran-4-carbonyl]amino]ethyl]benzoic acid, hydrochloride

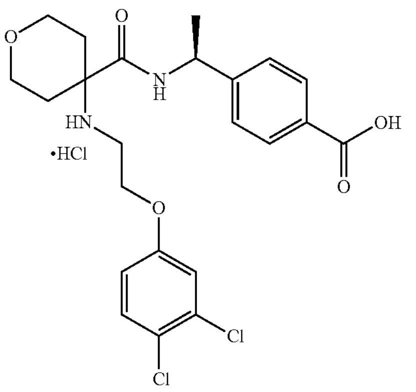 [SMILES: C[C@H](NC(=O)C1(NCCOc2ccc(Cl)c(Cl)c2)CCOCC1)c1ccc(C(=O)O)cc1 ; Cl]

Example 17 was obtained according to General Procedure IV-a, starting from Compound 16. Purification by preparative LC-MS, then HCl salt preparation (method 3) afforded Example 17 as a white solid in 49% yield. $^1$H-NMR (DMSO-d$_6$, 400 MHz) δ (ppm): 1.46 (d, J 6.9 Hz, 3H, CH—CH$_3$); 1.87-2.00 (m, 2H, CH$_2$); 2.36-2.47 (m, 2H, CH$_2$); 2.98-3.19 (m, 2H, NH—CH$_2$); 3.44-3.63 (m, 2H, O—CH$_2$); 3.84-3.93 (m, 2H, O—CH$_2$); 4.29-4.32 (m, 2H, Ph-O—CH$_2$); 5.05 (quint, J 6.9 Hz, 1H, CONH—CH—CH$_3$); 7.02 (d, J 8.9 Hz, 1H, Ar); 7.26 (s, 1H, Ar); 7.51 (d, J 8.0 Hz, 2H, Ar); 7.56 (d, J 8.9 Hz, 1H, Ar); 7.89 (d, J 8.0 Hz, 2H, Ar); 9.10-9.22 (m, 1H, CONH—CH); 9.76 (bs, 2H, NH+HCl salt); 12.91 (bs, 1H, CO$_2$H). M/Z (M[$^{35}$Cl]+H)$^+$: 481

Compound 17: Methyl 4-[(1S)-1-[[4-(3-phenylpropylamino)tetrahydropyran-4-carbonyl]amino]ethyl]benzoate Compound 17 was obtained according to General Procedure III-a, starting from Compound 2 and 3-phenylpropanal. Purification by flash chromatography (DCM/MeOH: 100/0 to 96/4) afforded compound 17 as a colorless oil in 41% yield. M/Z (M+H)$^+$: 425

Example 18: 4-[(1S)-1-[[4-(3-Phenylpropylamino)tetrahydropyran-4-carbonyl]amino]ethyl]benzoic acid, hydrochloride

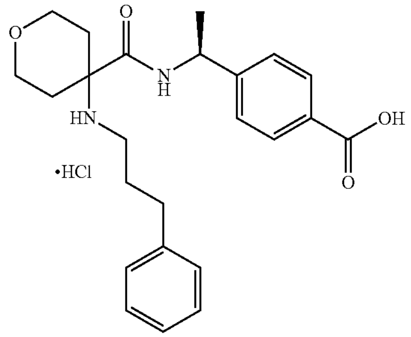 [SMILES: C[C@H](NC(=O)C1(NCCCc2ccccc2)CCOCC1)c1ccc(C(=O)O)cc1 ; Cl]

Example 18 was obtained according to General Procedure IV-a, starting from Compound 17, as a white solid in 69% yield. $^1$H-NMR (DMSO-d$_6$, 400 MHz) δ (ppm): 1.43 (d, J 7.1 Hz, 3H, CH—CH$_3$); 1.80-1.96 (m, 4H, CH$_2$); 2.34-2.75 (m, 6H, CH$_2$); 3.50-3.62 (m, 2H, O—CH$_2$); 3.82-3.91 (m, 2H, O—CH$_2$); 5.03 (quint, J 7.1 Hz, 1H, CONH—CH—CH$_3$); 7.15-7.23 (m, 3H, Ar); 7.29 (t, J 7.3 Hz, 2H, Ar); 7.51 (d, J 8.2 Hz, 2H, Ar); 7.92 (d, J 8.2 Hz, 2H, Ar); 9.14 (d, J 7.1 Hz, 1H, CONH—CH); 9.42-9.60 (m, 2H, NH+HCl salt); 12.87 (bs, 1H, CO$_2$H). M/Z (M+H)$^+$: 411

Compound 18: Methyl 4-[(1S)-1-[[4-(2-phenylethylamino)tetrahydropyran-4-carbonyl]amino]ethyl]benzoate Compound 18 was obtained according to General Procedure III-a, starting from Compound 2 and 2-phenylacetaldehyde. Purification by preparative LC-MS afforded Compound 18 as a brown oil in 53% yield. M/Z (M+H)$^+$: 411

Example 19: 4-[(1S)-1-[[4-(2-Phenylethylamino)tetrahydropyran-4-carbonyl]amino]ethyl]benzoic acid

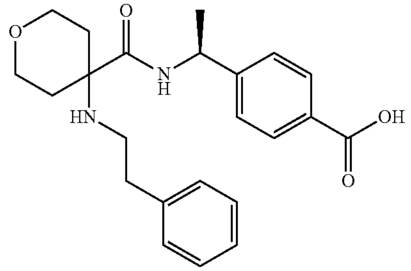 [SMILES: C[C@H](NC(=O)C1(NCCc2ccccc2)CCOCC1)c1ccc(C(=O)O)cc1]

Example 19 was obtained according to General Procedure IV-a, starting from Compound 18. Purification by preparative LC-MS afforded Example 19 as a beige powder in 25% yield. $^1$H-NMR (DMSO-d$_6$, 400 MHz) δ (ppm): 1.32 (d, J 7.2 Hz, 3H, CH—CH$_3$); 1.41-1.53 (m, 2H, CH$_2$); 1.78-1.91

(m, 2H, $CH_2$); 2.36-2.48 (m, 2H, Ph-$CH_2$); 2.64-2.70 (m, 2H, NH—$CH_2$); 3.46-3.54 (m, 2H, O—$CH_2$); 3.57-3.64 (m, 2H, O—$CH_2$); 4.90-5.00 (m, 1H, CONH—CH—$CH_3$); 7.11-7.19 (m, 3H, Ar); 7.21-7.27 (m, 2H, Ar); 7.37 (d, J 8.2 Hz, 2H, Ar); 7.87 (d, J 8.2 Hz, 2H, Ar); 8.04 (d, J 8.2 Hz, 1H, CONH—CH); 8.22 (bs, 1H, NH), $CO_2H$ signal not observed. M/Z $(M+H)^+$: 397

Compound 19: Methyl 4-[(1S)-1-[[4-[(3-fluorophenyl)methylamino]tetrahydropyran-4-carbonyl]amino]ethyl]benzoate Compound 19 was obtained according to General Procedure III-a, starting from Compound 2 and 3-fluorobenzaldehyde. Purification by flash chromatography (Cyclohexane/EtOAc: 100/0 to 0/100) afforded Compound 19 as a white powder in 53% yield. M/Z $(M+H)^+$: 415

Example 20: 4-[(1S)-1-[[4-[(3-Fluorophenyl)methylamino]tetrahydropyran-4-carbonyl]amino]ethyl]benzoic acid, hydrochloride

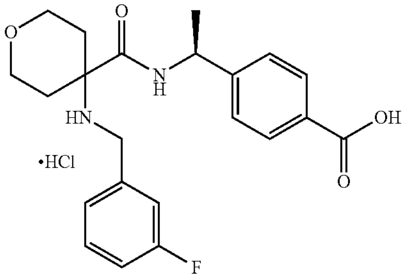 [SMILES: C[C@H](NC(=O)C1(NCc2cccc(F)c2)CCOCC1)c1ccc(C(=O)O)cc1 ; Cl]

Example 20 was obtained according to General Procedure IV-a, starting from Compound 19, as a white powder in 72% yield. $^1$H-NMR (DMSO-$d_6$ 400 MHz) δ (ppm): 1.50 (d, J 7.1 Hz, 3H, CH—$CH_3$); 1.88-2.00 (m, 2H, $CH_2$); 2.49-2.53 (m, 2H, $CH_2$); 3.35-3.49 (m, 2H, O—$CH_2$); 3.82-3.98 (m, 4H, NH—$CH_2$-Ph+O-$CH_2$); 5.05-5.14 (m, 1H, CONH—CH—$CH_3$); 7.21-7.40 (m, 3H, Ar); 7.42-7.51 (m, 1H, Ar); 7.54 (d, J 8.1 Hz, 2H, Ar); 7.91 (d, J 8.1 Hz, 2H, Ar); 9.05-9.27 (m, 1H, CONH—CH); 9.64-9.93 (m, 2H, NH+HCl salt); 12.85 (bs, 1H, $CO_2H$). M/Z $(M+H)^+$: 401

Compound 20: Methyl 4-[(1S)-1-[[4-(cyclohexylmethylamino)tetrahydropyran-4-carbonyl]amino]ethyl]benzoate Compound 20 was obtained according to General Procedure III-a, starting from Compound 2 and cyclohexanecarbaldehyde, as a white powder in 64% yield. M/Z $(M+H)^+$: 403

Example 21: 4-[(1S)-1-[[4-(Cyclohexylmethylamino)tetrahydropyran-4-carbonyl]amino]ethyl]benzoic acid, hydrochloride

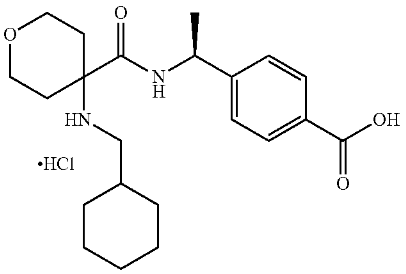 [SMILES: C[C@H](NC(=O)C1(NCC2CCCCC2)CCOCC1)c1ccc(C(=O)O)cc1 ; Cl]

Example 21 was obtained according to General Procedure IV-a, starting from Compound 20, as a white powder in 24% yield. $^1$H-NMR (DMSO-$d_6$, 400 MHz) δ (ppm): 0.70-0.87 (m, 2H, $CH_2$); 1.03-1.23 (m, 3H, CH+$CH_2$); 1.32-1.78 (m, 9H, $CH_2$+CH-$CH_3$); 1.78-1.96 (m, 2H, $CH_2$); 2.27-2.47 (m, 4H, $CH_2$); 3.28-3.37 (m, 2H, O—$CH_2$); 3.81-3.91 (m, 2H, O—$CH_2$); 5.05 (quint, J 7.1 Hz, 1H, CONH—CH—$CH_3$); 7.53 (d, J 8.2 Hz, 2H, Ar); 7.90 (d, J 8.2 Hz, 2H, Ar); 9.04-9.14 (m, 1H, NH); 9.19 (d, J 7.1 Hz, 1H, CONH—CH); 9.25-9.34 (m, 1H, HCl salt); 12.86 (bs, 1H, $CO_2H$). M/Z $(M+H)^+$: 389

Compound 21: Methyl 4-[(1S)-1-[[4-(3-pyridylmethylamino)tetrahydropyran-4-carbonyl]amino]ethyl]benzoate Compound 21 was obtained according to General Procedure III-a, starting from Compound 2 and pyridine-3-carbaldehyde, as a beige powder in quantitative yield. M/Z $(M+H)^+$: 398

Example 22: 4-[(1S)-1-[[4-(3-Pyridylmethylamino)tetrahydropyran-4-carbonyl]amino]ethyl]benzoic acid

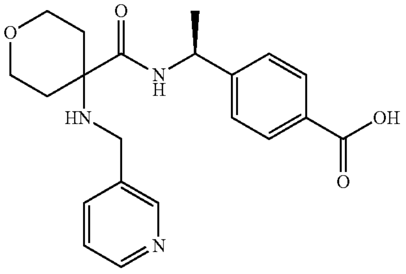 [SMILES: C[C@H](NC(=O)C1(NCc2cccnc2)CCOCC1)c1ccc(C(=O)O)cc1]

Example 22 was obtained according to General Procedure IV-a, starting from Compound 21. Purification by preparative LC-MS afforded Example 22 as a white powder in 7% yield. $^1$H-NMR (DMSO-$d_6$, 400 MHz) δ (ppm): $^1$H-NMR (400 MHz, DMSO-$d_6$): 1.40 (d, J 7.2 Hz, 3H, CH—$CH_3$); 1.55-1.64 (m, 2H, $CH_2$); 1.85-1.98 (m, 2H, $CH_2$); 3.45-3.57 (m, 4H, NH—$CH_2$-Ph+O-$CH_2$); 3.69-3.77 (m, 2H, O—$CH_2$); 4.99-5.09 (m, 1H, CONH—CH—$CH_3$); 7.34 (dd, J 7.6, 4.8 Hz, 1H, Ar); 7.43 (d, J 8.2 Hz, 2H, Ar); 7.71 (d, J 7.6 Hz, 1H, Ar); 7.87 (d, J 8.2 Hz, 2H, Ar); 8.22 (d, J 7.7

Hz, 1H, CONH—CH); 8.41-8.47 (m, 1H, Ar); 8.47-8.52 (m, 1H, Ar); NH signal not observed; $CO_2H$ signal not observed. M/Z $(M+H)^+$: 384

Compound 22: Methyl 4-[(1S)-1-[[4-(2-pyridylmethylamino)tetrahydropyran-4-carbonyl]amino]ethyl]benzoate Compound 22 was obtained according to General Procedure III-a, starting from Compound 2 and pyridine-2-carbaldehyde. Purification by preparative LC-MS afforded Compound 22 as a yellow oil in 59% yield. M/Z $(M+H)^+$: 398

Example 23: 4-[(1S)-1-[[4-(2-Pyridylmethylamino)tetrahydropyran-4-carbonyl]amino]ethyl]benzoic acid

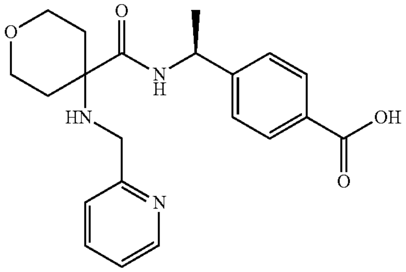 [SMILES: C[C@H](NC(=O)C1(NCc2ccccn2)CCOCC1)c1ccc(C(=O)O)cc1]

Example 23 was obtained according to General Procedure IV-a, starting from Compound 22. Purification by preparative LC-MS afforded Example 23 as a white powder in 4% yield. $^1$H-NMR (DMSO-$d_6$, 400 MHz) δ (ppm): 1.38 (d, J 6.9 Hz, 3H, CH—$CH_3$); 1.52-1.64 (m, 2H, $CH_2$); 1.87-2.02 (m, 2H, $CH_2$); 3.51-3.63 (m, 4H, NH—$CH_2$-Ph+O—$CH_2$); 3.64-3.74 (m, 2H, O—$CH_2$); 4.94-5.04 (m, 1H, CONH—CH—$CH_3$); 7.27 (ddd, J 7.7, 4.9, 0.6 Hz, 1H, Ar); 7.40 (d, J 8.2 Hz, 2H, Ar); 7.43 (d, J 7.7 Hz, 1H, Ar); 7.76 (td, J 7.7, 1.8 Hz, 1H, Ar); 7.81 (d, J 8.2 Hz, 2H, Ar); 8.49-8.52 (m, 1H, Ar); 8.57 (d, J 8.0 Hz, 1H, CONH—CH); NH signal not observed; $CO_2H$ signal not observed. M/Z $(M+H)^+$: 384

Compound 23: Methyl 4-[1-[[4-(tert-butoxycarbonylamino)tetrahydropyran-4-carbonyl]amino]cyclopropyl]benzoate Compound 23 was obtained according to General Procedure I-a, starting from 4-(tert-butoxycarbonylamino)tetrahydropyran-4-carboxylic acid and methyl 4-(1-aminocyclopropyl)benzoate. Purification by flash chromatography (Cyclohexane/EtOAc: 75/25 to 0/100) afforded Compound 23 as a white powder in 77% yield. M/Z $(M+H)^+$: 419

Compound 24: Methyl 4-[1-[(4-aminotetrahydropyran-4-carbonyl)amino]cyclopropyl]benzoate Compound 24 was obtained according to General Procedure II-a, starting from Compound 23. Purification by flash chromatography (KP-NH cartridge, DCM/EtOAc: 100/0 to 80/20) afforded Compound 24 as a beige powder in 60% yield. Compound 24 could also be obtained under its hydrochloride salt form according to General Procedure II-b, starting from Compound 23, in quantitative yield. M/Z $(M+H)^+$: 319

Compound 25: Methyl 4-[1-[[4-(2-phenoxyethylamino)tetrahydropyran-4-carbonyl]amino]cyclopropyl]benzoate Compound 25 was obtained according to General Procedure III-a, starting from Compound 24 and 2-phenoxyacetaldehyde. Purification by flash chromatography (Cyclohexane/EtOAc: 100/0 to 0/100) afforded Compound 25 as a colorless oil in 61% yield. M/Z $(M+H)^+$: 439

Example 24: 4-[1-[[4-(2-Phenoxyethylamino)tetrahydropyran-4-carbonyl]amino]cyclopropyl]benzoic acid, hydrochloride

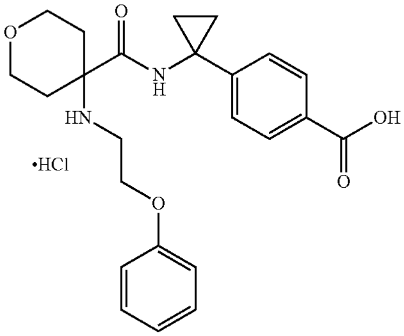 [SMILES: O=C(O)c1ccc(C2(NC(=O)C3(NCCOc4ccccc4)CCOCC3)CC2)cc1 ; Cl]

Example 24 was obtained according to General Procedure IV-a, starting from Compound 25, as a white powder in 91% yield. $^1$H-NMR (DMSO-$d_6$, 400 MHz) δ (ppm): 1.28-1.37 (m, 4H, C($CH_2$—$CH_2$)); 1.93-2.03 (m, 2H, $CH_2$); 2.37-2.47 (m, 2H, $CH_2$); 3.10-3.19 (m, 2H, NH—$CH_2$); 3.34-3.46 (m, 2H, O—$CH_2$); 3.88-3.96 (m, 2H, O—$CH_2$); 4.22-4.29 (m, 2H, PhO—$CH_2$); 6.96-7.02 (m, 3H, Ar); 7.29-7.36 (m, 4H, Ar); 7.85 (d, J 8.5 Hz, 2H, Ar); 9.50 (bs, 1H, CONH); 9.74-9.85 (m, 2H, NH+HCl salt); 13.32 (bs, 1H, $CO_2H$). M/Z $(M+H)^+$: 425

Compound 26: Methyl 4-[1-[[4-[methyl(2-phenoxyethyl)amino]tetrahydropyran-4-carbonyl]amino]cyclopropyl]benzoate Compound 26 was obtained according to General Procedure III-a, starting from Compound 25 and formaldehyde, as a colorless oil which was used as such in the next step. M/Z $(M+H)^+$: 439

Example 25: 4-[1-[[4-[Methyl(2-phenoxyethyl) amino]tetrahydropyran-4-carbonyl]amino]cyclopropyl]benzoic acid, hydrochloride N

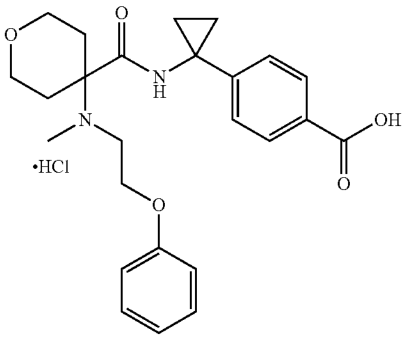 [SMILES: CN(CCOc1ccccc1)C1(C(=O)NC2(c3ccc(C(=O)O)cc3)CC2)CCOCC1 ; Cl]

Example 25 was obtained according to General Procedure IV-b, starting from Compound 26. Purification by preparative LC-MS, then HCl salt preparation (method 2) afforded Example 25 as a white powder in 29% yield over 2 steps. $^1$H-NMR (DMSO-de, 400 MHz, 80° C.): 1.27-1.30 (m, 4H, $C(CH_2—CH_2)$); 1.86-1.97 (m, 2H, $CH_2$); 2.16-2.26 (m, 2H, $CH_2$); 2.53-2.60 (m, 3H, N—$CH_3$); 3.03-3.13 (m, 2H, N—$CH_2$); 3.31-3.41 (m, 2H, O—$CH_2$); 3.82-3.90 (m, 2H, O—$CH_2$); 4.16-4.24 (m, 2H, PhO—$CH_2$); 6.92-6.98 (m, 3H, Ar); 7.27-7.32 (m, 2H, Ar); 7.37 (d, J 8.5 Hz, 2H, Ar); 7.85 (d, J 8.5 Hz, 2H, Ar); CONH signal not observed; $CO_2H$ signal not observed; HCl salt signal not observed. M/Z $(M+H)^+$: 439

Compound 27: Methyl 4-[1-[[4-[propyl(2-phenoxyethyl)amino]tetrahydropyran-4-carbonyl]amino]cyclopropyl]benzoate Compound 27 was obtained according to General Procedure III-b, starting from Compound 25 and propionaldehyde. Purification by flash chromatography (KP-NH cartridge, Cyclohexane/EtOAc: 100/0 to 70/30) afforded Compound 27 as a yellow oil in 60% yield. M/Z $(M+H)^+$: 481

Example 26: 4-[1-[[4-[Propyl(2-phenoxyethyl) amino]tetrahydropyran-4-carbonyl]amino]cyclopropyl]benzoic acid, hydrochloride

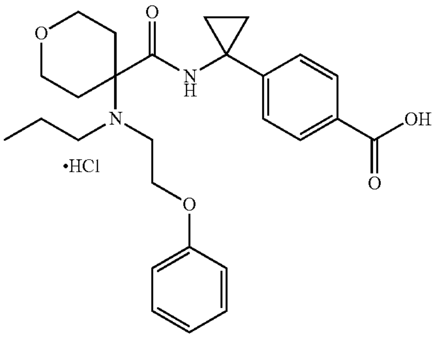 [SMILES: CCCN(CCOc1ccccc1)C1(C(=O)NC2(c3ccc(C(=O)O)cc3)CC2)CCOCC1 ; Cl]

Example 26 was obtained according to General Procedure IV-b, starting from Compound 27. Purification by preparative LC-MS, then HCl salt preparation (method 1) afforded Example 26 as a white powder in 40% yield. $^1$H-NMR ($DMSO-d_6/D_2O$ 400 MHz) δ (ppm): 0.77-0.84 (m, 3H, $CH_2—CH_2—CH_3$); 1.20-1.28 (m, 2H, $C(CH_2—CH_2)$); 1.28-1.35 (m, 2H, $C(CH_2—CH_2)$); 1.53-1.64 (m, 2H, $CH_2—CH_2—CH_3$); 1.84-1.95 (m, 2H, $CH_2$); 2.28-2.39 (m, 2H, $CH_2$); 2.81-2.95 (m, 2H, N—$CH_2$); 3.22 (t, J 11.6 Hz, 2H, O—$CH_2$); 3.29-3.43 (m, 2H, N—$CH_2$); 3.86-3.97 (m, 2H, O—$CH_2$); 4.07-4.16 (m, 2H, Ph-O—$CH_2$); 6.87-7.00 (m, 3H, Ar); 7.25-7.34 (m, 4H, Ar); 7.81-7.88 (m, 2H, Ar); CONH signal not observed; $CO_2H$ signal not observed; HCl salt signal not observed. M/Z $(M+H)^+$: 467

Compound 28: Methyl 4-[1-[[4-[cyclopropylmethyl (2-phenoxyethyl)amino]tetrahydropyran-4-carbonyl] amino]cyclopropyl]benzoate Compound 28 was obtained according to General Procedure III-b, starting from Compound 25 and cyclopropanecarbaldehyde. Purification by flash chromatography (KP-NH cartridge, Cyclohexane/EtOAc: 100/0 to 70/30) afforded Compound 28 as a colorless oil in 85% yield. M/Z $(M+H)^+$: 494

Example 27: 4-[1-[[4-[Cyclopropylmethyl(2-phenoxyethyl)amino]tetrahydropyran-4-carbonyl] amino]cyclopropyl]benzoic acid, hydrochloride

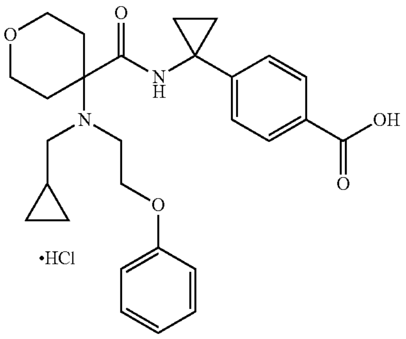 [SMILES: O=C(O)c1ccc(C2(NC(=O)C3(N(CCOc4ccccc4)CC4CC4)CCOCC3)CC2)cc1 ; Cl]

Example 27 was obtained according to General Procedure V-b, starting from Compound 28. Purification by preparative LC-MS, then HCl salt preparation (method 1) afforded Example 27 as a white powder in 42% yield. $^1$H-NMR ($DMSO-d_6/D_2O$, 400 MHz) δ (ppm): 0.23-0.33 (m, 2H, $CH(CH_2—CH_2)$); 0.54-0.63 (m, 2H, $CH(CH_2—CH_2)$); 1.00-1.09 (m, 1H, $CH(CH_2—CH_2)$); 1.21-1.34 (m, 4H, $C(CH_2—CH_2)$); 1.91-2.02 (m, 2H, $CH_2$); 2.34-2.43 (m, 2H, $CH_2$); 2.87-2.97 (m, 2H, N—$CH_2$); 3.16-3.25 (m, 2H, O—$CH_2$); 3.45-3.56 (m, 2H, N—$CH_2$); 3.89-3.96 (m, 2H, O—$CH_2$); 4.21-4.29 (m, 2H, PhO—$CH_2$); 6.91-6.99 (m, 3H, Ar); 7.27-7.34 (m, 4H, Ar); 7.85 (d, J 8.2 Hz, 2H, Ar); CONH signal not observed; $CO_2H$ signal not observed; HCl salt signal not observed. M/Z $(M+H)^+$: 479

Compound 29: Methyl 4-[1-[[4-[2-(3-chlorophenoxy)ethylamino]tetrahydropyran-4-carbonyl] amino]cyclopropyl]benzoate Compound 29 was obtained according to General Procedure III-a, starting from Compound 24 and 2-(3-chlorophenoxy)acetaldehyde. Purification by flash chromatography (KP-NH cartridge, Cyclohexane/EtOAc: 100/0 to 20/80) afforded Compound 29 as a colorless oil in 72% yield. M/Z $(M[^{35}Cl]+H)^+$: 473

Example 28: 4-[1-[[4-[2-(3-Chlorophenoxy)ethylamino]tetrahydropyran-4-carbonyl]amino]cyclopropyl]benzoic acid, hydrochloride

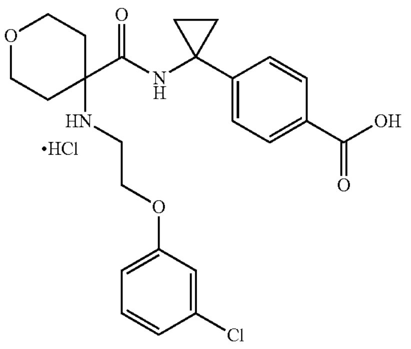 [SMILES: O=C(O)c1ccc(C2(NC(=O)C3(NCCOc4cccc(Cl)c4)CCOCC3)CC2)cc1 ; Cl]

Example 28 was obtained according to General Procedure IV-b, starting from Compound 29. Purification by preparative LC-MS, then HCl salt preparation (method 2) afforded Example 28 as a white powder in 50% yield. $^1$H-NMR (DMSO-$d_6$, 400 MHz) δ (ppm): 1.27-1.37 (m, 4H, C($CH_2$—$CH_2$)); 1.90-2.03 (m, 2H, $CH_2$); 2.38-2.47 (m, 2H, $CH_2$); 3.09-3.18 (m, 2H, N—$CH_2$); 3.35-3.45 (m, 2H, O—$CH_2$); 3.87-3.96 (m, 2H, O—$CH_2$); 4.25-4.32 (m, 2H, Ph-O—$CH_2$); 6.98 (dd, J 8.2, 1.8 Hz, 1H, Ar); 7.04-7.10 (m, 2H, Ar); 7.32 (d, J 8.5 Hz, 2H, Ar); 7.35 (t, J 8.2 Hz, 1H, Ar); 7.85 (d, J 8.5 Hz, 2H, Ar); 9.52 (bs, 1H, CONH); 9.80 (bs, 2H, NH+HCl salt); 12.75 (bs, 1H, $CO_2H$). MM/Z $(M[^{35}Cl]+H)^+$: 459

Compound 30: Methyl 4-[1-[[4-[2-(3-chlorophenoxy)ethyl-methyl-amino]tetrahydropyran-4-carbonyl]amino]cyclopropyl]benzoate Compound 30 was obtained according to General Procedure III-a, starting from Compound 29 and formaldehyde, as a colorless oil in 85% yield. M/Z $(M[^{35}Cl]+H)^+$: 487

Example 29: 4-[1-[[4-[2-(3-Chlorophenoxy)ethyl-methyl-amino]tetrahydropyran-4-carbonyl]amino]cyclopropyl]benzoic acid, hydrochloride

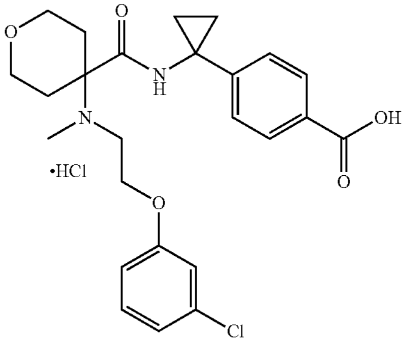 [SMILES: CN(CCOc1cccc(Cl)c1)C1(C(=O)NC2(c3ccc(C(=O)O)cc3)CC2)CCOCC1 ; Cl]

Example 29 was obtained according to General Procedure IV-b, starting from Compound 30. Purification by preparative LC-MS, then HCl salt preparation (method 2) afforded Example 29 as a white powder in 39% yield. $^1$H-NMR (DMSO-$d_6$ 400 MHz, 80° C.): 1.25-1.35 (m, 4H, C($CH_2$—$CH_2$)); 1.84-1.96 (m, 2H, $CH_2$); 2.16-2.26 (m, 2H, $CH_2$); 3.01-3.11 (m, 3H, N—$CH_3$); 3.20-3.40 (m, 4H, N-$CH_2$+O-$CH_2$); 3.81-3.89 (m, 2H, O—$CH_2$); 4.17-4.27 (m, 2H, PhO—$CH_2$); 6.90-6.94 (m, 1H, Ar); 6.98-7.03 (m, 2H, Ar); 7.32 (d, J 8.2 Hz, 1H, Ar); 7.37 (t, J 8.4 Hz, 2H, Ar); 7.85 (d, J 8.2 Hz, 2H, Ar); CONH signal not observed; $CO_2H$ signal not observed; HCl salt signal not observed. M/Z $(M[^{35}Cl]+H)^+$: 473

Compound 31: Methyl 4-[1-[[4-[2-(2-chlorophenoxy)ethylamino]tetrahydropyran-4-carbonyl]amino]cyclopropyl]benzoate Compound 31 was obtained according to General Procedure III-b, starting from Compound 24 (hydrochloride salt) and 2-(2-chlorophenoxy)acetaldehyde. Purification by flash chromatography (KP-NH cartridge, Cyclohexane/EtOAc: 100/0 to 50/50) afforded Compound 31 as a colorless oil in quantitative yield. M/Z $(M[^{35}Cl]+H)^+$: 473

Compound 32: Methyl 4-[1-[[4-[2-(2-chlorophenoxy)ethyl-methyl-amino]tetrahydropyran-4-carbonyl]amino]cyclopropyl]benzoate Compound 32 was obtained according to General Procedure III-b, starting from Compound 31 and formaldehyde, and was used as such in the next step. M/Z $(M[^{35}Cl]+H)^+$: 487

Example 30: 4-[1-[[4-[2-(2-Chlorophenoxy)ethyl-methyl-amino]tetrahydropyran-4-carbonyl]amino]cyclopropyl]benzoic acid, hydrochloride

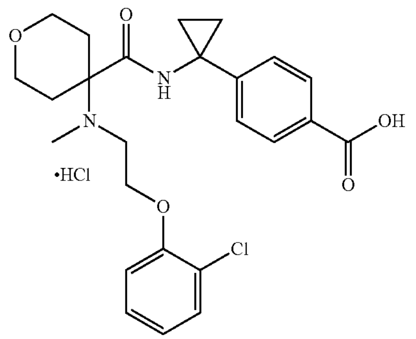 [SMILES: CN(CCOc1ccccc1Cl)C1(C(=O)NC2(c3ccc(C(=O)O)cc3)CC2)CCOCC1 ; Cl]

Example 30 was obtained according to General Procedure IV-b, starting from Compound 32. Purification by preparative LC-MS afforded Example 30 as a white powder in 75% yield over 2 steps. $^1$H-NMR (DMSO-$d_6$/$D_2O$, 400 MHz) δ (ppm): 1.22-1.34 (m, 4H, C($CH_2$—$CH_2$)); 1.85-1.95 (m, 2H, $CH_2$); 2.43-2.46 (m, 2H, $CH_2$); 2.82 (bs, 3H, N—$CH_3$); 3.18 (t, J 12.0 Hz, 2H, O—$CH_2$); 3.43 (bs, 2H, N—$CH_2$); 3.92-4.00 (m, 2H, O—$CH_2$); 4.26 (bs, 2H, PhO—$CH_2$); 6.99 (t, J 7.6 Hz, 1H, Ar); 7.04 (d, J 7.6 Hz, 1H, Ar); 7.29 (t, J 7.6 Hz, 1H, Ar); 7.33 (d, J 8.2 Hz, 2H, Ar); 7.40 (d, J 7.6 Hz, 1H, Ar); 7.85 (d, J 8.2 Hz, 2H, Ar); CONH signal not observed; $CO_2H$ signal not observed; HCl salt signal not observed. M/Z $(M[^{35}Cl]+H)^+$: 473

Compound 33: Methyl 4-[1-[[4-[2-(4-chlorophenoxy)ethylamino]tetrahydropyran-4-carbonyl]amino]cyclopropyl]benzoate Compound 33 was obtained according to General Procedure III-b, starting from Compound 24 (hydrochloride salt) and 2-(4-chlorophenoxy)acetaldehyde. Purification by flash chromatography (KP-NH cartridge, Cyclohexane/EtOAc: 100/0 to 50/50) afforded Compound 33 as a colorless oil in 65% yield. M/Z $(M[^{35}Cl]+H)^+$: 473

Compound 34: Methyl 4-[1-[[4-[2-(4-chlorophenoxy)ethyl-methyl-amino]tetrahydropyran-4-carbonyl]amino]cyclopropyl]benzoate Compound 34 was obtained according to General Procedure III-b, starting from Compound 33 and formaldehyde, and was used as such in the next step. M/Z $(M[^{35}Cl]+H)^+$: 487

Example 31: 4-[1-[[4-[2-(4-Chlorophenoxy)ethyl-methyl-amino]tetrahydropyran-4-carbonyl]amino]cyclopropyl]benzoic acid, hydrochloride

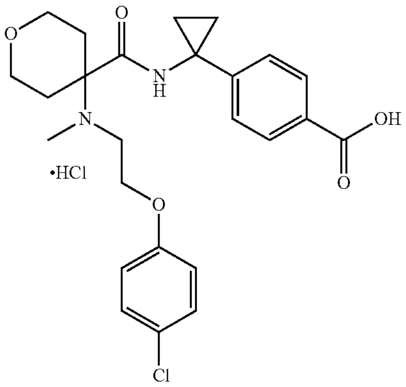

Example 31 was obtained according to General Procedure IV-b, starting from Compound 34. Purification by preparative LC-MS, then HCl salt preparation (method 1) afforded Example 31 as a white powder in 19% yield over 2 steps. $^1$H-NMR (DMSO-$d_6$/$D_2O$, 400 MHz) δ (ppm): 1.21-1.32 (m, 4H, $C(CH_2—CH_2)$); 1.79-1.88 (m, 2H, $CH_2$); 2.28-2.36 (m, 2H, $CH_2$); 2.65 (bs, 3H, N—$CH_3$); 3.19 (t, J 11.4 Hz, 2H, O—$CH_2$); 3.66-3.75 (m, 2H, N—$CH_2$); 3.86-3.93 (m, 2H, O—$CH_2$); 4.26 (t, J 4.3 Hz, 2H, PhO—$CH_2$); 6.92 (d, J 9.1 Hz, 2H, Ar); 7.28 (d, J 8.5 Hz, 2H, Ar); 7.30 (d, J 9.1 Hz, 2H, Ar); 7.81 (d, J 8.5 Hz, 2H, Ar); CONH signal not observed; $CO_2H$ signal not observed; HCl salt signal not observed. M/Z $(M[^{35}Cl]+H)^+$: 473

Compound 35: Methyl 4-[1-[[4-[2-(3-fluorophenoxy)ethylamino]tetrahydropyran-4-carbonyl]amino]cyclopropyl]benzoate Compound 35 was obtained according to General Procedure III-b, starting from Compound 24 (hydrochloride salt) and 2-(3-fluorophenoxy)acetaldehyde. Purification by flash chromatography (KP-NH cartridge, Cyclohexane/EtOAc: 100/0 to 50/50) afforded Compound 35 as a colorless oil in 68% yield. M/Z $(M+H)^+$: 457

Compound 36: Methyl 4-[1-[[4-[2-(3-fluorophenoxy)ethyl-methyl-amino]tetrahydropyran-4-carbonyl]amino]cyclopropyl]benzoate Compound 36 was obtained according to General Procedure III-b, starting from Compound 35 and formaldehyde, and was used as such in the next step. M/Z $(M+H)^+$: 471

Example 32: 4-[1-[[4-[2-(3-Fluorophenoxy)ethyl-methyl-amino]tetrahydropyran-4-carbonyl]amino]cyclopropyl]benzoic acid, hydrochloride

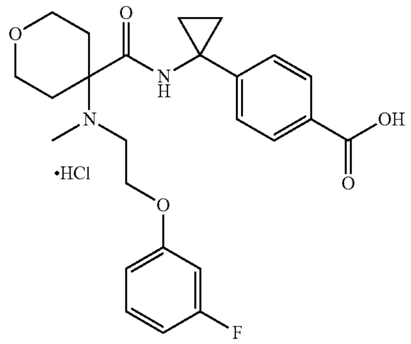 [SMILES: CN(CCOc1cccc(F)c1)C1(C(=O)NC2(c3ccc(C(=O)O)cc3)CC2)CCOCC1 ; Cl]

Example 32 was obtained according to General Procedure IV-b, starting from Compound 36. Purification by preparative LC-MS, then HCl salt preparation (method 1) afforded Example 32 as a white powder in 16% yield over 2 steps. $^1$H-NMR (DMSO-$d_4$, 400 MHz) δ (ppm): 1.26-1.39 (m, 4H, $C(CH_2—CH_2)$); 1.94-2.14 (m, 2H, $CH_2$); 2.35-2.47 (m, 2H, $CH_2$); 2.72 (s, 3H, $CH_3$); 3.19 (t, J 11.4 Hz, 2H, O—$CH_2$); 3.20-3.26 (m, 2H, N—$CH_2$); 3.88-4.04 (m, 2H, O—$CH_2$); 4.28-4.45 (m, 2H, Ph-O—$CH_2$); 6.78-6.91 (m, 3H, Ar); 7.30-7.39 (m, 3H, Ar); 7.86 (d, J 8.2 Hz, 2H, Ar), 9.56 (bs, 1H, CONH); 10.69 (bs, 1H, HCl salt); 12.77 (bs, 1H, $CO_2H$). M/Z $(M+H)^+$: 457

Compound 37: Methyl 4-[1-[[4-[2-(2-fluorophenoxy)ethylamino]tetrahydropyran-4-carbonyl]amino]cyclopropyl]benzoate Compound 37 was obtained according to General Procedure III-b, starting from Compound 24 (hydrochloride salt) and 2-(2-fluorophenoxy)acetaldehyde. Purification by flash chromatography (KP-NH cartridge, Cyclohexane/EtOAc: 100/0 to 50/50) afforded Compound 37 as a white powder in 49% yield. M/Z $(M+H)^+$: 457

Compound 38: Methyl 4-[1-[[4-[2-(2-fluorophenoxy)ethyl-methyl-amino]tetrahydropyran-4-carbonyl]amino]cyclopropyl]benzoate Compound 38 was obtained according to General Procedure III-b, starting from Compound 37 and formaldehyde, and was used as such in the next step. M/Z $(M+H)^+$: 471

Example 33: 4-[1-[[4-[2-(2-Fluorophenoxy)ethyl-methyl-amino]tetrahydropyran-4-carbonyl]amino]cyclopropyl]benzoic acid, hydrochloride

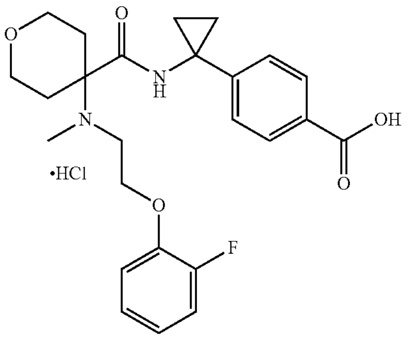 [SMILES: CN(CCOc1ccccc1F)C1(C(=O)NC2(c3ccc(C(=O)O)cc3)CC2)CCOCC1 ; Cl]

Example 33 was obtained according to General Procedure IV-b, starting from Compound 38. Purification by preparative LC-MS, then HCl salt preparation (method 1) afforded Example 33 as a white powder in 41% yield over 2 steps. $^1$H-NMR (DMSO-$d_6$/$D_2O$, 400 MHz) δ (ppm): 1.21-1.34 (m, 4H, C($CH_2$—$CH_2$)); 1.81-1.92 (m, 2H, $CH_2$); 2.33-2.43 (m, 2H, $CH_2$); 2.73 (s, 3H, N—$CH_3$); 3.21 (t, J 11.6 Hz, 2H, O—$CH_2$); 3.27-3.35 (m, 2H, N—$CH_2$); 3.89-3.98 (m, 2H, O—$CH_2$); 4.24 (t, J 4.4 Hz, 2H, PhO—$CH_2$); 6.94-7.00 (m, 1H, Ar); 7.06-7.15 (m, 2H, Ar); 7.15-7.22 (m, 1H, Ar); 7.31 (d, J 8.5 Hz, 2H, Ar); 7.84 (d, J 8.5 Hz, 2H, Ar); CONH signal not observed; $CO_2H$ signal not observed; HCl salt signal not observed. M/Z $(M+H)^+$: 457

Compound 39: Methyl 4-[1-[[4-[2-(4-fluorophenoxy)ethylamino]tetrahydropyran-4-carbonyl]amino]cyclopropyl]benzoate Compound 39 was obtained according to General Procedure III-b, starting from Compound 24 (hydrochloride salt) and 2-(4-fluorophenoxy)acetaldehyde. Purification by flash chromatography (KP-NH cartridge, Cyclohexane/EtOAc: 100/0 to 50/50) afforded Compound 39 as a colorless oil in 54% yield. M/Z $(M+H)^+$: 457

Compound 40: Methyl 4-[1-[[4-[2-(4-fluorophenoxy)ethyl-methyl-amino]tetrahydropyran-4-carbonyl]amino]cyclopropyl]benzoate Compound 40 was obtained according to General Procedure III-b, starting from Compound 39 and formaldehyde, and was used as such in the next step. M/Z $(M+H)^+$: 471

Example 34: 4-[1-[[4-[2-(4-Fluorophenoxy)ethyl-methyl-amino]tetrahydropyran-4-carbonyl]amino]cyclopropyl]benzoic acid, hydrochloride

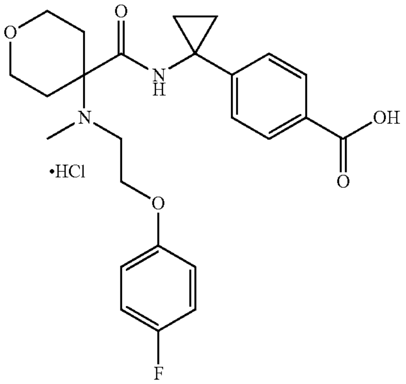 [SMILES: CN(CCOc1ccc(F)cc1)C1(C(=O)NC2(c3ccc(C(=O)O)cc3)CC2)CCOCC1 ; Cl]

Example 34 was obtained according to General Procedure IV-b, starting from Compound 40. Purification by preparative LC-MS, then HCl salt preparation (method 1) afforded Example 34 as a white powder in 25% yield over 2 steps. $^1$H-NMR (DMSO-$d_6$/$D_2O$, 400 MHz) δ (ppm): 1.21-1.34 (m, 4H, C($CH_2$—$CH_2$)); 1.83-1.93 (m, 2H, $CH_2$); 2.31-2.40 (m, 2H, $CH_2$); 2.71 (bs, 3H, N—$CH_3$); 3.20 (t, J 11.5 Hz, 2H, O—$CH_2$); 3.25 (bs, 2H, N—$CH_2$); 3.90-3.98 (m, 2H, O—$CH_2$); 4.11-4.16 (m, 2H, Ph-O—$CH_2$); 6.88-6.93 (m, 2H, Ar); 7.08 (t, J 9.0 Hz, 2H, Ar); 7.31 (d, J 8.5 Hz, 2H, Ar); 7.83 (d, J 8.5 Hz, 2H, Ar); CONH signal not observed; $CO_2H$ signal not observed; HCl salt signal not observed. M/Z $(M+H)^+$: 457

Compound 41: Methyl 4-[1-[[4-[2-(3-methylphenoxy)ethylamino]tetrahydropyran-4-carbonyl]amino]cyclopropyl]benzoate Compound 41 was obtained according to General Procedure III-b, starting from Compound 24 (hydrochloride salt) and 2-(3-methylphenoxy)acetaldehyde. Purification by flash chromatography (KP-NH cartridge, Cyclohexane/EtOAc: 100/0 to 50/50) afforded Compound 41 as a colorless oil in 77% yield. M/Z $(M+H)^+$: 453

Compound 42: Methyl 4-[1-[[4-[2-(3-methylphenoxy)ethyl-methyl-amino]tetrahydropyran-4-carbonyl]amino]cyclopropyl]benzoate Compound 42 was obtained according to General Procedure III-b, starting from Compound 41 and formaldehyde, and was used as such in the next step. M/Z $(M+H)^+$: 467

Example 35: 4-[1-[[4-[2-(3-Methylphenoxy)ethyl-methyl-amino]tetrahydropyran-4-carbonyl]amino]cyclopropyl]benzoic acid, hydrochloride

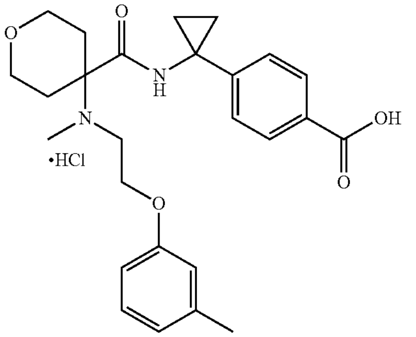 [SMILES: Cc1cccc(OCCN(C)C2(C(=O)NC3(c4ccc(C(=O)O)cc4)CC3)CCOCC2)c1 ; Cl]

Example 35 was obtained according to General Procedure IV-b, starting from Compound 42. Purification by preparative LC-MS, then HCl salt preparation (method 1) afforded Example 35 as a white powder in 68% yield over 2 steps. $^1$H-NMR (DMSO-d$_6$/D$_2$O, 400 MHz) δ (ppm): 1.21-1.34 (m, 4H, C(CH$_2$—CH$_2$)); 1.85-1.94 (m, 2H, CH$_2$); 2.21 (s, 3H, Ph-CH$_3$); 2.31-2.38 (m, 2H, CH$_2$); 2.72 (s, 3H, N—CH$_3$); 3.20 (t, J 12.0 Hz, 2H, O—CH$_2$); 3.27 (bs, 2H, N—CH$_2$); 3.91-3.98 (m, 2H, O—CH$_2$); 4.12 (t, J 4.3 Hz, 2H, PhO—CH$_2$); 6.64-6.69 (m, 2H, Ar); 6.77 (d, J 7.6 Hz, 1H, Ar); 7.13 (t, J 7.6 Hz, 1H, Ar); 7.32 (d, J 8.5 Hz, 2H, Ar); 7.82 (d, J 8.5 Hz, 2H, Ar); CONH signal not observed; CO$_2$H signal not observed; HCl salt signal not observed. M/Z (M+H)$^+$: 453

Compound 43: Methyl 4-[1-[[4-[2-(2-methylphenoxy)ethylamino]tetrahydropyran-4-carbonyl]amino]cyclopropyl]benzoate Compound 43 was obtained according to General Procedure III-b, starting from Compound 24 (hydrochloride salt) and 2-(2-methylphenoxy)acetaldehyde. Purification by flash chromatography (KP-NH cartridge, Cyclohexane/EtOAc: 100/0 to 50/50) afforded Compound 43 as a colorless oil in 86% yield. M/Z (M+H)$^+$: 453

Compound 44: Methyl 4-[1-[[4-[2-(2-methylphenoxy)ethyl-methyl-amino]tetrahydropyran-4-carbonyl]amino]cyclopropyl]benzoate Compound 44 was obtained according to General Procedure III-b, starting from Compound 43 and formaldehyde, and was used as such in the next step. M/Z (M+H)$^+$: 467

Example 36: 4-[1-[[4-[2-(2-Methylphenoxy)ethyl-methyl-amino]tetrahydropyran-4-carbonyl]amino]cyclopropyl]benzoic acid, hydrochloride

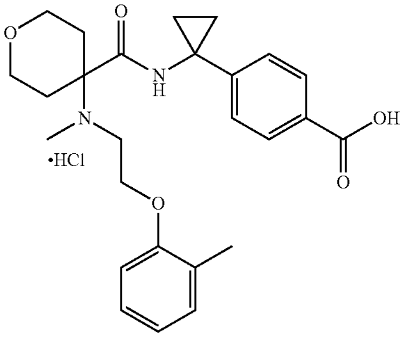 [SMILES: Cc1ccccc1OCCN(C)C1(C(=O)NC2(c3ccc(C(=O)O)cc3)CC2)CCOCC1 ; Cl]

Example 36 was obtained according to General Procedure IV-b, starting from Compound 44. Purification by preparative LC-MS, then HCl salt preparation (method 1) afforded Example 36 as a white powder in 44% yield over 2 steps. $^1$H-NMR (DMSO-d$_6$/D$_2$O, 400 MHz) δ (ppm): 1.21-1.34 (m, 4H, C(CH$_2$—CH$_2$)): 1.82-1.92 (m, 2H, CH$_2$); 2.09 (s, 3H, Ph-CH$_3$); 2.38-2.45 (m, 2H, CH$_2$); 2.74 (s, 3H, N—CH$_3$); 3.20 (t, J 11.7 Hz, 2H, O—CH$_2$); 3.32 (bs, 2H, N—CH$_2$); 3.91-3.98 (m, 2H, O—CH$_2$); 4.10-4.16 (m, 2H, PhO—CH$_2$); 6.82 (d, J 8.8 Hz, 1H, Ar); 6.87 (d, J 7.3 Hz, 1H, Ar); 7.10-7.15 (m, 2H, Ar); 7.33 (d, J 8.3 Hz, 2H, Ar); 7.84 (d, J 8.3 Hz, 2H, Ar); CONH signal not observed; CO$_2$H signal not observed; HCl salt signal not observed. M/Z (M+H)$^+$: 453

Compound 45: Methyl 4-[1-[[4-[2-(4-methylphenoxy)ethylamino]tetrahydropyran-4-carbonyl]amino]cyclopropyl]benzoate Compound 45 was obtained according to General Procedure III-b, starting from Compound 24 (hydrochloride salt) and 2-(4-methylphenoxy)acetaldehyde. Purification by flash chromatography (KP-NH cartridge, Cyclohexane/EtOAc: 100/0 to 50/50) afforded Compound 45 as a colorless oil in 90% yield. M/Z (M+H)$^+$: 453

Compound 46: Methyl 4-[1-[[4-[2-(4-methylphenoxy)ethyl-methyl-amino]tetrahydropyran-4-carbonyl]amino]cyclopropyl]benzoate Compound 46 was obtained according to General Procedure III-b, starting from Compound 45 and formaldehyde, and was used as such in the next step. M/Z (M+H)$^+$: 467

Example 37: 4-[1-[[4-[2-(4-Methylphenoxy)ethyl-methyl-amino]tetrahydropyran-4-carbonyl]amino]cyclopropyl]benzoic acid, hydrochloride

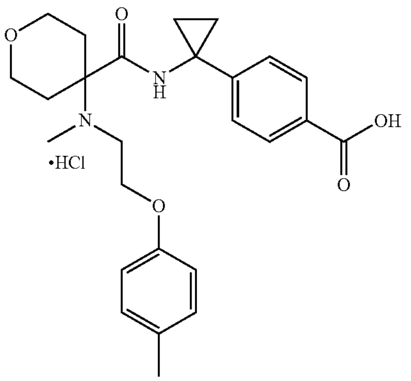 [SMILES: Cc1ccc(OCCN(C)C2(C(=O)NC3(c4ccc(C(=O)O)cc4)CC3)CCOCC2)cc1 ; Cl]

Example 37 was obtained according to General Procedure IV-b, starting from Compound 46. Concentration of the reaction mixture, then trituration in a DMSO/HCl 1 N mixture (2/1) afforded Example 37 as a white powder in 33% yield over 2 steps. $^1$H-NMR (DMSO-$d_6$/$D_2O$, 400 MHz) δ (ppm): 1.25-1.35 (m, 4H, C($CH_2$—$CH_2$)); 1.85-1.95 (m, 2H, $CH_2$); 2.21 (s, 3H, Ph-$CH_3$); 2.38-2.44 (m, 2H, $CH_2$); 2.75 (s, 3H, N—$CH_3$); 3.20 (t, J 12.0 Hz, 2H, O—$CH_2$); 3.30 (bs, 2H, N—$CH_2$); 3.91-3.98 (m, 2H, O—$CH_2$); 4.17 (t, J 4.7 Hz, 2H, PhO—$CH_2$); 6.82 (d, J 8.6 Hz, 2H, Ar); 7.10 (d, J 8.6 Hz, 2H, Ar); 7.32 (d, J 8.4 Hz, 2H, Ar); 7.85 (d, J 8.4 Hz, 2H, Ar); CONH signal not observed; $CO_2H$ signal not observed; HCl salt signal not observed. M/Z $(M+H)^+$: 453

Example 38: 4-[1-[[4-[2-(3-Methoxyphenoxy)ethyl-methyl-amino]tetrahydropyran-4-carbonyl]amino]cyclopropyl]benzoic acid, hydrochloride

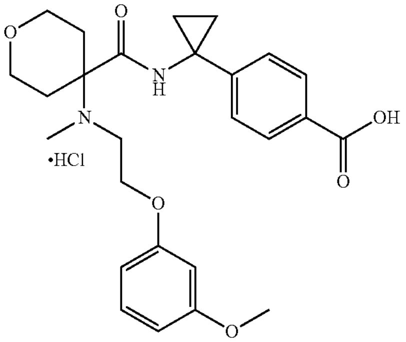 [SMILES: COc1cccc(OCCN(C)C2(C(=O)NC3(c4ccc(C(=O)O)cc4)CC3)CCOCC2)c1 ; Cl]

Example 38 was obtained according to General Procedure IV-b, starting from Compound 48. Purification by preparative LC-MS afforded Example 38 as a white powder in 75% yield over 2 steps. $^1$H-NMR (DMSO-$d_6$/$D_2O$, 400 MHz) δ (ppm): 1.26-1.37 (m, 4H, C($CH_2$—$CH_2$)); 1.88-1.97 (m, 2H, $CH_2$); 2.39-2.46 (m, 2H, $CH_2$); 2.76 (s, 3H, N—$CH_3$); 3.22 (t, J 11.6 Hz, 2H, O—$CH_2$); 3.26-3.41 (m, 2H, N—$CH_2$); 3.72 (s, 3H, O—$CH_3$); 3.93-3.99 (m, 2H, O—$CH_2$); 4.23 (t, J 4.2 Hz, 2H, Ph-O—$CH_2$); 6.49-6.59 (m, 3H, Ar); 7.21 (t, J 8.1 Hz, 1H, Ar); 7.33 (d, J 8.5 Hz, 2H, Ar); 7.86 (d, J 8.5 Hz, 2H, Ar); CONH signal not observed; $CO_2H$ signal not observed; HCl salt signal not observed. M/Z $(M+H)^+$: 469

Compound 47: Methyl 4-[1-[[4-[2-(3-methoxyphenoxy)ethylamino]tetrahydropyran-4-carbonyl]amino]cyclopropyl]benzoate Compound 47 was obtained according to General Procedure III-b, starting from Compound 24 (hydrochloride salt) and 2-(3-methoyphenoxy)acetaldehyde. Purification by flash chromatography (KP-NH cartridge, Cyclohexane/EtOAc: 100/0 to 40/60) afforded Compound 47 as a colorless oil in 53% yield. M/Z $(M+H)^+$: 469

Compound 48: Methyl 4-[1-[[4-[2-(3-methoxyphenoxy)ethyl-methyl-amino]tetrahydropyran-4-carbonyl]amino]cyclopropyl]benzoate Compound 48 was obtained according to General Procedure III-b, starting from Compound 47 and formaldehyde, and was used as such in the next step. M/Z $(M+H)^+$: 483

Compound 49: Methyl 4-[1-[[4-[2-(2-methoxyphenoxy)ethylamino]tetrahydropyran-4-carbonyl]amino]cyclopropyl]benzoate Compound 49 was obtained according to General Procedure III-b, starting from Compound 24 (hydrochloride salt) and 2-(2-methoyphenoxy)acetaldehyde. Purification by flash chromatography (KP-NH cartridge, Cyclohexane/EtOAc: 100/0 to 40/60) afforded Compound 49 as a colorless oil in 64% yield. M/Z $(M+H)^+$: 469

Compound 50: Methyl 4-[1-[[4-[2-(2-methoxyphenoxy)ethyl-methyl-amino]tetrahydropyran-4-carbonyl]amino]cyclopropyl]benzoate Compound 50 was obtained according to General Procedure III-b, starting from Compound 49 and formaldehyde, and was used as such in the next step. M/Z $(M+H)^+$: 483

Example 39: 4-[1-[[4-[2-(2-Methoxyphenoxy)ethyl-methyl-amino]tetrahydropyran-4-carbonyl]amino]cyclopropyl]benzoic acid, hydrochloride

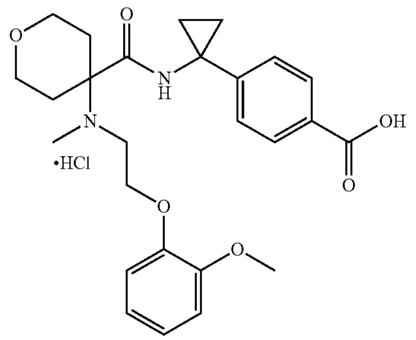 [SMILES: COc1ccccc1OCCN(C)C1(C(=O)NC2(c3ccc(C(=O)O)cc3)CC2)CCOCC1 ; Cl]

Example 39 was obtained according to General Procedure IV-b, starting from Compound 50. Purification by preparative LC-MS, then HCl salt preparation (method 1) afforded Example 39 as a white powder in 20% yield over 2 steps. $^1$H-NMR (DMSO-d/$D_2O$, 400 MHz) δ (ppm): 1.22-1.34 (m, 4H, C($CH_2$—$CH_2$)); 1.85-1.95 (m, 2H, $CH_2$); 2.39-2.45 (m, 2H, $CH_2$); 2.79 (s, 3H, N—$CH_3$); 3.19 (t, J 12.0 Hz, 2H, O—$CH_2$); 3.34 (bs, 2H, N—$CH_2$); 3.72 (s, 3H, O—$CH_3$); 3.92-3.99 (m, 2H, O—$CH_2$); 4.18 (t, J 3.8 Hz, 2H, PhO—$CH_2$); 6.85-7.01 (m, 4H, Ar); 7.31 (d, J 8.3 Hz, 2H, Ar); 7.84 (d, J 8.3 Hz, 2H, Ar); CONH signal not observed; $CO_2H$ signal not observed; HCl salt signal not observed. M/Z $(M+H)^+$: 469

Compound 51: Methyl 4-[1-[[4-[2-(4-methoxyphenoxy)ethylamino]tetrahydropyran-4-carbonyl]amino]cyclopropyl]benzoate Compound 51 was obtained according to General Procedure III-b, starting from Compound 24 (hydrochloride salt) and 2-(4-methoyphenoxy)acetaldehyde. Purification by flash chromatography (KP-NH cartridge, Cyclohexane/EtOAc: 100/0 to 40/60) afforded Compound 51 as a colorless oil in 57% yield. M/Z $(M+H)^+$: 469

Compound 52: Methyl 4-[1-[[4-[2-(4-methoxyphenoxy)ethyl-methyl-amino]tetrahydropyran-4-carbonyl]amino]cyclopropyl]benzoate Compound 52 was obtained according to General Procedure III-b, starting from Compound 51 and formaldehyde, and was used as such in the next step. M/Z $(M+H)^+$: 483

Example 40: 4-[1-[[4-[2-(4-Methoxyphenoxy)ethyl-methyl-amino]tetrahydropyran-4-carbonyl]amino]cyclopropyl]benzoic acid, hydrochloride

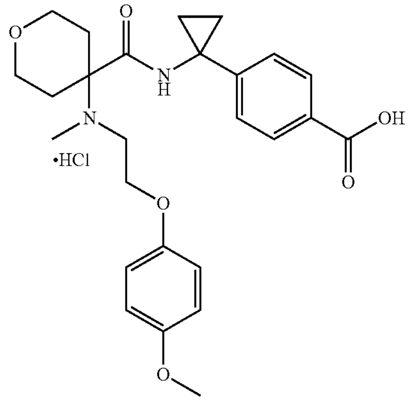 [SMILES: COc1ccc(OCCN(C)C2(C(=O)NC3(c4ccc(C(=O)O)cc4)CC3)CCOCC2)cc1 ; Cl]

Example 40 was obtained according to General Procedure IV-b, starting from Compound 52. Purification by preparative LC-MS, then HCl salt preparation (method 1) afforded Example 40 as a white powder in 16% yield over 2 steps. $^1$H-NMR (DMSO-$d_6$/$D_2O$, 400 MHz) δ (ppm): 1.15-1.22 (m, 2H, C($CH_2$—$CH_2$)); 1.22-1.30 (m, 2H, C($CH_2$—$CH_2$)); 1.62-1.71 (m, 2H, $CH_2$); 1.89-1.97 (m, 2H, $CH_2$); 2.27 (s, 3H, N—$CH_3$); 2.65-2.71 (m, 2H, N—$CH_2$); 3.35 (t, J 10.1 Hz, 2H, O—$CH_2$); 3.66 (s, 3H, O—$CH_3$); 3.72-3.79 (m, 2H, O—$CH_2$); 3.91 (t, J 5.8 Hz, 2H, PhO—$CH_2$); 6.82 (bs, 4H, Ar); 7.24 (d, J 8.5 Hz, 2H, Ar); 7.79 (d, J 8.5 Hz, 2H, Ar); CONH signal not observed; $CO_2H$ signal not observed; HCl salt signal not observed. M/Z $(M+H)^+$: 469

Compound 53: Methyl 4-[1-[[4-[2-(3-trifluoromethylphenoxy)ethylamino]tetrahydropyran-4-carbonyl]amino]cyclopropyl]benzoate Compound 53 was obtained according to General Procedure III-b, starting from Compound 24 (hydrochloride salt) and 2-(3-trifluoromethylphenoxy)acetaldehyde. Purification by flash chromatography (KP-NH cartridge, Cyclohexane/EtOAc: 100/0 to 50/50) afforded Compound 53 as a white powder in 40% yield. M/Z $(M+H)^+$: 507

Compound 54: Methyl 4-[1-[[4-[2-(3-trifluoromethylphenoxy)ethyl-methyl-amino]tetrahydropyran-4-carbonyl]amino]cyclopropyl]benzoate Compound 54 was obtained according to General Procedure III-b, starting from Compound 53 and formaldehyde, and was used as such in the next step. M/Z $(M+H)^+$: 521

Example 41: 4-[1-[[4-[2-(3-Trifluoromethylphenoxy)ethyl-methyl-amino]tetrahydropyran-4-carbonyl]amino]cyclopropyl]benzoic acid, hydrochloride

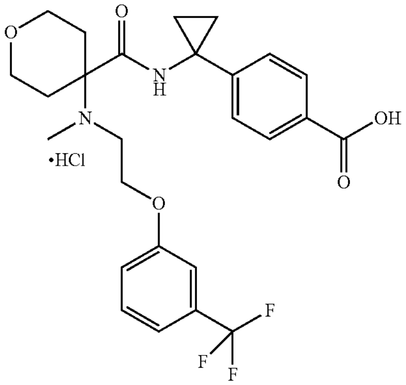 [SMILES: CN(CCOc1cccc(C(F)(F)F)c1)C1(C(=O)NC2(c3ccc(C(=O)O)cc3)CC2)CCOCC1 ; Cl]

Example 41 was obtained according to General Procedure IV-b, starting from Compound 54. Concentration of the reaction mixture, then trituration in a DMSO/HCl 1 N mixture (2/1) afforded Example 41 as a white powder in 46% yield over 2 steps. $^1$H-NMR (DMSO-$d_6$/$D_2O$, 400 MHz) δ (ppm): 1.26-1.36 (m, 4H, C($CH_2$—$CH_2$)); 1.86-1.96 (m, 2H, $CH_2$); 2.37-2.45 (m, 2H, $CH_2$); 2.75 (s, 3H, N—$CH_3$); 3.23 (t, J 11.7 Hz, 2H, O—$CH_2$); 3.29-3.39 (m, 2H, N—$CH_2$); 3.91-4.00 (m, 2H, O—$CH_2$); 4.27-4.37 (m, 2H, PhO—$CH_2$); 7.22-7.27 (m, 2H, Ar); 7.29-7.36 (m, 3H, Ar); 7.51-7.58 (m, 1H, Ar); 7.85 (d, J 8.5 Hz, 2H, Ar); CONH signal not observed; $CO_2H$ signal not observed; HCl salt signal not observed. M/Z $(M+H)^+$: 507

Compound 55: Methyl 4-[1-[[4-[2-(2-trifluoromethylphenoxy)ethylamino]tetrahydropyran-4-carbonyl]amino]cyclopropyl]benzoate Compound 55 was obtained according to General Procedure III-b, starting from Compound 24 (hydrochloride salt) and 2-(2-trifluoromethylphenoxy)acetaldehyde. Purification by flash chromatography (KP-NH cartridge, Cyclohexane/EtOAc: 100/0 to 50/50) afforded Compound 55 as a white powder in 57% yield. M/Z $(M+H)^+$: 507

Compound 56: Methyl 4-[1-[[4-[2-(2-trifluoromethylphenoxy)ethyl-methyl-amino]tetrahydropyran-4-carbonyl]amino]cyclopropyl]benzoate Compound 56 was obtained according to General Procedure III-b, starting from Compound 55 and formaldehyde, and was used as such in the next step. M/Z $(M+H)^+$: 521

Example 42: 4-[1-[[4-[2-(2-Trifluoromethylphenoxy)ethyl-methyl-amino]tetrahydropyran-4-carbonyl]amino]cyclopropyl]benzoic acid, hydrochloride

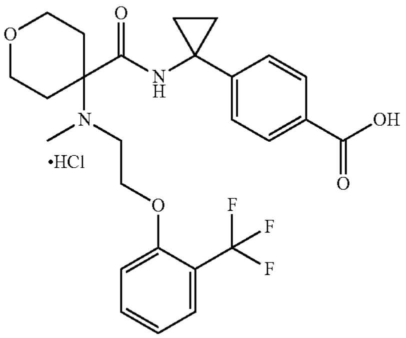 [SMILES: CN(CCOc1ccccc1C(F)(F)F)C1(C(=O)NC2(c3ccc(C(=O)O)cc3)CC2)CCOCC1 ; Cl]

Example 42 was obtained according to General Procedure IV-b, starting from Compound 56. Concentration of the reaction mixture, then trituration in a DMSO/HCl 1 N mixture (2/1) afforded Example 42 as a white powder in 41% yield over 2 steps. $^1$H-NMR (DMSO-$d_6$/$D_2O$, 400 MHz) δ (ppm): 1.24-1.35 (m, 4H, C($CH_2$—$CH_2$)); 1.80-1.90 (m, 2H, $CH_2$); 2.39-2.46 (m, 2H, $CH_2$); 2.71 (s, 3H, N—$CH_3$); 3.21 (t, J 11.5 Hz, 2H, O—$CH_2$); 3.28-3.37 (m, 2H, N—$CH_2$); 3.89-3.98 (m, 2H, O—$CH_2$); 4.32-4.37 (m, 2H, PhO—$CH_2$); 7.14 (t, J 7.6 Hz, 1H, Ar); 7.21 (d, J 8.8 Hz, 1H, Ar); 7.32 (d, J 8.5 Hz, 2H, Ar); 7.61-7.67 (m, 2H, Ar); 7.85 (d, J 8.5 Hz, 2H, Ar); CONH signal not observed; $CO_2H$ signal not observed; HCl salt signal not observed. M/Z $(M+H)^+$: 507

Compound 57: Methyl 4-[1-[[4-[2-(3-trifluoromethoxyphenoxy)ethylamino]tetrahydropyran-4-carbonyl]amino]cyclopropyl]benzoate Compound 57 was obtained according to General Procedure III-b, starting from Compound 24 (hydrochloride salt) and 2-(3-trifluoromethoxyphenoxy)acetaldehyde. Purification by flash chromatography (KP-NH cartridge, Cyclohexane/EtOAc: 100/0 to 40/60) afforded Compound 57 as a white powder in 40% yield. M/Z $(M+H)^+$: 523

Compound 58: Methyl 4-[1-[[4-[2-(3-trifluoromethoxyphenoxy)ethyl-methyl-amino]tetrahydropyran-4-carbonyl]amino]cyclopropyl]benzoate Compound 58 was obtained according to General Procedure III-b, starting from Compound 57 and formaldehyde, and was used as such in the next step. M/Z $(M+H)^+$: 537

Example 43: 4-[1-[[4-[2-(3-Trifluoromethoxyphenoxy)ethyl-methyl-amino]tetrahydropyran-4-carbonyl]amino]cyclopropyl]benzoic acid, hydrochloride Example 43 was obtained according to General Procedure IV-b, starting from 0

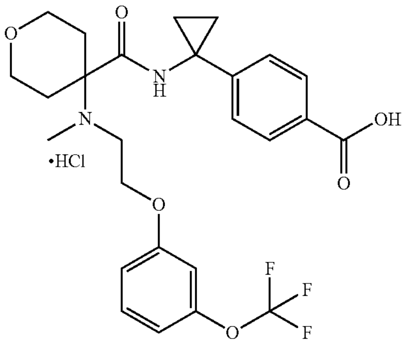 [SMILES: CN(CCOc1cccc(OC(F)(F)F)c1)C1(C(=O)NC2(c3ccc(C(=O)O)cc3)CC2)CCOCC1 ; Cl]

Compound 58. Purification by preparative LC-MS, then HCl salt preparation (method 1) afforded Example 43 as a white powder in 18% yield over 2 steps. $^1$H-NMR (DMSO-$d_6$/$D_2O$, 400 MHz) δ (ppm): 1.26-1.36 (m, 4H, C($CH_2$—$CH_2$)); 1.85-1.95 (m, 2H, $CH_2$); 2.36-2.43 (m, 2H, $CH_2$); 2.73 (s, 3H, N—$CH_3$); 3.23 (t, J 11.5 Hz, 2H, O—$CH_2$); 3.27-3.36 (m, 2H, N—$CH_2$); 3.91-3.98 (m, 2H, O—$CH_2$); 4.26 (t, J 4.3 Hz, 2H, PhO—$CH_2$); 6.93 (bs, 1H, Ar); 6.95-7.01 (m, 2H, Ar); 7.32 (d, J 8.5 Hz, 2H, Ar); 7.44 (t, J 8.2 Hz, 1H, Ar); 7.85 (d, J 8.5 Hz, 2H, Ar); CONH signal not observed; $CO_2H$ signal not observed; HCl salt signal not observed. M/Z $(M+H)^+$: 523

Example 44: 4-[1-[[4-[2-(2-Trifluoromethoxyphenoxy)ethyl-methyl-amino]tetrahydropyran-4-carbonyl]amino]cyclopropyl]benzoic acid, hydrochloride

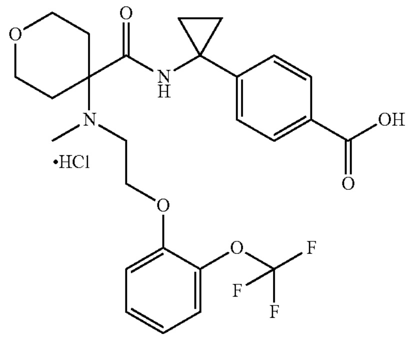 [SMILES: CN(CCOc1ccccc1OC(F)(F)F)C1(C(=O)NC2(c3ccc(C(=O)O)cc3)CC2)CCOCC1 ; Cl]

Example 44 was obtained according to General Procedure IV-b, starting from Compound 60. Purification by preparative LC-MS, then HCl salt preparation (method 1) afforded Example 44 as a white powder in 27% yield, over 2 steps. $^1$H-NMR (DMSO-$d_6$/$D_2O$, 400 MHz) δ (ppm): 1.23-1.29 (m, 2H, C($CH_2$—$CH_2$)); 1.29-1.35 (m, 2H, C($CH_2$—$CH_2$)); 1.81-1.91 (m, 2H, $CH_2$); 2.39-2.47 (m, 2H, $CH_2$); 2.71 (s, 3H, N—$CH_3$); 3.22 (t, J 11.5 Hz, 2H, O—$CH_2$); 3.27-3.38 (m, 2H, N—$CH_2$); 3.88-3.95 (m, 2H, O—$CH_2$); 4.28 (t, J 4.0 Hz, 2H, PhO—$CH_2$); 7.06 (td, J 8.2, 1.3 Hz, 1H, Ar); 7.18 (dd, J 8.8, 0.9 Hz, 1H, Ar); 7.32 (d, J 8.5 Hz, 2H, Ar); 7.34-7.39 (m, 2H, Ar); 7.85 (d, J 8.5 Hz, 2H, Ar); CONH signal not observed; $CO_2H$ signal not observed; HCl salt signal not observed. M/Z $(M+H)^+$: 523

Compound 59: Methyl 4-[1-[[4-[2-(2-trifluoromethoxyphenoxy)ethylamino]tetrahydropyran-4-carbonyl]amino]cyclopropyl]benzoate Compound 59 was obtained according to General Procedure III-b, starting from Compound 24 (hydrochloride salt) and 2-(2-trifluoromethoxyphenoxy)acetaldehyde. Purification by flash chromatography (KP-NH cartridge, Cyclohexane/EtOAc: 100/0 to 40/60) afforded Compound 59 as a white powder in 44% yield. M/Z $(M+H)^+$: 523

Compound 60: Methyl 4-[1-[[4-[2-(2-trifluoromethoxyphenoxy)ethyl-methyl-amino]tetrahydropyran-4-carbonyl]amino]cyclopropyl]benzoate Compound 60 was obtained according to General Procedure III-b, starting from Compound 59 and formaldehyde, and was used as such in the next step. M/Z $(M+H)^+$: 537

Compound 61: Methyl 4-[1-[[4-[2-(4-trifluoromethoxyphenoxy)ethylamino]tetrahydropyran-4-carbonyl]amino]cyclopropyl]benzoate Compound 61 was obtained according to General Procedure III-b, starting from Compound 24 (hydrochloride salt) and 2-(4-trifluoromethoxyphenoxy)acetaldehyde. Purification by flash chromatography (KP-NH cartridge, Cyclohexane/EtOAc: 100/0 to 40/60) afforded Compound 61 as a white powder in 58% yield. M/Z $(M+H)^+$: 523

Compound 62: Methyl 4-[1-[[4-[2-(4-trifluoromethoxyphenoxy)ethyl-methyl-amino]tetrahydropyran-4-carbonyl]amino]cyclopropyl]benzoate Compound 62 was obtained according to General Procedure III-b, starting from Compound 61 and formaldehyde, and was used as such in the next step. M/Z $(M+H)^+$: 537

Example 45: 4-[1-[[4-[2-(4-Trifluoromethoxyphenoxy)ethyl-methyl-amino]tetrahydropyran-4-carbonyl]amino]cyclopropyl]benzoic acid, hydrochloride

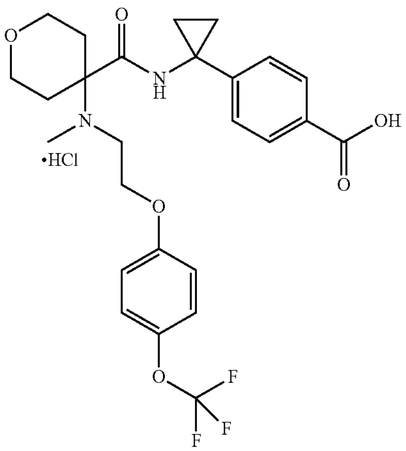 [SMILES: CN(CCOc1ccc(OC(F)(F)F)cc1)C1(C(=O)NC2(c3ccc(C(=O)O)cc3)CC2)CCOCC1 ; Cl]

Example 45 was obtained according to General Procedure IV-b, starting from Compound 62. Purification by preparative LC-MS, then HCl salt preparation (method 1) afforded Example 45 as a white powder in 39% yield over 2 steps. $^1$H-NMR (DMSO-$d_6$/$D_2O$, 400 MHz) δ (ppm): 1.26-1.36 (m, 4H, C($CH_2$—$CH_2$)); 1.84-1.94 (m, 2H, $CH_2$); 2.35-2.42 (m, 2H, $CH_2$); 2.72 (s, 3H, N—$CH_3$); 3.23 (t, J 11.4 Hz, 2H, O—$CH_2$); 3.26-3.33 (m, 2H, N—$CH_2$); 3.90-3.97 (m, 2H, O—$CH_2$); 4.22 (t, J 4.3 Hz, 2H, Ph-O—$CH_2$); 7.03 (d, J 9.1 Hz, 2H, Ar); 7.28-7.35 (m, 4H, Ar); 7.86 (d, J 8.5 Hz, 2H, Ar); CONH signal not observed; $CO_2H$ signal not observed; HCl salt signal not observed. M/Z $(M+H)^+$: 523

Compound 63: Methyl 4-[1-[[4-[2-(3-cyanophenoxy)ethylamino]tetrahydropyran-4-carbonyl]amino]cyclopropyl]benzoate Compound 63 was obtained according to General Procedure III-b, starting from Compound 24 (hydrochloride salt) and 2-(3-cyanophenoxy)acetaldehyde. Purification by flash chromatography (KP-NH cartridge, Cyclohexane/EtOAc: 100/0 to 40/60) afforded Compound 63 as a colorless oil in 39% yield. M/Z $(M+H)^+$: 464

Compound 64: Methyl 4-[1-[[4-[2-(3-cyanophenoxy)ethyl-methyl-amino]tetrahydropyran-4-carbonyl]amino]cyclopropyl]benzoate Compound 64 was obtained according to General Procedure III-b, starting from Compound 63 and formaldehyde, and was used as such in the next step. M/Z $(M+H)^+$: 478

Example 46: 4-[1-[[4-[2-(3-Cyanophenoxy)ethyl-methyl-amino]tetrahydropyran-4-carbonyl]amino]cyclopropyl]benzoic acid, hydrochloride

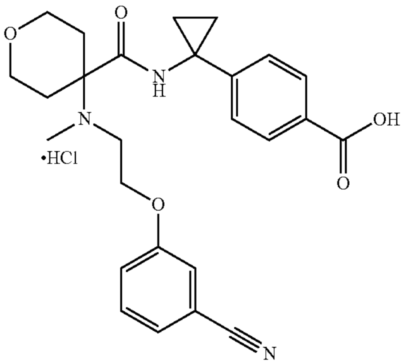 [SMILES: CN(CCOc1cccc(C#N)c1)C1(C(=O)NC2(c3ccc(C(=O)O)cc3)CC2)CCOCC1 ; Cl]

Example 46 was obtained according to General Procedure IV-b, starting from Compound 64. Purification by preparative LC-MS, then HCl salt preparation (method 1) afforded Example 46 as a white powder in 17% yield over 2 steps. $^1$H-NMR (DMSO-$d_6$/$D_2O$, 400 MHz) δ (ppm): 1.17-1.25 (m, 2H, C($CH_2$—$CH_2$)); 1.25-1.33 (m, 2H, C($CH_2$—$CH_2$)); 1.67 (dd, J 13.6, 10.0, 3.9 Hz, 2H, $CH_2$); 1.96-2.05 (m, 2H, $CH_2$); 2.30 (s, 3H, N—$CH_3$); 2.72-2.78 (m, 2H, O—$CH_2$); 3.31-3.41 (m, 2H, N—$CH_2$); 3.73-3.80 (m, 2H, O—$CH_2$); 4.07 (t, J 5.9 Hz, 2H, Ph-O—$CH_2$); 7.24-7.29 (m, 3H, Ar); 7.37-7.42 (m, 2H, Ar); 7.48 (d, J 8.0 Hz, 1H, Ar); 7.82 (d, J 8.5 Hz, 2H, Ar), 8.42 (s, 1H, CONH); $CO_2H$ signal not observed; HCl salt signal not observed. M/Z $(M+H)^+$: 464

Compound 65: Methyl 4-[1-[[4-[2-(2-cyanophenoxy)ethylamino]tetrahydropyran-4-carbonyl]amino]cyclopropyl]benzoate Compound 65 was obtained according to General Procedure III-b, starting from Compound 24 (hydrochloride salt) and 2-(2-cyanophenoxy)acetaldehyde. Purification by flash chromatography (KP-NH cartridge, Cyclohexane/EtOAc: 100/0 to 30/70) afforded Compound 65 as a colorless oil in 61% yield. M/Z $(M+H)^+$: 464

Compound 66: Methyl 4-[1-[[4-[2-(2-cyanophenoxy)ethyl-methyl-amino]tetrahydropyran-4-carbonyl]amino]cyclopropyl]benzoate Compound 66 was obtained according to General Procedure III-b, starting from Compound 65 and formaldehyde, and was used as such in the next step. M/Z $(M+H)^+$: 478

Example 47: 4-[1-[[4-[2-(2-Cyanophenoxy)ethyl-methyl-amino]tetrahydropyran-4-carbonyl]amino]cyclopropyl]benzoic acid, hydrochloride

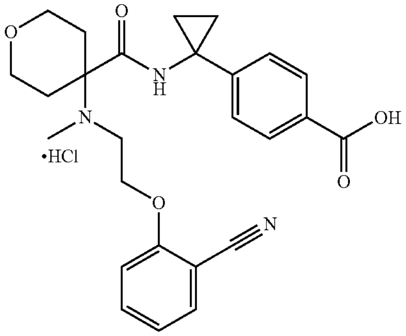 [SMILES: CN(CCOc1ccccc1C#N)C1(C(=O)NC2(c3ccc(C(=O)O)cc3)CC2)CCOCC1 ; Cl]

Example 47 was obtained according to General Procedure IV-b, starting from Compound 66. Purification by preparative LC-MS, then HCl salt preparation (method 1) afforded Example 47 as a white powder in 29% yield over 2 steps. $^1$H-NMR (DMSO-$d_6$/$D_2O$, 400 MHz) δ (ppm): 1.23-1.36 (m, 4H, C($CH_2$—$CH_2$)); 1.83-1.93 (m, 2H, $CH_2$); 2.38-2.47 (m, 2H, $CH_2$); 2.74 (s, 3H, N—$CH_3$); 3.22 (t, J 11.6 Hz, 2H, O—$CH_2$); 3.30-3.40 (m, 2H, N—$CH_2$); 3.87-3.97 (m, 2H, O—$CH_2$); 4.28-4.34 (m, 2H, Ph-O—$CH_2$); 7.10-7.18 (m, 2H, Ar); 7.30 (d, J 8.5 Hz, 2H, Ar); 7.64-7.69 (m, 1H, Ar); 7.72 (dd, J 7.5, 1.5 Hz, 1H, Ar); 7.85 (d, J 8.5 Hz, 2H, Ar); CONH signal not observed; signal not observed; HCl salt signal not observed. M/Z $(M+H)^+$: 464

Compound 67: Methyl 4-[1-[[4-[2-(4-cyanophenoxy)ethylamino]tetrahydropyran-4-carbonyl]amino]cyclopropyl]benzoate Compound 67 was obtained according to General Procedure III-b, starting from Compound 24 (hydrochloride salt) and 2-(4-cyanophenoxy)acetaldehyde. Purification by flash chromatography (KP-NH cartridge, Cyclohexane/EtOAc: 100/0 to 20/80) afforded Compound 67 as a white powder in 30% yield. M/Z $(M+H)^+$: 464

Compound 68: Methyl 4-[1-[[4-[2-(4-cyanophenoxy)ethyl-methyl-amino]tetrahydropyran-4-carbonyl]amino]cyclopropyl]benzoate Compound 68 was obtained according to General Procedure III-b, starting from Compound 67 and formaldehyde, and was used as such in the next step. M/Z $(M+H)^+$: 478

Example 48: 4-[1-[[4-[2-(4-Cyanophenoxy)ethyl-methyl-amino]tetrahydropyran-4-carbonyl]amino]cyclopropyl]benzoic acid, hydrochloride

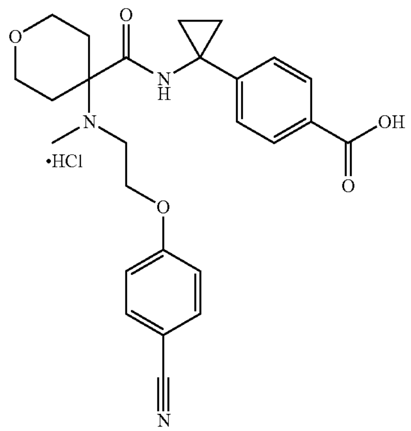 [SMILES: CN(CCOc1ccc(C#N)cc1)C1(C(=O)NC2(c3ccc(C(=O)O)cc3)CC2)CCOCC1 ; Cl]

Example 48 was obtained according to General Procedure IV-b, starting from Compound 68. Purification by preparative LC-MS, then HCl salt preparation (method 1) afforded Example 48 as a white powder in 15% yield over 2 steps. $^1$H-NMR (DMSO-$d_6$/$D_2O$, 400 MHz) δ (ppm): 1.24-1.35 (m, 4H, C($CH_2$—$CH_2$)); 1.81-1.92 (m, 2H, $CH_2$); 2.31-2.40 (m, 2H, $CH_2$); 2.69 (s, 3H, N—$CH_3$); 3.18-3.33 (m, 4H, N—$CH_2$+O—$CH_2$); 3.89-3.96 (m, 2H, O—$CH_2$); 4.24-4.30 (m, 2H, Ph-O—$CH_2$); 7.09 (d, J 9.0 Hz, 2H, Ar); 7.32 (d, J 8.5 Hz, 2H, Ar); 7.76 (d, J 9.0 Hz, 2H, Ar); 7.85 (d, J 8.5 Hz, 2H, Ar); CONH signal not observed; $CO_2$H signal not observed; HCl salt signal not observed. M/Z $(M+H)^+$: 464

Compound 69: Methyl 4-[1-[[4-(tert-butoxycarbonylamino)tetrahydropyran-4-carbonyl]amino]cyclopropyl]-2-fluoro-benzoate Compound 69 was obtained according to General Procedure I-a, starting from 4-(tert-butoxycarbonylamino)tetrahydropyran-4-carboxylic acid and methyl 4-(1-aminocyclopropyl)-2-fluoro-benzoate. Purification by flash chromatography (Cyclohexane/EtOAc: 80/20 to 20/80) afforded Compound 69 as a white powder in 72% yield. M/Z $(M+Na)^+$: 459

Compound 70: Methyl 4-[1-[(4-aminotetrahydropyran-4-carbonyl)amino]cyclopropyl]-2-fluoro-benzoate, hydrochloride Compound 70 was obtained according to General Procedure II-b, starting from Compound 69, as a white powder in quantitative yield. M/Z $(M+H)^+$: 337

Compound 71: Methyl 2-fluoro-4-[1-[[4-(2-phenoxyethylamino)tetrahydropyran-4-carbonyl]amino]cyclopropyl]benzoate Compound 71 was obtained according to General Procedure III-b, starting from Compound 70 and 2-phenoxyacetaldehyde. Purification by flash chromatography (Cyclohexane/EtOAc: 80/20 to 0/100) afforded Compound 71 as a colorless oil in 39% yield. M/Z $(M+H)^+$: 457

Compound 72: Methyl 2-fluoro-4-[1-[[4-[methyl(2-phenoxyethyl)amino]tetrahydropyran-4-carbonyl]amino]cyclopropyl]benzoate Compound 72 was obtained according to General Procedure III-b, starting from Compound 71 and formaldehyde, as a colorless oil which was used as such in the next step. M/Z $(M+H)^+$: 471

Example 49: 2-Fluoro-4-[1-[[4-[methyl(2-phenoxyethyl)amino]tetrahydropyran-4-carbonyl]amino]cyclopropyl]benzoic acid, hydrochloride

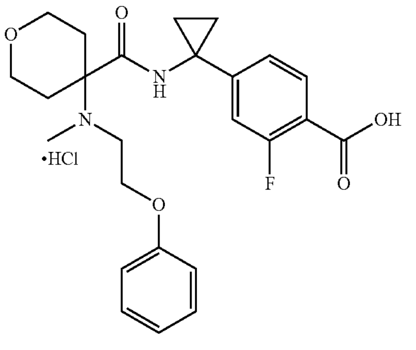 [SMILES: CN(CCOc1ccccc1)C1(C(=O)NC2(c3ccc(C(=O)O)c(F)c3)CC2)CCOCC1 ; Cl]

Example 49 was obtained according to General Procedure IV-b, starting from Compound 72. Purification by preparative LC-MS, then HCl salt preparation (method 1) afforded Example 49 as a beige powder in 30% yield over 2 steps. $^1$H-NMR (DMSO-$d_6$/$D_2O$, 400 MHz, 80° C.): 1.27-1.42 (m, 4H, C($CH_2$—$CH_2$)); 1.88-2.00 (m, 2H, $CH_2$); 2.38-2.46 (m, 2H, $CH_2$); 2.76 (s, 3H, N—$CH_3$); 3.15-3.26 (m, 2H, O—$CH_2$); 3.28-3.40 (m, 2H, N—$CH_2$); 3.93-4.02 (m, 2H, O—$CH_2$); 4.19-4.28 (m, 2H, Ph-O—$CH_2$); 6.91-7.02 (m, 3H, Ar); 7.08 (d, J 12.6 Hz, 1H, Ar); 7.15 (d, J 8.0 Hz, 1H, Ar); 7.28-7.34 (m, 2H, Ar); 7.80 (t, J 8.0 Hz, 1H, Ar); CONH signal not observed; $CO_2H$ signal not observed; HCl salt signal not observed. M/Z $(M+H)^+$: 457

Compound 73: Methyl 4-[1-[[4-(tert-butoxycarbonylamino)tetrahydropyran-4-carbonyl]amino]cyclopropyl]-3-fluoro-benzoate Compound 73 was obtained according to General Procedure I-a, starting from 4-(tert-butoxycarbonylamino)tetrahydropyran-4-carboxylic acid and methyl 4-(1-aminocyclopropyl)-3-fluoro-benzoate. Purification by flash chromatography (Cyclohexane/EtOAc: 100/0 to 20/80) afforded Compound 73 as a white powder in 96% yield. M/Z $(M+Na)^+$: 459

Compound 74: Methyl 4-[1-[(4-aminotetrahydropyran-4-carbonyl)amino]cyclopropyl]-3-fluoro-benzoate, hydrochloride Compound 74 was obtained according to General Procedure II-b, starting from Compound 73, as a white powder in quantitative yield. M/Z $(M+H)^+$: 337

Compound 75: Methyl 3-fluoro-4-[1-[[4-(2-phenoxyethylamino)tetrahydropyran-4-carbonyl]amino]cyclopropyl]benzoate Compound 75 was obtained according to General Procedure III-b, starting from Compound 74 and 2-phenoxyacetaldehyde. Purification by flash chromatography (KP-NH cartridge, Cyclohexane/EtOAc: 100/0 to 50/50) afforded Compound 75 as a colorless oil in 65% yield. M/Z $(M+H)^+$: 457

Compound 76: Methyl 3-fluoro-4-[1-[[4-[methyl(2-phenoxyethyl)amino]tetrahydropyran-4-carbonyl]amino]cyclopropyl]benzoate Compound 76 was obtained according to General Procedure III-b, starting from Compound 75 and formaldehyde, as a beige powder which was used as such in the next step. M/Z $(M+H)^+$: 471

Example 50: 3-Fluoro-4-[1-[[4-[methyl(2-phenoxyethyl)amino]tetrahydropyran-4-carbonyl]amino]cyclopropyl]benzoic acid, hydrochloride

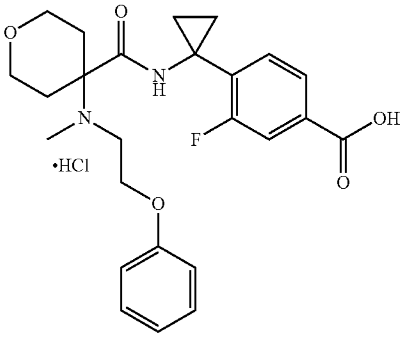 [SMILES: CN(CCOc1ccccc1)C1(C(=O)NC2(c3ccc(C(=O)O)cc3F)CC2)CCOCC1 ; Cl]

Example 50 was obtained according to General Procedure IV-b, starting from Compound 76. Purification by preparative LC-MS, then HCl salt preparation (method 1) afforded Example 50 as a white powder in 50% yield over 2 steps. $^1$H-NMR (DMSO-$d_6$/$D_2O$, 400 MHz, 80° C.): 1.21-1.28 (m, 4H, C($CH_2$—$CH_2$)); 1.78-1.90 (m, 2H, $CH_2$); 2.34-2.42 (m, 2H, $CH_2$); 2.69 (s, 3H, N—$CH_3$); 2.96-3.03 (m, 2H, O—$CH_2$); 3.13-3.35 (m, 2H, N—$CH_2$); 3.83-3.92 (m, 2H, O—$CH_2$); 4.13-4.22 (m, 2H, Ph-O—$CH_2$); 6.91 (d, J 8.2 Hz, 2H, Ar); 6.98 (t, J 7.6 Hz, 1H, Ar); 7.30 (dd, J 8.2, 7.6 Hz, 2H, Ar); 7.58 (d, J 11.1 Hz, 1H, Ar); 7.60-7.66 (m, 1H, Ar); 7.68-7.72 (m, 1H, Ar); CONH signal not observed; $CO_2H$ signal not observed; HCl salt signal not observed. M/Z $(M+H)^+$: 457

Compound 77: Methyl 4-[1-[[4-(tert-butoxycarbonylamino)tetrahydropyran-4-carbonyl]amino]cyclopropyl]-2-chloro-benzoate Compound 77 was obtained according to General Procedure I-a, starting from 4-(tert-butoxycarbonylamino)tetrahydropyran-4-carboxylic acid and methyl 4-(1-aminocyclopropyl)-2-chloro-benzoate. Purification by flash chromatography (DCM/MeOH: 100/0 to 96/4) afforded Compound 77 as a white powder in quantitative yield. M/Z $((M[^{35}Cl]-Boc)+H)^+$: 353

Compound 78: Methyl 4-[1-[(4-aminotetrahydropyran-4-carbonyl)amino]cyclopropyl]-2-chloro-benzoate, hydrochloride Compound 78 was obtained according to General Procedure II-b, starting from Compound 77, as a white powder in quantitative yield. M/Z $(M[^{35}Cl]+H)^+$: 353

Compound 79: Methyl 2-chloro-4-[1-[[4-(2-phenoxyethylamino)tetrahydropyran-4-carbonyl]amino]cyclopropyl]benzoate Compound 79 was obtained according to General Procedure III-b, starting from Compound 78 and 2-phenoxyacetaldehyde. Purification by flash chromatography (Cyclohexane/EtOAc: 100/0 to 60/40) afforded Compound 79 as a yellow oil in 64% yield. M/Z (M[35Cl]+H)$^+$: 473

Compound 80: Methyl 2-chloro-4-[1-[[4-[methyl(2-phenoxyethyl)amino]tetrahydropyran-4-carbonyl]amino]cyclopropyl]benzoate Compound 80 was obtained according to General Procedure III-b, starting from Compound 79 and formaldehyde, as a white powder which was used as such in the next step. M/Z (M[$^{35}$Cl]+H)$^+$: 487

Example 51: 2-Chloro-4-[1-[[4-[methyl(2-phenoxyethyl)amino]tetrahydropyran-4-carbonyl]amino]cyclopropyl]benzoic acid, hydrochloride

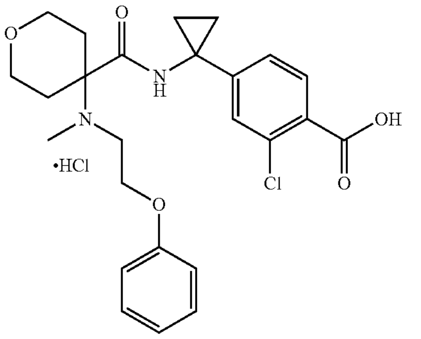 [SMILES: CN(CCOc1ccccc1)C1(C(=O)NC2(c3ccc(C(=O)O)c(Cl)c3)CC2)CCOCC1 ; Cl]

Example 51 was obtained according to General Procedure IV-b, starting from Compound 80. Purification by preparative LC-MS, then HCl salt preparation (method 1) afforded Example 51 as a beige powder in 64% yield over 2 steps. $^1$H-NMR (DMSO-d$_6$/D$_2$O, 400 MHz, 80° C.): 1.25-1.37 (m, 4H, C(CH$_2$—CH$_2$)); 1.84-1.94 (m, 2H, CH$_2$); 2.31-2.41 (m, 2H, CH$_2$); 2.70 (s, 3H, N—CH$_3$); 317-3.32 (m, 4H, O—CH$_2$+N-CH$_2$); 3.92-3.99 (m, 2H, O—CH$_2$); 4.14-4.23 (m, 2H, Ph-O—CH$_2$); 6.89-7.00 (m, 3H, Ar); 7.20-7.36 (m, 4H, Ar); 7.70-7.75 (m, 1H, Ar); CONH signal not observed; CO$_2$H signal not observed; HCl salt signal not observed. M/Z (M[$^{35}$Cl]+H)$^+$: 473

Compound 81: Methyl 4-[1-[[4-(tert-butoxycarbonylamino)tetrahydropyran-4-carbonyl]amino]cyclopropyl]-3-chloro-benzoate Compound 81 was obtained according to General Procedure I-a, starting from 4-(tert-butoxycarbonylamino)tetrahydropyran-4-carboxylic acid and methyl 4-(1-aminocyclopropyl)-3-chloro-benzoate. Purification by flash chromatography (DCM/MeOH: 100/0 to 97/3) afforded Compound 81 as a white powder in 89% yield. M/Z ((M[$^{35}$Cl]-Boc)+H)$^+$: 353

Compound 82: Methyl 4-[1-[(4-aminotetrahydropyran-4-carbonyl)amino]cyclopropyl]-3-chloro-benzoate, hydrochloride Compound 82 was obtained according to General Procedure II-b, starting from Compound 81, as a white powder in quantitative yield. M/Z (M[$^{35}$Cl]+H)$^+$: 353

Compound 83: Methyl 3-chloro-4-[1-[[4-(2-phenoxyethylamino)tetrahydropyran-4-carbonyl]amino]cyclopropyl]benzoate Compound 83 was obtained according to General Procedure III-b, starting from Compound 82 and 2-phenoxyacetaldehyde. Purification by flash chromatography (KP-NH cartridge, Cyclohexane/EtOAc: 100/0 to 70/30) afforded Compound 83 as a white powder in 86% yield. M/Z (M[$^{35}$Cl]+H)$^+$: 473

Compound 84: Methyl 3-chloro-4-[1-[[4-[methyl(2-phenoxyethyl)amino]tetrahydropyran-4-carbonyl]amino]cyclopropyl]benzoate Compound 84 was obtained according to General Procedure III-b, starting from Compound 83 and formaldehyde. Purification by flash chromatography (KP-NH cartridge, Cyclohexane/EtOAc: 100/0 to 70/30) afforded Compound 84 as a white powder in 70% yield. M/Z (M[$^{35}$Cl]+H)$^+$: 487

Example 52: 3-Chloro-4-[1-[[4-[methyl(2-phenoxyethyl)amino]tetrahydropyran-4-carbonyl]amino]cyclopropyl]benzoic acid, hydrochloride

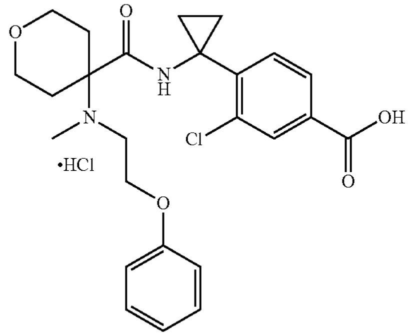 [SMILES: CN(CCOc1ccccc1)C1(C(=O)NC2(c3ccc(C(=O)O)cc3Cl)CC2)CCOCC1 ; Cl]

Example 52 was obtained according to General Procedure IV-b, starting from Compound 84. Purification by preparative LC-MS, then HCl salt preparation (method 1) afforded Example 52 as a white powder in 62% yield. $^1$H-NMR (DMSO-d$_6$/D$_2$O, 400 MHz, 80° C.): 1.14-1.21 (m, 2H, C(CH$_2$—CH$_2$)); 1.26-1.35 (m, 2H, C(CH$_2$—CH$_2$)); 1.75-1.87 (m, 2H, CH$_2$); 2.27-2.37 (m, 2H, CH$_2$); 2.61-2.70 (m, 3H, N—CH$_3$); 2.93-3.04 (m, 2H, O—CH$_2$); 3.07-3.25 (m, 2H, N—CH$_2$); 3.80-3.92 (m, 2H, O—CH$_2$); 4.09-4.22 (m, 2H, PhO—CH$_2$); 6.87-6.94 (m, 2H, Ar); 6.95-7.01 (m, 1H, Ar); 7.27-7.34 (m, 2H, Ar); 7.74-7.79 (m, 1H, Ar); 7.79-7.87 (m, 2H, Ar); CONH signal not observed CO$_2$H signal not observed; HCl salt signal not observed. M/Z (M[$^{35}$Cl]+H)$^+$: 473

Compound 85: Methyl 5-[1-[[4-(tert-butoxycarbonylamino)tetrahydropyran-4-carbonyl]amino]cyclopropyl]pyridine-2-carboxylate Compound 85 was obtained according to General Procedure I-a, starting from 4-(tert-butoxycarbonylamino)tetrahydropyran-4-carboxylic acid and methyl 5-(1-aminocyclopropyl)pyridine-2-carboxylate. Purification by flash chromatography (DCM/MeOH: 100/0 to 96/4) afforded Compound 85 as a yellow oil in quantitative yield. M/Z $(M+H)^+$: 420

Compound 86: Methyl 5-[1-[(4-aminotetrahydropyran-4-carbonyl)amino]cyclopropyl]pyridine-2-carboxylate, hydrochloride Compound 86 was obtained according to General Procedure II-b, starting from Compound 85, as a yellow powder in quantitative yield. M/Z $(M+H)^+$: 320

Compound 87: Methyl 5-[1-[[4-(2-phenoxyethylamino)tetrahydropyran-4-carbonyl]amino]cyclopropyl]pyridine-2-carboxylate Compound 87 was obtained according to General Procedure III-b, starting from Compound 86 and 2-phenoxyacetaldehyde. Purification by flash chromatography (KP-NH cartridge, Cyclohexane/EtOAc: 100/0 to 20/80) afforded Compound 87 as a colorless oil in 23% yield. M/Z $(M+H)^+$: 440

Compound 88: Methyl 5-[1-[[4-[methyl(2-phenoxyethyl)amino]tetrahydropyran-4-carbonyl]amino]cyclopropyl]pyridine-2-carboxylate Compound 88 was obtained according to General Procedure III-b, starting from Compound 87 and formaldehyde. Purification by flash chromatography (KP-NH cartridge, Cyclohexane/EtOAc: 50/50 to 20/80) afforded Compound 88 as a colorless oil in 46% yield. M/Z $(M+H)^+$: 454

Example 53: 5-[1-[[4-[Methyl(2-phenoxyethyl)amino]tetrahydropyran-4-carbonyl]amino]cyclopropyl]pyridine-2-carboxylic acid, hydrochloride

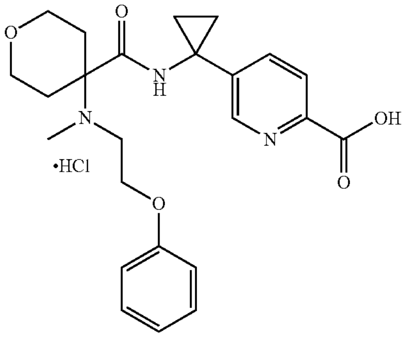 [SMILES: CN(CCOc1ccccc1)C1(C(=O)NC2(c3ccc(C(=O)O)nc3)CC2)CCOCC1 ; Cl]

Example 53 was obtained according to General Procedure V-e, starting from Compound 88. Purification by preparative LC-MS, then HCl salt preparation (method 1) afforded Example 53 as a white powder in 46% yield. $^1$H-NMR (DMSO-$d_6$/$D_2O$, 400 MHz, 80° C.): 1.29-1.49 (m, 4H, $C(CH_2—CH_2)$); 1.90-2.02 (m, 2H, $CH_2$); 2.42-2.48 (m, 2H, $CH_2$); 2.81 (s, 3H, N—$CH_3$); 3.12-3.23 (m, 2H, O—$CH_2$); 3.33-3.45 (m, 2H, N—$CH_2$); 3.93-4.02 (m, 2H, O—$CH_2$); 4.22-4.31 (m, 2H, Ph-O—$CH_2$); 6.91-7.02 (m, 3H, Ar); 7.26-7.34 (t, J 7.6 Hz, 2H, Ar); 7.82 (d, J 8.0 Hz, 1H, Ar); 8.00 (d, J 8.0 Hz, 1H, Ar); 8.59 (s, 1H, Ar); CONH signal not observed; $CO_2H$ signal not observed; HCl salt signal not observed. M/Z $(M+H)^+$: 440

Compound 89: Methyl 6-[1-[[4-(tert-butoxycarbonylamino)tetrahydropyran-4-carbonyl]amino]cyclopropyl]pyridine-3-carboxylate Compound 89 was obtained according to General Procedure I-a, starting from 4-(tert-butoxycarbonylamino)tetrahydropyran-4-carboxylic acid and methyl 6-(1-aminocyclopropyl)pyridine-3-carboxylate. Purification by flash chromatography (Cyclohexane/EtOAc: 50/50 to 10/90) afforded Compound 89 as a white powder in 69% yield. M/Z $(M+Na)^+$: 420

Compound 90: Methyl 6-[1-[(4-aminotetrahydropyran-4-carbonyl)amino]cyclopropyl]pyridine-3-carboxylate, hydrochloride Compound 90 was obtained according to General Procedure II-b, starting from Compound 89, as a beige powder in quantitative yield. M/Z $(M+H)^+$: 320

Compound 91: Methyl 6-[1-[[4-(2-phenoxyethylamino)tetrahydropyran-4-carbonyl]amino]cyclopropyl]pyridine-3-carboxylate Compound 91 was obtained according to General Procedure III-b, starting from Compound 90 and 2-phenoxyacetaldehyde. Purification by flash chromatography (KP-NH cartridge, Cyclohexane/EtOAc: 100/0 to 50/50) afforded Compound 91 as a colorless oil in 78% yield. M/Z $(M+H)^+$: 440

Compound 92: Methyl 6-[1-[[4-[methyl(2-phenoxyethyl)amino]tetrahydropyran-4-carbonyl]amino]cyclopropyl]pyridine-3-carboxylate Compound 92 was obtained according to General Procedure III-b, starting from Compound 91 and formaldehyde. Purification by flash chromatography (KP-NH cartridge, Cyclohexane/EtOAc: 100/0 to 50/50) afforded Compound 92 as a white powder. M/Z $(M+H)^+$: 454

Example 54: 6-[1-[[4-[Methyl(2-phenoxyethyl)amino]tetrahydropyran-4-carbonyl]amino]cyclopropyl]pyridine-3-carboxylic acid, hydrochloride

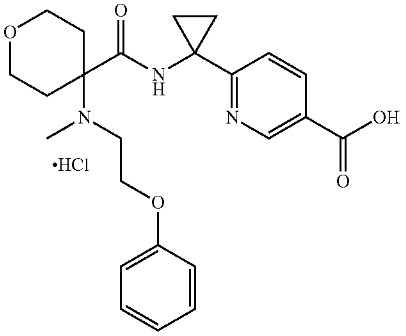 [SMILES: CN(CCOc1ccccc1)C1(C(=O)NC2(c3ccc(C(=O)O)cn3)CC2)CCOCC1 ; Cl]

Example 54 was obtained according to General Procedure IV-b, starting from Compound 92. Purification by preparative LC-MS, then HCl salt preparation (method 1) afforded Example 54 as a beige powder in 50% yield over 2 steps. $^1$H-NMR (DMSO-$d_6$/$D_2O$, 400 MHz, 80° C.): 1.39-1.44 (m, 2H, C($CH_2$—$CH_2$)); 1.52-1.58 (m, 2H, C($CH_2$—$CH_2$)); 1.89-2.04 (m, 2H, $CH_2$); 2.53-2.62 (m, 2H, $CH_2$); 2.96 (s, 3H, N—$CH_3$); 3.27-3.37 (m, 2H, O—$CH_2$); 3.73-3.79 (m, 2H, N—$CH_2$); 3.94-4.03 (m, 2H, O—$CH_2$); 4.31-4.40 (m, 2H, Ph-O—$CH_2$); 6.96-7.03 (m, 3H, Ar); 7.25 (d, J 8.4 Hz, 1H, Ar); 7.33 (t, J 7.3 Hz, 2H, Ar); 8.18 (d, J 8.4 Hz, 1H, Ar); 8.92 (s, 1H, Ar); CONH signal not observed; $CO_2H$ signal not observed; HCl salt signal not observed. M/Z $(M+H)^+$: 440

Compound 93: Methyl 4-[(1S)-1-[[1-(tert-butoxycarbonylamino)cyclohexanecarbonyl]amino]ethyl] benzoate Compound 93 was obtained according to General Procedure I-a, starting from 1-(tert-butoxycarbonylamino)cyclohexanecarboxylic acid and methyl 4-[(1S)-1-aminoethyl] benzoate. Purification by flash chromatography (Cyclohexane/EtOAc: 100/0 to 50/50) afforded Compound 93 as a white powder in 96% yield. M/Z $(M+H)^+$: 405

Compound 94: Methyl 4-[(1S)-1-[(1-aminocyclohexanecarbonyl)amino]ethyl]benzoate

Compound 94 was obtained according to General Procedure II-c, starting from Compound 93, as an hydrochloride salt in 95% yield. M/Z $(M+H)^+$: 305

Compound 95: Methyl 4-[(1S)-1-[[4-(2-phenoxyethylamino)cyclohexanecarbonyl]amino]ethyl]benzoate Compound 95 was obtained according to General Procedure III-a, starting from Compound 94 (hydrochloride salt) and 2-phenoxyacetaldehyde. Purification by flash chromatography (KP-NH cartridge, Cyclohexane/EtOAc: 100/0 to 70/30) afforded Compound 95 as a colorless oil in 17% yield. M/Z $(M+H)^+$: 425

Example 55: 4-[(1S)-1-[[1-(2-Phenoxyethylamino) cyclohexanecarbonyl]amino]ethyl]benzoic acid, hydrochloride

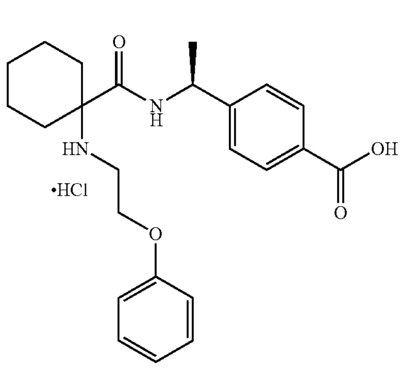 [SMILES: C[C@H](NC(=O)C1(NCCOc2ccccc2)CCCCC1)c1ccc(C(=O)O)cc1 ; Cl]

Example 55 was obtained according to General Procedure IV-a, starting from Compound 95. Purification by preparative LC-MS then HCl salt preparation (method 1) afforded Example 55 as a white powder in 10% yield. $^1$H-NMR (DMSO-$d_6$ 400 MHz) δ (ppm): 1.27-1.55 (m, 7H, $CH_2$+CH-$CH_3$); 1.64-1.84 (m, 4H, $CH_2$); 2.30-2.40 (m, 2H, $CH_2$);

3.02-3.17 (m, 2H, NH—$CH_2$); 4.20-4.30 (m, 2H, Ph-O—$CH_2$); 5.03 (quint, J 7.2 Hz, 1H, CONH—CH—$CH_3$); 6.92-7.01 (m, 3H, Ar); 7.32 (dd, J 8.6, 7.5 Hz, 2H, Ar); 7.49 (d, J 8.2 Hz, 2H, Ar); 7.89 (d, J 8.2 Hz, 2H, Ar); 8.94 (d, J 7.2 Hz, 1H, CONH—CH); 9.28-9.44 (m, 2H, NH+HCl salt); 12.85 (bs, 1H, $CO_2H$). M/Z $(M+H)^+$: 411

Compound 96: Methyl 4-[(1S)-1-[[1-[2-(3-chlorophenoxy)ethylamino]cyclohexanecarbonyl]amino] ethyl]benzoate Compound 96 was obtained according to General Procedure III-b, starting from Compound 94 (hydrochloride salt) and 2-(3-chlorophenoxy)acetaldehyde. Purification by flash chromatography (KP-NH cartridge, Cyclohexane/EtOAc: 100/0 to 70/30) afforded Compound 96 as a colorless oil in 77% yield. M/Z $(M[35Cl]+H)^+$: 459

Example 56: 4-[(1S)-1-[[1-[2-(3-Chlorophenoxy) ethylamino]cyclohexanecarbonyl]amino]ethyl]benzoic acid, hydrochloride

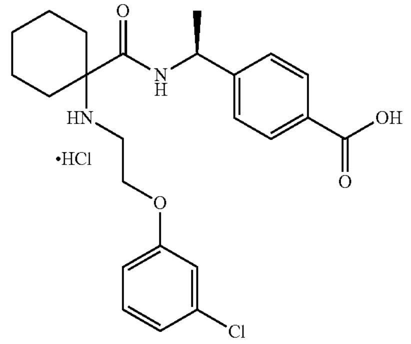 [SMILES: C[C@H](NC(=O)C1(NCCOc2cccc(Cl)c2)CCCCC1)c1ccc(C(=O)O)cc1 ; Cl]

Example 56 was obtained according to General Procedure IV-b, starting from Compound 96. Purification by preparative LC-MS, then HCl salt preparation (method 1) afforded Example 56 as a yellow powder in 10% yield. $^1$H-NMR (DMSO-$d_6$ 400 MHz) δ (ppm): 1.27-1.56 (m, 7H, $CH_2$+CH-$CH_3$); 1.64-1.83 (m, 4H, $CH_2$); 2.30-2.41 (m, 2H, $CH_2$); 3.02-3.18 (m, 2H, NH—$CH_2$); 4.24-4.32 (m, 2H, Ph-O—$CH_2$): 5.02 (quint, J 7.1 Hz, 1H, CONH—CH—$CH_3$); 6.96 (dd, J 8.3, 1.5 Hz, 1H, Ar); 7.03-7.08 (m, 2H, Ar); 7.34 (t, J 8.3 Hz, 1H, Ar); 7.49 (d, J 8.2 Hz, 2H, Ar); 7.89 (d, J 8.2 Hz, 2H, Ar); 8.98 (d, J 7.1 Hz, 1H, CONH—CH); 9.39 (bs, 2H, NH+HCl salt); 12.80 (bs, 1H, $CO_2H$). M/Z $(M[^{35}Cl]+H)^+$: 445

Compound 97: Methyl 4-[(1S)-1-[[1-[2-(3-chlorophenoxy)ethyl-methyl-amino]cyclohexanecarbonyl] amino]ethyl]benzoate Compound 97 was obtained according to General Procedure III-b, starting from Compound 96 and formaldehyde, and was used as such in the next step. M/Z $(M[35Cl]+H)^+$: 473

Example 57: 4-[(1S)-1-[[1-[2-(3-Chlorophenoxy)ethyl-methyl-amino]cyclohexanecarbonyl]amino]ethyl]benzoic acid, hydrochloride

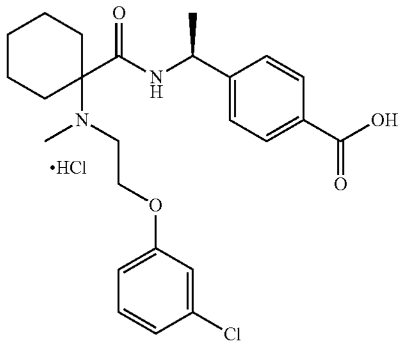 [SMILES: C[C@H](NC(=O)C1(N(C)CCOc2cccc(Cl)c2)CCCCC1)c1ccc(C(=O)O)cc1 ; Cl]

Example 57 was obtained according to General Procedure IV-b, starting from Compound 97. Purification by preparative LC-MS, then HCl salt preparation (method 2) afforded Example 57 as a white powder in 9% yield over 2 steps. $^1$H-NMR (DMSO-$d_6$ 400 MHz) δ (ppm): 1.12-1.32 (m, 3H, $CH_2$+$CH_aH_b$); 1.49 (d, J 6.7 Hz, 3H, CH—$CH_3$); 1.53-1.61 (m, 1H, $CH_aH_b$); 1.68-1.82 (m, 4H, $CH_2$); 2.51-2.62 (m, 2H, $CH_2$); 2.80 (bs, 3H, N—$CH_3$); 3.15-3.29 (m, 1H, N—$CH_aH_b$); 3.50-3.64 (m, 1H, N—$CH_aH_b$); 4.30-4.40 (m, 2H, PhO—$CH_2$); 5.05-5.14 (m, 1H, CONH—CH—$CH_3$); 6.89-6.94 (m, 1H, Ar); 7.03-7.08 (m, 2H, Ar); 7.33 (t, J 8.2 Hz, 1H, Ar); 7.47-7.55 (m, 2H, Ar); 7.86-7.94 (m, 2H, Ar); 8.95 (d, J 6.7 Hz, 1H, CONH—CH); 10.18 (bs, 1H, HCl salt); 12.85 (bs, 1H, $CO_2$H). M/Z (M[$^{35}$Cl]+H)$^+$: 459

Compound 98: Methyl 4-[(1S)-1-[[1-[2-(3-methylphenoxy)ethylamino]cyclohexanecarbonyl]amino]ethyl]benzoate Compound 98 was obtained according to General Procedure III-b, starting from Compound 94 (hydrochloride salt) and 2-(3-methylphenoxy)acetaldehyde. Purification by flash chromatography (KP-NH cartridge, Cyclohexane/EtOAc: 100/0 to 70/30) afforded Compound 98 as a colorless oil in 78% yield. M/Z (M+H)$^+$: 439

Example 58: 4-[(1S)-1-[[1-[2-(3-Methylphenoxy)ethylamino]cyclohexanecarbonyl]amino]ethyl]benzoic acid, hydrochloride

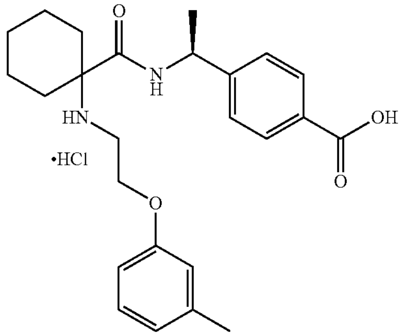 [SMILES: Cc1cccc(OCCNC2(C(=O)N[C@@H](C)c3ccc(C(=O)O)cc3)CCCCC2)c1 ; Cl]

Example 58 was obtained according to General Procedure IV-b, starting from Compound 98. Purification by preparative LC-MS, then HCl salt preparation (method 2) afforded Example 58 as a white powder in 51% yield. $^1$H-NMR (DMSO-$d_6$, 400 MHz) δ (ppm): 1.27-1.55 (m, 7H, $CH_2$+CH-$CH_3$); 1.63-1.83 (m, 4H, $CH_2$); 2.29 (s, 3H, Ph-$CH_3$); 2.30-2.38 (m, 2H, $CH_2$); 3.04-3.13 (m, 2H, NH—$CH_2$); 4.21 (t, J 5.1 Hz, 2H, PhO—$CH_2$); 5.03 (quint, J 7.2 Hz, 1H, CONH—CH—$CH_3$); 6.73-6.82 (m, 3H, Ar); 7.18 (t, J 7.8 Hz, 1H, Ar); 7.49 (d, J 8.2 Hz, 2H, Ar); 7.89 (d, J 8.2 Hz, 2H, Ar); 8.90 (d, J 7.2 Hz, 1H, CONH—CH); 9.32 (bs, 2H, NH+HCl salt); 12.84 (bs, 1H, $CO_2$H). M/Z (M+H)$^+$: 425

Compound 99: Methyl 4-[(1S)-1-[[1-[2-(3-methylphenoxy)ethyl-methyl-amino]cyclohexanecarbonyl]amino]ethyl]benzoate Compound 99 was obtained according to General Procedure III-b, starting from Compound 98 and formaldehyde, and was used as such in the next step. M/Z (M+H)$^+$: 452

Example 59: 4-[(1S)-1-[[1-[Methyl-[2-(3-methylphenoxy)ethyl]amino]cyclohexanecarbonyl]amino]ethyl]benzoic acid, hydrochloride

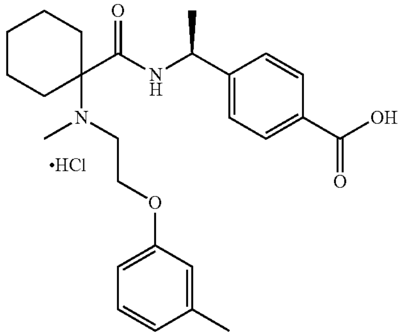 [SMILES: Cc1cccc(OCCN(C)C2(C(=O)N[C@@H](C)c3ccc(C(=O)O)cc3)CCCCC2)c1 ; Cl]

Example 59 was obtained according to General Procedure IV-b, starting from Compound 99. Purification by preparative LC-MS, then HCl salt preparation (method 2) afforded Example 59 as a white powder in 36% yield over 2 steps. $^1$H-NMR (DMSO-$d_6$, 400 MHz) δ (ppm): 1.12-1.34 (m, 3H, $CH_2$+$CH_aH_b$); 1.49 (d, J 6.9 Hz, 3H, CH—$CH_3$); 1.53-1.60 (m, 1H, $CH_aH_b$); 1.69-1.82 (m, 4H, $CH_2$); 2.28 (s, 3H, Ph-$CH_3$); 2.51-2.62 (m, 2H, $CH_2$); 2.76-2.84 (m, 3H, N—$CH_3$); 3.13-3.29 (m, 1H, N—$CH_aH_b$); 3.37-3.63 (m, 1H, N—$CH_aH_b$); 4.22-4.39 (m, 2H, Ph-O—$CH_2$); 5.10 (quint, J 6.9 Hz, 1H, CONH—CH—$CH_3$); 6.69-6.77 (m, 2H, Ar); 6.80 (d, J 7.5 Hz, 1H, Ar); 7.18 (t, J 7.5 Hz, 1H, Ar); 7.48-7.55 (m, 2H, Ar); 7.87-7.94 (m, 2H, Ar); 9.02 (bs, 1H, CONH—CH); 10.46 (bs, 1H, HCl salt); 12.86 (bs, 1H, $CO_2$H). M/Z (M+H)$^+$: 439

Compound 100: Methyl 4-[(1S)-1-[[1-[2-(3-methoxyphenoxy)ethylamino]cyclohexanecarbonyl]amino]ethyl]benzoate Compound 100 was obtained according to General Procedure III-b, starting from Compound 94 (hydrochloride salt) and 2-(3-methoxyphenoxy)acetaldehyde. Purification by flash chromatography (KP-NH cartridge, Cyclohexane/EtOAc: 100/0 to 70/30) afforded Compound 100 as a colorless oil in 76% yield. M/Z (M+H)$^+$: 455

Compound 101: Methyl 4-[(1S)-1-[[1-[2-(3-methoxyphenoxy)ethyl-methyl-amino]cyclohexanecarbonyl]amino]ethyl]benzoate Compound 101 was obtained according to General Procedure III-b, starting from Compound 100 and formaldehyde, and was used as such in the next step. M/Z $(M+H)^+$: 469

Example 60: 4-[(1S)-1-[[1-[2-(3-Methoxyphenoxy)ethyl-methyl-amino]cyclohexanecarbonyl]amino]ethyl]benzoic acid, hydrochloride

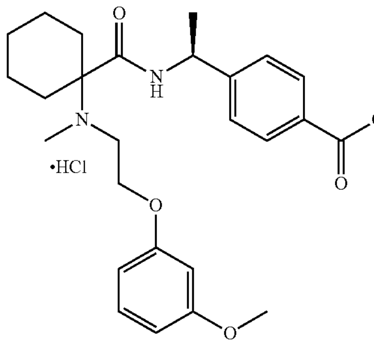

Example 60 was obtained according to General Procedure IV-b, starting from Compound 101. Purification by preparative LC-MS, then HCl salt preparation (method 2) afforded Example 60 as a white powder in 17% yield over 2 steps. $^1$H-NMR (DMSO-$d_6$, 400 MHz) δ (ppm): 1.12-1.35 (m, 3H, $CH_2$+$CH_aH_b$); 1.49 (d, J 6.8 Hz, 3H, CH—$CH_3$); 1.52-1.61 (m, 1H, $CH_aH_b$); 1.68-1.83 (m, 4H, $CH_2$); 2.52-2.63 (m, 2H, $CH_2$); 2.80 (bs, 3H, N—$CH_3$); 3.13-3.29 (m, 1H, N—$CH_aH_b$); 3.47-3.62 (m, 1H, N—$CH_aH_b$); 3.74 (s, 3H, O—$CH_3$); 4.24-4.41 (m, 2H, Ph-C—$CH_2$); 5.05-5.14 (m, 1H, CONH—CH—$CH_3$); 6.49-6.55 (m, 2H, Ar); 6.57 (d, J 8.3 Hz, 1H, Ar); 7.21 (t, J 8.3 Hz, 1H, Ar); 7.48-7.54 (m, 2H, Ar); 7.87-7.94 (m, 2H, Ar); 9.02 (d, J 6.8 Hz, 1H, CONH—CH); 10.46 (bs, 1H, HCl salt); 12.84 (bs, 1H, $CO_2H$). M/Z $(M+H)^+$: 455

Compound 102: Methyl 4-[(1S)-1-[[1-(tert-butoxycarbonylamino)cyclopentanecarbonyl]amino]ethyl]benzoate Compound 102 was obtained according to General Procedure I-a, starting from 1-(tert-butoxycarbonylamino)cyclopentanecarboxylic acid and methyl 4-[(1S)-1-aminoethyl]benzoate. Purification by flash chromatography (Cyclohexane/EtOAc: 100/0 to 50/50) afforded Compound 102 as a white powder in 88% yield. M/Z $(M+H)^+$: 391

Compound 103: Methyl 4-[(1S)-1-[(1-aminocyclopentanecarbonyl)amino]ethyl]benzoate Compound 103 was obtained according to General Procedure II-a, starting from Compound 102, in quantitative yield. M/Z $(M+H)^+$: 291

Compound 104: Methyl 4-[(1S)-1-[[4-(2-phenoxyethylamino)cyclopentanecarbonyl]amino]ethyl]benzoate Compound 104 was obtained according to General Procedure III-a, starting from Compound 103 and 2-phenoxyacetaldehyde. Purification by flash chromatography (Cyclohexane/EtOAc: 100/0 to 0/100) afforded Compound 104 as a white powder in 54% yield. M/Z $(M+H)^+$: 411

Example 61: 4-[(1S)-1-[[1-(2-Phenoxyethylamino)cyclopentanecarbonyl]amino]ethyl]benzoic acid, hydrochloride

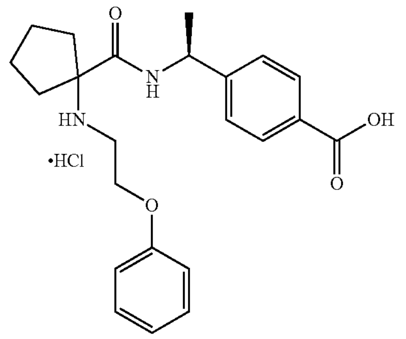 [SMILES: C[C@H](NC(=O)C1(NCCOc2ccccc2)CCCC1)c1ccc(C(=O)O)cc1 ; Cl]

Example 61 was obtained according to General Procedure IV-a, starting from Compound 104, as an orange powder in 55% yield. $^1$H-NMR (DMSO-$d_6$, 400 MHz) δ (ppm): 1.45 (d, J 7.1 Hz, 3H, CH—$CH_3$); 1.67-1.77 (m, 2H, $CH_2$); 1.77-1.88 (m, 2H, $CH_2$); 2.00-2.12 (m, 2H, $CH_2$); 2.18-2.30 (m, 2H, $CH_2$); 3.12-3.22 (m, 2H, NH—$CH_2$); 4.23 (t, J 4.4 Hz, 2H, Ph-O—$CH_2$); 5.03 (quint, J 7.1 Hz, 1H, CONH—CH—$CH_3$); 6.95-7.00 (m, 3H, Ar); 7.32 (dd, J 8.8, 7.2 Hz, 2H, Ar); 7.47 (d, J 8.2 Hz, 2H, Ar); 7.89 (d, J 8.2 Hz, 2H, Ar); 8.87 (d, J 7.1 Hz, 1H, CONH—CH); 9.49 (bs, 2H, NH+HCl salt); 12.85 (bs, 1H, $CO_2H$). M/Z $(M+H)^+$: 397

Compound 105: Methyl 4-[(1S)-1-[[1-[2-phenoxyethyl-methyl-amino]cyclopentanecarbonyl]amino]ethyl]benzoate Compound 105 was obtained according to General Procedure III-a, starting from Compound 104 and formaldehyde, and was used as such in the next step. M/Z $(M+H)^+$: 425

Example 62: 4-[(1S)-1-[[1-[Methyl(2-phenoxyethyl)amino]cyclopentanecarbonyl]amino]ethyl]benzoic acid, hydrochloride

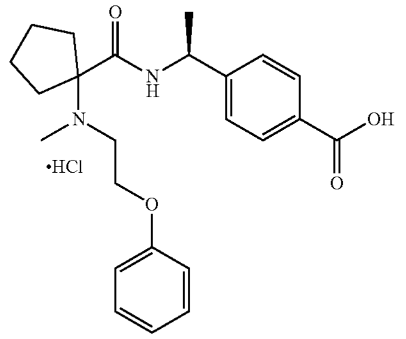 [SMILES: C[C@H](NC(=O)C1(N(C)CCOc2ccccc2)CCCC1)c1ccc(C(=O)O)cc1 ; Cl]

Example 62 was obtained according to General Procedure IV-b, starting from Compound 105. Purification by preparative LC-MS, then HCl salt preparation (method 1) afforded Example 62 as a white powder in 74% yield over 2 steps. $^1$H-NMR (DMSO-$d_6$ 400 MHz) δ (ppm): 1.47 (d, J 6.8 Hz, 3H, CH—$CH_3$); 1.59-1.87 (m, 4H, $CH_2$); 2.10-2.28 (m, 3H, $CH_2$+$CH_aH_b$); 2.36-2.45 (m, 1H, $CH_aH_b$); 2.87 (bs, 3H, N—$CH_3$); 3.26-3.40 (m, 2H, N—$CH_2$); 4.27-4.43 (m, 2H, PhO—$CH_2$); 5.06 (quint, J 6.8 Hz, 1H, CONH—CH—$CH_3$); 6.93-7.02 (m, 3H, Ar); 7.28-7.36 (m, 2H, Ar); 7.47 (d, J 8.1 Hz, 2H, Ar); 7.89 (d, J 8.1 Hz, 2H, Ar, signal of a rotamer); 7.91 (d, J 7.8 Hz, 2H, Ar, signal of a rotamer); 8.91 (bs, 1H, CONH—CH); 10.48 (bs, 1H, HCl salt); 12.86 (bs, 1H, $CO_2H$). M/Z $(M+H)^+$: 411

Compound 106: Methyl 4-[(13)-1-[[4-(2-(3-chlorophenoxy)ethylamino)cyclopentanecarbonyl]amino]ethyl]benzoate Compound 106 was obtained according to General Procedure III-a, starting from Compound 103 and 2-(3-chlorophenoxy)acetaldehyde. Purification by flash chromatography (Cyclohexane/EtOAc: 100/0 to 70/30) afforded Compound 106 as a white powder in 46% yield. M/Z $(M[^{35}Cl]+H)^+$: 445

Example 63: 4-[(1S)-1-[[1-[2-(3-Chlorophenoxy)ethylamino]cyclopentanecarbonyl]amino]ethyl]benzoic acid, hydrochloride

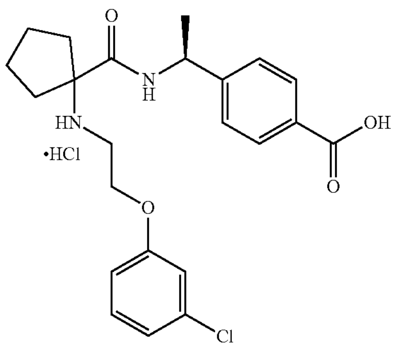 [SMILES: C[C@H](NC(=O)C1(NCCOc2cccc(Cl)c2)CCCC1)c1ccc(C(=O)O)cc1 ; Cl]

Example 63 was obtained according to General Procedure IV-a, starting from Compound 106, as a white powder in 44% yield. $^1$H-NMR (DMSO-$d_6$, 400 MHz) δ (ppm): 1.44 (d, J 7.1 Hz, 3H, CH—$CH_3$); 1.68-1.89 (m, 4H, $CH_2$); 1.99-2.13 (m, 2H, $CH_2$); 2.17-2.30 (m, 2H, $CH_2$); 3.13-3.23 (m, 2H, NH—$CH_2$); 4.26 (t, J 4.2 Hz, 2H, PhO—$CH_2$); 5.02 (quint, J 7.1 Hz, 1H, CONH—CH—$CH_3$); 6.93-6.99 (m, 1H, Ar); 7.03-7.07 (m, 2H, Ar); 7.34 (t, J 8.4 Hz, 1H, Ar); 7.46 (d, J 8.2 Hz, 2H, Ar); 7.89 (d, J 8.2 Hz, 2H, Ar); 8.84 (d, J 7.1 Hz, 1H, CONH—CH); 9.43 (bs, 2H, NH+HCl salt); 12.85 (bs, 1H, $CO_2H$). M/Z $(M[^{35}Cl]+H)^+$: 431

Compound 107: Methyl 3-[(1S)-1-[[1-(tert-butoxycarbonylamino)cyclopentanecarbonyl]amino]ethyl]bicyclo[1.1.1]pentane-1-carboxylate Compound 107 was obtained according to General Procedure I-a, starting from 1-(tert-butoxycarbonylamino)cyclopentanecarboxylic acid and methyl 3-[(1S)-1-aminoethyl]bicyclo[1.1.1]pentane-1-carboxylate. Purification by flash chromatography (Cyclohexane/EtOAc: 100/0 to 30/70) afforded Compound 107 as a white powder in 91% yield. M/Z $(M+H)^+$: 381

Compound 108: Methyl 3-[(1S)-1-[(1-aminocyclopentanecarbonyl)amino]ethyl]bicyclo[1.1.1]pentane-1-carboxylate Compound 108 was obtained according to General Procedure II-a, starting from Compound 107, in 75% yield. M/Z $(M+H)^+$: 281

Compound 109: Methyl 3-[(1S)-1-[[1-[2-(3-chlorophenoxy)ethylamino]cyclopentanecarbonyl]amino]ethyl]bicyclo[1.1.1]pentane-1-carboxylate Compound 109 was obtained according to General Procedure III-a, starting from Compound 108 and 2-(3-chlorophenoxy)acetaldehyde, and was used as such in the next step. M/Z $(M[^{35}Cl]+H)^+$: 435

Example 64: 3-[(1S)-1-[[1-[2-(3-Chlorophenoxy)ethylamino]cyclopentanecarbonyl]amino]ethyl]bicyclo[1.1.1]pentane-1-carboxylic acid, hydrochloride

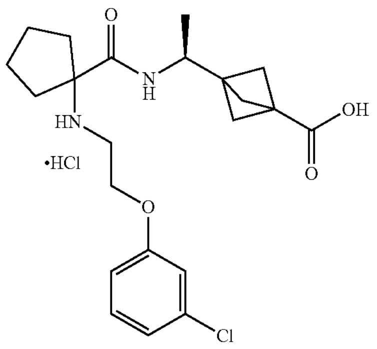 [SMILES: C[C@H](NC(=O)C1(NCCOc2cccc(Cl)c2)CCCC1)C12CC(C(=O)O)(C1)C2 ; Cl]

Example 64 was obtained according to General Procedure IV-a, starting from Compound 109. Purification by preparative LC-MS, then HCl salt preparation (method 1) afforded Example 64 as a beige powder in 8% yield over 2 steps. $^1$H-NMR (DMSO-$d_6$, 400 MHz) δ (ppm): 1.04 (d, J 6.9 Hz, 3H, CH—$CH_3$); 1.67-1.87 (m, 10H, $CH_2$); 1.99-2.08 (m, 2H, $CH_2$); 2.15-2.27 (m, 2H, $CH_2$); 3.15-3.24 (m, 2H, NH—$CH_2$); 3.96-4.04 (m, 1H, CONH—CH—$CH_3$); 4.28 (t, J 4.8 Hz, 2H, Ph-O—$CH_2$); 6.98 (dd, J 8.2, 1.5 Hz, 1H, Ar); 7.04-7.08 (m, 2H, Ar); 7.35 (t, J 8.2 Hz, 1H, Ar); 8.03 (d, J 8.3 Hz, 1H, CONH—CH); 9.36 (bs, 2H, NH+HCl salt); 12.30 (bs, 1H, $CO_2H$). M/Z $(M[^{35}Cl]+H)^+$: 421

Compound 110: Methyl 4-[(1S)-1-[[1-(tert-butoxycarbonylamino)-4,4-difluoro-cyclohexanecarbonyl]amino]ethyl]benzoate Compound 110 was obtained according to General Procedure I-a, starting from 1-(tert-butoxycarbonylamino)-4,4-difluoro-cyclohexanecarboxylic acid and methyl 4-[(1S)-1-aminoethyl]benzoate. Purification by flash chromatography (Cyclohexane/EtOAc: 100/0 to 50/50) afforded Compound 110 as a white powder in 40% yield. M/Z $(M+Na)^+$: 463

Compound 111: Methyl 4-[(1S)-1-[(1-amino-4,4-difluoro-cyclohexanecarbonyl)amino]ethyl]benzoate Compound 111 was obtained according to General Procedure II-a, starting from Compound 110, in 87% yield. M/Z $(M+H)^+$: 341

Compound 112: Methyl 4-[(1S)-1-[[4,4-difluoro-1-(2-phenoxyethylamino)cyclohexanecarbonyl]amino]ethyl]benzoate Compound 112 was obtained according to General Procedure III-a, starting from Compound 111 and 2-phenoxyacetaldehyde. Purification by flash chromatography (Cyclohexane/EtOAc: 100/0 to 60/40) afforded Compound 112 as a colorless oil in 36% yield. M/Z $(M+H)^+$: 461

Example 65: 4-[(1S)-1-[[4,4-Difluoro-1-(2-phenoxyethylamino)cyclohexanecarbonyl]amino]ethyl]benzoic acid, hydrochloride

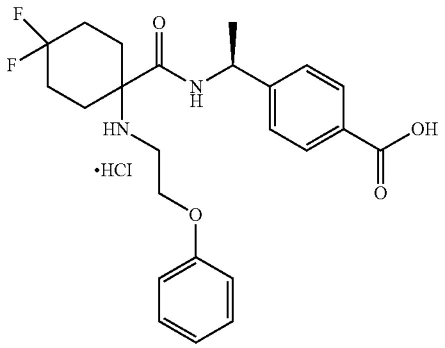 [SMILES: C[C@H](NC(=O)C1(NCCOc2ccccc2)CCC(F)(F)CC1)c1ccc(C(=O)O)cc1 ; "·HCI"]

Example 65 was obtained according to General Procedure IV-a, starting from Compound 112, as a white powder in 60% yield. $^1$H-NMR (DMSO-$d_6$, 400 MHz) δ (ppm): 1.46 (d, J 6.9 Hz, 3H, CH—$CH_3$); 1.81-2.29 (m, 7H, $CH_2$+$CH_aH_b$); 2.38-2.47 (m, 1H, $CH_aH_b$); 3.05-3.26 (m, 2H, NH—$CH_2$); 4.17-4.30 (m, 2H, Ph-O—$CH_2$); 5.03 (quint, J 6.9 Hz, 1H, CONH—CH—$CH_3$); 6.93-7.01 (m, 3H, Ar); 7.32 (t, J 7.8 Hz, 2H, Ar); 7.49 (d, J 8.2 Hz, 2H, Ar); 7.90 (d, J 8.2 Hz, 2H, Ar); 9.15 (bs, 1H, CONH—CH); 9.66 (bs, 2H, NH+HCl salt); 12.85 (bs, 1H, $CO_2H$). M/Z $(M+H)^+$: 447

Compound 113: Methyl 4-[(1S)-1-[[4-(tert-butoxycarbonylamino)tetrahydrothiopyran-4-carbonyl]amino]ethyl]benzoate Compound 113 was obtained according to General Procedure I-b, starting from 4-(tert-butoxycarbonylamino)tetrahydrothiopyran-4-carboxylic acid and methyl 4-[(1S)-1-aminoethyl]benzoate. Purification by flash chromatography (Cyclohexane/EtOAc: 100/0 to 50/50) afforded Compound 113 as a white powder in 91% yield. M/Z $(M+Na)^+$: 423

Compound 114: Methyl 4-[(1S)-1-[(4-aminotetrahydrothiopyran-4-carbonyl)amino]ethyl]benzoate Compound 114 was obtained according to General Procedure II-a, starting from Compound 113, as a yellow oil in quantitative yield. M/Z $(M+H)^+$: 323

Compound 115: Methyl 4-[(1S)-1-[[4-(2-phenoxyethylamino)tetrahydrothiopyran-4-carbonyl]amino]ethyl]benzoate Compound 115 was obtained according to General Procedure III-a, starting from Compound 114 and 2-phenoxyacetaldehyde. Purification by flash chromatography (DCM/MeOH: 100/0 to 90/10) afforded Compound 115 as a colorless oil in 73% yield. M/Z $(M+H)^+$: 443

Example 66: 4-[(1S)-1-[[4-(2-Phenoxyethylamino)tetrahydrothiopyran-4-carbonyl]amino]ethyl]benzoic acid

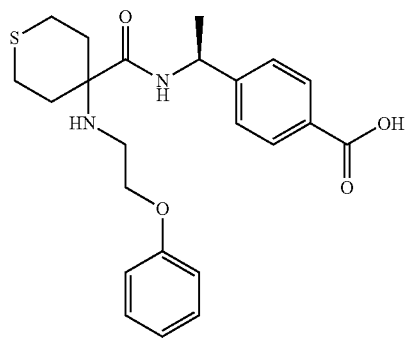 [SMILES: C[C@H](NC(=O)C1(NCCOc2ccccc2)CCSCC1)c1ccc(C(=O)O)cc1]

Example 66 was obtained according to General Procedure IV-a, starting from Compound 115. Purification by preparative LC-MS afforded Example 66 as a white powder in 41% yield. $^1$H-NMR (DMSO-$d_6$, 400 MHz) δ (ppm): 1.38 (d, J 7.1 Hz, 3H, CH—$CH_3$); 1.81-2.05 (m, 4H, $CH_2$); 2.34-2.47 (m, 2H, S—$CH_2$); 2.61-2.70 (m, 2H, NH—$CH_2$); 2.81-2.90 (m, 2H, S—$CH_2$); 4.02 (t, J 5.4 Hz, 2H, Ph-O—$CH_2$); 4.92-5.01 (m, 1H, CONH—CH—$CH_3$); 6.86-6.95 (m, 3H, Ar); 7.27 (dd, J 8.6, 7.5 Hz, 2H, Ar); 7.41 (d, J 8.2 Hz, 2H, Ar); 7.85 (d, J 8.2 Hz, 2H, Ar); 8.20 (d, J 8.0 Hz, 1H, CONH—CH); $CO_2H$ signal not observed; NH signal not observed. M/Z $(M+H)^+$: 429

Compound 116: Methyl 4-[(1S)-1-[[4-(tert-butoxycarbonylamino)-1,1-dioxo-thiane-4-carbonyl]amino]ethyl]benzoate To a solution of Compound 113 (1 equiv.) in DCM (0.1 M) was added mCPBA (2.5 equiv.). The reaction mixture was stirred for 3 h at rt. The reaction mixture was hydrolyzed with a saturated solution of sodium bicarbonate, extracted with DCM. The organic layer was washed with brine, dried, then concentrated to afford Compound 116 as a yellow powder in 98% yield. M/Z $(M+Na)^+$: 455

Compound 117: Methyl 4-[(1S)-1-[(4-amino-1,1-dioxo-thiane-4-carbonyl)amino]ethyl]benzoate Compound 117 was obtained according to General Procedure II-a, starting from Compound 116, as a white powder in 92% yield. M/Z $(M+H)^+$: 355

Compound 118: Methyl 4-[(1S)-1-[[1,1-dioxo-4-(2-phenoxyethylamino)thiane-4-carbonyl]amino]ethyl]benzoate Compound 118 was obtained according to General Procedure III-a, starting from Compound 117 and 2-phenoxyacetaldehyde. Purification by flash chromatography (Cyclohexane/EtOAc: 100/0 to 20/80) afforded Compound 118 as a colorless oil in 46% yield. M/Z $(M+H)^+$: 475

Example 67: 4-[(1S)-1-[[1,1-Dioxo-4-(2-phenoxyethylamino)thiane-4-carbonyl]amino]ethyl]benzoic acid

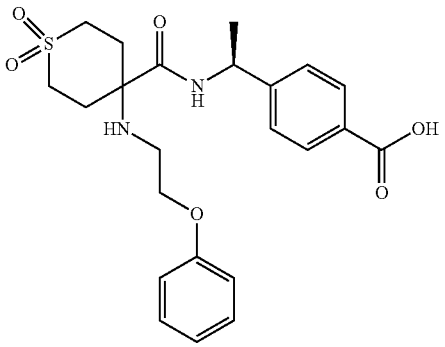 [SMILES: C[C@H](NC(=O)C1(NCCOc2ccccc2)CCS(=O)(=O)CC1)c1ccc(C(=O)O)cc1]

Example 67 was obtained according to General Procedure IV-a, starting from Compound 118. Purification by preparative LC-MS afforded Example 67 as a white powder in 21% yield. $^1$H-NMR (DMSO-$d_6$, 400 MHz) δ (ppm): 1.39 (d, J 7.1 Hz, 3H, CH—$CH_3$); 2.06-2.26 (m, 4H, $CH_2$); 2.63-2.73 (m, 2H, NH—$CH_2$); 2.89-3.02 (m, 2H, $SO_2$—$CH_2$); 3.20-3.31 (m, 2H, $SO_2$—$CH_2$); 4.03 (t, J 5.1 Hz, 2H, Ph-O—$CH_2$); 4.93-5.02 (m, 1H, CONH—CH—$CH_3$); 6.86-7.96 (m, 3H, Ar); 7.28 (dd, J 8.5, 7.6 Hz, 2H, Ar); 7.43 (d, J 8.2 Hz, 2H, Ar); 7.87 (d, J 8.2 Hz, 2H, Ar); 8.34 (d, J 7.9 Hz, 1H, CONH—CH); $CO_2H$ signal not observed; NH signal not observed. M/Z $(M+H)^+$: 461

Compound 119: Methyl 4-[(1S)-1-[[2-(tert-butoxycarbonylamino)spiro[3.3]heptane-2-carbonyl]amino]ethyl]benzoate Compound 119 was obtained according to General Procedure I-a, starting from 2-(tert-butoxycarbonylamino)spiro[3.3]heptane-2-carboxylic acid and methyl 4-[(1S)-1-aminoethyl]benzoate. Purification by flash chromatography (Cyclohexane/EtOAc: 100/0 to 50/50) afforded Compound 119 as a white powder in 84% yield. M/Z $(M+Na)^+$: 417

Compound 120: Methyl 4-[(1S)-1-[(2-aminospiro[3.3]heptane-2-carbonyl)amino]ethyl]benzoate Compound 120 was obtained according to General Procedure II-a, starting from Compound 119, as a yellow oil in quantitative yield. M/Z $(M+H)^+$: 317

Compound 121: Methyl 4-[(1S)-1-[[2-(2-phenoxyethylamino)spiro[3.3]heptane-2-carbonyl]amino]ethyl]benzoate Compound 121 was obtained according to General Procedure III-a, starting from Compound 120 and 2-phenoxyacetaldehyde. Purification by flash chromatography (DCM/MeOH: 100/0 to 60/40) afforded Compound 121 as a colorless oil in 50% yield. M/Z $(M+H)^+$: 437

Example 68: 4-[(1S)-1-[[2-(2-Phenoxyethylamino)spiro[3.3]heptane-2-carbonyl]amino]ethyl]benzoic acid, hydrochloride

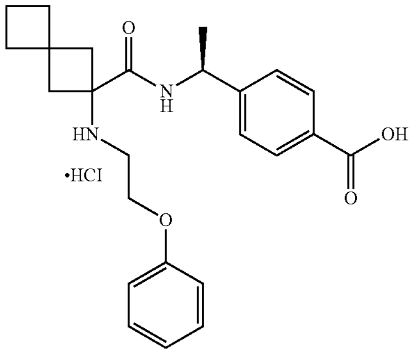 [SMILES: C[C@H](NC(=O)C1(NCCOc2ccccc2)CC2(CCC2)C1)c1ccc(C(=O)O)cc1 ; "·HCI"]

Example 68 was obtained according to General Procedure IV-a, starting from Compound 121, as a white powder in 53% yield. $^1$H-NMR (DMSO-$d_6$, 400 MHz) δ (ppm): 1.45 (d, J 7.1 Hz, 3H, CH—$CH_3$); 1.70-1.79 (m, 2H, $CH_2$); 1.93-2.02 (m, 4H, $CH_2$); 2.45-2.55 (m, 2H, $CH_2$); 2.64-2.73 (m, 2H, $CH_2$); 2.94-3.02 (m, 2H, NH—$CH_2$); 4.11-4.21 (m, 2H, PhO—$CH_2$); 5.05 (quint, J 7.1 Hz, 1H, CONH—CH—$CH_3$); 6.95-7.01 (m, 3H, Ar); 7.32 (dd, J 8.7, 7.3 Hz, 2H, Ar); 7.48 (d, J 8.2 Hz, 2H, Ar); 7.89 (d, J 8.2 Hz, 2H, Ar); 8.86 (bs, 1H, CONH—CH); 9.77 (bs, 2H, NH+HCl salt); 12.86 (bs, 1H, $CO_2H$). M/Z $(M+H)^+$: 423

Compound 122: Methyl 4-[(1S)-1-[[1-(tert-butoxycarbonylamino)cyclobutanecarbonyl]amino]ethyl]benzoate Compound 122 was obtained according to General Procedure I-a, starting from 2-(tert-butoxycarbonylamino)cyclobutanecarboxylic acid and methyl 4-[(1S)-1-aminoethyl]benzoate. Purification by flash chromatography (Cyclohexane/EtOAc: 100/0 to 50/50) afforded Compound 122 as a white powder in 90% yield. M/Z $(M+Na)^+$: 377

Compound 123: Methyl 4-[(1S)-1-[(1-aminocyclobutanecarbonyl)amino]ethyl]benzoate Compound 123 was obtained according to General Procedure II-a, starting from Compound 122, as a yellow oil in 90% yield. M/Z $(M+H)^+$: 277

Compound 124: Methyl 4-[(1S)-1-[[1-(2-phenoxyethylamino)cyclobutanecarbonyl]amino]ethyl]benzoate Compound 124 was obtained according to General Procedure III-a, starting from Compound 123 and 2-phenoxyacetaldehyde. Purification by flash chromatography (DCM/MeOH: 100/0 to 60/40) then by preparative LC-MS afforded Compound 124 as a colorless oil in 45% yield. M/Z $(M+H)^+$: 397

Example 69: 4-[(1S)-1-[[1-(2-Phenoxyethylamino)cyclobutanecarbonyl]amino]ethyl]benzoic acid, hydrochloride

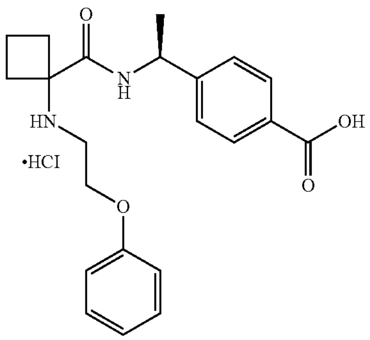 [SMILES: "·HCI" ; C[C@H](NC(=O)C1(NCCOc2ccccc2)CCC1)c1ccc(C(=O)O)cc1]

Example 69 was obtained according to General Procedure IV-a, starting from Compound 124. Purification by preparative LC-MS, then HCl salt preparation (method 2) afforded Example 69 as a beige powder in 27% yield. $^1$H-NMR (DMSO-$d_6$, 400 MHz) δ (ppm): 1.47 (d, J 7.1 Hz, 3H, CH—$CH_3$); 1.90-2.10 (m, 2H, $CH_2$); 2.52-2.63 (m, 4H, $CH_2$); 3.03-3.15 (m, 2H, NH—$CH_2$); 4.20 (t, J 4.8 Hz, 2H, Ph-O—$CH_2$); 5.07 (quint, J 7.1 Hz, 1H, CONH—CH—$CH_3$); 6.95-7.01 (m, 3H, Ar); 7.32 (dd, J 8.8, 7.2 Hz, 2H, Ar); 7.49 (d, J 8.2 Hz, 2H, Ar); 7.90 (d, J 8.2 Hz, 2H, Ar); 9.03 (bs, 1H, CONH—CH); 9.77 (bs, 2H, NH+HCl salt); 12.85 (bs, 1H, $CO_2$H). M/Z (M+H)$^+$: 383

Compound 125: Methyl 4-[(1S)-1-[[7-(tert-butoxycarbonylamino)-8,8-dimethyl-2-oxabicyclo[4.2.0]octane-7-carbonyl]amino]ethyl]benzoate Compound 125 was obtained according to General Procedure I-a, starting from 7-(tert-butoxycarbonylamino)-8,8-dimethyl-2-oxabicyclo[4.2.0]octane-7-carboxylic acid and methyl 4-[(1S)-1-aminoethyl]benzoate. Purification by flash chromatography (Cyclohexane/EtOAc: 80/20 to 60/40) afforded Compound 125 as a white powder in 67% yield. M/Z (M+H)$^+$: 461

Compound 126: Methyl 4-[(1S)-1-[(7-amino-8,8-dimethyl-2-oxabicyclo[4.2.0]octane-7-carbonyl)amino]ethyl]benzoate Compound 126 was obtained according to General Procedure II-a, starting from Compound 125, as a yellow oil in 87% yield. M/Z (M+H)$^+$: 361

Compound 127: Methyl 4-[(1S)-1-[[8,8-dimethyl-7-(2-phenoxyethylamino)-2-oxabicyclo[4.2.0]octane-7-carbonyl]amino]ethyl]benzoate Compound 127 was obtained according to General Procedure III-a, starting from Compound 126 and 2-phenoxyacetaldehyde. Purification by flash chromatography (DCM/MeOH: 100/0 to 40/60) afforded Compound 127 as a colorless oil in 18% yield. M/Z (M+H)$^+$: 481

Example 70: 4-[(1S)-1-[[8,8-Dimethyl-7-(2-phenoxyethylamino)-2-oxabicyclo[4.2.0]octane-7-carbonyl]amino]ethyl]benzoic acid, hydrochloride

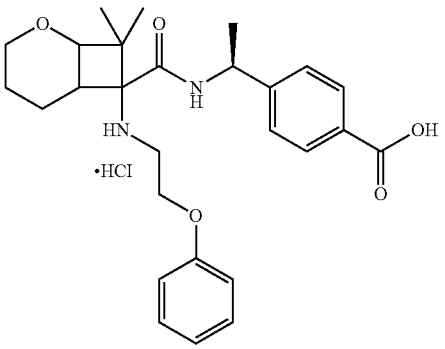 [SMILES: C[C@H](NC(=O)C1(NCCOc2ccccc2)C2CCCOC2C1(C)C)c1ccc(C(=O)O)cc1 ; "·HCI"]

Example 70 was obtained according to General Procedure IV-a, starting from Compound 127. Purification by preparative LC-MS, then HCl salt preparation (method 3) afforded Example 70 as a beige powder in 25% yield. $^1$H-NMR (DMSO-$d_6$ 400 MHz) δ (ppm): 0.86-1.01 (m, 3H, C—$(CH_3)_2$); 1.16-1.34 (bs, 3H, C—$(CH_3)_2$); 1.40-1.52 (m, 4H, $CH_aH_b$+CH-$CH_3$); 1.75-2.01 (m, 3H, $CH_2$+$CH_aH_b$); 2.89-3.07 (m, 1H, CH); 3.18-3.64 (m, 4H, $CH_2$+O-$CH_2$); 3.81-3.91 (m, 1H, O—CH); 4.15-4.34 (m, 2H, Ph-O—$CH_2$); 5.04-5.17 (m, 1H, CONH—CH—$CH_3$); 6.89-7.01 (m, 3H, Ar); 7.28-7.35 (m, 2H, Ar); 7.48-7.57 (m, 2H, Ar); 7.85-7.91 (m, 2H, Ar); 8.36 (bs, 1H, NH); 9.16 (bs, 1H, HCl salt); 10.15 (m, 1H, CONH—CH); 12.90 (bs, 1H, $CO_2$H). M/Z (M+H)$^+$: 467

Compound 128a and 128b: Methyl 4-[(1S)-1-[[4-(tert-butoxycarbonylamino)-2,2-dimethyl-tetrahydropyran-4-carbonyl]amino]ethyl]benzoate ((S,R) and (S,S) diastereoisomers)

Compound 128a and 128b were obtained according to General Procedure I-a, starting from 4-(tert-butoxycarbonylamino)-2,2-dimethyl-tetrahydropyran-4-carboxylic acid and methyl 4-[(1S)-1-aminoethyl]benzoate. Purification by flash chromatography (15 μm cartridge, Cyclohexane/EtOAc: 100/0 to 40/60) afforded Compound 128a, as the first eluting diastereoisomer, as a white powder in 41% yield and Compound 128b, as the second eluting diastereoisomer, as a white powder in 37% yield. 128a: M/Z (M+H)$^+$: 435; 128b: M/Z (M+H)$^+$: 435

Compound 129a and 129b: Methyl 4-[(1S)-1-[(4-amino-2,2-dimethyl-tetrahydropyran-4-carbonyl)amino]ethyl]benzoate ((S,R) and (S,S) diastereoisomers)

Compound 129a was obtained according to General Procedure II-a, starting from Compound 128a, as a yellow oil in 79% yield. Compound 129b was obtained according to General Procedure II-a, starting from Compound 128b, as a yellow oil in 76% yield. 129a: M/Z (M+H)$^+$: 335; 129b: M/Z (M+H)$^+$: 335

Compound 130a and 130b: Methyl 4-[(1S)-1-[[2,2-dimethyl-4-(2-phenoxyethylamino)tetrahydropyran-4-carbonyl]amino]ethyl]benzoate ((S,R) and (S,S) diastereoisomers)

Compound 130a was obtained according to General Procedure III-a, starting from Compound 129a and 2-phenoxy-acetaldehyde. Purification by flash chromatography (Cyclohexane/EtOAc: 100/0 to 40/60, then on a 15 μm cartridge, Cyclohexane/EtOAc: 100/0 to 40/60) afforded Compound 130a as a colorless oil in 57% yield. Compound 130b was obtained according to General Procedure III-a, starting from Compound 129b and 2-phenoxyacetaldehyde. Purification by flash chromatography (Cyclohexane/EtOAc: 100/0 to 40/60) afforded Compound 130b as a colorless oil in 51% yield. 130a: M/Z $(M+H)^+$: 455; 130b: M/Z $(M+H)^+$: 455

Example 71: 4-[(1S)-1-[[2,2-Dimethyl-4-(2-phenoxyethylamino)tetrahydropyran-4-carbonyl]amino]ethyl]benzoic acid, hydrochloride

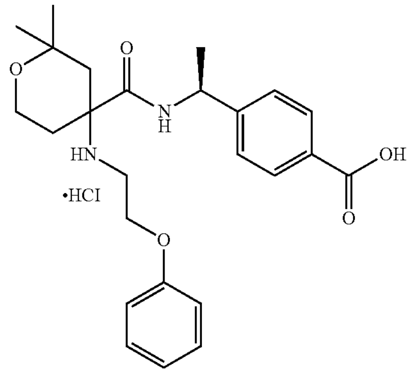 [SMILES: C[C@H](NC(=O)C1(NCCOc2ccccc2)CCOC(C)(C)C1)c1ccc(C(=O)O)cc1 ; "·HCI"]

Example 71 was obtained according to General Procedure IV-a, starting from Compound 130a. Purification by preparative LC-MS, then HCl salt preparation (method 3) afforded Example 71 as a beige powder in 19% yield. $^1$H-NMR (DMSO-$d_6$ 400 MHz) δ (ppm): 0.97 (s, 3H, C—$CH_3$); 1.18 (s, 3H, C—$CH_3$); 1.47 (d, J 6.8 Hz, 3H, CH—$CH_3$); 1.58-1.71 (m, 1H, $CH_aH_b$); 1.81-1.90 (m, 1H, $CH_aH_b$); 2.30-2.42 (m, 2H, $CH_2$); 2.52-2.72 (m, 2H, N—$CH_2$); 3.59-3.70 (m, 1H, O—$CH_aH_b$); 3.70-3.78 (m, 1H, O—$CH_aH_b$); 4.10-4.25 (m, 2H, Ph-O—$CH_2$); 5.05 (quint, J 6.8 Hz, 1H, CONH—CH—$CH_3$); 6.93-7.03 (m, 3H, Ar); 7.32 (t, J 7.7 Hz, 2H, Ar); 7.58 (d, J 8.0 Hz, 2H, Ar); 7.88 (d, J 8.0 Hz, 2H, Ar); 9.19 (bs, 1H, CONH—CH); 9.61 (bs, 1H, NH); 9.79 (bs, 1H, HCl salt); 12.77 (bs, 1H, $CO_2H$). M/Z $(M+H)^+$: 441

Example 72: 4-[(1S)-1-[[2,2-Dimethyl-4-(2-phenoxyethylamino)tetrahydropyran-4-carbonyl]amino]ethyl]benzoic acid, hydrochloride

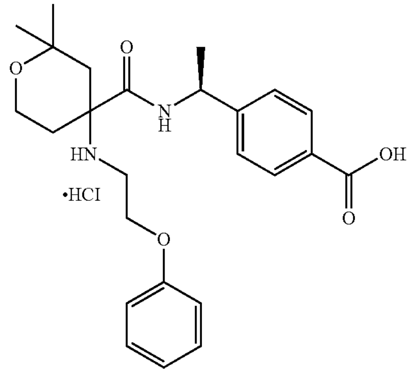 [SMILES: C[C@H](NC(=O)C1(NCCOc2ccccc2)CCOC(C)(C)C1)c1ccc(C(=O)O)cc1 ; "·HCI"]

Example 72 was obtained according to General Procedure IV-a, starting from Compound 130b. Purification by preparative LC-MS, then HCl salt preparation (method 3) afforded Example 72 as a white powder in 34% yield. $^1$H-NMR (DMSO-$d_6$ 400 MHz) δ (ppm): 0.83 (s, 3H, C—$CH_3$); 1.14 (s, 3H, C—$CH_3$); 1.48 (d, J 6.6 Hz, 3H, CH—$CH_3$); 1.64-1.76 (m, 1H, $CH_aH_b$); 1.80-1.87 (m, 1H, $CH_aH_b$); 2.41-2.49 (m, 2H, $CH_2$); 2.82-2.95 (m, 1H, NH—$CH_2$); 3.25-3.38 (m, 1H, NH—$CH_2$); 3.60-3.70 (m, 1H, O—$CH_aH_b$); 3.70-3.79 (m, 1H, O—$CH_aH_b$); 4.16-4.24 (m, 2H, Ph-O—$CH_2$); 5.08 (quint, J 6.6 Hz, 1H, CONH—CH—$CH_3$); 6.93-7.01 (m, 3H, Ar); 7.32 (t, J 7.7 Hz, 2H, Ar); 7.52 (d, J 8.0 Hz, 2H, Ar); 7.90 (d, J 8.0 Hz, 2H, Ar); 9.18 (d, J 6.6 Hz, 1H, CONH—CH); 9.56 (bs, 1H, NH); 9.78 (bs, 1H, HCl salt); 12.87 (bs, 1H, $CO_2H$). M/Z $(M+H)^+$: 441

Compound 131: Methyl 4-[(1S)-1-[[3-(tert-butoxycarbonylamino)tetrahydropyran-3-carbonyl]amino]ethyl]benzoate Compound 131 was obtained according to General Procedure I-a, starting from 3-(tert-butoxycarbonylamino)tetrahydropyran-3-carboxylic acid and methyl 4-[(1S)-1-aminoethyl]benzoate. Purification by flash chromatography (DCM/MeOH: 100/0 to 96/4) afforded Compound 131 as a white powder in 60% yield. M/Z $(M+H)^+$: 407

Compound 132: Methyl 4-[(1S)-1-[(3-aminotetrahydropyran-3-carbonyl)amino]ethyl]benzoate, hydrochloride Compound 132 was obtained according to General Procedure II-b, starting from Compound 131, as a white powder in quantitative yield. M/Z $(M+H)^+$: 307

Compound 133: Methyl 4-[(1S)-1-[[3-(2-phenoxyethylamino)tetrahydropyran-3-carbonyl]amino]ethyl]benzoate Compound 133 was obtained according to General Procedure III-b, starting from Compound 132 and 2-phenoxyacetaldehyde. Purification by flash chromatography (KP-NH cartridge, Cyclohexane/EtOAc: 100/0 to 60/40) afforded Compound 133 as a colorless oil in 69% yield. M/Z $(M+H)^+$: 427

Compound 134: Methyl 4-[(1S)-1-[[3-[methyl(2-phenoxyethyl)amino]tetrahydropyran-3-carbonyl]amino]ethyl]benzoate Compound 134 was obtained according to General Procedure III-b, starting from Compound 133 and formaldehyde. Purification by flash chromatography (KP-NH cartridge, Cyclohexane/EtOAc: 100/0 to 60/40) afforded Compound 134 as a colorless oil in 64% yield. M/Z $(M+H)^+$: 441

Example 73: 4-[(1S)-1-[[3-[Methyl(2-phenoxyethyl) amino]tetrahydropyran-3-carbonyl]amino]ethyl] benzoic acid, hydrochloride

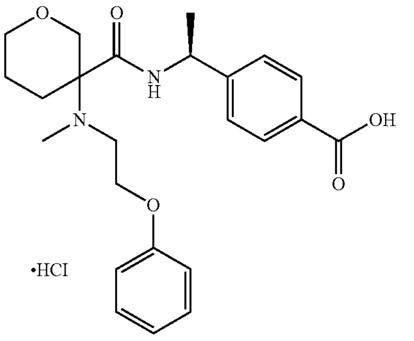 [SMILES: C[C@H](NC(=O)C1(N(C)CCOc2ccccc2)CCCOC1)c1ccc(C(=O)O)cc1 ; "·HCI"]

Example 73 was obtained according to General Procedure IV-b, starting from Compound 134. Purification by preparative LC-MS, then HCl salt preparation (method 1) afforded Example 73 as a white powder in 77% yield. $^1$H-NMR ($DMSO-d_6/D_2O$, 400 MHz) δ (ppm): 1.45 (d, J 7.1 Hz, 3H, CH—$CH_3$); 1.46-1.68 (m, 1H, $CH_aH_b$); 1.72-1.87 (m, 1H, $CH_aH_b$); 2.01-2.16 (m, 1H, $CH_aH_b$); 2.34-2.44 (m, 1H, $CH_aH_b$); 2.84 (s, 3H, N—$CH_3$, signal of a diastereoisomer); 2.85 (s, 3H, N—$CH_3$, signal of a diastereoisomer); 3.34-3.47 (m, 1H, N—$CH_aH_b$); 3.47-3.58 (m, 1H, N—$CH_aH_b$); 3.84 (d, J 12.1 Hz, 2H, O—$CH_a$H); 4.16-4.24 (m, 2H, Ph-O—$CH_2$); 4.32 (d, J 12.1 Hz, 1H, O—$CH_aH_b$); 4.39 (d, J 12.1 Hz, 1H, O—$CH_aH_b$); 5.00-5.08 (m, 1H, CONH—CH—$CH_3$); 6.89 (d, J 8.3 Hz, 2H, Ar, signal of a diastereoisomer); 6.92 (d, J 8.3 Hz, 2H, Ar, signal of a diastereoisomer); 6.97 (t, J 7.3 Hz, 1H, Ar, signal of a diastereoisomer); 6.98 (t, J 7.3 Hz, 1H, Ar, signal of a diastereoisomer); 7.26-7.33 (m, 2H, Ar); 7.46 (d, J 8.2 Hz, 2H, Ar, signal of a diastereoisomer); 7.47 (d, J 8.2 Hz, 2H, Ar, signal of a diastereoisomer); 7.89 (d, J 8.2 Hz, 2H, Ar, signal of a diastereoisomer); 7.90 (d, J 8.2 Hz, 2H, Ar, signal of a diastereoisomer); CONH signal not observed; $CO_2H$ signal not observed; HCl salt signal not observed. M/Z $(M+H)^+$: 427

Compound 135: Methyl 4-[(1S)-1-[[3-(tert-butoxycarbonylamino)tetrahydrofuran-3-carbonyl]amino] ethyl]benzoate Compound 135 was obtained according to General Procedure I-a, starting from 3-(tert-butoxycarbonylamino)tetrahydrofuran-3-carboxylic acid and methyl 4-[(1S)-1-aminoethyl]benzoate. Purification by flash chromatography (DCM/MeOH: 100/0 to 96/4) afforded Compound 135 as a white powder in 53% yield. M/Z $(M+Na)^+$: 415

Compound 136: Methyl 4-[(1S)-1-[(3-aminotetrahydrofuran-3-carbonyl)amino]ethyl]benzoate, hydrochloride Compound 136 was obtained according to General Procedure II-b, starting from Compound 135, as a white powder in quantitative yield. M/Z $(M+H)^+$: 293

Compound 137: Methyl 4-[(1S)-1-[[3-(2-phenoxyethylamino)tetrahydrofuran-3-carbonyl]amino]ethyl] benzoate Compound 137 was obtained according to General Procedure III-b, starting from Compound 136 and 2-phenoxyacetaldehyde. Purification by flash chromatography (KP-NH cartridge, Cyclohexane/EtOAc: 100/0 to 60/40) afforded Compound 137 as a colorless oil in 85% yield. M/Z $(M+H)^+$: 413

Compound 138: Methyl 4-[(1S)-1-[[3-[methyl(2-phenoxyethyl)amino]tetrahydrofuran-3-carbonyl] amino]ethyl]benzoate Compound 138 was obtained according to General Procedure III-b, starting from Compound 137 and formaldehyde. Purification by flash chromatography (KP-NH cartridge, Cyclohexane/EtOAc: 100/0 to 70/30) afforded Compound 138 as a colorless oil in 62% yield. M/Z $(M+H)^+$: 427

Example 74: 4-[(1S)-1-[[3-[Methyl(2-phenoxyethyl) amino]tetrahydrofuran-3-carbonyl]amino]ethyl]benzoic acid, hydrochloride

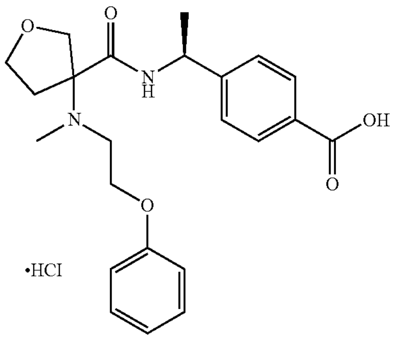 [SMILES: "·HCI" ; C[C@H](NC(=O)C1(N(C)CCOc2ccccc2)CCOC1)c1ccc(C(=O)O)cc1]

Example 74 was obtained according to General Procedure IV-b, starting from Compound 138. Purification by preparative LC-MS, then HCl salt preparation (method 1) afforded Example 74 as a white powder in 62% yield. $^1$H-NMR ($DMSO-d_6/D_2O$ 400 MHz) δ (ppm): 1.36 (d, J 6.9 Hz, 3H, CH—$CH_3$); 1.88-1.99 (m, 1H, $CH_aH_b$); 2.17 (s, 3H, N—$CH_3$, signal of a diastereoisomer); 2.21 (s, 3H, N—$CH_3$, signal of a diastereoisomer); 2.22-2.34 (m, 1H, $CH_aH_b$); 2.41-2.70 (m, 2H, N—$CH_2$); 3.42-3.59 (m, 2H, O—$CH_2$); 3.86-3.95 (m, 2H, O—$CH_2$); 4.00-4.06 (m, 2H, PhO—$CH_2$); 4.94 (q, J 6.9 Hz, 1H, CONH—CH—$CH_2$); 6.81 (d, J 8.3 Hz, 2H, Ar, signal of a diastereoisomer); 6.84 (d, J 8.3 Hz, 2H, Ar, signal of a diastereoisomer); 6.90 (t, J 7.3 Hz, 1H, Ar); 7.23 (dd, J 8.3, 7.3 Hz, 2H, Ar); 7.38 (d, J 8.2 Hz, 2H, Ar, signal of a diastereoisomer); 7.41 (d, J 8.2 Hz, 2H, Ar, signal of a diastereoisomer); 7.80 (d, J 8.2 Hz, 2H, Ar, signal of a diastereoisomer); 7.84 (d, J 8.2 Hz, 2H, Ar, signal of a diastereoisomer); CONH signal not observed; $CO_2H$ signal not observed; HCl salt signal not observed. M/Z $(M+H)^+$: 413

Compound 139: Methyl 4-[(1S)-1-[[3-[2-(3-chlorophenoxy)ethylamino]tetrahydrofuran-3-carbonyl] amino]ethyl]benzoate Compound 139 was obtained according to General Procedure III-b, starting from Compound 136 and 2-(3-chlorophenoxy)acetaldehyde. Purification by flash chromatography (KP-NH cartridge, Cyclohexane/EtOAc: 100/0 to 50/50) afforded Compound 139 as a colorless oil in 64% yield. M/Z $(M[^{35}Cl]+H)^+$: 447

Compound 140: Methyl 4-[(1S)-1-[[3-[2-(3-chlorophenoxy)ethyl-methyl-amino]tetrahydrofuran-3-carbonyl]amino]ethyl]benzoate Compound 140 was obtained according to General Procedure III-b, starting from Compound 139 and formaldehyde. Purification by flash chromatography (KP-NH cartridge, Cyclohexane/EtOAc: 100/0 to 60/40) afforded Compound 140 as a colorless oil in 76% yield. M/Z $(M[^{35}Cl]+H)^+$: 461

Example 75: 4-[(1S)-1-[[3-[2-(3-Chlorophenoxy)ethyl-methyl-amino]tetrahydrofuran-3-carbonyl]amino]ethyl]benzoic acid, hydrochloride

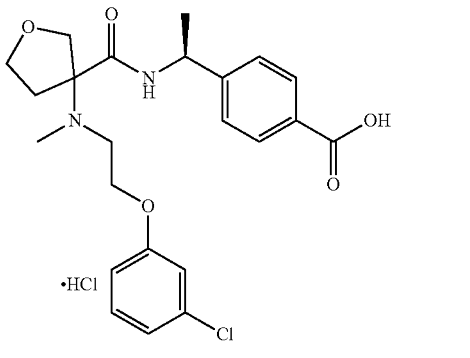 [SMILES: C[C@H](NC(=O)C1(N(C)CCOc2cccc(Cl)c2)CCOC1)c1ccc(C(=O)O)cc1 ; Cl]

Example 75 was obtained according to General Procedure IV-b, starting from Compound 140. Purification by preparative LC-MS, then HCl salt preparation (method 1) afforded Example 75 as a white powder in 64% yield. $^1$H-NMR (DMSO-$d_6$/$D_2O$, 400 MHz) δ (ppm): 1.42 (d, J 6.9 Hz, 3H, CH—$CH_3$, signal of a rotamer); 1.43 (d, J 6.9 Hz, 3H, CH—$CH_3$, signal of a rotamer); 2.28-2.44 (m, 1H, $CH_aH_b$); 2.52-2.60 (m, 1H, $CH_aH_b$); 2.67 (s, 3H, N—$CH_3$); 3.03-3.17 (m, 1H, N—$CH_aH_b$); 3.17-3.31 (m, 1H, N—$CH_aH_b$); 3.67-3.87 (m, 2H, O—$CH_2$); 4.00-4.10 (m, 2H, O—$CH_2$); 4.13-4.27 (m, 2H, Ph-O—$CH_2$); 4.93-5.04 (m, 1H, CONH—CH—$CH_3$); 6.86-6.92 (m, 1H, Ar); 6.96-7.03 (m, 2H, Ar); 7.26-7.33 (m, 1H, Ar); 7.42 (d, J 8.2 Hz, 2H, Ar, signal of a rotamer); 7.43 (d, J 8.2 Hz, 2H, Ar, signal of a rotamer); 7.86 (d, J 8.2 Hz, 2H, Ar, signal of a rotamer); 7.88 (d, J 8.2 Hz, 2H, Ar, signal of a rotamer); CONH signal not observed; $CO_2H$ signal not observed; HCl salt signal not observed. M/Z $(M[^{35}Cl]+H)^+$: 447

Compound 141: Methyl 4-[1-[[3-(tert-butoxycarbonylamino)tetrahydrofuran-3-carbonyl]amino]cyclopropyl]benzoate Compound 141 was obtained according to General Procedure I-a, starting from 3-(tert-butoxycarbonylamino)tetrahydrofuran-3-carboxylic acid and methyl 4-(1-aminocyclopropyl)benzoate. Purification by flash chromatography (Cyclohexane/EtOAc: 90/10 to 20/80) afforded Compound 141 as an orange powder in 98% yield. M/Z $(M+Na)^+$: 427

Compound 142: Methyl 4-[1-[(3-aminotetrahydrofuran-3-carbonyl)amino]cyclopropyl]benzoate, hydrochloride Compound 142 was obtained according to General Procedure II-b, starting from Compound 141, as an orange powder in quantitative yield. M/Z $(M+H)^+$: 305

Compound 143: Methyl 4-[1-[[3-(2-phenoxyethylamino)tetrahydrofuran-3-carbonyl]amino]cyclopropyl]benzoate Compound 143 was obtained according to General Procedure III-b, starting from Compound 142 and 2-phenoxyacetaldehyde. Purification by flash chromatography (KP-NH cartridge, Cyclohexane/EtOAc: 100/0 to 50/50) afforded Compound 143 as a colorless oil in 61% yield. M/Z $(M+H)^+$: 425

Compound 144: Methyl 4-[1-[[3-[methyl(2-phenoxyethyl)amino]tetrahydrofuran-3-carbonyl]amino]cyclopropyl]benzoate Compound 144 was obtained according to General Procedure III-b, starting from Compound 143 and formaldehyde. Purification by flash chromatography (KP-NH cartridge, Cyclohexane/EtOAc: 100/0 to 60/40) afforded Compound 144 as a colorless oil in 53% yield. M/Z $(M+H)^+$: 439

Example 76: 4-[1-[[3-[Methyl(2-phenoxyethyl)amino]tetrahydrofuran-3-carbonyl]amino]cyclopropyl]benzoic acid, hydrochloride

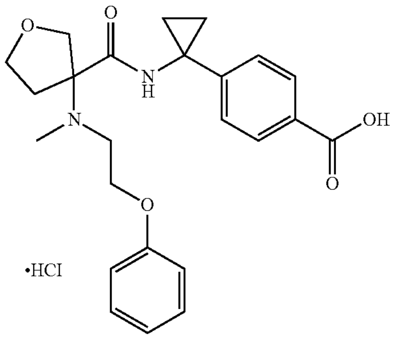 [SMILES: "·HCI" ; CN(CCOc1ccccc1)C1(C(=O)NC2(c3ccc(C(=O)O)cc3)CC2)CCOC1]

Example 76 was obtained according to General Procedure IV-b, starting from Compound 144. Purification by preparative LC-MS, then HCl salt preparation (method 1) afforded Example 76 as a white powder in 89% yield. $^1$H-NMR (DMSO-$d_6$/$D_2O$, 400 MHz) δ (ppm): 1.25-1.35 (m, 4H, C($CH_2$—$CH_2$)); 2.35-2.46 (m, 1H, $CH_aH_b$); 2.54-2.62 (m, 1H, $CH_aH_b$); 2.73 (s, 3H, N—$CH_3$); 3.14-3.24 (m, 1H, N—$CH_aH_b$); 3.24-3.36 (m, 1H, N—$CH_aH_b$); 3.80-3.92 (m, 2H, O—$CH_2$); 4.03-4.12 (m, 1H, O—$CH_aH_b$); 4.19-4.28 (m, 3H, O-$CH_aH_b$+Ph-O—$CH_2$); 6.91-6.98 (m, 3H, Ar); 7.23 (d, J 8.2 Hz, 2H, Ar); 7.31 (dd, J 8.0, 7.6 Hz, 2H, Ar); 7.83 (d, J 8.2 Hz, 2H, Ar, signal of a rotamer); CONH signal not observed; $CO_2H$ signal not observed; HCl salt signal not observed. M/Z $(M+H)^+$: 425

Compound 145: Methyl 4-[1-[[3-[2-(3-chlorophenoxy)ethylamino]tetrahydrofuran-3-carbonyl]amino]cyclopropyl]benzoate Compound 145 was obtained according to General Procedure III-b, starting from Compound 142 and 2-(3-chlorophenoxy)acetaldehyde. Purification by flash chromatography (KP-NH cartridge, Cyclohexane/EtOAc: 100/0 to 50/50) afforded Compound 145 as a colorless oil in 59% yield. M/Z $(M[^{35}Cl]+H)^+$: 459

Compound 146: Methyl 4-[1-[[3-[2-(3-chlorophenoxy)ethyl-methyl-amino]tetrahydrofuran-3-carbonyl]amino]cyclopropyl]benzoate Compound 146 was obtained according to General Procedure III-b, starting from Compound 145 and formaldehyde. Purification by flash chromatography (KP-NH cartridge, Cyclohexane/EtOAc: 100/0 to 60/40) afforded Compound 146 as a colorless oil in 93% yield. M/Z (M[$^{35}$Cl]+H)$^+$: 473

Example 77: 4-[1-[[3-[2-(3-Chlorophenoxy)ethyl-methyl-amino]tetrahydrofuran-3-carbonyl]amino]cyclopropyl]benzoic acid, hydrochloride

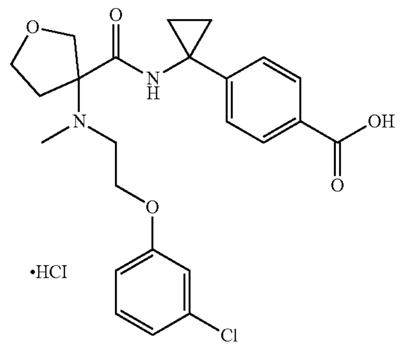 [SMILES: "·HCI" ; CN(CCOc1cccc(Cl)c1)C1(C(=O)NC2(c3ccc(C(=O)O)cc3)CC2)CCOC1]

Example 77 was obtained according to General Procedure IV-b, starting from Compound 146. Purification by preparative LC-MS, then HCl salt preparation (method 1) afforded Example 77 as a white powder in 63% yield. $^1$H-NMR (DMSO-$d_6$/$D_2O$, 400 MHz) δ (ppm): 1.25-1.33 (m, 4H, C($CH_2$—$CH_2$)); 2.31-2.43 (m, 1H, $CH_aH_b$); 2.53-2.72 (m, 4H, $CH_aH_b$+N-$CH_3$); 3.05-3.19 (m, 1H, N—$CH_aH_b$); 3.19-3.36 (m, 1H, N—$CH_aH_b$); 3.72-3.89 (m, 2H, O—$CH_2$); 4.01-4.11 (m, 1H, $CH_aH_b$); 4.16-4.32 (m, 3H, O-$CH_aH_b$+PhO—$CH_2$); 6.92 (d, J 7.7 Hz, 1H, Ar); 6.98-7.04 (m, 2H, Ar); 7.23 (d, J 8.2 Hz, 2H, Ar); 7.31 (dd, J 8.1, 7.7 Hz, 1H, Ar); 7.83 (d, J 8.2 Hz, 2H, Ar, signal of a rotamer); CONH signal not observed; $CO_2H$ signal not observed; HCl salt signal not observed. M/Z (M[$^{35}$Cl]+H)$^+$: 459

Compound 147: Benzyl 2,4-dioxo-1,3,8-triazaspiro[4.5]decane-8-carboxylate

To a solution of benzyl 4-oxopiperidine-1-carboxylate (1 equiv.) in methanol (0.95 M) were added a solution of ammonium carbonate (2 equiv.) in water (0.75 M) and potassium cyanide (2 equiv.). The reaction mixture was stirred at rt for 72 h. The resulting yellow suspension was filtered, washed with water. The resulting solid was dried overnight under vacuum with $P_2O_5$ to afford Compound 147 as a beige powder in 81% yield. TLC (Cyclohexane/EtOAc, $KMnO_4$ staining): Rf=0.25.

Compound 148: 8-Benzyl 1,3-di-tert-butyl 2,4-dioxo-1,3,8-triazaspiro[4.5]decane-1,3,8-tricarboxylate To a solution of Compound 147 (1 equiv.) in DME (0.1 M) were added DMAP (0.015 equiv.), triethylamine (1.1 equiv.) and di-tert-butyl dicarbonate (4 equiv.). The yellow solution was stirred at rt for 7 h. The reaction mixture was half concentrated. The resulting suspension was filtered, washed with diethyl ether (3 times), then dried under vacuum overnight to afford Compound 148 as a white powder in 79% yield. M/Z (M+Na)$^+$: 526

Compound 149: 4-Amino-1-benzyloxycarbonyl-piperidine-4-carboxylic acid, hydrochloride To a solution of Compound 148 (1 equiv.) in THF (0.12 M) was added LiOH 1 M in water (4 equiv.). The reaction mixture was stirred at rt for 48 h. The reaction mixture was concentrated, then acidified with aqueous HCl 1 M. The resulting suspension was filtered, washed with water and diisopropyl ether, then dried overnight under vacuum with $P_2O_5$ to afford Compound 149 as a white powder in 77% yield. M/Z (M+H)$^+$: 279

Compound 150: 1-Benzyloxycarbonyl-4-(tert-butoxycarbonylamino)piperidine-4-carboxylic acid To a suspension of Compound 149 (1 equiv.) in a dioxane/water mixture (1/1, 0.15 M) were added triethylamine (5 equiv.) and di-tert-butyl dicarbonate (1.6 equiv.). The reaction mixture was stirred at rt for 72 h. The reaction mixture was acidified with formic acid to pH 4, then extracted with EtOAc. The organic layer was washed with brine, dried, then concentrated. Purification by flash chromatography (DCM/MeOH: 100/0 to 90/10) afforded Compound 150 as a beige powder in 83% yield. M/Z (M+Na)$^+$: 400

Compound 151: Benzyl 4-(tert-butoxycarbonylamino)-4-[[(1S)-1-(4-methoxycarbonylphenyl)ethyl]carbamoyl]piperidine-1-carboxylate Compound 151 was obtained according to General Procedure I-a, starting from Compound 150 and methyl 4-[(1S)-1-aminoethyl]benzoate. Purification by flash chromatography (Cyclohexane/EtOAc: 95/5 to 0/100) afforded Compound 151 as a beige powder in 44% yield. M/Z (M+Na)$^+$: 562

Compound 152: Methyl 4-[(1S)-1-[[4-(tert-butoxycarbonylamino)piperidine-4-carbonyl]amino]ethyl]benzoate To a suspension of Compound 151 in ethanol (0.1 M) was added Pd/C (10 wt %). The reaction mixture was stirred overnight at rt under hydrogen (6 bars). The reaction mixture was filtered on a celite pad. The resulting filtrate was concentrated. Purification by flash chromatography (KP-NH cartridge, DCM/MeOH: 100/0 to 93/7) afforded Compound 152 as colorless crystals in 90% yield. M/Z (M+Na)$^+$: 406

Compound 153: Methyl 4-[(1S)-1-[[4-(tert-butoxycarbonylamino)-1-methyl-piperidine-4-carbonyl]amino]ethyl]benzoate Compound 153 was obtained according to General Procedure III-a, starting from Compound 152 and formaldehyde.

Purification by flash chromatography (KP-NH cartridge, DCM/MeOH: 100/0 to 95/5) afforded Compound 153 as a beige powder in 73% yield. M/Z (M+H)$^+$: 420

Compound 154: Methyl 4-[(1S)-1-[(4-amino-1-methyl-piperidine-4-carbonyl)amino]ethyl]benzoate Compound 154 was obtained according to General Procedure II-a, starting from Compound 153, as an beige powder in 93% yield. M/Z (M+H)$^+$: 320

Compound 155: Methyl 4-[(1S)-1-[[1-methyl-4-(2-phenoxyethylamino)piperidine-4-carbonyl]amino]ethyl]benzoate Compound 155 was obtained according to General Procedure III-a, starting from Compound 154 and 2-phenoxy-acetaldehyde. Purification by flash chromatography (DCM/MeOH: 100/0 to 90/10), then by preparative LC-MS afforded Compound 155 as a yellow oil in 44% yield. M/Z $(M+H)^+$: 440

Example 78: 4-[(1S)-1-[[1-Methyl-4-(2-phenoxyethylamino)piperidine-4-carbonyl]amino]ethyl]benzoic acid, hydrochloride

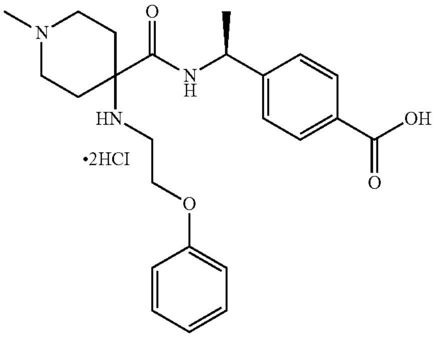

Example 78 was obtained according to General Procedure IV-a, starting from Compound 155, as a beige solid in 75% yield. $^1$H-NMR (DMSO-$d_6$, 400 MHz) δ (ppm): 1.44 (t, J 7.1 Hz, 3H, CH—$CH_3$, minor rotamer); 1.48 (t, J 7.1 Hz, 3H, CH—$CH_3$, major rotamer); 2.14-2.44 (m, 4H, $CH_2$); 2.69 (s, 3H, $CH_3$, major rotamer); 2.78 (s, 3H, N—$CH_3$, minor rotamer); 2.81-2.98 (m, 2H, N—$CH_2$); 3.08-3.34 (m, 2H, N—$CH_2$); 3.38-3.57 (m, 2H, N—$CH_2$); 4.18-4.26 (m, 2H, PhO—$CH_2$); 5.04 (quint, J 7.1 Hz, 1H, CONH—CH—$CH_3$); 6.92-7.02 (m, 3H, Ar); 7.27-7.35 (m, 2H, Ar); 7.49 (d, J 8.2 Hz, 2H, Ar, minor rotamer); 7.57 (d, J 8.2 Hz, 2H, Ar, major rotamer); 7.88 (d, J 8.2 Hz, 2H, Ar, minor rotamer); 7.89 (d, J 8.2 Hz, 2H, Ar, major rotamer); 9.56-9.72 (m, 1H, CONH—CH); 10.10-10.86 (m, 3H, NH+HCl salts); 12.76 (bs, 1H, $CO_2H$). M/Z $(M+H)^+$: 426

Compound 156: Methyl 4-[(1S)-1-[[4-(tert-butoxycarbonylamino)-1-(2-methoxyethyl)piperidine-4-carbonyl]amino]ethyl]benzoate To a suspension of Compound 152 (1 equiv.) in DMF (0.1 M) were added potassium carbonate (2 equiv.) and 1-bromo-2-methoxy-ethane (1 equiv.). The reaction mixture was stirred overnight at rt. The reaction mixture was extracted with EtOAc, washed with a saturated solution of sodium bicarbonate, dried, then concentrated. Purification by flash chromatography (DCM/MeOH: 100/0 to 90/10) afforded Compound 156 as a beige powder in 72% yield. M/Z $(M+H)^+$: 464

Compound 157: Methyl 4-[(1S)-1-[[4-amino-1-(2-methoxyethyl)piperidine-4-carbonyl]amino]ethyl]benzoate Compound 157 was obtained according to General Procedure II-a, starting from Compound 156, as a beige powder in 92% yield. M/Z $(M+H)^+$: 364

Compound 158: Methyl 4-[(1S)-1-[[1-(2-methoxyethyl)-4-(2-phenoxyethylamino)piperidine-4-carbonyl]amino]ethyl]benzoate Compound 158 was obtained according to General Procedure III-a, starting from Compound 157 and 2-phenoxy-acetaldehyde. Purification by flash chromatography (KP-NH cartridge, Cyclohexane/EtOAc: 100/0 to 0/100) afforded Compound 158 as a yellow oil in 58% yield. M/Z $(M+H)^+$: 484

Example 79: 4-[(1S)-1-[[1-(2-Methoxyethyl)-4-(2-phenoxyethylamino)piperidine-4-carbonyl]amino]ethyl]benzoic acid, hydrochloride

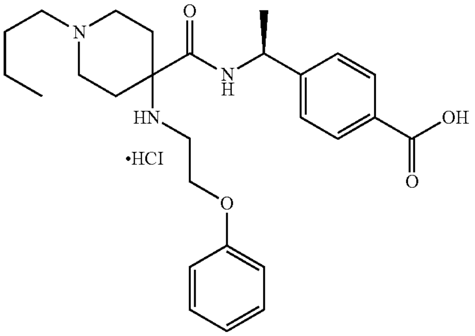 [SMILES: CCCCN1CCC(NCCOc2ccccc2)(C(=O)N[C@@H](C)c2ccc(C(=O)O)cc2)CC1 ; "·HCI"]

Example 79 was obtained according to General Procedure IV-a, starting from Compound 158, as a beige solid in 88% yield. $^1$H-NMR (DMSO-$d_6$, 400 MHz, 80° C.): 1.48 (d, J 6.8 Hz, 3H, CH—$CH_3$); 2.18-2.46 (m, 4H, $CH_2$); 2.83-3.11 (m, 3H, N—$CH_2$+N-$CH_aH_b$); 3.17-3.35 (m, 2H, N—$CH_2$); 3.31 (s, 3H, O—$CH_3$); 3.42-3.58 (m, 3H, N—$CH_2$+N-$CH_aH_b$); 3.70-3.76 (m, 2H, O—$CH_2$); 4.16-4.23 (m, 2H, Ph-O—$CH_2$); 5.00-5.09 (m, 1H, CONH—CH—$CH_3$); 6.94-6.99 (m, 3H, Ar); 7.26-7.33 (m, 2H, Ar); 7.47-7.55 (m, 2H, Ar); 7.89 (d, J 8.3 Hz, 2H, Ar); 8.64 (bs, 1H, CONH—CH); 9.24 (bs, 1H, NH); 10.22 (bs, 1H, HCl salt); $CO_2H$ signal not observed at 80° C. M/Z $(M+H)^+$: 470

Compound 159: Methyl 4-[(1S)-1-[[4-(tert-butoxycarbonylamino)-1-(cyclopropylmethyl)piperidine-4-carbonyl]amino]ethyl]benzoate To a suspension of Compound 152 (1 equiv.) in DMF (0.1 M) were added potassium carbonate (2 equiv.) and iodomethylcyclopropane (1.05 equiv.). The reaction mixture was stirred overnight at rt. A saturated solution of sodium bicarbonate was poured into the reaction mixture. The resulting precipitate was filtered, washed with water, then dried overnight under vacuum with $P_2O_5$. Purification by flash chromatography (DCM/MeOH: 100/0 to 90/10) afforded Compound 159 as a beige powder in 47% yield. M/Z $(M+H)^+$: 460

Compound 160: Methyl 4-[(1S)-1-[[4-amino-1-(cyclopropylmethyl)piperidine-4-carbonyl]amino]ethyl]benzoate Compound 160 was obtained according to General Procedure II-a, starting from Compound 159, as a yellow oil in quantitative yield. M/Z $(M+H)^+$: 360

Compound 161: Methyl 4-[(1S)-1-[[1-(cyclopropylmethyl)-4-(2-phenoxyethylamino)piperidine-4-carbonyl]amino]ethyl]benzoate Compound 161 was obtained according to General Procedure III-a, starting from Compound 160 and 2-phenoxyacetaldehyde. Purification by flash chromatography (KP-NH cartridge, DCM/MeOH: 100/0 to 90/10) afforded Compound 161 as a yellow oil in 74% yield. M/Z $(M+H)^+$: 480

Example 80: 4-[(1S)-1-[[1-(Cyclopropylmethyl)-4-(2-phenoxyethylamino)piperidine-4-carbonyl]amino]ethyl]benzoic acid, hydrochloride

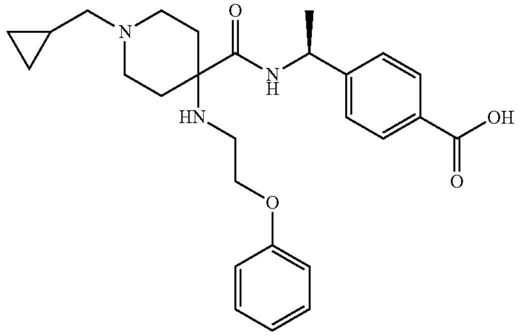 [SMILES: C[C@H](NC(=O)C1(NCCOc2ccccc2)CCN(CC2CC2)CC1)c1ccc(C(=O)O)cc1]

Example 80 was obtained according to General Procedure IV-a, starting from Compound 161, as a beige powder in 76% yield. $^1$H-NMR (DMSO-$d_6$, 400 MHz, 80° C.): 0.36-0.45 (m, 2H, $CH(CH_2—CH_2)$); 0.58-0.71 (m, 2H, $CH(CH_2—CH_2)$); 1.05-1.18 (m, 1H, $CH(CH_2—CH_2)$); 1.42-1.52 (m, 3H, $CH—CH_3$); 2.13-2.44 (m, 4H, $CH_2$); 2.83-3.11 (m, 5H, $N—CH_2$+N-$CH_aH_b$); 3.32-3.50 (m, 2H, $N—CH_2$); 3.51-3.36 (m, 1H, N—$CH_aH_b$); 4.12-4.23 (m, 2H, PhO—$CH_2$); 4.98-5.10 (m, 1H, CONH—CH—$CH_3$); 6.92-6.99 (m, 3H, Ar); 7.29 (t, J 7.8 Hz, 2H, Ar); 7.45-7.55 (m, 2H, Ar); 7.89 (d, J 8.3 Hz, 2H, Ar); 8.52 (bs, 1H, CONH—CH); 9.16 (bs, 1H, NH); 10.20 (bs, 1H, HCl salt); $CO_2H$ signal not observed at 80° C. M/Z $(M+H)^+$: 466

Compound 162: 3-Iodopropoxybenzene

To a solution of 3-phenoxypropan-1-ol (1 equiv.) in DCM (0.2 M) were added iodine (1.3 equiv.), imidazole (3 equiv.) and PS-triphenylphosphine (2.1 equiv.). The reaction mixture was shaked at rt for 2 h. The reaction mixture was filtered, then washed with a saturated solution of sodium thiosulphate and water. The organic layer was dried, then concentrated to afford Compound 162 as a yellow oil in 90% yield. $^1$H NMR (DMSO-$d_6$, 400 MHz) δ (ppm): 2.19 (quint, J 6.1 Hz, 2H, $CH_2$); 3.39 (t, J 6.1 Hz, 2H, I—$CH_2$); 4.01 (t, J 6.1 Hz, 2H, PhO—$CH_2$); 6.91-6.97 (m, 3H, Ar); 7.25-7.32 (m, 2H, Ar).

Compound 163: Methyl 4-(3-phenoxypropyl)tetrahydropyran-4-carboxylate

To a solution of methyl tetrahydropyran-4-carboxylate (1 equiv.) in THF (0.1 M) at −15° C. was added dropwise LDA 1 M in THF (1.2 equiv.). The reaction mixture was stirred at −15° C. for 10 min then at rt for 30 min. Compound 162 (1.2 equiv.) was added. The reaction mixture was stirred at rt for 1 h, then hydrolyzed with aqueous HCl 1 N and extracted with DCM. The organic layer was dried, then concentrated. Purification by flash chromatography (Cyclohexane/EtOAc: 100/0 to 50/50) afforded Compound 163 as a colorless oil in 60% yield. $^1$H NMR (DMSO-$d_6$, 400 MHz) δ (ppm): 1.39-1.51 (m, 2H, $CH_2$); 1.53-1.61 (m, 2H, $CH_2$); 1.61-1.68 (m, 2H, $CH_2$); 1.93-2.00 (m, 2H, $CH_2$); 3.26-3.33 (m, 2H, O—$CH_2$); 3.65 (s, 3H, O—$CH_3$); 3.73 (dt, J 11.6, 3.8 Hz, 2H, O—$CH_2$); 3.91 (t, J 6.1 Hz, 2H, PhO—$CH_2$), 6.87-6.93 (m, 3H, Ar); 7.24-7.30 (m, 2H, Ar).

Compound 164: Lithium 4-(3-phenoxypropyl)tetrahydropyran-4-carboxylate

Compound 164 was obtained according to General Procedure V-a, starting from Compound 163, as a white solid in quantitative yield. $^1$H NMR (DMSO-$d_6$, 400 MHz) δ (ppm): 1.13 (td, J 11.0, 3.2 Hz, 2H, $CH_2$); 1.35-1.42 (m, 2H, $CH_2$); 1.61-1.71 (m, 2H, $CH_2$); 1.93-2.00 (m, 2H, $CH_2$); 3.41 (td, J 11.0, 3.2 Hz, 2H, O—$CH_2$); 3.73 (dt, J 11.0, 3.2 Hz, 2H, O—$CH_2$); 3.91 (t, J 6.1 Hz, 2H, PhO—$CH_2$), 6.86-6.91 (m, 3H, Ar); 7.22-7.29 (m, 2H, Ar).

Compound 165: Methyl 4-[(1S)-1-[[4-(3-phenoxypropyl)tetrahydropyran-4-carbonyl]amino]ethyl]benzoate Compound 165 was obtained according to General Procedure I-a, starting from Compound 164 and methyl 4-[(1S)-1-aminoethyl]benzoate. Purification by flash chromatography (Cyclohexane/EtOAc: 100/0 to 50/50) afforded Compound 165 as a beige powder in 67% yield. M/Z $(M+Na)^+$: 426

Example 81: 4-[(1S)-1-[[4-(3-Phenoxypropyl)tetrahydropyran-4-carbonyl]amino]ethy]benzoic Acid

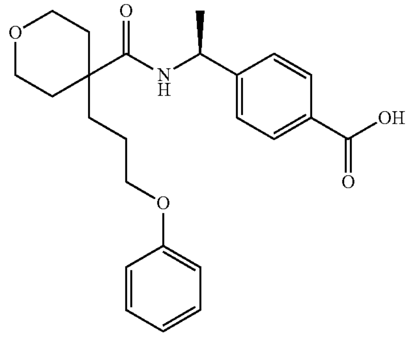 [SMILES: C[C@H](NC(=O)C1(CCCOc2ccccc2)CCOCC1)c1ccc(C(=O)O)cc1]

Example 81 was obtained according to General Procedure V-b, starting from Compound 165. Purification by flash chromatography (Cyclohexane/EtOAc: 80/20 to 0/100) afforded Example 81 as a white powder in 13% yield. $^1$H-NMR (DMSO-$d_6$, 400 MHz) δ (ppm): 1.33-1.72 (m, 6H, $CH_2$); 1.39 (d, J 7.2 Hz, 3H, CH—$CH_3$); 2.04-2.12 (m, 2H, $CH_2$); 3.25-3.35 (m, 2H, O—$CH_2$); 3.63-3.70 (m, 2H, O—$CH_2$); 3.86 (t, J 6.2 Hz, 2H, PhO—$CH_2$); 5.03-5.12 (m, 1H, CONH—CH—$CH_3$); 6.85-6.93 (m, 3H, Ar); 7.27 (dd, J 8.7, 7.3 Hz, 2H, Ar); 7.43 (d, J 8.3 Hz, 2H, Ar); 7.87 (d, J 8.3 Hz, 2H, Ar); 8.07 (d, J 7.8 Hz, 1H, CONH—CH); 12.80 (bs, 1H, $CO_2H$). M/Z $(M+H)^+$: 412

Compound 166: 2-[2-(3-Chlorophenoxy)ethoxy]acetonitrile

To a solution of 3-chlorophenol (1 equiv.) in DMA (0.2 M) were added potassium carbonate (2 equiv.) and 2-(2-chloroethoxy)acetonitrile (1.2 equiv.). The reaction mixture was stirred overnight at 120° C. The reaction mixture was hydrolyzed with a saturated solution of ammonium carbonate, extracted with EtOAc. The organic layer was washed with brine, dried, then concentrated. Purification by flash chromatography (Cyclohexane/EtOAc: 100/0 to 70/30) afforded Compound 166 as white powder in quantitative yield. $^1$H-NMR (DMSO-$d_6$, 400 MHz) δ (ppm): 3.83-3.87 (m, 2H, O—$CH_2$); 4.15-4.19 (m, 2H, O—$CH_2$); 4.55 (s, 2H, O—$CH_2$—CN); 6.93 (ddd, J 8.2, 2.1, 0.8 Hz, 1H, Ar); 7.00 (ddd, J 8.2, 2.1, 0.8 Hz, 1H, Ar); 7.04 (t, J 2.1, 1H, Ar); 7.31 (t, J 8.2 Hz, 1H, Ar).

Compound 167: 4-[2-(3-Chlorophenoxy)ethoxy]tetrahydropyran-4-carbonitrile

To a solution of Compound 166 (1 equiv.) and 2-bromoethylether (1.5 equiv.) in a THF/DMPU mixture (1/1, 0.2 M) at −78° C. was added dropwise LDA 1 M in THE (2.5 equiv.). The reaction mixture was stirred at −78° C. for 1.5 h. The reaction mixture was hydrolyzed with a saturated solution of ammonium carbonate, extracted with EtOAc. The organic layer was washed with brine, dried, then concentrated. Purification by flash chromatography (Cyclohexane/EtOAc: 100/0 to 70/30) afforded Compound 167 as a yellow oil in 53% yield. $^1$H-NMR (DMSO-$d_6$, 400 MHz) δ (ppm): 1.84 (ddd, J 12.3, 8.6, 3.9 Hz, 2H, $CH_2$); 2.11-2.18 (m, 2H, $CH_2$); 3.50 (ddd, J 12.3, 8.6, 2.9 Hz, 2H, O—$CH_2$); 3.79-3.85 (m, 2H, O—$CH_2$); 3.90-3.93 (m, 2H, O—$CH_2$); 4.19-4.22 (m, 2H, O—$CH_2$); 6.94 (ddd, J 8.2, 2.1, 0.9 Hz, 1H, Ar); 7.00 (ddd, J 8.2, 2.1, 0.9 Hz, 1H, Ar); 7.04 (t, J 2.1, 1H, Ar); 7.31 (t, J 8.2 Hz, 1H, Ar).

Compound 168: 4-[2-(3-Chlorophenoxy)ethoxy]tetrahydropyran-4-carboxylic acid

To a suspension of Compound 167 (1 equiv.) in water (0.1 M) was added potassium hydroxide (1.2 equiv.). The reaction mixture was heated overnight at 100° C. The reaction mixture was cooled down, hydrolyzed with aqueous HCl 1 N, extracted with DCM. The organic layer was dried, then concentrated. The resulting residue was dissolved in a HCl 6 N/dioxane mixture (3/1, 0.1 M). The reaction mixture was heated overnight at 100° C. The reaction mixture was cooled down, diluted with water, extracted with DCM. The organic layer was dried, then concentrated to afford Compound 168 as a colorless oil in 82% yield. M/Z (M[$^{35}$Cl]+H)$^+$: 301

Compound 169: Methyl 4-[1-[[4-[2-(3-chlorophenoxy)ethoxy]tetrahydropyran-4-carbonyl]amino]cyclopropyl]benzoate Compound 169 was obtained according to General Procedure I-a, starting from Compound 168 and methyl 4-(1-aminocyclopropyl)benzoate. Purification by flash chromatography (Cyclohexane/EtOAc: 100/0 to 30/70) afforded Compound 169 as a yellow powder in 75% yield. M/Z (M[$^{35}$Cl]+H)$^+$: 474

Example 82: 4-[1-[[4-[2-(3-Chlorophenoxy)ethoxy]tetrahydropyran-4-carbonyl]amino]cyclopropyl]benzoic acid

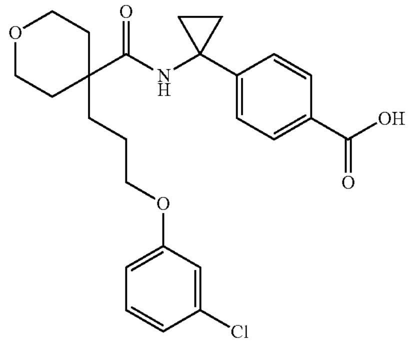 [SMILES: O=C(O)c1ccc(C2(NC(=O)C3(CCCOc4cccc(Cl)c4)CCOCC3)CC2)cc1]

Example 82 was obtained according to General Procedure V-b, starting from Compound 169. Purification by flash chromatography (Cyclohexane/EtOAc: 50/50 to 0/100) afforded Example 82 as a beige powder in 57% yield. $^1$H-NMR (DMSO-$d_6$, 400 MHz) δ (ppm): 1.21-1.27 (m, 2H, C($CH_2$—$CH_2$)); 1.28-1.33 (m, 2H, C($CH_2$—$CH_2$)); 1.72-1.80 (m, 2H, $CH_2$); 1.92 (ddd, J 14.4, 10.7, 4.4 Hz, 2H, $CH_2$); 3.53-3.69 (m, 6H, O—$CH_2$); 4.23 (dd, J 4.5, 2.9 Hz, 2H, Ph-O—$CH_2$); 6.93 (ddd, J 8.2, 2.1, 0.8 Hz, 1H, Ar): 7.00 (ddd, J 8.2, 2.1, 0.8 Hz, 1H, Ar); 7.04 (t, J 2.1 Hz, 1H, Ar); 7.23 (d, J 8.5 Hz, 2H, Ar); 7.31 (t, J 8.2 Hz, 1H, Ar); 7.82 (d, J 8.5 Hz, 2H, Ar); 8.58 (s, 1H, CONH); 12.72 (bs, 1H, $CO_2$H). M/Z (M[$^{35}$Cl]+H)$^+$: 460

Compound 170: Methyl 4-(3-fluorophenyl)tetrahydropyran-4-carboxylate

Compound 170 was obtained according to General Procedure VI-a, starting from methyl tetrahydropyran-4-carboxylate and 1-bromo-3-fluorobenzene. Purification by flash chromatography (Cyclohexane/EtOAc: 100/0 to 75/25) afforded Compound 170 as a yellow oil in 29% yield. M/Z (M[—H—$CO_2$Me]+H)$^+$: 179

Compound 171: 4-(3-Fluorophenyl)tetrahydropyran-4-carboxylic acid

Compound 171 was obtained according to General Procedure V-b, starting from Compound 170, as a brown powder in quantitative yield. M/Z (M[—H—$CO_2$H]+H)$^+$: 179

Compound 172: Methyl 4-[(1S)-1-[[4-(3-fluorophenyl)tetrahydropyran-4-carbonyl]amino]ethyl]benzoate Compound 172 was obtained according to General Procedure I-b, starting from Compound 171 and methyl 4-[(1S)-1-aminoethyl]benzoate. Purification by flash chromatography (Cyclohexane/EtOAc: 100/0 to 50/50) afforded Compound 172 as a colorless oil in 83% yield. M/Z (M+H)$^+$: 386

Example 83: 4-[(1S)-1-[[4-(3-Fluorophenyl)tetrahydropyran-4-carbonyl]amino]ethyl]benzoic acid

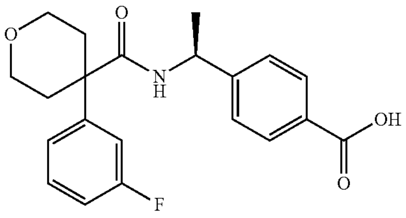 [SMILES: C[C@H](NC(=O)C1(c2cccc(F)c2)CCOCC1)c1ccc(C(=O)O)cc1]

Example 83 was obtained according to General Procedure V-c, starting from

Compound 172, as a white powder in 88% yield. $^1$H-NMR (DMSO-$d_6$, 400 MHz) δ (ppm): 1.31 (d, J 7.2 Hz, 3H, CH—$CH_3$); 1.79 (ddd, J 14.0, 10.9, 3.8 Hz, 1H, $CH_aH_b$); 1.92 (ddd, J 14.0, 10.9, 3.8 Hz, 1H, $CH_aH_b$); 2.43-2.48 (m, 2H, $CH_2$); 3.37-3.48 (m, 2H, O—$CH_2$); 3.69-3.81 (m, 2H, O—$CH_2$); 4.95-5.04 (m, 1H, CONH—CH—$CH_3$); 7.07-7.21 (m, 5H, Ar); 7.39 (ddd, J 8.1, 7.9, 6.4 Hz, 1H, Ar); 7.76 (d, J 8.2 Hz, 2H, Ar); 8.01 (d, J 7.9 Hz, 1H, CONH—CH); 12.83 (bs, 1H, $CO_2H$). M/Z $(M+H)^+$: 372

Compound 173: 1-Bromo-4-(2-methylpentoxy)benzene

Compound 173 was obtained according to General Procedure IX-a, starting from 4-bromophenol and 2-methylpentan-1-ol. Purification by flash chromatography (Cyclohexane/EtOAc: 100/0 to 50/50) afforded Compound 173 as a colorless oil in 96% yield. M/Z $(M[^{19}Br]+H)^+$: 257

Compound 174: Methyl 4-[4-(2-methylpentoxy)phenyl]tetrahydropyran-4-carboxylate

Compound 174 was obtained according to General Procedure VI-a, starting from methyl tetrahydropyran-4-carboxylate and compound 173. Purification by flash chromatography (Cyclohexane/EtOAc: 100/0 to 75/25) afforded Compound 174 as a yellow oil in 89% yield. M/Z $(M[—H—CO_2Me]+H)^+$: 261

Compound 175: Lithium 4-[4-(2-Methylpentoxy)phenyl]tetrahydropyran-4-carboxylate Compound 175 was obtained according to General Procedure V-a, starting from Compound 174, as a beige powder in quantitative yield. M/Z $(M[—H—COO_2H]+H)^+$: 261

Compound 176: Methyl 4-[(1S)-1-[[4-[4-(2-methylpentoxy)phenyl]tetrahydropyran-4-carbonyl]amino]ethyl]benzoate Compound 176 was obtained according to General Procedure I-b, starting from Compound 175 and methyl 4-[(1S)-1-aminoethyl]benzoate. Purification by flash chromatography (Cyclohexane/EtOAc: 100/0 to 30/70) afforded Compound 176 as a yellow oil in 58% yield. M/Z $(M+H)^+$: 468

Example 84: 4-[(1S)-1-[[4-[4-(2-Methylpentoxy)phenyl]tetrahydropyran-4-carbonyl]amino]ethyl]benzoic acid

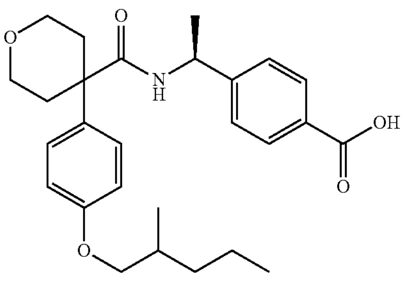 [SMILES: CCCC(C)COc1ccc(C2(C(=O)N[C@@H](C)c3ccc(C(=O)O)cc3)CCOCC2)cc1]

Example 84 was obtained according to General Procedure V-c, starting from Compound 176, as a white powder in 63% yield. $^1$H-NMR (DMSO-$d_6$, 400 MHz) δ (ppm): 0.88 (t, J 7.2 Hz, 3H, $CH_2$—$CH_3$); 0.97 (d, J 6.7 Hz, 3H, CH—$CH_3$); 1.14-1.23 (m, 1H, $CH_aH_b$); 1.31 (d, J 7.1 Hz, 3H, CONH—CH—$CH_3$); 1.32-1.50 (m, 3H, $CH_2$+$CH_aH_b$); 1.73-1.82 (m, 1H, CH—$CH_3$); 1.83-1.92 (m, 2H, $CH_2$); 2.41-2.48 (m, 2H, $CH_2$); 3.36-3.46 (m, 2H, O—$CH_2$); 3.67-3.76 (m, 2H, O—$CH_2$); 3.79-3.85 (m, 2H, PhO—$CH_2$); 4.95-5.04 (m, 1H, CONH—CH—$CH_3$); 6.89 (d, J 8.9 Hz, 2H, Ar); 7.15 (d, J 8.3 Hz, 2H, Ar); 7.24 (d, J 8.9 Hz, 2H, Ar); 7.75 (d, J 8.3 Hz, 2H, Ar); 7.87 (d, J 7.8 Hz, 1H, CONH—CH); $CO_2H$ signal was not observed. M/Z $(M+H)^+$: 454

Compound 177: Methyl 4-(4-methoxyphenyl)tetrahydropyran-4-carboxylate

Compound 177 was obtained according to General Procedure VI-a, starting from methyl tetrahydropyran-4-carboxylate and 1-bromo-4-methoxybenzene. Purification by flash chromatography (Cyclohexane/EtOAc: 100/0 to 75/25) afforded Compound 177 as a yellow oil in 48% yield. M/Z $(M[—H—CO_2Me]+H)^+$: 191

Compound 178: 4-(4-Methoxyphenyl)tetrahydropyran-4-carboxylic acid

Compound 178 was obtained according to General Procedure V-b, starting from Compound 177, as a brown powder in quantitative yield. M/Z $(M[—H—CO_2H]+H)^+$: 191

Compound 179: Methyl 4-[(1S)-1-[[4-(4-methoxyphenyl)tetrahydropyran-4-carbonyl]amino]ethyl]benzoate Compound 179 was obtained according to General Procedure I-a, starting from Compound 178 and methyl 4-[(1S)-1-aminoethyl]benzoate. Purification by flash chromatography (Cyclohexane/EtOAc: 100/0 to 40/60) afforded Compound 179 as a yellow oil in 69% yield. M/Z $(M+H)^+$: 398

Example 85: 4-[(1S)-1-[[4-(4-Methoxyphenyl)tetrahydropyran-4-carbonyl]amino]ethyl]benzoic acid

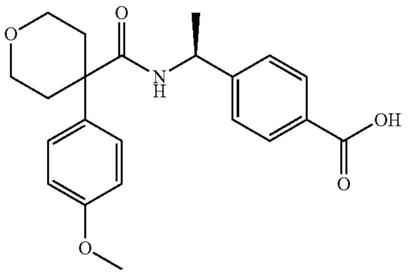 [SMILES: COc1ccc(C2(C(=O)N[C@@H](C)c3ccc(C(=O)O)cc3)CCOCC2)cc1]

Example 85 was obtained according to General Procedure V-c, starting from Compound 179, as a beige powder in 71% yield. $^1$H-NMR (DMSO-$d_6$, 400 MHz) δ (ppm): 1.31 (d, J 7.1 Hz, 3H, CH—$CH_3$); 1.78 (ddd, J 14.3, 10.6, 3.9 Hz, 1H, $CH_aH_b$); 1.87 (ddd, J 14.3, 10.6, 3.9 Hz, 1H, $CH_aH_b$); 2.42-2.48 (m, 2H, $CH_2$); 3.37-3.45 (m, 2H, O—$CH_2$); 3.68-3.74 (m, 2H, O—$CH_2$); 3.75 (s, 3H, O—$CH_3$); 4.95-5.05 (m, 1H, CONH—CH—$CH_3$); 6.90 (d, J 6.8 Hz, 2H, Ar); 7.17 (d, J 8.3 Hz, 2H, Ar); 7.26 (d, J 6.8 Hz, 2H, Ar); 7.76 (d, J 8.3 Hz, 2H, Ar); 7.88 (d, J 7.8 Hz, 1H, CONH—CH); 12.79 (bs, 1H, $CO_2H$). M/Z $(M+H)^+$: 384

Compound 180: Methyl 4-(3-isopropoxyphenyl)tetrahydropyran-4-carboxylate

Compound 180 was obtained according to General Procedure VI-b, starting from methyl tetrahydropyran-4-carboxylate and 1-bromo-3-isopropoxybenzene. Purification by flash chromatography (Cyclohexane/EtOAc: 100/0 to 70/30) afforded Compound 180 as a yellow oil in 62% yield. M/Z $(M[—H—CO_2Me]+H)^+$: 219

Compound 181: 4-(3-Isopropoxyphenyl)tetrahydropyran-4-carboxylic acid

Compound 181 was obtained according to General Procedure V-b, starting from Compound 180, as a beige powder in 98% yield. M/Z $(M[—H—CO_2H]+H)^+$: 219

Compound 182: Methyl 4-[(1S)-1-[[4-(3-isopropoxyphenyl)tetrahydropyran-4-carbonyl]amino]ethyl]benzoate Compound 182 was obtained according to General Procedure I-a, starting from Compound 181 and methyl 4-[(1S)-1-aminoethyl]benzoate. Purification by flash chromatography (Cyclohexane/EtOAc: 100/0 to 40/60) afforded Compound 182 as a beige powder in 78% yield. M/Z $(M+H)^+$: 426

Example 86: 4-[(1S)-1-[[4-(3-Isopropoxyphenyl)tetrahydropyran-4-carbonyl]amino]ethyl]benzoic acid

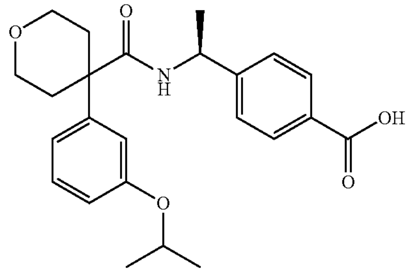 [SMILES: CC(C)Oc1cccc(C2(C(=O)N[C@@H](C)c3ccc(C(=O)O)cc3)CCOCC2)c1]

Example 86 was obtained according to General Procedure V-c, starting from Compound 182, as a beige powder in 82% yield. $^1$H-NMR (DMSO-$d_6$, 400 MHz) δ (ppm): 1.21 (d, J 5.9 Hz, 3H, CH—$(CH_3)_2$); 1.23 (d, J 5.9 Hz, 3H, CH—$(CH_3)_2$); 1.32 (d, J 7.2 Hz, 3H, CONH—CH—$CH_3$); 1.75 (ddd, J 14.1, 11.0, 3.9 Hz, 1H, $CH_aH_b$); 1.92 (ddd, J 14.1, 11.0, 3.9 Hz, 1H, $CH_aH_b$); 2.42-2.48 (m, 2H, $CH_2$); 3.39-3.45 (m, 2H, O—$CH_2$); 3.68-3.80 (m, 2H, O—$CH_2$); 4.52 (septuplet, J 5.9 Hz, 1H, O—CH); 4.97-5.07 (m, 1H, CONH—CH—$CH_3$); 6.79-6.84 (m, 2H, Ar); 6.89 (d, J 8.0 Hz, 1H, Ar); 7.15 (d, J 8.3 Hz, 2H, Ar); 7.23 (dd, J 8.8, 8.0 Hz, 1H, Ar); 7.75 (d, J 8.3 Hz, 2H, Ar); 7.96 (d, J 8.0 Hz, 1H, CONH—CH); 12.78 (bs, 1H, $CO_2H$). M/Z $(M+H)^+$: 412

Compound 183: Methyl 4-[3-(2,2,2-trifluoroethoxy)phenyl]tetrahydropyran-4-carboxylate Compound 183 was obtained according to General Procedure VI-b, starting from methyl tetrahydropyran-4-carboxylate and 1-bromo-3-(2,2,2-trifluoroethoxy)benzene. Purification by flash chromatography (Cyclohexane/EtOAc: 100/0 to 50/50) afforded Compound 183 as a yellow oil in 42% yield. M/Z $(M[—H—CO_2Me]+H)^+$: 259

Compound 184: 4-[3-(2,2,2-Trifluoroethoxy)phenyl]tetrahydropyran-4-carboxylic acid Compound 184 was obtained according to General Procedure V-b, starting from Compound 183, as a beige powder in 90% yield. M/Z $(M[—H—COO_2H]+H)^+$: 259

Compound 185: Methyl 4-[(1S)-1-[[4-[3-(2,2,2-trifluoroethoxy)phenyl]tetrahydropyran-4-carbonyl]amino]ethyl]benzoate Compound 185 was obtained according to General Procedure I-a, starting from Compound 184 and methyl 4-[(1S)-1-aminoethyl]benzoate. Purification by flash chromatography (Cyclohexane/EtOAc: 100/0 to 40/60) afforded Compound 185 as a beige powder in quantitative yield. M/Z $(M+H)^+$: 466

Example 87: 4-[(1S)-1-[[4-[3-(2,2,2-Trifluoroethoxy)phenyl]tetrahydropyran-4-carbonyl]amino]ethyl]benzoic acid

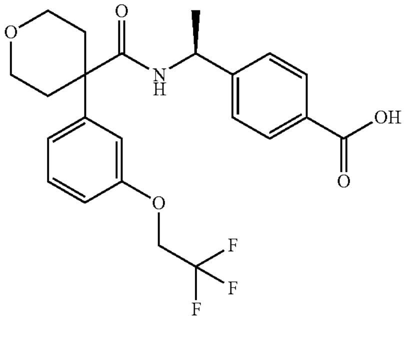 [SMILES: C[C@H](NC(=O)C1(c2cccc(OCC(F)(F)F)c2)CCOCC1)c1ccc(C(=O)O)cc1]

Example 87 was obtained according to General Procedure V-c, starting from Compound 185, as a beige powder in 89% yield. $^1$H-NMR (DMSO-$d_6$, 400 MHz) δ (ppm): 1.31 (d, J 7.1 Hz, 3H, CH—$CH_3$); 1.79 (ddd, J 14.1, 11.0, 3.9 Hz, 1H, $CH_aH_b$); 1.92 (ddd, J 14.1, 11.0, 3.9 Hz, 1H, $CH_aH_b$); 2.42-2.49 (m, 2H, $CH_2$); 3.37-3.48 (m, 2H, O—$CH_2$); 3.68-3.80 (m, 2H, O—$CH_2$); 4.65-4.75 (m, 2H, PhO—$CH_2$—$CF_3$); 4.94-5.04 (m, 1H, CONH—CH—$CH_3$); 6.95-7.03 (m, 3H, Ar); 7.16 (d, J 8.3 Hz, 2H, Ar); 7.31 (t, J 8.0 Hz, 1H, Ar); 7.75 (d, J 8.3 Hz, 2H, Ar); 7.96 (d, J 8.0 Hz, 1H, CONH—CH); 12.75 (bs, 1H, $CO_2$H). M/Z $(M+H)^+$: 452

Compound 186: Methyl 4-[4-[tert-butyl(dimethyl)silyl]oxyphenyl]tetrahydropyran-4-carboxylate Compound 186 was obtained according to General Procedure VI-b, starting from methyl tetrahydropyran-4-carboxylate and (4-bromophenoxy)-tert-butyl-dimethyl-silane. Purification by flash chromatography (Cyclohexane/EtOAc: 100/0 to 75/25) afforded Compound 186 as a yellow oil in 45% yield. M/Z $(M[—H—CO_2Me]+H)^+$: 291

Compound 187: Methyl 4-(4-hydroxyphenyl)tetrahydropyran-4-carboxylate

Compound 187 was obtained according to General Procedure XV-a, starting from Compound 186. Purification by flash chromatography (DCM/EtOAc: 100/0 to 80/20) afforded Compound 187 as a white powder in 93% yield. M/Z $(M[—H—CO_2Me]+H)^+$: 177

Compound 188: Methyl 4-(4-benzyloxyphenyl)tetrahydropyran-4-carboxylate

Compound 188 was obtained according to General Procedure X, starting from Compound 187 and benzyle bromide, as a white powder in 32% yield. M/Z $(M[—H—CO_2Me]+H)^+$: 267

Compound 189: 4-(4-Benzyloxyphenyl)tetrahydropyran-4-carboxylic acid

Compound 189 was obtained according to General Procedure V-b, starting from Compound 188, as a white powder in 40% yield. M/Z $(M[—H—CO_2H]+H)^+$: 267

Compound 190: Methyl 4-[(1S)-1-[[4-(4-benzyloxyphenyl)tetrahydropyran-4-carbonyl]amino]ethyl]benzoate Compound 190 was obtained according to General Procedure I-a, starting from Compound 189 and methyl 4-[(1S)-1-aminoethyl]benzoate, Purification by flash chromatography (Cyclohexane/EtOAc: 100/0 to 50/50) afforded Compound 190 as a white powder in 53% yield. M/Z $(M+H)^+$: 474

Example 88: 4-[(1S)-1-[[4-(4-Benzyloxyphenyl)tetrahydropyran-4-carbonyl]amino]ethyl]benzoic acid

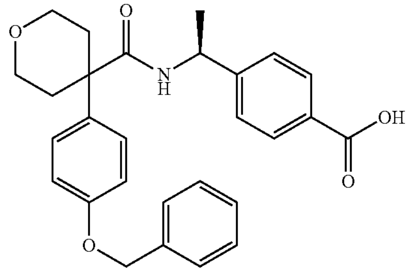 [SMILES: C[C@H](NC(=O)C1(c2ccc(OCc3ccccc3)cc2)CCOCC1)c1ccc(C(=O)O)cc1]

Example 88 was obtained according to General Procedure V-c, starting from Compound 190, as a beige powder in 76% yield. $^1$H-NMR (DMSO-$d_6$, 400 MHz) δ (ppm): 1.31 (d, J 7.2 Hz, 3H, CH—$CH_3$); 1.76 (ddd, J 14.1, 10.8, 3.9 Hz, 1H, $CH_aH_b$); 1.87 (ddd, J 14.1, 10.8, 3.9 Hz, 1H, $CH_aH_b$); 2.41-2.49 (m, 2H, $CH_2$); 3.36-3.45 (m, 2H, O—$CH_2$); 3.67-3.77 (m, 2H, O—$CH_2$); 4.95-5.05 (m, 1H, CONH—CH—$CH_3$); 5.10 (s, 2H, Ph-O—$CH_2$-Ph); 6.97 (d, J 8.8 Hz, 2H, Ar); 7.15 (d, J 8.3 Hz, 2H, Ar); 7.26 (d, J 8.8 Hz, 2H, Ar); 7.30-7.34 (m, 1H, Ar); 7.37-7.41 (m, 2H, Ar); 7.41-7.47 (m, 2H, Ar); 7.76 (d, J 8.3 Hz, 2H, Ar); 7.88 (d, J 7.8 Hz, 1H, CONH—CH); 12.80 (bs, 1H, $CO_2$H). M/Z $(M+H)^+$: 460

Compound 191: Methyl 4-[4-(cyclohexylmethoxy)phenyl]tetrahydropyran-4-carboxylate Compound 191 was obtained according to General Procedure IX-a, starting from Compound 187 and cyclohexylmethanol. Purification by flash chromatography (Cyclohexane/EtOAc: 100/0 to 50/50) afforded Compound 191 as a white powder in 64% yield. M/Z $(M+H)^+$: 333

Compound 192: 4-[4-(Cyclohexylmethoxy)phenyl]tetrahydropyran-4-carboxylic acid

Compound 192 was obtained according to General Procedure V-b, starting from Compound 191, as a white powder in 72% yield. M/Z $(M+H)^+$: 319

Compound 193: Methyl 4-[(1S)-1-[[4-[4-(cyclohexylmethoxy)phenyl]tetrahydropyran-4-carbonyl]amino]ethyl]benzoate Compound 193 was obtained according to General Procedure I-a, starting from Compound 192 and methyl 4-[(1S)-1-aminoethyl]benzoate. Purification by flash chromatography (Cyclohexane/EtOAc: 100/0 to 50/50) afforded Compound 193 as a white powder in 74% yield. M/Z $(M+H)^+$: 480

Example 89: 4-[(1S)-1-[[4-[4-(Cyclohexylmethoxy) phenyl]tetrahydropyran-4-carbonyl]amino]ethyl] benzoic acid

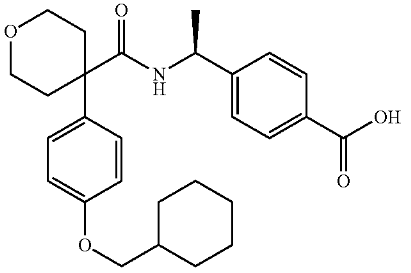 [SMILES: C[C@H](NC(=O)C1(c2ccc(OCC3CCCCC3)cc2)CCOCC1)c1ccc(C(=O)O)cc1]

Example 89 was obtained according to General Procedure V-c, starting from Compound 193, as a beige powder in 64% yield. $^1$H-NMR (DMSO-$d_6$, 400 MHz) δ (ppm): 0.98-1.09 (m, 2H, $CH_2$); 1.13-1.28 (m, 3H, CH, $CH_2$); 1.30 (d, J 7.2 Hz, 3H, CH—$CH_3$); 1.61-1.92 (m, 8H, $CH_2$); 2.41-2.49 (m, 2H, $CH_2$); 3.34-3.45 (m, 2H, O—$CH_2$); 3.66-3.76 (m, 2H, O—$CH_2$); 3.77 (d, J 6.3 Hz, 2H, Ph-O—$CH_2$); 4.95-5.05 (m, 1H, CONH—CH—$CH_3$); 6.88 (d, J 8.8 Hz, 2H, Ar); 7.14 (d, J 8.3 Hz, 2H, Ar); 7.23 (d, J 8.8 Hz, 2H, Ar); 7.75 (d, J 8.3 Hz, 2H, Ar); 7.86 (d, J 7.8 Hz, 1H, CONH—CH); 12.75 (bs, 1H, $CO_2H$). M/Z $(M+H)^+$: 466

Compound 194: Methyl 4-[4-(tetrahydropyran-4-ylmethoxy)phenyl]tetrahydropyran-4-carboxylate Compound 194 was obtained according to General Procedure IX-a, starting from Compound 187 and tetrahydropyran-4-ylmethanol. Purification by flash chromatography (Cyclohexane/EtOAc: 100/0 to 50/50) afforded Compound 194 as a white powder in 58% yield. M/Z $(M+H)^+$: 335

Compound 195: 4-[4-(Tetrahydropyran-4-ylmethoxy)phenyl]tetrahydropyran-4-carboxylic acid Compound 195 was obtained according to General Procedure V-b, starting from Compound 194, as a white powder in 70% yield. M/Z $(M+H)^+$: 321

Compound 196: Methyl 4-[(1S)-1-[[4-[4-(cyclohexylmethoxy)phenyl]tetrahydropyran-4-carbonyl]amino]ethyl]benzoate Compound 196 was obtained according to General Procedure I-a, starting from Compound 195 and methyl 4-[(1S)-1-aminoethyl]benzoate. Purification by flash chromatography (Cyclohexane/EtOAc: 100/0 to 40/60) afforded Compound 196 as a white powder in 57% yield. M/Z $(M+H)^+$: 482

Example 90: 4-[(1S)-1-[[4-[4-(Tetrahydropyran-4-ylmethoxy)phenyl]tetrahydropyran-4-carbonyl]amino]ethyl]benzoic acid

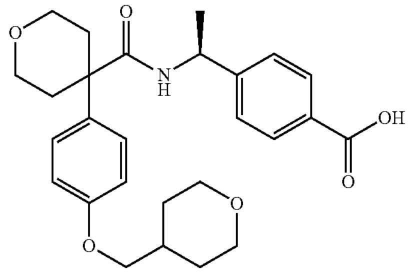 [SMILES: C[C@H](NC(=O)C1(c2ccc(OCC3CCOCC3)cc2)CCOCC1)c1ccc(C(=O)O)cc1]

Example 90 was obtained according to General Procedure V-c, starting from Compound 196, as a beige powder in 41% yield. $^1$H-NMR (DMSO-$d_6$, 400 MHz) δ (ppm): 1.27-1.38 (m, 2H, $CH_2$); 1.31 (d, J 7.1 Hz, 3H, CH—$CH_3$); 1.65-1.71 (m, 2H, $CH_2$); 1.76 (ddd, J 14.1, 10.7, 3.9 Hz, 1H, $CH_aH$); 1.88 (ddd, J 14.1, 10.7, 3.9 Hz, 1H, $CH_aH_b$); 194-2.05 (m, 1H, CH); 2.41-2.49 (m, 2H, $CH_2$); 3.30-3.37 (m, 2H, O—$CH_2$); 3.37-3.47 (m, 2H, O—$CH_2$); 3.67-3.77 (m, 2H, O—$CH_2$); 3.82 (t, J 6.4 Hz, 2H, Ph-O—$CH_2$); 3.85-3.91 (m, 2H, O—$CH_2$); 4.95-5.05 (m, 1H, CONH—CH—$CH_3$); 6.90 (d, J 9.0 Hz, 2H, Ar); 7.14 (d, J 8.2 Hz, 2H, Ar); 7.25 (d, J 9.0 Hz, 2H, Ar); 7.75 (d, J 8.2 Hz, 2H, Ar); 7.87 (d, J 8.0 Hz, 1H, CONH—CH); 12.80 (bs, 1H, $CO_2H$). M/Z $(M+H)^+$: 468

Compound 197: Methyl 4-[4-(2,2,2-trifluoroethoxy) phenyl]tetrahydropyran-4-carboxylate Compound 197 was obtained according to General Procedure X, starting from Compound 187 and 2,2,2-trifluoroethyl trifluoromethanesulfonate. Purification by flash chromatography (Cyclohexane/EtOAc: 100/0 to 50/50) afforded Compound 197 as a white powder in 72% yield. M/Z $(M+H)^+$: 319

Compound 198: 4-[4-(2,2,2-Trifluoroethoxy)phenyl] tetrahydropyran-4-carboxylic acid Compound 198 was obtained according to General Procedure V-d, starting from Compound 197, as a white powder in quantitative yield. M/Z $(M[-H-CO_2H]+H)^+$: 259

Compound 199: Methyl 4-[(1S)-1-[[4-[4-(2,2,2-trifluoroethoxy)phenyl]tetrahydropyran-4-carbonyl]amino]ethyl]benzoate Compound 199 was obtained according to General Procedure I-a, starting from Compound 198 and methyl 4-[(1S)-1-aminoethyl]benzoate. Purification by flash chromatography (Cyclohexane/EtOAc: 100/0 to 50/50) afforded Compound 199 as a white powder in 78% yield. M/Z $(M+H)^+$: 466

Example 91: 4-[(1S)-1-[[4-[4-(2,2,2-Trifluoroethoxy)phenyl]tetrahydropyran-4-carbonyl]amino]ethyl]benzoic acid

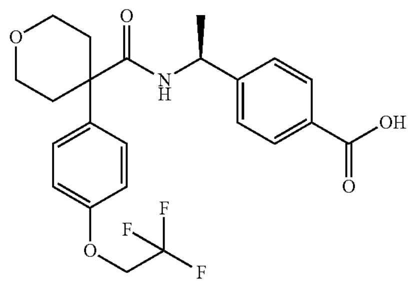 [SMILES: C[C@H](NC(=O)C1(c2ccc(OCC(F)(F)F)cc2)CCOCC1)c1ccc(C(=O)O)cc1]

Example 91 was obtained according to General Procedure V-c, starting from Compound 199, as a white powder in 80% yield. $^1$H-NMR (DMSO-$d_6$, 400 MHz) δ (ppm): 1.30 (d, J 7.1 Hz, 3H, CH—$CH_3$); 1.78 (ddd, J 14.1, 10.9, 3.9 Hz, 1H, $CH_aH_b$); 1.87 (ddd, J 14.1, 10.9, 3.9 Hz, 1H, $CH_aH_b$); 2.41-2.49 (m, 2H, $CH_2$); 3.37-3.46 (m, 2H, O—$CH_2$); 3.68-3.77 (m, 2H, O—$CH_2$); 4.74 (q, J 8.8 Hz, 2H, PhO—$CH_2$—$CF_3$); 4.95-5.05 (m, 1H, CONH—CH—$CH_3$); 7.03 (d, J 9.0 Hz, 2H, Ar); 7.17 (d, J 8.2 Hz, 2H, Ar); 7.30 (d, J 9.0 Hz, 2H, Ar); 7.77 (d, J 8.2 Hz, 2H, Ar); 7.92 (d, J 8.0 Hz, 1H, CONH—CH); 12.78 (bs, 1H, $CO_2H$). M/Z $(M+H)^+$: 452

Compound 200: Methyl 4-[4-(3-phenylpropoxy)phenyl]tetrahydropyran-4-carboxylate

Compound 200 was obtained according to General Procedure IX-a, starting from Compound 187 and 3-phenylpropan-1-ol. Purification by flash chromatography (Cyclohexane/EtOAc: 100/0 to 50/50) afforded Compound 200 as a white powder in 65% yield. M/Z $(M[—H—CO_2Me]+H)^+$: 295

Compound 201: 4-[4-(3-Phenylpropoxy)phenyl]tetrahydropyran-4-carboxylic acid

Compound 201 was obtained according to General Procedure V-d, starting from Compound 200, as a white powder in 88% yield. M/Z $(M[—H—CO_2H]+H)^+$: 295

Compound 202: Methyl 4-[(1S)-1-[[4-[4-(3-phenylpropoxy)phenyl]tetrahydropyran-4-carbonyl]amino]ethyl]benzoate Compound 202 was obtained according to General Procedure I-a, starting from Compound 201 and methyl 4-[(1S)-1-aminoethyl]benzoate. Purification by flash chromatography (Cyclohexane/EtOAc: 100/0 to 50/50) afforded Compound 202 as a white powder in 69% yield. M/Z $(M+H)^+$: 502

Example 92: 4-[(1S)-1-[[4-[4-(3-Phenylpropoxy)phenyl]tetrahydropyran-4-carbonyl]amino]ethyl]benzoic acid

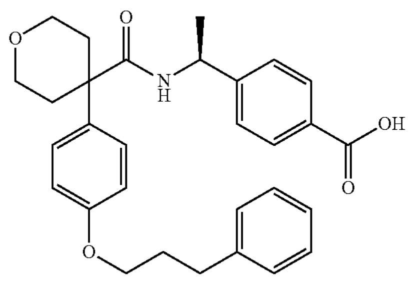 [SMILES: C[C@H](NC(=O)C1(c2ccc(OCCCc3ccccc3)cc2)CCOCC1)c1ccc(C(=O)O)cc1]

Example 92 was obtained according to General Procedure V-c, starting from Compound 202, as a white powder in 36% yield. $^1$H-NMR (DMSO-$d_6$, 400 MHz) δ (ppm): 1.31 (d, J 7.1 Hz, 3H, CH—$CH_3$); 1.76 (ddd, J 14.1, 10.8, 3.9 Hz, 1H, $CH_aH_b$); 1.87 (ddd, J 14.1, 10.8, 3.9 Hz, 1H, $CH_aH_b$); 1.98-2.05 (m, 2H, $CH_2$); 2.41-2.49 (m, 2H, $CH_2$); 2.75 (dd, J 8.0, 7.3 Hz, 2H, $CH_2$); 3.36-3.45 (m, 2H, O—$CH_2$); 3.67-3.77 (m, 2H, O—$CH_2$); 3.95 (t, J 6.3 Hz, 2H, PhO—$CH_2$); 4.95-5.05 (m, 1H, CONH—CH—$CH_3$); 6.88 (d, J 8.8 Hz, 2H, Ar); 7.16 (d, J 8.3 Hz, 2H, Ar); 7.17-7.31 (m, 7H, Ar); 7.76 (d, J 8.3 Hz, 2H, Ar); 7.88 (d, J 7.8 Hz, 1H, CONH—CH); 12.79 (bs, 1H, $CO_2H$). M/Z $(M+H)^+$: 488

Compound 203: Methyl 4-[4-(2-tetrahydropyran-4-ylethoxy)phenyl]tetrahydropyran-4-carboxylate Compound 203 was obtained according to General Procedure IX-a, starting from Compound 187 and 2-(tetrahydropyran-4-yl)ethanol. Purification by flash chromatography (Cyclohexane/EtOAc: 100/0 to 70/30) afforded Compound 203 as a white powder in 45% yield. M/Z $(M[—H—CO_2Me]+H)^+$: 289

Compound 204: 4-[4-(2-Tetrahydropyran-4-ylethoxy)phenyl]tetrahydropyran-4-carboxylic acid Compound 204 was obtained according to General Procedure V-d, starting from Compound 203, as a white powder in quantitative yield. M/Z $(M[—H—CO_2H]+H)^+$: 289

Compound 205: Methyl 4-[(1S)-1-[[4-[4-(2-tetrahydropyran-4-ylethoxy)phenyl]tetrahydropyran-4-carbonyl]amino]ethyl]benzoate Compound 205 was obtained according to General Procedure I-a, starting from Compound 204 and methyl 4-[(1S)-1-aminoethyl]benzoate. Purification by flash chromatography (Cyclohexane/EtOAc: 100/0 to 10/90) afforded Compound 205 as a white powder in 61% yield. M/Z $(M+H)^+$: 496

Example 93: 4-[(1S)-1-[[4-[4-(2-Tetrahydropyran-4-ylethoxy)phenyl]tetrahydropyran-4-carbonyl]amino]ethyl]benzoic acid

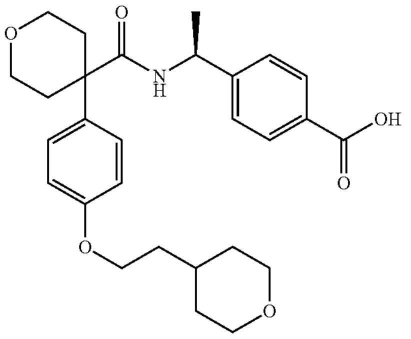 [SMILES: C[C@H](NC(=O)C1(c2ccc(OCCC3CCOCC3)cc2)CCOCC1)c1ccc(C(=O)O)cc1]

Example 93 was obtained according to General Procedure V-c, starting from Compound 205, as a white powder in 61% yield. $^{1}$H-NMR (DMSO-$d_6$, 400 MHz) δ (ppm): 1.16-1.28 (m, 2H, $CH_2$); 1.30 (d, J 7.1 Hz, 3H, CH—$CH_3$); 158-1.80 (m, 6H, CH+2 $CH_2$+$CH_aH_b$); 1.88 (ddd, J 14.1, 10.5, 3.7 Hz, 1H, $CH_aH_b$); 2.41-2.49 (m, 2H, $CH_2$); 3.24-3.30 (m, 2H, O—$CH_2$); 3.37-3.47 (m, 2H, O—$CH_2$); 3.67-3.77 (m, 2H, O—$CH_2$); 3.79-3.86 (m, 2H, O—$CH_2$); 4.01 (t, J 6.4 Hz, 2H, Ph-O—$CH_2$); 4.95-5.05 (i, 1H, CONH—CH—$CH_3$); 6.89 (d, J 8.9 Hz, 2H, Ar); 7.14 (d, J 8.3 Hz, 2H, Ar); 7.24 (d, J 8.9 Hz, 2H, Ar); 7.75 (d, J 8.3 Hz, 2H, Ar); 7.87 (d, J 8.0 Hz, 1H, CONH—CH); 12.78 (bs, 1H, $CO_2H$). M/Z $(M+H)^+$: 482

Compound 206: Methyl 4-[4-(2-phenylethoxy)phenyl]tetrahydropyran-4-carboxylate

Compound 206 was obtained according to General Procedure IX-a, starting from Compound 187 and 2-phenylethan-1-ol. Purification by flash chromatography (Cyclohexane/EtOAc: 100/0 to 70/30) afforded Compound 206 as a white powder in 74% yield. M/Z $(M[—H—CO_2Me]+H)^+$: 281

Compound 207: 4-[4-(2-Phenylethoxy)phenyl]tetrahydropyran-4-carboxylic acid

Compound 207 was obtained according to General Procedure V-d, starting from Compound 206, as a white powder in 95% yield. M/Z $(M[—H—COO_2H]+H)^+$: 281

Compound 208: Methyl 4-[(1S)-1-[[4-[4-(2-phenylethoxy)phenyl]tetrahydropyran-4-carbonyl]amino]ethyl]benzoate Compound 208 was obtained according to General Procedure I-a, starting from Compound 207 and methyl 4-[(1S)-1-aminoethyl]benzoate. Purification by flash chromatography (Cyclohexane/EtOAc: 100/0 to 30/70) afforded Compound 208 as a white powder in 60% yield. M/Z $(M+H)^+$: 488

Example 94: 4-[(1S)-1-[[4-[4-(3-Phenylethoxy)phenyl]tetrahydropyran-4-carbonyl]amino]ethyl]benzoic acid

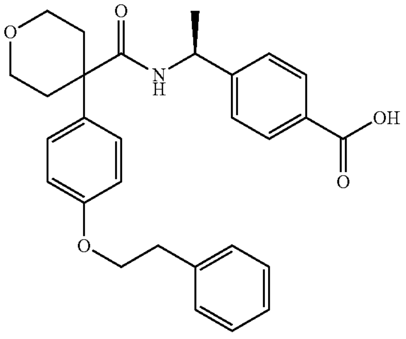 [SMILES: C[C@H](NC(=O)C1(c2ccc(OCCc3ccccc3)cc2)CCOCC1)c1ccc(C(=O)O)cc1]

Example 94 was obtained according to General Procedure V-c, starting from Compound 208, as a white powder in 60% yield. $^{1}$H-NMR (DMSO-$d_6$, 400 MHz) δ (ppm): 1.30 (d, J 7.1 Hz, 3H, CH—$CH_3$); 1.76 (ddd, J 14.0, 10.8, 3.9 Hz, 1H, $CH_aH_b$); 1.86 (ddd, J 14.0, 10.8, 3.9 Hz, 1H, $CH_aH_b$); 2.41-2.49 (m, 2H, $CH_2$); 3.03 (t, 6.8 Hz, 2H, Ph-$CH_2$); 3.36-3.46 (m, 2H, O—$CH_2$); 3.67-3.76 (m, 2H, O—$CH_2$); 4.18 (t, J 6.8 Hz, 2H, Ph-C—$CH_2$); 4.95-5.04 (m, 1H, CONH—CH—$CH_3$); 6.90 (d, J 8.8 Hz, 2H, Ar); 7.16 (d, J 8.2 Hz, 2H, Ar); 7.19-7.24 (m, 1H, Ar); 7.24 (d, J 8.8 Hz, 2H, Ar); 7.28-7.34 (m, 4H, Ar); 7.76 (d, J 8.2 Hz, 2H, Ar); 7.88 (d, J 8.0 Hz, 1H, CONH—CH); 12.76 (bs, 1H, $CO_2H$). M/Z $(M+H)^+$: 474

Compound 209: Methyl 4-[4-(2-cyclohexylethoxy)phenyl]tetrahydropyran-4-carboxylate Compound 209 was obtained according to General Procedure VI-b, starting from methyl tetrahydropyran-4-carboxylate and 1-bromo-4-(2-cyclohexylethoxy)benzene. Purification by flash chromatography (Cyclohexane/EtOAc: 100/0 to 70/30) afforded Compound 209 as a yellow powder in 61% yield. M/Z $(M[—H—CO_2Me]+H)^+$: 287

Compound 210: 4-[4-(2-Cyclohexylethoxy)phenyl]tetrahydropyran-4-carboxylic acid

Compound 210 was obtained according to General Procedure V-b, starting from Compound 209, as a yellow powder in 76% yield. M/Z $(M[—H—CO_2H]+H)^+$: 287

Compound 211: Methyl 4-[(1S)-1-[[4-[4-(2-Cyclohexylethoxy)phenyl]tetrahydropyran-4-carbonyl]amino]ethyl]benzoate Compound 211 was obtained according to General Procedure I-a, starting from Compound 210 and methyl 4-[(1S)-1-aminoethyl]benzoate. Purification by flash chromatography (Cyclohexane/EtOAc: 100/0 to 50/50) afforded Compound 211 as a white powder in 96% yield. M/Z $(M+H)^+$: 494

Example 95: 4-[(1S)-1-[[4-[4-(2-Cyclohexylethoxy)phenyl]tetrahydropyran-4-carbonyl]amino]ethyl]benzoic acid

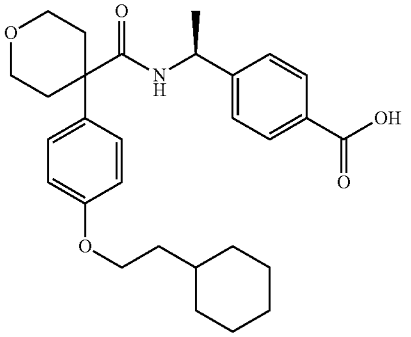

Example 95 was obtained according to General Procedure V-c, starting from Compound 211, as a white powder in 67% yield. $^1$H-NMR (DMSO-$d_6$, 400 MHz) δ (ppm): 0.89-1.01 (m, 2H, $CH_2$); 1.10-1.27 (m, 3H, CH, $CH_2$); 1.30 (d, J 7.1 Hz, 3H, CH—$CH_3$); 1.42-1.51 (m, 1H, $CH_aH_b$); 1.57-1.80 (m, 8H, $CH_2$); 1.87 (ddd, J 14.1, 10.6, 3.7 Hz, 1H, $CH_aH_b$); 2.42-2.49 (m, 2H, $CH_2$); 3.36-3.46 (m, 2H, O—$CH_2$); 3.67-3.78 (m, 2H, O—$CH_2$); 3.99 (t, J 6.6 Hz, 2H, Ph-O—$CH_2$); 4.95-5.04 (m, 1H, CONH—CH—$CH_3$); 6.88 (d, J 8.8 Hz, 2H, Ar); 7.15 (d, J 8.2 Hz, 2H, Ar); 7.24 (d, J 8.8 Hz, 2H, Ar); 7.76 (d, J 8.2 Hz, 2H, Ar); 7.87 (d, J 8.0 Hz, 1H, CONH—CH); 12.78 (bs, 1H, $CO_2H$). M/Z $(M+H)^+$: 480

Compound 212: Methyl 4-[4-(3-pyridylmethoxy)phenyl]tetrahydropyran-4-carboxylate Compound 212 was obtained according to General Procedure X, starting from Compound 187 and 3-(bromomethyl)pyridine hydrobromide. In that specific case, 3 equivalents of potassium carbonate were used. Purification by flash chromatography (Cyclohexane/EtOAc: 100/0 to 0/100) afforded Compound 212 as a white powder in 54% yield. M/Z $(M[—H—CO_2Me]+H)^+$: 177

Compound 213: 4-[4-(3-Pyridylmethoxy)phenyl]tetrahydropyran-4-carboxylic acid

Compound 213 was obtained according to General Procedure V-d, starting from Compound 212, as a white powder in quantitative yield. M/Z $(M+H)^+$: 314

Compound 214: Methyl 4-[(1S)-1-[[4-[4-(3-pyridylmethoxy)phenyl]tetrahydropyran-4-carbonyl]amino]ethyl]benzoate Compound 214 was obtained according to General Procedure I-a, starting from Compound 213 and methyl 4-[(1S)-1-aminoethyl]benzoate. Purification by flash chromatography (DCM/MeOH: 100/0 to 90/10) afforded Compound 214 as a white powder in 80% yield. M/Z $(M+H)^+$: 475

Example 96: 4-[(1S)-1-[[4-[4-(3-Pyridylmethoxy)phenyl]tetrahydropyran-4-carbonyl]amino]ethyl]benzoic acid

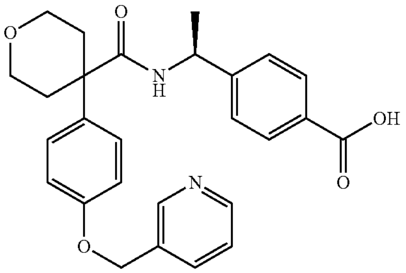 [SMILES: C[C@H](NC(=O)C1(c2ccc(OCc3cccnc3)cc2)CCOCC1)c1ccc(C(=O)O)cc1]

Example 96 was obtained according to General Procedure V-c, starting from Compound 214, as a brown powder in 20% yield. $^1$H-NMR (DMSO-$d_6$, 400 MHz) δ (ppm): 1.31 (d, J 7.0 Hz, 3H, CH—$CH_3$); 1.72-1.82 (m, 1H, $CH_aH_b$); 1.82-1.92 (m, 1H, $CH_aH_b$); 2.41-2.49 (m, 2H, $CH_2$); 3.35-3.45 (m, 2H, O—$CH_2$); 3.67-3.76 (m, 2H, O—$CH_2$); 4.95-5.03 (m, 1H, CONH—CH—$CH_3$); 5.27 (s, 2H, Ph-O—$CH_2$); 7.02 (d, J 8.7 Hz, 2H, Ar); 7.17 (d, J 8.1 Hz, 2H, Ar); 7.29 (d, J 8.7 Hz, 2H, Ar); 7.76 (d, J 8.1 Hz, 2H, Ar); 7.80-7.85 (m, 1H, Ar); 7.92 (d, J 7.9 Hz, 1H, Ar); 8.34 (d, J 7.9 Hz, 1H, CONH—CH); 8.76 (d, J 4.4 Hz, 1H, Ar); 8.89 (s, 1H, Ar), $CO_2H$ signal was not observed. M/Z $(M+H)^+$: 461

Compound 215: Methyl 4-(3-hydroxyphenyl)tetrahydropyran-4-carboxylate

Compound 215 was obtained according to General Procedure VI-b, starting from methyl tetrahydropyran-4-carboxylate and (3-bromophenoxy)-trimethyl-silane. Purification by flash chromatography (DCM/MeOH: 100/0 to 96/4) afforded Compound 215 as a white powder in 54% yield. M/Z $(M[—H—CO_2Me]+H)^+$: 177

Compound 216: Methyl 4-[3-(cyclohexylmethoxy)phenyl]tetrahydropyran-4-carboxylate Compound 216 was obtained according to General Procedure IX-a, starting from Compound 215 and cyclohexylmethanol. Purification by flash chromatography (Cyclohexane/EtOAc: 100/0 to 70/30) afforded Compound 216 as a beige powder in 55% yield. M/Z $(M[—H—CO_2Me]+H)^+$: 273

Compound 217: 4-[3-(Cyclohexylmethoxy)phenyl]tetrahydropyran-4-carboxylic acid

Compound 217 was obtained according to General Procedure V-d, starting from Compound 216, as a white powder in 90% yield. M/Z $(M[—H—CO_2H]+H)^+$: 273

Compound 218: Methyl 4-[(1S)-1-[[4-[3-(cyclohexylmethoxy)phenyl]tetrahydropyran-4-carbonyl]amino]ethyl]benzoate Compound 218 was obtained according to General Procedure I-a, starting from Compound 217 and methyl 4-[(1S)-1-aminoethyl]benzoate. Purification by flash chromatography (Cyclohexane/EtOAc: 100/0 to 40/60) afforded Compound 218 as a white powder in 85% yield. M/Z $(M+H)^+$: 480

Example 97: 4-[(1S)-1-[[4-[3-(Cyclohexylmethoxy)phenyl]tetrahydropyran-4-carbonyl]amino]ethyl]benzoic acid

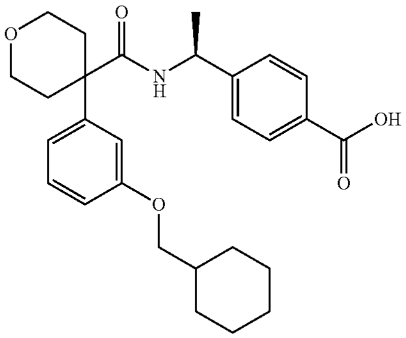

Example 97 was obtained according to General Procedure V-c, starting from Compound 218, as a beige powder in 58% yield. $^1$H-NMR (DMSO-$d_6$, 400 MHz) δ (ppm): 0.95-1.07 (m, 2H, $CH_2$); 1.12-1.27 (m, 3H, CH, $CH_2$); 1.32 (d, J 7.2 Hz, 3H, CH—$CH_3$); 1.59-1.81 (m, 7H, $CH_2$+$CH_aH_b$); 1.93 (ddd, J 14.3, 11.2, 3.9 Hz, 1H, $CH_aH_b$); 2.40-2.48 (m, 2H, $CH_2$); 3.37-3.47 (m, 2H, O—$CH_2$); 3.62-3.80 (m, 4H, PhO—$CH_2$+O—$CH_2$); 4.97-5.06 (m, 1H, CONH—CH—$CH_3$); 6.79-6.84 (m, 2H, Ar); 6.91 (d, J 7.8 Hz, 1H, Ar); 7.14 (d, J 8.3 Hz, 2H, Ar); 7.24 (t, J 7.8 Hz, 1H, Ar); 7.75 (d, J 8.3 Hz, 2H, Ar); 7.96 (d, J 7.8 Hz, 1H, CONH—CH); 12.73 (bs, 1H, $CO_2H$). M/Z $(M+H)^+$: 466

Compound 219: Methyl 4-[3-(tetrahydropyran-4-ylmethoxy)phenyl]tetrahydropyran-4-carboxylate Compound 219 was obtained according to General Procedure IX-a, starting from Compound 215 and tetrahydropyran-4-ylmethanol. Purification by flash chromatography (Cyclohexane/EtOAc: 100/0 to 50/50) afforded Compound 219 as a beige powder in 56% yield. M/Z $(M[—H—CO_2Me]+H)^+$: 275

Compound 220: 4-[3-(Tetrahydropyran-4-ylmethoxy)phenyl]tetrahydropyran-4-carboxylic acid Compound 220 was obtained according to General Procedure V-d, starting from Compound 219, as a beige powder in 76% yield. M/Z $(M[—H—COO_2H]+H)^+$: 275

Compound 221: Methyl 4-[(1S)-1-[[4-[3-(tetrahydropyran-4-ylmethoxy)phenyl]tetrahydropyran-4-carbonyl]amino]ethyl]benzoate Compound 221 was obtained according to General Procedure I-a, starting from Compound 220 and methyl 4-[(1S)-1-aminoethyl]benzoate. Purification by flash chromatography (Cyclohexane/EtOAc: 90/10 to 0/100) afforded Compound 221 as a white powder in 91% yield. M/Z $(M+H)^+$: 482

Example 98: 4-[(1S)-1-[[4-[3-(Tetrahydropyran-4-ylmethoxy)phenyl]tetrahydropyran-4-carbonyl]amino]ethyl]benzoic acid

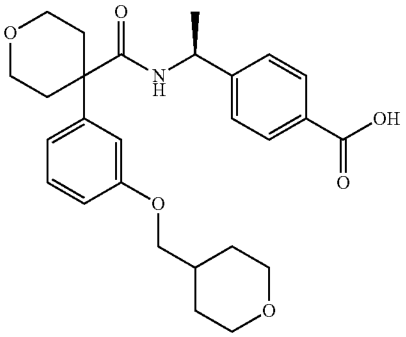 [SMILES: C[C@H](NC(=O)C1(c2cccc(OCC3CCOCC3)c2)CCOCC1)c1ccc(C(=O)O)cc1]

Example 98 was obtained according to General Procedure V-c, starting from Compound 221, as a beige powder in 95% yield. $^1$H-NMR (DMSO-$d_6$, 400 MHz) δ (ppm): 1.23-1.36 (m, 2H, $CH_2$); 1.32 (d, J 7.1 Hz, 3H, CH—$CH_3$); 1.60-1.68 (m, 2H, $CH_2$); 1.74 (ddd, J 14.0, 10.9, 3.9 Hz, 1H, $CH_aH_b$); 1.89-2.00 (m, 2H, CH+$CH_aH_b$); 2.40-2.48 (m, 2H, $CH_2$); 3.26-3.30 (m, 2H, O—$CH_2$); 3.39-3.48 (m, 2H, O—$CH_2$); 3.68-3.81 (m, 4H, O—$CH_2$); 3.83-3.89 (m, 2H, PhO—$CH_2$); 4.97-5.06 (m, 1H, CONH—CH—$CH_3$); 6.79-6.85 (m, 2H, Ar); 6.92 (d, J 7.9 Hz, 1H, Ar); 7.14 (d, J 8.2 Hz, 2H, Ar); 7.25 (t, J 7.9 Hz, 1H, Ar); 7.75 (d, J 8.2 Hz, 2H, Ar); 7.96 (d, J 7.8 Hz, 1H, CONH—CH); 12.80 (bs, 1H, $CO_2H$). M/Z $(M+H)^+$: 468

Compound 222: Methyl 4-(3-benzyloxyphenyl)tetrahydropyran-4-carboxylate

Compound 222 was obtained according to General Procedure X, starting from Compound 215 and benzyle bromide. Purification by flash chromatography (Cyclohexane/EtOAc: 100/0 to 70/30) afforded Compound 222 as a colorless oil in 72% yield. M/Z $(M[—H—CO_2Me]+H)^+$: 267

Compound 223: 4-(3-Benzyloxyphenyl)tetrahydropyran-4-carboxylic acid

Compound 223 was obtained according to General Procedure V-d, starting from Compound 222, as a beige powder in 98% yield. M/Z $(M[—H—CO_2H]+H)^+$: 267

Compound 224: Methyl 4-[(1S)-1-[[4-(3-benzyloxyphenyl)tetrahydropyran-4-carbonyl]amino]ethyl]benzoate Compound 224 was obtained according to General Procedure I-a, starting from Compound 223 and methyl 4-[(1S)-1-aminoethyl]benzoate. Purification by flash chromatography (Cyclohexane/EtOAc: 100/0 to 40/60) afforded Compound 224 as a colorless oil in 95% yield. M/Z $(M+H)^+$: 474

Example 99: 4-[(1S)-1-[[4-(3-Benzyloxyphenyl)tetrahydropyran-4-carbonyl]amino]ethyl]benzoic acid

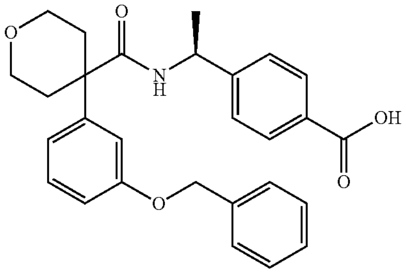 [SMILES: C[C@H](NC(=O)C1(c2cccc(OCc3ccccc3)c2)CCOCC1)c1ccc(C(=O)O)cc1]

Example 99 was obtained according to General Procedure V-c, starting from Compound 224, as a beige powder in 85% yield. $^1$H-NMR (DMSO-$d_6$, 400 MHz) δ (ppm): 1.30 (d, J 7.2 Hz, 3H, CH—$CH_3$); 1.72-1.82 (m, 1H, $CH_aH_b$); 1.86-1.97 (m, 1H, $CH_aH_b$); 2.41-2.49 (m, 2H, $CH_2$); 3.37-3.47 (m, 2H, O—$CH_2$); 3.67-3.78 (m, 2H, O—$CH_2$); 4.96-5.08 (m, 3H, CONH—CH—$CH_3$+PhO—$CH_2$); 6.90-6.97 (m, 3H, Ar); 7.16 (d, J 8.2 Hz, 2H, Ar); 7.26 (t, J 7.8 Hz, 2H, Ar); 7.30-7.46 (m, 4H, Ar); 7.76 (d, J 8.2 Hz, 2H, Ar); 7.97 (d, J 7.9 Hz, 1H, CONH—CH); 12.80 (s, 1H, $CO_2H$). M/Z $(M+H)^+$: 460

Compound 225: Methyl 4-[3-(cyclohexoxy)phenyl]tetrahydropyran-4-carboxylate

Compound 225 was obtained according to General Procedure IX-a, starting from Compound 215 and cyclohexanol. Purification by flash chromatography (Cyclohexane/EtOAc: 100/0 to 50/50) afforded Compound 225 as a beige powder in 39% yield. M/Z $(M+H)^+$: 319

Compound 226: 4-[3-(Cyclohexoxy)phenyl]tetrahydropyran-4-carboxylic acid

Compound 226 was obtained according to General Procedure V-d, starting from Compound 225, as a white powder in 91% yield. M/Z $(M[—H—CO_2H]+H)^+$: 259

Compound 227: Methyl 4-[(1S)-1-[[4-[3-(cyclohexoxy)phenyl]tetrahydropyran-4-carbonyl]amino]ethyl]benzoate Compound 227 was obtained according to General Procedure I-a, starting from Compound 226 and methyl 4-[(1S)-1-aminoethyl]benzoate. Purification by flash chromatography (Cyclohexane/EtOAc: 100/0 to 50/50) afforded Compound 227 as a white powder in 73% yield. M/Z $(M+H)^+$: 466

Example 100: 4-[(1S)-1-[[4-[3-(Cyclohexoxy)phenyl]tetrahydropyran-4-carbonyl]amino]ethyl]benzoic acid

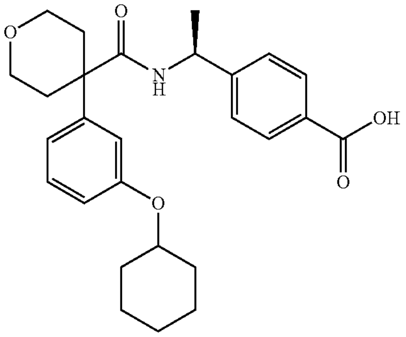 [SMILES: C[C@H](NC(=O)C1(c2cccc(OC3CCCCC3)c2)CCOCC1)c1ccc(C(=O)O)cc1]

Example 100 was obtained according to General Procedure Vc, starting from Compound 227, as a white powder in 63% yield. $^1$H-NMR (DMSO-$d_6$, 400 MHz) δ (ppm): 1.20-1.44 (m, 8H, 2 $CH_2$+CH-$CH_3$+$CH_aH_b$); 1.48-1.54 (m, 1H, $CH_aH_n$); 1.65-1.79 (m, 3H, $CH_2$+$CH_aH_b$); 1.84-1.96 (m, 3H, $CH_2$+$CH_aH_b$); 2.42-2.49 (m, 2H, $CH_2$); 3.36-3.48 (m, 2H, O—$CH_2$); 3.68-3.79 (m, 2H, O—$CH_2$); 4.21-4.29 (m, 1H, Ph-O—CH); 4.97-5.06 (m, 1H, CONH—CH—$CH_3$); 6.80-6.85 (m, 2H, Ar); 6.89 (d, J 7.8 Hz, 1H, Ar); 7.14 (d, J 8.2 Hz, 2H, Ar); 7.23 (t, J 7.8 Hz, 1H, Ar); 7.74 (d, J 8.2 Hz, 2H, Ar); 7.96 (d, J 7.8 Hz, 1H, CONH—CH); 12.74 (bs, 1H, $CO_2H$). M/Z $(M+H)^+$: 452

Compound 228: Methyl 4-[3-(cyclopropylmethoxy)phenyl]tetrahydropyran-4-carboxylate Compound 228 was obtained according to General Procedure IX-a, starting from Compound 215 and cyclopropylimethanol. Purification by flash chromatography (Cyclohexane/EtOAc: 100/0 to 65/35) afforded Compound 228 as a beige powder in 85% yield. M/Z $(M+H)^+$: 291

Compound 229: 4-[3-(Cyclopropylmethoxy)phenyl]tetrahydropyran-4-carboxylic acid

Compound 229 was obtained according to General Procedure V-d, starting from Compound 228, as a white powder in quantitative yield. M/Z $(M[—H—COO_2H]+H)^+$: 231

Compound 230: Methyl 4-[(1S)-1-[[4-[3-(cyclopropylmethoxy)phenyl]tetrahydropyran-4-carbonyl]amino]ethyl]benzoate Compound 230 was obtained according to General Procedure I-a, starting from Compound 229 and methyl 4-[(1S)-1-aminoethyl]benzoate. Purification by flash chromatography (Cyclohexane/EtOAc: 100/0 to 40/60) afforded Compound 230 as a white powder in 63% yield. M/Z $(M+H)^+$: 438

Example 101: 4-[(1S)-1-[[4-[3-(Cyclopropylmethoxy)phenyl]tetrahydropyran-4-carbonyl]amino]ethyl]benzoic acid

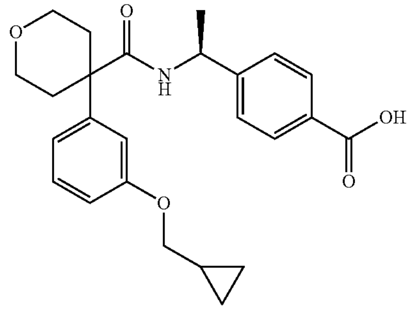 [SMILES: C[C@H](NC(=O)C1(c2cccc(OCC3CC3)c2)CCOCC1)c1ccc(C(=O)O)cc1]

Example 101 was obtained according to General Procedure V-c, starting from Compound 230 as a white powder in 54% yield. $^1$H-NMR (DMSO-$d_6$, 400 MHz) δ (ppm): 0.27-0.31 (m, 2H, $CH(CH_2—CH_2)$); 0.52-0.57 (m, 2H, $CH(CH_2—CH_2)$); 1.13-1.21 (m, 1H, $CH(CH_2—CH_2)$); 1.31 (d, J 7.1 Hz, 3H, $CH—CH_3$); 1.76 (ddd, J 14.1, 10.9, 3.9 Hz, 1H, $CH_aH_b$); 1.92 (ddd, J 14.1, 10.9, 3.9 Hz, 1H, $CH_aH_b$); 2.40-2.47 (m, 2H, $CH_2$); 3.37-3.47 (m, 2H, $O—CH_2$); 3.67-3.80 (m, 4H, Ph-$O—CH_2$+$O—CH_2$); 4.96-5.05 (m, 1H, CONH—CH—$CH_3$); 6.79-6.85 (m, 2H, Ar); 6.90 (d, J 8.6 Hz, 1H, Ar); 7.14 (d, J 8.3 Hz, 2H, Ar); 7.24 (t, J 8.0 Hz, 1H, Ar); 7.75 (d, J 8.3 Hz, 2H, Ar); 7.94 (d, J 7.8 Hz, 1H, CONH—CH); 12.79 (bs, 1H, $CO_2H$). M/Z $(M+H)^+$: 424

Compound 231: Methyl 4-[3-(cyclopentylmethoxy)phenyl]tetrahydropyran-4-carboxylate Compound 231 was obtained according to General Procedure IX-a, starting from Compound 215 and cyclopentylmethanol. Purification by flash chromatography (Cyclohexane/EtOAc: 100/0 to 50/50) afforded Compound 231 as a beige powder in 87% yield. M/Z $(M[—H—CO_2Me]+H)^+$: 259

Compound 232: 4-[3-(Cyclopentylmethoxy)phenyl]tetrahydropyran-4-carboxylic acid

Compound 232 was obtained according to General Procedure V-d, starting from Compound 231, as a white powder in quantitative yield. M/Z $(M[—H—CO_2H]+H)^+$: 259

Compound 233: Methyl 4-[(1S)-1-[[4-[3-(cyclopentylmethoxy)phenyl]tetrahydropyran-4-carbonyl]amino]ethyl]benzoate Compound 233 was obtained according to General Procedure I-a, starting from Compound 232 and methyl 4-[(1S)-1-aminoethyl]benzoate. Purification by flash chromatography (Cyclohexane/EtOAc: 100/0 to 50/50) afforded Compound 233 as a white powder in 57% yield. M/Z $(M+H)^+$: 466

Example 102: 4-[(1S)-1-[[4-[3-(Cyclopentylmethoxy)phenyl]tetrahydropyran-4-carbonyl]amino]ethyl]benzoic acid

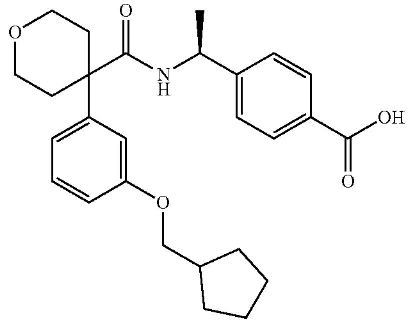 [SMILES: C[C@H](NC(=O)C1(c2cccc(OCC3CCCC3)c2)CCOCC1)c1ccc(C(=O)O)cc1]

Example 102 was obtained according to General Procedure V-c, starting from Compound 233, as a white powder in 51% yield. $^1$H-NMR (DMSO-$d_6$, 400 MHz) δ (ppm): 124-1.34 (m, 2H, $CH_2$); 1.32 (d, J 7.1 Hz, 3H, $CH—CH_3$); 1.47-1.65 (m, 4H, $CH_2$): 1.70-1.80 (m, 3H, $CH_2$+$CH_a$Ho); 1.93 (ddd, J 14.1, 10.9, 3.9 Hz, 1H, $CH_aH_b$); 2.22-2.31 (m, 1H, CH); 2.40-2.47 (m, 2H, $CH_2$); 3.37-3.48 (m, 2H, $O—CH_2$); 3.69-3.80 (m, 4H, Ph-$O—CH_2$+O-$CH_2$); 4.98-5.06 (m, 1H, CONH—CH—$CH_3$); 6.81-6.85 (m, 2H, Ar); 6.92 (d, J 8.1 Hz, 1H, Ar); 7.15 (d, J 8.3 Hz, 2H, Ar); 7.24 (t, J 8.1 Hz, 1H, Ar); 7.75 (d, J 8.3 Hz, 2H, Ar); 7.96 (d, J 7.8 Hz, 1H, CONH—CH); 12.76 (bs, 1H, $CO_2H$). M/Z $(M+H)^+$: 452

Compound 234: Methyl 4-[3-(cycloheptylmethoxy)phenyl]tetrahydropyran-4-carboxylate Compound 234 was obtained according to General Procedure IX-a, starting from Compound 215 and cycloheptylmethanol. Purification by flash chromatography (Cyclohexane/EtOAc: 100/0 to 60/40) afforded Compound 234 as a beige powder in 48% yield. M/Z $(M[—H—CO_2Me]+H)^+$: 287

Compound 235: 4-[3-(Cycloheptylmethoxy)phenyl]tetrahydropyran-4-carboxylic acid

Compound 235 was obtained according to General Procedure V-d, starting from Compound 234, as a white powder in quantitative yield. M/Z $(M[—H—CO_2H]+H)^+$: 287

Compound 236: Methyl 4-[(1S)-1-[[4-[3-(cycloheptylmethoxy)phenyl]tetrahydropyran-4-carbonyl]amino]ethyl]benzoate Compound 236 was obtained according to General Procedure I-a, starting from Compound 235 and methyl 4-[(1S)-1-aminoethyl]benzoate. Purification by flash chromatography (Cyclohexane/EtOAc: 100/0 to 50/50) afforded Compound 236 as a white powder in 76% yield. M/Z $(M+H)^+$: 494

Example 103: 4-[(1S)-1-[[4-[3-(Cycloheptylmethoxy)phenyl]tetrahydropyran-4-carbonyl]amino]ethyl]benzoic acid

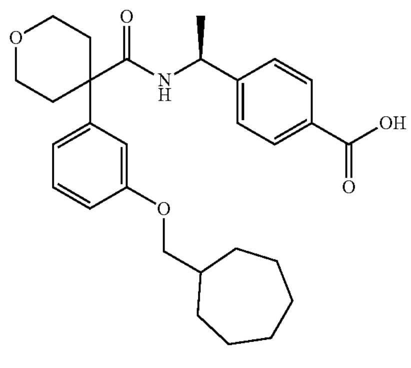 [SMILES: C[C@H](NC(=O)C1(c2cccc(OCC3CCCCCC3)c2)CCOCC1)c1ccc(C(=O)O)cc1]

Example 103 was obtained according to General Procedure V-c, starting from Compound 236, as a white powder in 64% yield. $^1$H-NMR (DMSO-$d_6$, 400 MHz) δ (ppm): 1.19-1.30 (m, 2H, $CH_2$); 1.32 (d, J 7.1 Hz, 3H, CH—$CH_3$); 1.37-1.99 (m, 13H, CH, $CH_2$); 2.39-2.47 (m, 2H, $CH_2$); 3.37-3.48 (m, 2H, O—$CH_2$); 3.61-3.81 (m, 4H, Ph-O—$CH_2$+O-$CH_2$); 4.97-5.07 (m, 1H, CONH—CH—$CH_3$); 6.81-6.85 (m, 2H, Ar); 6.92 (d, J 7.8 Hz, 1H, Ar); 7.15 (d, J 8.3 Hz, 2H, Ar); 7.24 (dd, J 8.6, 7.8 Hz, 1H, Ar); 7.75 (d, J 8.3 Hz, 2H, Ar); 7.96 (d, J 7.8 Hz, 1H, CONH—CH); 12.80 (bs, 1H, $CO_2$H). M/Z $(M+H)^+$: 480

Compound 237: Methyl 4-(3-isopentyloxyphenyl)tetrahydropyran-4-carboxylate

Compound 237 was obtained according to General Procedure IX-a, starting from Compound 215 and 3-isopentanol. Purification by flash chromatography (Cyclohexane/EtOAc: 100/0 to 60/40) afforded Compound 237 as a beige powder in 68% yield. M/Z $(M+H)^+$: 307

Compound 238: 4-(3-Isopentyloxyphenyl)tetrahydropyran-4-carboxylic acid

Compound 238 was obtained according to General Procedure V-d, starting from Compound 237, as a white powder in 97% yield. M/Z $(M+H)^+$: 293

Compound 239: Methyl 4-[(1S)-1-[[4-(3-isopentyloxyphenyl)tetrahydropyran-4-carbonyl]amino]ethyl]benzoate Compound 239 was obtained according to General Procedure I-a, starting from Compound 238 and methyl 4-[(1S)-1-aminoethyl]benzoate. Purification by flash chromatography (Cyclohexane/EtOAc: 100/0 to 40/60) afforded Compound 239 as a white powder in 75% yield. M/Z $(M+H)^+$: 454

Example 104: 4-[(1S)-1-[[4-(3-Isopentyloxyphenyl)tetrahydropyran-4-carbonyl]amino]ethyl]benzoic acid

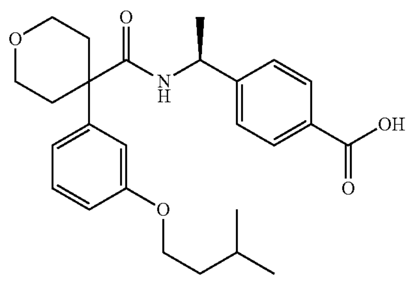 [SMILES: CC(C)CCOc1cccc(C2(C(=O)N[C@@H](C)c3ccc(C(=O)O)cc3)CCOCC2)c1]

Example 104 was obtained according to General Procedure V-c, starting from Compound 239, as a white powder in 55% yield. $^1$H-NMR (DMSO-$d_6$, 400 MHz) δ (ppm): 0.91 (d, J 6.6 Hz, 6H, $CH(CH_3)_2$); 1.32 (d, J 7.2 Hz, 3H, CH—$CH_3$); 1.58 (q, J 6.6 Hz, 2H, $CH_2$); 1.70-1.81 (m, 2H, $CH(CH_3)_2$+$CH_aH_b$); 1.93 (ddd, J 14.1, 10.9, 3.9 Hz, 1H, $CH_aH_b$); 2.41-2.49 (m, 2H, $CH_2$); 3.37-3.48 (m, 2H, O—$CH_2$); 3.68-3.80 (m, 2H, O—$CH_2$); 3.85-3.96 (m, 2H, PhO—$CH_2$); 4.97-5.07 (m, 1H, CONH—CH—$CH_3$); 6.81-6.85 (m, 2H, Ar); 6.91 (d, J 8.1 Hz, 1H, Ar); 7.15 (d, J 8.2 Hz, 2H, Ar); 7.24 (dd, J 8.6, 8.1 Hz, 1H, Ar); 7.74 (d, J 8.2 Hz, 2H, Ar); 7.95 (d, J 8.0 Hz, 1H, CONH—CH); 12.78 (bs, 1H, $CO_2$H). M/Z $(M+H)^+$: 440

Compound 240: Methyl 4-[3-(2-cyclohexylethoxy)phenyl]tetrahydropyran-4-carboxylate Compound 240 was obtained according to General Procedure IX-a, starting from Compound 215 and 2-cyclohexylethanol. Purification by flash chromatography (Cyclohexane/EtOAc: 100/0 to 60/40) afforded Compound 240 as a beige powder in 44% yield. M/Z $(M[—H—CO_2Me]+H)^+$: 287

Compound 241: 4-[3-(2-Cyclohexylethoxy)phenyl]tetrahydropyran-4-carboxylic acid

Compound 241 was obtained according to General Procedure V-d, starting from Compound 240, as a white powder in 82% yield. M/Z $(M[—H—CO_2H]+H)^+$: 287

Compound 242: Methyl 4-[(1S)-1-[[4-[3-(2-cyclohexylethoxy)phenyl]tetrahydropyran-4-carbonyl]amino]ethyl]benzoate Compound 242 was obtained according to General Procedure I-a, starting from Compound 241 and methyl 4-[(1S)-1-aminoethyl]benzoate. Purification by flash chromatography (Cyclohexane/EtOAc: 100/0 to 40/60) afforded Compound 242 as a white powder in 81% yield. M/Z $(M+H)^+$: 494

Example 105: 4-[(1S)-1-[[4-[3-(2-Cyclohexylethoxy)phenyl]tetrahydropyran-4-carbonyl]amino]ethyl]benzoic acid

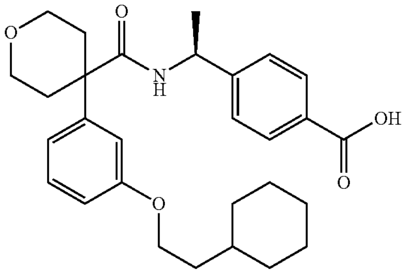 [SMILES: C[C@H](NC(=O)C1(c2cccc(OCCC3CCCCC3)c2)CCOCC1)c1ccc(C(=O)O)cc1]

Example 105 was obtained according to General Procedure V-c, starting from Compound 242, as a white powder in 43% yield. $^1$H-NMR (DMSO-d$_6$, 400 MHz) δ (ppm): 0.87-0.98 (m, 2H, $CH_2$); 1.07-1.26 (m, 3H, CH+$CH_2$); 1.32 (d, J 7.1 Hz, 3H, CH—$CH_3$); 1.38-1.48 (m, 1H, $CH_aH_b$); 1.58 (q, J 6.7 Hz, 2H, $CH_2$); 1.61-1.80 (m, 6H, $CH_2$); 1.93 (ddd, J 14.1, 10.9, 3.9 Hz, 1H, $CH_aH_b$); 2.41-2.49 (m, 2H, $CH_2$); 3.37-3.48 (m, 2H, O—$CH_2$); 3.68-3.79 (m, 2H, O—$CH_2$); 3.86-3.96 (m, 2H, PhO—$CH_2$); 4.97-5.06 (m, 1H, CONH—CH—$CH_3$); 6.81-6.85 (m, 2H, Ar); 6.91 (d, J 7.8 Hz, 1H, Ar); 7.15 (d, J 8.2 Hz, 2H, Ar); 7.24 (dd, J 8.7, 7.8 Hz, 1H, Ar); 7.74 (d, J 8.2 Hz, 2H, Ar); 7.95 (d, J 7.8 Hz, 1H, CONH—CH); 12.79 (bs, 1H, $CO_2H$). M/Z $(M+H)^+$: 480

Compound 243: Methyl 4-[3-[[(3S)-tetrahydrofuran-3-yl]methoxy]phenyl]tetrahydropyran-4-carboxylate Compound 243 was obtained according to General Procedure IX-a, starting from Compound 215 and [(3R)-tetrahydrofuran-3-yl]methanol. Purification by flash chromatography (Cyclohexane/EtOAc: 100/0 to 50/50) afforded Compound 243 as a beige powder. M/Z $(M[—H—CO_2Me]+H)^+$: 261

Compound 244: 4-[3-[[(3S)-Tetrahydrofuran-3-yl]methoxy]phenyl]tetrahydropyran-4-carboxylic acid Compound 244 was obtained according to General Procedure V-d, starting from Compound 243, as a white powder in 26% yield over 2 steps. M/Z $(M[—H—CO_2H]+H)^+$: 261

Compound 245: Methyl 4-[(1S)-1-[[4-[3-[[(3S)-tetrahydrofuran-3-yl]methoxy]phenyl]tetrahydropyran-4-carbonyl]amino]ethyl]benzoate Compound 245 was obtained according to General Procedure I-a, starting from Compound 244 and methyl 4-[(1S)-1-aminoethyl]benzoate. Purification by flash chromatography (Cyclohexane/EtOAc: 50/50 to 0/100) afforded Compound 245 as a beige powder. M/Z $(M+H)^+$: 468

Example 106: 4-[(1S)-1-[[4-[3-[[(3S)-Tetrahydrofuran-3-yl]methoxy]phenyl]tetrahydropyran-4-carbonyl]amino]ethyl]benzoic acid

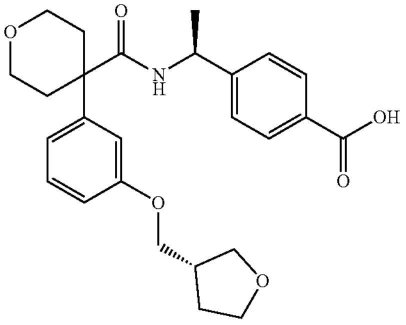 [SMILES: C[C@H](NC(=O)C1(c2cccc(OC[C@H]3CCOC3)c2)CCOCC1)c1ccc(C(=O)O)cc1]

Example 106 was obtained according to General Procedure V-c, starting from Compound 245, as a white powder in 13% yield over 2 steps. $^1$H-NMR (DMSO-d$_6$, 400 MHz) δ (ppm): 1.32 (d, J 7.1 Hz, 3H, CH—$CH_3$); 1.59-1.68 (m, 1H, $CH_aH_b$); 1.75 (ddd, J 14.1, 10.9, 3.9 Hz, 1H, $CH_aH_b$); 1.92 (ddd, J 14.1, 10.9, 3.9 Hz, 1H, $CH_aH_b$); 1.97-2.05 (m, 1H, $CH_aH_b$); 2.40-2.47 (m, 2H, $CH_2$); 2.56-2.65 (m, 1H, CH); 3.37-3.47 (m, 2H, O—$CH_2$); 3.50 (dd, J 8.6, 5.7 Hz, 1H, $CH_aH_b$); 3.61-3.83 (m, 6H, PhO—$CH_2$+2O—$CH_2$); 3.88 (dd, J 9.3, 6.8 Hz, 1H, O—$CH_aH_b$); 4.97-5.05 (m, 1H, CONH—CH—$CH_3$); 6.82-6.87 (m, 2H, Ar); 6.93 (d, J 7.8 Hz, 1H, Ar); 7.15 (d, J 8.3 Hz, 2H, Ar); 7.24 (dd, J 8.6, 7.8 Hz, 1H, Ar); 7.75 (d, J 8.3 Hz, 2H, Ar); 7.95 (d, J 8.0 Hz, 1H, CONH—CH); 12.79 (bs, 1H, $CO_2H$). M/Z $(M+H)^+$: 454

Compound 246: Methyl 4-[3-[[(3R)-tetrahydrofuran-3-yl]methoxy]phenyl]tetrahydropyran-4-carboxylate Compound 246 was obtained according to General Procedure IX-a, starting from Compound 215 and [(3S)-tetrahydrofuran-3-yl]methanol. Purification by flash chromatography (Cyclohexane/EtOAc: 100/0 to 60/40) afforded Compound 246 as a beige powder. M/Z $(M[—H—COO_2Me]+H)^+$: 261

Compound 247: 4-[3-[[(3R)-Tetrahydrofuran-3-yl]methoxy]phenyl]tetrahydropyran-4-carboxylic acid Compound 247 was obtained according to General Procedure V-d, starting from Compound 246, as a white powder in 38% yield over 2 steps. M/Z $(M[—H—COO_2H]+H)^+$: 261

Compound 248: Methyl 4-[(1S)-1-[[4-[3-[[(3R)-tetrahydrofuran-3-yl]methoxy]phenyl]tetrahydropyran-4-carbonyl]amino]ethyl]benzoate Compound 248 was obtained according to General Procedure I-a, starting from Compound 247 and methyl 4-[(1S)-1-aminoethyl]benzoate. Purification by flash chromatography (Cyclohexane/EtOAc: 0/100 to 0/100) afforded Compound 248 as a beige powder. M/Z $(M+H)^+$: 468

Example 107: 4-[(1S)-1-[[4-[3-[[(3R)-Tetrahydrofuran-3-yl]methoxy]phenyl]tetrahydropyran-4-carbonyl]amino]ethyl]benzoic acid

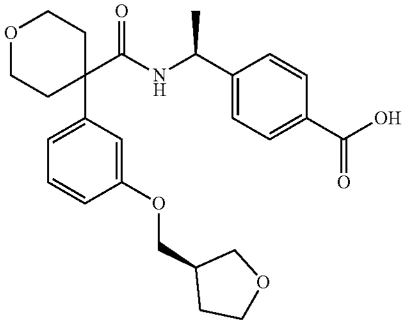 [SMILES: C[C@H](NC(=O)C1(c2cccc(OC[C@@H]3CCOC3)c2)CCOCC1)c1ccc(C(=O)O)cc1]

Example 107 was obtained according to General Procedure V-c, starting from Compound 248, as a white powder in 10% yield over 2 steps. $^1$H-NMR (DMSO-$d_6$, 400 MHz) δ (ppm): 1.31 (d, J 7.1 Hz, 3H, CH—$CH_3$); 1.58-1.67 (m, 1H, $CH_aH_b$); 1.75 (ddd, J 14.1, 10.9, 3.9 Hz, 1H, $CH_aH_b$); 1.93 (ddd, J 14.1, 10.9, 3.9 Hz, 1H, $CH_aH_b$); 1.97-2.05 (m, 1H, $CH_aH_b$); 2.40-2.47 (m, 2H, $CH_2$); 2.56-2.65 (m, 1H, CH); 3.38-3.48 (m, 2H, O—$CH_2$); 3.50 (dd, J 8.6, 5.6 Hz, 1H, O—$CH_aH_b$); 3.61-3.85 (m, 7H, Ph-O—$CH_2$+O—$CH_2$+O-$CH_aH_b$); 4.97-5.05 (m, 1H, CONH—CH—$CH_3$); 6.82-6.87 (m, 2H, Ar); 6.93 (d, J 7.7 Hz, 1H, Ar); 7.14 (d, J 8.2 Hz, 2H, Ar); 7.24 (dd, J 8.3, 7.7 Hz, 1H, Ar); 7.75 (d, J 8.2 Hz, 2H, Ar); 7.95 (d, J 7.8 Hz, 1H, CONH—CH); 12.80 (bs, 1H, $CO_2H$). M/Z $(M+H)^+$: 454

Compound 249: Methyl 1-[4-[tert-butyl(dimethyl)silyl]oxyphenyl]cyclopentanecarboxylate Compound 249 was obtained according to General Procedure VI-b, starting from methyl cyclopentanecarboxylate and (4-bromophenoxy)-tert-butyl-dimethyl-silane. Purification by flash chromatography (Cyclohexane/EtOAc: 100/0 to 90/10) afforded Compound 249 as a yellow oil in 45% yield. M/Z $(M[—H—CO_2Me]+H)^+$: 291

Compound 250: Methyl 1-(4-hydroxyphenyl)cyclopentanecarboxylate

Compound 250 was obtained according to General Procedure XV-a, starting from Compound 249. Purification by flash chromatography (DCM/EtOAc: 100/0 to 60/40) afforded Compound 250 as an orange powder in 64% yield. M/Z $(M[—H—CO_2Me]+H)^+$: 161

Compound 251: Methyl 1-[4-(cyclohexylmethoxy)phenyl]cyclopentanecarboxylate

Compound 251 was obtained according to General Procedure IX-a, starting from Compound 250 and cyclohexylmethanol. Purification by flash chromatography (Cyclohexane/EtOAc: 100/0 to 70/30) afforded Compound 251 as a white powder in 42% yield. M/Z $(M[—H—COO_2Me]+H)^+$: 257

Compound 252: 1-[4-(Cyclohexylmethoxy)phenyl]cyclopentanecarboxylic acid

Compound 252 was obtained according to General Procedure V-b, starting from Compound 251, as a white powder in 86% yield. M/Z $(M[—H—COO_2H]+H)^+$: 257

Compound 253: Methyl 4-[(1S)-1-[[1-[4-(cyclohexylmethoxy)phenyl]cyclopentanecarbonyl]amino]ethyl]benzoate Compound 253 was obtained according to General Procedure I-a, starting from Compound 252 and methyl 4-[(1S)-1-aminoethyl]benzoate. Purification by flash chromatography (Cyclohexane/EtOAc: 100/0 to 60/40) afforded Compound 253 as a white powder in 68% yield. M/Z $(M+H)^+$: 464

Example 108: 4-[(1S)-1-[[1-[4-(Cyclohexylmethoxy)phenyl]cyclopentanecarbonyl]amino]ethyl]benzoic acid

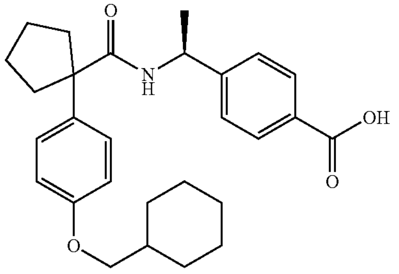

Example 108 was obtained according to General Procedure V-c, starting from Compound 253, as a white powder in 66% yield. $^1$H-NMR (DMSO-$d_6$, 400 MHz) δ (ppm): 0.98-1.26 (m, 5H, CH, $CH_2$); 1.29 (d, J 7.2 Hz, 3H, CH—$CH_3$); 1.48-1.85 (m, 12H, $CH_2$); 2.41-2.49 (m, 2H, $CH_2$); 3.77 (d, J 6.3 Hz, 2H, Ph-O—$CH_2$); 4.88-4.96 (m, 1H, CONH—CH—$CH_3$); 6.86 (d, J 8.7 Hz, 2H, Ar); 7.17 (d, J 8.2 Hz, 2H, Ar); 7.23 (d, J 8.7 Hz, 2H, Ar); 7.74 (d, J 8.0 Hz, 1H, CONH—CH); 7.77 (d, J 8.2 Hz, 2H, Ar); 12.80 (bs, 1H, $CO_2H$). M/Z $(M+H)^+$: 450

Compound 254: Methyl 1-(4-benzyloxyphenyl)cyclopentanecarboxylate

Compound 254 was obtained according to General Procedure X, starting from Compound 250 and benzyle bromide. Purification by flash chromatography (Cyclohexane/EtOAc: 100/0 to 70/30) afforded Compound 254 as a white powder in 83% yield. M/Z $(M[—H—CO_2Me]+H)^+$: 251

Compound 255: 1-(4-Benzyloxyphenyl)cyclopentanecarboxylic acid

Compound 255 was obtained according to General Procedure V-b, starting from Compound 254, as a white powder in quantitative yield. M/Z $(M[—H—CO_2H]+H)^+$: 251

Compound 256: Methyl 4-[(1S)-1-[[1-(4-benzyloxyphenyl)cyclopentanecarbonyl]amino]ethyl]benzoate Compound 256 was obtained according to General Procedure I-a, starting from Compound 255 and methyl 4-[(1S)-

1-aminoethyl]benzoate. Purification by flash chromatography (Cyclohexane/EtOAc: 100/0 to 60/40) afforded Compound 256 as a white powder in 59% yield. M/Z $(M+H)^+$: 458

Example 109: 4-[(1S)-1-[[1-(4-Benzyloxyphenyl) cyclopentanecarbonyl]amino]ethyl]benzoic acid

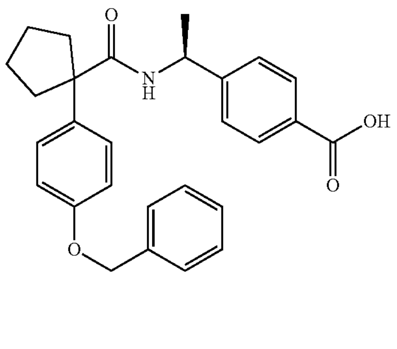 [SMILES: C[C@H](NC(=O)C1(c2ccc(OCc3ccccc3)cc2)CCCC1)c1ccc(C(=O)O)cc1]

Example 109 was obtained according to General Procedure V-c, starting from Compound 256, as a beige powder in 80% yield. $^1$H-NMR (DMSO-$d_6$, 400 MHz) δ (ppm): 1.28 (d, J 7.2 Hz, 3H, CH—$CH_3$); 1.47-1.66 (m, 4H, $CH_2$); 1.69-1.85 (m, 2H, $CH_2$); 2.41-2.49 (m, 2H, $CH_2$); 4.87-4.95 (m, 1H, CONH—CH—$CH_3$); 5.09 (s, 2H, PhO—$CH_2$); 6.94 (d, J 8.7 Hz, 2H, Ar); 7.16 (d, J 8.2 Hz, 2H, Ar); 7.24 (d, J 8.7 Hz, 2H, Ar); 7.32 (t, J 7.2 Hz, 1H, Ar); 7.39 (t, J 7.2 Hz, 2H, Ar); 7.45 (d, J 7.2 Hz, 2H, Ar); 7.75 (d, J 8.0 Hz, 1H, CONH—CH); 7.77 (d, J 8.2 Hz, 2H, Ar); 12.80 (bs, 1H, $CO_2H$). M/Z $(M+H)^+$: 444

Compound 257: Methyl 1-[4-(2-cyclohexylethoxy) phenyl]cyclopentanecarboxylate

Compound 257 was obtained according to General Procedure IX-a, starting from Compound 250 and 2-cyclohexylethanol. Purification by flash chromatography (Cyclohexane/EtOAc: 100/0 to 50/50) afforded Compound 257 as a white powder in 77% yield. M/Z $(M+H)^+$: 331

Compound 258: 1-[4-(2-Cyclohexylethoxy)phenyl] cyclopentanecarboxylic acid

Compound 258 was obtained according to General Procedure V-b, starting from Compound 257, as a white powder in 92% yield. M/Z $(M[—H—CO_2H]+H)^+$: 271

Compound 259: Methyl 4-[(1S)-1-[[4-[4-(2-cyclohexylethoxy)phenyl]cyclopentanecarbonyl]amino] ethyl]benzoate Compound 259 was obtained according to General Procedure I-a, starting from Compound 258 and methyl 4-[(1S)-1-aminoethyl]benzoate. Purification by flash chromatography (Cyclohexane/EtOAc: 100/0 to 70/30) afforded Compound 259 as a white powder in 93% yield. M/Z $(M+H)^+$: 478

Example 110: 4-[(1S)-1-[[1-[4-(2-Cyclohexylethoxy)phenyl]cyclopentanecarbonyl]amino]ethyl] benzoic acid

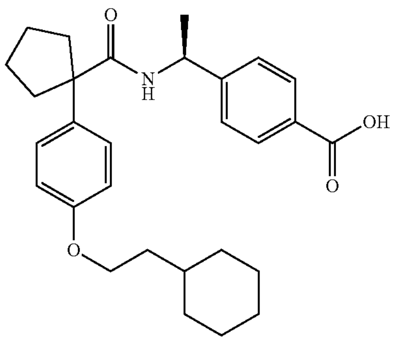

Example 110 was obtained according to General Procedure V-c, starting from Compound 259, as a white powder in 55% yield. $^1$H-NMR (DMSO-$d_6$, 400 MHz) δ (ppm): 0.89-1.00 (m, 2H, $CH_2$); 1.09-1.25 (m, 3H, CH, $CH_2$); 1.28 (d, J 7.2 Hz, 3H, CH—$CH_3$); 1.41-1.84 (m, 14H, $CH_2$); 2.52-2.57 (m, 2H, $CH_2$); 3.98 (t, J 6.6 Hz, 2H, PhO—$CH_2$); 4.88-4.96 (m, 1H, CONH—CH—$CH_3$); 6.86 (d, J 8.8 Hz, 2H, Ar); 7.17 (d, J 8.2 Hz, 2H, Ar); 7.23 (d, J 8.8 Hz, 2H, Ar); 7.72 (d, J 8.0 Hz, 1H, CONH—CH); 7.76 (d, J 8.2 Hz, 2H, Ar); 12.77 (bs, 1H, $CO_2H$). M/Z $(M+H)^+$: 464

Compound 260: Methyl 4-[(1S)-1-[[1-[4-(2-cyclohexylethoxy)phenyl]cyclopentanecarbonyl]-methyl-amino]ethyl]benzoate To a solution of Compound 259 (1 equiv.) in DMF (0.1 M) at 0° C., sodium hydride (1.2 equiv.) was added. The reaction mixture was stirred at 0° C. for 15 min, then allowed to warm up to rt. Methyl iodide (1.2 equiv.) was added. The reaction mixture was stirred at rt for 1.5 h, then hydrolyzed. The reaction mixture was extracted with EtOAc. The organic layer was washed with brine, dried, then concentrated. Purification by flash chromatography (Cyclohexane/EtOAc: 100/0 to 65/35) afforded Compound 260 as a white powder. M/Z $(M+H)^+$: 478

Example 111: 4-[(1S)-1-[[1-[4-(2-Cyclohexylethoxy)phenyl]cyclopentanecarbonyl]-methyl-amino]ethyl]benzoic acid

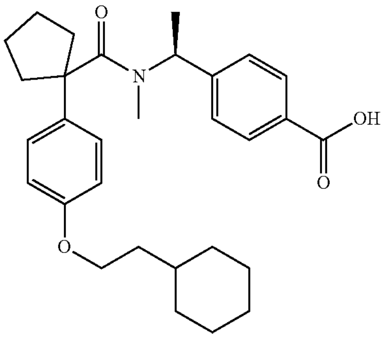 [SMILES: C[C@@H](c1ccc(C(=O)O)cc1)N(C)C(=O)C1(c2ccc(OCCC3CCCCC3)cc2)CCCC1]

Example 111 was obtained according to General Procedure V-c, starting from Compound 260, as a white powder in 33% yield over 2 steps. $^1$H-NMR (DMSO-$d_6$, 400 MHz, 80° C.): 0.94-1.06 (m, 2H, $CH_2$); 1.15-1.29 (m, 3H, CH, $CH_2$); 1.28 (d, J 6.7 Hz, 3H, CH—$CH_3$); 1.43-1.53 (m, 1H, $CH_aH_b$); 1.57-1.77 (m, 11H, $CH_2$+$CH_aH_b$); 1.91-2.02 (m, 2H, $CH_2$); 2.33 (s, 3H, N—$CH_3$); 2.34-2.44 (m, 2H, $CH_2$); 3.99 (t, J 6.6 Hz, 2H, PhO—$CH_2$); 5.61-5.75 (m, 1H, CON—CH—$CH_3$); 6.87 (d, J 8.8 Hz, 2H, Ar); 7.13 (d, J 8.8 Hz, 2H, Ar); 7.21 (bd, J 8.2 Hz, 2H, Ar); 7.86 (d, J 8.2 Hz, 2H, Ar); 12.21-12.50 (m, 1H, $CO_2H$). M/Z $(M+H)^+$: 478

Compound 261: Methyl 1-(3-hydroxyphenyl)cyclopentanecarboxylate

Compound 261 was obtained according to General Procedure VI-b, starting from methyl cyclopentanecarboxylate and (3-bromophenoxy)-trimethyl-silane. Purification by flash chromatography (Cyclohexane/EtOAc: 100/0 to 50/50) afforded Compound 261 as a beige powder in 19% yield. M/Z $(M[—H—COO_2Me]+H)^+$: 161

Compound 262: Methyl 1-[3-(cyclohexylmethoxy)phenyl]cyclopentanecarboxylate

Compound 262 was obtained according to General Procedure IX-a, starting from Compound 261 and cyclohexylmethanol. Purification by flash chromatography (Cyclohexane/EtOAc: 100/0 to 60/40) afforded Compound 262 as a white powder in 45% yield. M/Z $(M[—H—CO_2Me]+H)^+$: 257

Compound 263: 1-[3-(Cyclohexylmethoxy)phenyl]cyclopentanecarboxylic acid

Compound 263 was obtained according to General Procedure V-b, starting from Compound 262, as a white powder in 84% yield. M/Z $(M[—H—CO_2H]+H)^+$: 257

Compound 264: Methyl 4-[(1S)-1-[[1-[3-(cyclohexylmethoxy)phenyl]cyclopentanecarbonyl]amino]ethyl]benzoate Compound 264 was obtained according to General Procedure I-a, starting from Compound 263 and methyl 4-[(1S)-1-aminoethyl]benzoate. Purification by flash chromatography (Cyclohexane/EtOAc: 100/0 to 60/40) afforded Compound 264 as a white powder in 80% yield. M/Z $(M+H)^+$: 464

Example 112: 4-[(1S)-1-[[1-[3-(Cyclohexylmethoxy)phenyl]cyclopentanecarbonyl]amino]ethyl]benzoic acid

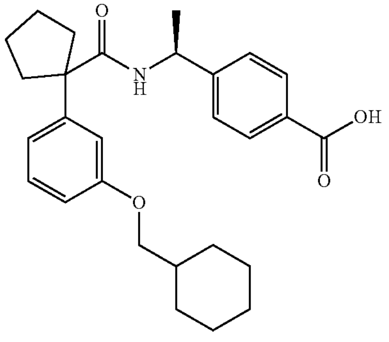 [SMILES: C[C@H](NC(=O)C1(c2cccc(OCC3CCCCC3)c2)CCCC1)c1ccc(C(=O)O)cc1]

Example 112 was obtained according to General Procedure V-c, starting compound 264, as a white powder in 54% yield. $^1$H-NMR (DMSO-$d_6$, 400 MHz) δ (ppm): 0.96-1.09 (m, 2H, $CH_2$); 1.14-1.28 (m, 3H, CH, $CH_2$); 1.29 (d, J 7.1 Hz, 3H, CH—$CH_3$); 1.50-1.82 (m, 10H, $CH_2$); 1.83-1.92 (m, 2H, $CH_2$); 2.52-2.61 (m, 2H, $CH_2$); 3.64-3.73 (m, 2H, PhO—$CH_2$); 4.89-4.97 (m, 1H, CONH—CH—$CH_3$); 6.76-6.82 (m, 2H, Ar); 6.89 (d, J 8.0 Hz, 1H, Ar); 7.16 (d, J 8.2 Hz, 2H, Ar); 7.20 (t, J 8.0 Hz, 1H, Ar); 7.75 (d, J 8.2 Hz, 2H, Ar); 7.80 (d, J 8.0 Hz, 1H, CONH—CH); 12.77 (bs, 1H, $CO_2H$). M/Z $(M+H)^+$: 450

Compound 265: Methyl 1-(3-benzyloxyphenyl)cyclopentanecarboxylate

Compound 265 was obtained according to General Procedure X, starting from Compound 261 and benzyle bromide. Purification by flash chromatography (Cyclohexane/EtOAc: 100/0 to 60/40) afforded Compound 265 as a white powder in 79% yield. M/Z $(M[—H—CO_2Me]+H)^+$: 251

Compound 266: 1-(3-Benzyloxyphenyl)cyclopentanecarboxylic acid

Compound 266 was obtained according to General Procedure V-b, starting from Compound 265, as a white powder in 89% yield. M/Z $(M[—H—CO_2H]+H)^+$: 251

Compound 267: Methyl 4-[(1S)-1-[[1-(3-benzyloxyphenyl)cyclopentanecarbonyl]amino]ethyl]benzoate Compound 267 was obtained according to General Procedure I-a, starting from Compound 266 and methyl 4-[(1S)-1-aminoethyl]benzoate. Purification by flash chromatography (Cyclohexane/EtOAc: 100/0 to 60/40) afforded Compound 267 as a white powder in 83% yield. M/Z $(M+H)^+$: 458

Example 113: 4-[(1S)-1-[[1-(3-Benzyloxyphenyl)cyclopentanecarbonyl]amino]ethyl]benzoic acid

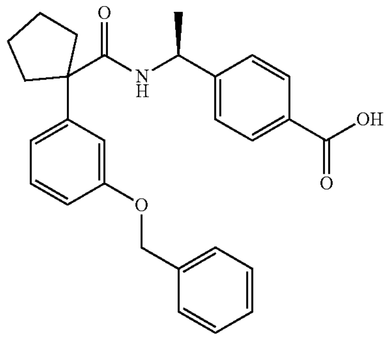 [SMILES: C[C@H](NC(=O)C1(c2cccc(OCc3ccccc3)c2)CCCC1)c1ccc(C(=O)O)cc1]

Example 113 was obtained according to General Procedure V-c, starting compound 267, as a beige powder in 55% yield. $^1$H-NMR (DMSO-$d_6$, 400 MHz) δ (ppm): 1.29 (d, J 7.1 Hz, 3H, CH—$CH_3$); 1.48-1.66 (m, 4H, $CH_2$); 1.71-1.80 (m, 1H, $CH_aH_b$); 1.80-1.88 (m, 1H, $CH_aH_b$); 2.51-2.60 (m, 2H, $CH_2$); 4.89-4.98 (m, 1H, CONH—CH—$CH_3$); 5.03 (d, J 11.9 Hz, 1H, Ph-O—$CH_2$); 5.06 (d, J 11.9 Hz, 1H, Ph-O—$CH_2$); 6.86-6.93 (m, 2H, Ar); 6.95-6.97 (m, 1H, Ar); 7.18 (d, J 8.2 Hz, 2H, Ar); 7.23 (t, J 8.0 Hz, 1H, Ar); 7.30-7.35 (m, 1H, Ar); 7.36-7.42 (m, 2H, Ar); 7.42-7.46 (m, 2H, Ar); 7.77 (d, J 8.2 Hz, 2H, Ar); 7.79 (d, J 8.2 Hz, 1H, CONH—CH); 12.80 (bs, 1H, $CO_2H$). M/Z $(M+H)^+$: 444

Compound 268: 2-[2-(Cyclohexylmethoxy)phenyl]acetonitrile

Compound 268 was obtained according to General Procedure X, starting from 2-(2-hydroxyphenyl)acetonitrile and bromomethylcyclohexane. In that specific case, the reaction was performed in DMA, the reaction mixture was stirred at 150° C. for 15 min under microwave irradiation. Purification by flash chromatography (Cyclohexane/EtOAc: 100/0 to 95/5) afforded Compound 268 as a yellow oil in 77% yield. M/Z $(M+H)^+$: 230

Compound 269: 2-[2-(Cyclohexylmethoxy)phenyl]acetamide

Compound 269 was obtained according to General Procedure XI-a, starting from Compound 268, as a white powder in 86% yield. M/Z $(M+H)^+$: 248

Compound 270: Methyl 2-[2-(cyclohexylmethoxy)phenyl]acetate

Compound 270 was obtained according to General Procedure XII, starting from Compound 269. Purification by flash chromatography (Cyclohexane/EtOAc: 100/0 to 95/5) afforded Compound 270 as a colorless oil in 93% yield. M/Z $(M+H)^+$: 263

Compound 271: Methyl 1-[2-(cyclohexylmethoxy)phenyl]cyclopentanecarboxylate

Compound 271 was obtained according to General Procedure VIII-a, starting from Compound 270 and 1,4-dibromobutane. Purification by flash chromatography (Cyclohexane/EtOAc: 100/0 to 90/10) afforded Compound 271 as a colorless oil in 45% yield. M/Z $(M[—H—CO_2Me]+H)^+$: 257

Compound 272: 1-[2-(Cyclohexylmethoxy)phenyl]cyclopentanecarboxylic acid

Compound 272 was obtained according to General Procedure V-b, starting from Compound 271, as a white powder in quantitative yield. M/Z $(M[—H—CO_2H]+H)^+$: 257

Compound 273: Methyl 4-[(1S)-1-[[1-[2-(cyclohexylmethoxy)phenyl]cyclopentanecarbonyl]amino]ethyl]benzoate Compound 273 was obtained according to General Procedure I-a, starting from Compound 272 and methyl 4-[(1S)-1-aminoethyl]benzoate. Purification by flash chromatography (Cyclohexane/EtOAc: 100/0 to 80/20) afforded Compound 273 as a colorless oil in 63% yield. M/Z $(M+H)^+$: 464

Example 114: 4-[(1S)-1-[[1-[2-(Cyclohexylmethoxy)phenyl]cyclopentanecarbonyl]amino]ethyl]benzoic acid

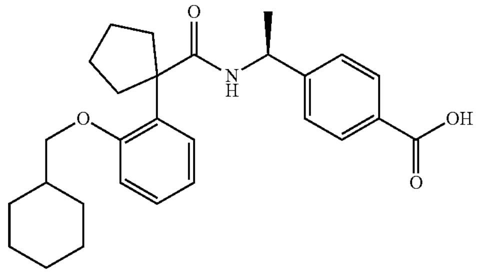 [SMILES: C[C@H](NC(=O)C1(c2ccccc2OCC2CCCCC2)CCCC1)c1ccc(C(=O)O)cc1]

Example 114 was obtained according to General Procedure V-c, starting from Compound 273. Purification by flash chromatography (Cyclohexane/EtOAc: 100/0 to 50/50) afforded Example 114 as a white powder in 56% yield. $^1$H-NMR (DMSO-$d_6$, 400 MHz) δ (ppm): 0.81-0.99 (m, 2H, $CH_2$); 1.05-1.19 (m, 3H, CH, $CH_2$); 1.22 (d, J 7.1 Hz, 3H, CH—$CH_3$); 1.28-1.41 (m, 1H, $CH_aH_b$); 1.45-1.68 (m, 8H, $CH_2$); 1.67-1.83 (m, 2H, $CH_2$); 1.94-2.03 (m, 1H, $CH_aH_b$); 2.18-2.27 (m, 1H, $CH_aH_b$); 2.35-2.45 (m, 1H, $CH_aH_b$); 3.50-3.61 (m, 2H, Ph-O—$CH_2$); 4.89-4.99 (m, 1H, CONH—CH—$CH_3$); 6.81 (d, J 8.1 Hz, 1H, Ar); 6.88-6.95 (m, 2H, Ar+CONH-CH); 7.19-7.25 (m, 3H, Ar); 7.32 (dd, J 8.1, 1.6 Hz, 1H, Ar); 7.80 (d, J 8.2 Hz, 2H, Ar); 12.56 (bs, 1H, $CO_2H$). M/Z $(M+H)^+$: 450

Compound 274: 2-(6-Chloro-2-pyridyl)acetonitrile

Compound 274 was obtained according to General Procedure VII-b, starting from 2,6-dichloropyridine. Purification by flash chromatography (Cyclohexane/EtOAc: 100/0 to 60/40) afforded Compound 274 as a colorless oil in 82% yield. M/Z $(M[^{35}Cl]+H)^+$: 153

Compound 275: 4-(6-Chloro-2-pyridyl)tetrahydropyran-4-carbonitrile

Compound 275 was obtained according to General Procedure VIII-a, starting from Compound 275 and 1-bromo-2-(2-bromoethoxy)ethane. Purification by flash chromatography (Cyclohexane/EtOAc: 100/0 to 80/20) afforded Compound 275 as a yellow powder in 85% yield. M/Z $(M[^{35}Cl]+H)^+$: 223

Compound 276: 4-[6-(Cyclohexylmethoxy)-2-pyridyl]tetrahydropyran-4-carbonitrile

Compound 276 was obtained according to General Procedure VII-c, starting from Compound 275 and cyclohexylmethanol. Purification by flash chromatography (Cyclohexane/EtOAc: 100/0 to 90/10) afforded Compound 276 as a beige powder in 76% yield. M/Z $(M+H)^+$: 301

Compound 277: 4-[6-(Cyclohexylmethoxy)-2-pyridyl]tetrahydropyran-4-carboxamide

Compound 277 was obtained according to General Procedure XI-b, starting from Compound 276, as a yellow powder in 99% yield. M/Z $(M+H)^+$: 319

Compound 278: Methyl 4-[6-(cyclohexylmethoxy)-2-pyridyl]tetrahydropyran-4-carboxylate Compound 278 was obtained according to General Procedure XII, starting from Compound 277. Purification by flash chromatography (Cyclohexane/EtOAc: 100/0 to 80/20) afforded Compound 278 as a colorless oil in 87% yield. M/Z $(M+H)^+$: 334

Compound 279: Lithium 4-[6-(cyclohexylmethoxy)-2-pyridyl]tetrahydropyran-4-carboxylate Compound 279 was obtained according to General Procedure V-a, starting from Compound 278, as a beige powder in 97% yield. M/Z $(M[—H—CO_2H]+H)^+$: 320

Compound 280: Methyl 4-[(1S)-1-[[4-[6-(cyclohexylmethoxy)-2-pyridyl]tetrahydropyran-4-carbonyl]amino]ethyl]benzoate Compound 280 was obtained according to General Procedure I-a, starting from Compound 279 and methyl 4-[(1S)-1-aminoethyl]benzoate. Purification by flash chromatography (Cyclohexane/EtOAc: 100/0 to 50/50) afforded Compound 280 as a colorless oil in 85% yield. M/Z $(M+H)^+$: 481

Example 115: 4-[(1S)-1-[[4-[6-(Cyclohexylmethoxy)-2-pyridyl]tetrahydropyran-4-carbonyl]amino]ethyl]benzoic acid

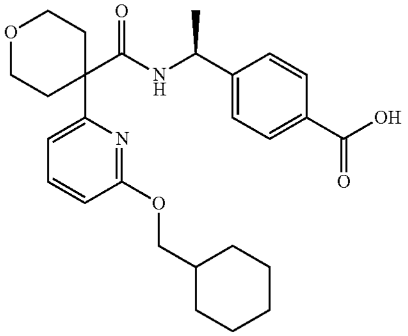

Example 115 was obtained according to General Procedure V-b, starting from Compound 280, as a beige powder in 52% yield. $^1$H-NMR (MeOD-$d_4$, 400 MHz) δ (ppm): 0.96-1.07 (m, 2H, $CH_2$); 1.17-1.34 (m, 3H, CH, $CH_2$); 1.42 (d, J 7.1 Hz, 3H, CH—$CH_3$); 1.65-1.83 (m, 6H, $CH_2$); 2.13-2.20 (m, 1H, $CH_aH_b$); 2.26-2.34 (m, 1H, $CH_aH_b$); 2.38-2.47 (m, 2H, $CH_2$); 3.63-3.79 (m, 4H, O—$CH_2$); 3.94-4.00 (m, 2H, Pyr-O—$CH_2$); 5.02-5.11 (m, 1H, CONH—CH—$CH_3$); 6.66 (d, J 8.2 Hz, 1H, Ar); 6.92 (d, J 7.5 Hz, 1H, Ar); 7.20 (d, J 8.3 Hz, 2H, Ar); 7.20 (dd, J 8.2, 7.5 Hz, 1H, Ar); 7.68 (d, J 8.0 Hz, 1H, CONH—CH); 7.88 (d, J 8.3 Hz, 2H, Ar); $CO_2H$ signal was not observed. M/Z $(M+H)^+$: 467

Compound 281: 2-(2-Chloro-4-pyridyl)acetonitrile

Compound 281 was obtained according to General Procedure VII-b, starting from 2-chloro-4-fluoropyridine. Purification by flash chromatography (Cyclohexane/EtOAc: 100/0 to 50/50) afforded Compound 281 as a white powder in 76% yield. M/Z $(M[^{35}Cl]+H)^+$: 153

Compound 282: 4-(2-Chloro-4-pyridyl)tetrahydropyran-4-carbonitrile

Compound 282 was obtained according to General Procedure VIII-a, starting from Compound 281 and 1-bromo-2-(2-bromoethoxy)ethane. Purification by flash chromatography (Cyclohexane/EtOAc: 100/0 to 50/50) afforded Compound 282 as a white powder in 85% yield. M/Z $(M[^{35}Cl]+H)^+$: 223

Compound 283: 4-[2-(Cyclohexylmethoxy)-4-pyridyl]tetrahydropyran-4-carbonitrile

Compound 283 was obtained according to General Procedure VII-c, starting from Compound 282 and cyclohexylmethanol. Purification by flash chromatography (Cyclohexane/EtOAc: 100/0 to 80/20) afforded Compound 283 as a colorless oil in 91% yield. M/Z $(M+H)^+$: 301

Compound 284: 4-[2-(Cyclohexylmethoxy)-4-pyridyl]tetrahydropyran-4-carboxamide

Compound 284 was obtained according to General Procedure XI-b, starting from Compound 283, as a white powder in 87% yield. M/Z $(M+H)^+$: 319

Compound 285: Methyl 4-[2-(cyclohexylmethoxy)-4-pyridyl]tetrahydropyran-4-carboxylate Compound 285 was obtained according to General Procedure XII, starting from Compound 280. Purification by flash chromatography (Cyclohexane/EtOAc: 100/0 to 80/20) afforded Compound 285 as a yellow oil in 74% yield. M/Z $(M+H)^+$: 334

Compound 286: Lithium 4-[2-(cyclohexylmethoxy)-4-pyridyl]tetrahydropyran-4-carboxylate Compound 286 was obtained according to General Procedure V-a, starting from Compound 285, as a white powder in quantitative yield. M/Z $(M[—H—CO_2H]+H)^+$: 320

Compound 287: Methyl 4-[(1S)-1-[[4-[2-(cyclohexylmethoxy)-4-pyridyl]tetrahydropyran-4-carbonyl]amino]ethyl]benzoate Compound 287 was obtained according to General Procedure I-a, starting from Compound 286 and methyl 4-[(1S)-1-aminoethyl]benzoate. Purification by flash chromatography (Cyclohexane/EtOAc: 100/0 to 50/50) afforded Compound 287 as a colorless oil in 49% yield. M/Z $(M+H)^+$: 481

Example 116: 4-[(1S)-1-[[4-[2-(Cyclohexylmethoxy)-4-pyridyl]tetrahydropyran-4-carbonyl]amino]ethyl]benzoic acid

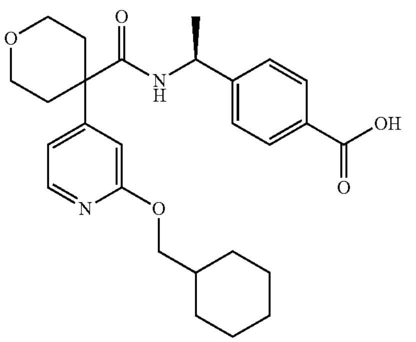

Example 116 was obtained according to General Procedure V-b, starting from Compound 287, as a white powder in 68% yield. $^1$H-NMR (MeOD-$d_4$, 400 MHz) δ (ppm): 1.02-1.12 (m, 2H, $CH_2$); 1.20-1.38 (m, 3H, CH, $CH_2$); 1.40 (d, J 6.9 Hz, 3H, CH—$CH_3$); 1.66-1.97 (m, 7H, $CH_2$+ $CH_aH_b$); 2.10 (ddd, J 14.1, 10.5, 3.8 Hz, 1H, $CH_aH_b$); 2.40-2.50 (m, 2H, $CH_2$); 3.46-3.56 (m, 2H, O—$CH_2$); 3.76-3.89 (m, 2H, O—$CH_2$); 4.01 (d, J 6.2 Hz, 2H, Pyr-O—$CH_2$); 5.04-5.13 (m, 1H, CONH—CH—$CH_3$); 6.69 (d, J 1.6 Hz, 1H, Ar); 6.84 (dd, J 5.6, 1.6 Hz, 1H, Ar); 7.17 (d, J 8.2 Hz, 2H, Ar); 7.87 (d, J 8.2 Hz, 2H, Ar); 7.98 (d, J 7.8 Hz, 1H, CONH—CH); 8.05 (d, J 5.6 Hz, 1H, Ar); $CO_2H$ signal was not observed. M/Z $(M+H)^+$: 467

Compound 288: 2-(4-Bromo-2-pyridyl)acetonitrile

Compound 288 was obtained according to General Procedure VII-b, starting from 4-bromo-2-fluoropyridine. Purification by flash chromatography (Cyclohexane/EtOAc: 100/0 to 60/40) afforded Compound 288 as a white powder in 84% yield. M/Z $(M[^{79}Br]+H)^+$: 197

Compound 289: 4-(4-Bromo-2-pyridyl)tetrahydropyran-4-carbonitrile

Compound 289 was obtained according to General Procedure VIII-a, starting from Compound 288 and 1-bromo-2-(2-bromoethoxy)ethane. Purification by flash chromatography (Cyclohexane/EtOAc: 100/0 to 80/20) afforded Compound 289 as a yellow powder in 82% yield. M/Z $(M[^{79}Br]+H)^+$: 267

Compound 290: 4-[4-(Cyclohexylmethoxy)-2-pyridyl]tetrahydropyran-4-carbonitrile

Compound 290 was obtained according to General Procedure VII-c, starting from Compound 289 and cyclohexylmethanol. Purification by flash chromatography (Cyclohexane/EtOAc: 100/0 to 80/20) afforded Compound 290 as a colorless oil in 67% yield. M/Z $(M+H)^+$: 301

Compound 291: 4-[4-(Cyclohexylmethoxy)-2-pyridyl]tetrahydropyran-4-carboxylic acid Compound 291 was obtained according to General Procedure XI-c, starting from Compound 290, as a white powder in quantitative yield. M/Z $(M[—H—CO_2H]+H)^+$: 320

Compound 292: Methyl 4-[(1S)-1-[[4-[4-(cyclohexylmethoxy)-2-pyridyl]tetrahydropyran-4-carbonyl]amino]ethyl]benzoate Compound 292 was obtained according to General Procedure I-a, starting from Compound 291 and methyl 4-[(1S)-1-aminoethyl]benzoate. Purification by flash chromatography (Cyclohexane/EtOAc: 100/0 to 50/50) afforded Compound 292 as a colorless oil in 49% yield. M/Z $(M+H)^+$: 481

Example 117: 4-[(1S)-1-[[4-[4-(Cyclohexylmethoxy)-2-pyridyl]tetrahydropyran-4-carbonyl]amino]ethyl]benzoic acid

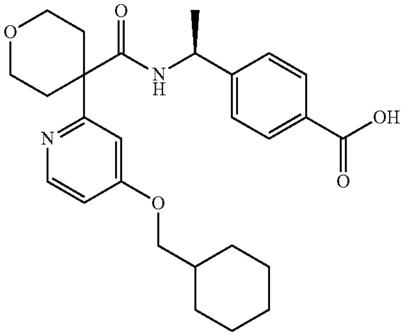 [SMILES: C[C@H](NC(=O)C1(c2cc(OCC3CCCCC3)ccn2)CCOCC1)c1ccc(C(=O)O)cc1]

Example 117 was obtained according to General Procedure V-b, starting from Compound 292, as a white powder in 38% yield. $^1$H-NMR (DMSO-$d_6$, 400 MHz) δ (ppm): 0.94-1.06 (m, 2H, $CH_2$); 1.12-1.28 (m, 3H, CH, $CH_2$); 1.33 (d, J 7.1 Hz, 3H, CH—$CH_3$); 1.61-1.78 (m, 6H, $CH_2$); 1.97 (ddd, J 13.4, 9.5, 3.7 Hz, 1H, $CH_aH_b$); 2.10 (ddd, J 13.4, 9.5, 3.7 Hz, 1H, $CH_aH_b$); 2.29-2.40 (m, 2H, $CH_2$); 3.43-3.53 (m, 2H, O—$CH_2$); 3.60-3.73 (m, 3H, Pyr-O—$CH_2$+O-$CH_2$); 3.77 (dd, J 9.5, 6.3 Hz, 1H, Pyr-O—$CH_2$); 4.97-5.06 (m, 1H, CONH—CH—$CH_3$); 6.73 (d, J 2.3 Hz, 1H, Ar); 6.86 (dd, J 5.7, 2.3 Hz, 1H, Ar); 7.21 (d, J 8.2 Hz, 2H, Ar); 7.77 (d, J 8.2 Hz, 2H, Ar); 7.96 (d, J 8.0 Hz, 1H, CONH—CH); 8.36 (d, J 5.7 Hz, 1H, Ar); $CO_2H$ signal was not observed. M/Z $(M+H)^+$: 467

Compound 293: 4-(5-Bromo-3-pyridyl)tetrahydropyran-4-carbonitrile

Compound 293 was obtained according to General Procedure VIII-a, starting from 2-(5-Bromo-3-pyridyl)acetonitrile and 1-bromo-2-(2-bromoethoxy)ethane. Purification by flash chromatography (Cyclohexane/EtOAc: 100/0 to 50/50) afforded Compound 293 as a yellow powder in 89% yield. M/Z $(M[^{79}Br]+H)^+$: 267

Compound 294: 4-(5-Bromo-3-pyridyl)tetrahydropyran-4-carboxamide

Compound 294 was obtained according to General Procedure XI-b, starting from Compound 293, as a white powder in 61% yield. M/Z $(M[^{79}Br]+H)^+$: 285

Compound 295: Methyl 4-(5-bromo-3-pyridyl)tetrahydropyran-4-carboxylate

Compound 295 was obtained according to General Procedure XII, starting from Compound 294. Purification by flash chromatography (Cyclohexane/EtOAc: 100/0 to 50/50) afforded Compound 295 as a colorless oil in 83% yield. M/Z (M[$^{79}$Br]+H)$^+$: 300

Compound 296: Methyl 4-[5-(cyclohexylmethoxy)-3-pyridyl]tetrahydropyran-4-carboxylate Compound 296 was obtained according to General Procedure XIII, starting from Compound 295 and cyclohexylmethanol. Purification by flash chromatography (Cyclohexane/EtOAc: 100/0 to 50/50) afforded Compound 296 as a orange powder in 63% yield. M/Z (M+H)$^+$: 334

Compound 297: Lithium 4-[5-(cyclohexylmethoxy)-3-pyridyl]tetrahydropyran-4-carboxylate Compound 297 was obtained according to General Procedure V-a, starting from Compound 296, as a white powder in quantitative yield. M/Z (M[—H—$CO_2$H]+H)$^+$: 320

Compound 298: Methyl 4-[(1S)-1-[[4-[5-(cyclohexylmethoxy)-3-pyridyl]tetrahydropyran-4-carbonyl]amino]ethyl]benzoate Compound 298 was obtained according to General Procedure I-a, starting from Compound 297 and methyl 4-[(1S)-1-aminoethyl]benzoate. Purification by flash chromatography (Cyclohexane/EtOAc: 50/50 to 0/100) afforded Compound 298 as a colorless oil in quantitative yield. M/Z (M+H)$^+$: 481

Example 118: 4-[(1S)-1-[[4-[5-(Cyclohexylmethoxy)-3-pyridyl]tetrahydropyran-4-carbonyl]amino]ethyl]benzoic acid

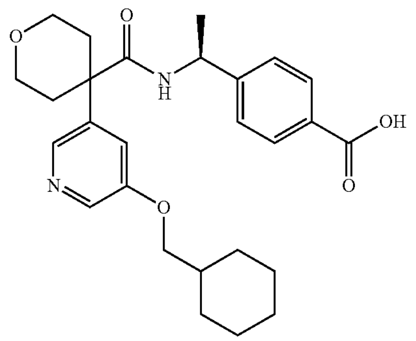

Example 118 was obtained according to General Procedure V-b, starting compound 298, as a white powder in 21% yield. $^1$H-NMR (MeOD-d$_4$, 400 MHz) δ (ppm): 1.01-1.12 (m, 2H, $CH_2$); 1.21-1.38 (m, 3H, CH, $CH_2$); 1.41 (d, J 7.1 Hz, 3H, CH—$CH_3$); 1.67-1.87 (m, 6H, $CH_2$); 1.90 (ddd, J 14.0, 10.7, 4.2 Hz, 1H, $CH_aH_b$); 2.20 (ddd, J 14.0, 10.7, 4.2 Hz, 1H, $CH_aH_b$); 2.44-2.56 (m, 2H, $CH_2$); 3.58-3.69 (m, 3H, O-$CH_2$+O-$CH_aH_b$); 3.73 (dd, J 9.1, 6.4 Hz, 1H, O—$CH_aH_b$); 3.77 (dd, J 11.7, 3.8 Hz, 1H, Pyr-O—$CH_2$); 3.91 (dd, J 11.7, 3.8 Hz, 1H, Pyr-O—$CH_2$); 5.05-5.12 (m, 1H, CONH—CH—$CH_3$); 7.14 (d, J 8.2 Hz, 2H, Ar); 7.16 (t, J 2.4 Hz, 1H, Ar); 7.86 (d, J 8.2 Hz, 2H, Ar); 8.06 (d, J 8.0 Hz, 1H, CONH—CH); 8.14 (d, J 2.4 Hz, 1H, Ar); 8.16 (d, J 2.4 Hz, 1H, Ar); $CO_2$H signal was not observed. M/Z (M+H)$^+$: 467

Compound 299: 2-(5-Bromo-2-pyridyl)acetonitrile

Compound 299 was obtained according to General Procedure VII-b, starting from 5-bromo-2-fluoropyridine. Purification by flash chromatography (Cyclohexane/EtOAc: 100/0 to 60/40) afforded Compound 299 as a yellow oil in 81% yield. M/Z (M[$^{79}$Br]+H)$^+$: 197

Compound 300: 4-(5-Bromo-2-pyridyl)tetrahydropyran-4-carbonitrile

Compound 300 was obtained according to General Procedure VIII-a, starting from Compound 299 and 1-bromo-2-(2-bromoethoxy)ethane. Purification by flash chromatography (Cyclohexane/EtOAc: 100/0 to 80/20) afforded Compound 300 as a yellow oil in 86% yield. M/Z (M[$^{79}$Br]+H)$^+$: 267

Compound 301: 4-(5-Bromo-2-pyridyl)tetrahydropyran-4-carboxamide

Compound 301 was obtained according to General Procedure XI-b, starting from Compound 300, as a white powder in 88% yield. M/Z (M[$^{79}$Br]+H)$^+$: 285

Compound 302: Methyl 4-(5-bromo-2-pyridyl)tetrahydropyran-4-carboxylate

Compound 302 was obtained according to General Procedure XII, starting from Compound 301. Purification by flash chromatography (Cyclohexane/EtOAc: 100/0 to 80/20) afforded Compound 302 as a white powder in 96% yield. M/Z (M[$^{79}$Br]+H)$^+$: 300

Compound 303: Methyl 4-[5-(cyclohexylmethoxy)-2-pyridyl]tetrahydropyran-4-carboxylate Compound 303 was obtained according to General Procedure XIII, starting from Compound 302 and cyclohexylmethanol. Purification by flash chromatography (Cyclohexane/EtOAc: 100/0 to 80/20) afforded Compound 303 as a yellow oil in quantitative yield. M/Z (M+H)$^+$: 334

Compound 304: Lithium 4-[5-(cyclohexylmethoxy)-2-pyridyl]tetrahydropyran-4-carboxylate Compound 304 was obtained according to General Procedure V-a, starting from Compound 303, as a white powder in quantitative yield. M/Z (M[—H—$CO_2$H]+H)$^+$: 320

Compound 305: Methyl 4-[(1S)-1-[[4-[5-(cyclohexylmethoxy)-2-pyridyl]tetrahydropyran-4-carbonyl]amino]ethyl]benzoate Compound 305 was obtained according to General Procedure I-a, starting from Compound 304 and methyl 4-[(1S)-1-aminoethyl]benzoate. Purification by flash chromatography (Cyclohexane/EtOAc: 100/0 to 50/50) afforded Compound 305 as a colorless oil in 50% yield. M/Z (M+H)$^+$: 481

Example 119: 4-[(1S)-1-[[4-[5-(Cyclohexylmethoxy)-2-pyridyl]tetrahydropyran-4-carbonyl]amino]ethyl]benzoic acid

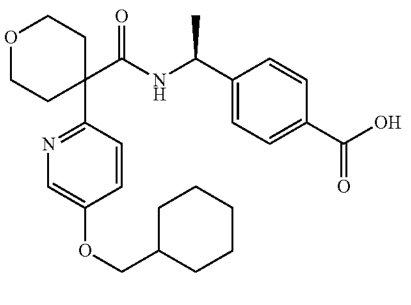 [SMILES: C[C@H](NC(=O)C1(c2ccc(OCC3CCCCC3)cn2)CCOCC1)c1ccc(C(=O)O)cc1]

Example 119 was obtained according to General Procedure V-b, starting from Compound 305. Purification by flash chromatography (Cyclohexane/EtOAc: 50/50 to 0/100 then DCM/MeOH: 80/20) afforded Example 119 as a white powder in 37% yield. $^1$H-NMR (DMSO-d$_6$, 400 MHz) δ (ppm): 0.99-1.10 (m, 2H, $CH_2$); 1.14-1.29 (m, 3H, CH, $CH_2$); 1.31 (d, J 7.2 Hz, 3H, CH—$CH_3$); 1.61-1.84 (m, 6H, $CH_2$); 2.02 (ddd, J 13.3, 9.3, 3.5 Hz, 1H, $CH_aH_b$); 2.10 (ddd, J 13.3, 9.3, 3.5 Hz, 1H, $CH_aH_b$); 2.32-2.41 (m, 2H, $CH_2$); 3.43-3.51 (m, 2H, O—$CH_2$); 3.57-3.67 (m, 2H, O—$CH_2$); 3.85 (d, J 6.3 Hz, 2H, Pyr-O—$CH_2$); 4.94-5.03 (m, 1H, CONH—CH—$CH_3$); 7.19 (d, J 8.2 Hz, 2H, Ar); 7.24 (d, J 8.8 Hz, 1H, Ar); 7.34 (dd, J 8.8, 3.0 Hz, 1H, Ar); 7.78 (d, J 8.2 Hz, 2H, Ar); 7.86 (d, J 8.0 Hz, 1H, CONH—CH); 8.26 (d, J 3.0 Hz, 1H, Ar); $CO_2H$ signal was not observed. M/Z $(M+H)^+$: 467

Compound 306: Methyl 4-[5-(2-cyclohexylethoxy)-2-pyridyl]tetrahydropyran-4-carboxylate Compound 306 was obtained according to General Procedure XIII, starting from Compound 302 and 2-cyclohexylethanol. Purification by flash chromatography (Cyclohexane/EtOAc: 100/0 to 80/20) afforded Compound 306 as a yellow oil in quantitative yield. M/Z $(M+H)^+$: 348

Compound 307: Lithium 4-[5-(2-cyclohexylethoxy)-2-pyridyl]tetrahydropyran-4-carboxylate Compound 307 was obtained according to General Procedure V-a, starting from Compound 306, as a white powder in quantitative yield. M/Z $(M[—H—CO_2H]+H)^+$: 334

Compound 308: Methyl 4-[(1S)-1-[[4-[5-(2-cyclohexylethoxy)-2-pyridyl]tetrahydropyran-4-carbonyl]amino]ethyl]benzoate Compound 308 was obtained according to General Procedure I-a, starting from Compound 307 and methyl 4-[(1S)-1-aminoethyl]benzoate. Purification by flash chromatography (Cyclohexane/EtOAc: 100/0 to 50/50) afforded Compound 308 as a colorless oil in 64% yield. M/Z $(M+H)^+$: 495

Example 120: 4-[(1S)-1-[[4-[5-(2-Cyclohexylethoxy)-2-pyridyl]tetrahydropyran-4-carbonyl]amino]ethyl]benzoic acid

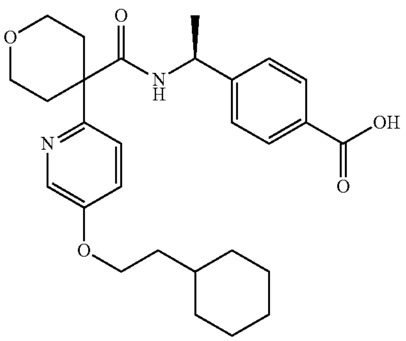 [SMILES: C[C@H](NC(=O)C1(c2ccc(OCCC3CCCCC3)cn2)CCOCC1)c1ccc(C(=O)O)cc1]

Example 120 was obtained according to General Procedure V-b, starting from Compound 308. Purification by flash chromatography (DCM/MeOH: 100/0 to 90/100) afforded Example 120 as a beige powder in 70% yield. $^1$H-NMR (DMSO-d$_6$, 400 MHz) δ (ppm): 0.90-1.01 (m, 2H, $CH_2$); 1.09-1.28 (m, 3H, CH, $CH_2$); 1.31 (d, J 7.2 Hz, 3H, CH—$CH_3$); 1.41-1.52 (m, 1H, $CH_aH_b$); 1.57-1.77 (m, 7H, $CH_2$+$CH_aH_b$); 2.02 (ddd, J 13.4, 9.3, 3.5 Hz, 1H, $CH_aH_b$); 2.10 (ddd, J 13.4, 9.3, 3.5 Hz, 1H, $CH_aH_b$); 2.31-2.41 (m, 2H, $CH_2$); 3.41-3.53 (m, 2H, O—$CH_2$); 3.57-3.68 (m, 2H, O—$CH_2$); 4.08 (t, J 6.6 Hz, 2H, Pyr-O—$CH_2$); 4.94-5.03 (m, 1H, CONH—CH—$CH_3$); 7.21 (d, J 8.2 Hz, 2H, Ar); 7.25 (d, J 8.8 Hz, 1H, Ar); 7.34 (dd, J 8.8, 3.0 Hz, 1H, Ar); 7.78 (d, J 8.2 Hz, 2H, Ar); 7.87 (d, J 8.0 Hz, 1H, CONH—CH); 8.26 (d, J 3.0 Hz, 1H, Ar); 12.75 (bs, 1H, $CO_2H$). M/Z $(M+H)^+$: 481

Compound 309: (6-Bromo-3-pyridyl)methyl methanesulfonate

To a solution of 6-bromopyridine-3-methanol (1 equiv.) in THF (0.2 M) at 0° C. were added DIPEA (1.1 equiv.) and methane sulfonyl chloride (1.1 equiv.). The reaction mixture was stirred at rt for 1 h. The reaction mixture was hydrolyzed with water, extracted with DCM, dried, then concentrated to afford Compound 309 as a yellow powder in quantitative yield. M/Z $(M[^{79}Br]+H)^+$: 266

Compound 310: 2-(6-Bromo-3-pyridyl)acetonitrile

To a solution of Compound 309 (1 equiv.) in DMSO (0.1 M) was added potassium cyanide (1.5 equiv.). The reaction mixture was stirred overnight at rt. The reaction mixture was hydrolyzed with a saturated solution of sodium bicarbonate, extracted with EtOAc. The organic layer was washed with brine, dried, then concentrated. Purification by flash chromatography (Cyclohexane/EtOAc: 100/0 to 50/50) afforded Compound 310 as a yellow powder in 73% yield. M/Z $(M[^{79}Br]+H)^+$: 197

Compound 311: 4-(6-Bromo-3-pyridyl)tetrahydropyran-4-carbonitrile

Compound 311 was obtained according to General Procedure VIII-a, starting from Compound 310 and 1-bromo-2-(2-bromoethoxy)ethane. Purification by flash chromatography (Cyclohexane/EtOAc: 100/0 to 50/50) afforded Compound 311 as a yellow powder in 87% yield. M/Z $(M[^{79}Br]+H)^+$: 267

Compound 312: 4-[6-(Cyclohexylmethoxy)-3-pyridyl]tetrahydropyran-4-carbonitrile

Compound 312 was obtained according to General Procedure VII-c, starting from Compound 311 and cyclohexylmethanol. Purification by flash chromatography (Cyclohexane/EtOAc: 100/0 to 90/10) afforded Compound 312 as a white powder in 83% yield. M/Z $(M+H)^+$: 301

Compound 313: 4-[6-(Cyclohexylmethoxy)-3-pyridyl]tetrahydropyran-4-carboxamide

Compound 313 was obtained according to General Procedure XI-b, starting from Compound 312, as a white powder in 88% yield. M/Z $(M+H)^+$: 319

Compound 314: Methyl 4-[6-(cyclohexylmethoxy)-3-pyridyl]tetrahydropyran-4-carboxylate Compound 314 was obtained according to General Procedure XII, starting from Compound 313. Purification by flash chromatography (Cyclohexane/EtOAc: 100/0 to 80/20) afforded Compound 314 as a white powder in 88% yield. M/Z $(M+H)^+$: 334

Compound 315: Lithium 4-[6-(Cyclohexylmethoxy)-3-pyridyl]tetrahydropyran-4-carboxylate Compound 315 was obtained according to General Procedure V-a, starting from Compound 314, as a white powder in quantitative yield. M/Z $(M[—H—CO_2H]+H)^+$: 320

Compound 316: Methyl 4-[(1S)-1-[[4-[6-(cyclohexylmethoxy)-3-pyridyl]tetrahydropyran-4-carbonyl]amino]ethyl]benzoate Compound 316 was obtained according to General Procedure I-a, starting from Compound 315 and methyl 4-[(1S)-1-aminoethyl]benzoate. Purification by flash chromatography (Cyclohexane/EtOAc: 100/0 to 50/50) afforded Compound 316 as a colorless oil in 71% yield. M/Z $(M+H)^+$: 481

Example 121: 4-[(1S)-1-[[4-[6-(Cyclohexylmethoxy)-3-pyridyl]tetrahydropyran-4-carbonyl]amino]ethyl]benzoic acid

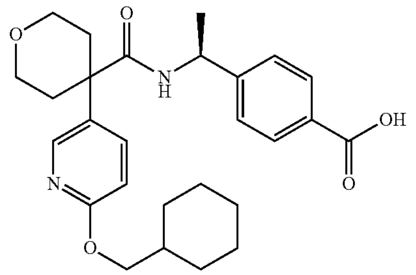 [SMILES: C[C@H](NC(=O)C1(c2ccc(OCC3CCCCC3)nc2)CCOCC1)c1ccc(C(=O)O)cc1]

Example 121 was obtained according to General Procedure V-b, starting from Compound 316, as a beige powder in 61% yield. $^1$H-NMR (DMSO-$d_6$, 400 MHz) δ (ppm): 0.96-1.08 (m, 2H, $CH_2$); 1.14-1.28 (m, 3H, CH, $CH_2$); 1.31 (d, J 7.2 Hz, 3H, CH—$CH_3$); 1.60-1.84 (m, 7H, $CH_2$+$CH_aH_b$); 1.92 (ddd, J 13.8, 10.6, 3.4 Hz, 1H, $CH_aH_b$); 2.40-2.49 (m, 2H, $CH_2$); 3.37-3.48 (m, 2H, O—$CH_2$); 3.67-3.78 (m, 2H, O—$CH_2$); 4.01-4.10 (m, 2H, Pyr-O—$CH_2$); 5.00 (quint, J 7.2 Hz, 1H, CONH—CH—$CH_3$); 6.76 (d, J 8.8 Hz, 1H, Ar); 7.16 (d, J 8.2 Hz, 2H, Ar); 7.59 (dd, J 8.8, 2.7 Hz, 1H, Ar); 7.77 (d, J 8.2 Hz, 2H, Ar); 8.00 (d, J 8.0 Hz, 1H, CONH—CH); 8.09 (d, J 2.7 Hz, 1H, Ar); 12.80 (bs, 1H, $CO_2H$). M/Z $(M+H)^+$: 467

Compound 317: 4-[6-(2-Cyclohexylethoxy)-3-pyridyl]tetrahydropyran-4-carbonitrile Compound 317 was obtained according to General Procedure VII-c, starting from Compound 311 and 2-cyclohexylethanol. Purification by flash chromatography (Cyclohexane/EtOAc: 100/0 to 90/10) afforded Compound 317 as colorless oil in 98% yield. M/Z $(M+H)^+$: 315

Compound 318: 4-[6-(2-Cyclohexylethoxy)-3-pyridyl]tetrahydropyran-4-carboxamide

Compound 318 was obtained according to General Procedure XI-b, starting from Compound 317, as a white powder in 78% yield. M/Z $(M+H)^+$: 333

Compound 319: Methyl 4-[6-(2-cyclohexylethoxy)-3-pyridyl]tetrahydropyran-4-carboxylate Compound 319 was obtained according to General Procedure XII, starting from Compound 318. Purification by flash chromatography (Cyclohexane/EtOAc: 100/0 to 80/20) afforded Compound 319 as a colorless oil in 94% yield. M/Z $(M+H)^+$: 348

Compound 320: Lithium 4-[6-(2-cyclohexylethoxy)-3-pyridyl]tetrahydropyran-4-carboxylate Compound 320 was obtained according to General Procedure V-a, starting from Compound 319, as a white powder in quantitative yield. M/Z $(M[—H—CO_2H]+H)^+$: 334

Compound 321: Methyl 4-[(1S)-1-[[4-[6-(2-cyclohexylethoxy)-3-pyridyl]tetrahydropyran-4-carbonyl]amino]ethyl]benzoate Compound 321 was obtained according to General Procedure I-a, starting from Compound 320 and methyl 4-[(1S)-1-aminoethyl]benzoate. Purification by flash chromatography (Cyclohexane/EtOAc: 100/0 to 50/50) afforded Compound 321 as a colorless oil in 81% yield. M/Z $(M+H)^+$: 495

Example 122: 4-[(1S)-1-[[4-[6-(2-Cyclohexylethoxy)-3-pyridyl]tetrahydropyran-4-carbonyl]amino]ethyl]benzoic acid

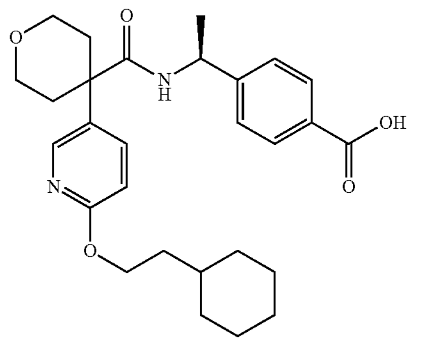 [SMILES: C[C@H](NC(=O)C1(c2ccc(OCCC3CCCCC3)nc2)CCOCC1)c1ccc(C(=O)O)cc1]

Example 122 was obtained according to General Procedure V-b, starting from Compound 321, as a white powder in 64% yield. $^1$H-NMR (DMSO-$d_6$, 400 MHz) δ (ppm): 0.89-0.99 (m, 2H, $CH_2$); 1.07-1.27 (m, 3H, CH, $CH_2$); 1.31 (d, J 7.2 Hz, 3H, CH—$CH_3$); 1.38-1.48 (m, 1H, $CH_aH_b$); 1.57-1.75 (m, 7H, $CH_2$+$CH_aH_b$); 1.80 (ddd, J 13.8, 10.6, 3.4 Hz, 1H, $CH_aH_b$); 1.92 (ddd, J 13.8, 10.6, 3.4 Hz, 1H, $CH_aH_b$); 2.42-2.49 (m, 2H, $CH_2$); 3.37-3.47 (m, 2H, O—$CH_2$); 3.67-3.78 (m, 2H, O—$CH_2$); 4.23-4.33 (m, 2H, Pyr-O—$CH_2$); 4.95-5.05 (m, 1H, CONH—CH—$CH_3$); 6.75 (d, J 8.7 Hz, 1H, Ar); 7.16 (d, J 8.2 Hz, 2H, Ar); 7.59 (dd, J 8.7, 2.7 Hz, 1H, Ar); 7.76 (d, J 8.2 Hz, 2H, Ar); 8.01 (d, J 7.8 Hz, 1H, CONH—CH); 8.10 (d, J 2.7 Hz, 1H, Ar); 12.76 (bs, 1H, $CO_2H$). M/Z $(M+H)^+$: 481

Compound 322: 1-(6-Chloro-2-pyridyl)cyclopentanecarbonitrile

Compound 322 was obtained according to General Procedure VII-a, starting from Compound 2,6-dichloropyridine and cyclopentanecarbonitrile. Purification by flash chromatography (Cyclohexane/EtOAc: 100/0 to 95/5) afforded Compound 322 as a white powder in quantitative yield. M/Z $(M[^{35}Cl]+H)^+$: 207

Compound 323: 4-[6-(Cyclohexylmethoxy)-2-pyridyl]cyclopentanecarbonitrile

Compound 323 was obtained according to General Procedure VII-c, starting from Compound 322 and cyclohexylmethanol. Purification by flash chromatography (Cyclohexane/EtOAc: 100/0 to 97/3) afforded Compound 323 as a beige powder in 60% yield. M/Z $(M+H)^+$: 285

Compound 324: 1-[6-(Cyclohexylmethoxy)-2-pyridyl]cyclopentanecarboxylic acid

Compound 324 was obtained according to General Procedure XI-c, starting from Compound 323, as a white powder in quantitative yield. M/Z $(M+H)^+$: 304

Compound 325: Methyl 4-[(1S)-1-[[1-[6-(cyclohexylmethoxy)-2-pyridyl]cyclopentanecarbonyl]amino]ethyl]benzoate Compound 325 was obtained according to General Procedure I-a, starting from Compound 324 and methyl 4-[(1S)-

1-aminoethyl]benzoate. Purification by flash chromatography (Cyclohexane/EtOAc: 100/0 to 80/20) afforded Compound 325 as a colorless oil in 67% yield. M/Z $(M+H)^+$: 465

Example 123: 4-[(1S)-1-[[1-[6-(Cyclohexylmethoxy)-2-pyridyl]cyclopentanecarbonyl]amino]ethyl]benzoic acid

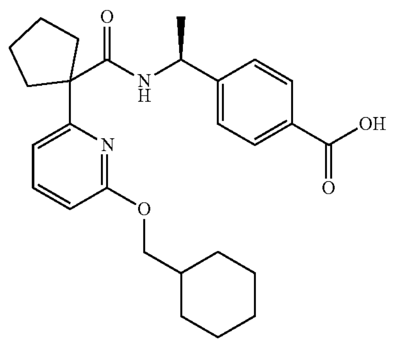 [SMILES: C[C@H](NC(=O)C1(c2cccc(OCC3CCCCC3)n2)CCCC1)c1ccc(C(=O)O)cc1]

Example 123 was obtained according to General Procedure V-b, starting from Compound 325, as a beige powder in 46% yield. $^1$H-NMR (DMSO-$d_6$, 400 MHz) δ (ppm): 0.93-1.05 (m, 2H, $CH_2$); 1.12-1.26 (m, 3H, CH, $CH_2$); 1.32 (d, J 7.1 Hz, 3H, CH—$CH_3$); 1.54-1.79 (m, 10H, $CH_2$); 2.01-2.18 (m, 2H, $CH_2$): 2.27-2.39 (m, 2H, $CH_2$); 3.97-4.04 (m, 2H, Pyr-O—$CH_2$); 4.94-5.01 (m, 1H, CONH—CH—$CH_3$); 6.63 (d, J 8.1 Hz, 1H, Ar); 6.84 (d, J 7.3 Hz, 1H, Ar); 7.27 (d, J 8.3 Hz, 2H, Ar); 7.20 (dd, J 8.1, 7.3 Hz, 1H, Ar); 7.69 (d, J 8.0 Hz, 1H, CONH—CH); 7.81 (d, J 8.3 Hz, 2H, Ar); $CO_2H$ signal was not observed. M/Z $(M+H)^+$: 451

Compound 326: 1-(2-Chloro-4-pyridyl)cyclopentanecarbonitrile

Compound 326 was obtained according to General Procedure VII-a, starting from 2-chloro-4-fluoropyridine and cyclopentanecarbonitrile. Purification by flash chromatography (Cyclohexane/EtOAc: 100/0 to 80/20) afforded Compound 326 as a colorless oil in 68% yield. M/Z $(M[^{35}Cl]+H)^+$: 207

Compound 327: 4-[2-(Cyclohexylmethoxy)-4-pyridyl]cyclopentanecarbonitrile

Compound 327 was obtained according to General Procedure VII-c, starting from Compound 326 and cyclohexylmethanol. Purification by flash chromatography (Cyclohexane/EtOAc: 100/0 to 90/10) afforded Compound 327 as a yellow oil in 70% yield. M/Z $(M+H)^+$: 285

Compound 328: 1-[2-(Cyclohexylmethoxy)-4-pyridyl]cyclopentanecarboxylic acid

Compound 328 was obtained according to General Procedure XI-c, starting from Compound 327, as a white powder in quantitative yield. M/Z $(M+H)^+$: 304

Compound 329: Methyl 4-[(1S)-1-[[1-[2-(Cyclohexylmethoxy)-4-pyridyl]cyclopentanecarbonyl]amino]ethyl]benzoate Compound 329 was obtained according to General Procedure I-a, starting from Compound 328 and methyl 4-[(1S)-

1-aminoethyl]benzoate. Purification by flash chromatography (Cyclohexane/EtOAc: 100/0 to 80/20) afforded Compound 329 as a colorless oil in 31% yield. M/Z $(M+H)^+$: 465

Example 124: 4-[(1S)-1-[[1-[2-(Cyclohexylmethoxy)-4-pyridyl]cyclopentanecarbonyl]amino]ethyl]benzoic acid

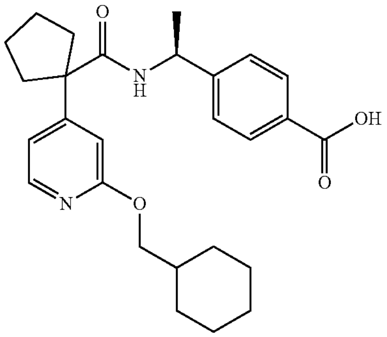 [SMILES: C[C@H](NC(=O)C1(c2ccnc(OCC3CCCCC3)c2)CCCC1)c1ccc(C(=O)O)cc1]

Example 124 was obtained according to General Procedure V-b, starting from Compound 329, as a white powder in 69% yield. $^1$H-NMR (DMSO-$d_6$, 400 MHz) δ (ppm): 0.96-1.07 (m, 2H, $CH_2$); 1.13-1.27 (m, 3H, CH, $CH_2$); 1.29 (d, J 7.1 Hz, 3H, CH—$CH_3$); 1.50-1.81 (m, 11H, $CH_2$+$CH_aH_b$); 1.82-1.90 (m, 1H, $CH_aH_b$); 2.42-2.59 (m, 2H, $CH_2$); 4.04 (d, J 6.3 Hz, 2H, Pyr-O—$CH_2$); 4.90-4.98 (m, 1H, CONH—CH—$CH_3$); 6.66 (d, J 1.5 Hz, 1H, Ar); 6.84 (dd, J 5.4, 1.5 Hz, 1H, Ar); 7.20 (d, J 8.2 Hz, 2H, Ar); 7.78 (d, J 8.2 Hz, 2H, Ar); 7.95 (d, J 7.8 Hz, 1H, CONH—CH); 8.03 (d, J 5.4 Hz, 1H, Ar); $CO_2H$ signal was not observed. M/Z $(M+H)^+$: 451

Compound 330: 1-(4-Bromo-2-pyridyl)cyclopentanecarbonitrile

Compound 330 was obtained according to General Procedure VII-a, starting from 4-bromo-2-fluoropyridine and cyclopentanecarbonitrile. Purification by flash chromatography (Cyclohexane/EtOAc: 100/0 to 90/10) afforded Compound 330 as a colorless oil in 54% yield. M/Z $(M[^{79}Br]+H)^+$: 251

Compound 331: 4-[4-(Cyclohexylmethoxy)-2-pyridyl]cyclopentanecarbonitrile

Compound 331 was obtained according to General Procedure VII-c, starting from Compound 330 and cyclohexylmethanol. Purification by flash chromatography (Cyclohexane/EtOAc: 100/0 to 80/20) afforded Compound 331 as a yellow oil in 70% yield. M/Z $(M+H)^+$: 285

Compound 332: 1-[4-(Cyclohexylmethoxy)-2-pyridyl]cyclopentanecarboxamide

Compound 332 was obtained according to General Procedure XI-b, starting from Compound 331, as a white powder in 56% yield. M/Z $(M+H)^+$: 303

Compound 333: Methyl 1-[4-(cyclohexylmethoxy)-2-pyridyl]cyclopentanecarboxate

Compound 333 was obtained according to General Procedure XII, starting from Compound 332. Purification by flash chromatography (Cyclohexane/EtOAc: 100/0 to 50/50) afforded Compound 333 as a yellow oil in 50% yield. M/Z $(M+H)^+$: 318

Compound 334: Lithium 4-[4-(cyclohexylmethoxy)-2-pyridyl]tetrahydropyran-4-carboxylate Compound 334 was obtained according to General Procedure V-a, starting from Compound 333, as a white powder in quantitative yield. M/Z $(M[—H—CO_2H]+H)^+$: 304

Compound 335: Methyl 4-[(1S)-1-[[1-[4-(cyclohexylmethoxy)-2-pyridyl]cyclopentanecarbonyl]amino]ethyl]benzoate Compound 335 was obtained according to General Procedure I-a, starting from Compound 334 and methyl 4-[(1S)-1-aminoethyl]benzoate. Purification by flash chromatography (Cyclohexane/EtOAc: 100/0 to 70/30) afforded Compound 335 as a colorless oil in 39% yield. M/Z $(M+H)^+$: 465

Example 125: 4-[(1S)-1-[[1-[4-(Cyclohexylmethoxy)-2-pyridyl]cyclopentanecarbonyl]amino]ethyl]benzoic acid

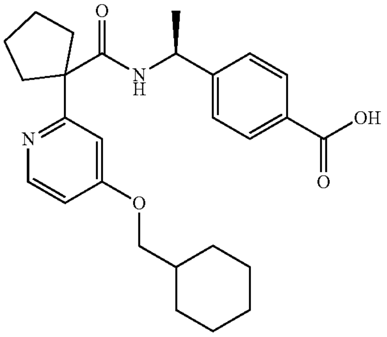 [SMILES: C[C@H](NC(=O)C1(c2cc(OCC3CCCCC3)ccn2)CCCC1)c1ccc(C(=O)O)cc1]

Example 125 was obtained according to General Procedure V-b, starting from Compound 335, as a grey powder in 62% yield. $^1$H-NMR (DMSO-$d_6$, 400 MHz) δ (ppm): 0.94-1.07 (m, 2H, $CH_2$); 1.13-1.27 (m, 3H, CH, $CH_2$); 1.30 (d, J 7.1 Hz, 3H, CH—$CH_3$); 1.51-1.78 (m, 10H, $CH_2$); 1.92-2.00 (m, 1H, $CH_aH_b$); 2.21-2.34 (m, 2H, $CH_2$); 2.38-2.46 (m, 1H, $CH_aH_b$); 3.68 (dd, J 9.3, 6.3 Hz, 1H, Pyr-O—$CH_2$); 3.76 (dd, J 9.3, 6.3 Hz, 1H, Pyr-O—$CH_2$); 4.92-5.01 (m, 1H, CONH—CH—$CH_3$); 6.67 (d, J 2.2 Hz, 1H, Ar); 6.83 (dd, J 5.7, 2.2 Hz, 1H, Ar); 7.24 (d, J 8.3 Hz, 2H, Ar); 7.79 (d, J 8.3 Hz, 2H, Ar); 7.82 (d, J 8.1 Hz, 1H, CONH—CH); 8.33 (d, J 5.7 Hz, 1H, Ar); $CO_2H$ signal was not observed. M/Z $(M+H)^+$: 451

Compound 336: 4-(5-Bromo-3-pyridyl)cyclopentanecarbonitrile

Compound 336 was obtained according to General Procedure VIII-a, starting from 2-(5-Bromo-3-pyridyl)acetonitrile and 1,4-dibromoethane. Purification by flash chromatography (Cyclohexane/EtOAc: 100/0 to 80/20) afforded Compound 336 as a colorless oil in 81% yield. M/Z $(M[^{79}Br]+H)^+$: 251

Compound 337: 4-(5-Bromo-3-pyridyl)cyclopentanecarboxamide

Compound 337 was obtained according to General Procedure XI-b, starting from Compound 336, as a white powder in 55% yield. M/Z $(M[^{79}Br]+H)^+$: 269

Compound 338: Methyl 4-(5-bromo-3-pyridyl)cyclopentanecarboxylate

Compound 338 was obtained according to General Procedure XII, starting from Compound 337. Purification by flash chromatography (Cyclohexane/EtOAc: 100/0 to 70/30) afforded Compound 338 as a colorless oil in 69% yield. M/Z (M[19Br]+H)$^+$: 284

Compound 339: Methyl 4-[5-(cyclohexylmethoxy)-3-pyridyl]cyclopentanecarboxylate

Compound 339 was obtained according to General Procedure XIII, starting from Compound 338 and cyclohexylmethanol. Purification by flash chromatography (Cyclohexane/EtOAc: 100/0 to 70/30) afforded Compound 339 as a colorless oil in 61% yield. M/Z $(M+H)^+$: 318

Compound 340: Lithium 4-[5-(cyclohexylmethoxy)-3-pyridyl]cyclopentanecarboxylate Compound 340 was obtained according to General Procedure V-a, starting from Compound 339, as a beige powder in quantitative yield. M/Z $(M+H)^+$: 304

Compound 341: Methyl 4-[(1S)-1-[[1-[5-(cyclohexylmethoxy)-3-pyridyl]cyclopentanecarbonyl]amino]ethyl]benzoate Compound 341 was obtained according to General Procedure I-a, starting from Compound 340 and methyl 4-[(1S)-1-aminoethyl]benzoate. Purification by flash chromatography (Cyclohexane/EtOAc: 100/0 to 50/50) afforded Compound 341 as a colorless oil in 52% yield. M/Z $(M+H)^+$: 465

Example 126: 4-[(1S)-1-[[1-[5-(Cyclohexylmethoxy)-3-pyridyl]cyclopentanecarbonyl]amino]ethyl]benzoic acid

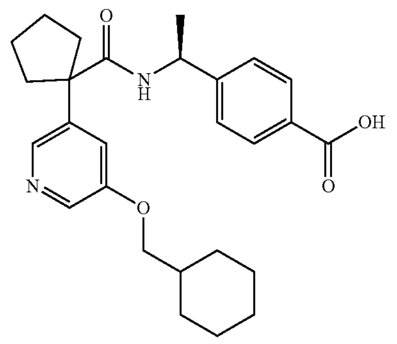 [SMILES: C[C@H](NC(=O)C1(c2cncc(OCC3CCCCC3)c2)CCCC1)c1ccc(C(=O)O)cc1]

Example 126 was obtained according to General Procedure V-b, starting from Compound 341, as a beige powder in 46% yield. $^1H$-NMR (DMSO-$d_6$, 400 MHz) δ (ppm): 0.97-1.08 (m, 2H, $CH_2$); 1.14-1.28 (m, 3H, CH, $CH_2$); 1.29 (d, J 7.1 Hz, 3H, CH—$CH_3$); 1.54-1.82 (m, 10H, $CH_2$); 1.88-1.97 (m, 1H, $CH_aH_b$); 2.51-2.63 (m, 3H, $CH_2$+$CH_aH_b$); 3.72 (dd, J 9.2, 6.3 Hz, 1H, Pyr-O—$CH_2$); 3.79 (dd, J 9.2, 6.3 Hz, 1H, Pyr-O—$CH_2$); 4.89-4.98 (m, 1H, CONH—CH—$CH_3$); 7.13 (bs, 1H, Ar); 7.17 (d, J 8.2 Hz, 2H, Ar); 7.77 (d, J 8.2 Hz, 2H, Ar); 7.96 (d, J 8.0 Hz, 1H, CONH—CH); 8.11-8.16 (m, 2H, Ar); $CO_2H$ signal was not observed. M/Z $(M+H)^+$: 451

Compound 342: 4-(5-Bromo-2-pyridyl)cyclopentanecarbonitrile

Compound 342 was obtained according to General Procedure VIII-a, starting from Compound 241 and 1,4-dibromoethane. Purification by flash chromatography (Cyclohexane/EtOAc: 100/0 to 95/5) afforded Compound 342 as a white powder in 89% yield. M/Z (M[$^{7\prime}$Br]+H)$^+$: 251

Compound 343: 4-(5-Bromo-2-pyridyl)cyclopentanecarboxamide

Compound 343 was obtained according to General Procedure XI-b, starting from Compound 342, as a white powder in 87% yield. M/Z (M[?Br]+H)$^+$: 269

Compound 344: Methyl 4-(5-bromo-2-pyridyl)cyclopentanecarboxylate

Compound 344 was obtained according to General Procedure XII, starting from Compound 343. Purification by flash chromatography (Cyclohexane/EtOAc: 100/0 to 90/10) afforded Compound 344 as a colorless oil in 91% yield. M/Z $(M[^{79}Br]+H)^+$: 284

Compound 345: Methyl 4-[5-(cyclohexylmethoxy)-2-pyridyl]cyclopentanecarboxylate

Compound 345 was obtained according to General Procedure XIII, starting from Compound 344 and cyclohexylmethanol. Purification by flash chromatography (Cyclohexane/EtOAc: 100/0 to 90/10) afforded Compound 345 as a colorless oil in 69% yield. M/Z $(M+H)^+$: 318

Compound 346: Lithium 4-[5-(cyclohexylmethoxy)-2-pyridyl]cyclopentanecarboxylate Compound 346 was obtained according to General Procedure V-a, starting from Compound 345, as a white powder in quantitative yield. M/Z (M[—H—$CO_2$H]+H)$^+$: 304

Compound 347: Methyl 4-[(1S)-1-[[4-[5-(cyclohexylmethoxy)-2-pyridyl]cyclopentanecarbonyl]amino]ethyl]benzoate Compound 347 was obtained according to General Procedure I-a, starting from Compound 346 and methyl 4-[(1S)-1-aminoethyl]benzoate. Purification by flash chromatography (Cyclohexane/EtOAc: 100/0 to 80/20) afforded Compound 347 as a colorless oil in 91% yield. M/Z $(M+H)^+$: 465

Example 127: 4-[(1S)-1-[[1-[5-(Cyclohexylmethoxy)-2-pyridyl]cyclopentanecarbonyl]amino]ethyl]benzoic acid

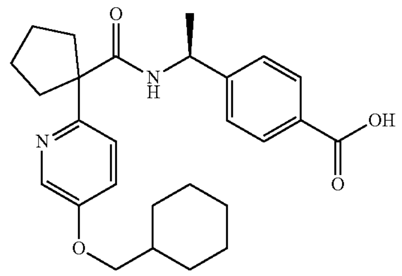 [SMILES: C[C@H](NC(=O)C1(c2ccc(OCC3CCCCC3)cn2)CCCC1)c1ccc(C(=O)O)cc1]

Example 127 was obtained according to General Procedure V-b starting from Compound 347. Purification by flash chromatography (Cyclohexane/EtOAc: 100/0 to 50/50) afforded Example 127 as a white powder in 43% yield. $^1$H-NMR (DMSO-$d_6$, 400 MHz) δ (ppm): 0.99-1.11 (m, 2H, $CH_2$); 1.14-1.27 (m, 3H, CH, $CH_2$); 1.29 (d, J 7.2 Hz, 3H, CH—$CH_3$); 1.51-1.59 (m, 4H, $CH_2$); 1.62-1.85 (m, 6H, $CH_2$); 2.00-2.16 (m, 2H, $CH_2$); 2.31-2.42 (m, 2H, $CH_2$); 3.84 (d, J 6.3 Hz, 2H, Pyr-O—$CH_2$); 4.89-4.98 (m, 1H, CONH—CH—$CH_3$); 7.20 (d, J 8.7 Hz, 1H, Ar); 7.23 (d, J 8.2 Hz, 2H, Ar); 7.31 (dd, J 8.7, 3.0 Hz, 1H, Ar); 7.70 (d, J 8.0 Hz, 1H, CONH—CH); 7.79 (d, J 8.2 Hz, 2H, Ar); 8.2 (d, J 3.0 Hz, 1H, Ar); 12.76 (bs, 1H, $CO_2$H). M/Z $(M+H)^+$: 451

Compound 348: Methyl 4-[5-(2-cyclohexylethoxy)-2-pyridyl]cyclopentanecarboxylate Compound 348 was obtained according to General Procedure XIII, starting from Compound 344 and 2-cyclohexylethanol. Purification by flash chromatography (Cyclohexane/EtOAc: 100/0 to 90/10) afforded Compound 348 as a colorless oil in 79% yield. M/Z $(M+H)^+$: 332

Compound 349: Lithium 4-[5-(2-cyclohexylethoxy)-2-pyridyl]cyclopentanecarboxylate Compound 349 was obtained according to General Procedure V-a, starting from Compound 348, as a white powder in quantitative yield. M/Z $(M[—H—CO_2H]+H)^+$: 318

Compound 350: Methyl 4-[(1S)-1-[[4-[5-(2-cyclohexylethoxy)-2-pyridyl]cyclopentanecarbonyl]amino]ethyl]benzoate Compound 350 was obtained according to General Procedure I-a, starting from Compound 349 and methyl 4-[(1S)-1-aminoethyl]benzoate. Purification by flash chromatography (Cyclohexane/EtOAc: 100/0 to 80/20) afforded Compound 350 as a colorless oil in 74% yield. M/Z $(M+H)^+$: 479

Example 128: 4-[(1S)-1-[[1-[5-(2-Cyclohexylethoxy)-2-pyridyl]cyclopentanecarbonyl]amino]ethyl]benzoic acid

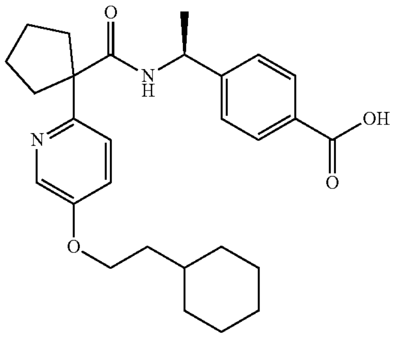 [SMILES: C[C@H](NC(=O)C1(c2ccc(OCCC3CCCCC3)cn2)CCCC1)c1ccc(C(=O)O)cc1]

Example 128 was obtained according to General Procedure V-b, starting from Compound 350. Purification by flash chromatography (Cyclohexane/EtOAc: 100/0 to 50/50) afforded Example 128 as a white powder in 32% yield. $^1$H-NMR (DMSO-$d_6$, 400 MHz) δ (ppm): 0.89-1.00 (m, 2H, $CH_2$); 1.11-1.27 (m, 3H, CH, $CH_2$); 1.29 (d, J 7.2 Hz, 3H, CH—$CH_3$); 1.42-1.50 (m, 1H, $CH_aH_b$); 1.52-1.77 (m, 11H, $CH_2$+$CH_aH_b$); 2.00-2.15 (m, 2H, $CH_2$); 2.31-2.43 (m, 2H, $CH_2$); 4.06 (t, J 6.6 Hz, 2H, Pyr-O—$CH_2$); 4.89-4.98 (m, 1H, CONH—CH—$CH_3$); 7.21 (d, J 8.7 Hz, 1H, Ar); 7.23 (d, J 8.2 Hz, 2H, Ar); 7.32 (dd, J 8.7, 3.0 Hz, 1H, Ar); 7.71 (d, J 8.0 Hz, 1H, CONH—CH); 7.80 (d, J 8.2 Hz, 2H, Ar); 8.26 (d, J 3.0 Hz, 1H, Ar); 12.77 (bs, 1H, $CO_2$H). M/Z $(M+H)^+$: 465

Compound 351: 4-(6-Bromo-3-pyridyl)cyclopentanecarbonitrile

Compound 351 was obtained according to General Procedure VIII-a, starting from Compound 299 and 1,4-dibromoethane. Purification by flash chromatography (Cyclohexane/EtOAc: 100/0 to 80/20) afforded Compound 351 as a colorless oil in 81% yield. M/Z $(M[^{79}Br]+H)^+$: 251

Compound 352: 4-[6-(Cyclohexylmethoxy)-3-pyridyl]cyclopentanecarbonitrile

Compound 352 was obtained according to General Procedure VII-c, starting from Compound 351 and cyclohexylmethanol. Purification by flash chromatography (Cyclohexane/EtOAc: 100/0 to 90/10) afforded Compound 352 as colorless oil in 81% yield. M/Z $(M+H)^+$: 285

Compound 353: 4-[6-(Cyclohexylmethoxy)-3-pyridyl]cyclopentanecarboxamide

Compound 353 was obtained according to General Procedure XI-b, starting from Compound 352, as a white powder in quantitative yield. M/Z $(M+H)^+$: 303

Compound 354: Methyl 4-[6-(cyclohexylmethoxy)-3-pyridyl]cyclopentanecarboxylate

Compound 354 was obtained according to General Procedure XII, starting from Compound 353. Purification by flash chromatography (Cyclohexane/EtOAc: 100/0 to 90/10) afforded Compound 354 as a white powder in 71% yield. M/Z $(M+H)^+$: 318

Compound 355: Lithium 4-[6-(cyclohexylmethoxy)-3-pyridyl]cyclopentanecarboxylate Compound 355 was obtained according to General Procedure V-a, starting from Compound 354, as a yellow powder in quantitative yield. M/Z $(M[—H—CO_2H]+H)^+$: 304

Compound 356: Methyl 4-[(1S)-1-[[4-[6-(cyclohexylmethoxy)-3-pyridyl]cyclopentane carbonyl]amino] ethyl]benzoate Compound 356 was obtained according to General Procedure I-a, starting from Compound 355 and methyl 4-[(1S)-1-aminoethyl]benzoate. Purification by flash chromatography (Cyclohexane/EtOAc: 100/0 to 80/20) afforded Compound 356 as a colorless oil in 85% yield. M/Z $(M+H)^+$: 465

Example 129: 4-[(1S)-1-[[1-[6-(Cyclohexylmethoxy)-3-pyridyl]cyclopentanecarbonyl]amino] ethyl]benzoic acid

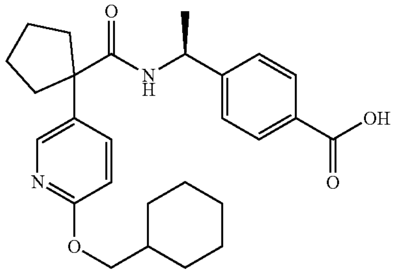 [SMILES: C[C@H](NC(=O)C1(c2ccc(OCC3CCCCC3)nc2)CCCC1)c1ccc(C(=O)O)cc1]

Example 129 was obtained according to General Procedure V-b, starting from Compound 356, as a white powder in 80% yield. $^1$H-NMR (DMSO-$d_6$, 400 MHz) δ (ppm): 0.96-1.08 (m, 2H, $CH_2$); 1.13-1.27 (m, 3H, CH, $CH_2$); 1.29 (d, J 7.3 Hz, 3H, CH—$CH_3$); 1.49-1.87 (m, 12H, $CH_2$); 2.52-2.60 (m, 2H, $CH_2$); 4.01-4.08 (m, 2H, Pyr-O—$CH_2$); 4.88-4.98 (m, 1H, CONH—CH—$CH_3$); 6.73 (d, J 8.8 Hz, 1H, Ar); 7.18 (d, J 8.2 Hz, 2H, Ar); 7.57 (dd, J 8.8, 2.5 Hz, 1H, Ar); 7.77 (d, J 8.2 Hz, 2H, Ar); 7.88 (d, J 8.0 Hz, 1H, CONH—CH); 8.09 (d, J 2.5 Hz, 1H, Ar); 12.78 (bs, 1H, $CO_2$H). M/Z $(M+H)^+$: 451

Compound 357: 4-[6-(2-cyclohexylethoxy)-3-pyridyl]cyclopentanecarbonitrile

Compound 357 was obtained according to General Procedure VII-c, starting from Compound 351 and 2-cyclohexylethanol. Purification by flash chromatography (Cyclohexane/EtOAc: 100/0 to 90/10) afforded Compound 357 as colorless oil in 67% yield. M/Z $(M+H)^+$: 299

Compound 358: 4-[6-(2-Cyclohexylethoxy)-3-pyridyl]cyclopentanecarboxamide

Compound 358 was obtained according to General Procedure XI-b, starting from Compound 357, as a white powder in 87% yield. M/Z $(M+H)^+$: 317

Compound 359: Methyl 4-[6-(2-cyclohexylethoxy)-3-pyridyl]cyclopentanecarboxylate Compound 359 was obtained according to General Procedure XII, starting from Compound 358. Purification by flash chromatography (Cyclohexane/EtOAc: 100/0 to 90/10) afforded Compound 359 as a colorless oil in 90% yield. M/Z $(M+H)^+$: 332

Compound 360: Lithium 4-[6-(2-cyclohexylethoxy)-3-pyridyl]cyclopentanecarboxylate Compound 360 was obtained according to General Procedure V-a, starting from Compound 359, as a white powder in quantitative yield. M/Z $(M[—H—CO_2H]+H)^+$: 318

Compound 361: Methyl 4-[(1S)-1-[[4-[6-(2-cyclohexylethoxy)-3-pyridyl]cyclopentane carbonyl]amino]ethyl]benzoate Compound 361 was obtained according to General Procedure I-a, starting from Compound 360 and methyl 4-[(1S)-1-aminoethyl]benzoate. Purification by flash chromatography (Cyclohexane/EtOAc: 100/0 to 80/20) afforded Compound 361 as a colorless oil in 93% yield. M/Z $(M+H)^+$: 479

Example 130: 4-[(1S)-1-[[1-[6-(2-Cyclohexylethoxy)-3-pyridyl]cyclopentanecarbonyl]amino] ethyl]benzoic acid

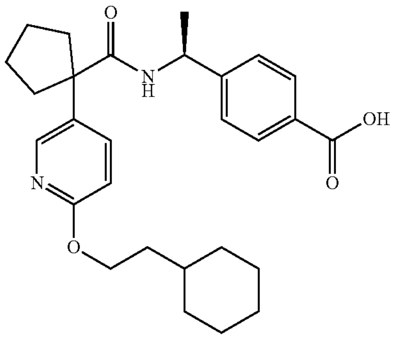 [SMILES: C[C@H](NC(=O)C1(c2ccc(OCCC3CCCCC3)nc2)CCCC1)c1ccc(C(=O)O)cc1]

Example 130 was obtained according to General Procedure V-b, starting from Compound 361. Purification by flash chromatography (Cyclohexane/EtOAc: 100/0 to 50/50) afforded Example 130 as a beige powder in 30% yield. $^1$H-NMR (DMSO-$d_6$, 400 MHz) δ (ppm): 0.88-1.00 (m, 2H, $CH_2$); 1.10-1.27 (m, 3H, CH, $CH_2$); 1.29 (d, J 7.1 Hz, 3H, CH—$CH_3$); 1.38-1.49 (m, 1H, $CH_aH_b$); 1.50-1.87 (m, 13H, $CH_2$+$CH_aH_b$); 2.52-2.60 (m, 2H, $CH_2$); 4.22-4.31 (m, 2H, Pyr-O—$CH_2$); 4.88-4.96 (m, 1H, CONH—CH—$CH_3$); 6.72 (d, J 8.6 Hz, 1H, Ar); 7.18 (d, J 8.2 Hz, 2H, Ar); 7.57 (dd, J 8.6, 2.7 Hz, 1H, Ar); 7.77 (d, J 8.2 Hz, 2H, Ar); 7.88 (d, J 7.8 Hz, 1H, CONH—CH); 8.10 (d, J 2.7 Hz, 1H, Ar); 12.76 (bs, 1H, $CO_2$H). M/Z $(M+H)^+$: 465

Compound 362: tert-Butyl 4-(3-chlorophenoxy)piperidine-1-carboxylate

Compound 362 was obtained according to General Procedure IX-b, starting from tert-butyl 4-hydroxypiperidine-1-carboxylate and 3-chlorophenol. Purification by flash chromatography (Cyclohexane/EtOAc: 100/0 to 90/10) afforded Compound 362 as a colorless oil in 83% yield. M/Z ((M[$^{35}$Cl]-tBu)+H)$^+$: 256

Compound 363: (3-Chlorophenoxy)piperidine

Compound 363 was obtained according to General Procedure II-c, starting from Compound 362. Filtration through a SCX resin afforded Compound 363 as a yellow oil in quantitative yield. M/Z (M[$^{35}$Cl]+H)$^+$: 212

Compound 364: 4-[4-(3-Chlorophenoxy)-1-piperidyl]tetrahydropyran-4-carbonitrile

To a solution of Compound 363 (1 equiv.) in DMA (0.1 M) were added tetrahydro-4H-pyran-4-one (1.05 equiv.), magnesium sulphate (5 equiv.) and acetone cyanohydrin (1 equiv.). The reaction mixture was stirred overnight at 50° C. The reaction mixture was hydrolyzed with water, extracted with etyl acetate. The organic layer was dried, then concentrated. Purification by flash chromatography (Cyclohexane/EtOAc: 100/0 to 50/50) afforded Compound 364 as a white powder in 58% yield. M/Z (M[$^{35}$Cl]+H)$^+$: 321

Compound 365: 4-[4-(3-Chlorophenoxy)-1-piperidyl]tetrahydropyran-4-carboxamide

Compound 365 was obtained according to General Procedure XI-a, starting from Compound 364. Purification by flash chromatography (Cyclohexane/EtOAc: 50/50 to 0/100) afforded Compound 365 as a white powder in 34% yield. M/Z (M[$^{35}$Cl]+H)$^+$: 339

Compound 366: 4-[4-(3-Chlorophenoxy)-1-piperidyl]tetrahydropyran-4-carboxylic acid A solution of Compound 365 in HCl 12 N (0.1 M) in a sealed tube (1 equiv.) was stirred at 150° C. for 24 h. The reaction mixture was concentrated to dryness to afford Compound 366 as a green powder which was used as such in the next step. M/Z (M[$^{35}$Cl]+H)$^+$: 340

Compound 367: Methyl 4-[(1S)-1-[[4-[4-(3-chlorophenoxy)-1-piperidyl]tetrahydropyran-4-carbonyl]amino]ethyl]benzoate Compound 367 was obtained according to General Procedure I-a, starting from Compound 366 and methyl 4-[(1S)-1-aminoethyl]benzoate. Purification by flash chromatography (Cyclohexane/EtOAc: 100/0 to 30/70) afforded Compound 367 as a brown powder in 14% yield over 2 steps. M/Z (M[$^{35}$Cl]+H)$^+$: 501

Example 131: 4-[(1S)-1-[[4-[4-(3-Chlorophenoxy)-1-piperidyl]tetrahydropyran-4-carbonyl]amino]ethyl]benzoic acid, hydrochloride

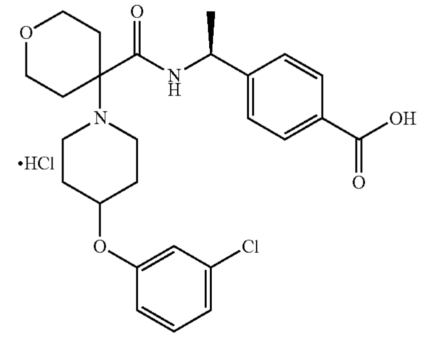 [SMILES: Cl ; C[C@H](NC(=O)C1(N2CCC(Oc3cccc(Cl)c3)CC2)CCOCC1)c1ccc(C(=O)O)cc1]

Example 131 was obtained according to General Procedure IV-b, starting from Compound 367. Purification by preparative LC-MS, then HCl salt preparation (method 1) afforded Example 131 as a beige powder in 38% yield. $^1$H-NMR (DMSO-d$_6$/D$_2$O 400 MHz) δ (ppm): 1.48 (d, J 7.1 Hz, 3H, CH—CH$_3$); 1.77-2.16 (m, 6H, CH$_2$); 2.82-3.34 (m, 6H, CH$_2$+N-CH$_2$+O-CH$_2$); 3.67-3.84 (m, 2H, N—CH$_2$); 3.89-3.98 (m, 2H, O—CH$_2$); 4.61 (bs, 1H, Ph-O—CH); 5.14 (q, J 7.1 Hz, 1H, CONH—CH—CH$_3$); 6.72-6.82 (m, 1H, Ar); 6.87-6.94 (m, 1H, Ar); 6.98 (d, J 8.2 Hz, 1H, Ar); 7.27 (t, J 8.2 Hz, 1H, Ar); 7.49 (d, J 8.1 Hz, 2H, Ar); 7.91 (d, J 8.1 Hz, 2H, Ar); CONH signal was not observed; CO$_2$H signal was not observed; HCl salt not observed. M/Z (M[$^{35}$Cl]+H)$^+$: 487

Compound 368: (3-Chlorophenyl)methyl 2,2,2-trichloroethanimidate

To a solution of 3-chlorobenzyl alcohol (1 equiv.) in diethyl ether (0.3M) was added sodium hydride (0.1 equiv.). The reaction mixture was stirred at rt for 10 min, cooled down to 0° C., then trichloroacetonitrile (1 equiv.) was added. The reaction mixture was stirred at rt for 2 h. The reaction mixture was diluted with pentane. The resulting precipitate was filtered off. The filtrate was concentrated to dryness to afford Compound 368 as a yellow oil in quantitative yield. Compound 369: Dimethyl 3-[(3-chlorophenyl)methoxy]pentanedioate To a solution of Compound 368 (1.2 equiv.) in a cyclohexane/DCM mixture (2/1, 0.5 M) were added dimethyl 3-hydroxypentanedioate (1 equiv.) and trifluoromethanesulfonic acid (0.15 equiv.). The reaction mixture was stirred overnight at rt. The resulting precipitate was filtered off. The filtrate was washed with a saturated solution of sodium bicarbonate and brine, dried, then concentrated. The resulting yellow oil was purified by flash chromatography (Cyclohexane/EtOAc: 100/0 to 80/20) to afford Compound 369 as a colorless oil in 68% yield. $^1$H-NMR (DMSO-d$_6$, 400 MHz) δ (ppm): 2.65 (d, J 6.2 Hz, 4H, CH$_2$—CO$_2$—CH$_3$); 3.60 (s, 6H, CH$_2$—CO$_2$—CH$_3$); 4.18 (quint, J 6.2 Hz, 1H, O—CH); 4.52 (s, 2H, Ph-CH$_2$—O); 7.19-7.22 (m, 1H, Ar); 7.28-7.39 (m, 3H, Ar).

Compound 370: 3-[(3-Chlorophenyl)methoxy]pentane-1,5-diol

To a solution of Compound 369 (1 equiv.) in THF (0.3 M) at 0° C. was added dropwise LiAlH$_4$ 1 M in THF (4 equiv.).

The reaction mixture was stirred overnight at rt. The reaction mixture was diluted with diethyl ether, then were successively added water, NaOH 20 mol %, and finally water. The resulting precipitate was filtered off. The filtrate was concentrated, then purified by flash chromatography (DCM/MeOH: 100/0 to 95/5) to afford Compound 370 as a colorless oil in 77% yield. M/Z (M[$^{35}$Cl]+H)$^+$: 245

Compound 371: 1-[[3-Bromo-1-(2-bromoethyl)propoxy]methyl]-3-chloro-benzene

Compound 371 was obtained according to General Procedure XVI, starting from Compound 370. Purification by flash chromatography (Cyclohexane/EtOAc: 100/0 to 90/10) afforded Compound 371 as a colorless oil in 50% yield. $^1$H-NMR (DMSO-d$_6$ 400 MHz) δ (ppm): 1.95-2.15 (m, 4H, CH$_2$); 3.53-3.60 (m, 4H, Br—CH$_2$); 3.68-3.76 (m, 1H, O—CH); 4.54 (m, 2H, Ph-CH$_2$—O); 7.30-7.43 (m, 4H, Ar).

Compound 372: Methyl 4-[4-[(3-chlorophenyl)methoxy]-1-piperidyl]tetrahydropyran-4-carboxylate Compound 372 was obtained according to General Procedure VIII-b, starting from Compound 371 and methyl 4-aminotetrahydropyran-4-carboxylate. Purification by flash chromatography (Cyclohexane/EtOAc: 100/0 to 80/20) afforded Compound 372 as a white powder in 83% yield. M/Z (M[$^{35}$Cl]+H)$^+$: 368

Compound 373: 4-[4-[(3-Chlorophenyl)methoxy]-1-piperidyl]tetrahydropyran-4-carboxylic acid Compound 373 was obtained according to General Procedure V-d, starting from Compound 372, as a white powder in quantitative yield. M/Z (M[$^{35}$Cl]+H)$^+$: 354

Compound 374: Methyl 4-[(1S)-1-[[4-[4-[(3-chlorophenyl)methoxy]-1-piperidyl]tetrahydropyran-4-carbonyl]amino]ethyl]benzoate Compound 374 was obtained according to General Procedure I-b, starting from Compound 373 and methyl 4-[(1S)-1-aminoethyl]benzoate. Purification by flash chromatography (KP-NH cartridge, Cyclohexane/EtOAc: 100/0 to 50/50) afforded Compound 374 as a colorless oil in 90% yield. M/Z (M[$^{35}$Cl]+H)$^+$: 515

Example 132: 4-[(1S)-1-[[4-[4-[(3-chlorophenyl)methoxy]-1-piperidyl]tetrahydropyran-4-carbonyl]amino]ethyl]benzoic acid, hydrochloride

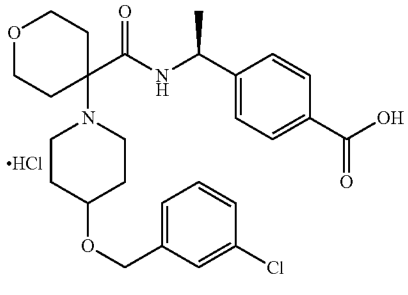 [SMILES: Cl ; C[C@H](NC(=O)C1(N2CCC(OCc3cccc(Cl)c3)CC2)CCOCC1)c1ccc(C(=O)O)cc1]

Example 132 was obtained according to General Procedure V-e, starting from Compound 374. Purification by preparative LC-MS, then HCl salt preparation (method 1) afforded Example 132 as a white powder in 59% yield. $^1$H-NMR (DMSO-d$_6$/D$_2$O 400 MHz) δ (ppm): 1.43 (d, J 6.9 Hz, 3H, CH—CH$_3$); 1.77-2.16 (m, 6H, CH$_2$); 2.80-3.03 (m, 2H, CH$_2$); 3.04-3.21 (m, 2H, CH$_2$); 3.20-3.77 (m, 5H, O-CH+N-CH$_2$); 3.84-3.96 (m, 2H, O—CH$_2$); 4.45 (s, 2H, Ph-CH$_2$O); 5.14 (q, J 6.9 Hz, 1H, CONH—CH—CH$_3$); 7.20-7.24 (m, 1H, Ar); 7.29-7.39 (m, 3H, Ar); 7.45 (d, J 8.2 Hz, 1H, Ar); 7.87 (d, J 8.2 Hz, 1H, Ar); CONH signal was not observed; CO$_2$H signal was not observed; HCl salt not observed. M/Z (M[$^{35}$Cl]+H)$^+$: 501

Compound 375: Methyl 4-[1-[[4-[4-[(3-chlorophenyl)methoxy]-1-piperidyl]tetrahydropyran-4-carbonyl]amino]cyclopropyl]benzoate Compound 375 was obtained according to General Procedure I-b, starting from Compound 373 and methyl 4-(1-aminocyclopropyl)benzoate. Purification by flash chromatography (KP-NH cartridge, Cyclohexane/EtOAc: 100/0 to 50/50) afforded Compound 375 as a colorless oil in 52% yield. M/Z (M[$^{35}$Cl]+H)$^+$: 527

Example 133: 4-[1-[[4-[4-[(3-Chlorophenyl)methoxy]-1-piperidyl]tetrahydropyran-4-carbonyl]amino]cyclopropyl]benzoic acid, hydrochloride

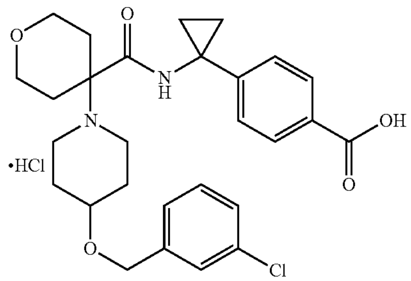 [SMILES: Cl ; O=C(O)c1ccc(C2(NC(=O)C3(N4CCC(OCc5cccc(Cl)c5)CC4)CCOCC3)CC2)cc1]

Example 133 was obtained according to General Procedure V-e, starting from Compound 375. Purification by preparative LC-MS, then HCl salt preparation (method 1) afforded Example 133 as a white powder in 67% yield. $^1$H-NMR (DMSO-d$_6$/D$_2$O, 400 MHz) δ (ppm): 1.15-1.34 (m, 4H, C(CH$_2$—CH$_2$)); 1.68-2.18 (m, 6H, CH$_2$); 2.79-3.03 (m, 2H, CH$_2$); 3.10-3.23 (m, 2H, O—CH$_2$); 3.23-3.46 (m, 2H, N—CH$_2$); 3.52-3.77 (m, 3H, O-CH+N-CH$_2$); 3.89 3.97 (m, 2H, O—CH$_2$); 4.47 (s, 2H, Ph-CHO$_2$—); 7.23-7.39 (m, 6H, Ar); 7.83 (d, J 8.2 Hz, 2H, Ar); CONH signal was not observed; CO$_2$H signal was not observed; HCl salt not observed. M/Z (M[$^{35}$Cl]+H)$^+$: 513

Compound 376: (2R)-Pentane-1,2,5-triol

To a solution of (2R)-5-oxotetrahydrofuran-2-carboxylic acid (1 equiv.) in chloroform (0.2 M) was added BH$_3$·Me$_2$S (1.2 equiv.). The reaction mixture was stirred overnight at 70° C. The reaction mixture was cooled down to 0° C., methanol was added. The reaction mixture was concentrated to dryness to afford Compound 376 as a colorless oil in 95% yield. $^1$H-NMR (D$_2$O 400 MHz) δ (ppm): 1.41-1.53 (m, 1H, CH$_a$H$_b$); 1.54-1.79 (m, 3H, CH$_2$+CH H$_b$), 3.48-3.55 (m, 1H, O—CH$_a$H$_b$); 3.60-3.70 (m, 3H, O-CH$_2$+O-CH$_a$H$_b$); 3.71-3.79 (m, 1H, HO—CH), OH signals were not observed.

Compound 377: (2R)-1,5-Bis[[tert-butyl(dimethyl) silyl]oxy]pentan-2-ol

Compound 377 was obtained according to General Procedure XIV, starting from Compound 376. Purification by flash chromatography (Cyclohexane/EtOAc: 100/0 to 90/10) afforded Compound 377 as a colorless oil in 68% yield. $^1$H-NMR (DMSO-$d_6$, 400 MHz) δ (ppm): 0.01-0.03 (m, 12H, Si—$CH_3$); 0.86 (s, 18H, $C(CH_3)_3$); 1.16-1.27 (m, 1H, $CH_aH_b$); 1.40-1.50 (m, 1H, $CH_aH_b$); 1.52-1.63 (m, 2H, $CH_2$); 3.31-3.37 (m, 1H, O—$CH_aH_b$); 3.38-3.46 (m, 1H, O—$CH_aH_b$); 3.46-3.53 (m, 1H, O—$CH_aH_b$); 3.54-3.62 (m, 2H, HO-CH+O-$CH_aH_b$); 4.41 (d, J 4.9 Hz, 1H, OH).

Compound 378: tert-Butyl-[(2S)-5-[tert-butyl(dimethyl)silyl]oxy-2-(3-chlorophenoxy)pentoxy]-dimethyl-silane Compound 378 was obtained according to General Procedure IX-b, starting from Compound 377 and 3-chlorophenol.

Purification by flash chromatography (Pentane/EtOAc: 100/0 to 95/5) afforded Compound 378 as a colorless oil in 38% yield. $^1$H-NMR (DMSO-de, 400 MHz) δ (ppm): −0.05-0.05 (m, 12H, Si—$CH_3$); 0.81-0.87 (m, 18H, $C(CH_3)_3$); 1.45-1.73 (m, 4H, $CH_2$); 3.31-3.37 (m, 1H, O—$CH_aH_b$); 3.55-3.63 (m, 1H, O—$CH_aH_b$); 3.66-3.76 (m, 2H, O—$CH_2$); 4.41-4.47 (m, 1H, Ph-O—CH); 6.89-6.97 (m, 2H, Ar); 7.02 (t, J 2.1 Hz, 1H, Ar); 7.26 (t, J 8.2 Hz, 1H, Ar).

Compound 379: (2S)-2-(3-Chlorophenoxy)pentane-1,5-diol

Compound 379 was obtained according to General Procedure XV-b, starting from Compound 378. Purification by flash chromatography (DCM/MeOH: 100/0 to 95/5) afforded Compound 379 as a colorless oil in 82% yield. $^1$H-NMR (DMSO-$d_6$ 400 MHz) δ (ppm): 1.39-1.72 (m, 4H, $CH_2$); 3.38 (q, J 6.0 Hz, 2H, HO—$CH_2$—$CH_2$); 3.51 (t, J 5.3 Hz, 2H, HO—$CH_2$—CH); 4.29-4.36 (m, 1H, Ph-O—CH); 4.39 (t, J 5.3 Hz, 1H, HO—$CH_2$—CH); 4.80 (t, J 6.0 Hz, 1H, HO—$CH_2$—$CH_2$); 6.89-6.97 (m, 2H, Ar); 7.03 (t, J 2.1 Hz, 1H, Ar); 7.26 (t, J 8.2 Hz, 1H, Ar).

Compound 380: 1-[(1S)-4-Bromo-1-(bromomethyl) butoxy]-3-chloro-benzene

Compound 380 was obtained according to General Procedure XVI, starting from Compound 379. Purification by flash chromatography (Cyclohexane/EtOAc: 100/0 to 95/5) afforded Compound 380 as a colorless oil in 68% yield. $^1$H-NMR (DMSO-$d_6$ 400 MHz) δ (ppm): 1.80-2.00 (m, 4H, $CH_2$); 3.57 (t, J 6.2 Hz, 2H, Br—$CH_2$—$CH_2$); 3.67 (dd, J 11.2, 4.8 Hz, 1H, Br—$CH_2$—CH); 3.83 (dd, J 11.2, 4.0 Hz, 1H, Br—$CH_2$—CH); 4.67-4.73 (m, 1H, Ph-O—CH); 6.96-7.04 (m, 2H, Ar); 7.10 (t, J 2.1 Hz, 1H, Ar); 7.32 (t, J 8.2 Hz, 1H, Ar).

Compound 381: [4-[(3S)-3-(3-Chlorophenoxy)-1-piperidyl]tetrahydropyran-4-yl]methanol Compound 381 was obtained according to General Procedure VIII-b, starting from Compound 380 and (4-aminotetrahydropyran-4-yl)methanol. Purification by flash chromatography (DCM/MeOH: 100/0 to 97/3) afforded Compound 381 as a colorless oil in 70% yield. M/Z (M[$^{35}$Cl]+H)$^+$: 326

Compound 382: 4-[(3S)-3-(3-Chlorophenoxy)-1-piperidyl]tetrahydropyran-4-carboxylic acid Compound 382 was obtained according to General Procedure XVII, starting from Compound 381, as a brown powder in 43% yield. M/Z (M[$^{35}$Cl]+H)$^+$: 340

Compound 383: Methyl 4-[(1S)-1-[[4-[(3S)-3-(3-chlorophenoxy)-1-piperidyl]tetrahydropyran-4-carbonyl]amino]ethyl]benzoate Compound 383 was obtained according to General Procedure I-a, starting from Compound 382 and methyl 4-[(1S)-1-aminoethyl]benzoate. Purification by flash chromatography (Cyclohexane/EtOAc: 100/0 to 30/70) afforded Compound 383 as a yellow powder in 70% yield. M/Z (M[$^{35}$Cl]+H)$^+$: 501

Example 134: 4-[(1S)-1-[[4-[(3S)-3-(3-Chlorophenoxy)-1-piperidyl]tetrahydropyran-4-carbonyl] amino]ethyl]benzoic acid, hydrochloride

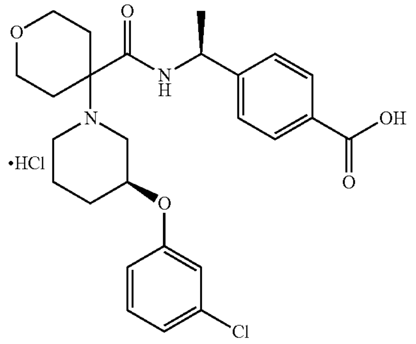 [SMILES: Cl ; C[C@H](NC(=O)C1(N2CCC[C@H](Oc3cccc(Cl)c3)C2)CCOCC1)c1ccc(C(=O)O)cc1]

Example 134 was obtained according to General Procedure V-e, starting from Compound 383. Purification by preparative LC-MS, then HCl salt preparation (method 1) afforded Example 134 as a white powder in 59% yield. $^1$H-NMR (DMSO-$d_6$/$D_2O$, 400 MHz) δ (ppm): 1.41-1.51 (m, 3H, CH—$CH_3$); 1.51-1.78 (m, 2H, $CH_2$); 1.78-2.04 (m, 4H, $CH_2$); 2.25-2.41 (m, 2H, $CH_2$); 2.95-3.35 (m, 4H, N—$CH_2$+O-$CH_2$); 3.58-3.71 (m, 2H, N—$CH_2$); 3.84-3.94 (m, 2H, O—$CH_2$); 4.71 (bs, 1H, Ph-O—CH); 5.02-5.13 (m, 1H, CONH—CH—$CH_3$); 6.92-7.00 (m, 1H, Ar); 7.00-7.11 (m, 2H, Ar); 7.29-7.36 (m, 1H, Ar); 7.42-7.50 (m, 2H, Ar); 7.82-7.89 (m, 2H, Ar); CONH signal was not observed; $CO_2H$ signal was not observed; HCl salt not observed. M/Z (M[$^{35}$Cl]+H)$^+$: 487

Compound 384: Methyl 4-[1-[[4-[(3S)-3-(3-chlorophenoxy)-1-piperidyl]tetrahydropyran-4-carbonyl] amino]cyclopropyl]benzoate Compound 384 was obtained according to General Procedure I-b, starting from Compound 382 and methyl 4-(1-aminocyclopropyl)benzoate. Purification by flash chromatography (Cyclohexane/EtOAc: 100/0 to 40/60) afforded Compound 384 as a yellow oil in 42% yield. M/Z (M[$^{35}$Cl]+H)$^+$: 513

Example 135: 4-[1-[[4-[(3S)-3-(3-Chlorophenoxy)-1-piperidyl]tetrahydropyran-4-carbonyl]amino]cyclopropyl]benzoic acid, hydrochloride

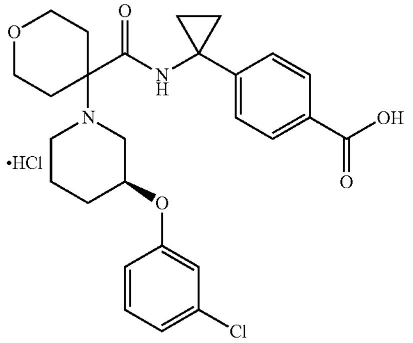 [SMILES: Cl ; O=C(O)c1ccc(C2(NC(=O)C3(N4CCC[C@H](Oc5cccc(Cl)c5)C4)CCOCC3)CC2)cc1]

Example 135 was obtained according to General Procedure V-e, starting from Compound 384. Purification by preparative LC-MS, then HCl salt preparation (method 1) afforded Example 135 as a white powder in 54% yield. $^1$H-NMR (DMSO-$d_6$/$D_2O$ 400 MHz) δ (ppm): 1.16-1.32 (m, 4H, C($CH_2$—$CH_2$)); 1.52-1.77 (m, 2H, $CH_2$); 1.81-1.99 (m, 4H, $CH_2$); 2.26-2.36 (m, 2H, $CH_2$); 2.71-3.31 (m, 6H, 2 N—$CH_2$+O—$CH_2$); 3.84-3.94 (m, 2H, O—$CH_2$); 4.67 (bs, 1H, PhO—CH); 6.90-7.12 (m, 3H, Ar); 7.25-7.39 (m, 3H, Ar); 7.76-7.89 CI (m, 2H, Ar); CONH signal was not observed; $CO_2H$ signal was not observed; HCl salt not observed. M/Z (M[$^{35}$Cl]+H)$^+$: 499

Compound 385: (2S)-Pentane-1,2,5-triol

To a solution of (2S)-5-oxotetrahydrofuran-2-carboxylic acid (1 equiv.) in chloroform (0.2M) was added $BH_3$·$Me_2S$ (1.2 equiv.). The reaction mixture was stirred overnight at 70° C. The reaction mixture was cooled down to 0° C., methanol was added. The reaction mixture was concentrated to dryness to afford Compound 385 as a colorless oil in 95% yield. $^1$H-NMR ($D_2O$, 400 MHz) δ (ppm): 1.41-1.53 (m, 1H, $CH_aH_b$); 1.54-1.79 (m, 3H, $CH_2$+$CH_aH_b$), 3.48-3.55 (m, 1H, O—$CH_aH_b$); 3.60-3.70 (m, 3H, O—$CH_2$+O—$CH_aH_b$); 3.71-3.79 (m, 3H, O—CH), OH signals were not observed.

Compound 386: (2S)-1,5-Bis[[tert-butyl(dimethyl)silyl]oxy]pentan-2-ol

Compound 386 was obtained according to General Procedure XIV, starting from Compound 385. Purification by flash chromatography (Cyclohexane/EtOAc: 100/0 to 90/10) afforded Compound 386 as a colorless oil in 58% yield. $^1$H-NMR (DMSO-$d_6$, 400 MHz) δ (ppm): 0.01-0.03 (m, 12H, Si—$CH_3$); 0.86 (s, 18H, C($CH_3$)$_3$); 1.16-1.27 (m, 1H, $CH_aH_b$); 1.40-1.50 (m, 1H, $CH_aH_b$); 1.52-1.63 (m, 2H, $CH_2$); 3.31-3.37 (m, 1H, O—$CH_aH_b$); 3.38-3.46 (m, 1H, O—$CH_aH_b$); 3.46-3.53 (m, 1H, O—$CH_aH_b$); 3.54-3.62 (m, 2H, O-CH+O-$CH_aH_b$); 4.41 (d, J 4.9 Hz, 1H, OH).

Compound 387: tert-Butyl-[(2R)-5-[tert-butyl(dimethyl)silyl]oxy-2-(3-chlorophenoxy)pentoxy]-dimethyl-silane Compound 387 was obtained according to General Procedure IX-b, starting from Compound 386 and 3-chlorophenol. Purification by flash chromatography (Pentane/EtOAc: 100/0 to 95/5) afforded Compound 387 as a colorless oil in 36% yield. $^1$H-NMR (DMSO-$d_6$, 400 MHz) δ (ppm): −0.05-0.05 (m, 12H, Si—$CH_3$); 0.81-0.87 (m, 18H, C($CH_3$)$_3$); 1.45-1.73 (m, 4H, $CH_2$); 3.31-3.37 (m, 1H, O—$CH_aH_b$); 3.55-3.63 (m, 1H, O—$CH_aH_b$); 3.66-3.76 (m, 2H, O—$CH_2$); 4.41-447 (m, 1H, PhO—CH); 6.89-6.97 (m, 2H, Ar); 7.02 (t, J 2.1 Hz, 1H, Ar); 7.26 (t, J 8.2 Hz, 1H, Ar).

Compound 388: (2R)-2-(3-Chlorophenoxy)pentane-1,5-diol

Compound 388 was obtained according to General Procedure XV-b, starting from Compound 387. Purification by flash chromatography (DCM/MeOH: 100/0 to 95/5) afforded Compound 388 as a colorless oil in 86% yield. $^1$H-NMR (DMSO-$d_6$ 400 MHz) δ (ppm): 1.39-1.72 (m, 4H, $CH_2$); 3.38 (q, J 6.0 Hz, 2H, HO—$CH_2$—$CH_2$); 3.51 (t, J 5.3 Hz, 2H, HO—$CH_2$—CH); 4.29-4.36 (m, 1H, PhO—CH); 4.39 (t, J 5.3 Hz, 1H, HO—$CH_2$—CH); 4.80 (t, J 6.0 Hz, 1H, HO—$CH_2$—$CH_2$); 6.89-6.97 (m, 2H, Ar); 7.03 (t, J 2.1 Hz, 1H, Ar); 7.26 (t, J 8.2 Hz, 1H, Ar).

Compound 389: 1-[(1R)-4-Bromo-1-(bromomethyl)butoxy]-3-chloro-benzene

Compound 389 was obtained according to General Procedure XVI, starting from Compound 388. Purification by flash chromatography (Cyclohexane/EtOAc: 100/0 to 95/5) afforded Compound 389 as a colorless oil in 68% yield. $^1$H-NMR (DMSO-$d_6$, 400 MHz) δ (ppm): 1.80-2.00 (m, 4H, $CH_2$); 3.57 (t, J 6.2 Hz, 2H, Br—$CH_2$—$CH_2$); 3.67 (dd, J 11.2, 4.8 Hz, 1H, Br—$CH_2$—CH); 3.83 (dd, J 11.2, 4.0 Hz, 1H, Br—$CH_2$—CH); 4.67-4.73 (m, 1H, Ph-O—CH); 6.96-7.04 (m, 2H, Ar); 7.10 (t, J 2.1 Hz, 1H, Ar); 7.32 (t, J 8.2 Hz, 1H, Ar).

Compound 390: [4-[(3R)-3-(3-Chlorophenoxy)-1-piperidyl]tetrahydropyran-4-yl]methanol Compound 390 was obtained according to General Procedure VIII-b, starting from Compound 389 and (4-aminotetrahydropyran-4-yl)methanol. Purification by flash chromatography (DCM/MeOH: 100/0 to 97/3) afforded Compound 390 as a colorless oil in 71% yield. M/Z (M[$^{35}$Cl]+H)$^+$: 326

Compound 391: 4-[(3R)-3-(3-Chlorophenoxy)-1-piperidyl]tetrahydropyran-4-carboxylic acid Compound 391 was obtained according to General Procedure XVII, starting from Compound 390, as a brown powder in 53% yield. M/Z (M[$^{35}$Cl]+H)$^+$: 340

Compound 392: Methyl 4-[(1S)-1-[[4-[(3R)-3-(3-chlorophenoxy)-1-piperidyl]tetrahydropyran-4-carbonyl]amino]ethyl]benzoate Compound 392 was obtained according to General Procedure I-a, starting from Compound 391 and methyl 4-[(1S)-1-aminoethyl]benzoate. Purification by flash chromatography (Cyclohexane/EtOAc: 100/0 to 30/70) afforded Compound 392 as a colorless oil in 51% yield. M/Z (M[$^{35}$Cl]+H)$^+$: 501

Example 136: 4-[(1S)-1-[[4-[(3R)-3-(3-Chlorophenoxy)-1-piperidyl]tetrahydropyran-4-carbonyl]amino]ethyl]benzoic acid, hydrochloride

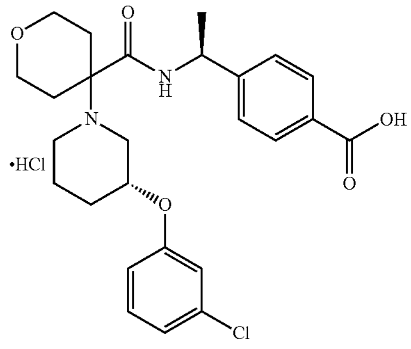 [SMILES: Cl ; C[C@H](NC(=O)C1(N2CCC[C@@H](Oc3cccc(Cl)c3)C2)CCOCC1)c1ccc(C(=O)O)cc1]

Example 136 was obtained according to Procedure V-e, starting from Compound 392. Purification by preparative LC-MS, then HCl salt preparation (method 1) afforded Example 136 as a white powder in 67% yield. $^1$H-NMR (DMSO-$d_6$/$D_2O$, 400 MHz) δ (ppm): 1.41 (d, J 7.1 Hz, 3H, CH—$CH_3$); 1.46-1.81 (m, 2H, $CH_2$); 1.81-2.04 (m, 4H, $CH_2$); 2.30-2.46 (m, 2H, $CH_2$); 3.02-3.33 (m, 4H, N—$CH_2$+O-$CH_2$); 3.58-3.71 (m, 2H, N—$CH_2$); 3.84-3.92 (m, 2H, O—$CH_2$); 4.69 (bs, 1H, Ph-O—CH); 5.06 (q, J 7.1 Hz, 1H, CONH—CH—$CH_3$); 6.92-6.98 (m, 1H, Ar); 7.01-7.09 (m, 2H, Ar); 7.32 (t, J 8.2 Hz, 1H, Ar); 7.45 (d, J 8.3 Hz, 2H, Ar); 7.88 (d, J 8.3 Hz, 2H, Ar); CONH signal was not observed; $CO_2H$ signal was not observed; HCl salt not observed. M/Z (M[$^{35}$Cl]+H)$^+$: 487

Compound 393: Methyl 4-[1-[[4-[(3R)-3-(3-chlorophenoxy)-1-piperidyl]tetrahydropyran-4-carbonyl]amino]cyclopropyl]benzoate Compound 393 was obtained according to General Procedure I-b, starting from Compound 391 and methyl 4-(1-aminocyclopropyl)benzoate. Purification by flash chromatography (Cyclohexane/EtOAc: 100/0 to 40/60) afforded Compound 393 as a yellow oil in 42% yield. M/Z (M[$^{35}$Cl]+H)$^+$: 513

Example 137: 4-[1-[[4-[(3R)-3-(3-Chlorophenoxy)-1-piperidyl]tetrahydropyran-4-carbonyl]amino]cyclopropyl]benzoic acid, hydrochloride

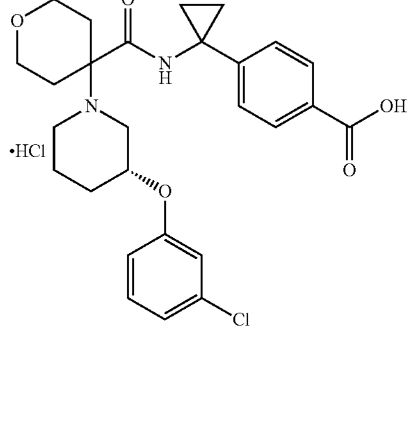

Example 137 was obtained according to General Procedure V-e, starting from Compound 393. Purification by preparative LC-MS, then HCl salt preparation (method 1) afforded Example 137 as a white powder in 66% yield. $^1$H-NMR (DMSO-$d_6$/$D_2O$, 400 MHz) δ (ppm): 1.16-1.32 (m, 4H, C($CH_2$—$CH_2$)); 1.55-1.77 (m, 2H, $CH_2$); 1.81-1.99 (m, 4H, $CH_2$); 2.26-2.36 (m, 2H, $CH_2$); 2.80-2.94 (m, 3H, N—$CH_2$+N-$CH_aH_b$); 3.13-3.26 (m, 3H, N-$CH_aH_b$+O-$CH_2$); 3.84-3.94 (m, 2H, O—$CH_2$); 4.67 (bs, 1H, Ph-C—CH); 6.92-6.97 (m, 1H, Ar); 6.99-7.07 (m, 2H, Ar); 7.28-7.35 (m, 3H, Ar); 7.81 (d, J 8.2 Hz, 2H, Ar); CONH signal was not observed; $CO_2H$ signal was not observed; HCl salt not observed. M/Z (M[$^{35}$Cl]+H)$^+$: 499

Compound 394: (2R)-1,4-Bis[[tert-butyl(dimethyl)silyl]oxy]butan-2-ol

Compound 394 was obtained according to General Procedure XIV, starting from (2R)-butane-1,2,4-triol. Purification by flash chromatography (Cyclohexane/EtOAc: 100/0 to 80/20) afforded Compound 394 as a colorless oil in 87% yield. $^1$H-NMR (DMSO-$d_6$, 400 MHz) δ (ppm): 0.01-0.03 (m, 12H, Si—CH); 0.85 (s, 9H, C($CH_3$)$_3$); 0.86 (s, 9H, C($CH_3$)$_3$); 1.34-1.43 (m, 1H, $CH_aH_b$); 1.64-1.74 (m, 1H, $CH_aH_b$); 3.34-3.39 (m, 1H, O—$CH_aH_b$); 3.47-3.53 (m, 1H, O—$CH_aH_b$); 3.52-3.59 (m, 1H, O—CH); 3.68 (dd, J 7.6, 5.6 Hz, 2H, O—$CH_2$); 4.41 (d, J 5.1 Hz, 1H, OH).

Compound 395: tert-Butyl-[(2S)-4-[tert-butyl(dimethyl)silyl]oxy-2-(3-chlorophenoxy)butoxy]-dimethyl-silane Compound 395 was obtained according to General Procedure IX-b, starting from Compound 394 and 3-chlorophenol.

Purification by flash chromatography (Pentane/EtOAc: 100/0 to 95/5) afforded Compound 395 as a colorless oil in 37% yield. $^1$H-NMR (DMSO-$d_6$ 400 MHz) δ (ppm): −0.09-0.06 (m, 12H, Si—$CH_3$); 0.79-0.87 (m, 18H, C($CH_3$)$_3$); 1.74-1.83 (m, 2H, $CH_2$); 3.64-3.75 (m, 3H. O-$CH_2$+O-$CH_aH_b$); 3.79 (dd, J 11.2, 3.8 Hz, 1H, O—$CH_aH_b$); 4.49-4.56 (m, 1H, Ph-O—CH); 6.89-6.97 (m, 2H, Ar); 7.03 (t, J 2.1 Hz, 1H, Ar); 7.26 (t, J 8.2 Hz, 1H, Ar).

Compound 396: (2S)-2-(3-Chlorophenoxy)butane-1,4-diol

Compound 396 was obtained according to General Procedure XV-b, starting from Compound 395. Purification by flash chromatography (DCM/MeOH: 100/0 to 94/6) afforded Compound 396 as a colorless oil in 91% yield. $^1$H-NMR (DMSO-$d_6$ 400 MHz) δ (ppm): 1.65-1.82 (m, 2H, $CH_2$); 3.44-3.56 (m, 4H, HO—$CH_2$); 4.41-4.48 (m, 1H, Ph-C—CH); 4.55 (t, J 5.1 Hz, 1H, HO—$CH_2$—CH); 4.82 (t, J 5.7 Hz, 1H, HO—$CH_2$—$CH_2$); 6.91-6.97 (m, 2H, Ar); 7.05 (t, J 2.1 Hz, 1H, Ar); 7.27 (t, J 8.2 Hz, 1H, Ar).

Compound 397: 1-[(1S)-3-Bromo-1-(bromomethyl)propoxy]-3-chloro-benzene

Compound 397 was obtained according to General Procedure XVI, starting from Compound 396. Purification by flash chromatography (Cyclohexane/EtOAc: 100/0 to 95/5) afforded Compound 397 as a colorless oil in 68% yield. $^1$H-NMR (DMSO-$d_6$ 400 MHz) δ (ppm): 2.17-2.37 (m, 2H, $CH_2$); 3.55-3.70 (m, 2H, Br—$CH_2$—$CH_2$); 3.73 (dd, J 11.2, 4.5 Hz, 1H, Br—$CH_2$—CH); 3.83 (dd, J 11.2, 4.0 Hz, 1H, Br—$CH_2$—CH); 4.70-4.77 (m, 1H, Ph-C—CH); 6.99-7.07 (m, 2H, Ar); 7.12 (t, J 2.1 Hz, 1H, Ar); 7.34 (t, J 8.2 Hz, 1H, Ar).

Compound 398: [4-[(3S)-3-(3-Chlorophenoxy)pyrrolidin-1-yl]tetrahydropyran-4-yl]methanol Compound 398 was obtained according to General Procedure VIII-b, starting from Compound 397 and (4-aminotetrahydropyran-4-yl)methanol. Purification by flash chromatography (DCM/MeOH: 100/0 to 95/5) afforded Compound 398 as a colorless oil in 66% yield. M/Z $(M[^{35}Cl]+H)^+$: 312

Compound 399: 4-[(3S)-3-(3-Chlorophenoxy)pyrrolidin-1-yl]tetrahydropyran-4-carboxylic acid Compound 399 was obtained according to General Procedure XVII, starting from Compound 398, as a brown powder in 58% yield. M/Z $(M[^{35}Cl]+H)^+$: 326

Compound 400: Methyl 4-[(1S)-1-[[4-[(3S)-3-(3-chlorophenoxy)pyrrolidin-1-yl]tetrahydropyran-4-carbonyl]amino]ethyl]benzoate Compound 400 was obtained according to General Procedure I-a, starting from Compound 399 and methyl 4-[(1S)-1-aminoethyl]benzoate. Purification by flash chromatography (Cyclohexane/EtOAc: 100/0 to 30/70) afforded Compound 400 as a colorless oil in 86% yield. M/Z $(M[^{35}Cl]+H)^+$: 487

Example 138: 4-[(1S)-1-[[4-[(3S)-3-(3-Chlorophenoxy)pyrrolidin-1-yl]tetrahydropyran-4-carbonyl]amino]ethyl]benzoic acid, hydrochloride

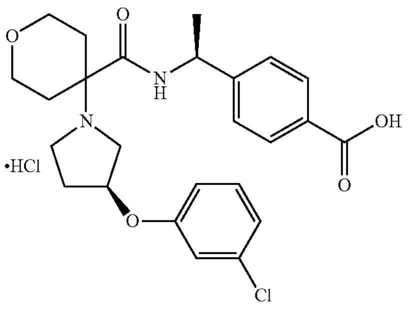 [SMILES: Cl ; C[C@H](NC(=O)C1(N2CC[C@H](Oc3cccc(Cl)c3)C2)CCOCC1)c1ccc(C(=O)O)cc1]

Example 138 was obtained according to General Procedure V-e, starting from Compound 400. Purification by preparative LC-MS, then HCl salt preparation (method 1) afforded Example 138 as a white powder in 24% yield, $^1$H-NMR (DMSO-$d_6$/$D_2$O 400 MHz) δ (ppm): 1.33-1.42 (m, 3H, CH—$CH_3$); 1.84-2.00 (m, 2H, $CH_2$); 2.06-2.13 (m, 2H, $CH_2$); 2.36-2.48 (m, 2H, $CH_2$); 3.03-3.14 (m, 1H, O—$CH_aH_b$); 3.14-3.24 (m, 1H, O—$CH_aH_b$); 3.29-3.46 (m, 3H, N—$CH_2$+N-$CH_aH_b$); 3.59-3.69 (m, 1H, N—$CH_aH_b$); 3.83-3.94 (m, 2H, O—$CH_2$); 5.03-5.12 (m, 2H, Ph-O-CH+CONH—CH—$CH_3$); 6.78-6.85 (m, 1H, Ar); 6.86-6.95 (m, 1H, Ar); 7.01-7.06 (m, 1H, Ar); 7.27-7.34 (m, 1H, Ar); 7.43-7.49 (m, 2H, Ar); 7.90 (d, J 8.2 Hz, 2H, Ar); CONH signal was not observed; $CO_2$H signal was not observed; HCl salt not observed. M/Z $(M[^{35}Cl]+H)^+$: 473

Compound 401: Methyl 4-[1-[[4-[(3S)-3-(3-Chlorophenoxy)pyrrolidin-1-yl]tetrahydropyran-4-carbonyl]amino]cyclopropyl]benzoate Compound 401 was obtained according to General Procedure I-a, starting from Compound 399 and methyl 4-(1-aminocyclopropyl)benzoate. Purification by flash chromatography (Cyclohexane/EtOAc: 100/0 to 30/70) afforded Compound 401 as an orange oil which was used as such in the next step. M/Z $(M[^{35}Cl]+H)^+$: 499

Example 139: 4-[1-[[4-[(3S)-3-(3-Chlorophenoxy)pyrrolidin-1-yl]tetrahydropyran-4-carbonyl]amino]cyclopropyl]benzoic acid, hydrochloride

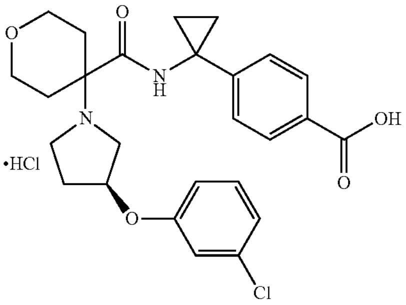 [SMILES: Cl ; O=C(O)c1ccc(C2(NC(=O)C3(N4CC[C@H](Oc5cccc(Cl)c5)C4)CCOCC3)CC2)cc1]

Example 139 was obtained according to General Procedure V-e, starting from Compound 401. Purification by preparative LC-MS, then HCl salt preparation (method 1) afforded Example 139 as a white powder in 11% yield over 2 steps. $^1$H-NMR (DMSO-$d_6$/$D_2$, 400 MHz) δ (ppm): 1.19-1.37 (m, 4H, C($CH_2$—$CH_2$)); 1.85-2.00 (m, 2H, $CH_2$); 2.06-2.17 (m, 2H, $CH_2$); 2.34-2.43 (m, 2H, $CH_2$); 3.13-3.26 (m, 2H, O—$CH_2$); 3.26-3.47 (m, 3H, N—$CH_2$+N-$CH_aH_b$); 3.59-3.69 (m, 1H, N—$CH_aH_b$); 3.86-3.94 (m, 2H, O—$CH_2$); 5.09 (bs, 1H, PhO—CH); 6.84-6.90 (m, 1H, Ar); 6.94-6.99 (m, 1H, Ar); 7.02-7.07 (m, 1H, Ar); 7.29-7.36 (m, 3H, Ar); 7.82-7.88 (m, 2H, Ar); CONH signal was not observed; $CO_2$H signal was not observed; HCl salt not observed. M/Z $(M[^{35}Cl]+H)^+$: 485

Compound 402: (2S)-1,4-Bis[[tert-butyl(dimethyl)silyl]oxy]butan-2-ol

Compound 402 was obtained according to General Procedure XIV, starting from (2S)-butane-1,2,4-triol. Purification by flash chromatography (Cyclohexane/EtOAc: 100/0 to 80/20) afforded Compound 402 as a colorless oil in 86% yield. $^1$H-NMR (DMSO-$d_6$ 400 MHz) δ (ppm): 0.01-0.03 (m, 12H, Si—$CH_3$); 0.85 (s, 9H, C$(CH_3)_3$); 0.86 (s, 9H, C$(CH_3)_3$); 1.34-1.43 (m, 1H, $CH_aH_b$); 1.64-1.74 (m, 1H, CH $H_b$); 3.34-3.39 (m, 1H, O—$CH_aH_b$); 3.47-3.53 (m, 1H, O—$CH_aH_b$); 3.52-3.59 (m, 1H, O—CH); 3.68 (dd, J 7.6, 5.6 Hz, 2H, O—$CH_2$); 4.41 (d, J 5.1 Hz, 1H, OH).

Compound 403: tert-Butyl-[(2R)-4-[tert-butyl(dimethyl)silyl]oxy-2-(3-chlorophenoxy)butoxy]-dimethyl-silane Compound 403 was obtained according to General Procedure IX-b, starting from Compound 402 and 3-chlorophenol. Purification by flash chromatography (Pentane/EtOAc: 100/0 to 95/5) afforded Compound 403 as a colorless oil in 39% yield. $^1$H-NMR (DMSO-$d_6$, 400 MHz) δ (ppm): −0.09-0.06 (m, 12H, Si—$CH_3$); 0.79-0.87 (m, 18H, $C(CH_3)_3$); 1.74-1.83 (m, 2H, $CH_2$); 3.64-3.75 (m, 3H, O-$CH_2$+O-$CH_aH_b$); 3.79 (dd, J 11.2, 3.8 Hz, 1H, O—$CH_aH_b$); 4.49-4.56 (m, 1H, Ph-O—CH); 6.89-6.97 (m, 2H, Ar); 7.03 (t, J 2.1 Hz, 1H, Ar); 7.26 (t, J 8.2 Hz, 1H, Ar).

Compound 404: (2R)-2-(3-Chlorophenoxy)butane-1,4-diol

Compound 404 was obtained according to General Procedure XV-b, starting from Compound 403. Purification by flash chromatography (DCM/MeOH: 100/0 to 94/6) afforded Compound 404 as a colorless oil in 89% yield. $^1$H-NMR (DMSO-$d_6$ 400 MHz) δ (ppm): 1.65-1.82 (m, 2H, $CH_2$); 3.44-3.56 (m, 4H, HO—$CH_2$); 4.41-4.48 (m, 1H, Ph-O—CH); 4.55 (t, J 5.1 Hz, 1H, HO—$CH_2$—CH); 4.82 (t, J 5.7 Hz, 1H, HO—$CH_2$—$CH_2$); 6.91-6.97 (m, 2H, Ar); 7.05 (t, J 2.1 Hz, 1H, Ar); 7.27 (t, J 8.2 Hz, 1H, Ar).

Compound 405: 1-[(1R)-3-Bromo-1-(bromomethyl)propoxy]-3-chloro-benzene

Compound 405 was obtained according to General Procedure XVI, starting from Compound 404. Purification by flash chromatography (Cyclohexane/EtOAc: 100/0 to 95/5) afforded Compound 405 as a colorless oil in 68% yield. $^1$H-NMR (DMSO-$d_6$ 400 MHz) δ (ppm): 2.17-2.37 (m, 2H, $CH_2$); 3.55-3.70 (m, 2H, Br—$CH_2$—$CH_2$); 3.73 (dd, J 11.2, 4.5 Hz, 1H, Br—$CH_2$—CH); 3.83 (dd, J 11.2, 4.0 Hz, 1H, Br—$CH_2$—CH); 4.70-4.77 (m, 1H, Ph-O—CH); 6.99-7.07 (m, 2H, Ar); 7.12 (t, J 2.1 Hz, 1H, Ar); 7.34 (t, J 8.2 Hz, 1H, Ar).

Compound 406: [4-[(3R)-3-(3-Chlorophenoxy)pyrrolidin-1-yl]tetrahydropyran-4-yl]methanol Compound 406 was obtained according to General Procedure VIII-b, starting from Compound 405 and (4-aminotetrahydropyran-4-yl)methanol. Purification by flash chromatography (DCM/MeOH: 100/0 to 95/5) afforded Compound 406 as a colorless oil in 44% yield. M/Z (M[$^{35}$Cl]+H)$^+$: 312

Compound 407: 4-[(3R)-3-(3-Chlorophenoxy)pyrrolidin-1-yl]tetrahydropyran-4-carboxylic acid Compound 407 was obtained according to General Procedure XVII, starting from Compound 406, as a brown powder in 77% yield. M/Z (M[$^{35}$Cl]+H)$^+$: 326

Compound 408: Methyl 4-[(1S)-1-[[4-[(3R)-3-(3-chlorophenoxy)pyrrolidin-1-yl]tetrahydropyran-4-carbonyl]amino]ethyl]benzoate Compound 408 was obtained according to General Procedure I-a, starting from Compound 407 and methyl 4-[(1S)-1-aminoethyl]benzoate. Purification by flash chromatography (Cyclohexane/EtOAc: 100/0 to 30/70) afforded Compound 408 as a colorless oil in 53% yield. M/Z (M[$^{35}$Cl]+H)$^+$: 487

Example 140: 4-[(1S)-1-[[4-[(3R)-3-(3-Chlorophenoxy)pyrrolidin-1-yl]tetrahydropyran-4-carbonyl]amino]ethyl]benzoic acid, hydrochloride

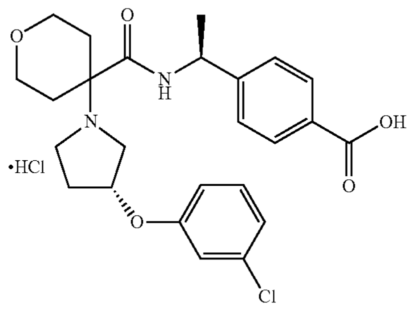 [SMILES: Cl ; C[C@H](NC(=O)C1(N2CC[C@@H](Oc3cccc(Cl)c3)C2)CCOCC1)c1ccc(C(=O)O)cc1]

Example 140 was obtained according to General Procedure V-e, starting from Compound 408. Purification by preparative LC-MS, then HCl salt preparation (method 1) afforded Example 140 as a white powder in 54% yield. $^1$H-NMR (DMSO-$d_6$/$D_2O$ 400 MHz) δ (ppm): 1.40-1.54 (m, 3H, CH—$CH_3$); 1.80-1.93 (m, 2H, $CH_2$); 2.02-2.13 (m, 2H, $CH_2$); 2.35-2.45 (m, 2H, $CH_2$); 3.06-3.20 (m, 2H, O—$CH_2$); 3.30-3.46 (m, 3H, N—$CH_2$+N-$CH_aH_b$); 3.59-3.69 (m, 1H, N—$CH_aH_b$); 3.85-3.94 (m, 2H, O—$CH_2$); 5.01-5.14 (m, 2H, Ph-O-CH+CONH—CH—$CH_3$); 6.78-6.94 (m, 2H, Ar); 6.98-7.05 (m, 1H, Ar); 7.25-7.34 (m, 1H, Ar); 7.40-7.48 (m, 2H, Ar); 7.82-7.91 (m, 2H, Ar); CONH signal was not observed; $CO_2H$ signal was not observed; HCl salt not observed. M/Z (M[$^{35}$Cl]+H)$^+$: 473

Compound 409: Methyl 4-[1-[[4-[(3R)-3-(3-Chlorophenoxy)pyrrolidin-1-yl]tetrahydropyran-4-carbonyl]amino]cyclopropyl]benzoate Compound 409 was obtained according to General Procedure I-a, starting from Compound 407 and methyl 4-(1-aminocyclopropyl)benzoate. Purification by flash chromatography (Cyclohexane/EtOAc: 100/0 to 30/70) afforded Compound 409 as an orange oil. M/Z (M[$^{35}$Cl]+H)$^+$: 499

Example 141: 4-[1-[[4-[(3R)-3-(3-Chlorophenoxy)pyrrolidin-1-yl]tetrahydropyran-4-carbonyl]amino]cyclopropyl]benzoic acid, hydrochloride

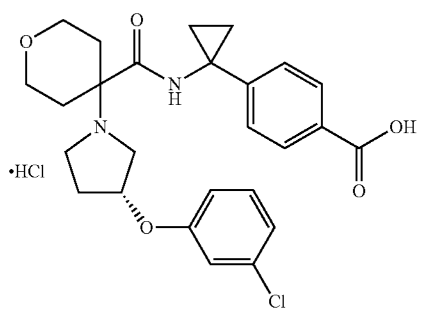 [SMILES: Cl ; O=C(O)c1ccc(C2(NC(=O)C3(N4CC[C@@H](Oc5cccc(Cl)c5)C4)CCOCC3)CC2)cc1]

Example 141 was obtained according to General Procedure V-e, starting from Compound 409. Purification by preparative LC-MS, then HCl salt preparation (method 1) afforded Example 141 as a white powder in 11% yield over 2 steps. $^1$H-NMR (DMSO-de/$D_2O$, 400 MHz) δ (ppm): 1.19-1.37 (m, 4H, $C(CH_2—CH_2)$); 1.85-2.00 (m, 2H, $CH_2$); 2.06-2.17 (m, 2H, $CH_2$); 2.34-2.43 (m, 2H, $CH_2$); 3.13-3.41 (m, 5H, N—$CH_2$+N-$CH_aH_b$+O—$CH_2$); 3.59-3.69 (m, 1H, N—$CH_aH_b$); 3.86-3.94 (m, 2H, O—$CH_2$); 5.09 (bs, 1H, PhO—CH); 6.84-6.90 (m, 1H, Ar); 6.94-6.99 (m, 1H, Ar); 7.02-7.07 (m, 1H, Ar); 7.29-7.36 (m, 3H, Ar); 7.82-7.88 (m, 2H, Ar); CONH signal was not observed; $CO_2H$ signal was not observed; HCl salt not observed. M/Z (M[$^{35}$Cl]+H)$^+$: 485

Compound 410: tert-Butyl-[(2R)-4-[tert-butyl(dimethyl)silyl]oxy-2-(3-fluorophenoxy)butoxy]-dimethyl-silane Compound 410 was obtained according to General Procedure IX-b, starting from Compound 402 and 3-fluorophenol. Purification by flash chromatography (Pentane/EtOAc: 100/0 to 85/15) afforded Compound 410 as a pale yellow oil in 44% yield. $^1$H-NMR (DMSO-$d_6$ 400 MHz) δ (ppm): −0.07-0.05 (m, 12H, Si—$CH_3$); 0.78-0.88 (m, 18H, $C(CH_3)_3$); 1.72-1.84 (m, 2H, $CH_2$); 3.66-3.75 (m, 3H, O—$CH_2$+ 0—$CH_aH_b$); 3.79 (dd, J 11.2, 3.8 Hz, 1H, O—$CH_aH_b$); 4.48-4.54 (m, 1H, Ph-C—CH); 6.68-6.74 (m, 1H, Ar); 6.76-6.83 (m, 2H, Ar); 7.23-7.29 (m, 1H, Ar).

Compound 411: (2R)-2-(3-Fluorophenoxy)butane-1,4-diol

Compound 411 was obtained according to General Procedure XV-b, starting from Compound 410. Purification by flash chromatography (DCM/MeOH: 100/0 to 93/7) afforded Compound 411 as a colorless oil in 88% yield. $^1$H-NMR (DMSO-$d_6$, 400 MHz) δ (ppm): 1.65-1.82 (m, 2H, $CH_2$); 3.44-3.56 (m, 4H, HO—$CH_2$); 4.40-4.47 (m, 1H, PhO—CH); 4.54 (bs, 1H, HO—CH—CH); 4.80 (bs, 1H, HO—$CH_2$—$CH_2$); 6.68-6.74 (m, 1H, Ar); 6.78-6.86 (m, 2H, Ar); 7.24-7.31 (m, 1H, Ar).

Compound 412: 1-[(1R)-3-Fluoro-1-(bromomethyl)propoxy]-3-chloro-benzene

Compound 412 was obtained according to General Procedure XVI, starting from Compound 411. Purification by flash chromatography (Cyclohexane/EtOAc: 100/0 to 90/10) afforded Compound 412 as a colorless oil in 60% yield. $^1$H-NMR (DMSO-$d_6$ 400 MHz) δ (ppm): 2.18-2.28 (m, 1H, $CH_aH_b$); 2.28-2.38 (m, 1H, $CH_aH_b$); 3.54-3.69 (m, 2H, Br—$CH_2$—$CH_2$); 3.73 (dd, J 11.2, 4.4 Hz, 1H, Br—CH—CH); 3.84 (dd, J 11.2, 4.0 Hz, 1H, Br—$CH_2$—CH); 4.69-4.75 (m, 1H, Ph-O—CH); 6.79-6.85 (m, 1H, Ar); 6.85-6.94 (m, 2H, Ar); 7.30-7.37 (m, 1H, Ar).

Compound 413: Methyl 4-[(3R)-3-(3-fluorophenoxy)pyrrolidin-1-yl]tetrahydropyran-4-carboxylate Compound 413 was obtained according to General Procedure VIII-b, starting from Compound 412 and methyl 4-aminotetrahydropyran-4-carboxylate. Purification by flash chromatography (Cyclohexane/EtOAc: 100/0 to 60/40) afforded Compound 413 as a pale brown oil in 52% yield. M/Z (M+H)$^+$: 324

Compound 414: Lithium 4-[(3R)-3-(3-fluorophenoxy)pyrrolidin-1-yl]tetrahydropyran-4-carboxylate Compound 414 was obtained according to General Procedure V-f, starting from Compound 413, as a yellow powder in quantitative yield. M/Z (M+H)$^+$: 310

Compound 415: Methyl 4-[(1S)-1-[[4-[(3R)-3-(3-fluorophenoxy)pyrrolidin-1-yl]tetrahydropyran-4-carbonyl]amino]ethyl]benzoate Compound 415 was obtained according to General Procedure I-a, starting from Compound 414 and methyl 4-[(1S)-1-aminoethyl]benzoate. Purification by flash chromatography (Cyclohexane/EtOAc: 100/0 to 40/60) afforded Compound 415 as a colorless oil in 53% yield. M/Z (M+H)$^+$: 471

Example 142: 4-[(1S)-1-[[4-[(3R)-3-(3-Fluorophenoxy)pyrrolidin-1-yl]tetrahydropyran-4-carbonyl]amino]ethyl]benzoic acid, hydrochloride

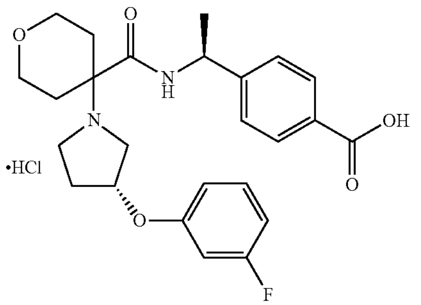 [SMILES: Cl ; C[C@H](NC(=O)C1(N2CC[C@@H](Oc3cccc(F)c3)C2)CCOCC1)c1ccc(C(=O)O)cc1]

Example 142 was obtained according to General Procedure V-e, starting from Compound 415. Purification by preparative LC-MS, then HCl salt preparation (method 1) afforded Example 142 as a white powder in 48% yield. $^1$H-NMR (DMSO-$d_6$/$D_2O$ 400 MHz) δ (ppm): 1.45-1.52 (m, 3H, CH—$CH_3$); 1.87-2.02 (m, 2H, $CH_2$); 2.05-2.15 (m, 2H, $CH_2$); 2.39-2.48 (m, 2H, $CH_2$); 3.08-3.20 (m, 2H, O—$CH_2$); 3.30-3.46 (m, 3H, N-$CH_2$+N-$CH_aH_b$); 3.59-3.69 (m, 1H, N—$CH_aH_b$); 3.84-3.94 (m, 2H, O—$CH_2$); 5.02-5.15 (m, 2H, Ph-O-CH+CONH—CH—$CH_3$); 6.69-6.83 (m, 3H, Ar); 7.28-7.36 (m, 1H, Ar); 7.47 (d, J 8.0 Hz, 2H, Ar); 7.88 (d, J 8.0 Hz, 2H, Ar); CONH signal was not observed; $CO_2H$ signal was not observed; HCl salt not observed. M/Z (M+H)$^+$: 457

Compound 416: Methyl 4-[1-[[4-[(3R)-3-(3-fluorophenoxy)pyrrolidin-1-yl]tetrahydropyran-4-carbonyl]amino]cyclopropyl]benzoate Compound 416 was obtained according to General Procedure I-b, starting from Compound 414 and methyl 4-(1-aminocyclopropyl)benzoate. Purification by flash chromatography (Cyclohexane/EtOAc: 100/0 to 40/60) afforded Compound 416 as a colorless oil in quantitative yield. M/Z (M+H)$^+$: 483

Example 143: 4-[1-[[4-[(3R)-3-(3-Fluorophenoxy)pyrrolidin-1-yl]tetrahydropyran-4-carbonyl]amino]cyclopropyl]benzoic acid, hydrochloride

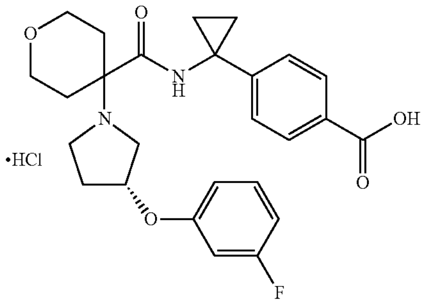 [SMILES: Cl ; O=C(O)c1ccc(C2(NC(=O)C3(N4CC[C@@H](Oc5cccc(F)c5)C4)CCOCC3)CC2)cc1]

Example 143 was obtained according to General Procedure V-e, starting from Compound 416. Purification by preparative LC-MS, then HCl salt preparation (method 1) afforded Example 143 as a white powder in 12% yield. $^1$H-NMR (DMSO-$d_6$/$D_2O$ 400 MHz) δ (ppm): 1.16-1.40 (m, 4H, $C(CH_2—CH_2)$); 1.90-2.03 (m, 2H, $CH_2$); 2.10-2.19 (m, 2H, $CH_2$); 2.35-2.45 (m, 2H, $CH_2$); 3.13-3.26 (m, 2H, O—$CH_2$); 3.26-3.47 (m, 3H, N—$CH_2$+N-$CH_aH_b$); 3.63-3.78 (m, 1H, N—$CH_aH_b$); 3.88-3.97 (m, 2H, O—$CH_2$); 5.09 (bs, 1H, PhO—CH); 6.72-6.85 (m, 3H, Ar); 7.29-7.36 (m, 3H, Ar); 7.86 (d, J 8.5 Hz, 2H, Ar); CONH signal was not observed; $CO_2H$ signal was not observed; HCl salt not observed. M/Z (M[$^{35}$Cl]+H)$^+$: 469

Compound 417: tert-Butyl-[(2R)-4-[tert-butyl(dimethyl)silyl]oxy-2-[3-(trifluoromethyl)phenoxy]butoxy]-dimethyl-silane Compound 417 was obtained according to General Procedure IX-b, starting from Compound 402 and 3-(trifluoromethyl)phenol. Purification by flash chromatography (Pentane/EtOAc: 100/0 to 85/15) afforded Compound 417 as a colorless oil in 57% yield. $^1$H-NMR (DMSO-$d_6$ 400 MHz) δ (ppm): −0.09-0.05 (m, 12H, Si—$CH_3$); 0.78-0.81 (m, 18H, $C(CH_3)_3$); 1.71-1.86 (m, 2H, $CH_2$); 3.65-3.77 (m, 3H, O-$CH_2$+O-$CH_aH_b$); 3.81 (dd, J 11.2, 3.8 Hz, 1H, O—$CH_aH_b$); 4.59-4.65 (m, 1H, PhO—CH); 7.22-7.27 (m, 3H, Ar); 7.45-7.50 (m, 1H, Ar).

Compound 418: (2R)-2-[3-(Trifluoromethyl)phenoxy]butane-1,4-diol

Compound 418 was obtained according to General Procedure XV-b, starting from Compound 417. Purification by flash chromatography (DCM/MeOH: 100/0 to 93/7) afforded Compound 418 as a colorless oil in 91% yield. $^1$H-NMR (DMSO-$d_6$, 400 MHz) δ (ppm): 1.68-1.84 (m, 2H, $CH_2$); 3.47-3.59 (m, 4H, HO—$CH_2$); 4.50-4.55 (m, 1H, PhO—CH); 4.57 (t, J 4.9 Hz, 1H, HO—$CH_2$—CH); 4.85 (t, J 4.9 Hz, 1H, HO—$CH_2$—$CH_2$); 7.22-7.30 (m, 3H, Ar); 7.49 (t, J 7.8 Hz, 1H, Ar).

Compound 419: 1-[(1R)-3-Bromo-1-(bromomethyl)propoxy]-3-(trifluoromethyl)benzene Compound 419 was obtained according to General Procedure XVI, starting from Compound 418. Purification by flash chromatography (Cyclohexane/EtOAc: 100/0 to 90/10) afforded Compound 419 as a colorless oil in 64% yield. $^1$H-NMR (DMSO-$d_6$ 400 MHz) δ (ppm): 2.20-2.30 (m, 1H, $CH_aH_b$); 2.30-2.40 (m, 1H, $CH_aH_b$); 3.54-3.71 (m, 2H, Br—$CH_2$—$CH_2$); 3.76 (dd, J 11.2, 4.4 Hz, 1H, Br—$CH_2$—CH); 3.95 (dd, J 11.2, 4.0 Hz, 1H, Br—$CH_2$—CH); 4.80-4.86 (m, 1H, Ph-O—CH); 6.79-6.85 (m, 1H, Ar); 7.32-7.37 (m, 2H, Ar); 7.56 (t, J 7.8 Hz, 1H, Ar).

Compound 420: Methyl 4-[(3R)-3-[3-(trifluoromethyl)phenoxy]pyrrolidin-1-yl]tetrahydropyran-4-carboxylate Compound 420 was obtained according to General Procedure VIII-b, starting from Compound 419 and methyl 4-aminotetrahydropyran-4-carboxylate. Purification by flash chromatography (Cyclohexane/EtOAc: 100/0 to 60/40) afforded Compound 420 as a brown oil in 39% yield. M/Z (M+H)$^+$: 374

Compound 421: Lithium 4-[(3R)-3-[3-Trifluoromethyl)phenoxy]pyrrolidin-1-yl]tetrahydropyran-4-carboxylate Compound 421 was obtained according to General Procedure V-f, starting from Compound 420, as a white powder in quantitative yield. M/Z (M+H)$^+$: 360

Compound 422: Methyl 4-[(1S)-1-[[4-[(3R)-3-[3-(trifluoromethyl)phenoxy]pyrrolidin-1-yl]tetrahydropyran-4-carbonyl]amino]ethyl]benzoate Compound 422 was obtained according to General Procedure I-a, starting from Compound 421 and methyl 4-[(1S)-1-aminoethyl]benzoate. Purification by flash chromatography (Cyclohexane/EtOAc: 100/0 to 40/60) afforded Compound 422 as a colorless oil in 63% yield. M/Z (M+H)$^+$: 521

Example 144: 4-[(1S)-1-[[4-[(3R)-3-[3-(Trifluoromethyl)phenoxy]pyrrolidin-1-yl]tetrahydropyran-4-carbonyl]amino]ethyl]benzoic acid, hydrochloride

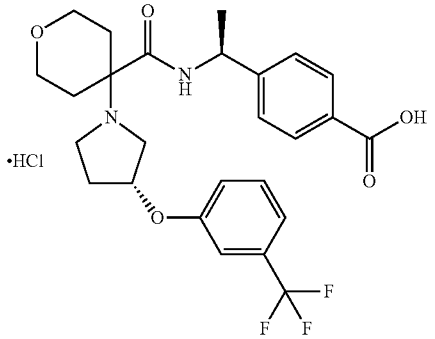 [SMILES: Cl ; C[C@H](NC(=O)C1(N2CC[C@@H](Oc3cccc(C(F)(F)F)c3)C2)CCOCC1)c1ccc(C(=O)O)cc1]

Example 144 was obtained according to General Procedure V-e, starting from Compound 422. Purification by preparative LC-MS, then HCl salt preparation (method 1) afforded Example 144 as a white powder in 55% yield. $^1$H-NMR (DMSO-$d_6$/$D_2O$ 400 MHz) δ (ppm): 1.48 (d, J 7.1 Hz, 3H, CH—$CH_3$); 1.86-1.98 (m, 2H, $CH_2$); 2.06-2.16 (m, 2H, $CH_2$); 2.39-2.47 (m, 2H, $CH_2$); 3.07-3.21 (m, 2H, O—$CH_2$); 3.31-3.47 (m, 3H, N—$CH_2$+N-$CH_aH_b$); 3.59-3.69 (m, 1H, N—$CH_aH_b$); 3.85-3.95 (m, 2H, O—$CH_2$);

5.07-5.14 (m, 1H, CONH—CH—$CH_3$); 5.17 (bs, 1H, Ph-O—CH); 7.14 (bs, 1H, Ar); 7.18 (d, J 8.0 Hz, 1H, Ar); 7.32 (d, J 8.0 Hz, 1H, Ar); 7.45 (d, J 8.2 Hz, 2H, Ar); 7.53 (t, J 8.0 Hz, 1H, Ar); 7.86 (d, J 8.2 Hz, 2H, Ar); CONH signal was not observed; $CO_2H$ signal was not observed; HCl salt not observed. M/Z $(M+H)^+$: 507

Compound 423: Methyl 4-[1-[[4-[(3R)-3-[3-(trifluoromethyl)phenoxy]pyrrolidin-1-yl]tetrahydropyran-4-carbonyl]amino]cyclopropyl]benzoate Compound 423 was obtained according to General Procedure I-b, starting from Compound 421 and methyl 4-(1-aminocyclopropyl)benzoate. Purification by flash chromatography (Cyclohexane/EtOAc: 100/0 to 40/60) afforded Compound 423 as a colorless oil in 68% yield. M/Z $(M+H)^+$: 533

Example 145: 4-[1-[[4-[(3R)-3-[3-(Trifluoromethyl)phenoxy]pyrrolidin-1-yl]tetrahydropyran-4-carbonyl]amino]cyclopropyl]benzoic acid, hydrochloride

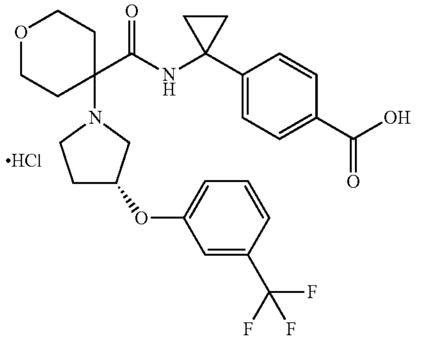 [SMILES: Cl ; O=C(O)c1ccc(C2(NC(=O)C3(N4CC[C@@H](Oc5cccc(C(F)(F)F)c5)C4)CCOCC3)CC2)cc1]

Example 145 was obtained according to General Procedure V-e, starting from Compound 423. Purification by preparative LC-MS, then HCl salt preparation (method 1) afforded Example 145 as a white powder in 22% yield. $^1$H-NMR (DMSO-$d_6$/$D_2O$, 400 MHz) δ (ppm): 1.19-1.37 (m, 4H, C($CH_2$—$CH_2$)); 1.87-1.99 (m, 2H, $CH_2$); 2.08-2.19 (m, 2H, $CH_2$); 2.30-2.42 (m, 2H, $CH_2$); 3.15-3.26 (m, 2H, O—$CH_2$); 3.27-3.44 (m, 3H, N—$CH_2$+N-$CH_aH_b$); 3.63-3.69 (m, 1H, N—$CH_aH_b$); 3.87-3.96 (m, 2H, O—$CH_2$); 5.17 (bs, 1H, Ph-O—CH); 7.17-7.24 (m, 2H, Ar); 7.29-7.36 (m, 3H, Ar); 7.54 (t, J 8.0 Hz, 1H, Ar); 7.84 (d, J 8.5 Hz, 2H, Ar); CONH signal was not observed; $CO_2H$ signal was not observed; HCl salt not observed. M/Z $(M+H)^+$: 519

Compound 424: tert-Butyl-[(2R)-4-[tert-butyl(dimethyl)silyl]oxy-2-[3-(trifluoromethoxy)phenoxy]butoxy]-dimethyl-silane Compound 424 was obtained according to General Procedure IX-b, starting from Compound 402 and 3-(trifluoromethoxy)phenol. Purification by flash chromatography (Pentane/EtOAc: 100/0 to 95/5) afforded Compound 424 as a yellow oil in 42% yield. $^1$H-NMR (DMSO-$d_6$ 400 MHz) δ (ppm): −0.07-0.05 (m, 12H, Si—$CH_3$); 0.78-0.83 (m, 18H, C($CH_3$)$_3$); 1.73-1.83 (m, 2H, $CH_2$); 3.66-3.75 (m, 3H, O—$CH_2$+0—$CH_aH_b$); 3.80 (dd, J 11.2, 3.8 Hz, 1H, O—$CH_aH_b$); 4.50-4.57 (m, 1H, Ph-O—CH); 6.86-7.00 (m, 3H, Ar); 7.34-7.39 (m, 1H, Ar).

Compound 425: (2R)-2-[3-(Trifluoromethoxy)phenoxy]butane-1,4-diol

Compound 425 was obtained according to General Procedure XV-b, starting from Compound 424. Purification by flash chromatography (DCM/MeOH: 100/0 to 95/5) afforded Compound 425 as a colorless oil in 87% yield. $^1$H-NMR (DMSO-$d_6$ 400 MHz) δ (ppm): 1.71-1.83 (m, 2H, $CH_2$); 3.45-3.60 (m, 4H, HO—$CH_2$); 4.45-4.51 (m, 1H, Ph-O—CH); 4.58 (t, J 5.3 Hz, 1H, HO—$CH_2$—CH); 4.85 (t, J 5.3 Hz, 1H, HO—$CH_2$—$CH_2$); 6.88-6.92 (m, 1H, Ar); 6.97 (bs, 1H, Ar); 7.01-7.05 (m, 1H, Ar); 7.39 (t, J 8.2 Hz, 1H, Ar).

Compound 426: 1-[(1R)-3-Bromo-1-(bromomethyl)propoxy]-3-(trifluoromethoxy)benzene Compound 426 was obtained according to General Procedure XVI, starting from Compound 425. Purification by flash chromatography (Cyclohexane/EtOAc: 100/0 to 95/5) afforded Compound 426 as a colorless oil in 68% yield. $^1$H-NMR (DMSO-$d_6$ 400 MHz) δ (ppm): 2.18-2.38 (m, 2H, $CH_2$); 3.54-3.71 (m, 2H, Br—$CH_2$—$CH_2$); 3.74 (dd, J 11.2, 4.4 Hz, 1H, Br—$CH_2$—CH); 3.84 (dd, J 11.2, 4.0 Hz, 1H, Br—$CH_2$—CH); 4.73-4.79 (m, 1H, Ph-O—CH); 6.96-7.00 (m, 1H, Ar); 7.03 (bs, 1H, Ar); 7.06-7.10 (m, 1H, Ar); 7.44 (t, J 8.2 Hz, 1H, Ar).

Compound 427: Methyl 4-[(3R)-3-[3-(trifluoromethoxy)phenoxy]pyrrolidin-1-yl]tetrahydropyran-4-carboxylate Compound 427 was obtained according to General Procedure VIII-b, starting from Compound 426 and methyl 4-aminotetrahydropyran-4-carboxylate. Purification by flash chromatography (Cyclohexane/EtOAc: 100/0 to 60/40) afforded Compound 427 as a colorless oil in 56% yield. M/Z $(M+H)^+$: 390

Compound 428: Lithium 4-[(3R)-3-[3-trifluoromethoxy)phenoxy]pyrrolidin-1-yl]tetrahydropyran-4-carboxylate Compound 428 was obtained according to General Procedure V-f, starting from Compound 427, as a white powder in quantitative yield. M/Z $(M+H)^+$: 376

Compound 429: Methyl 4-[(1S)-1-[[4-[(3R)-3-[3-(trifluoromethoxy)phenoxy]pyrrolidin-1-yl]tetrahydropyran-4-carbonyl]amino]ethyl]benzoate Compound 429 was obtained according to General Procedure I-b, starting from Compound 428 and methyl 4-[(1S)-1-aminoethyl]benzoate. Purification by flash chromatography (Cyclohexane/EtOAc: 100/0 to 50/50) afforded Compound 429 as a yellow oil in 77% yield. M/Z $(M+H)^+$: 537

Example 146: 4-[(1S)-1-[[4-[(3R)-3-[3-(Trifluoromethoxy)phenoxy]pyrrolidin-1-yl]tetrahydropyran-4-carbonyl]amino]ethyl]benzoic acid, hydrochloride

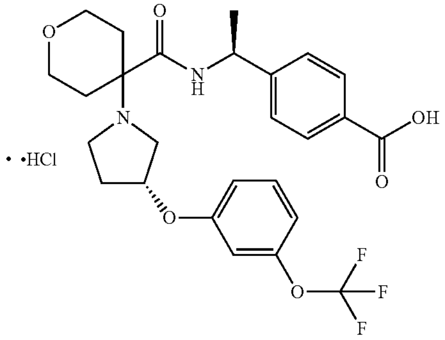 [SMILES: Cl ; C[C@H](NC(=O)C1(N2CC[C@@H](Oc3cccc(OC(F)(F)F)c3)C2)CCOCC1)c1ccc(C(=O)O)cc1]

Example 146 was obtained according to General Procedure V-e, starting from Compound 429. Purification by preparative LC-MS, then HCl salt preparation (method 1) afforded Example 146 as a white powder in 62% yield. $^1$H-NMR (DMSO-$d_6$/$D_2O$ 400 MHz) δ (ppm): 1.46 (d, J 7.1 Hz, 3H, CH—$CH_3$); 1.80-1.94 (m, 2H, $CH_2$); 2.05-2.13 (m, 2H, $CH_2$); 2.36-2.46 (m, 2H, $CH_2$); 3.06-3.19 (m, 2H, O—$OH_2$); 3.31-3.44 (m, 3H, N—$CH_2$+N-$CH_aH_b$); 3.60-3.68 (m, 1H, N—$CH_aH_b$); 3.85-3.95 (m, 2H, O—$CH_2$); 5.04-5.11 (m, 2H, CONH—CH—$CH_3$+Ph-O—CH); 6.79 (bs, 1H, Ar); 6.89 (dd, J 8.2, 2.0 Hz, 1H, Ar); 6.95 (d, J 8.2 Hz, 1H, Ar); 7.40 (t, J 8.2 Hz, 1H, Ar); 7.43 (d, J 8.2 Hz, 2H, Ar); 7.86 (d, J 8.2 Hz, 2H, Ar); CONH signal was not observed; $CO_2H$ signal was not observed; HCl salt not observed. M/Z $(M+H)^+$: 523

Compound 430: Methyl 4-[1-[[4-[(3R)-3-[3-(trifluoromethoxy)phenoxy]pyrrolidin-1-yl]tetrahydropyran-4-carbonyl]amino]cyclopropyl]benzoate Compound 430 was obtained according to General Procedure I-b, starting from Compound 428 and methyl 4-(1-aminocyclopropyl)benzoate. Purification by flash chromatography (Cyclohexane/EtOAc: 100/0 to 50/50) afforded Compound 430 as a colorless oil in 79% yield. M/Z $(M+H)^+$: 549

Example 147: 4-[1-[[4-[(3R)-3-[3-(Trifluoromethoxy)phenoxy]pyrrolidin-1-yl]tetrahydropyran-4-carbonyl]amino]cyclopropyl]benzoic acid, hydrochloride

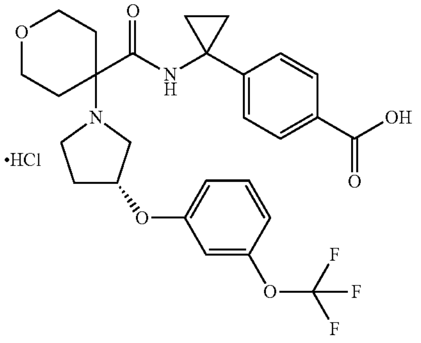 [SMILES: Cl ; O=C(O)c1ccc(C2(NC(=O)C3(N4CC[C@@H](Oc5cccc(OC(F)(F)F)c5)C4)CCOCC3)CC2)cc1]

Example 147 was obtained according to General Procedure V-e, starting from Compound 430. Purification by preparative LC-MS, then HCl salt preparation (method 1) afforded Example 147 as a white powder in 21% yield. $^1$H-NMR (DMSO-$d_6$/$D_2O$ 400 MHz) δ (ppm): 1.16-1.35 (m, 4H, C($CH_2$—$CH_2$)); 1.79-1.93 (m, 2H, $CH_2$); 2.07-2.17 (m, 2H, $CH_2$); 2.30-2.41 (m, 2H, $CH_2$); 3.12-3.24 (m, 2H, O—$CH_2$); 3.24-3.46 (m, 3H, N—$CH_2$+N-$CH_aH_b$); 3.59-3.89 (m, 1H, $CH_aH_b$); 3.85-3.95 (m, 2H, O—$CH_2$); 5.06 (bs, 1H, Ph-O—CH); 6.78 (bs, 1H, Ar); 6.89 (d, J 8.2 Hz, 1H, Ar); 6.94 (d, J 8.2 Hz, 1H, Ar); 7.30 (d, J 8.5 Hz, 2H, Ar); 7.40 (t, J 8.2 Hz, 1H, Ar); 7.82 (d, J 8.5 Hz, 2H, Ar); CONH signal was not observed; $CO_2H$ signal was not observed; HCl salt not observed. M/Z $(M+H)^+$: 535

Compound 431: tert-Butyl-[(2R)-4-[tert-butyl(dimethyl)silyl]oxy-2-(3-bromophenoxy)butoxy]-dimethyl-silane Compound 431 was obtained according to General Procedure IX-b, starting from Compound 402 and 3-bromophenol. Purification by flash chromatography (Pentane/EtOAc: 100/0 to 95/5) afforded Compound 431 as a colorless oil in 45% yield. $^1$H-NMR (DMSO-$d_6$ 400 MHz) δ (ppm): −0.06-0.03 (m, 12H, Si—$CH_3$); 0.79-0.87 (m, 18H, $C(CH_3)_3$); 1.70-1.83 (m, 2H, $CH_2$); 3.64-3.75 (m, 3H, O-$CH_2$+O-$CH_aH_b$); 3.78 (dd, J 11.4, 3.8 Hz, 1H, O—$CH_aH_b$); 4.49-4.56 (m, 1H, Ph-O—CH); 6.93-6.97 (m, 1H, Ar); 7.06-7.11 (m, 1H, Ar); 7.15-7.23 (m, 2H, Ar).

Compound 432: (2R)-2-(3-Bromophenoxy)butane-1,4-diol

Compound 432 was obtained according to General Procedure XV-b, starting from Compound 431. Purification by flash chromatography (DCM/MeOH: 100/0 to 95/5) afforded Compound 431 as a colorless oil in 95% yield. $^1$H-NMR (DMSO-$d_6$ 400 MHz) δ (ppm): 1.66-1.82 (m, 2H, $CH_2$); 3.44-3.56 (m, 4H, HO—$CH_2$); 4.40-4.57 (m, 1H, Ph-O—CH); 4.55 (t, J 5.3 Hz, 1H, HO—$CH_2$—CH); 4.81 (t, J 5.3 Hz, 1H, HO—$CH_2$—$CH_2$); 6.98 (ddd, J 8.2, 2.4, 0.8 Hz, 1H, Ar); 7.08 (ddd, J 8.2, 1.8, 0.8 Hz, 1H, Ar); 7.18-7.24 (m, 2H, Ar).

Compound 433: 1-[(1R)-3-Bromo-1-(bromomethyl)propoxy]-3-bromobenzene

Compound 433 was obtained according to General Procedure XVI, starting from Compound 432. Purification by flash chromatography (Cyclohexane/EtOAc: 100/0 to 90/0) afforded Compound 433 as a colorless oil in 55% yield. $^1$H-NMR (DMSO-$d_6$ 400 MHz) S (ppm): 2.17-2.37 (m, 2H, $CH_2$); 3.55-3.70 (m, 2H, Br—$CH_2$—$CH_2$); 3.73 (dd, J 11.2, 4.4 Hz, 1H, Br—$CH_2$—CH); 3.83 (dd, J 11.2, 4.2 Hz, 1H, Br—$CH_2$—CH); 4.70-4.76 (m, 1H, Ph-O—CH); 7.05 (ddd, J 8.2, 2.4, 0.8 Hz, 1H, Ar); 7.18 (ddd, J 8.2, 1.8, 0.8 Hz, 1H, Ar); 7.24-7.30 (m, 2H, Ar).

Compound 434: Methyl 4-[(3R)-3-(3-bromophenoxy)pyrrolidin-1-yl]tetrahydropyran-4-carboxylate Compound 434 was obtained according to General Procedure VIII-b, starting from Compound 433 and methyl 4-aminotetrahydropyran-4-carboxylate. Purification by flash chromatography (Cyclohexane/EtOAc: 100/0 to 50/50) afforded Compound 434 as a yellow oil in 33% yield. M/Z $(M[^{19}Br]+H)^+$: 384

Compound 435: Methyl 4-[(3R)-3-(3-methoxyphenoxy)pyrrolidin-1-yl]tetrahydropyran-4-carboxylate To a solution of Compound 434 (1.0 equiv.) in dioxane (0.1 M) was added sodium tert-butoxide (1.4 equiv.). The reaction mixture was degassed with argon, then tBuBrettPhos Pd G3 (10 mol %) and methanol (5 equiv.) were added. The reaction mixture was stirred at rt for 1.5 h. The reaction mixture was filtered over celite. The filtrate was concentrated to dryness. The obtained crude was purified by flash chromatography (Cyclohexane/EtOAc: 100/0 to 50/50) to afford Compound 435 as a beige solid in 93% yield. M/Z $(M+H)^+$: 336

Compound 436: Lithium 4-[(3R)-3-(3-methoxyphenoxy)pyrrolidin-1-yl]tetrahydropyran-4-carboxylate Compound 436 was obtained according to General Procedure V-f, starting from Compound 435, as a white powder in quantitative yield. M/Z $(M+H)^+$: 322

Compound 437: Methyl 4-[(1S)-1-[[4-[(3R)-3-(3-methoxyphenoxy)pyrrolidin-1-yl]tetrahydropyran-4-carbonyl]amino]ethyl]benzoate Compound 437 was obtained according to General Procedure I-b, starting from Compound 436 and methyl 4-[(1S)-1-aminoethyl]benzoate. Purification by flash chromatography (Cyclohexane/EtOAc: 100/0 to 20/80) afforded Compound 437 as a yellow oil in 47% yield. M/Z $(M+H)^+$: 483

Example 148: 4-[(1S)-1-[[4-[(3R)-3-(3-Methoxyphenoxy)pyrrolidin-1-yl]tetrahydropyran-4-carbonyl]amino]ethyl]benzoic acid, hydrochloride

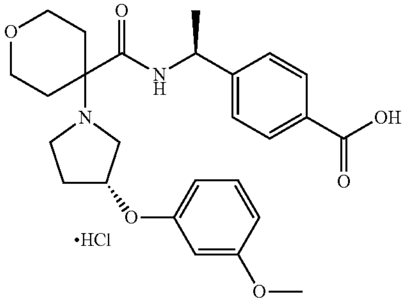 [SMILES: COc1cccc(O[C@@H]2CCN(C3(C(=O)N[C@@H](C)c4ccc(C(=O)O)cc4)CCOCC3)C2)c1 ; Cl]

Example 148 was obtained according to General Procedure V-e, starting from Compound 437. Purification by preparative LC-MS, then HCl salt preparation (method 1) afforded Example 148 as a white powder in 59% yield. $^1$H-NMR (DMSO-$d_6$/$D_2$, 400 MHz) δ (ppm): 1.46 (d, J 7.1 Hz, 3H, CH—$CH_3$); 1.80-1.91 (m, 2H, $CH_2$); 2.01-2.12 (m, 2H, $CH_2$); 2.31-2.43 (m, 2H, $CH_2$); 3.09-3.20 (m, 2H, O—$CH_2$); 3.27-3.36 (m, 3H, N—$CH_2$+N-$CH_aH_b$); 3.53-3.62 (m, 1H, N—$CH_aH_b$); 3.69 (s, 3H, O—$CH_3$); 3.85-3.95 (m, 2H, O—$CH_2$); 4.98 (bs, 1H, Ph-O—CH); 5.09 (q, J 7.1 Hz, 1H, CONH—CH—$CH_3$); 6.37-6.41 (m, 1H, Ar); 6.44 (dd, J 8.2, 2.0 Hz, 1H, Ar); 6.55 (dd, J 8.2, 2.0 Hz, 1H, Ar); 7.18 (t, J 8.2 Hz, 1H, Ar); 7.44 (d, J 8.2 Hz, 2H, Ar); 7.86 (d, J 8.2 Hz, 2H, Ar); CONH signal was not observed; $CO_2H$ signal was not observed; HCl salt not observed. M/Z $(M+H)^+$: 469

Compound 438: Methyl 4-[1-[[4-[(3R)-3-(3-methoxyphenoxy)pyrrolidin-1-yl]tetrahydropyran-4-carbonyl]amino]cyclopropyl]benzoate Compound 438 was obtained according to General Procedure I-b, starting from Compound 436 and methyl 4-(1-aminocyclopropyl)benzoate. Purification by flash chromatography (Cyclohexane/EtOAc: 100/0 to 30/70) afforded Compound 438 as a colorless oil in 32% yield. M/Z $(M+H)^+$: 495

Example 149: 4-[1-[[4-[(3R)-3-(3-Methoxyphenoxy)pyrrolidin-1-yl]tetrahydropyran-4-carbonyl]amino]cyclopropyl]benzoic acid, hydrochloride

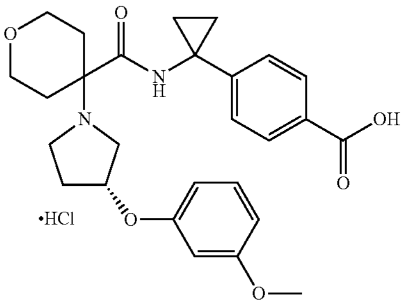 [SMILES: COc1cccc(O[C@@H]2CCN(C3(C(=O)NC4(c5ccc(C(=O)O)cc5)CC4)CCOCC3)C2)c1 ; Cl]

Example 149 was obtained according to General Procedure IV-b, starting from Compound 438. Purification by preparative LC-MS, then HCl salt preparation (method 1) afforded Example 149 as a white powder in 48% yield. $^1$H-NMR (DMSO-$d_6$/$D_2O$, 400 MHz) δ (ppm): 1.18-1.34 (m, 4H, C($CH_2$—$CH_2$)); 1.80-1.91 (m, 2H, $CH_2$); 2.06-2.13 (m, 2H, $CH_2$); 2.29-2.36 (m, 2H, $CH_2$); 3.13-3.36 (m, 5H, O-$CH_2$+N-$CH_2$+N-$CH_aH_b$); 3.54-3.62 (m, 1H, N—$CH_aH_b$); 3.69 (s, 3H, O—$CH_3$); 3.85-3.95 (m, 2H, O—$CH_2$); 5.01 (bs, 1H, Ph-O—CH); 6.40-6.43 (m, 1H, Ar); 6.46 (dd, J 8.2, 2.0 Hz, 1H, Ar); 6.56 (dd, J 8.2, 2.0 Hz, 1H, Ar); 7.19 (t, J 8.2 Hz, 1H, Ar); 7.29 (d, J 8.5 Hz, 2H, Ar); 7.83 (d, J 8.5 Hz, 2H, Ar); CONH signal was not observed; $CO_2H$ signal was not observed; HCl salt not observed. M/Z $(M+H)^+$: 481

Compound 439: Methyl 4-[(3R)-3-(3-methylphenoxy)pyrrolidin-1-yl]tetrahydropyran-4-carboxylate To a solution of Compound 434 (1.0 equiv.) in dioxane (0.1 M) was added dimethylzinc 2 M in toluene (1.5 equiv.). The reaction mixture was degassed with argon, then $Pd(PtBu_3)_2$ (10 mol %) was added. The reaction mixture was stirred at 100° C. for 1 h. The reaction mixture was filtered over celite. The filtrate was concentrated to dryness. The obtained crude was purified by flash chromatography (Cyclohexane/EtOAc: 100/0 to 50/50) to afford Compound 439 as a yellow solid in 90% yield. M/Z $(M+H)^+$: 320

Compound 440: Lithium 4-[(3R)-3-(3-methylphenoxy)pyrrolidin-1-yl]tetrahydropyran-4-carboxylate Compound 440 was obtained according to General Procedure V-f, starting from Compound 439, as a brown powder in quantitative yield. M/Z $(M+H)^+$: 306

Compound 441: Methyl 4-[(1S)-1-[[4-[(3R)-3-(3-methylphenoxy)pyrrolidin-1-yl]tetrahydropyran-4-carbonyl]amino]ethyl]benzoate Compound 441 was obtained according to General Procedure I-b, starting from Compound 440 and methyl 4-[(1S)-1-aminoethyl]benzoate. Purification by flash chromatography (Cyclohexane/EtOAc: 100/0 to 20/80) afforded Compound 441 as a yellow oil in 54% yield. M/Z $(M+H)^+$: 467

Example 150: 4-[(1S)-1-[[4-[(3R)-3-(3-Methylphenoxy)pyrrolidin-1-yl]tetrahydropyran-4-carbonyl]amino]ethyl]benzoic acid, hydrochloride

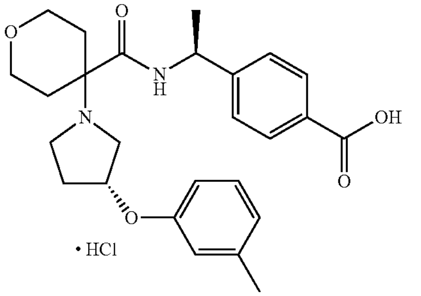 [SMILES: Cc1cccc(O[C@@H]2CCN(C3(C(=O)N[C@@H](C)c4ccc(C(=O)O)cc4)CCOCC3)C2)c1 ; Cl]

Example 150 was obtained according to General Procedure IV-b, starting from Compound 441. Purification by preparative LC-MS, then HCl salt preparation (method 1) afforded Example 150 as a white powder in 71% yield. $^1$H-NMR ($DMSO-d_6/D_2O$ 400 MHz) δ (ppm): 1.47 (d, J 7.1 Hz, 3H, CH—$CH_3$); 1.82-1.93 (m, 2H, $CH_2$); 2.02-2.11 (m, 2H, $CH_2$); 2.24 (s, 3H, Ph-$CH_3$); 2.38-2.47 (m, 2H, $CH_2$); 3.09-3.19 (m, 2H, O—$CH_2$); 3.29-3.42 (m, 3H, N—$CH_2$+N-$CH_aH_b$); 3.60-3.69 (m, 1H, N—$CH_aH_b$); 3.86-3.93 (m, 2H, O—$CH_2$); 4.99 (bs, 1H, PhO—CH); 5.09 (q, J 7.1 Hz, 1H, CONH—CH—$CH_3$); 6.62-6.66 (m, 2H, Ar); 6.78 (d, J 7.8 Hz, 1H, Ar); 7.18 (dd, J 8.8, 7.8 Hz, 1H, Ar); 7.45 (d, J 8.2 Hz, 2H, Ar); 7.86 (d, J 8.2 Hz, 2H, Ar); CONH signal was not observed; $CO_2H$ signal was not observed; HCl salt not observed. M/Z $(M+H)^+$: 453

Compound 442: Methyl 4-[1-[[4-[(3R)-3-(3-methylphenoxy)pyrrolidin-1-yl]tetrahydropyran-4-carbonyl]amino]cyclopropyl]benzoate Compound 442 was obtained according to General Procedure I-b, starting from Compound 440 and methyl 4-(1-aminocyclopropyl)benzoate. Purification by flash chromatography (Cyclohexane/EtOAc: 100/0 to 20/80) afforded Compound 442 as a yellow oil in 49% yield. M/Z $(M+H)^+$: 479

Example 151: 4-[1-[[4-[(3R)-3-(3-Methylphenoxy)pyrrolidin-1-yl]tetrahydropyran-4-carbonyl]amino]cyclopropyl]benzoic acid, hydrochloride

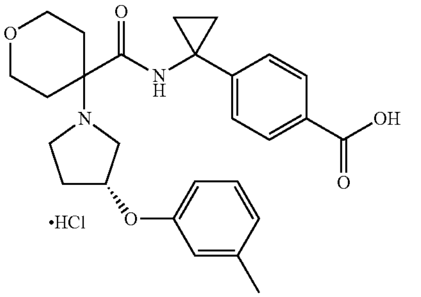 [SMILES: Cc1cccc(O[C@@H]2CCN(C3(C(=O)NC4(c5ccc(C(=O)O)cc5)CC4)CCOCC3)C2)c1 ; Cl]

Example 151 was obtained according to General Procedure IV-b, starting from Compound 442. Purification by preparative LC-MS, then HCl salt preparation (method 1) afforded Example 151 as a white powder in 45% yield. $^1$H-NMR ($DMSO-d_6/D_2O$, 400 MHz) δ (ppm): 1.20-1.36 (m, 4H, C($CH_2$—$CH_2$)); 1.84-1.96 (m, 2H, $CH_2$); 2.06-2.13 (m, 2H, $CH_2$); 2.24 (s, 3H, Ph-$CH_3$); 2.34-2.42 (m, 2H, $CH_2$); 3.13-3.24 (m, 2H, O—$CH_2$); 3.25-3.45 (m, 3H, N—$CH_2$+N-$CH_aH_b$); 3.62-3.71 (m, 1H, N—$CH_aH_b$): 3.87-3.95 (m, 2H, O—$CH_2$); 5.01 (bs, 1H, Ph-O—CH); 6.65-6.70 (m, 2H, Ar); 6.79 (d, J 7.6 Hz, 1H, Ar); 7.16 (t, J 7.6 Hz, 1H, Ar); 7.31 (d, J 8.5 Hz, 2H, Ar); 7.84 (d, J 8.5 Hz, 2H, Ar); CONH signal was not observed; $CO_2H$ signal was not observed; HCl salt not observed. M/Z $(M+H)^+$: 465

Compound 443: Methyl 4-((3R)-3-phenoxypyrrolidin-1-yl)tetrahydropyran-4-carboxylate A solution of Compound 434 (1.0 equiv.) in methanol (0.1 M) was degassed with argon, then Pd/C 10% wt (10 wt %) was added. The reaction mixture was stirred at rt for 1 h under hydrogen atmosphere ($P_{atm}$). The reaction mixture was filtered over celite. The filtrate was concentrated to dryness. The obtained crude was purified by flash chromatography (Cyclohexane/EtOAc: 100/0 to 40/60, then DCM/MeOH: 90/10) to afford Compound 443 as a yellow solid in quantitative yield. M/Z $(M+H)^+$ 306

Compound 444: Lithium 4-((3R)-3-phenoxypyrrolidin-1-yl)tetrahydropyran-4-carboxylate Compound 444 was obtained according to General Procedure V-f, starting from Compound 443, as a white powder in quantitative yield. M/Z $(M+H)^+$: 292

Compound 445: Methyl 4-[(1S)-1-[[4-((3R)-3-phenoxypyrrolidin-1-yl)tetrahydropyran-4-carbonyl]amino]ethyl]benzoate Compound 445 was obtained according to General Procedure I-b, starting from Compound 444 and methyl 4-[(1S)-1-aminoethyl]benzoate. Purification by flash chromatography (Cyclohexane/EtOAc: 100/0 to 20/80) afforded Compound 445 as a yellow oil in 87% yield. M/Z $(M+H)^+$: 453

Example 152: 4-[(1S)-1-[[4-((3R)-3-Phenoxypyrrolidin-1-yl)tetrahydropyran-4-carbonyl]amino]ethyl] benzoic acid, hydrochloride

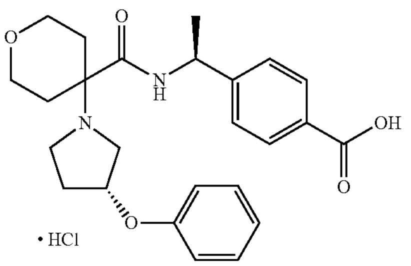 [SMILES: C[C@H](NC(=O)C1(N2CC[C@@H](Oc3ccccc3)C2)CCOCC1)c1ccc(C(=O)O)cc1 ; Cl]

Example 152 was obtained according to General Procedure V-e, starting from Compound 445. Purification by preparative LC-MS, then HCl salt preparation (method 1) afforded Example 152 as a white powder in 31% yield. $^1$H-NMR (DMSO-d/$D_2O$ 400 MHz) δ (ppm): 1.48 (d, J 7.1 Hz, 3H, CH—$CH_3$); 1.84-1.95 (m, 2H, $CH_2$); 2.03-2.13 (m, 2H, $CH_2$); 2.37-2.47 (m, 2H, $CH_2$); 3.09-3.20 (m, 2H, O—$CH_2$); 3.29-3.41 (m, 3H, N—$CH_2$+N-$CH_aH_b$); 3.60-3.69 (m, 1H, N—$CH_aH_b$); 3.85-3.93 (m, 2H, O—$CH_2$); 5.02 (bs, 1H, Ph-O—CH); 5.10 (q, J 7.1 Hz, 1H, CONH—CH—$CH_3$); 6.86 (d, J 8.2 Hz, 2H, Ar); 6.97 (t, J 7.4 Hz, 1H, Ar); 7.29 (dd, J 8.2, 7.4 Hz, 2H, Ar); 7.46 (d, J 8.2 Hz, 2H, Ar); 7.87 (d, J 8.2 Hz, 2H, Ar); CONH signal was not observed; $CO_2H$ signal was not observed; HCl salt not observed. M/Z $(M+H)^+$: 439

Compound 446: Methyl 4-[1-[[4-((3R)-3-Phenoxypyrrolidin-1-yl)tetrahydropyran-4-carbonyl]amino] cyclopropyl]benzoate Compound 446 was obtained according to General Procedure 1-b, starting from Compound 444 and methyl 4-(1-aminocyclopropyl)benzoate. Purification by flash chromatography (Cyclohexane/EtOAc: 100/0 to 20/80) afforded Compound 446 as a yellow oil in 31% yield. M/Z $(M+H)^+$: 465

Example 153: 4-[1-[[4-((3R)-3-Phenoxypyrrolidin-1-yl)tetrahydropyran-4-carbonyl]amino]cyclopropyl] benzoic acid, hydrochloride

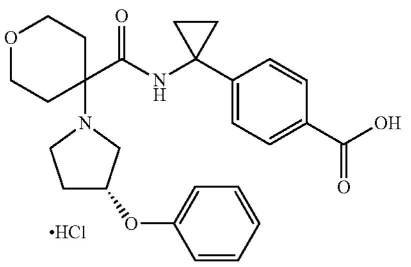 [SMILES: O=C(O)c1ccc(C2(NC(=O)C3(N4CC[C@@H](Oc5ccccc5)C4)CCOCC3)CC2)cc1 ; Cl]

Example 153 was obtained according to General Procedure IV-b, starting from Compound 446. Purification by preparative LC-MS, then HCl salt preparation (method 1) afforded Example 153 as a white powder in 22% yield. $^1$H-NMR (DMSO-de/$D_2O$ 400 MHz) δ (ppm): 1.18-1.34 (m, 4H, C($CH_2$—$CH_2$)); 1.81-1.92 (m, 2H, $CH_2$); 2.05-2.13 (m, 2H, $CH_2$); 2.29-2.37 (m, 2H, $CH_2$); 3.14-3.36 (m, 5H, O-$CH_2$+N-$CH_2$+N-$CH_aH_b$); 3.55-3.62 (m, 1H, N—$CH_aH_b$); 3.87-3.95 (m, 2H, O—$CH_2$); 5.00 (bs, 1H, Ph-O—CH); 6.87 (d, J 8.0 Hz, 2H, Ar); 6.97 (t, J 7.2 Hz, 1H, Ar); 7.26-7.33 (m, 4H, Ar); 7.83 (d, J 8.5 Hz, 2H, Ar); CONH signal was not observed; $CO_2H$ signal was not observed; HCl salt not observed. M/Z $(M+H)^+$: 451

Compound 447: Methyl 4-[(3R)-3-(cyclohexyloxy) pyrrolidin-1-yl]tetrahydropyran-4-carboxylate A solution of Compound 443 (1.0 equiv.) in toluene (0.1 M) was degassed with argon, then Rh/C 5% wt (20 wt %) was added. The reaction mixture was stirred at 100° C. for 5 days under hydrogen atmosphere. The reaction mixture was filtered over celite. The filtrate was concentrated to dryness to afford Compound 447 as a colorless oil in 76% yield, M/Z $(M+H)^+$: 312

Compound 448: Lithium 4-[(3R)-3-(cyclohexyloxy) pyrrolidin-1-yl]tetrahydropyran-4-carboxylate Compound 448 was obtained according to General Procedure V-f, starting from Compound 447, as a white powder in quantitative yield. M/Z $(M+H)^+$: 298

Compound 449: Methyl 4-[(1S)-1-[[4-[(3R)-3-(cyclohexyloxy]pyrrolidin-1-yl)tetrahydropyran-4-carbonyl]amino]ethyl]benzoate Compound 449 was obtained according to General Procedure I-a, starting from Compound 448 and methyl 4-[(1S)-1-aminoethyl]benzoate. Purification by flash chromatography (Cyclohexane/EtOAc: 100/0 to 70/30) afforded Compound 449 as a colorless oil in 66% yield. M/Z $(M+H)^+$: 459

Example 154: 4-[(1S)-1-[[4-[(3R)-3-(Cyclohexyloxy]pyrrolidin-1-yl]tetrahydropyran-4-carbonyl] amino]ethyl]benzoic acid, hydrochloride

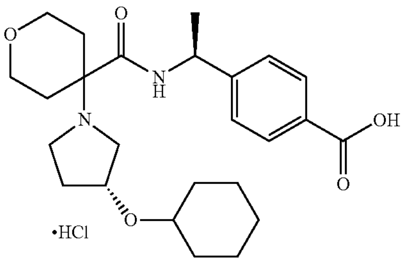 [SMILES: C[C@H](NC(=O)C1(N2CC[C@@H](OC3CCCCC3)C2)CCOCC1)c1ccc(C(=O)O)cc1 ; Cl]

Example 154 was obtained according to General Procedure IV-b, starting from Compound 449. Purification by preparative LC-MS, then HCl salt preparation (method 1) afforded Example 154 as a white powder in 29% yield. $^1$H-NMR (DMSO-$d_6$/$D_2O$, 400 MHz) δ (ppm): 1.00-1.21 (m, 5H, $CH_2$+$CH_aH_b$); 1.37-1.42 (m, 1H, $CH_aH_b$); 1.45 (d, J 7.1 Hz, 3H, CH—$CH_3$); 1.53-1.61 (m, 2H, $CH_2$); 1.65-1.74 (m, 2H, $CH_2$); 1.75-1.88 (m, 4H, $CH_2$); 2.33-2.43 (m, 2H, $CH_2$); 3.03 (bs, 1H, Pyrrolidinyl-O—CH); 2.99-3.30 (m, 5H, O-$CH_2$+N-$CH_2$+N-$CH_aH_b$); 3.30-3.40 (m, 1H, N—$CH_aH_b$); 3.83-3.93 (m, 2H, O—$CH_2$); 4.11-4.19 (m, 1H, Cyclohexyl-O—CH); 5.07 (q, J 7.1 Hz, 1H, CONH—CH—$CH_3$); 7.45 (d, J 8.3 Hz, 2H, Ar); 7.89 (d, J 8.3 Hz, 2H, Ar); CONH signal was not observed; $CO_2H$ signal was not observed; HCl salt not observed. M/Z $(M+H)^+$: 445

Compound 450: Methyl 1-[(3R)-3-(3-chlorophenoxy)pyrrolidin-1-yl]cyclohexane-1-carboxylate Compound 450 was obtained according to General Procedure VIII-b, starting from Compound 405 and methyl 1-aminocyclohexane-1-carboxylate. Purification by flash chromatography (DCM/MeOH: 100/0 to 80/20) afforded Compound 450 as a colorless oil. M/Z $(M[^{35}Cl]+H)^+$: 338

Compound 451: Lithium 1-[(3R)-3-(3-Chlorophenoxy)pyrrolidin-1-yl]cyclohexane-1-carboxylate Compound 451 was obtained according to General Procedure V-f, starting from Compound 450. M/Z $(M[^{35}Cl]+H)^+$: 324

Compound 452: Methyl 4-[(1S)-1-[[1-[(3R)-3-(3-chlorophenoxy)pyrrolidin-1-yl]cyclohexane-1-carbonyl]amino]ethyl]benzoate Compound 452 was obtained according to General Procedure I-a, starting from Compound 451 and methyl 4-[(1S)-1-aminoethyl]benzoate. Purification by flash chromatography (Cyclohexane/EtOAc: 100/0 to 70/30) afforded Compound 452 as a colorless oil in 34% yield over 3 steps. M/Z $(M[^{35}Cl]+H)^+$: 485

Example 155: 4-[(1S)-1-[[1-[(3R)-3-(3-Chlorophenoxy)pyrrolidin-1-yl]cyclohexane-1-carbonyl]amino]ethyl]benzoic acid, hydrochloride

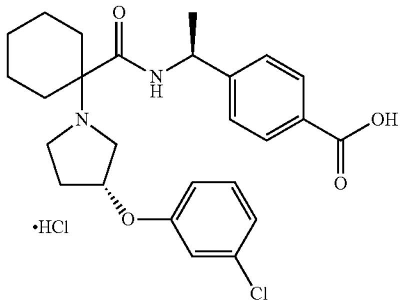 [SMILES: C[C@H](NC(=O)C1(N2CC[C@@H](Oc3cccc(Cl)c3)C2)CCCCC1)c1ccc(C(=O)O)cc1 ; Cl]

Example 155 was obtained according to General Procedure IV-b, starting from Compound 452. Purification by preparative LC-MS, then HCl salt preparation (method 1) afforded Example 155 as a white powder in 25% yield. $^1$H-NMR (DMSO-$d_6$/$D_2O$, 400 MHz) δ (ppm): 1.06-1.20 (m, 3H, $CH_2$+$CH_aH_b$); 1.46 (d, J 7.1 Hz, 3H, CH—$CH_3$); 1.50-1.65 (m, 3H, $CH_2$+$CH_aH_b$); 1.66-1.77 (m, 2H, $CH_2$); 2.02-2.13 (m, 2H, $CH_2$); 2.39-2.47 (m, 2H, $CH_2$); 3.30-3.47 (m, 3H, N—$CH_2$+N-$CH_aH_b$); 3.60-3.71 (m, 1H, N—$CH_aH_b$); 5.02-5.11 (m, 2H, Ph-O-CH+CONH—CH—$CH_3$); 6.82 (bd, J 8.1 Hz, 1H, Ar); 6.90 (bs, 1H, Ar); 7.02 (dd, J 8.1, 1.0 Hz, 1H, Ar); 7.30 (t, J 8.1 Hz, 1H, Ar); 7.44 (d, J 8.2 Hz, 2H, Ar); 7.86 (d, J 8.2 Hz, 2H, Ar); CONH signal was not observed; $CO_2H$ signal was not observed; HCl salt not observed. M/Z $(M[^{35}Cl]+H)^+$: 471

Compound 453: Methyl 1-[(3R)-3-(3-chlorophenoxy)pyrrolidin-1-yl]-4,4-difluorocyclohexane-1-carboxylate Compound 453 was obtained according to General Procedure VIII-b, starting from Compound 405 and methyl 1-amino-4,4-difluorocyclohexane-1-carboxylate. Purification by flash chromatography (DCM/MeOH: 100/0 to 80/20) afforded Compound 453 as a colorless oil in 28% yield. M/Z $(M[^{35}Cl]+H)^+$: 374

Compound 454: Lithium 1-[(3R)-3-(3-Chlorophenoxy)pyrrolidin-1-yl]-4,4-difluorocyclohexane-1-carboxylate Compound 454 was obtained according to General Procedure V-f, starting from Compound 453. M/Z $(M[^{35}Cl]+H)^+$: 360

Compound 455: Methyl 4-[(1S)-1-[[1-[(3R)-3-(3-chlorophenoxy)pyrrolidin-1-yl]-4,4-difluorocyclohexane-1-carbonyl]amino]ethyl]benzoate Compound 455 was obtained according to General Procedure I-a, starting from Compound 454 and methyl 4-[(1S)-1-aminoethyl]benzoate. Purification by flash chromatography (Cyclohexane/EtOAc: 100/0 to 80/20) afforded Compound 455 as a colorless oil in 66% yield over 2 steps. M/Z $(M[^{35}Cl]+H)^+$: 521

Example 156: 4-[(1S)-1-[[1-[(3R)-3-(3-Chlorophenoxy)pyrrolidin-1-yl]-4,4-difluorocyclohexane-1-carbonyl]amino]ethyl]benzoic acid, hydrochloride

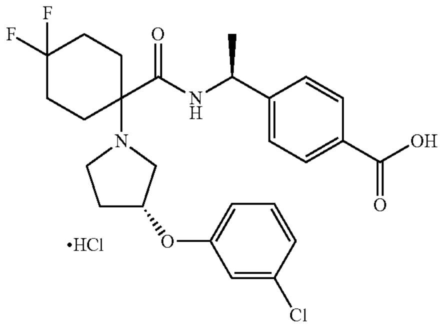 [SMILES: C[C@H](NC(=O)C1(N2CC[C@@H](Oc3cccc(Cl)c3)C2)CCC(F)(F)CC1)c1ccc(C(=O)O)cc1 ; Cl]

Example 156 was obtained according to General Procedure IV-b, starting from Compound 452. Purification by preparative LC-MS, then HCl salt preparation (method 1) afforded Example 156 as a white powder in 22% yield. $^1$H-NMR (DMSO-$d_6$/$D_2O$ 400 MHz) δ (ppm): 1.44 (d, J 7.1 Hz, 3H, CH—$CH_3$); 1.55-1.75 (m, 2H, $CH_2$); 1.86-1.97 (m, 2H, $CH_2$); 1.98-2.18 (m, 4H, $CH_2$); 2.38-2.48 (m, 2H, $CH_2$); 3.22-3.34 (m, 3H, N—$CH_2$+N-$CH_aH_b$); 3.51-3.59 (m, 1H, N—$CH_aH_b$); 5.00 (bs, 1H, Ph-O—CH); 5.05 (q, J 7.1 Hz, 1H, CONH—CH—$CH_3$); 6.80 (dd, J 8.2, 1.8 Hz, 1H, Ar); 6.86 (bs, 1H, Ar); 7.00 (d, J 8.2 Hz, 1H, Ar); 7.28 (t, J 8.2 Hz, 1H, Ar); 7.42 (d, J 8.3 Hz, 2H, Ar); 7.84 (d, J 8.3 Hz, 2H, Ar); CONH signal was not observed; $CO_2H$ signal was not observed; HCl salt not observed. M/Z $(M[^{35}Cl]+H)^+$: 507

Compound 456: Methyl 1-[(3R)-3-(3-chlorophenoxy)pyrrolidin-1-yl]cyclopentane-1-carboxylate Compound 456 was obtained according to General Procedure VIII-b, starting from Compound 405 and methyl 1-aminocyclopentane-1-carboxylate. Purification by flash chromatography (DCM/MeOH: 100/0 to 80/20) afforded Compound 456 as a colorless oil in 81% yield. M/Z $(M[^{35}Cl]+H)^+$: 324

Compound 457: Lithium 1-[(3R)-3-(3-Chlorophenoxy)pyrrolidin-1-yl]cyclopentane-1-carboxylate Compound 457 was obtained according to General Procedure V-f, starting from Compound 456. M/Z $(M[^{35}Cl]+H)^+$: 310

Compound 458: Methyl 4-[(1S)-1-[[1-[(3R)-3-(3-chlorophenoxy)pyrrolidin-1-yl]cyclopentane-1-carbonyl]amino]ethyl]benzoate Compound 458 was obtained according to General Procedure I-a, starting from Compound 457 and methyl 4-[(1S)-1-aminoethyl]benzoate. Purification by flash chromatography (Cyclohexane/EtOAc: 100/0 to 70/30) afforded Compound 458 as a colorless oil in 55% yield over 2 steps. M/Z $(M[35Cl]+H)^+$: 471

Example 157: 4-[(1S)-1-[[1-[(3R)-3-(3-Chlorophenoxy)pyrrolidin-1-yl]cyclopentane-1-carbonyl]amino]ethyl]benzoic acid, hydrochloride

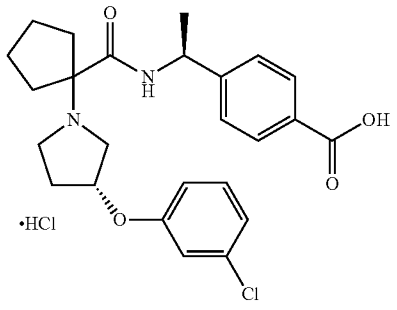 [SMILES: C[C@H](NC(=O)C1(N2CC[C@@H](Oc3cccc(Cl)c3)C2)CCCC1)c1ccc(C(=O)O)cc1 ; Cl]

Example 157 was obtained according to General Procedure IV-b, starting from Compound 458. Purification by preparative LC-MS, then HCl salt preparation (method 1) afforded Example 157 as a white powder in 25% yield. $^1$H-NMR (DMSO-$d_6$/$D_2O$ 400 MHz) δ (ppm): 1.42 (d, J 7.1 Hz, 3H, CH—$CH_3$); 1.66-1.84 (m, 4H, $CH_2$); 1.95-2.27 (m, 6H, $CH_2$); 3.15-3.74 (m, 4H, N—$CH_2$); 4.98 (q, J 7.1 Hz, 1H, CONH—CH—$CH_3$); 5.09 (bs, 1H, Ph-O—CH); 6.88 (dd, J 8.2, 1.6 Hz, 1H, Ar); 6.98 (bs, 1H, Ar); 7.02 (d, J 8.2 Hz, 1H, Ar); 7.30 (t, J 8.2 Hz, 1H, Ar); 7.40 (d, J 8.2 Hz, 2H, Ar); 7.86 (d, J 8.2 Hz, 2H, Ar); CONH signal was not observed; $CO_2H$ signal was not observed; HCl salt not observed. M/Z $(M[^{35}Cl]+H)^+$: 457

Compound 459: Methyl 4-[1-[[4-[(3R)-3-(3-Chlorophenoxy)pyrrolidin-1-yl]cyclopentane-1-carbonyl]amino]cyclopropyl]benzoate Compound 459 was obtained according to General Procedure I-b, starting from Compound 457 and methyl 4-(1-aminocyclopropyl)benzoate. Purification by flash chromatography (Cyclohexane/EtOAc: 100/0 to 60/40) afforded Compound 459 as an brown oil in 54% yield. M/Z $(M[^{35}Cl]+H)^+$: 483

Example 158: 4-[1-[[4-[(3R)-3-(3-Chlorophenoxy)pyrrolidin-1-yl]cyclopentane-1-carbonyl]amino]cyclopropyl]benzoic acid, hydrochloride

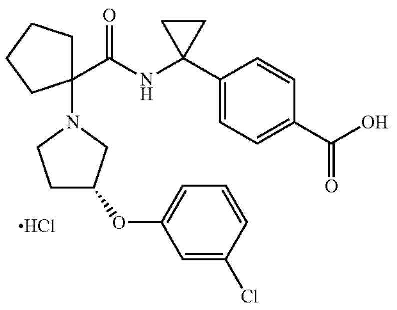 [SMILES: O=C(O)c1ccc(C2(NC(=O)C3(N4CC[C@@H](Oc5cccc(Cl)c5)C4)CCCC3)CC2)cc1 ; Cl]

Example 158 was obtained according to General Procedure V-e, starting from Compound 459. Purification by preparative LC-MS, then HCl salt preparation (method 1) afforded Example 158 as a white powder in 40% yield. $^1$H-NMR (DMSO-de/$D_2O$ 400 MHz) δ (ppm): 1.20-1.35 (m, 4H, C($CH_2$—$CH_2$)); 1.70-1.84 (m, 4H, $CH_2$); 1.98-2.25 (m, 6H, $CH_2$); 3.17-3.50 (m, 3H, N—$CH_2$+N-$CH_aH_b$); 3.51-3.75 (m, 1H, N—$CH_aH_b$); 5.10 (bs, 1H, Ph-O—CH); 6.90 (dd, J 8.2, 1.8 Hz, 1H, Ar); 6.98-7.05 (m, 2H, Ar); 7.17 (d, J 8.5 Hz, 2H, Ar); 7.32 (t, J 8.2 Hz, 1H, Ar); 7.82 (d, J 8.5 Hz, 2H, Ar); CONH signal was not observed; $CO_2H$ signal was not observed; HCl salt not observed. M/Z $(M[^{35}Cl]+H)^+$: 469

Compound 460: Methyl 1-[(3R)-3-(3-chlorophenoxy)pyrrolidin-1-yl]cyclobutane-1-carboxylate Compound 460 was obtained according to General Procedure VIII-b, starting from Compound 405 and methyl 1-aminocyclobutane-1-carboxylate hydrochloride. In that specific case, the reaction was performed with 4 equiv. of potassium carbonate. Purification by flash chromatography (DCM/MeOH: 100/0 to 80/20) afforded Compound 460 as a colorless oil in 33% yield. M/Z $(M[^{35}Cl]+H)^+$: 310

Compound 461: Lithium 1-[(3R)-3-(3-Chlorophenoxy)pyrrolidin-1-yl]cyclobutane-1-carboxylate Compound 461 was obtained according to General Procedure V-f, starting from Compound 460. M/Z $(M[^{35}Cl]+H)^+$: 296

Compound 462: Methyl 4-[(1S)-1-[[1-[(3R)-3-(3-chlorophenoxy)pyrrolidin-1-yl]cyclobutane-1-carbonyl]amino]ethyl]benzoate Compound 462 was obtained according to General Procedure I-a, starting from Compound 461 and methyl 4-[(1S)-1-aminoethyl]benzoate. Purification by flash chromatography (Cyclohexane/EtOAc: 100/0 to 85/15) afforded Compound 462 as a colorless oil in 88% yield over 2 steps. M/Z $(M[^{35}Cl]+H)^+$: 457

Example 159: 4-[(1S)-1-[[1-[(3R)-3-(3-Chlorophenoxy)pyrrolidin-1-yl]cyclobutane-1-carbonyl]amino]ethyl]benzoic acid, hydrochloride

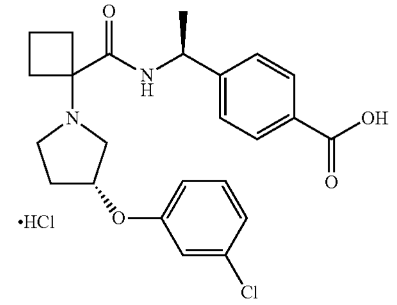 [SMILES: Cl ; C[C@H](NC(=O)C1(N2CC[C@@H](Oc3cccc(Cl)c3)C2)CCC1)c1ccc(C(=O)O)cc1]

Example 159 was obtained according to General Procedure IV-b, starting from Compound 462. Purification by preparative LC-MS, then HCl salt preparation (method 1) afforded Example 159 as a white powder in 40% yield. $^1$H-NMR (DMSO-$d_6$/$D_2O$, 400 MHz) δ (ppm): 1.46 (d, J 7.1 Hz, 3H, CH—$CH_3$); 1.91-2.06 (m, 2H, $CH_2$); 2.08-2.31 (m, 2H, $CH_2$); 2.44-2.55 (m, 4H, $CH_2$); 3.22-3.33 (m, 1H, N—$CH_aH_b$); 3.40-3.54 (m, 2H, N—$CH_2$); 3.57-3.74 (m, 1H, N—$CH_aH_b$); 5.03 (q, J 7.1 Hz, 1H, CONH—CH—$CH_3$); 5.12 (bs, 1H, Ph-O—CH); 6.89 (dd, J 8.2, 2.0 Hz, 1H, Ar); 6.99 (t, J 2.0 Hz, 1H, Ar); 7.03 (dd, J 8.2, 2.0 Hz, 1H, Ar); 7.31 (t, J 8.2 Hz, 1H, Ar); 7.44 (d, J 8.3 Hz, 2H, Ar); 7.88 (d, J 8.3 Hz, 2H, Ar); CONH signal was not observed; $CO_2H$ signal was not observed; HCl salt not observed. M/Z $(M[^{35}Cl]+H)^+$: 443

Compound 463: Methyl 1-[(3R)-3-(3-chlorophenoxy)pyrrolidin-1-yl]cyclopropane-1-carboxylate Compound 463 was obtained according to General Procedure VIII-b, starting from Compound 405 and methyl 1-aminocyclopropane-1-carboxylate. Purification by flash chromatography (DCM/MeOH: 100/0 to 80/20) afforded Compound 463 as a colorless oil in 85% yield. M/Z $(M[35Cl]+H)^+$: 296

Compound 464: Lithium 1-[(3R)-3-(3-Chlorophenoxy)pyrrolidin-1-yl]cyclopropane-1-carboxylate Compound 464 was obtained according to General Procedure V-f, starting from Compound 463. M/Z $(M[35Cl]+H)^+$: 288

Compound 465: Methyl 4-[(1S)-1-[[1-[(3R)-3-(3-chlorophenoxy)pyrrolidin-1-yl]cyclopropane-1-carbonyl]amino]ethyl]benzoate Compound 465 was obtained according to General Procedure I-a, starting from Compound 464 and methyl 4-[(1S)-1-aminoethyl]benzoate. Purification by flash chromatography (Cyclohexane/EtOAc: 100/0 to 60/40) afforded Compound 465 as a colorless oil in 73% yield over 2 steps. M/Z $(M[35Cl]+H)^+$: 443

Example 160: 4-[(1S)-1-[[1-[(3R)-3-(3-Chlorophenoxy)pyrrolidin-1-yl]cyclopropane-1-carbonyl]amino]ethyl]benzoic acid, hydrochloride

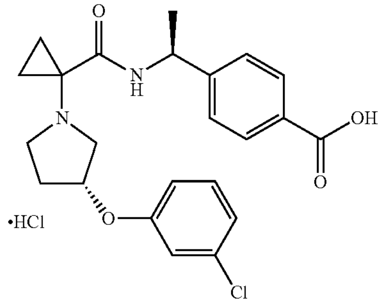 [SMILES: Cl ; C[C@H](NC(=O)C1(N2CC[C@@H](Oc3cccc(Cl)c3)C2)CC1)c1ccc(C(=O)O)cc1]

Example 160 was obtained according to General Procedure IV-b, starting from Compound 465. Purification by preparative LC-MS, then HCl salt preparation (method 1) afforded Example 160 as a white powder in 72% yield. $^1$H-NMR (MeOD 400 MHz) δ (ppm): 1.48 (d, J 7.1 Hz, 3H, CH—$CH_3$); 1.50-1.66 (m, 3H, $CH_2$+$CH_aH$); 2.15-2.28 (m, 1H, $CH_aH_b$); 2.44-2.55 (m, 2H, $CH_2$); 3.20-3.82 (m, 4H, N—$CH_2$); 5.07-5.19 (m, 2H, CONH—CH—$CH_3$+Ph-O—CH); 6.88 (dd, J 8.6, 2.0 Hz, 1H, Ar); 6.97-7.02 (m, 2H, Ar); 7.28 (dd, J 8.6, 7.8 Hz, 1H, Ar); 7.41 (d, J 8.4 Hz, 2H, Ar); 7.99 (d, J 8.4 Hz, 2H, Ar); CONH signal was not observed; $CO_2H$ signal was not observed; HCl salt not observed. M/Z $(M[^{35}Cl]+H)^+$: 429

Compound 466: Methyl 2-[(3R)-3-(3-chlorophenoxy)pyrrolidin-1-yl]-2-methylpropanoate Compound 466 was obtained according to General Procedure VIII-b, starting from Compound 405 and methyl 2-amino-2-methylpropanoate hydrochloride. In that specific case, the reaction was performed with 3 equiv. of potassium carbonate. Purification by flash chromatography (DCM/MeOH: 100/0 to 80/20) afforded Compound 466 as a pale brown oil in 45% yield. M/Z $(M[^{35}Cl]+H)^+$: 298

Compound 467: Lithium 2-[(3R)-3-(3-Chlorophenoxy)pyrrolidin-1-yl]-2-methylpropanoate Compound 467 was obtained according to General Procedure V-f, starting from Compound 466. M/Z $(M[^{35}Cl]+H)^+$: 284

Compound 468: Methyl 4-[(1S)-1-[[2-[(3R)-3-(3-chlorophenoxy)pyrrolidin-1-yl]-2-methylpropanecarbonyl]amino]ethyl]benzoate Compound 468 was obtained according to General Procedure I-a, starting from Compound 467 and methyl 4-[(1S)-1-aminoethyl]benzoate. Purification by flash chromatography (Cyclohexane/EtOAc: 100/0 to 40/60) afforded Compound 468 as a colorless oil in 64% yield over 2 steps. M/Z $(M[^{35}Cl]+H)^+$: 445

Example 161: 4-[(1S)-1-[[2-[(3R)-3-(3-Chlorophenoxy)pyrrolidin-1-yl]-2-methylpropane-carbonyl]amino]ethyl]benzoic acid, hydrochloride

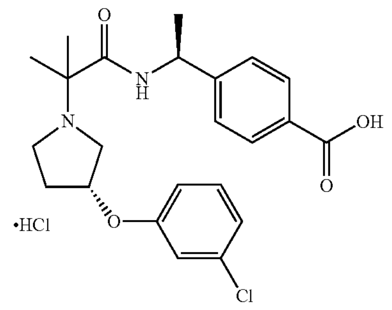 [SMILES: Cl ; C[C@H](NC(=O)C(C)(C)N1CC[C@@H](Oc2cccc(Cl)c2)C1)c1ccc(C(=O)O)cc1]

Example 161 was obtained according to General Procedure V-e, starting from Compound 468. Purification by preparative LC-MS, then HCl salt preparation (method 1) afforded Example 161 as a white powder in 55% yield. $^{1}H$-NMR (DMSO-$d_6$/$D_2O$ 400 MHz) δ (ppm): 1.38 (d, J 6.9 Hz, 3H, CH—$CH_3$); 1.49 (s, 3H, C—$(CH_3)_2$); 1.54 (s, 3H, C—$(CH_3)_2$); 2.03-2.20 (m, 2H, $CH_2$); 3.31-3.72 (m, 4H, N—$CH_2$); 4.87-4.97 (m, 1H, CONH—CH—$CH_3$); 5.09 (bs, 1H, Ph-O—CH); 6.89 (dd, J 8.2, 1.6 Hz, 1H, Ar); 6.98-7.05 (m, 2H, Ar); 7.31 (t, J 8.2 Hz, 1H, Ar); 7.39 (d, J 8.3 Hz, 2H, Ar); 7.87 (d, J 8.3 Hz, 2H, Ar); CONH signal was not observed; $CO_2H$ signal was not observed; HCl salt not observed. M/Z (M[$^{35}$Cl]+H)$^+$: 431

Compound 469: Methyl 1-[(3R)-3-[3-(trifluoromethyl)phenoxy]pyrrolidin-1-yl]cyclohexane-1-carboxylate Compound 469 was obtained according to General Procedure VIII-b, starting from Compound 419 and methyl 1-aminocyclohexane-1-carboxylate. Purification by flash chromatography (DCM/MeOH: 100/0 to 70/3) afforded Compound 469 as a pale orange oil. M/Z (M+H)$^+$: 372

Compound 470: Lithium 1-[(3R)-3-[3-(trifluoromethyl)phenoxy]pyrrolidin-1-yl]cyclohexane-1-carboxylate Compound 470 was obtained according to General Procedure V-f, starting from Compound 469. M/Z (M+H)$^+$: 358

Compound 471: Methyl 4-[(1S)-1-[[1-[(3R)-3-[3-(trifluoromethyl)phenoxy]pyrrolidin-1-yl]cyclohexane-1-carbonyl]amino]ethyl]benzoate Compound 471 was obtained according to General Procedure I-a, starting from Compound 470 and methyl 4-[(1S)-1-aminoethyl]benzoate. Purification by flash chromatography (Cyclohexane/EtOAc: 100/0 to 50/50) afforded Compound 471 as a colorless oil in 41% yield over 2 steps. M/Z (M+H)$^+$: 519

Example 162: 4-[(1S)-1-[[1-[(3R)-3-[3-(Trifluoromethyl)phenoxy]pyrrolidin-1-yl]cyclohexane-1-carbonyl]amino]ethyl]benzoic acid, hydrochloride

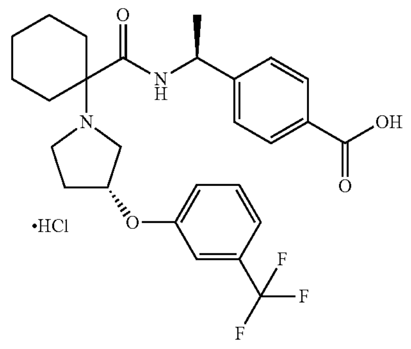 [SMILES: C[C@H](NC(=O)C1(N2CC[C@@H](Oc3cccc(C(F)(F)F)c3)C2)CCCCC1)c1ccc(C(=O)O)cc1 ; Cl]

Example 162 was obtained according to General Procedure IV-b, starting from Compound 471. Purification by preparative LC-MS, then HCl salt preparation (method 1) afforded Example 162 as a white powder in 52% yield. $^{1}H$-NMR (DMSO-d/$D_2O$ 400 MHz) δ (ppm): 1.03-1.22 (m, 3H, $CH_2$+$CH_aH_b$); 1.46 (d, J 7.1 Hz, 3H, CH—$CH_3$); 1.50-1.66 (m, 3H, $CH_2$+$CH_aH_b$); 1.66-1.78 (m, 2H, $CH_2$); 2.02-2.15 (m, 2H, $CH_2$); 2.40-2.48 (m, 2H, $CH_2$); 3.33-3.51 (m, 3H, N-$CH_2$+N-$CH_a$Ho); 3.62-3.74 (m, 1H, N—$CH_aH_b$); 5.06 (q, J 7.1 Hz, 1H, CONH—CH—$CH_3$); 5.13 (bs, 1H, Ph-O—CH); 7.08-7.19 (m, 2H, Ar); 7.31 (d, J 7.7 Hz, 1H, Ar); 7.43 (d, J 8.3 Hz, 2H, Ar); 7.52 (dd, J 8.1, 7.7 Hz, 1H, Ar); 7.84 (d, J 8.3 Hz, 2H, Ar); CONH signal was not observed; $CO_2H$ signal was not observed; HCl salt not observed. M/Z (M+H)$^+$: 505

Compound 472: Methyl 1-[(3R)-3-[3-(trifluoromethyl)phenoxy]pyrrolidin-1-yl]-4,4-difluorocyclohexane-1-carboxylate Compound 472 was obtained according to General Procedure VIII-b, starting from Compound 419 and methyl 1-amino-4,4-difluorocyclohexane-1-carboxylate. Purification by flash chromatography (DCM/MeOH: 100/0 to 80/20) afforded Compound 472 as a colorless oil in 30% yield. M/Z (M+H)$^+$: 408

Compound 473: Lithium 1-[(3R)-3-[3-(trifluoromethyl)phenoxy]pyrrolidin-1-yl]-4,4-difluorocyclohexane-1-carboxylate Compound 473 was obtained according to General Procedure V-f, starting from Compound 472. M/Z (M+H)$^+$: 394

Compound 474: Methyl 4-[(1S)-1-[[1-[(3R)-3-[3-(trifluoromethyl)phenoxy]pyrrolidin-1-yl]-4,4-difluorocyclohexane-1-carbonyl]amino]ethyl]benzoate Compound 474 was obtained according to General Procedure I-a, starting from Compound 473 and methyl 4-[(1S)-1-aminoethyl]benzoate. Purification by flash chromatography (Cyclohexane/EtOAc: 100/0 to 70/30) afforded Compound 474 as a colorless oil in 53% yield over 2 steps. M/Z (M+H)$^+$: 555

Example 163: 4-[(1S)-1-[[1-[(3R)-3-[3-(Trifluoromethyl)phenoxy]pyrrolidin-1-yl]-4,4-difluorocyclohexane-1-carbonyl]amino]ethyl]benzoic acid, hydrochloride

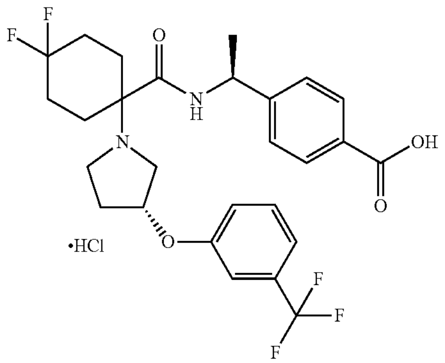 [SMILES: C[C@H](NC(=O)C1(N2CC[C@@H](Oc3cccc(C(F)(F)F)c3)C2)CCC(F)(F)CC1)c1ccc(C(=O)O)cc1 ; Cl]

Example 163 was obtained according to General Procedure IV-b, starting from Compound 474. Purification by preparative LC-MS, then HCl salt preparation (method 1) afforded Example 163 as a white powder in 55% yield. $^{1}$H-NMR (DMSO-$d_6$/$D_2O$, 400 MHz) δ (ppm): 1.43 (d, J 7.1 Hz, 3H, $CH_3$); 1.53-1.74 (m, 2H, $CH_2$); 1.85-1.97 (m, 2H, $CH_2$); 1.98-2.16 (m, 4H, $CH_2$); 2.36-2.46 (m, 2H, $CH_2$); 3.24-3.33 (m, 3H, N—$CH_2$+N-$CH_aH_b$); 3.51-3.59 (m, 1H, N—$CH_aH_b$); 5.00-5.08 (m, 2H, Ph-O-CH+CONH—CH—$CH_3$); 7.06 (bs, 1H, Ar); 7.12 (d, J 8.3 Hz, 1H, Ar); 7.29 (d, J 7.7 Hz, 1H, Ar); 7.41 (d, J 8.2 Hz, 2H, Ar); 7.50 (dd, J 8.3, 7.7 Hz, 1H, Ar); 7.82 (d, J 8.2 Hz, 2H, Ar); CONH signal was not observed; $CO_2H$ signal was not observed; HCl salt not observed. M/Z $(M+H)^+$: 541

Compound 475: Methyl 1-[(3R)-3-[3-(trifluoromethyl)phenoxy]pyrrolidin-1-yl]cyclopentane-1-carboxylate Compound 475 was obtained according to General Procedure VIII-b, starting from Compound 419 and methyl 1-aminocyclopentane-1-carboxylate. Purification by flash chromatography (DCM/MeOH: 100/0 to 70/30) afforded Compound 475 as a colorless oil in 60% yield. M/Z $(M+H)^+$: 358

Compound 476: Lithium 1-[(3R)-3-[3-(trifluoromethyl)phenoxy]pyrrolidin-1-yl]cyclopentane-1-carboxylate Compound 476 was obtained according to General Procedure V-f, starting from Compound 475. M/Z $(M+H)^+$: 344

Compound 477: Methyl 4-[(1S)-1-[[1-[(3R)-3-[3-(trifluoromethyl)phenoxy]pyrrolidin-1-yl]cyclopentane-1-carbonyl]amino]ethyl]benzoate Compound 477 was obtained according to General Procedure I-a, starting from Compound 476 and methyl 4-[(1S)-1-aminoethyl]benzoate. Purification by flash chromatography (Cyclohexane/EtOAc: 100/0 to 70/30) afforded Compound 477 as a colorless oil in 79% yield over 2 steps. M/Z $(M+H)^+$: 505

Example 164: 4-[(1S)-1-[[1-[(3R)-3-[3-Trifluoromethyl)phenoxy]pyrrolidin-1-yl]cyclopentane-1-carbonyl]amino]ethyl]benzoic acid, hydrochloride

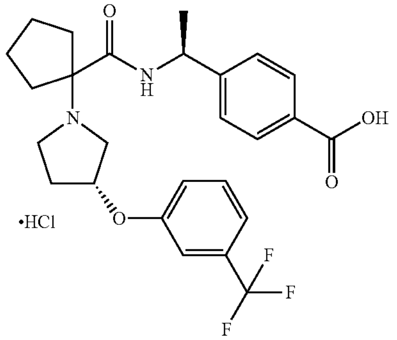 [SMILES: C[C@H](NC(=O)C1(N2CC[C@@H](Oc3cccc(C(F)(F)F)c3)C2)CCCC1)c1ccc(C(=O)O)cc1 ; Cl]

Example 164 was obtained according to General Procedure IV-b, starting from Compound 477. Purification by preparative LC-MS, then HCl salt preparation (method 1) afforded Example 164 as a white powder in 60% yield. $^{1}$H-NMR (DMSO-$d_6$/$D_2O$, 400 MHz) δ (ppm): 1.40 (d, J 7.1 Hz, 3H, CH—$CH_3$); 1.66-1.83 (m, 4H, $CH_2$); 1.93-2.08 (m, 2H, $CH_2$); 2.09-2.28 (m, 4H, $CH_2$); 3.15-3.74 (m, 4H, N—$CH_2$); 4.97 (q, J 7.1 Hz, 1H, CONH—CH—$CH_3$); 5.16 (bs, 1H, Ph-O—CH); 7.17-7.22 (m, 2H, Ar); 7.31 (d, J 7.6 Hz, 1H, Ar); 7.39 (d, J 8.2 Hz, 2H, Ar); 7.50 (dd, J 8.2, 7.6 Hz, 1H, Ar); 7.85 (d, J 8.2 Hz, 2H, Ar); CONH signal was not observed; $CO_2H$ signal was not observed; HCl salt not observed. M/Z $(M+H)^+$: 491

Compound 478: Methyl 1-[(3R)-3-[3-(trifluoromethyl)phenoxy]pyrrolidin-1-yl]cyclobutane-1-carboxylate Compound 478 was obtained according to General Procedure VIII-b, starting from Compound 419 and methyl 1-aminocyclobutane-1-carboxylate hydrochloride. In that specific case, the reaction was performed with 4 equiv. of potassium carbonate. Purification by flash chromatography (DCM/MeOH: 100/0 to 70/30) afforded Compound 478 as a colorless oil in 12% yield. M/Z $(M+H)^+$: 344

Compound 479: Lithium 1-[(3R)-3-[3-(trifluoromethyl)phenoxy]pyrrolidin-1-yl]cyclobutane-1-carboxylate Compound 479 was obtained according to General Procedure V-f, starting from Compound 478. M/Z $(M+H)^+$: 330

Compound 480: Methyl 4-[(1S)-1-[[1-[(3R)-3-[3-(trifluoromethyl)phenoxy]pyrrolidin-1-yl]cyclobutane-1-carbonyl]amino]ethyl]benzoate Compound 480 was obtained according to General Procedure I-a, starting from Compound 479 and methyl 4-[(1S)-1-aminoethyl]benzoate. Purification by flash chromatography (Cyclohexane/EtOAc: 100/0 to 70/30) afforded Compound 480 as a colorless oil in 86% yield over 2 steps. M/Z $(M+H)^+$: 491

Example 165: 4-[(1S)-1-[[1-[(3R)-3-[3-(Trifluoromethyl)phenoxy]pyrrolidin-1-yl]cyclobutane-1-carbonyl]amino]ethyl]benzoic acid, hydrochloride

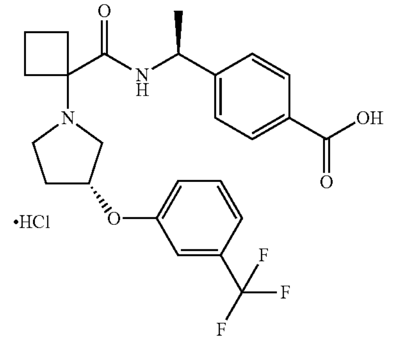 [SMILES: Cl ; C[C@H](NC(=O)C1(N2CC[C@@H](Oc3cccc(C(F)(F)F)c3)C2)CCC1)c1ccc(C(=O)O)cc1]

Example 165 was obtained according to General Procedure IV-b, starting from Compound 480. Purification by preparative LC-MS, then HCl salt preparation (method 1) afforded Example 165 as a white powder in 48% yield. $^1$H-NMR (DMSO-$d_6$/$D_2O$, 400 MHz) δ (ppm): 1.43 (d, J 7.1 Hz, 3H, CH—$CH_3$); 1.88-2.01 (m, 2H, $CH_2$); 2.08-2.17 (m, 1H, $CH_aH_b$); 2.19-2.31 (m, 1H, $CH_aH_b$); 2.42-2.48 (m, 4H, $CH_2$); 3.18-3.26 (m, 1H, N—$CH_aH_b$); 3.33-3.51 (m, 2H, N—$CH_2$); 3.51-3.63 (m, 1H, N—$CH_aH_b$); 5.00 (q, J 7.1 Hz, 1H, CONH—CH—$CH_3$); 5.16 (bs, 1H, Ph-O—CH); 7.15-7.21 (m, 2H, Ar); 7.30 (d, J 7.6 Hz, 1H, Ar); 7.42 (d, J 8.2 Hz, 2H, Ar); 7.51 (dd, J 8.2, 7.6 Hz, 1H, Ar); 7.85 (d, J 8.2 Hz, 2H, Ar); CONH signal was not observed; $CO_2H$ signal was not observed; HCl salt not observed. M/Z $(M+H)^+$: 477

Compound 481: Methyl 1-[(3R)-3-[3-(trifluoromethyl)phenoxy]pyrrolidin-1-yl]cyclopropane-1-carboxylate Compound 481 was obtained according to General Procedure VIII-b, starting from Compound 419 and methyl 1-aminocyclopropane-1-carboxylate. Purification by flash chromatography (DCM/MeOH: 100/0 to 50/50) afforded Compound 481 as a colorless oil in 72% yield. M/Z $(M+H)^+$: 330

Compound 482: Lithium 1-[(3R)-3-[3-(trifluoromethyl)phenoxy]pyrrolidin-1-yl]cyclopropane-1-carboxylate Compound 482 was obtained according to General Procedure V-f, starting from Compound 481. M/Z $(M+H)^+$: 322

Compound 483: Methyl 4-[(1S)-1-[[1-[(3R)-3-[3-(trifluoromethyl)phenoxy]pyrrolidin-1-yl]cyclopropane-1-carbonyl]amino]ethyl]benzoate Compound 483 was obtained according to General Procedure I-a, starting from Compound 482 and methyl 4-[(1S)-1-aminoethyl]benzoate. Purification by flash chromatography (Cyclohexane/EtOAc: 100/0 to 50/50) afforded Compound 483 as a pale brown oil in 42% yield over 2 steps. M/Z $(M+H)^+$: 477

Example 166: 4-[(1S)-1-[[1-[(3R)-3-[3-(Trifluoromethyl)phenoxy]pyrrolidin-1-yl]cyclopropane-1-carbonyl]amino]ethyl]benzoic acid, hydrochloride

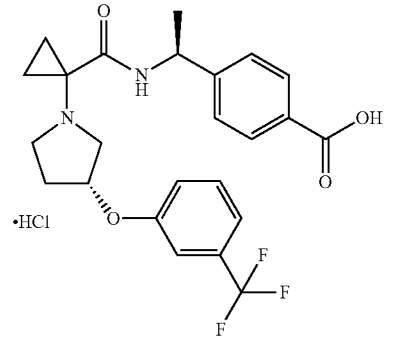 [SMILES: Cl ; C[C@H](NC(=O)C1(N2CC[C@@H](Oc3cccc(C(F)(F)F)c3)C2)CC1)c1ccc(C(=O)O)cc1]

Example 166 was obtained according to General Procedure IV-b, starting from Compound 483. Purification by preparative LC-MS, then HCl salt preparation (method 1) afforded Example 166 as a white powder in 59% yield. $^1$H-NMR (DMSO-$d_6$/$D_2O$, 400 MHz) δ (ppm): 1.30-1.44 (m, 5H, CH—$CH_3$+$CH_2$); 1.97-2.05 (m, 1H, $CH_2$, signal of a rotamer); 2.27-2.38 (m, 1H, $CH_2$, signal of a rotamer); 2.42-2.48 (m, 2H, $CH_2$); 3.01-3.09 (m, 1H, N—$CH_aH_b$); 3.11-3.25 (m, 2H, N—$CH_2$); 3.46-3.56 (m, 1H, N—$CH_aH_b$); 4.95 (q, J 7.1 Hz, 1H, CONH—CH—$CH_3$); 5.13 (bs, 1H, Ph-O—CH); 7.18 (bs, 1H, Ar); 7.21 (bd, J 8.4 Hz, 1H, Ar); 7.30 (d, J 7.8 Hz, 1H, Ar); 7.38 (d, J 8.3 Hz, 2H, Ar); 7.52 (dd, J 8.4, 7.8 Hz, 1H, Ar); 7.87 (d, J 8.3 Hz, 2H, Ar); CONH signal was not observed; $CO_2H$ signal was not observed; HCl salt not observed. M/Z $(M+H)^+$: 463

Compound 484: Methyl 2-[(3R)-3-[3-(trifluoromethyl)phenoxy]pyrrolidin-1-yl]-2-methylpropanoate Compound 484 was obtained according to General Procedure VIII-b, starting from Compound 419 and methyl 2-amino-2-methylpropanoate hydrochloride. In that specific case, the reaction was performed with 4 equiv. of potassium carbonate and 3 equiv. of sodium iodide were added. Purification by flash chromatography (DCM/MeOH: 100/0 to 60/40) afforded Compound 484 as a pale yellow oil in 70% yield. M/Z $(M+H)^+$: 332

Compound 485: Lithium 2-[(3R)-3-[3-(trifluoromethyl)phenoxy]pyrrolidin-1-yl]-2-methylpropanoate Compound 485 was obtained according to General Procedure V-f, starting from Compound 485. M/Z $(M+H)^+$: 318

Compound 486: Methyl 4-[(1S)-1-[[2-[(3R)-3-[3-(trifluoromethyl)phenoxy]pyrrolidin-1-yl]-2-methylpropane-carbonyl]amino]ethyl]benzoate Compound 486 was obtained according to General Procedure I-a, starting from Compound 485 and methyl 4-[(1S)-1-aminoethyl]benzoate. Purification by flash chromatography (Cyclohexane/EtOAc: 100/0 to 60/40) afforded Compound 486 as a colorless oil in 60% yield over 2 steps. M/Z $(M+H)^+$: 479

Example 167: 4-[(1S)-1-[[2-[(3R)-3-[3-(Trifluoromethyl)phenoxy]pyrrolidin-1-yl]-2-methylpropanecarbonyl]amino]ethyl]benzoic acid, hydrochloride

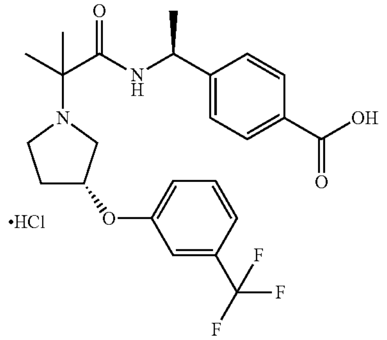 [SMILES: Cl ; C[C@H](NC(=O)C(C)(C)N1CC[C@@H](Oc2cccc(C(F)(F)F)c2)C1)c1ccc(C(=O)O)cc1]

Example 167 was obtained according to General Procedure V-e, starting from Compound 486. Purification by preparative LC-MS, then HCl salt preparation (method 1) afforded Example 167 as a white powder in 57% yield. $^1$H-NMR (DMSO-$d_6$/$D_2O$, 400 MHz) δ (ppm): 1.38 (d, J 6.9 Hz, 3H, CH—$CH_3$); 1.50 (s, 3H, C—$(CH_3)_2$); 1.55 (s, 3H, C—$(CH_3)_2$); 2.10-2.29 (m, 2H, $CH_2$); 3.27-3.71 (m, 4H, N—$CH_2$); 4.91 (q, J 6.9 Hz, 1H, CONH—CH—$CH_3$); 5.16 (bs, 1H, Ph-O—CH); 7.17-7.23 (m, 2H, Ar); 7.31 (d, J 7.7 Hz, 1H, Ar); 7.38 (d, J 8.2 Hz, 2H, Ar); 7.52 (dd, J 8.2, 7.7 Hz, 1H, Ar); 7.86 (d, J 8.2 Hz, 2H, Ar); CONH signal was not observed; $CO_2H$ signal was not observed; HCl salt not observed. M/Z $(M+H)^+$: 465

Example 168: 4-[(1S)-1-[[4-[(3R)-3-[3-(Trifluoromethyl)phenoxy]pyrrolidin-1-yl]tetrahydropyran-4-carbonyl]amino]ethyl]benzamide, hydrochloride

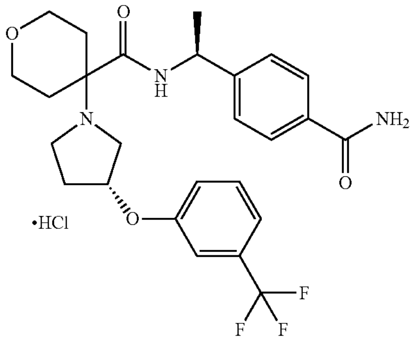 [SMILES: C[C@H](NC(=O)C1(N2CC[C@@H](Oc3cccc(C(F)(F)F)c3)C2)CCOCC1)c1ccc(C(N)=O)cc1 ; Cl]

Example 168 was obtained according to General Procedure I-a, starting from Compound 421 and (S)-4-(1-aminoethyl)benzamide. Purification by preparative LC-MS, then HCl salt preparation (method 1) afforded Example 168 as a white powder in 60% yield. $^1$H-NMR (DMSO-$d_6$/$D_2O$, 400 MHz) δ (ppm): 1.49 (d, J 7.1 Hz, 3H, CH—$CH_3$); 1.89-2.04 (m, 2H, $CH_2$); 2.06-2.20 (m, 2H, $CH_2$); 2.38-2.47 (m, 2H, $CH_2$); 3.04-3.19 (m, 2H, O—$CH_2$); 3.31-3.53 (m, 3H, N—$CH_2$+N-$CH_aH_b$); 3.67-3.77 (m, 1H, N—$CH_aH_b$); 3.86-3.96 (m, 2H, $CH_2$); 5.06-5.15 (m, 1H, CONH—CH—$CH_3$); 5.20 (bs, 1H, PhO—CH); 7.17-7.24 (m, 2H, Ar); 7.34 (d, J 7.8 Hz, 1H, Ar); 7.41 (d, J 8.2 Hz, 2H, Ar); 7.55 (dd, J 8.2, 7.8 Hz, 1H, Ar); 7.81 (d, J 8.2 Hz, 2H, Ar); CONH signal was not observed; $CONH_2$ signal was not observed; HCl salt not observed. M/Z $(M+H)^+$: 506

Example 169: 4-[(1S)-1-[[4-[(3R)-3-[3-(Trifluoromethyl)phenoxy]pyrrolidin-1-yl]tetrahydropyran-4-carbonyl]methylamino]ethyl]benzamide, hydrochloride

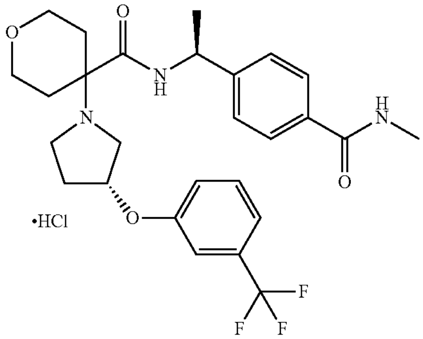 [SMILES: CNC(=O)c1ccc([C@H](C)NC(=O)C2(N3CC[C@@H](Oc4cccc(C(F)(F)F)c4)C3)CCOCC2)cc1 ; Cl]

Example 169 was obtained according to General Procedure I-a, starting from Example 144 and methylamine 2 M in THF. Purification by preparative LC-MS, then HCl salt preparation (method 1) afforded Example 169 as a white powder in 55% yield. $^1$H-NMR (DMSO-$d_6$/$D_2O$, 400 MHz) δ (ppm): 1.48 (d, J 7.1 Hz, 3H, CH—$CH_3$); 1.89-2.00 (m, 2H, $CH_2$); 2.06-2.16 (m, 2H, $CH_2$); 2.35-2.47 (m, 2H, $CH_2$); 2.75 (s, 3H, CONH—$CH_3$); 3.06-3.20 (m, 2H, O—$CH_2$); 3.31-3.51 (m, 3H, N—$CH_2$+N-$CH_aH_b$); 3.60-3.71 (m, 1H, N—$CH_aH_b$); 3.84-3.94 (m, 2H, O—$CH_2$); 5.06-5.13 (m, 1H, CONH—CH—$CH_3$); 5.18 (bs, 1H, Ph-C—CH); 7.17-7.22 (m, 2H, Ar); 7.33 (d, J 7.8 Hz, 1H, Ar); 7.41 (d, J 8.3 Hz, 2H, Ar); 7.54 (dd, J 8.2, 7.8 Hz, 1H, Ar); 7.81 (d, J 8.3 Hz, 2H, Ar); CONH—CH—$CH_3$ signal was not observed; CONH—$CH_3$ signal was not observed: HCl salt not observed. M/Z $(M+H)^+$: 520

Example 170: 4-[(1S)-1-[[4-[(3R)-3-[3-(Trifluoromethyl)phenoxy]pyrrolidin-1-yl]tetrahydropyran-4-carbonyl]dimethylamino]ethyl]benzamide, hydrochloride

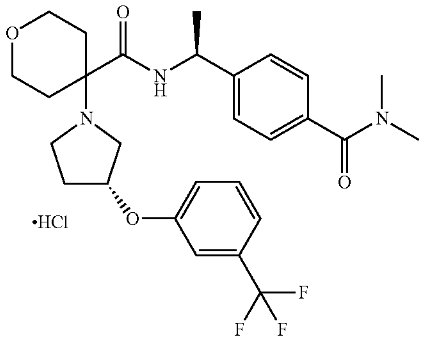 [SMILES: C[C@H](NC(=O)C1(N2CC[C@@H](Oc3cccc(C(F)(F)F)c3)C2)CCOCC1)c1ccc(C(=O)N(C)C)cc1 ; Cl]

Example 170 was obtained according to General Procedure I-a, starting from Example 144 and dimethylamine 2 M in THF. Purification by preparative LC-MS, then HCl salt preparation (method 1) afforded Example 170 as a white powder in 53% yield. $^1$H-NMR (DMSO-dc/$D_2O$ 400 MHz) δ (ppm): 1.49 (d, J 7.1 Hz, 3H, CH—$CH_3$); 1.85-1.97 (m, 2H, $CH_2$); 2.04-2.13 (m, 2H, $CH_2$); 2.37-2.48 (m, 2H, $CH_2$); 2.83 (bs, 3H, CON$(CH_3)_2$); 2.94 (bs, 3H, CON$(CH_3)_2$); 3.09-3.21 (m, 2H, O—$CH_2$); 3.32-3.47 (m, 3H, N—$CH_2$+N-$CH_aH_b$); 3.62-3.70 (m, 1H, N—$CH_aH_b$); 3.85-3.94 (m, 2H, O—$CH_2$); 5.08 (q, J 7.1 Hz, 1H, CONH—CH—$CH_3$); 5.16 (bs, 1H, Ph-C—CH); 7.17-7.23 (m, 2H, Ar); 7.30-7.36 (m, 3H, Ar); 7.39 (d, J 8.1 Hz, 2H, Ar); 7.55 (t, J 8.0 Hz, 1H, Ar); CONH signal was not observed; HCl salt not observed. M/Z $(M+H)^+$: 534

Example 171: 4-[(1S)-1-[[1-[(3R)-3-[3-(Trifluoromethyl)phenoxy]pyrrolidin-1-yl]cyclobutane-1-carbonyl]amino]ethyl]benzamide, hydrochloride

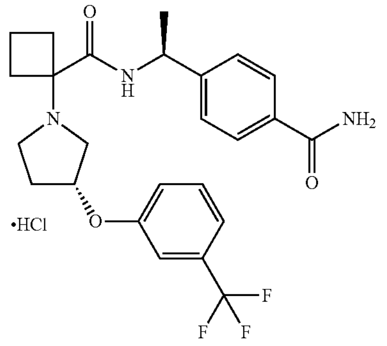 [SMILES: C[C@H](NC(=O)C1(N2CC[C@@H](Oc3cccc(C(F)(F)F)c3)C2)CCC1)c1ccc(C(N)=O)cc1 ; Cl]

Example 171 was obtained according to General Procedure I-a, starting from Compound 479 and (S)-4-(1-aminoethyl)benzamide. Purification by preparative LC-MS, then HCl salt preparation (method 1) afforded Example 171 as a white powder in 94% yield. $^1$H-NMR (DMSO-$d_6$/$D_2O$, 400 MHz) δ (ppm): 1.47 (d, J 7.1 Hz, 3H, CH—$CH_3$); 1.92-2.06 (m, 2H, $CH_2$); 2.11-2.31 (m, 2H, $CH_2$); 2.53-2.59 (m, 4H, $CH_2$); 3.28-3.56 (m, 3H, N—$CH_2$+N-$CH_aH_b$); 3.67-3.77 (m, 1H, N—$CH_aH_b$); 5.00-5.07 (m, 1H, CONH—CH—$CH_3$); 5.23 (bs, 1H, PhO—CH); 7.22-7.27 (m, 2H, Ar); 7.34 (d, J 7.8 Hz, 1H, Ar); 7.40 (d, J 8.3 Hz, 2H, Ar); 7.55 (dd, J 8.2, 7.8 Hz, 1H, Ar); 7.79 (d, J 8.3 Hz, 2H, Ar); CONH signal was not observed; $CONH_2$ signal was not observed; HCl salt not observed. M/Z $(M+H)^+$: 476

Example 172: 4-[(1S)-1-[[1-[(3R)-3-(3-Chlorophenoxy)pyrrolidin-1-yl]cyclobutane-1-carbonyl]amino]ethyl]benzamide, hydrochloride

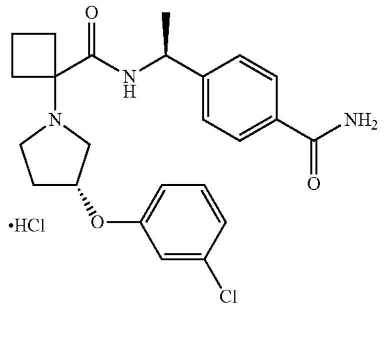 [SMILES: Cl ; C[C@H](NC(=O)C1(N2CC[C@@H](Oc3cccc(Cl)c3)C2)CCC1)c1ccc(C(N)=O)cc1]

Example 172 was obtained according to General Procedure I-a, starting from Compound 461 and (S)-4-(1-aminoethyl)benzamide. Purification by preparative LC-MS, then HCl salt preparation (method 1) afforded Example 172 as a white powder in 32% yield. $^1$H-NMR (DMSO-$d_6$/$D_2O$ 400 MHz) δ (ppm): 1.45 (d, J 7.1 Hz, 3H, CH—$CH_3$); 1.89-2.03 (m, 2H, $CH_2$); 2.07-2.29 (m, 2H, $CH_2$); 2.39-2.48 (m, 4H, $CH_2$); 3.16-3.51 (m, 3H, N—$CH_2$+N-$CH_aH_b$); 3.59-3.64 (m, 1H, N—$CH_aH_b$); 5.03 (q, J 7.1 Hz, 1H, CONH—CH—$CH_3$); 5.13 (bs, 1H, PhO—CH); 6.91 (dd, J 8.2, 1.8 Hz, 1H, Ar); 7.01-7.06 (m, 2H, Ar); 7.32 (t, J 8.2 Hz, 1H, Ar); 7.40 (d, J 8.3 Hz, 2H, Ar); 7.80 (d, J 8.3 Hz, 2H, Ar); CONH signal was not observed; $CONH_2$ signal was not observed; HCl salt not observed. M/Z $(M[^{35}Cl]+H)^+$: 442

Example 173: 4-[(1S)-1-[[2-[(3R)-3-[3-(Trifluoromethyl)phenoxy]pyrrolidin-1-yl]-2-methylpropanecarbonyl]amino]ethyl]benzamide, hydrochloride

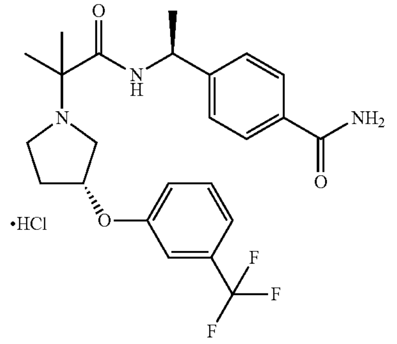 [SMILES: Cl ; C[C@H](NC(=O)C(C)(C)N1CC[C@@H](Oc2cccc(C(F)(F)F)c2)C1)c1ccc(C(N)=O)cc1]

Example 173 was obtained according to General Procedure I-a, starting from Example 167 and $NH_3$ 0.5 M in dioxane. Purification by preparative LC-MS, then HCl salt preparation (method 1) afforded Example 173 as a white powder in 70% yield. $^1$H-NMR (DMSO-$d_6$/$D_2O$ 400 MHz) δ (ppm): 1.39 (d, J 7.1 Hz, 3H, CH—$CH_3$); 1.50 (s, 3H, C—$(CH_3)_2$); 1.57 (s, 3H, C—$(CH_3)_2$); 2.03-2.23 (m, 2H, $CH_2$); 3.26-3.46 (m, 3H, N—$CH_2$+N-$CH_aH_b$); 3.46-3.60 (m, 1H, N—$CH_aH_b$); 4.85-4.97 (m, 1H, CONH—CH—$CH_3$); 5.16 (bs, 1H, PhO—CH); 7.19-7.25 (m, 2H, Ar); 7.29-7.37 (m, 3H, Ar); 7.52 (t, J 8.0 Hz, 1H, Ar); 7.76 (d, J 8.2 Hz, 2H, Ar); CONH signal was not observed; $CO_2H$ signal was not observed; HCl salt not observed. M/Z $(M+H)^+$: 464

Example 174: 4-[(1S)-1-[[2-[(3R)-3-(3-Chlorophenoxy)pyrrolidin-1-yl]-2-methylpropane-carbonyl]amino]ethyl]benzamide, hydrochloride

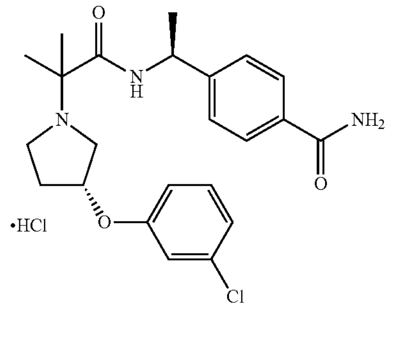 [SMILES: Cl ; C[C@H](NC(=O)C(C)(C)N1CC[C@@H](Oc2cccc(Cl)c2)C1)c1ccc(C(N)=O)cc1]

Example 174 was obtained according to General Procedure I-a, starting from Compound 467 and and (S)-4-(1-aminoethyl)benzamide. Purification by preparative LC-MS, then HCl salt preparation (method 1) afforded Example 174 as a beige powder in 42% yield. $^1$H-NMR (DMSO-$d_6$/$D_2O$, 400 MHz) δ (ppm): 1.37 (d, J 7.1 Hz, 3H, CH—$CH_3$); 1.49 (s, 3H, C—$(CH_3)_2$); 1.54 (s, 3H, C—$(CH_3)_2$); 2.06-2.20 (m, 2H, $CH_2$); 3.20-3.79 (m, 4H, N—$CH_2$); 4.85-4.94 (m, 1H, CONH—CH—$CH_3$); 5.07 (bs, 1H, Ph-O—CH); 6.87 (dd, J 8.2, 1.4 Hz, 1H, Ar); 6.97-7.03 (m, 2H, Ar); 7.29 (t, J 8.2 Hz, 1H, Ar); 7.34 (d, J 8.3 Hz, 2H, Ar); 7.74 (d, J 8.3 Hz, 2H, Ar); CONH signal was not observed; $CO_2H$ signal was not observed; HCl salt not observed. M/Z $(M+H)^+$: 430

Example 175: N—((S)-1-(4-(2H-Tetrazol-5-yl)phenyl)ethyl)-4-((R)-3-(3-(trifluoromethyl)phenoxy)pyrrolidin-1-yl)tetrahydro-2H-pyran-4-carboxamide, hydrochloride

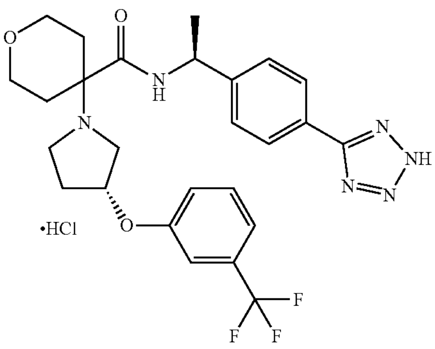

Example 175 was obtained according to General Procedure I-a, starting from Compound 421 and (S)-1-(4-(2H-tetrazol-5-yl)phenyl)ethan-1-amine. Purification by preparative LC-MS, then HCl salt preparation (method 1) afforded Example 175 as a white powder in 23% yield. $^1$H-NMR (DMSO-$d_6$/$D_2O$ 400 MHz) δ (ppm): 1.51 (d, J 7.1 Hz, 3H, CH—$CH_3$); 1.84-1.97 (m, 2H, $CH_2$); 2.04-2.15 (m, 2H, $CH_2$); 2.35-2.46 (m, 2H, $CH_2$); 3.12-3.23 (m, 2H, O—$CH_2$); 3.28-3.44 (m, 3H, N—$CH_2$+N-$CH_aH_b$); 3.57-3.69 (m, 1H, N—$CH_aH_b$); 3.84-3.95 (m, 2H, O—$CH_2$); 5.09-5.18 (m, 1H, CONH—CH—$CH_3$); 5.20 (bs, 1H, PhO—CH); 7.13-7.21 (m, 2H, Ar); 7.30 (d, J 7.8 Hz, 1H, Ar); 7.51 (dd, J 8&2, 7.8 Hz, 1H, Ar); 7.57 (d, J 8.2 Hz, 2H, Ar); 7.97 (d, J 8.2 Hz, 2H, Ar); CONH signal was not observed; tetrazole-NH signal was not observed; HCl salt not observed. M/Z $(M+H)^+$: 531

Compound 487: (S)-1-(4-(1H-Pyrazol-4-yl)phenyl)ethan-1-amine, hydrochloride

To a solution of tert-butyl (S)-(1-(4-bromophenyl)ethyl)carbamate (1 equiv.) in a n-butanol/water mixture (7/3, 0.07 M) were added 1-(tetrahydro-2H-pyran-2-yl)-4-(4,4,5,5-tetramethyl-1,3,2-dioxaborolan-2-yl)-1H-pyrazole (1.5 equiv.) and tripotassium phosphate (2 equiv.). The reaction mixture was degassed for 10 min with argon, then SPhosPd G2 (10 mol %) was added. The reaction mixture was heated overnight at 100° C. The reaction mixture was filtered through a celite pad. The filtrate was diluted with EtOAc, washed with a saturated solution of ammonium chloride. The aqueous layer was extracted with EtOAc. The combined organic layers were washed with brine, dried, then concentrated. The crude was purified by flash chromatography (Cyclohexane/EtOAc: 90/10 to 50/50) to afford a white solid in 88% yield. M/Z $(M+H)^+$: 372. This white solid was dissolved in a DCM/TFA mixture (1/1, 0.1 M). The reaction mixture was stirred overnight at rt, then concentrated to dryness. The resulting residue was co-evaporated 3 times with HCl 2 N in diethyl ether to afford Compound 487 as a grey solid in quantitative yield. M/Z $(M+H)^+$: 188

Example 176: N—((S)-1-(4-(1H-Pyrazol-4-yl)phenyl)ethyl)-4-((R)-3-(3-(trifluoromethyl)phenoxy)pyrrolidin-1-yl)tetrahydro-2H-pyran-4-carboxamide, hydrochloride

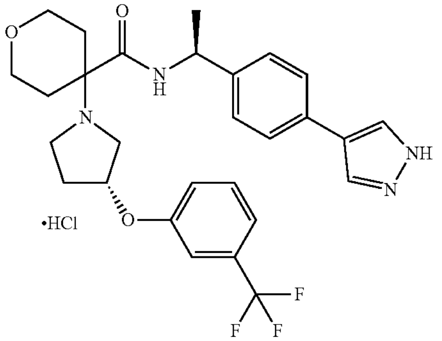 [SMILES: C[C@H](NC(=O)C1(N2CC[C@@H](Oc3cccc(C(F)(F)F)c3)C2)CCOCC1)c1ccc(-c2cn[nH]c2)cc1 ; Cl]

Example 176 was obtained according to General Procedure I-a, starting from Compound 421 and Compound 487. In that specific case, 4 equiv. of diisopropylethylamine were used. Purification by preparative LC-MS, then HCl salt preparation (method 1) afforded Example 176 as a white powder in 36% yield. $^1$H-NMR (DMSO-$d_6$/$D_2O$ 400 MHz) δ (ppm): 1.49 (d, J 7.1 Hz, 3H, CH—$CH_3$); 1.87-2.01 (m, 2H, $CH_2$); 2.06-2.20 (m, 2H, $CH_2$); 2.46-2.56 (m, 2H, $CH_2$); 3.04-3.19 (m, 2H, O—$CH_2$); 3.39-3.58 (m, 3H, N—$CH_2$+N-$CH_aH_b$); 3.69-3.78 (m, 1H, N—$CH_aH_b$); 3.86-3.96 (m, 2H, O—$CH_2$); 5.02-5.10 (m, 1H, CONH—CH—$CH_3$); 5.19 (bs, 1H, PhO—CH); 7.17-7.22 (m, 2H, Ar); 7.29-7.35 (m, 3H, Ar); 7.49-7.55 (m, 3H, Ar); 7.98 (s, 2H, Ar); 8.86 (d, J 7.1 Hz, 1H, CONH); indazole-NH signal was not observed; HCl salt not observed. M/Z $(M+H)^+$: 529

Compound 488: (S)-1-(4-(1H-Pyrazol-5-yl)phenyl)ethan-1-amine, hydrochloride

To a solution of tert-butyl (S)-(1-(4-bromophenyl)ethyl)carbamate (1 equiv.) in a n-butanol/water mixture (7/3, 0.07 M) were added 1-(tetrahydro-2H-pyran-2-yl)-5-(4,4,5,5-tetramethyl-1,3,2-dioxaborolan-2-yl)-1H-pyrazole (1.5 equiv.) and tripotassium phosphate (2 equiv.). The reaction mixture was degassed for 10 min with argon, then SPhosPd G2 (10 mol %) was added. The reaction mixture was heated overnight at 100° C. The reaction mixture was filtered through a celite pad. The filtrate was diluted with EtOAc, washed with a saturated solution of ammonium chloride. The aqueous layer was extracted with EtOAc. The combined organic layers were washed with brine, dried, then concentrated. The crude was purified by flash chromatography (Cyclohexane/EtOAc: 100/0 to 50/50) to afford a white solid in quantitative yield. M/Z $(M+H)^+$: 372. This white solid was dissolved in a DCM/TFA mixture (1/1, 0.1 M). The reaction mixture was stirred overnight at rt, then concentrated to dryness. The resulting residue was co-evaporated 3 times with HCl 2 N in diethyl ether to afford Compound 487 as a grey solid in quantitative yield. M/Z $(M+H)^+$: 188

Example 177: N—((S)-1-(4-(1H-Pyrazol-5-yl)phenyl)ethyl)-4-((R)-3-(3-(trifluoromethyl)phenoxy)pyrrolidin-1-yl)tetrahydro-2H-pyran-4-carboxamide, hydrochloride

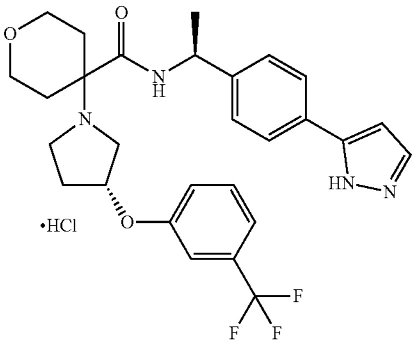 [SMILES: C[C@H](NC(=O)C1(N2CC[C@@H](Oc3cccc(C(F)(F)F)c3)C2)CCOCC1)c1ccc(-c2ccn[nH]2)cc1 ; Cl]

Example 177 was obtained according to General Procedure I-a, starting from Compound 421 and Compound 488. In that specific case, 4 equiv. of diisopropylethylamine were used. Purification by preparative LC-MS, then HCl salt preparation (method 1) afforded Example 176 as a white powder in 50% yield. $^1$H-NMR (DMSO-d/$D_2O$ 400 MHz) δ (ppm): 1.51 (d, J 7.1 Hz, 3H, CH—$CH_3$); 1.92-2.06 (m, 2H, $CH_2$); 2.07-2.21 (m, 2H, $CH_2$); 2.42-2.57 (m, 2H, $CH_2$); 3.05-3.21 (m, 2H, O—$CH_2$); 3.35-3.58 (m, 3H, N—$CH_2$+N-$CH_aH_b$); 3.69-3.81 (m, 1H, N—$CH_aH_b$); 3.87-3.98 (m, 2H, O—$CH_2$); 5.06-5.14 (m, 1H, CONH—CH—$CH_3$); 5.21 (bs, 1H, Ph-O—CH); 6.65 (d, J 2.2 Hz, 1H, Ar); 7.18-7.24 (m, 2H, Ar); 7.33 (d, J 7.8 Hz, 1H, Ar); 7.39 (d, J 8.2 Hz, 2H, Ar); 7.50-7.56 (m, 1H, Ar); 7.69 (d, J 2.2 Hz, 1H, Ar); 7.73 (d, J 8.2 Hz, 2H, Ar); 8.91 (d, J 7.1 Hz, 1H, CONH); indazole-NH signal was not observed; HCl salt not observed. M/Z $(M+H)^+$: 529

Example 178: N—((S)-1-(4-Sulfamoylphenyl)ethyl)-4-((R)-3-(3-(trifluoromethyl)phenoxy)pyrrolidin-1-yl)tetrahydro-2H-pyran-4-carboxamide, hydrochloride

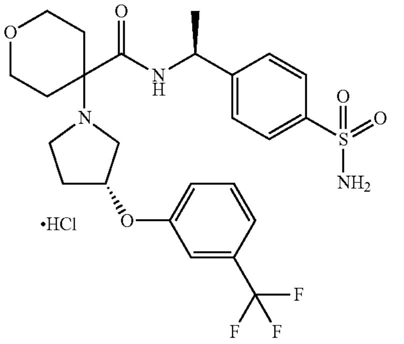 [SMILES: C[C@H](NC(=O)C1(N2CC[C@@H](Oc3cccc(C(F)(F)F)c3)C2)CCOCC1)c1ccc(S(N)(=O)=O)cc1 ; Cl]

Example 178 was obtained according to General Procedure I-a, starting from Compound 421 and (S)-4-(1-aminoethyl)benzenesulfonamide. Purification by preparative LC-MS, then HCl salt preparation (method 1) afforded Example 178 as a white powder in 60% yield. $^1$H-NMR (DMSO-$d_6$/$D_2O$ 400 MHz) δ (ppm): 1.49 (d, J 6.9 Hz, 3H, CH—$CH_3$); 1.89-2.05 (m, 2H, $CH_2$); 2.07-2.20 (m, 2H, $CH_2$); 2.39-2.47 (m, 2H, $CH_2$); 3.02-3.19 (m, 2H, O—$CH_2$); 3.34-3.44 (m, 3H, N—$CH_2$+N-$CH_aH_b$); 3.65-3.80 (m, 1H, N—$CH_aH_b$); 3.85-3.98 (m, 2H, O—$CH_2$); 5.06-5.15 (m, 1H, CONH—CH—$CH_3$); 5.19 (bs, 1H, PhO—CH); 7.18-7.24 (m, 2H, Ar); 7.34 (d, J 7.8 Hz, 1H, Ar); 7.41 (d, J 8.1 Hz, 2H, Ar); 7.55 (dd, J 8.2, 7.8 Hz, 1H, Ar); 7.81 (d, J 8.1 Hz, 2H, Ar); CONH signal was not observed; $SO_2$—$NH_2$ signal was not observed; HCl salt not observed. M/Z $(M+H)^+$: 542

Example 179: N—((S)-1-(4-(Methylsulfonyl)phenyl)ethyl)-4-((R)-3-(3-(trifluoromethyl)phenoxy)pyrrolidin-1-yl)tetrahydro-2H-pyran-4-carboxamide, hydrochloride

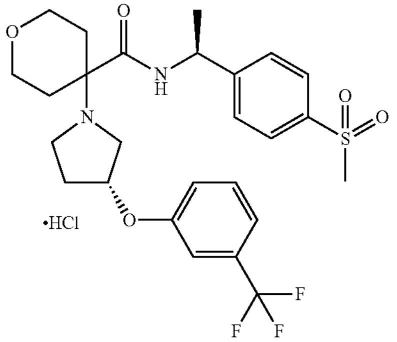 [SMILES: C[C@H](NC(=O)C1(N2CC[C@@H](Oc3cccc(C(F)(F)F)c3)C2)CCOCC1)c1ccc(S(C)(=O)=O)cc1 ; Cl]

Example 179 was obtained according to General Procedure I-a, starting from Compound 421 and (S)-1-(4-(methylsulfonyl)phenyl)ethan-1-amine. Purification by preparative LC-MS, then HCl salt preparation (method 1) afforded Example 179 as a white powder in 28% yield. $^1$H-NMR (DMSO-de/$D_2O$ 400 MHz) δ (ppm): 1.49 (d, J 6.9 Hz, 3H, CH—$CH_3$); 1.83-1.98 (m, 2H, $CH_2$); 2.03-2.15 (m, 2H, $CH_2$); 2.35-2.44 (m, 2H, $CH_2$); 3.09-3.23 (m, 5H, O-$CH_2$+$SO_2$—$CH_3$); 3.29-3.47 (m, 3H, N-$CH_2$+N-$CH_aH_b$); 3.65-3.71 (m, 1H, N—$CH_aH_b$); 3.84-3.95 (m, 2H, O—$CH_2$); 5.09-5.20 (m, 2H, CONH—CH—$CH_3$+PhO—CH); 7.16-7.24 (m, 2H, Ar); 7.34 (d, J 7.5 Hz, 1H, Ar); 7.52-7.53 (m, 3H, Ar); 7.87 (d, J 7.7 Hz, 2H, Ar); CONH signal was not observed; HCl salt not observed. M/Z $(M+H)^+$: 541

Example 180: N-((1S)-1-(4-(S-Methylsulfonimidoyl)phenyl)ethyl)-4-((R)-3-(3-(trifluoromethyl)phenoxy)pyrrolidin-1-yl)tetrahydro-2H-pyran-4-carboxamide, hydrochloride

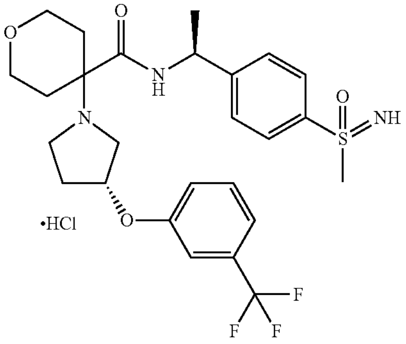 [SMILES: C[C@H](NC(=O)C1(N2CC[C@@H](Oc3cccc(C(F)(F)F)c3)C2)CCOCC1)c1ccc(S(C)(=N)=O)cc1 ; Cl]

Example 180 was obtained according to General Procedure I-a, starting from Compound 421 and (4-((S)-1-aminoethyl)phenyl)(imino)(methyl)-sulfanone. Purification by preparative LC-MS, then HCl salt preparation (method 1) afforded Example 180 as a white powder in 27% yield. $^1$H-NMR ($D_2O$ 400 MHz) δ (ppm): 1.65 (d, J 7.1 Hz, 3H, CH—$CH_3$); 2.05-2.25 (m, 3H, $CH_2$+$CH_aH_b$); 2.33.2.42 (m, 1H, $CH_aH_b$); 2.56-2.68 (m, 2H, $CH_2$); 3.32-3.43 (m, 2H, O—$CH_2$); 3.43-3.49 (m, 3H, SO(NH)—$CH_3$); 3.66-3.81 (m, 3H, N—$CH_2$+N-$CH_aH_b$); 3.83-3.91 (m, 1H, N—$CH_aH_b$); 4.06-4.18 (m, 2H, O—$CH_2$); 5.22-5.29 (m, 2H, CONH—CH—$CH_3$+PhO—CH); 7.16 (d, J 8.2 Hz, 1H, Ar); 7.21 (bs, 1H, Ar); 7.43 (d, J 7.8 Hz, 1H, Ar); 7.56 (dd, J 8.2, 7.8 Hz, 1H, Ar); 7.75 (d, J 8.2 Hz, 2H, Ar); 8.02 (d, J 8.2 Hz, 2H, Ar); CONH signal was not observed; SO(NH)—$CH_3$ signal was not observed; HCl salt not observed. M/Z $(M+H)^+$: 540

Example 181: N—((S)-1-(4-Hydroxyphenyl)ethyl)-4-((R)-3-(3-(trifluoromethyl)phenoxy)pyrrolidin-1-yl)tetrahydro-2H-pyran-4-carboxamide, hydrochloride

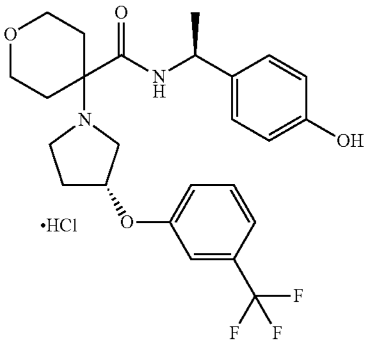 [SMILES: C[C@H](NC(=O)C1(N2CC[C@@H](Oc3cccc(C(F)(F)F)c3)C2)CCOCC1)c1ccc(O)cc1 ; Cl]

Example 181 was obtained according to General Procedure I-a, starting from Compound 421 and (S)-1-(4-hydroxyphenyl)ethan-1-amine. Purification by preparative LC-MS, then HCl salt preparation (method 1) afforded Example 181 as a white powder in 43% yield. $^1$H-NMR (DMSO-$d_6$/$D_2O$, 400 MHz) δ (ppm): 1.34-1.43 (m, 3H, CH—$CH_3$); 1.73-1.87 (m, 2H, $CH_2$); 1.99-2.15 (m, 2H, $CH_2$); 2.21-2.38 (m, 2H, $CH_2$); 3.06-3.58 (m, 6H, O-$CH_2$, 2 N—$CH_2$); 3.79-3.87 (m, 2H, O—$CH_2$); 4.91-4.98 (m, 1H, CONH—CH—$CH_3$); 5.07 (bs, 1H, PhO—CH); 6.66 (d, J 8.3 Hz, 2H, Ar); 7.11 (d, J 8.3 Hz, 2H, Ar); 7.13-7.19 (m, 2H, Ar); 7.28-7.34 (m, 1H, Ar); 7.49-7.56 (m, 1H, Ar); observed; HCl salt not observed. M/Z $(M+H)^+$: 515

Example 182: N—((S)-1-(4-Cyanophenyl)ethyl)-4-((R)-3-(3-(trifluoromethyl)phenoxy)pyrrolidin-1-yl)tetrahydro-2H-pyran-4-carboxamide, hydrochloride

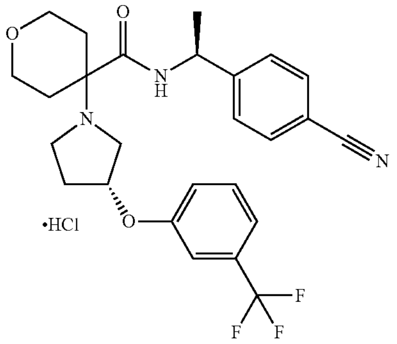 [SMILES: C[C@H](NC(=O)C1(N2CC[C@@H](Oc3cccc(C(F)(F)F)c3)C2)CCOCC1)c1ccc(C#N)cc1 ; Cl]

Example 182 was obtained according to General Procedure I-a, starting from Compound 421 and (S)-4-(1-aminoethyl)benzonitrile. Purification by preparative LC-MS, then HCl salt preparation (method 1) afforded Example 182 as a white powder in 39% yield. $^1$H-NMR (DMSO-$d_6$/$D_2O$, 400 MHz) δ (ppm): 1.40-1.48 (m, 3H, CH—$CH_3$); 1.76-1.89 (m, 2H, $CH_2$); 1.95-2.16 (m, 2H, $CH_2$); 2.22-2.35 (m, 2H, $CH_2$); 3.11-3.29 (m, 5H, O—$CH_2$, N—$CH_2$+N-$CH_aH_b$); 3.41-3.52 (m, 1H, N—$CH_aH_b$); 3.81-3.95 (m, 2H, O—$CH_2$); 5.01-5.11 (m, 2H, CONH—CH—$CH_3$+PhO—CH); 7.06-7.19 (m, 2H, Ar); 7.27-7.35 (m, 1H, Ar); 7.47-7.57 (m, 3H, Ar); 7.67-7.76 (m, 2H, Ar); CONH signal was not observed; HCl salt not observed. M/Z $(M+H)^+$: 488

Example 183: N—((S)-1-Phenylethyl)-4-((R)-3-(3-(trifluoromethyl)phenoxy)pyrrolidin-1-yl)tetrahydro-2H-pyran-4-carboxamide, hydrochloride

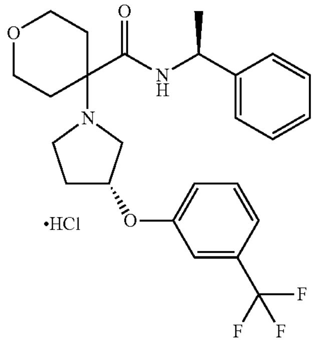 [SMILES: C[C@H](NC(=O)C1(N2CC[C@@H](Oc3cccc(C(F)(F)F)c3)C2)CCOCC1)c1ccccc1 ; Cl]

Example 183 was obtained according to General Procedure I-a, starting from Compound 421 and (S)-1-phenylethan-1-amine. Purification by preparative LC-MS, then HCl salt preparation (method 1) afforded Example 183 as a white powder in 76% yield. $^1$H-NMR (DMSO-$d_6$/$D_2O$ 400 MHz) δ (ppm): 1.45 (d, J 7.1 Hz, 3H, CH—$CH_3$); 1.79-1.92 (m, 2H, $CH_2$); 2.05-2.13 (m, 2H, $CH_2$); 2.31-2.39 (m, 2H, $CH_2$); 3.06-3.20 (m, 2H, O—$CH_2$); 3.30-3.44 (m, 3H, N—$CH_2$+N-$CH_aH_b$); 3.57-3.64 (m, 1H, N—$CH_aH_b$); 3.85-3.91 (m, 2H, O—$CH_2$); 5.04 (q, J 7.1 Hz, 1H, CONH—CH—$CH_3$); 5.12 (bs, 1H, PhO—CH); 7.13-7.22 (m, 3H, Ar); 7.25-7.35 (m, 5H, Ar); 7.54 (t, J 8.0 Hz, 1H, Ar); CONH signal was not observed; HCl salt not observed. M/Z $(M+H)^+$: 463

Example 184: N—((S)-1-(Pyridin-4-yl)ethyl)-4-((R)-3-(3-(trifluoromethyl)phenoxy)pyrrolidin-1-yl) tetrahydro-2H-pyran-4-carboxamide, hydrochloride

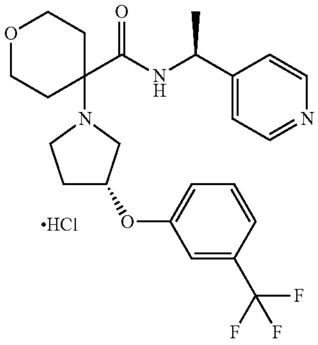 [SMILES: C[C@H](NC(=O)C1(N2CC[C@@H](Oc3cccc(C(F)(F)F)c3)C2)CCOCC1)c1ccncc1 ; Cl]

Example 184 was obtained according to General Procedure I-a, starting from Compound 421 and (S)-1-(pyridin-4-yl)ethan-1-amine. Purification by preparative LC-MS, then HCl salt preparation (method 1) afforded Example 184 as a white powder in 50% yield. $^1$H-NMR (DMSO-$d_6$/$D_2O$ 400 MHz) δ (ppm): 1.50 (d, J 7.2 Hz, 3H, CH—$CH_3$); 1.84-1.99 (m, 2H, $CH_2$); 2.05-2.22 (m, 2H, $CH_2$); 2.34-2.46 (m, 2H, $CH_2$); 3.14-3.26 (m, 2H, O—$CH_2$); 3.26-3.42 (m, 3H, N—$CH_2$+N-$CH_aH_b$); 3.57-3.64 (m, 1H, N—$CH_aH_b$); 3.84-3.95 (m, 2H, O—$CH_2$); 5.12-5.20 (m, 2H, CONH—CH—$CH_3$+PhO—CH); 7.18 (bs, 1H, Ar); 7.22 (bd, J 8.6 Hz, 1H, Ar); 7.34 (d, J 7.8 Hz, 1H, Ar); 7.55 (dd, J 8.6, 7.8 Hz, 1H, Ar); 7.79 (d, J 6.4 Hz, 2H, Ar); 8.71 (d, J 6.4 Hz, 2H, Ar); CONH signal was not observed; HCl salt not observed. M/Z $(M+H)^+$: 464

Example 185: N—((S)-1-(Pyridin-3-yl)ethyl)-4-((R)-3-(3-(trifluoromethyl)phenoxy)pyrrolidin-1-yl) tetrahydro-2H-pyran-4-carboxamide, hydrochloride

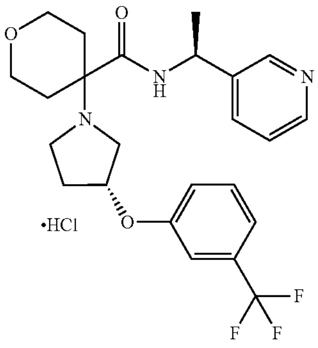 [SMILES: C[C@H](NC(=O)C1(N2CC[C@@H](Oc3cccc(C(F)(F)F)c3)C2)CCOCC1)c1cccnc1 ; Cl]

Example 185 was obtained according to General Procedure I-a, starting from Compound 421 and (S)-1-(pyridin-3-yl)ethan-1-amine. Purification by preparative LC-MS, then HCl salt preparation (method 1) afforded Example 185 as a white powder in 31% yield. $^1$H-NMR (DMSO-$d_6$/$D_2O$ 400 MHz) δ (ppm): 1.53 (d, J 7.1 Hz, 3H, CH—$CH_3$); 1.85-1.98 (m, 2H, $CH_2$); 2.07-2.15 (m, 2H, $CH_2$); 2.34-2.46 (m, 2H, $CH_2$); 3.08-3.19 (m, 2H, O—$CH_2$); 3.31-3.47 (m, 3H, N—$CH_2$+N-$CH_aH_b$); 3.57-3.64 (m, 1H, N—$CH_aH_b$); 3.85-3.94 (m, 2H, O—$CH_2$); 5.14-5.22 (m, 2H, CONH—CH—$CH_3$+Ph-O—CH); 7.18 (bs, 1H, Ar); 7.24 (bd, J 8.4 Hz, 1H, Ar); 7.35 (d, J 7.8 Hz, 1H, Ar); 7.55 (dd, J 8.4, 7.8 Hz, 1H, Ar); 7.71 (dd, J 8.0, 5.2 Hz, 1H, Ar); 8.20 (bd, J 8.0 Hz, 1H, Ar); 8.62 (dd, J 5.2, 1.5 Hz, 1H, Ar); 8.74 (d, J 1.5 Hz, 1H, Ar); CONH signal was not observed; HCl salt not observed. M/Z $(M+H)^+$: 464

Example 186: N—((S)-1-(Pyridin-2-yl)ethyl)-4-((R)-3-(3-(trifluoromethyl)phenoxy)pyrrolidin-1-yl) tetrahydro-2H-pyran-4-carboxamide, hydrochloride

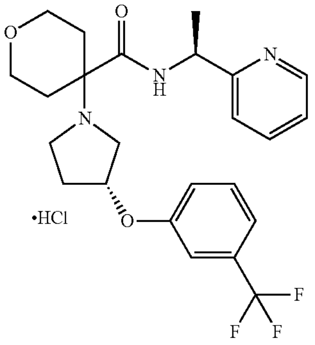 [SMILES: C[C@H](NC(=O)C1(N2CC[C@@H](Oc3cccc(C(F)(F)F)c3)C2)CCOCC1)c1ccccn1 ; Cl]

Example 186 was obtained according to General Procedure I-a, starting from Compound 421 and (S)-1-(pyridin-2-yl)ethan-1-amine. Purification by preparative LC-MS, then HCl salt preparation (method 1) afforded Example 186 as a white powder in 38% yield. $^1$H-NMR (DMSO-$d_6$/$D_2O$ 400 MHz) δ (ppm): 1.50 (d, J 7.2 Hz, 3H, CH—$CH_3$); 1.88-1.99 (m, 2H, $CH_2$); 2.12-2.24 (m, 2H, $CH_2$); 2.42-2.47 (m, 2H, $CH_2$); 3.12-3.21 (m, 1H, O—$CH_aH_h$); 3.24-3.32 (m, 1H, O—$CH_aH_b$); 3.42-3.51 (m, 1H, N—$CH_aH_b$); 3.54-3.60 (m, 2H, N—$CH_2$); 3.68-3.75 (m, 1H, N—$CH_aH_b$); 3.86-3.96 (m, 2H, O—$CH_2$); 5.14 (q, J 7.2 Hz, 1H, CONH—CH—$CH_3$); 5.20 (bs, 1H, PhO—CH); 7.19 (bs, 1H, Ar); 7.23 (dd, J 8.4, 1.8 Hz, 1H, Ar); 7.33-7.37 (m, 2H, Ar); 7.48 (d, J 7.8 Hz, 1H, Ar); 7.55 (dd, J 8.4, 7.8 Hz, 1H, Ar); 7.87 (td, J 7.8, 1.8 Hz, 1H, Ar); 8.49-8.51 (m, 1H, Ar); CONH signal was not observed; HCl salt not observed. M/Z $(M+H)^+$: 464

Example 187: N—((S)-1-(4-Fluorophenyl)ethyl)-4-((R)-3-(3-(trifluoromethyl)phenoxy)pyrrolidin-1-yl) tetrahydro-2H-pyran-4-carboxamide, hydrochloride

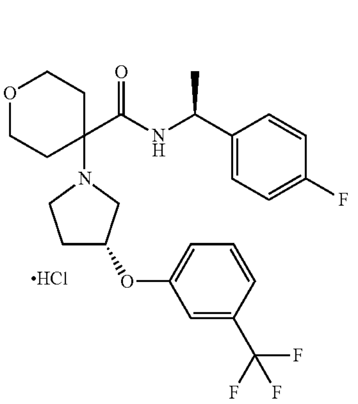 [SMILES: C[C@H](NC(=O)C1(N2CC[C@@H](Oc3cccc(C(F)(F)F)c3)C2)CCOCC1)c1ccc(F)cc1 ; Cl]

Example 187 was obtained according to General Procedure I-a, starting from Compound 421 and (S)-1-(4-fluorophenyl)ethan-1-amine. Purification by preparative LC-MS, then HCl salt preparation (method 1) afforded Example 187 as a white powder in 56% yield. $^1$H-NMR (DMSO-$d_6$/$D_2O$ 400 MHz) δ (ppm): 1.49 (d, J 7.1 Hz, 3H, CH—$CH_3$); 1.85-1.97 (m, 2H, $CH_2$); 2.06-2.15 (m, 2H, $CH_2$); 2.34-2.46 (m, 2H, $CH_2$); 3.12-3.24 (m, 2H, O—$CH_2$); 3.28-3.45 (m, 3H, N—$CH_2$+N-$CH_aH_b$); 3.57-3.70 (m, 1H, N—$CH_aH_b$); 3.84-3.94 (m, 2H, O—$CH_2$); 5.09-5.18 (m, 2H, CONH—CH-$CH_3$+PhO—CH); 7.12-7.21 (m, 2H, Ar); 7.30 (d, J 8.0 Hz, 1H, Ar); 7.51 (t, J 8.0 Hz, 1H, Ar); 7.57 (d, J 8.2 Hz, 2H, Ar); 7.97 (d, J 8.2 Hz, 2H, Ar); CONH signal was not observed; HCl salt not observed. M/Z $(M+H)^+$: 491

Example 188: N—((S)-1-(3-Fluorophenyl)ethyl)-4-((R)-3-(3-(trifluoromethyl)phenoxy)pyrrolidin-1-yl)tetrahydro-2H-pyran-4-carboxamide, hydrochloride

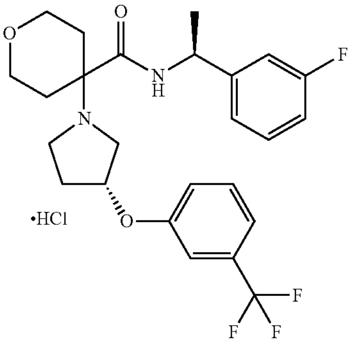 [SMILES: C[C@H](NC(=O)C1(N2CC[C@@H](Oc3cccc(C(F)(F)F)c3)C2)CCOCC1)c1cccc(F)c1 ; Cl]

Example 188 was obtained according to General Procedure I-a, starting from Compound 421 and (S)-1-(3-fluorophenyl)ethan-1-amine. Purification by preparative LC-MS, then HCl salt preparation (method 1) afforded Example 188 as a white powder in 40% yield. $^1$H-NMR (DMSO-$d_6$/$D_2O$ 400 MHz) δ (ppm): 1.47 (d, J 7.1 Hz, 3H, CH—$CH_3$); 1.89-2.03 (m, 2H, $CH_2$); 2.05-2.17 (m, 2H, $CH_2$); 2.37-2.46 (m, 2H, $CH_2$); 3.09-3.20 (m, 2H, O—$CH_2$); 3.27-3.50 (m, 3H, N—$CH_2$+N-$CH_aH_b$); 3.60-3.74 (m, 1H, N—$CH_aH_b$); 3.84-3.96 (m, 2H, O—$CH_2$); 5.04-5.12 (m, 1H, CONH—CH—$CH_3$); 5.18 (bs, 1H, PhO—CH); 7.00-7.07 (m, 1H, Ar); 7.13-7.25 (m, 4H, Ar); 7.30-7.38 (m, 2H, Ar); 7.55 (t, J 8.0 Hz, 1H, Ar); CONH signal was not observed; HCl salt not observed. M/Z $(M+H)^+$: 491

Example 189: N—((S)-1-(2-Fluorophenyl)ethyl)-4-((R)-3-(3-(trifluoromethyl)phenoxy)pyrrolidin-1-yl)tetrahydro-2H-pyran-4-carboxamide, hydrochloride

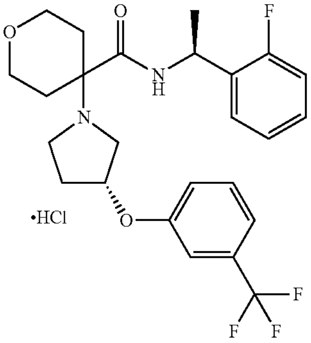 [SMILES: C[C@H](NC(=O)C1(N2CC[C@@H](Oc3cccc(C(F)(F)F)c3)C2)CCOCC1)c1ccccc1F ; Cl]

Example 189 was obtained according to General Procedure I-a, starting from Compound 421 and (S)-1-(2-fluorophenyl)ethan-1-amine. Purification by preparative LC-MS, then HCl salt preparation (method 1) afforded Example 189 as a beige powder in 40% yield. $^1$H-NMR (DMSO-$d_6$/$D_2O$, 400 MHz) δ (ppm): 1.46 (d, J 7.1 Hz, 3H, CH—$CH_3$); 1.82-1.96 (m, 2H, $CH_2$); 2.06-2.19 (m, 2H, $CH_2$); 2.37-2.46 (m, 2H, $CH_2$); 3.06-3.15 (m, 1H, O—$CH_aH_b$); 3.15-3.23 (m, 1H, O—$CH_aH_b$); 3.28-3.45 (m, 3H, N—$CH_2$+N-$CH_aH_b$); 3.59-3.66 (m, 1H, N—$CH_aH_b$); 3.83-3.93 (m, 2H, O—$CH_2$); 5.16 (bs, 1H, Ph-O—CH); 5.29 (q, J 7.1 Hz, 1H, CONH—CH—$CH_3$); 7.09-7.18 (m, 3H, Ar); 7.21 (bd, J 8.4 Hz, 1H, Ar); 7.25-7.31 (m, 1H, Ar); 7.34 (d, J 7.8 Hz, 1H, Ar); 7.42 (td, J 7.8, 1.5 Hz, 1H, Ar); 7.51 (dd, J 8.4, 7.8 Hz, 1H, Ar); CONH signal was not observed; HCl salt not observed. M/Z $(M+H)^+$: 491

Example 190: N—((S)-1-(4-Bromophenyl)ethyl)-4-((R)-3-(3-(trifluoromethyl)phenoxy)pyrrolidin-1-yl)tetrahydro-2H-pyran-4-carboxamide, hydrochloride

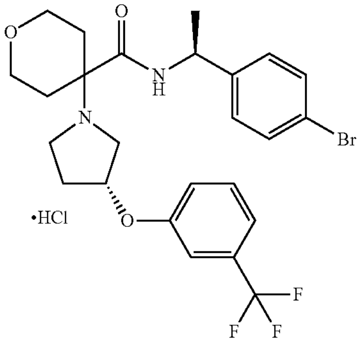 [SMILES: C[C@H](NC(=O)C1(N2CC[C@@H](Oc3cccc(C(F)(F)F)c3)C2)CCOCC1)c1ccc(Br)cc1 ; Cl]

Example 190 was obtained according to General Procedure I-a, starting from Compound 421 and (S)-1-(4-bromophenyl)ethan-1-amine. Purification by flash chromatography (Cyclohexane/EtOAc: 80/20 to 0/100), then HCl salt preparation (method 1) afforded Example 190 as a white powder in 87% yield. $^1$H-NMR (DMSO-$d_6$/$D_2O$, 400 MHz) δ (ppm): 1.39-1.47 (m, 3H, CH—$CH_3$); 1.79-1.93 (m, 2H, $CH_2$); 2.01-2.16 (m, 2H, $CH_2$); 2.31-2.41 (m, 2H, $CH_2$); 3.09-3.19 (m, 2H, O—$CH_2$); 3.24-3.37 (m, 3H, N—$CH_2$+

N-$CH_aH_b$); 3.57-3.70 (m, 1H, N—$CH_aH_b$); 3.76-3.82 (m, 2H, O—$CH_2$); 4.95-5.05 (m, 1H, CONH—CH—$CH_3$); 5.11 (bs, 1H, PhO—CH); 7.12-7.20 (m, 2H, Ar); 7.24-7.35 (m, 3H, Ar); 7.42-7.48 (m, 2H, Ar); 7.51-7.57 (m, 1H, Ar); CONH signal was not observed; HCl salt not observed. M/Z $(M[^{79}Br]+H)^+$: 541

Example 191: N—((S)-1-(3-Chlorophenyl)ethyl)-4-((R)-3-(3-(trifluoromethyl)phenoxy)pyrrolidin-1-yl) tetrahydro-2H-pyran-4-carboxamide, hydrochloride

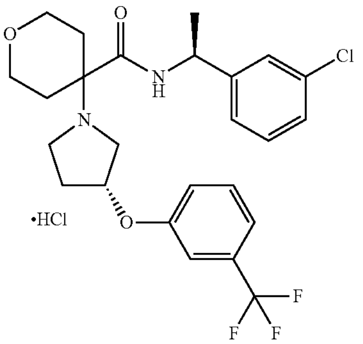 [SMILES: C[C@H](NC(=O)C1(N2CC[C@@H](Oc3cccc(C(F)(F)F)c3)C2)CCOCC1)c1cccc(Cl)c1 ; Cl]

Example 191 was obtained according to General Procedure I-a, starting from Compound 421 and (S)-1-(3-chlorophenyl)ethan-1-amine. Purification by preparative LC-MS, then HCl salt preparation (method 1) afforded Example 191 as a white powder in 44% yield. $^1$H-NMR (DMSO-$d_6$/$D_2O$ 400 MHz) δ (ppm): 1.44 (d, J 7.1 Hz, 3H, CH—$CH_3$); 1.79-1.91 (m, 2H, $CH_2$); 2.00-2.14 (m, 2H, $CH_2$); 2.35-2.42 (m, 2H, $CH_2$); 3.06-3.20 (m, 2H, O—$CH_2$); 3.28-3.39 (m, 3H, N—$CH_2$+N-$CH_aH_b$); 3.53-3.61 (m, 1H, N—$CH_aH_b$); 3.83-3.93 (m, 2H, O—$CH_2$); 5.02 (q, J 7.1 Hz, 1H, CONH—CH—$CH_3$); 5.12 (bs, 1H, Ph-C—CH); 7.13 (bs, 1H, Ar); 7.17 (bd, J 8.4 Hz, 1H, Ar); 7.23-7.34 (m, 4H, Ar); 7.36 (bs, 1H, Ar); 7.53 (dd, J 8.4, 7.8 Hz, 1H, Ar); CONH signal was not observed; HCl salt not observed. M/Z $(M[35Cl]+H)^+$: 497

Example 192: N—((S)-1-(2-Chlorophenyl)ethyl)-4-((R)-3-(3-(trifluoromethyl)phenoxy)pyrrolidin-1-yl) tetrahydro-2H-pyran-4-carboxamide, hydrochloride

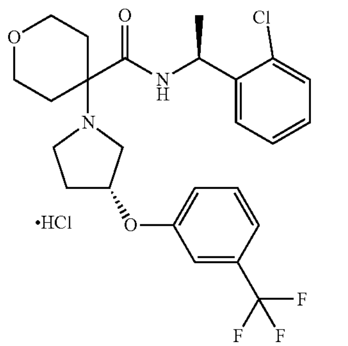 [SMILES: C[C@H](NC(=O)C1(N2CC[C@@H](Oc3cccc(C(F)(F)F)c3)C2)CCOCC1)c1ccccc1Cl ; Cl]

Example 192 was obtained according to General Procedure I-a, starting from Compound 421 and (S)-1-(2-chlorophenyl)ethan-1-amine. Purification by preparative LC-MS, then HCl salt preparation (method 1) afforded Example 191 as a beige powder in 42% yield. $^1$H-NMR (DMSO-$d_6$/$D_2O$ 400 MHz) δ (ppm): 1.44 (d, J 7.1 Hz, 3H, OH—$CH_3$); 1.83-1.99 (m, 2H, $CH_2$); 2.08-2.20 (m, 2H, $CH_2$); 2.35-2.47 (m, 2H, $CH_2$); 3.07 3.17 (m, 1H, O—$CH_aH_b$); 3.19-3.28 (m, 1H, O—$CH_aH_b$); 3.32-3.51 (m, 3H, N—$CH_2$+N-$CH_aH_b$); 3.61-3.70 (m, 1H, N—$CH_aH_b$); 3.82-3.96 (m, 2H, O—$CH_2$); 5.17 (bs, 1H, Ph-O—CH); 5.35 (q, J 7.1 Hz, 1H, CONH—CH—$CH_3$); 7.16 (bs, 1H, Ar); 7.19-7.32 (m, 3H, Ar); 7.33 (d, J 7.8 Hz, 1H, Ar); 7.39 (dd, J 7.8, 1.4 Hz, 1H, Ar); 7.48 (dd, J 7.6, 1.4 Hz, 1H, Ar); 7.55 (dd, J 8.4, 7.8 Hz, 1H, Ar); CONH signal was not observed; HCl salt not observed. M/Z $(M[^{35}Cl]+H)^+$: 497

Example 193: N—((S)-1-(4-Methylphenyl)ethyl)-4-((R)-3-(3-(trifluoromethyl)phenoxy)pyrrolidin-1-yl) tetrahydro-2H-pyran-4-carboxamide, hydrochloride

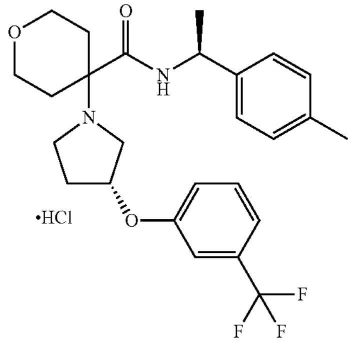 [SMILES: Cc1ccc([C@H](C)NC(=O)C2(N3CC[C@@H](Oc4cccc(C(F)(F)F)c4)C3)CCOCC2)cc1 ; Cl]

Example 193 was obtained according to General Procedure I-a, starting from Compound 421 and (S)-1-(4-methylphenyl)ethan-1-amine. Purification by preparative LC-MS, then HCl salt preparation (method 1) afforded Example 193 as a white powder in 53% yield. $^1$H-NMR (DMSO-$d_6$/$D_2O$ 400 MHz) δ (ppm): 1.42 (d, J 6.9 Hz, 3H, CH—$CH_3$); 1.79-1.92 (m, 2H, $CH_2$); 2.04-2.14 (m, 2H, $CH_2$); 2.21 (s, 3H, $CH_3$); 2.30-2.44 (m, 2H, $CH_2$); 3.08-3.19 (m, 2H, O—$CH_2$); 3.27-3.40 (m, 3H, N—$CH_2$+N-$CH_aH_b$); 3.57-3.70 (m, 1H, N—$CH_aH_b$); 3.84-3.91 (m, 2H, O—$CH_2$); 4.97-5.05 (m, 1H, CONH—CH—$CH_3$); 5.13 (bs, 1H, Ph-O—CH); 7.07 (d, J 7.3 Hz, 2H, Ar); 7.13-7.22 (m, 4H, Ar); 7.34 (d, J 8.0 Hz, 1H, Ar); 7.51 (t, J 8.0 Hz, 1H, Ar); CONH signal was not observed; HCl salt not observed. M/Z $(M+H)^+$: 477

Example 194: N—((S)-1-(3-Methylphenyl)ethyl)-4-((R)-3-(3-(trifluoromethyl)phenoxy)pyrrolidin-1-yl)tetrahydro-2H-pyran-4-carboxamide, hydrochloride

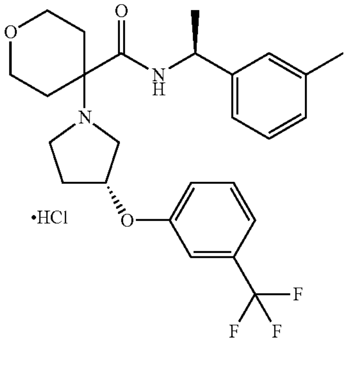 [SMILES: Cc1cccc([C@H](C)NC(=O)C2(N3CC[C@@H](Oc4cccc(C(F)(F)F)c4)C3)CCOCC2)c1 ; Cl]

Example 194 was obtained according to General Procedure I-a, starting from Compound 421 and (S)-1-(3-methylphenyl)ethan-1-amine. Purification by preparative LC-MS, then HCl salt preparation (method 1) afforded Example 194 as a white powder in 57% yield. $^1$H-NMR (DMSO-$d_6$/$D_2O$, 400 MHz) δ (ppm): 1.42 (d, J 7.1 Hz, 3H, CH—$CH_3$); 1.76-1.89 (m, 2H, $CH_2$); 2.04-2.14 (m, 2H, $CH_2$); 2.21 (s, 3H, $CH_3$); 2.33-2.45 (m, 2H, $CH_2$); 3.06-3.20 (m, 2H, O—$CH_2$); 3.29-3.42 (m, 3H, N—$CH_2$+N-$CH_aH_b$); 3.54-3.62 (m, 1H, N—$CH_aH_b$); 3.83-3.92 (m, 2H, O—$CH_2$); 4.98 (q, J 7.1 Hz, 1H, CONH—CH—$CH_3$); 5.10 (bs, 1H, PhO—CH); 7.00 (d, J 7.2 Hz, 1H, Ar); 7.04-7.18 (m, 5H, Ar); 7.32 (d, J 7.6 Hz, 1H, Ar); 7.53 (dd, J 8.4, 7.6 Hz, 1H, Ar); CONH signal was not observed; HCl salt not observed. M/Z $(M+H)^+$: 477

Example 195: N—((S)-1-(4-Methoxyphenyl)ethyl)-4-((R)-3-(3-(trifluoromethyl)phenoxy)pyrrolidin-1-yl)tetrahydro-2H-pyran-4-carboxamide, hydrochloride

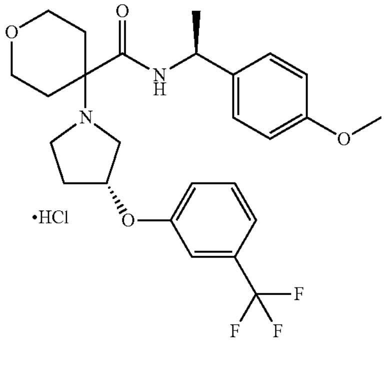 [SMILES: COc1ccc([C@H](C)NC(=O)C2(N3CC[C@@H](Oc4cccc(C(F)(F)F)c4)C3)CCOCC2)cc1 ; Cl]

Example 195 was obtained according to General Procedure I-a, starting from Compound 421 and (S)-1-(4-methoxyphenyl)ethan-1-amine. Purification by preparative LC-MS, then HCl salt preparation (method 1) afforded Example 195 as a white powder in 35% yield. $^1$H-NMR (DMSO-$d_6$/$D_2O$ 400 MHz) δ (ppm): 1.44 (d, J 7.1 Hz, 3H, CH—$CH_3$); 1.81-1.94 (m, 2H, $CH_2$); 2.06-2.13 (m, 2H, $CH_2$); 2.35-2.45 (m, 2H, $CH_2$); 3.08-3.17 (m, 2H, O—$CH_2$); 3.30-3.46 (m, 3H, N—$CH_2$+N-$CH_aH_b$); 3.60-3.67 (m, 1H, N—$CH_aH_b$); 3.68 (s, 3H, O—$CH_3$); 3.85-3.91 (m, 2H, O—$CH_2$); 4.98-5.07 (m, 1H, CONH—CH—$CH_3$); 5.16 (bs, 1H, PhO—CH); 6.84 (d, J 8.7 Hz, 2H, Ar); 7.16-7.22 (m, 2H, Ar); 7.25 (d, J 8.7 Hz, 2H, Ar); 7.34 (d, J 8.0 Hz, 1H, Ar); 7.55 (t, J 8.0 Hz, 1H, Ar); CONH signal was not observed; HCl salt not observed. M/Z $(M+H)^+$: 493

Example 196: N—((S)-1-(3-Methoxyphenyl)ethyl)-4-((R)-3-(3-(trifluoromethyl)phenoxy)pyrrolidin-1-yl)tetrahydro-2H-pyran-4-carboxamide, hydrochloride

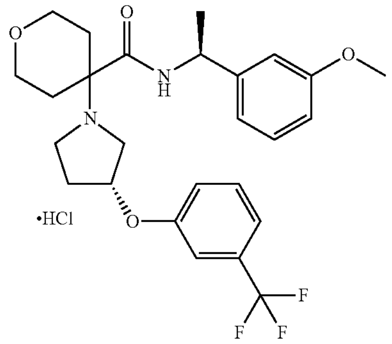 [SMILES: COc1cccc([C@H](C)NC(=O)C2(N3CC[C@@H](Oc4cccc(C(F)(F)F)c4)C3)CCOCC2)c1 ; Cl]

Example 196 was obtained according to General Procedure I-a, starting from Compound 421 and (S)-1-(3-methoxyphenyl)ethan-1-amine. Purification by preparative LC-MS, then HCl salt preparation (method 1) afforded Example 196 as a white powder in 55% yield. $^1$H-NMR (DMSO-$d_6$/$D_2O$, 400 MHz) δ (ppm): 1.46 (d, J 7.1 Hz, 3H, CH—$CH_3$); 1.86-2.02 (m, 2H, $CH_2$); 2.06-2.17 (m, 2H, $CH_2$); 2.35-2.47 (m, 2H, $CH_2$); 3.10-3.24 (m, 2H, O—$CH_2$); 3.26-3.46 (m, 3H, N—$CH_2$+N-$CH_aH_b$); 3.56-3.69 (m, 1H, N—$CH_aH_b$); 3.71 (s, 3H, O—$CH_3$); 3.84-3.94 (m, 2H, O—$CH_2$); 4.98-5.07 (m, 1H, CONH—CH—$CH_3$); 5.16 (bs, 1H, PhO—CH); 6.77-6.81 (m, 1H, Ar); 6.89-6.94 (m, 2H, Ar); 7.15-7.25 (m, 3H, Ar); 7.34 (d, J 7.8 Hz, 1H, Ar); 7.55 (dd, J 8.4, 7.8 Hz, 1H, Ar); CONH signal was not observed; HCl salt not observed. M/Z $(M+H)^+$: 493

Example 197: N—((S)-1-(2-Methoxyphenyl)ethyl)-4-((R)-3-(3-(trifluoromethyl)phenoxy)pyrrolidin-1-yl)tetrahydro-2H-pyran-4-carboxamide, hydrochloride

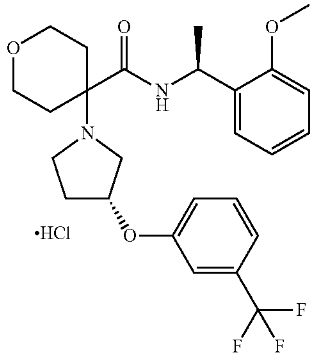 [SMILES: COc1ccccc1[C@H](C)NC(=O)C1(N2CC[C@@H](Oc3cccc(C(F)(F)F)c3)C2)CCOCC1 ; Cl]

Example 197 was obtained according to General Procedure I-a, starting from Compound 421 and (S)-1-(2-methoxyphenyl)ethan-1-amine. Purification by preparative LC-MS, then HCl salt preparation (method 1) afforded Example 197 as a beige powder in 32% yield. $^1$H-NMR ($DMSO-d_6/D_2O$ 400 MHz) δ (ppm): 1.38 (d, J 7.1 Hz, 3H, CH—$CH_3$); 1.82-1.96 (m, 2H, $CH_2$); 2.08-2.20 (m, 2H, $CH_2$); 2.35-2.47 (m, 2H, $CH_2$); 3.09-3.25 (m, 2H, O—$CH_2$); 3.28-3.51 (m, 3H, N—$CH_2$+N-$CH_aH_b$); 3.56-3.69 (m, 1H, N—$CH_aH_b$); 3.77 (s, 3H, O—$CH_3$); 3.84-3.93 (m, 2H, O—$CH_2$); 5.17 (bs, 1H, Ph-O—CH); 5.27-5.35 (m, 1H, CONH—CH—$CH_3$); 6.88 (t, J 7.4 Hz, 1H, Ar); 6.96 (d, J 8.0 Hz, 1H, Ar); 7.15-7.25 (m, 3H, Ar); 7.27 (dd, J 7.6, 1.1 Hz, 1H, Ar); 7.34 (d, J 7.8 Hz, 1H, Ar); 7.55 (dd, J 8.4, 7.8 Hz, 1H, Ar); CONH signal was not observed; HCl salt not observed. M/Z $(M+H)^+$: 493

Compound 489: Methyl (R)-2-methyl-4-(1-(4-(3-(3-(trifluoromethyl)phenoxy)pyrrolidin-1-yl)tetrahydro-2H-pyran-4-carboxamido)cyclopropyl)benzoate Compound 489 was obtained according to General Procedure I-a, starting from Compound 421 and methyl 4-(1-aminocyclopropyl)-2-methylbenzoate. Purification by flash chromatography (Cyclohexane/EtOAc: 50/50 to 0/100) afforded Compound 489 as a pink oil in 80% yield. M/Z $(M+H)^+$: 547

Example 198: (R)-2-Methyl-4-(1-(4-(3-(3-(trifluoromethyl)phenoxy)pyrrolidin-1-yl)tetrahydro-2H-pyran-4-carboxamido)cyclopropyl)benzoic acid, hydrochloride

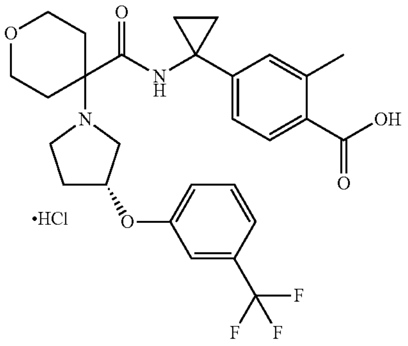 [SMILES: Cc1cc(C2(NC(=O)C3(N4CC[C@@H](Oc5cccc(C(F)(F)F)c5)C4)CCOCC3)CC2)ccc1C(=O)O ; Cl]

Example 198 was obtained according to General Procedure V-e, starting from Compound 489. Purification by preparative LC-MS, then HCl salt preparation (method 1) afforded Example 198 as a white powder in 40% yield. $^1$H-NMR ($DMSO-d_6/D_2O$ 400 MHz) δ (ppm): 1.15-1.36 (m, 4H, C($CH_2$—$CH_2$)); 1.85-1.98 (m, 2H, $CH_2$); 2.10-2.18 (m, 2H, $CH_2$); 2.31-2.42 (m, 2H, $CH_2$); 2.45 (s, 3H, $CH_3$); 3.17-3.43 (m, 5H, O-$CH_2$+N-$CH_2$+N-$CH_aH_b$); 3.63-3.69 (m, 1H, N—$CH_aH_b$); 3.90-3.97 (m, 2H, O—$CH_2$); 5.17 (bs, 1H, PhO—CH); 7.07-7.12 (m, 2H, Ar); 7.15-7.22 (m, 2H, Ar); 7.33 (d, J 8.0 Hz, 1H, Ar); 7.54 (t, J 8.0 Hz, 1H, Ar); 7.73 (d, J 8.3 Hz, 1H, Ar); CONH signal was not observed; $CO_2H$ signal was not observed; HCl salt not observed. M/Z $(M+H)^+$: 533

Compound 490: Methyl (R)-6-(4-(3-(3-(trifluoromethyl)phenoxy)pyrrolidin-1-yl)tetrahydro-2H-pyran-4-carboxamido)spiro[3.3]heptane-2-carboxylate Compound 490 was obtained according to General Procedure I-a, starting from Compound 421 and methyl 6-aminospiro[3.3]heptane-2-carboxylate. Purification by flash chromatography (Cyclohexane/EtOAc: 50/50 to 0/100) afforded Compound 490 as a colorless oil in 70% yield. M/Z $(M+H)^+$: 511

Example 199: (R)-6-(4-(3-(3-(Trifluoromethyl)phenoxy)pyrrolidin-1-yl)tetrahydro-2H-pyran-4-carboxamido)spiro[3.3]heptane-2-carboxylic acid, hydrochloride

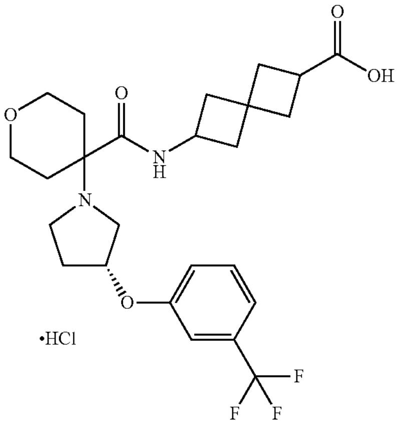 [SMILES: O=C(O)C1CC2(CC(NC(=O)C3(N4CC[C@@H](Oc5cccc(C(F)(F)F)c5)C4)CCOCC3)C2)C1 ; Cl]

Example 199 was obtained according to General Procedure V-e, starting from Compound 490. Purification by preparative LC-MS, then HCl salt preparation (method 1) afforded Example 199 as a white powder in 57% yield. $^1$H-NMR ($D_2O$ 400 MHz) δ (ppm): 1.87-2.60 (m, 14H, $CH_2$); 3.07-3.16 (m, 1H, CO—NH—CH); 3.36-3.49 (m, 2H, O—$CH_2$); 3.70-3.81 (m, 3H, N—$CH_2$+N-$CH_aH_b$); 3.87 (dd, J 13.4, 4.0 Hz, 1H, N—$CH_aH_b$); 4.06-4.17 (m, 3H, O-$CH_2$+CH-$CO_2$H); 5.29 (t, J 4.2 Hz, 1H, Ph-O—CH); 7.23 (dd, J 8.0, 2.1 Hz, 1H, Ar); 7.30 (bs, 1H, Ar); 7.45 (d, J 8.0 Hz, 1H, Ar); 7.59 (t, J 8.0 Hz, 1H, Ar); CONH signal was not observed; $CO_2H$ signal was not observed; HCl salt not observed. M/Z $(M+H)^+$: 497

Compound 491: Methyl (1R,4R)-4-((4-((R)-3-(3-(trifluoromethyl)phenoxy)pyrrolidin-1-yl)tetrahydro-2H-pyran-4-carboxamido)methyl)cyclohexane-1-carboxylate Compound 491 was obtained according to General Procedure I-a, starting from Compound 421 and methyl (1R,4R)-4-(aminomethyl)cyclohexane-1-carboxylate hydrochloride. In that specific case, 4 equiv. of diisopropylethylamine were used. Purification by flash chromatography (Cyclohexane/EtOAc: 50/50 to 0/100) afforded Compound 491 as a colorless oil in 76% yield. M/Z $(M+H)^+$: 513

Example 200: (1R,4R)-4-((4-((R)-3-(3-(Trifluoromethyl)phenoxy)pyrrolidin-1-yl)tetrahydro-2H-pyran-4-carboxamido)methyl)cyclohexane-1-carboxylic acid, hydrochloride

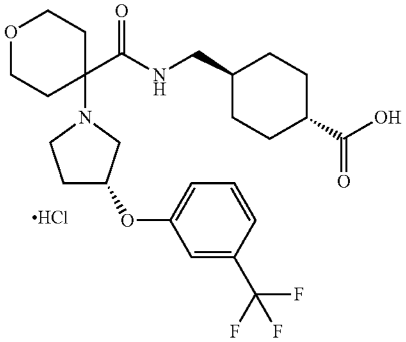 [SMILES: O=C(NC[C@H]1CC[C@H](C(=O)O)CC1)C1(N2CC[C@@H](Oc3cccc(C(F)(F)F)c3)C2)CCOCC1 ; Cl]

Example 200 was obtained according to General Procedure V-e, starting from Compound 491. Purification by preparative LC-MS, then HCl salt preparation (method 1) afforded Example 200 as a white powder in 60% yield. $^{1}H$-NMR ($D_2O$, 400 MHz) δ (ppm): 0.95-1.08 (m, 2H, $CH_2$); 1.24-1.37 (m, 2H, $CH_2$); 1.50-1.61 (m, 1H, CO—NH—$CH_2$—CH); 1.72-1.84 (m, 2H, $CH_2$); 1.91-2.00 (m, 2H, $CH_2$); 2.06-2.16 (m, 2H, $CH_2$); 2.24-2.39 (m, 2H, $CH_2$); 2.42-2.59 (m, 3H, $CH_2$+CH-$CO_2H$); 3.08 (dd, J 13.4, 6.8 Hz, 1H, CO—NH—$CH_2$); 3.20 (dd, J 13.4, 6.8 Hz, 1H, CO—NH—$CH_2$); 3.40-3.52 (m, 2H, O—$CH_2$); 3.72-3.80 (m, 3H, N—$CH_2$+N-$CH_aH_b$); 3.89 (dd, J 13.4, 4.4 Hz, 1H, N—$CH_aH_b$); 4.12 (dd, J 12.3, 3.7, 2H, O—$CH_2$); 5.30 (t, J 4.2 Hz, 1H, Ph-O—CH); 7.24 (dd, J 8.0, 2.1 Hz, 1H, Ar); 7.32 (bs, 1H, Ar); 7.44 (d, J 8.0 Hz, 1H, Ar); 7.58 (t, J 8.0 Hz, 1H, Ar); CONH signal was not observed; $CO_2H$ signal was not observed; HCl salt not observed. M/Z $(M+H)^+$: 499

Compound 492: Methyl (1R,4R)-4-((2-methyl-2-((R)-3-(3-(trifluoromethyl)phenoxy)pyrrolidin-1-yl)propanamido)methyl)cyclohexane-1-carboxylate Compound 492 was obtained according to General Procedure I-a, starting from Compound 485 and methyl (1R,4R)-4-(aminomethyl)cyclohexane-1-carboxylate hydrochloride. In that specific case, 4 equiv. of diisopropylethylamine were used. Purification by flash chromatography (Cyclohexane/EtOAc: 100/0 to 50/50) afforded Compound 492 as a yellow oil in 58% yield. M/Z $(M+H)^+$: 471

Example 201: (1R,4R)-4-((2-Methyl-2-((R)-3-(3-(trifluoromethyl)phenoxy)pyrrolidin-1-yl)propanamido)methyl)cyclohexane-1-carboxylic acid, hydrochloride

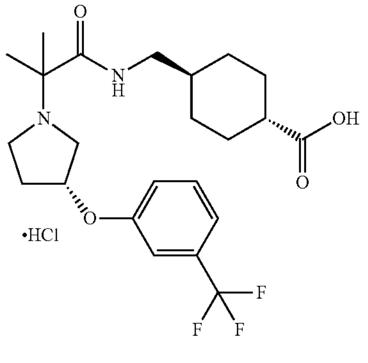 [SMILES: CC(C)(C(=O)NC[C@H]1CC[C@H](C(=O)O)CC1)N1CC[C@@H](Oc2cccc(C(F)(F)F)c2)C1 ; Cl]

Example 201 was obtained according to General Procedure V-e, starting from Compound 492. Purification by preparative LC-MS, then HCl salt preparation (method 1) afforded Example 201 as a white powder in 67% yield. $^{1}H$-NMR ($D_2O$, 400 MHz) δ (ppm): 0.92-1.07 (m, 2H, $CH_2$); 1.30-1.42 (m, 2H, $CH_2$); 1.48-1.60 (m, 1H, CO—NH—$CH_aCH_b$); 1.66 (s, 6H, $(CH_3)_2$); 1.73-1.82 (m, 2H, $CH_2$); 1.95-2.02 (m, 2H, $CH_2$); 2.24-2.53 (m, 3H, $CH_2$+CH-$CO_2H$); 3.13 (d, J 6.9 Hz, 2H, CO—NH—$CH_2$); 3.51-3.95 (m, 4H, N—$CH_2$); 5.34 (bs, 1H, Ph-O—CH); 7.28 (bd, J 8.2 Hz, 1H, Ar); 7.36 (bs, 1H, Ar); 7.44 (d, J 7.8 Hz, 1H, Ar); 7.58 (dd, J 8.2, 7.8 Hz, 1H, Ar); CONH signal was not observed; $CO_2H$ signal was not observed; HCl salt not observed. M/Z $(M+H)^+$: 457

Example 202: (1R,4R)-4-((2-Methyl-2-((R)-3-(3-(trifluoromethyl)phenoxy)pyrrolidin-1-yl)propanamido)methyl)cyclohexane-1-carboxamide, hydrochloride

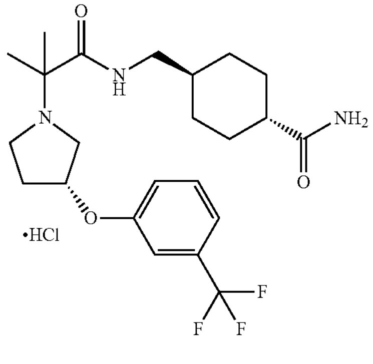 [SMILES: CC(C)(C(=O)NC[C@H]1CC[C@H](C(N)=O)CC1)N1CC[C@@H](Oc2cccc(C(F)(F)F)c2)C1 ; Cl]

Example 202 was obtained according to General Procedure I-a, starting from Example 201 and $NH_3$ 0.5 M in dioxane. Purification by preparative LC-MS, then HCl salt preparation (method 1) afforded Example 202 as a white powder in 62% yield. $^{1}H$-NMR (DMSO-$d_6$/$D_2O$ 400 MHz) δ (ppm): 0.78-0.91 (m, 2H, $CH_2$); 1.18-1.30 (m, 2H, $CH_2$); 1.35-1.45 (m, 1H, CO—NH—$CH_2$—CH); 1.50 (s, 6H, $(CH_3)_2$); 1.60-1.75 (m, 4H, $CH_2$); 1.96-2.06 (m, 1H, CH—$CO_2H$); 2.11-2.24 (m, 1H, $CH_aH_b$); 2.53-2.61 (m, 1H, $CH_aH_b$); 2.92-3.00 (m, 2H, CO—NH—$CH_2$); 3.22 3.60 (m, 4H, N—$CH_2$); 5.21 (bs, 1H, Ph-O—CH); 7.22-7.29 (m, 2H, Ar); 7.34 (d, J 7.8 Hz, 1H, Ar); 7.55 (t, J 7.8 Hz, 1H, Ar); CONH signal was not observed; $CO_2H$ signal was not observed; HCl salt not observed. M/Z $(M+H)^+$: 456

Example 203: 2-Methyl-N—((S)-1-(4-sulfamoylphenyl)ethyl)-2-((R)-3-(3-(trifluoromethyl)phenoxy)pyrrolidin-1-yl)propanamide, hydrochloride

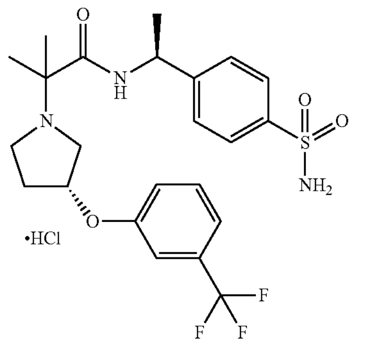 [SMILES: C[C@H](NC(=O)C(C)(C)N1CC[C@@H](Oc2cccc(C(F)(F)F)c2)C1)c1ccc(S(N)(=O)=O)cc1 ; Cl]

Example 203 was obtained according to General Procedure I-a, starting from Compound 485 and (S)-4-(1-aminoethyl)benzenesulfonamide. Purification by preparative LC-MS, then HCl salt preparation (method 1) afforded Example 203 as a white powder in 47% yield. $^1$H-NMR (DMSO-$d_6$/$D_2O$ 400 MHz) δ (ppm): 1.38 (d, J 6.8 Hz, 3H, CH—$CH_3$); 1.49 (bs, 3H, $CH_3$); 1.54 (bs, 3H, $CH_3$); 2.05-2.20 (m, 2H, $CH_2$); 3.24-3.45 (m, 3H, N—$CH_2$+N-$CH_aH_b$); 3.65-3.61 (m, 1H, N—$CH_aH_b$); 4.87-4.95 (m, 1H, CONH—CH—$CH_3$); 5.17 (bs, 1H, Ph-O—CH); 7.21-7.25 (m, 2H, Ar); 7.32 (d, J 7.2 Hz, 1H, Ar); 7.44 (d, J 8.3 Hz, 2H, Ar); 7.50-7.56 (m, 1H, Ar); 7.74 (d, J 8.3 Hz, 2H, Ar); CONH signal was not observed; $SO_2$—$NH_2$ signal was not observed; HCl salt not observed. M/Z $(M+H)^+$: 500

Example 204: 2-Methyl-N—((S)-1-(4-(methylsulfonyl)phenyl)ethyl)-2-((R)-3-(3-(trifluoromethyl)phenoxy)pyrrolidin-1-yl)propanamide, hydrochloride

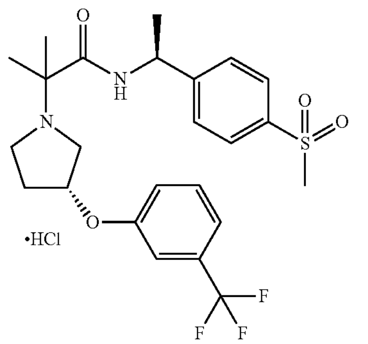 [SMILES: C[C@H](NC(=O)C(C)(C)N1CC[C@@H](Oc2cccc(C(F)(F)F)c2)C1)c1ccc(S(C)(=O)=O)cc1 ; Cl]

Example 204 was obtained according to General Procedure I-a, starting from Compound 485 and (S)-1-(4-(methylsulfonyl)phenyl)ethan-1-amine. Purification by preparative LC-MS, then HCl salt preparation (method 1) afforded Example 204 as a white powder in 20% yield. $^1$H-NMR (DMSO-$d_6$/$D_2O$ 400 MHz) δ (ppm): 1.35-1.44 (m, 3H, CH—$CH_3$); 1.45-1.64 (m, 6H, $(CH_3)_2$); 2.04-2.35 (m, 2H, $CH_2$); 3.14 (s, 3H, $SO_2$—$CH_3$); 3.29-3.46 (m, 3H, N-$CH_2$+N-$CH_aH_b$); 3.46-3.59 (m, 1H, N—$CH_aH_b$); 4.90-4.99 (m, 1H, CONH—CH—$CH_3$); 5.18 (bs, 1H, PhO—CH); 7.20-7.26 (m, 2H, Ar); 7.32 (d, J 7.5 Hz, 1H, Ar); 7.51-7.57 (m, 3H, Ar); 7.85 (d, J 8.3 Hz, 2H, Ar); CONH signal was not observed; HCl salt not observed. M/Z $(M+H)^+$: 499

Example 205: 2-Methyl-N-((1S)-1-(4-(S-methylsulfonimidoyl)phenyl)ethyl)-2-((R)-3-(3-(trifluoromethyl)phenoxy)pyrrolidin-1-yl)propanamide, hydrochloride

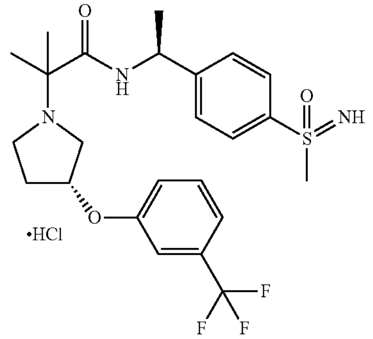 [SMILES: C[C@H](NC(=O)C(C)(C)N1CC[C@@H](Oc2cccc(C(F)(F)F)c2)C1)c1ccc(S(C)(=N)=O)cc1 ; Cl]

Example 205 was obtained according to General Procedure I-a, starting from Compound 485 and (4-((S)-1-aminoethyl)phenyl)(imino)(methyl)-sulfanone. Purification by preparative LC-MS, then HCl salt preparation (method 1) afforded Example 205 as a white powder in 60% yield. $^1$H-NMR ($D_2O$ 400 MHz) δ (ppm): 1.40 (d, J 6.9 Hz, 3H, CH—$CH_3$); 1.53 (s, 3H, $CH_3$); 1.58 (s, 3H, $CH_3$); 2.07-2.35 (m, 2H, $CH_2$); 3.31 (s, 3H, SO(NH)—$CH_3$); 3.33-3.45 (m, 3H, N—$CH_2$+N-$CH_aH_b$); 3.46-3.59 (m, 1H, N—$CH_aH_b$); 4.92-5.01 (m, 1H, CONH—CH—$CH_3$); 5.19 (bs, 1H, PhO—CH); 7.20-7.26 (m, 2H, Ar); 7.32 (d, J 7.6 Hz, 1H, Ar); 7.50-7.58 (m, 3H, Ar); 7.91 (d, J 8.5 Hz, 2H, Ar); CONH signal was not observed; SO(NH)—$CH_3$ signal was not observed; HCl salt not observed. M/Z $(M+H)^+$: 498

Example 206: N—((S)-1-(4-(1,2,4-Oxadiazol-3-yl)phenyl)ethyl)-2-methyl-2-((R)-3-(3-(trifluoromethyl)phenoxy)pyrrolidin-1-yl)propanamide, hydrochloride

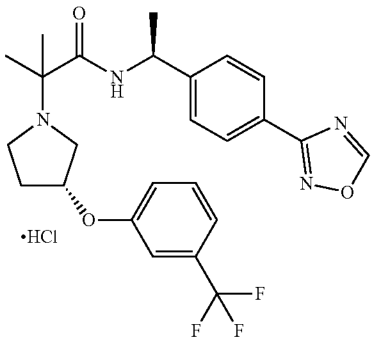 [SMILES: C[C@H](NC(=O)C(C)(C)N1CC[C@@H](Oc2cccc(C(F)(F)F)c2)C1)c1ccc(-c2ncon2)cc1 ; Cl]

Example 206 was obtained according to General Procedure I-a, starting from Compound 485 and (S)-1-(4-(1,2,4-oxadiazol-3-yl)phenyl)ethan-1-amine. Purification by preparative LC-MS, then HCl salt preparation (method 1) afforded Example 206 as a white powder in 41% yield. $^1$H-NMR ($D_2$, 400 MHz, 80° C.): 1.45 (d, J 7.0 Hz, 3H, CH—$CH_3$); 1.50 (s, 3H, $CH_3$); 1.54 (s, 3H, $CH_3$); 2.09-2.17 (m, 1H, $CH_aH_b$); 2.24-2.32 (m, 1H, $CH_aH_b$); 3.26-3.38 (m, 3H, N—$CH_2$+N-$CH_aH_b$); 3.53-3.63 (m, 1H, N—$CH_aH_b$); 4.99 (q, J 7.0 Hz, 1H, CONH—CH—$CH_3$); 5.12-5.17 (m, 1H, PhO—CH); 7.16-7.22 (m, 2H, Ar); 7.28 (d, J 7.7 Hz, 1H, Ar); 7.45-7.54 (m, 3H, Ar); 7.95 (d, J 8.3 Hz, 2H, Ar); 9.38 (s, 1H, Ar); CONH signal was not observed; HCl salt not observed. M/Z $(M+H)^+$: 525

Example 207: N—((S)-1-(4-(1,2,4-Oxadiazol-5-yl)phenyl)ethyl)-2-methyl-2-((R)-3-(3-(trifluoromethyl)phenoxy)pyrrolidin-1-yl)propanamide, hydrochloride

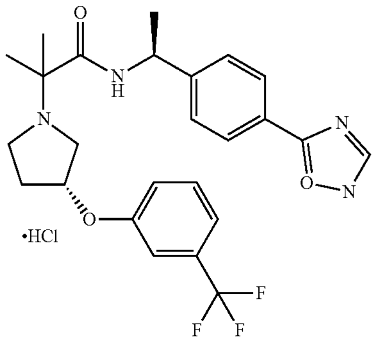

Example 207 was obtained according to General Procedure I-a, starting from Compound 485 and (S)-1-(4-(1,2,4-oxadiazol-5-yl)phenyl)ethan-1-amine. Purification by preparative LC-MS, then HCl salt preparation (method 1) afforded Example 207 as a white powder in 23% yield. $^1$H-NMR (DMSO/$D_2O$ 400 MHz) δ (ppm): 1.43 (d, J 6.9 Hz, 3H, CH—$CH_3$); 1.54 (bs, 3H, $CH_3$); 1.58 (bs, 3H, $CH_3$); 2.06-2.25 (m, 2H, $CH_2$); 3.30-3.46 (m, 3H, N—$CH_2$+N-$CH_aH_b$); 3.46-3.60 (n, 1H, N—$CH_aH_b$); 4.91-5.00 (m, 1H, CONH—CH—$CH_3$); 5.19 (bs, 1H, Ph-C—CH); 7.19-7.26 (m, 2H, Ar); 7.28-7.35 (m, 1H, Ar); 7.48-7.56 (m, 3H, Ar): 8.06 (d, J 8.3 Hz, 2H, Ar); 8.97 (s, 1H, Ar); CONH signal was not observed; HCl salt not observed. M/Z $(M+H)^+$: 525

Compound 493: (4-Bromo-2-(bromomethyl)butyl)benzene

Compound 493 was obtained according to General Procedure XVI, starting from 2-benzylbutane-1,4-diol. Purification by flash chromatography (Cyclohexane/EtOAc: 100/0 to 90/10) afforded Compound 493 as a colorless oil in 73% yield. $^1$H-NMR (DMSO-$d_6$ 400 MHz) δ (ppm): 1.79-1.98 (m, 2H, $CH_2$); 2.10-2.19 (m, 1H, Ph-$CH_2$—CH); 2.60-2.72 (m, 2H, Ph-$CH_2$—CH); 3.43 (dd, J 10.2, 4.0 Hz, 1H, $CH_aH_b$—Br); 3.52-3.65 (m, 3H, $CH_aH_b$-Br+CH-Br); 7.19-7.25 (m, 2H, Ar); 7.29-7.34 (m, 3H, Ar).

Compound 494: Methyl 2-(3-benzylpyrrolidin-1-yl)-2-methylpropanoate

Compound 494 was obtained according to General Procedure VIII-b, starting from Compound 493 and methyl 2-amino-2-methylpropanoate hydrochloride. Purification by flash chromatography (Cyclohexane/EtOAc: 100/0 to 70/30) afforded Compound 494 as a colorless oil in 74% yield. M/Z $(M+H)^+$: 262

Compound 495: Lithium 2-(3-benzylpyrrolidin-1-yl)-2-methylpropanoate

Compound 495 was obtained according to General Procedure V-f, starting from Compound 494, as a beige powder in quantitative yield. M/Z $(M+H)^+$: 248

Compound 496: Methyl 4-((1S)-1-(2-(3-benzylpyrrolidin-1-yl)-2-methylpropanamido)ethyl)benzoate Compound 496 was obtained according to General Procedure I-a, starting from Compound 495 and methyl 4-[(1S)-1-aminoethyl]benzoate. Purification by flash chromatography (Cyclohexane/EtOAc: 100/0 to 50/50) afforded Compound 496 as a colorless oil in 50% yield. M/Z $(M+H)^+$: 409

Example 208: 4-((1S)-1-(2-(3-Benzylpyrrolidin-1-yl)-2-methylpropanamido)ethyl)benzoic acid, hydrochloride

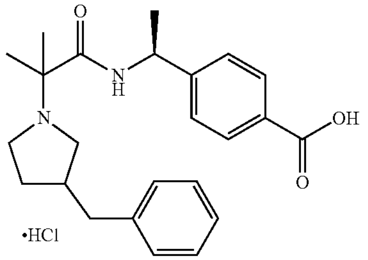 [SMILES: C[C@H](NC(=O)C(C)(C)N1CCC(Cc2ccccc2)C1)c1ccc(C(=O)O)cc1 ; Cl]

Example 208 was obtained according to General Procedure V-e, starting from Compound 496. Purification by preparative LC-MS, then HCl salt preparation (method 1) afforded Example 208 as a white powder in 48% yield. $^1$H-NMR (DMSO-$d_6$/$D_2O$ 400 MHz) δ (ppm): 1.38 (d, J 6.9 Hz, 3H, CH—$CH_3$); 1.43-1.53 (m, 6H, C—$(CH_3)_2$); 1.87-1.98 (m, 1H, Ph-$CH_2$—CH); 2.37-2.71 (m, 4H, $CH_2$+Ph-$CH_2$—CH); 2.79-2.90 (m, 1H, N—$CH_aH_b$); 3.09-3.33 (m, 3H, N—$CH_2$+N-$CH_aH_b$); 4.85-4.96 (m, 1H, CONH—CH—$CH_3$); 7.11-7.21 (m, 3H, Ar); 7.21-7.30 (m, 2H, Ar); 7.36 (d, J 8.0 Hz, 2H, Ar); 7.85 (d, J 8.0 Hz, 2H, Ar); CONH signal was not observed; $CO_2H$ signal was not observed; HCl salt not observed. M/Z $(M+H)^+$: 431

Compound 497: Dimethyl (S)-2-((3-chlorophenoxy)methyl)succinate

To a solution of Compound 368 (1.2 equiv.) in a cyclohexane/DCM mixture (2/1, 0.5 M) were added dimethyl (R)-hydroxysuccinate (1 equiv.) and trifluoromethanesulfonic acid (0.15 equiv.). The reaction mixture was stirred overnight at rt. The resulting precipitate was filtered off. The filtrate was washed with a saturated solution of sodium bicarbonate and brine, dried, then concentrated. The resulting yellow oil was purified by flash chromatography (Cyclohexane/EtOAc: 100/0 to 80/20) to afford Compound 497 as a colorless oil in 41% yield. $^1$H-NMR (DMSO-$d_6$ 400 MHz) δ (ppm): 2.74 (dd, J 16.0, 8.0 Hz, 1H, $CH_aH_b$—

$CO_2$—$CH_3$); 2.85 (dd, J 16.0, 4.7 Hz, 1H, $CH_aH_b$—$CO_2CH_3$); 3.60 (s, 3H, $CH_2$—$CO_2$—$CH_3$); 3.69 (s, 3H, CH—$CO_2$—$CH_3$); 4.40 (dd, J 8.0, 4.7 Hz, 1H, CH—$CO_2$—$CH_3$); 4.50 (d, J 12.3 Hz, 1H, Ph-$CH_aH_b$—O); 4.67 (d, J 12.3 Hz, 1H, Ph-$CH_aH_b$—O); 7.25-7.28 (m, 1H, Ar); 7.34-7.39 (m, 3H, Ar).

Compound 498: (R)-2-((3-Chlorophenoxy)methyl)butane-1,4-diol

To a solution of Compound 497 (1 equiv.) in THF (0.3 M) at 0° C. was added dropwise $LiAlH_4$ 1 M in THF (4 equiv.). The reaction mixture was stirred overnight at rt. The reaction mixture was diluted with diethyl ether, then were successively added water, NaOH 20 mol %, and finally water. The resulting precipitate was filtered off. The filtrate was concentrated, then purified by flash chromatography (DCM/MeOH: 100/0 to 96/4) to afford Compound 498 as a colorless oil in 62% yield. M/Z $(M[^{35}Cl]+H)^+$: 231

Compound 499: (S)-1-(4-Bromo-2-(bromomethyl)butoxy)-3-chlorobenzene

Compound 499 was obtained according to General Procedure XVI, starting from Compound 498. Purification by flash chromatography (Cyclohexane/EtOAc: 100/0 to 90/10) afforded Compound 499 as a colorless oil in 92% yield. $^1H$-NMR (DMSO-$d_6$, 400 MHz) δ (ppm): 2.02-2.20 (m, 2H, $CH_2$); 3.51-3.64 (m, 2H, Br—$CH_2$); 3.66-3.72 (m, 1H, O—CH); 3.73-3.83 (m, 2H, Br—$CH_2$); 4.49 (d, J 11.5 Hz, 1H, Ph-$CH_aH_b$—O); 4.66 (d, J 11.5 Hz, 1H, Ph-$CH_aH_b$—O); 7.28-7.45 (m, 4H, Ar).

Compound 500: Methyl (R)-2-(3-((3-chlorophenoxy)methyl)pyrrolidin-1-yl)-2-methylpropanoate Compound 500 was obtained according to General Procedure VIII-b, starting from Compound 499 and methyl 2-amino-2-methylpropanoate hydrochloride. Purification by flash chromatography (Cyclohexane/EtOAc: 100/0 to 60/40) afforded Compound 500 as a yellow oil in 66% yield. M/Z $(M[^{35}Cl]+H)^+$: 312

Compound 501: Lithium (R)-2-(3-((3-chlorophenoxy)methyl)pyrrolidin-1-yl)-2-methylpropanoate Compound 501 was obtained according to General Procedure V-f, starting from Compound 500, as a beige powder in quantitative yield. M/Z $(M[^{35}Cl]+H)^+$: 298

Compound 502: Methyl 4-((S)-1-(2-((R)-3-((3-chlorophenoxy)methyl)pyrrolidin-1-yl)-2-methylpropanamido)ethyl)benzoate Compound 502 was obtained according to General Procedure I-a, starting from Compound 501 and methyl 4-[(1S)-1-aminoethyl]benzoate. Purification by flash chromatography (Cyclohexane/EtOAc: 100/0 to 50/50) afforded Compound 502 as a yellow oil in 56% yield. M/Z $(M[^{35}Cl]+H)^+$: 459

Example 209: 4-((S)-1-(2-((R)-3-((3-Chlorophenoxy)methyl)pyrrolidin-1-yl)-2-methylpropanamido)ethyl)benzoic acid

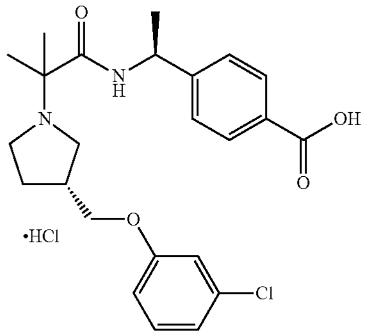 [SMILES: C[C@H](NC(=O)C(C)(C)N1CC[C@@H](COc2cccc(Cl)c2)C1)c1ccc(C(=O)O)cc1 ; Cl]

Example 209 was obtained according to General Procedure V-e, starting from Compound 502. Purification by preparative LC-MS, then HCl salt preparation (method 1) afforded Example 209 as a white powder in 72% yield. $^1H$-NMR ($D_2O$ 400 MHz) δ (ppm): 1.54 (d, J 7.1 Hz, 3H, CH—$CH_3$); 1.65 (s, 3H, C—$(CH_3)_2$); 1.68 (s, 3H, C—$(CH_3)_2$); 2.02-2.40 (m, 2H, $CH_2$); 3.31-3.73 (m, 4H, N—$CH_2$); 4.44 (bs, 1H, Ph-O—$CH_2$—CH); 4.47-4.60 (m, 1H, Ph-O—$CH_2$—CH); 5.03 (q, J 7.1 Hz, 1H, CONH—CH—$CH_3$); 7.26-7.34 (m, 1H, Ar); 7.35-7.45 (m, 3H, Ar); 7.49 (d, J 8.3 Hz, 2H, Ar); 8.01 (d, J 8.3 Hz, 2H, Ar); CONH signal was not observed; $CO_2H$ signal was not observed; HCl salt not observed. M/Z $(M[^{35}Cl]+H)^+$: 445

Compound 503: Methyl 2-[(3R)-3-(3-chlorophenoxy)pyrrolidin-1-yl]-2-ethylbutanoate Compound 503 was obtained according to General Procedure VIII-b, starting from Compound 405 and methyl 2-amino-2-ethylbutanoate. Purification by flash chromatography (Cyclohexane/AcOEt: 100/0 to 70/30) afforded Compound 503 as a yellow oil in 60% yield. M/Z $(M[^{35}Cl]+H)^+$: 326

Compound 504: Lithium 2-[(3R)-3-(3-Chlorophenoxy)pyrrolidin-1-yl]-2-ethylbutanoate Compound 504 was obtained according to General Procedure V-f, starting from Compound 503, as a yellow powder. M/Z $(M[^{35}Cl]+H)^+$: 312

Compound 505: Methyl 4-[(1S)-1-[[2-[(3R)-3-(3-chlorophenoxy)pyrrolidin-1-yl]-2-ethylbutane-carbonyl]amino]ethyl]benzoate Compound 505 was obtained according to General Procedure I-a, starting from Compound 504 and methyl 4-[(1S)-1-aminoethyl]benzoate. Purification by flash chromatography (Cyclohexane/EtOAc: 100/0 to 70/30) afforded Compound 505 as a yellow oil in 16% yield over 2 steps. M/Z $(M[^{35}Cl]+H)^+$: 473

Example 210: 4-[(1S)-1-[[2-[(3R)-3-(3-Chlorophenoxy)pyrrolidin-1-yl]-2-ethylbutane-carbonyl]amino]ethyl]benzoic acid, hydrochloride

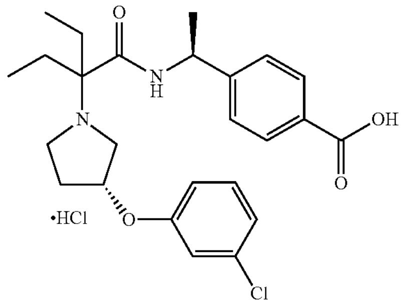 [SMILES: CCC(CC)(C(=O)N[C@@H](C)c1ccc(C(=O)O)cc1)N1CC[C@@H](Oc2cccc(Cl)c2)C1 ; Cl]

Example 210 was obtained according to General Procedure V-e, starting from Compound 505. Purification by preparative LC-MS, then HCl salt preparation (method 1) afforded Example 210 as a white powder in 90% yield. $^1$H-NMR (DMSO-d$_6$/D$_2$O, 400 MHz) δ (ppm): 0.73 (t, J 6.9 Hz, 3H, $CH_2$—$CH_3$); 0.93 (t, J 6.9 Hz, 3H, $CH_2$—$CH_3$); 1.40 (d, J 7.1 Hz, 3H, CH—$CH_3$); 1.89-2.25 (m, 6H, $CH_2$); 3.27-3.45 (m, 3H, N—$CH_2$+N-$CH_aH_b$); 3.65-3.79 (m, 1H, N—$CH_aH_b$); 5.00 (q, J 7.1 Hz, 1H, CONH—CH—$CH_3$); 5.07 (bs, 1H, Ph-O—CH); 6.87 (dd, J 8.2, 1.9 Hz, 1H, Ar); 6.96 (bs, 1H, Ar); 7.01 (dd, J 8.2, 1.0 Hz, 1H, Ar); 7.31 (t, J 8.2 Hz, 1H, Ar); 7.43 (d, J 8.2 Hz, 2H, Ar); 7.87 (d, J 8.2 Hz, 2H, Ar); CONH signal was not observed; $CO_2H$ signal was not observed; HCl salt not observed. M/Z (M[$^{35}$Cl]+H)$^+$: 459

Biological Experiments

Example 211: In Vitro Human $EP_4$ Functional Antagonist Activity Using BRET Biosensors Examples of the present invention were tested successively for their agonist and antagonist activities on human $EP_4$ (h$EP_4$) receptor transiently over-expressed in HEK-293 T cells. Compounds exert agonist activity if, by themselves in absence of TCS 2510 (Highly selective $EP_4$ agonist), they activate h$EP_4$; they exert antagonist activity if they decrease the action of TCS2510 on the receptor. The assay used to measure compound activity is based on the BRET technology. The unimolecular cAMP biosensor used to detect intracellular cAMP levels following GPCR stimulation consists of the EPAC protein fused to N- and C-terminal of Luciferase and GFP respectively.

Cell Culture and Transfection: HEK-293 T cells are maintained in Dulbecco's Modified Eagle's Medium supplemented with 10% Foetal Calf Serum, 1% Penicillin/Streptomycin at 37° C./5% $CO_2$. Cells are co-transfected using polyethylenimine (25 kDa linear) with two DNA plasmids encoding h$EP_4$, EPAC fused to luciferase (BRET donor) and to GFP (BRET acceptor). After transfection, cells are cultured (40,000 cells per well) for 48 h at 37° C./5% $CO_2$.

BRET assay: Receptor activity is detected by changes in BRET signal. On the day of the assay, cells are rinsed and incubated in assay buffer (1.8 mM $CaCl_2$, 1 mM $MgCl_2$, 2.7 mM KCl, 137 mM NaCl, 0.4 mM $NaH_2PO_4$, 5.5 mM D-Glucose, 11.9 mM $NaHCO_3$, 25 mM Hepes). Then, plates are equilibrated 1 h at 22° C. before adding compounds. Compounds and luciferase substrate are added to the cells using an automated device (Freedom Evo®, Tecan) and BRET readings are collected on EnVision (PerkinElmer) with specific filters (410 nm BW 80 nm, 515 nm BW 30 nm). Agonist and antagonist activities of compounds are consecutively evaluated on the same cell plate. Agonist activity is first measured after 5 min incubation with compound alone on the cells. Then, cells are stimulated by an $EC_{60}$ TCS2510 concentration and luminescence is recorded for additional 10 min. $EC_{60}$ TCS2510 concentration is the concentration giving 60% of the maximal TCS2510 response. Agonist or antagonist activities are evaluated in comparison to basal signals evoked by assay buffer or $EC_{60}$ TCS2510 alone, respectively.

For $IC_{50}$ determination, a dose-response test is performed using 10 concentrations (ranging over 4.5 logs) of each compound. Dose-response curves are fitted using the sigmoidal dose-response (variable slope) analysis in GraphPad Prism software (GraphPad Software) and $IC_{50}$ of antagonist activity is calculated. Dose-response experiments are performed in duplicate, in two independent experiments. $IC_{50}$ values are categorized as following: A: $IC_{50}<0.1$ μM; B: $IC_{50}<1$ μM.

| Example | $IC_{50}$ |
|---|---|
| 1 | A |
| 2 | A |
| 3 | B |
| 4 | B |
| 5 | B |
| 8 | A |
| 9 | A |
| 10 | A |
| 11 | B |
| 12 | A |
| 13 | A |
| 14 | A |
| 16 | A |
| 17 | B |
| 18 | B |
| 20 | B |
| 21 | B |
| 24 | B |
| 25 | A |
| 26 | B |
| 27 | B |
| 28 | A |
| 29 | A |
| 30 | A |
| 31 | B |
| 32 | A |
| 33 | A |
| 34 | A |
| 35 | A |
| 36 | A |
| 37 | B |
| 38 | A |
| 39 | B |
| 40 | B |
| 41 | A |
| 42 | B |
| 43 | A |
| 44 | A |
| 45 | B |
| 46 | B |
| 49 | B |
| 50 | A |
| 51 | B |
| 52 | A |
| 53 | B |
| 54 | B |
| 55 | B |
| 56 | A |
| 57 | A |
| 58 | A |

-continued

| Example | $IC_{50}$ |
|---|---|
| 59 | A |
| 60 | A |
| 61 | A |
| 62 | A |
| 63 | A |
| 64 | B |
| 65 | B |
| 66 | A |
| 68 | B |
| 69 | B |
| 72 | A |
| 73 | B |
| 74 | A |
| 75 | A |
| 76 | B |
| 77 | A |
| 81 | A |
| 82 | A |
| 84 | B |
| 88 | B |
| 89 | B |
| 91 | B |
| 92 | A |
| 94 | B |
| 95 | B |
| 96 | B |
| 97 | B |
| 98 | B |
| 99 | B |
| 100 | B |
| 101 | B |
| 102 | B |
| 103 | A |
| 104 | B |
| 105 | B |
| 108 | A |
| 109 | A |
| 110 | A |
| 112 | A |
| 113 | A |
| 115 | B |
| 116 | B |
| 117 | B |
| 119 | B |
| 120 | B |
| 121 | B |
| 122 | B |
| 123 | B |
| 124 | A |
| 127 | B |
| 128 | B |
| 129 | A |
| 130 | B |
| 134 | B |
| 135 | B |
| 136 | A |
| 137 | A |
| 138 | B |
| 139 | B |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |

-continued

| Example | $IC_{50}$ |
|---|---|
| 158 | A |
| 159 | A |
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | B |
| 182 | A |
| 183 | B |
| 184 | B |
| 185 | B |
| 186 | B |
| 187 | B |
| 188 | B |
| 189 | B |
| 190 | B |
| 191 | B |
| 192 | B |
| 193 | B |
| 194 | B |
| 195 | A |
| 196 | B |
| 197 | B |
| 198 | A |
| 200 | A |
| 201 | A |
| 203 | B |
| 204 | B |
| 205 | A |
| 209 | A |
| 210 | A |

These results demonstrate that the compounds of formula (I), including the compounds of Examples 1 to 210, exhibit potent antagonistic activity on the human $EP_a$ receptor. Moreover, no agonistic activity was observed for any of these compounds.

Example 212: In Vivo Anti-Tumoral Activity of the Compound of Example 25 in a CT26 Tumor Model CT26 tumor cells were maintained in vitro as a monolayer culture in RPM11640 medium supplemented with 10% fetal bovine serum at 37° C. in an atmosphere of 5% $CO_2$ in air. The cells were routinely subcultured twice weekly by trypsin-EDTA treatment. The cells in an exponential growth phase were harvested and counted for tumor inoculation.

Female BALB/c mice were inoculated subcutaneously in the right rear flank region with CT26 tumor cells ($5\times10^5$) in 0.1 ml of PBS for tumor development on day 0. Tumor volumes were measured thrice per week in two dimensions using a caliper, and the volume was expressed in $mm^3$ using the formula: "V=(L×W×W)/2", where V is tumor volume, L is tumor length (the longest tumor dimension) and W is tumor width (the longest tumor dimension perpendicular to L). When the mean tumor size reached approximately 100 $mm^3$, mice were randomly allocated into groups (12 mice per group) and treated with either a control antibody (rIgG2a (2A3), 200 μg/mouse, iv, Q3D) or an anti-PD-1 antibody (RPM1-14, 200 μg/mouse, iv, Q3D), with or without the compound of Example 25 (150 mg/kg, po, 0.5% MC, BID, BID time interval: 8 h) for at least 3 weeks.

Animals were checked daily for morbidity and mortality. During routine monitoring, the animals were checked for any effects on tumor growth and treatments on behavior such as mobility, food and water consumption, body weight gain/loss (body weights were measured thrice per week), eye/hair matting and any other abnormalities. Dosing as well as tumor and body weight measurements were conducted in a Laminar Flow Cabinet. The body weights and tumor volumes were monitored by using StudyDirector™ software (version 3.1.399.19).

Example 25 administered at 150 mg/kg BID combined with anti-PD-1 immunotherapy resulted in 5 cases of complete tumor regression in total (corresponding to 42% of the test animals), compared with 2 cases of complete regression (i.e., 17%) in the anti-PD-1 group (see FIG. 1).

These results show that the administration of a compound of formula (I), such as Example 25, in combination with an anti-PD-1 antibody results in a remarkable increase in the cases of complete tumor regression in this xenograft mouse model. This finding is indicative of an outstanding therapeutic benefit of the compounds provided herein.

Example 213: In Vivo Anti-Tumoral Activity of the Compound of Example 25 in a Pan02 Tumor Model Pan02 tumor cells were maintained in vitro as a monolayer culture in RPM11640 medium supplemented with 10% fetal bovine serum at 37° C. in an atmosphere of 5% $CO_2$ in air. The cells were routinely subcultured twice weekly by trypsin-EDTA treatment. The cells in an exponential growth phase were harvested and counted for tumor inoculation.

Female C57BL/6 mice were inoculated subcutaneously in the right rear flank region with Pan02 tumor cells ($3\times10^6$) in 0.1 ml of PBS for tumor development on day 0. Tumor volumes were measured thrice per week in two dimensions using a caliper, and the volume was expressed in $mm^3$ using the formula: "V=(L×W×W)/2", where V is tumor volume, L is tumor length (the longest tumor dimension) and W is tumor width (the longest tumor dimension perpendicular to L). When the mean tumor size reached approximately 100 $mm^3$, mice were randomly allocated into groups (10 mice per group) and treated with either a control antibody (rIgG2a (2A3), 200 μg/mouse, iv, Q3D) or an anti-PD-1 antibody (RPM1-14, 200 μg/mouse, iv, Q3D), with or without the compound of Example 25 (150 mg/kg, po, 0.5% MC, BID, BID time interval: 8 h) for at least 3 weeks.

Animals were checked daily for morbidity and mortality. During routine monitoring, the animals were checked for any effects on tumor growth and treatments on behavior such as mobility, food and water consumption, body weight gain/loss (body weights were measured thrice per week), eye/hair matting and any other abnormalities. Dosing as well as tumor and body weight measurements were conducted in a Laminar Flow Cabinet. The body weights and tumor volumes were monitored by using StudyDirector™ software (version 3.1.399.19).

Example 25 administered at 150 mg/kg BID plus rIgG2a demonstrated significant anti-tumor efficacy with tumor growth inhibition (TGI) value of 68.5% on day 21 (P<0.001 vs control group) (see FIG. 2 and Table 1). Example 25 administered at 150 mg/kg BID combined with anti-PD-1 antibody (0.2 mg/animal, Q3D) displayed significant anti-tumor efficacy with TGI value of 71.0% on day 21 (P<0.001 vs control group).

TABLE 1

Tumor Growth Inhibition (TGI) in Pan02 tumor model.

| Study | TGI (%) | | | | | | |
|---|---|---|---|---|---|---|---|
| days | 0 | 3 | 7 | 10 | 14 | 17 | 21 |
| Group 2 | 0.1% | 9.3% | 15.6% | 10.9% | 28.8% | 31.7% | 32.7% |
| Group 3 | 0.0% | 15.6% | 22.5% | 25.1% | 51.5% | 61.8% | 68.5% |
| Group 4 | 0.1% | 10.9% | 16.9% | 26.1% | 51.1% | 62.8% | 71.0% |

(Group 2: anti-PD1 antibody; Group 3: Example 25 + rIgG2a; Group 4: Example 25 + anti-PD1 antibody)

These results demonstrate that the compounds of formula (I), including Example 25, exhibit an advantageously potent anti-tumor activity, which can be further enhanced by combined treatment with an anti-PD-1 antibody.

Example 214: In Vivo Anti-Tumoral Activity of the Compound of Example 166 in a Pan02 Tumor Model Pan02 tumor cells were maintained in vitro as a monolayer culture in RPM11640 medium supplemented with 10% fetal bovine serum at 37° C. in an atmosphere of 5% $CO_2$ in air. The cells were routinely subcultured twice weekly by trypsin-EDTA treatment. The cells in an exponential growth phase were harvested and counted for tumor inoculation.

Female C57BL/6 mice were inoculated subcutaneously in the right rear flank region with Pan02 tumor cells ($3\times10^6$) in 0.1 ml of PBS for tumor development on day 0. Tumor volumes were measured thrice per week in two dimensions using a caliper, and the volume was expressed in $mm^3$ using the formula: "V=(L×W×W)/2", where V is tumor volume, L is tumor length (the longest tumor dimension) and W is tumor width (the longest tumor dimension perpendicular to L). When the mean tumor size reached approximately 100 $mm^3$, mice were randomly allocated into groups (10 mice per group) and treated with or without the compound of Example 166 (3, 10, 30, 100 or 300 mg/kg, po, QD, 5% DMSO/95% (10% w/v solution of HP-β-CD in water) v/v) for at least 3 weeks).

Animals were checked daily for morbidity and mortality. During routine monitoring, the animals were checked for any effects on tumor growth and treatments on behavior such as mobility, food and water consumption, body weight gain/loss (body weights were measured thrice per week), eye/hair matting and any other abnormalities. Dosing as well as tumor and body weight measurements were conducted in a Laminar Flow Cabinet. The body weights and tumor volumes were monitored by using StudyDirector™ software (version 3.1.399.19).

Example 166 administered at 100 mg/kg QD demonstrated significant anti-tumor efficacy with tumor growth inhibition (TGI) value of 48.2% on day 18 (P<0.05 vs control group) (see FIG. 3 and Table 2). Example 166 administered at 300 mg/kg displayed anti-tumor efficacy with TGI value of 32.9% on day 18.

TABLE 2

| Tumor Growth Inhibition (TGI) in a Pan02 tumor model. | | | | | | | | | |
|---|---|---|---|---|---|---|---|---|---|
| Study | TGI (%) | | | | | | | | |
| days | 0 | 4 | 7 | 9 | 11 | 14 | 16 | 18 | 21 |
| Group 2 | 0.0% | 8.2% | 2.9% | 2.3% | −8.0% | −5.6% | 10.7% | 9.1% | −1.4% |
| Group 3 | 0.0% | 14.3% | −2.3% | 0.8% | 2.4% | 11.1% | 21.1% | 22.4% | 16.2% |
| Group 4 | 0.0% | 17.5% | 19.0% | 16.3% | −8.2% | 5.7% | 9.7% | 13.9% | 7.4% |
| Group 5 | 0.0% | 17.1% | 21.4% | 20.8% | 23.7% | 44.3% | 42.2% | 48.2% | 42.6% |
| Group 6 | 0.0% | 14.3% | −2.5% | −0.7% | −5.6% | 11.8% | 24.7% | 32.9% | 32.8% |

(Group 2: 3 mg/kg; Group 3: 10 mg/kg; Group 4: 30 mg/kg; Group 5: 100 mg/kg; Group 6: 300 mg/kg)

These results demonstrate that the compounds of formula (I), including Example 166, exhibit an advantageously potent anti-tumor activity, even as a monotherapy.

Example 215: In Vivo Anti-Tumoral Activity of the Compound of Example 166 in a MCA205 Tumor Model Sarcoma MCA205 tumor cell line was cultured in vitro in DMEM supplemented with 10% FBS, 1% Penicillin-Streptomycin, 1 mM HEPES. Before inoculation in mice, cell viability was assessed by flow cytometry analysis and viable cell gating. A cell suspension was prepared according to the viable cell count.

Female C57BL/6 mice were inoculated subcutaneously in the right flank region with MCA205 tumor cells ($0.5\times10^6$) in 0.1 ml of PBS for tumor development on day 1. Tumor volumes were measured thrice per week in two dimensions using a caliper, and the volume was expressed in $mm^3$ using the formula: "V=(L×W×W)/2", where V is tumor volume, L is tumor length (the longest tumor dimension) and W is tumor width (the longest tumor dimension perpendicular to L). When the mean tumor size reached approximately 80 $mm^3$, mice were randomly allocated into groups (10 mice per group) and treated with or without an anti-PD-1 antibody (RPM1-14, 5 mg/kg, ip, on days 1, 4, 7, 10), with or without the compound of Example 166 (30 or 100 mg/kg, po, QD, 5% DMSO/95% (10% w/v solution of HP-3-CD in water) v/v) for 23 days).

Animals were checked daily for morbidity and mortality. During routine monitoring, the animals were checked for any effects on tumor growth and treatments on behavior such as mobility, food and water consumption, body weight gain/loss (body weights were measured thrice per week), eye/hair matting and any other abnormalities.

Example 166 administered at 100 mg/kg QD demonstrated anti-tumor efficacy with tumor growth inhibition (TGI) value of 31.0% on day 17 (see FIG. 4 and Table 3). Example 166 administered at 100 mg/kg combined with anti-PD-1 antibody (5 mg/kg) displayed significant anti-tumor efficacy with TGI value of 68.0% on day 17.

TABLE 3

| Tumor Growth Inhibition (TGI) in a MCA205 tumor model | | | | | | | | |
|---|---|---|---|---|---|---|---|---|
| Study | TGI (%) | | | | | | | |
| days | 1 | 3 | 6 | 8 | 10 | 13 | 15 | 17 |
| Group 2 | −0.8% | −0.8% | 12.2% | 32.9% | 45.9% | 40.4% | 40.3% | 38.4% |
| Group 3 | −6.1% | −6.3% | −22.4% | 9.8% | 10.2% | 6.4% | 4.3% | 10.8% |
| Group 4 | −0.7% | 13.2% | 12.1% | 16.7% | 25.7% | 32.6% | 23.6% | 31.0% |
| Group 5 | 0.1% | 8.3% | 30.6% | 47.4% | 58.6% | 55.7% | 49.3% | 52.2% |
| Group 6 | 1.4% | 12.2% | 34.3% | 50.2% | 66.6% | 70.4% | 67.3% | 68.1% |

(Group 2: anti-PD1 antibody; Group 3: Example 166 at 30 mg/kg; Group 4: Example 166 at 100 mg/kg; Group 5: Example 166 at 30 mg/kg + anti-PD1 antibody; Group 6: Example 166 at 100 mg/kg + anti-PD1 antibody)

These results confirm that the compounds of formula (I), including Example 166, exhibit an advantageously potent anti-tumor activity, particularly in combination with an anti-PD-1 antibody.

The invention claimed is:

1. A compound of the following formula (I)

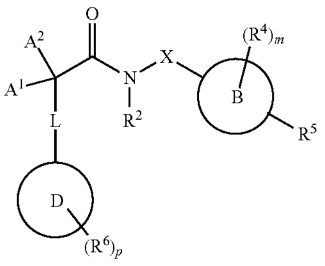

(I)

wherein:

$A^1$ and $A^2$ are each independently $C_{1-5}$ alkyl;

ring B is a carbocyclic group or a heterocyclic group;

ring D is carbocyclyl or heterocyclyl;

L is-heterocyclylene-$(CH_2)_{1-2}$—, wherein one —$CH_2$— unit comprised in said-heterocyclylene-$(CH_2)_{1-2}$— is optionally replaced by a group selected from —O13 , —CO—, —NH—, —N($C_{1-5}$ alkyl)-and-N [—CO—($C_{1-5}$ alkyl)]-, wherein the heterocyclylene in said-heterocyclylene-$(CH_2)_{1-2}$— is optionally substituted with one or more groups -$L^A$-$R^A$, and further wherein L is attached to ring D via —$CH_2$— r via —O— contained in said L;

m is an integer of 0 to 4;

p is an integer of 0 to 4;

$R^2$ is selected from hydrogen, $C_{1-5}$ alkyl, and —CO ($C_{1-5}$ alkyl);

X is $C(R^{3a})(R^{3b})$ or $N(R^{3c})$;

$R^{3a}$ is selected from $C_{1-5}$ alkyl and $C_{2-5}$ alkenyl, and $R^{3b}$ is selected from hydrogen, $C_{1-5}$ alkyl, and $C_{2-5}$ alkenyl; or $R^{3a}$ and $R^{3b}$ are mutually linked to form, together with the carbon atom that they are attached to, a cycloalkyl or a heterocycloalkyl, wherein said cycloalkyl or said heterocycloalkyl is optionally substituted with one or more groups $R^{31}$; or $R^{3a}$ is a divalent group selected from linear $C_{2-4}$ alkylene and linear $C_{2-4}$ alkenylene, wherein said divalent group is attached via one end to the carbon atom carrying $R^{3b}$ and is attached via the other end to a ring atom of ring B which is adjacent to the ring atom carrying the group X, wherein said alkylene or said alkenylene is optionally substituted with one or more groups $R^{31}$, wherein one —$CH_2$— unit in said alkylene or said alkenylene is optionally replaced by —O—, —S—, —NH— or —N($C_{1-5}$ alkyl)-, and $R^{3b}$ is selected from hydrogen, $C_{1-5}$ alkyl, and $C_{2-5}$ alkenyl;

$R^{3c}$ is selected from hydrogen, $C_{1-5}$ alkyl, and $C_{2-5}$ alkenyl;

each $R^{31}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH ($C_{1-5}$ alkyl), —N($C_{1-5}$ alkyl) ($C_{1-5}$ alkyl), halogen, $C_{1-5}$ haloalkyl, —O—($C_{1-5}$ haloalkyl), —CN, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl) ($C_{1-5}$ alkyl), —NH—CO—($C_{1-5}$ alkyl), —N($C_{1-5}$ alkyl)-CO—($C_{1-5}$ alkyl), —NH—COO($C_{1-5}$ alkyl), —N($C_{1-5}$ alkyl)-COO($C_{1-5}$ alkyl), —O—CO—NH ($C_{1-5}$ alkyl), —O—CO—N($C_{1-5}$ alkyl) ($C_{1-5}$ alkyl), —$SO_2$—$NH_2$, —$SO_2$—NH($C_{1-5}$ alkyl), —$SO_2$—N ($C_{1-5}$ alkyl) ($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), and —$SO_2$—($C_{1-5}$ alkyl);

each $R^4$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O ($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S ($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl) ($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl) ($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl) ($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl) ($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^A$-$R^A$;

$R^5$ is selected from —COOH, —CO—$NH_2$, —CO—NH($C_{1-5}$ alkyl), —CO—N($C_{1-5}$ alkyl) ($C_{1-5}$ alkyl), —$SO_2$—OH, —$SO_2$—O—($C_{1-5}$ alkyl), —$SO_2$—$NH_2$, —$SO_2$—NH($C_{1-5}$ alkyl), —$SO_2$—N($C_{1-5}$ alkyl) ($C_{1-5}$ alkyl), —$SO_2$—($C_{1-5}$ alkyl), —S(═O)(=NH)—($C_{1-5}$ alkyl), halogen, $C_{1-5}$ haloalkyl, —CN, $C_{1-4}$ alkyl, —OH, —O($C_{1-4}$ alkyl), carbocyclyl, and heterocyclyl, wherein said carbocyclyl or said heterocyclyl is optionally substituted with one or more groups-LA-RA;

each $R^6$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-6}$ alkyl), —($C_{0-3}$ alkylene)-O($C_{1-5}$ alkylene)-O($C_{1-5}$ alkylene)-O($C_{1-5}$ alkyl), —($C_{0-3}$ alkylene)-OH, —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S ($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl) ($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CN, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl) ($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-NH—COO($C_{1-5}$ alkyl), —($C_{0-3}$ alkylene)-N($C_{1-5}$ alkyl)-COO($C_{1-5}$ alkyl), —($C_{0-3}$ alkylene)-O—CO—NH($C_{1-5}$ alkyl), —($C_{0-3}$ alkylene)-O—CO—N($C_{1-5}$ alkyl) ($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl) ($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, —($C_{0-3}$ alkylene)-heterocycloalkyl, and -$L^1$-$R^{61}$;

$L^1$ is $C_{1-6}$ alkylene or a covalent bond, wherein one or more —$CH_2$— units comprised in said $C_{1-6}$ alkylene are each optionally replaced by a group independently selected from —O—, —CO—, —NH—, —$N(C_{1-5}$ alkyl)-, —N [—CO—$(C_{1-5}$ alkyl)]-, —S—, —SO—, —$SO_2$—, —$CH(C_{1-5}$ alkyl)-and-$C(C_{1-5}$ alkyl) $(C_{1-5}$ alkyl)-;

$R^{61}$ is carbocyclyl or heterocyclyl, wherein said carbocyclyl or said heterocyclyl is optionally substituted with one or more groups $R^{62}$;

each $R^{62}$ is independently selected from $C_{1-5}$ alkyl, $C_{2-5}$ alkenyl, $C_{2-5}$ alkynyl, —$(C_{0-3}$ alkylene)-OH, —$(C_{0-3}$ alkylene)-$O(C_{1-5}$ alkyl), —$(C_{0-3}$ alkylene)-$O(C_{1-5}$ alkylene)-OH, —$(C_{0-3}$ alkylene)-$O(C_{1-5}$ alkylene)-$O(C_{1-5}$ alkyl), —$(C_{0-3}$ alkylene)-SH, —$(C_{0-3}$ alkylene)-$S(C_{1-5}$ alkyl), —$(C_{0-3}$ alkylene)-$S(C_{1-5}$ alkylene)-SH, —$(C_{0-3}$ alkylene)-$S(C_{1-5}$ alkylene)-$S(C_{1-5}$ alkyl), —$(C_{0-3}$ alkylene)-$NH_2$, —$(C_{0-3}$ alkylene)-$NH(C_{1-5}$ alkyl), —$(C_{0-3}$ alkylene)-$N(C_{1-5}$ alkyl) $(C_{1-5}$ alkyl), —$(C_{0-3}$ alkylene)-halogen, —$(C_{0-3}$ alkylene)-$(C_{1-5}$ haloalkyl), —$(C_{0-3}$ alkylene)-O—$(C_{1-5}$ haloalkyl), —$(C_{0-3}$ alkylene)-CN, —$(C_{0-3}$ alkylene)-CHO, —$(C_{0-3}$ alkylene)-CO—$(C_{1-5}$ alkyl), —$(C_{0-3}$ alkylene)-COOH, —$(C_{0-3}$ alkylene)-CO—O—$(C_{1-5}$ alkyl), —$(C_{0-3}$ alkylene)-O—CO—$(C_{1-5}$ alkyl), —$(C_{0-3}$ alkylene)-CO—$NH_2$, —$(C_{0-3}$ alkylene)-CO—$NH(C_{1-5}$ alkyl), —$(C_{0-3}$ alkylene)-CO—$N(C_{1-5}$ alkyl) $(C_{1-5}$ alkyl), —$(C_{0-3}$ alkylene)-NH—CO—$(C_{1-5}$ alkyl), —$(C_{0-3}$ alkylene)-$N(C_{1-5}$ alkyl)-CO—$(C_{1-5}$ alkyl), —$(C_{0-3}$ alkylene)-NH—$COO(C_{1-5}$ alkyl), —$(C_{0-3}$ alkylene)-$N(C_{1-5}$ alkyl)-$COO(C_{1-5}$ alkyl), —$(C_{0-3}$ alkylene)-O—CO—$NH(C_{1-5}$ alkyl), —$(C_{0-3}$ alkylene)-O—CO—$N(C_{1-5}$ alkyl) $(C_{1-5}$ alkyl), —$(C_{0-3}$ alkylene)-$SO_2$—$NH_2$, —$(C_{0-3}$ alkylene)-$SO_2$—$NH(C_{1-5}$ alkyl), —$(C_{0-3}$ alkylene)-$SO_2$—$N(C_{1-5}$ alkyl) $(C_{1-5}$ alkyl), —$(C_{0-3}$ alkylene)-NH—$SO_2$—$(C_{1-5}$ alkyl), —$(C_{0-3}$ alkylene)-$N(C_{1-5}$ alkyl)-$SO_2$—$(C_{1-5}$ alkyl), —$(C_{0-3}$ alkylene)-SO—$(C_{1-5}$ alkyl), —$(C_{0-3}$ alkylene)-$SO_2$—$(C_{1-5}$ alkyl), —$(C_{0-3}$ alkylene)-cycloalkyl, and —$(C_{0-3}$ alkylene)-heterocycloalkyl;

each $L^A$ is independently selected from a covalent bond, $C_{1-5}$ alkylene, $C_{2-5}$ alkenylene, and $C_{2-5}$ alkynylene, wherein said alkylene, said alkenylene and said alkynylene are each optionally substituted with one or more groups independently selected from halogen, $C_{1-5}$ haloalkyl, —CN, —OH, —$O(C_{1-5}$ alkyl), —SH, —$S(C_{1-5}$ alkyl), —$NH_2$, —$NH(C_{1-5}$ alkyl), and —$N(C_{1-5}$ alkyl) $(C_{1-5}$ alkyl), and further wherein one or more —$CH_2$— units comprised in said alkylene, said alkenylene or said alkynylene are each optionally replaced by a group independently selected from —O—, —NH—, —$N(C_{1-5}$ alkyl)-, —CO—, —S—, —SO—, and —$SO_2$—; and each $R^A$ is independently selected from —OH, —$O(C_{1-5}$ alkyl), —$O(C_{1-5}$ alkylene)-OH, —$O(C_{1-5}$ alkylene)-$O(C_{1-5}$ alkyl), —SH, —$S(C_{1-5}$ alkyl), —$S(C_{1-5}$ alkylene)-SH, —$S(C_{1-5}$ alkylene)-$S(C_{1-5}$ alkyl), —$NH_2$, —$NH(C_{1-5}$ alkyl), —$N(C_{1-5}$ alkyl) $(C_{1-5}$ alkyl), halogen, $C_{1-5}$ haloalkyl, —$O(C_{1-5}$ haloalkyl), —CN, —CHO, —$CO(C_{1-5}$ alkyl), —COOH, —$COO(C_{1-5}$ alkyl), —O—$CO(C_{1-5}$ alkyl), —CO—$NH_2$, —CO—$NH(C_{1-5}$ alkyl), —CO—$N(C_{1-5}$ alkyl) $(C_{1-5}$ alkyl), —NH—$CO(C_{1-5}$ alkyl), —$N(C_{1-5}$ alkyl)-$CO(C_{1-5}$ alkyl), —NH—$COO(C_{1-5}$ alkyl), —$N(C_{1-5}$ alkyl)-$COO(C_{1-5}$ alkyl), —O—CO—$NH(C_{1-5}$ alkyl), —O—CO—$N(C_{1-5}$ alkyl) $(C_{1-5}$ alkyl), —$SO_2$—$NH_2$, —$SO_2$—$NH(C_{1-5}$ alkyl), —$SO_2$—$N(C_{1-5}$ alkyl) $(C_{1-5}$ alkyl), —NH—$SO_2$—$(C_{1-5}$ alkyl), —$N(C_{1-5}$ alkyl)-$SO_2$—$(C_{1-5}$ alkyl), —$SO_2$—$(C_{1-5}$ alkyl), —SO—$(C_{1-5}$ alkyl), hydrogen, aryl, heteroaryl, cycloalkyl, and heterocycloalkyl, wherein said aryl, said heteroaryl, said cycloalkyl, and said heterocycloalkyl are each optionally substituted with one or more groups independently selected from $C_{1-5}$ alkyl, $C_{2-5}$ alkenyl, $C_{2-5}$ alkynyl, halogen, $C_{1-5}$ haloalkyl, —CN, —OH, —$O(C_{1-5}$ alkyl), —SH, —$S(C_{1-5}$ alkyl), —$NH_2$, —$NH(C_{1-5}$ alkyl), and —$N(C_{1-5}$ alkyl) $(C_{1-5}$ alkyl);

or a pharmaceutically acceptable salt thereof.

2. The compound of claim 1, wherein:

$A^1$ and $A^2$ are each independently $C_{1-4}$ alkyl;

X is $C(R^{3a})(R^{3b})$;

$R^{3a}$ is selected from $C_{1-5}$ alkyl and $C_{2-5}$ alkenyl, and $R^{3b}$ is selected from hydrogen, $C_{1-5}$ alkyl, and $C_{2-5}$ alkenyl; or $R^{3a}$ and $R^{3b}$ are mutually linked to form, together with the carbon atom that they are attached to, a cycloalkyl or a heterocycloalkyl, wherein said cycloalkyl or said heterocycloalkyl is optionally substituted with one or more groups $R^{31}$; and L is -heterocycloalkylene-$CH_2$—, wherein the —$CH_2$-unit in said-heterocycloalkylene-$CH_2$— is optionally replaced by —O—, and further wherein L is attached to ring D via —$CH_2$— or via —O— contained in said L.

3. The compound of claim 1, wherein $A^1$ and $A^2$ are each methyl.

4. The compound of claim 1, wherein ring B is phenylene or cyclohexylene.

5. The compound of claim 1, wherein X is $C(R^{3a})(R^{3b})$; and wherein $R^{3a}$ is $C_{1-5}$ alkyl and $R^{3b}$ is hydrogen or $C_{1-5}$ alkyl, or $R^{3a}$ and $R^{3b}$ are mutually linked to form, together with the carbon atom that they are attached to, a cyclopropyl.

6. The compound of claim 1, wherein $R^5$ is selected from —COOH, —CO—$NH_2$, —CO—$NH(C_{1-5}$ alkyl), —CO—$N(C_{1-5}$ alkyl) $(C_{1-5}$ alkyl), —$SO_2$—$(C_{1-5}$ alkyl), —S(═O)(═NH)—$(C_{1-5}$ alkyl), and tetrazolyl.

7. The compound of claim 1, wherein the moiety

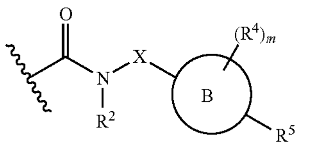

is

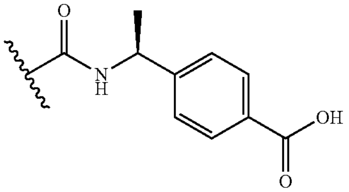

or

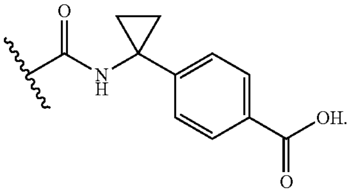

8. The compound of claim 1, wherein ring D is selected from phenyl, pyridinyl, azetidinyl, pyrrolidinyl, piperidinyl, and cyclohexyl.

9. The compound of claim 1, wherein L is -heterocycloalkylene-$CH_2$—, wherein the —$CH_2$-unit in said -heterocycloalkylene-$CH_2$— is optionally replaced by —O—, and further wherein L is attached to ring D via —$CH_2$— or via —O— contained in said L.

10. The compound of claim 1, wherein L is -heterocycloalkylene-O— which is attached to ring D via the oxygen atom in said group -heterocycloalkylene-O—, and wherein the heterocycloalkylene in said -heterocycloalkylene-O— is attached in a 1,3-orientation.

11. The compound of claim 1, wherein L is selected from

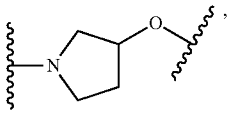

, and

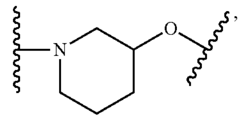

, wherein each of the aforementioned groups is attached to ring D via the terminal oxygen atom contained therein.

12. The compound of claim 1, wherein:

$A^1$ and $A^2$ are each independently methyl or ethyl;

X is $C(R^{3a})(R^{3b})$, wherein $R^{3a}$ is $C_{1-5}$ alkyl and $R^{3b}$ is hydrogen or $C_{1-5}$ alkyl, or wherein $R^{3a}$ and $R^{3b}$ are mutually linked to form, together with the carbon atom that they are attached to, a cyclopropyl; and L is selected from

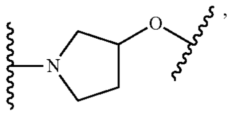

, and

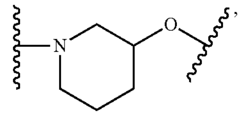

, wherein each of the aforementioned groups is attached to ring D via the terminal oxygen atom contained therein.

13. The compound of claim 1, wherein p is 1, wherein $R^6$ is attached to ring D in a 1,3-orientation with respect to the attachment point of group L to ring D, and wherein $R^6$ is selected from —$CH_3$, —OH, —$OCH_3$, halogen, —$CF_3$, —$OCF_3$, —CN, and -$L^1$-$R^{61}$.

14. The compound of claim 1, wherein said compound is selected from:

4-[(1S)-1-[[2-[(3R)-3-[3-(Trifluoromethyl)phenoxy]pyrrolidin-1-yl]-2-methylpropane-carbonyl]amino]ethyl]benzoic acid;

4-[(1S)-1-[[2-[(3R)-3-[3-(Trifluoromethyl)phenoxy]pyrrolidin-1-yl]-2-methylpropane-carbonyl]amino]ethyl]benzamide;

4-[(1S)-1-[[2-[(3R)-3-(3-Chlorophenoxy)pyrrolidin-1-yl]-2-methylpropane-carbonyl]amino]ethyl]benzamide;

2-Methyl-N—((S)-1-(4-sulfamoylphenyl)ethyl)-2-((R)-3-(3-(trifluoromethyl)phenoxy)pyrrolidin-1-yl)propanamide;

2-Methyl-N—((S)-1-(4-(methylsulfonyl)phenyl)ethyl)-2-((R)-3-(3-(trifluoromethyl)phenoxy)pyrrolidin-1-yl)propanamide;

2-Methyl-N-((1S)-1-(4-(S-methylsulfonimidoyl)phenyl)ethyl)-2-((R)-3-(3-(trifluoromethyl)phenoxy)pyrrolidin-1-yl)propanamide;

N—((S)-1-(4-(1,2,4-Oxadiazol-3-yl)phenyl)ethyl)-2-methyl-2-((R)-3-(3-(trifluoromethyl)phenoxy)pyrrolidin-1-yl)propanamide;

N—((S)-1-(4-(1,2,4-Oxadiazol-5-yl)phenyl)ethyl)-2-methyl-2-((R)-3-(3-(trifluoromethyl)phenoxy)pyrrolidin-1-yl)propanamide;

4-((1S)-1-(2-(3-Benzylpyrrolidin-1-yl)-2-methylpropanamido)ethyl)benzoic acid;

4-((S)-1-(2-((R)-3-((3-Chlorophenoxy)methyl)pyrrolidin-1-yl)-2-methylpropanamido)ethyl)benzoic acid; and 4-[(1S)-1-[2-[(3R)-3-(3-Chlorophenoxy)pyrrolidin-1-yl]-2-ethylbutane-carbonyl]amino]ethyl]benzoic acid;

or a pharmaceutically acceptable salt thereof.

15. The compound of claim 1, wherein said compound is 4-[(1S)-1-[2-[(3R)-3-[3-(Trifluoromethyl)phenoxy]pyrrolidin-1-yl]-2-methylpropane-carbonyl]amino]ethyl]benzoic acid or a pharmaceutically acceptable salt thereof.

16. A pharmaceutical composition comprising the compound of claim 1 and a pharmaceutically acceptable excipient.

17. A method of treating cancer, inflammatory pain, an inflammatory disease, or a neovascular eye disease, the method comprising administering a therapeutically effective amount of the compound of claim 1 to a subject in need thereof, wherein the cancer is selected from lung cancer, non-small cell lung cancer, renal carcinoma, gastro-intestinal cancer, stomach cancer, colorectal cancer, colon cancer, malignantfamilial adenomatouspolyposis, anal cancer, genitourinary cancer, bladder cancer, liver cancer, pancreatic cancer, ovarian cancer, cervical cancer, endometrial cancer, vaginal cancer, vulvar cancer, prostate cancer, testicular cancer, biliary tract cancer, hepatobiliary cancer, neuroblastoma, brain cancer, breast cancer, head and/or neck cancer, skin cancer, melanoma, Merkel-cell carcinoma, epidermoid cancer, squamous cell carcinoma, bone cancer, fibrosarcoma, Ewing's sarcoma, malignant mesothelioma, esophageal cancer, laryngeal cancer, mouth cancer, thymoma, neuroendocrine cancer, hematological cancer, leukemia, acute myeloid leukemia, lymphoma, and multiple myeloma.

18. The method of claim 17, wherein the disease is cancer.

19. The method of claim 17, wherein the disease is inflammatory pain.

20. The method of claim 17, wherein the disease is an inflammatory disease.

21. The method of claim 17, wherein the disease is a neovascular eye disease.

22. The method of claim 18, wherein said compound is administered in combination with one or more immune checkpoint inhibitors.

23. The method of claim 20, wherein said inflammatory disease is selected from multiple sclerosis, rheumatoid arthritis, endometriosis, and osteoarthritis.

24. The method of claim 21, wherein said neovascular eye disease is selected from neovascular degenerative maculopathy, proliferative diabetic retinopathy, neovascular glaucoma, and retinopathy of prematurity.

25. The method of claim 22, wherein said one or more immune checkpoint inhibitors are selected from anti-CTLA-4 antibodies, anti-PD-1 antibodies and anti-PD-L1 antibodies.

26. The method of claim 22, wherein said one or more immune checkpoint inhibitors are selected from ipilimumab, tremelimumab, nivolumab, pembrolizumab, cemiplimab, spartalizumab, camrelizumab, sintilimab, tislelizumab, AMP-224, AMP-514, atezolizumab, avelumab, durvalumab, KN035, and CK-301.

* * * * *